US011350959B2

(12) United States Patent
Messerly et al.

(10) Patent No.: US 11,350,959 B2
(45) Date of Patent: Jun. 7, 2022

(54) ULTRASONIC TRANSDUCER TECHNIQUES FOR ULTRASONIC SURGICAL INSTRUMENT

(71) Applicant: Ethicon LLC, Guaynabo, PR (US)

(72) Inventors: Jeffrey D. Messerly, Cincinnati, OH (US); Brian D. Black, Loveland, OH (US); William A. Olson, Lebanon, OH (US); Frederick Estera, Cincinnati, OH (US); William E. Clem, Bozeman, MT (US); Jerome R. Morgan, Cincinnati, OH (US); Jeffrey L. Aldridge, Lebanon, OH (US); Stephen M. Leuck, Milford, OH (US)

(73) Assignee: Cilag GmbH International, Zug (CH)

( * ) Notice: Subject to any disclaimer, the term of this patent is extended or adjusted under 35 U.S.C. 154(b) by 224 days.

(21) Appl. No.: 15/679,940

(22) Filed: Aug. 17, 2017

(65) Prior Publication Data

US 2018/0055529 A1 Mar. 1, 2018

Related U.S. Application Data

(60) Provisional application No. 62/379,550, filed on Aug. 25, 2016.

(51) Int. Cl.
*A61B 17/00* (2006.01)
*H01L 41/09* (2006.01)
(Continued)

(52) U.S. Cl.
CPC ............. *A61B 17/320068* (2013.01); *A61B 17/00234* (2013.01); *A61N 7/02* (2013.01);
(Continued)

(58) Field of Classification Search
CPC .............. H01L 41/0536; H01L 41/083; H01L 41/0835; H01L 41/0986; B29C 65/4805;
(Continued)

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| CA | 837241 A | 3/1970 |
| CA | 2535467 A1 | 4/1993 |

(Continued)

OTHER PUBLICATIONS

Technology Overview, printed from www.harmonicscalpel.com, Internet site, website accessed on Jun. 13, 2007, (3 pages).
(Continued)

*Primary Examiner* — A. Dexter Tugbang

(57) ABSTRACT

A method of fabricating an ultrasonic medical device is presented. The method includes machining a surgical tool from a flat metal stock, contacting a face of a first transducer with a first face of the surgical tool, and contacting a face of a second transducer with an opposing face of the surgical tool opposite the first transducer. The first and second transducers are configured to operate in a D31 mode with respect to the longitudinal portion of the surgical tool. Upon activation, the first transducer and the second transducer are configured to induce a standing wave in the surgical tool and the induced standing wave comprises a node at a node location in the surgical tool and an antinode at an antinode location in the surgical tool.

13 Claims, 133 Drawing Sheets

(51) Int. Cl.
  *A61B 17/32* (2006.01)
  *H01L 41/053* (2006.01)
  *H01L 41/083* (2006.01)
  *B29C 65/48* (2006.01)
  *A61N 7/02* (2006.01)
  *A61B 17/22* (2006.01)
  *A61B 17/29* (2006.01)
  *B29L 31/00* (2006.01)
  *A61B 17/16* (2006.01)
  *A61B 18/00* (2006.01)

(52) U.S. Cl.
  CPC ...... B29C 65/4805 (2013.01); H01L 41/0536 (2013.01); H01L 41/083 (2013.01); H01L 41/0835 (2013.01); H01L 41/0986 (2013.01); *A61B 17/1628* (2013.01); *A61B 2017/00017* (2013.01); *A61B 2017/0088* (2013.01); *A61B 2017/00402* (2013.01); *A61B 2017/00477* (2013.01); *A61B 2017/00526* (2013.01); *A61B 2017/22027* (2013.01); *A61B 2017/294* (2013.01); *A61B 2017/32007* (2017.08); *A61B 2017/320074* (2017.08); *A61B 2017/320082* (2017.08); *A61B 2017/320088* (2013.01); *A61B 2017/320089* (2017.08); *A61B 2017/320098* (2017.08); *A61B 2018/00565* (2013.01); *A61B 2018/00589* (2013.01); *A61B 2018/00595* (2013.01); *B29L 2031/7546* (2013.01); *Y10T 29/42* (2015.01)

(58) Field of Classification Search
  CPC ....... B29L 2031/7546; A61B 17/00234; A61B 17/1628; A61B 17/320068; A61B 2017/00017; A61B 2017/00477; A61B 2017/00402; A61B 2017/00526; A61B 2017/0088; A61B 2017/294; A61B 2017/22027; A61B 2017/32007; A61B 2017/320074; A61B 2017/320082; A61B 2017/320088; A61B 2017/320089; A61B 2017/320098; A61B 2018/00565; A61B 2018/00589; A61B 2018/00595; Y10T 29/42; A61N 7/02
  See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,743,726 A | 5/1956 | Grieshaber |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,503,396 A | 3/1970 | Pierie et al. |
| 3,503,397 A | 3/1970 | Fogarty et al. |
| 3,503,398 A | 3/1970 | Fogarty et al. |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,792,701 A | 2/1974 | Kloz et al. |
| 3,805,787 A | 4/1974 | Banko |
| 3,809,977 A | 5/1974 | Balamuth et al. |
| 3,830,098 A | 8/1974 | Antonevich |
| 3,832,776 A | 9/1974 | Sawyer |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,057,660 A | 11/1977 | Yoshida et al. |
| 4,058,126 A | 11/1977 | Leveen |
| 4,074,719 A | 2/1978 | Semm |
| 4,085,893 A | 4/1978 | Durley, III |
| 4,156,187 A | 5/1979 | Murry et al. |
| 4,167,944 A | 9/1979 | Banko |
| 4,169,984 A | 10/1979 | Parisi |
| 4,173,725 A | 11/1979 | Asai et al. |
| 4,188,927 A | 2/1980 | Harris |
| 4,193,009 A | 3/1980 | Durley, III |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Helges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,352,459 A | 10/1982 | Berger et al. |
| 4,445,063 A | 4/1984 | Smith |
| 4,452,473 A | 6/1984 | Ruschke |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |

(56) References Cited

U.S. PATENT DOCUMENTS

| | | |
|---|---|---|
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,663,677 A | 5/1987 | Griffith et al. |
| 4,674,502 A | 6/1987 | Imonti |
| 4,696,667 A | 9/1987 | Masch |
| 4,708,127 A | 11/1987 | Abdelghani |
| 4,712,722 A | 12/1987 | Hood et al. |
| 4,735,603 A | 4/1988 | Goodson et al. |
| 4,750,488 A | 6/1988 | Wuchinich et al. |
| 4,761,871 A | 8/1988 | O'Connor et al. |
| 4,783,997 A | 11/1988 | Lynnworth |
| 4,808,154 A | 2/1989 | Freeman |
| 4,819,635 A | 4/1989 | Shapiro |
| 4,821,719 A | 4/1989 | Fogarty |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,869,715 A | 9/1989 | Sherburne |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,978,067 A | 12/1990 | Berger et al. |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,047,043 A | 9/1991 | Kubota et al. |
| 5,057,119 A | 10/1991 | Clark et al. |
| 5,058,570 A | 10/1991 | Idemoto et al. |
| 5,059,210 A | 10/1991 | Clark et al. |
| 5,061,269 A | 10/1991 | Muller |
| 5,084,052 A | 1/1992 | Jacobs |
| 5,088,687 A | 2/1992 | Stender |
| 5,096,532 A | 3/1992 | Neuwirth et al. |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| D330,253 S | 10/1992 | Burek |
| 5,152,762 A | 10/1992 | McElhenney |
| 5,156,613 A | 10/1992 | Sawyer |
| 5,156,633 A | 10/1992 | Smith |
| 5,159,226 A | 10/1992 | Montgomery |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,209,776 A | 5/1993 | Bass et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,385 A | 9/1993 | Strukel |
| 5,242,460 A | 9/1993 | Klein et al. |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,289,436 A | 2/1994 | Terhune |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| 5,306,280 A | 4/1994 | Bregen et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,327 A | 5/1994 | Bales et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |

(56) References Cited

U.S. PATENT DOCUMENTS

| | | |
|---|---|---|
| 5,323,055 A | 6/1994 | Yamazaki |
| 5,324,297 A | 6/1994 | Hood et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,339,723 A | 8/1994 | Huitema |
| 5,342,292 A | 8/1994 | Nita et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,354,265 A | 10/1994 | Mackool |
| 5,356,064 A | 10/1994 | Green et al. |
| 5,357,164 A | 10/1994 | Imabayashi et al. |
| 5,357,423 A | 10/1994 | Weaver et al. |
| 5,358,506 A | 10/1994 | Green et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,372,585 A | 12/1994 | Tiefenbrun et al. |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,883 A | 1/1995 | Wilk et al. |
| 5,387,207 A | 2/1995 | Dyer et al. |
| 5,387,215 A | 2/1995 | Fisher |
| 5,389,098 A | 2/1995 | Tsuruta et al. |
| 5,391,144 A | 2/1995 | Sakurai et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,397,293 A | 3/1995 | Alliger et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| 5,409,453 A | 4/1995 | Lundquist et al. |
| D358,887 S | 5/1995 | Feinberg |
| 5,411,481 A | 5/1995 | Allen et al. |
| 5,413,107 A | 5/1995 | Oakley et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatia |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,496,411 A | 3/1996 | Candy |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,273 A | 6/1996 | Manna et al. |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,575,799 A | 11/1996 | Bolanos et al. |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tai et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,578 A | 5/1997 | Tihon |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,643,301 A | 7/1997 | Mollenauer |
| 5,647,851 A | 7/1997 | Pokras |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |

(56) References Cited

U.S. PATENT DOCUMENTS

| | | |
|---|---|---|
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,735,875 A | 4/1998 | Bonutti et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,310 A | 9/1998 | Hood |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,810,869 A | 9/1998 | Kaplan et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,290 A | 12/1998 | Winston |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,363 A | 3/1999 | Urich |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,893,880 A | 4/1999 | Egan et al. |
| 5,895,412 A | 4/1999 | Tucker |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,910,150 A | 6/1999 | Saadat |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,941,887 A | 8/1999 | Steen et al. |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,971,949 A | 10/1999 | Levin et al. |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,001,120 A | 12/1999 | Levin |
| 6,003,517 A | 12/1999 | Sheffield et al. |
| 6,004,335 A | 12/1999 | Vaitekunas et al. |
| 6,007,552 A | 12/1999 | Fogarty et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,053,906 A | 4/2000 | Honda et al. |
| 6,056,735 A | 5/2000 | Okada et al. |
| 6,063,050 A | 5/2000 | Manna et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,544 A | 7/2000 | Hibner et al. |
| 6,086,584 A | 7/2000 | Miller |
| 6,090,120 A | 7/2000 | Wright et al. |

(56) References Cited

U.S. PATENT DOCUMENTS

| | | |
|---|---|---|
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| 6,120,519 A | 9/2000 | Weber et al. |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,165,186 A | 12/2000 | Fogarty et al. |
| 6,165,191 A | 12/2000 | Shibata et al. |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,217,591 B1 | 4/2001 | Egan et al. |
| 6,228,080 B1 | 5/2001 | Gines |
| 6,228,104 B1 | 5/2001 | Fogarty et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,471 B1 | 8/2001 | Hechel et al. |
| 6,270,831 B2 | 8/2001 | Kumar et al. |
| 6,273,852 B1 | 8/2001 | Lehe et al. |
| 6,273,902 B1 | 8/2001 | Fogarty et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,293,954 B1 | 9/2001 | Fogarty et al. |
| 6,299,591 B1 | 10/2001 | Banko |
| 6,299,621 B1 | 10/2001 | Fogarty et al. |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,312,445 B1 | 11/2001 | Fogarty et al. |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,333,488 B1 | 12/2001 | Lawrence et al. |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,387,112 B1 | 5/2002 | Fogarty et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| 6,409,743 B1 | 6/2002 | Fenton, Jr. |
| H2037 H | 7/2002 | Yates et al. |
| 6,416,469 B1 | 7/2002 | Phung et al. |
| 6,416,486 B1 | 7/2002 | Wampler |
| 6,416,525 B1 | 7/2002 | Shibata |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,425,907 B1 | 7/2002 | Shibata et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,286 B2 | 10/2002 | Mastri et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |

(56) References Cited

U.S. PATENT DOCUMENTS

| | | |
|---|---|---|
| 6,491,701 B2 | 12/2002 | Tierney et al. |
| 6,491,708 B2 | 12/2002 | Madan et al. |
| 6,497,715 B2 | 12/2002 | Satou |
| 6,498,421 B1 | 12/2002 | Oh et al. |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,526,976 B1 | 3/2003 | Baran |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B2 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,562,059 B2 | 5/2003 | Edwards et al. |
| 6,565,558 B1 | 5/2003 | Lindenmeier et al. |
| 6,569,109 B2 | 5/2003 | Sakurai et al. |
| 6,569,178 B1 | 5/2003 | Miyawaki et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,929 B2 | 6/2003 | Sussman et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,229 B2 | 8/2003 | Coss |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,444 B2 | 9/2003 | Babaev |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,839 B2 | 11/2003 | Manna et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,124 B2 | 12/2003 | Flesch et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,086 B1 | 2/2004 | Nita et al. |
| 6,689,145 B2 | 2/2004 | Lee et al. |
| 6,689,146 B1 | 2/2004 | Himes |
| 6,690,960 B2 | 2/2004 | Chen et al. |
| 6,695,782 B2 | 2/2004 | Ranucci et al. |
| 6,695,840 B2 | 2/2004 | Schulze |
| 6,699,214 B2 | 3/2004 | Gellman |
| 6,702,761 B1 | 3/2004 | Damadian et al. |
| 6,702,821 B2 | 3/2004 | Bonutti |
| 6,712,805 B2 | 3/2004 | Weimann |
| 6,716,215 B1 | 4/2004 | David et al. |
| 6,719,692 B2 | 4/2004 | Kleffner et al. |
| 6,719,765 B2 | 4/2004 | Bonutti |
| 6,719,766 B1 | 4/2004 | Buelna et al. |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,154 B2 | 6/2004 | Fogarty et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |

(56) References Cited

U.S. PATENT DOCUMENTS

| | | |
|---|---|---|
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,832,988 B2 | 12/2004 | Sproul |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,221 B1 | 5/2005 | Baillargeon et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,466 B1 | 6/2005 | Bonutti et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,932,876 B1 | 8/2005 | Statnikov |
| 6,933,656 B2 | 8/2005 | Matsushita et al. |
| D509,589 S | 9/2005 | Wells |
| 6,942,660 B2 | 9/2005 | Pantera et al. |
| 6,942,676 B2 | 9/2005 | Buelna |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,989,017 B2 | 1/2006 | Howell et al. |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,002,283 B2 | 2/2006 | Li et al. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,354 B2 | 3/2006 | Tazi |
| 7,018,389 B2 | 3/2006 | Camerlengo |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,131,983 B2 | 11/2006 | Murakami |
| 7,135,018 B2 | 11/2006 | Ryan et al. |
| 7,135,029 B2 | 11/2006 | Makin et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,201 B2 | 1/2007 | Peshkovskiy et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,182,762 B2 | 2/2007 | Bortkiewicz |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |

(56) References Cited

U.S. PATENT DOCUMENTS

| | | |
|---|---|---|
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,282,836 B2 | 10/2007 | Kwon et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,338,463 B2 | 3/2008 | Vigil |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckal et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,413,123 B2 | 8/2008 | Ortenzi |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,168 B2 | 10/2008 | Novak et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,533,830 B1 | 5/2009 | Rose |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,563,259 B2 | 7/2009 | Takahashi |
| 7,563,269 B2 | 7/2009 | Hashiguchi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,166 B2 | 8/2009 | Ethridge et al. |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,617,961 B2 | 11/2009 | Viola |
| 7,621,930 B2 | 11/2009 | Houser |
| 7,625,370 B2 | 12/2009 | Hart et al. |
| 7,627,936 B2 | 12/2009 | Bromfield |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |

(56) References Cited

U.S. PATENT DOCUMENTS

| | | |
|---|---|---|
| 7,644,848 B2 | 1/2010 | Swayze et al. |
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,763 B2 | 3/2010 | Vaezy et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,734,476 B2 | 6/2010 | Wildman et al. |
| 7,738,969 B2 | 6/2010 | Bleich |
| 7,740,594 B2 | 6/2010 | Hibner |
| 7,749,240 B2 | 7/2010 | Takahashi et al. |
| 7,749,273 B2 | 7/2010 | Cauthen, III et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,815,658 B2 | 10/2010 | Murakami |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,834,521 B2 | 11/2010 | Habu et al. |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,465 B2 | 2/2011 | Donofrio et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,716 B2 | 4/2011 | Malecki et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,006,358 B2 | 8/2011 | Cooke et al. |
| 8,016,843 B2 | 9/2011 | Escaf |

(56) References Cited

U.S. PATENT DOCUMENTS

| | | |
|---|---|---|
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,011 B2 | 11/2011 | Okabe |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,467 B2 | 11/2011 | Faller et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,137,263 B2 | 3/2012 | Marescaux et al. |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,501 B2 | 5/2012 | Houser et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,306 B2 | 7/2012 | Okada et al. |
| 8,221,415 B2 | 7/2012 | Francischelli |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,096 B2 | 3/2013 | Moses et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stabler et al. |

(56) References Cited

U.S. PATENT DOCUMENTS

| | | |
|---|---|---|
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,161 B2 | 4/2013 | Nagaya et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,435,258 B2 | 5/2013 | Young et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,460,326 B2 | 6/2013 | Houser et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,610,334 B2 | 12/2013 | Bromfield |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,651,230 B2 | 2/2014 | Peshkovsky et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,691,268 B2 | 4/2014 | Weimann |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,715,306 B2 | 5/2014 | Faller et al. |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,734,476 B2 | 5/2014 | Rhee et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |

(56) References Cited

U.S. PATENT DOCUMENTS

| | | |
|---|---|---|
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,870,867 B2 | 10/2014 | Walberg et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,071 B2 | 5/2015 | Miller et al. |
| 9,023,072 B2 | 5/2015 | Young et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,705 B2 | 5/2015 | Takashino |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,125,722 B2 | 9/2015 | Schwartz |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,192,380 B2 | 11/2015 | Racenet et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |

(56) References Cited

U.S. PATENT DOCUMENTS

| | | |
|---|---|---|
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,301,772 B2 | 4/2016 | Kimball et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,235 B2 | 11/2016 | Harrington et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |

(56) References Cited

U.S. PATENT DOCUMENTS

| | | |
|---|---|---|
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,064 B2 | 4/2019 | Rhee et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,363,058 B2 | 7/2019 | Roberson et al. |
| 10,368,892 B2 | 8/2019 | Stulen et al. |
| 10,368,894 B2 | 8/2019 | Madan et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov |
| 10,561,436 B2 | 2/2020 | Asher et al. |
| 10,677,764 B2 | 6/2020 | Ross et al. |
| 10,779,848 B2 | 9/2020 | Houser |
| 10,856,896 B2 | 12/2020 | Eichmann et al. |
| 10,874,418 B2 | 12/2020 | Houser et al. |
| 10,881,451 B2 | 1/2021 | Worrell et al. |
| 10,912,603 B2 | 2/2021 | Boudreaux et al. |
| 11,033,292 B2 | 6/2021 | Green et al. |
| D924,400 S | 7/2021 | Kimball |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0032002 A1 | 10/2001 | McClurken et al. |
| 2001/0039419 A1 | 11/2001 | Francischelli et al. |
| 2002/0002377 A1 | 1/2002 | Cimino |
| 2002/0002378 A1 | 1/2002 | Messerly |
| 2002/0016603 A1 | 2/2002 | Wells |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0099373 A1 | 7/2002 | Schulze et al. |
| 2002/0107446 A1 | 8/2002 | Rabiner et al. |
| 2002/0107517 A1 | 8/2002 | Witt et al. |
| 2002/0120266 A1 | 8/2002 | Truckai et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0120306 A1 | 6/2003 | Burbank et al. |
| 2003/0130675 A1 | 7/2003 | Kasahara et al. |
| 2003/0130693 A1 | 7/2003 | Levin et al. |
| 2003/0139741 A1 | 7/2003 | Goble et al. |
| 2003/0144652 A1 | 7/2003 | Baker et al. |
| 2003/0144680 A1 | 7/2003 | Kellogg et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |

(56) References Cited

U.S. PATENT DOCUMENTS

| | | |
|---|---|---|
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0039242 A1 | 2/2004 | Tolkoff et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0147946 A1 | 7/2004 | Mastri et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0199194 A1 | 10/2004 | Witt et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0085728 A1 | 4/2005 | Fukuda |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0228425 A1 | 10/2005 | Boukhny et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0095046 A1 | 5/2006 | Trieu et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0241580 A1 | 10/2006 | Mittelstein et al. |
| 2006/0247558 A1 | 11/2006 | Yamada |
| 2006/0253050 A1 | 11/2006 | Yoshimine et al. |
| 2006/0257819 A1 | 11/2006 | Johnson |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0276419 A1 | 11/2007 | Rosenthal |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097281 A1 | 4/2008 | Zusman et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |

(56) References Cited

U.S. PATENT DOCUMENTS

| | | |
|---|---|---|
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0294051 A1 | 11/2008 | Koshigoe et al. |
| 2008/0296346 A1 | 12/2008 | Shelton, IV et al. |
| 2008/0300588 A1 | 12/2008 | Groth et al. |
| 2008/0303384 A1* | 12/2008 | Sakamoto ........... H01L 41/0913 310/334 |
| 2009/0012516 A1 | 1/2009 | Curtis et al. |
| 2009/0023985 A1 | 1/2009 | Ewers |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1* | 3/2009 | Mulvihill ....... A61B 17/320068 606/171 |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042126 A1 | 2/2010 | Houser et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228191 A1 | 9/2010 | Alvarez et al. |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0298851 A1* | 11/2010 | Nield ............. A61B 17/320068 606/169 |
| 2010/0312186 A1 | 12/2010 | Suchdev et al. |
| 2010/0331742 A1 | 12/2010 | Masuda |
| 2010/0331873 A1 | 12/2010 | Dannaher et al. |
| 2011/0004233 A1 | 1/2011 | Muir et al. |
| 2011/0028964 A1 | 2/2011 | Edwards |
| 2011/0106141 A1 | 5/2011 | Nakamura |
| 2011/0125151 A1 | 5/2011 | Strauss et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0291526 A1 | 12/2011 | Abramovich et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0078249 A1 | 3/2012 | Eichmann et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0136279 A1 | 5/2012 | Tanaka et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2012/0330338 A1 | 12/2012 | Messerly |
| 2013/0023925 A1 | 1/2013 | Mueller |
| 2013/0035685 A1 | 2/2013 | Fischer et al. |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0231691 A1 | 9/2013 | Houser |
| 2013/0253256 A1 | 9/2013 | Griffith et al. |
| 2013/0277410 A1 | 10/2013 | Fernandez et al. |
| 2013/0296843 A1 | 11/2013 | Boudreaux et al. |
| 2013/0331873 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0081299 A1 | 3/2014 | Dietz et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0207163 A1 | 7/2014 | Eichmann et al. |
| 2014/0323926 A1 | 10/2014 | Akagane |
| 2014/0371735 A1 | 12/2014 | Long |
| 2015/0011889 A1 | 1/2015 | Lee |
| 2015/0080876 A1 | 3/2015 | Worrell et al. |
| 2015/0083774 A1 | 3/2015 | Measamer et al. |
| 2015/0112335 A1 | 4/2015 | Boudreaux et al. |
| 2015/0157356 A1 | 6/2015 | Gee |

(56) References Cited

U.S. PATENT DOCUMENTS

| | | |
|---|---|---|
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0257780 A1 | 9/2015 | Houser |
| 2015/0272659 A1 | 10/2015 | Boudreaux et al. |
| 2015/0289854 A1 | 10/2015 | Cho et al. |
| 2016/0045248 A1 | 2/2016 | Unger et al. |
| 2016/0051316 A1 | 2/2016 | Boudreaux |
| 2016/0074108 A1 | 3/2016 | Woodruff et al. |
| 2016/0114355 A1 | 4/2016 | Sakai et al. |
| 2016/0121143 A1 | 5/2016 | Mumaw et al. |
| 2016/0128769 A1 | 5/2016 | Rontal et al. |
| 2016/0157927 A1 | 6/2016 | Corbett et al. |
| 2016/0175029 A1 | 6/2016 | Witt et al. |
| 2016/0199125 A1 | 7/2016 | Jones |
| 2016/0206342 A1 | 7/2016 | Robertson et al. |
| 2016/0213395 A1 | 7/2016 | Anim |
| 2016/0240768 A1 | 8/2016 | Fujii et al. |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0346001 A1 | 12/2016 | Vakharia et al. |
| 2016/0367281 A1 | 12/2016 | Gee et al. |
| 2016/0374709 A1 | 12/2016 | Timm et al. |
| 2017/0000541 A1 | 1/2017 | Yates et al. |
| 2017/0014152 A1 | 1/2017 | Noui et al. |
| 2017/0027624 A1 | 2/2017 | Wilson et al. |
| 2017/0036044 A1 | 2/2017 | Ito |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0105757 A1 | 4/2017 | Weir et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0189095 A1 | 7/2017 | Danziger et al. |
| 2017/0189096 A1 | 7/2017 | Danziger et al. |
| 2017/0196586 A1 | 7/2017 | Witt et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202592 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2018/0014845 A1 | 1/2018 | Dannaher |
| 2018/0014848 A1 | 1/2018 | Messerly et al. |
| 2018/0049767 A1 | 2/2018 | Gee et al. |
| 2018/0055531 A1 | 3/2018 | Messerly et al. |
| 2018/0055532 A1 | 3/2018 | Messerly et al. |
| 2018/0055533 A1 | 3/2018 | Conlon et al. |
| 2018/0056095 A1 | 3/2018 | Messerly et al. |
| 2018/0078268 A1 | 3/2018 | Messerly et al. |
| 2018/0092660 A1 | 4/2018 | Houser et al. |
| 2018/0125523 A1 | 5/2018 | Johnson |
| 2018/0146975 A1 | 5/2018 | Zhang |
| 2018/0168680 A1 | 6/2018 | Houser et al. |
| 2018/0177521 A1 | 6/2018 | Faller et al. |
| 2018/0199957 A1 | 7/2018 | Robertson et al. |
| 2018/0206881 A1 | 7/2018 | Price et al. |
| 2018/0221049 A1 | 8/2018 | Faller et al. |
| 2019/0008543 A1 | 1/2019 | Scoggins et al. |
| 2019/0053822 A1 | 2/2019 | Robertson et al. |
| 2019/0090900 A1 | 3/2019 | Rhee et al. |
| 2019/0133633 A1 | 5/2019 | Neurohr et al. |
| 2019/0239919 A1 | 8/2019 | Witt et al. |
| 2019/0262029 A1 | 8/2019 | Messerly et al. |
| 2019/0350615 A1 | 11/2019 | Messerly et al. |
| 2019/0380733 A1 | 12/2019 | Stulen et al. |
| 2019/0381339 A1 | 12/2019 | Voegele et al. |
| 2019/0381340 A1 | 12/2019 | Voegele et al. |
| 2020/0008857 A1 | 1/2020 | Conlon et al. |
| 2020/0015798 A1 | 1/2020 | Wiener et al. |
| 2020/0015838 A1 | 1/2020 | Robertson |
| 2020/0046401 A1 | 2/2020 | Witt et al. |
| 2020/0054386 A1 | 2/2020 | Houser et al. |
| 2020/0054899 A1 | 2/2020 | Wiener et al. |
| 2020/0085462 A1 | 3/2020 | Robertson |
| 2020/0085466 A1 | 3/2020 | Faller et al. |
| 2020/0323551 A1 | 10/2020 | Faller et al. |
| 2021/0038248 A1 | 2/2021 | Houser |
| 2021/0121197 A1 | 4/2021 | Houser et al. |
| 2021/0128191 A1 | 5/2021 | Messerly et al. |
| 2021/0145531 A1 | 5/2021 | Gee et al. |
| 2021/0236157 A1 | 8/2021 | Rhee et al. |
| 2021/0315605 A1 | 10/2021 | Gee et al. |

FOREIGN PATENT DOCUMENTS

| | | |
|---|---|---|
| CA | 2214413 A1 | 9/1996 |
| CN | 2460047 Y | 11/2001 |
| CN | 1634601 A | 7/2005 |
| CN | 1775323 A | 5/2006 |
| CN | 1922563 A | 2/2007 |
| CN | 2868227 Y | 2/2007 |
| CN | 202027624 U | 11/2011 |
| CN | 102335778 A | 2/2012 |
| CN | 103668171 A | 3/2014 |
| CN | 103921215 A | 7/2014 |
| CN | 106077718 A | 11/2016 |
| DE | 2065681 A1 | 3/1975 |
| DE | 3904558 A1 | 8/1990 |
| DE | 9210327 U1 | 11/1992 |
| DE | 4300307 A1 | 7/1994 |
| DE | 4434938 C1 | 2/1996 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1543854 A1 | 6/2005 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2510891 B1 | 6/2016 |
| FR | 2454351 A1 | 11/1980 |
| FR | 2964554 A1 | 3/2012 |

(56) References Cited

FOREIGN PATENT DOCUMENTS

| | | |
|---|---|---|
| GB | 2032221 A | 4/1980 |
| GB | 2317566 A | 4/1998 |
| GB | 2318298 A | 4/1998 |
| GB | 2425480 A | 11/2006 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | 04161078 A * | 6/1992 |
| JP | H04161078 A | 6/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |
| JP | H07185457 A | 7/1995 |
| JP | H07299415 A | 11/1995 |
| JP | H0824266 A | 1/1996 |
| JP | H08229050 A | 9/1996 |
| JP | H08275950 A | 10/1996 |
| JP | H08275951 A | 10/1996 |
| JP | H08299351 A | 11/1996 |
| JP | H08336545 A | 12/1996 |
| JP | H09135553 A | 5/1997 |
| JP | H09140722 A | 6/1997 |
| JP | H105236 A | 1/1998 |
| JP | H105237 A | 1/1998 |
| JP | H10295700 A | 11/1998 |
| JP | H11128238 A | 5/1999 |
| JP | 2000139943 A | 5/2000 |
| JP | 2000210296 A | 8/2000 |
| JP | 2000210299 A | 8/2000 |
| JP | 2000271145 A | 10/2000 |
| JP | 2000287987 A | 10/2000 |
| JP | 2000312682 A | 11/2000 |
| JP | 2001029353 A | 2/2001 |
| JP | 2001057985 A | 3/2001 |
| JP | 2001170066 A | 6/2001 |
| JP | 2001198137 A | 7/2001 |
| JP | 2002186901 A | 7/2002 |
| JP | 2002233533 A | 8/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003230567 A | 8/2003 |
| JP | 2003339730 A | 12/2003 |
| JP | 2004129871 A | 4/2004 |
| JP | 2004147701 A | 5/2004 |
| JP | 2004209043 A | 7/2004 |
| JP | 2005027026 A | 1/2005 |
| JP | 2005074088 A | 3/2005 |
| JP | 2005094552 A | 4/2005 |
| JP | 2005253674 A | 9/2005 |
| JP | 2006217716 A | 8/2006 |
| JP | 2006288431 A | 10/2006 |
| JP | 3841627 B2 | 11/2006 |
| JP | D1339835 S | 8/2008 |
| JP | 2009071439 A | 4/2009 |
| JP | 2009297352 A | 12/2009 |
| JP | 2010009686 A | 1/2010 |
| JP | 2010121865 A | 6/2010 |
| JP | 2011160586 A | 8/2011 |
| JP | 2012235658 A | 11/2012 |
| JP | 2015529140 A | 10/2015 |
| JP | 2016022136 A | 2/2016 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9805437 A1 | 2/1998 |
| WO | WO-9816157 A1 | 4/1998 |
| WO | WO-9920213 A1 | 4/1999 |
| WO | WO-9923960 A1 | 5/1999 |
| WO | WO-0024322 A1 | 5/2000 |
| WO | WO-0024330 A1 | 5/2000 |
| WO | WO-0064358 A2 | 11/2000 |
| WO | WO-0128444 A1 | 4/2001 |
| WO | WO-0132087 A1 | 5/2001 |
| WO | WO-0167970 A1 | 9/2001 |
| WO | WO-0195810 A2 | 12/2001 |
| WO | WO-02076685 A1 | 10/2002 |
| WO | WO-02080799 A1 | 10/2002 |
| WO | WO-2004037095 A2 | 5/2004 |
| WO | WO-2004078051 A2 | 9/2004 |
| WO | WO-2004098426 A1 | 11/2004 |
| WO | WO-2005084250 A2 | 9/2005 |
| WO | WO-2007008710 A2 | 1/2007 |
| WO | WO-2008118709 A1 | 10/2008 |
| WO | WO-2008130793 A1 | 10/2008 |
| WO | WO-2008154338 A1 | 12/2008 |
| WO | WO-2010104755 A1 | 9/2010 |
| WO | WO-2011008672 A2 | 1/2011 |
| WO | WO-2011052939 A2 | 5/2011 |
| WO | WO-2011060031 A1 | 5/2011 |
| WO | WO-2012044606 A2 | 4/2012 |
| WO | WO-2012066983 A1 | 5/2012 |
| WO | WO-2013048963 A2 | 4/2013 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008], Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in Physical Properties of Tissue (1990).

Campbell et al., "Thermal Imaging in Surgery," p. 19-3, in Medical Infrared Imaging, N. A. Diakides and J. D. Bronzino, Eds. (2008).

(56) References Cited

OTHER PUBLICATIONS

AST Products, Inc., "Principles of Video Contact Angle Analysis," 20 pages, (2006).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
http://www.apicalinstr.com/generators.htm.
http://www.dotmed.eom/listing/electrosurical-unit/ethicon/ultracision-g110-/1466724.
http:/www.ethicon.com/gb-en/healthcare-professionals/products/energy-devices/capital//ge . . . .
http://www.medicalexpo.com/medical-manufacturer/electrosurgical-generator-6951.html.
http://www.megadyne.com/es_generator.php.
http://www.valleylab.com/product/es/generators/index.html.
Sullivan, "Optimal Choice for Number of Strands in a Litz-Wire Transformer Winding," IEEE Transactions on Power Electronics, vol. 14, No. 2, Mar. 1999, pp. 283-291.
Covidien 501 (k) Summary Sonicision, dated Feb. 24, 2011 (7 pages).
http://www.4-traders.com/JOHNSON-JOHNSON-4832/news/Johnson-Johnson-Ethicon-E . . . .
Weir, C.E., "Rate of shrinkage of tendon collagen-heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Meeh. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, Engineering Formulas § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Douglas, S.C. "Introduction to Adaptive Filter". Digital Signal Processing Handbook. Ed. Vijay K. Madisetti and Douglas B. Williams. Boca Raton: CRC Press LLC, 1999.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe,Integrated Circuit Engineering, Addison-Wesley Publishing, Reading, MA (1979). (book—not attached).
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages accessed Mar. 31, 2014 at http://www.erbe-med. com/erbe/media/Marketing materialien/85140170 ERBE EN VIO 200 S D027541.
Sadiq Muhammad et al: "High-performance planar ultrasonic tool based on d31-mode piezocrystal", IEEE Transactions on Ultrasonics, Ferroelectricsand Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.

(56) References Cited

OTHER PUBLICATIONS

Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.

Emam, Tarek A. et al., "How Safe is High-Power Ultrasonic Dissection?," Annals of Surgery, (2003), pp. 186-191, vol. 237, No. 2, Lippincott Williams & Wilkins, Inc., Philadelphia, PA.

Feil, Wolfgang, M.D., et al., "Ultrasonic Energy for Cutting, Coagulating, and Dissecting," (2005), pp. IV, 17, 21, and 23; ISBN 3-13-127521-9 (New York, NY, Thieme, New York).

McCarus, Steven D. M.D., "Physiologic Mechanism of the Ultrasonically Activated Scalpel," The Journal of the American Association of Gynecologic Laparoscopists; (Aug. 1996), vol. 3, No. 4., pp. 601-606 and 608.

\* cited by examiner

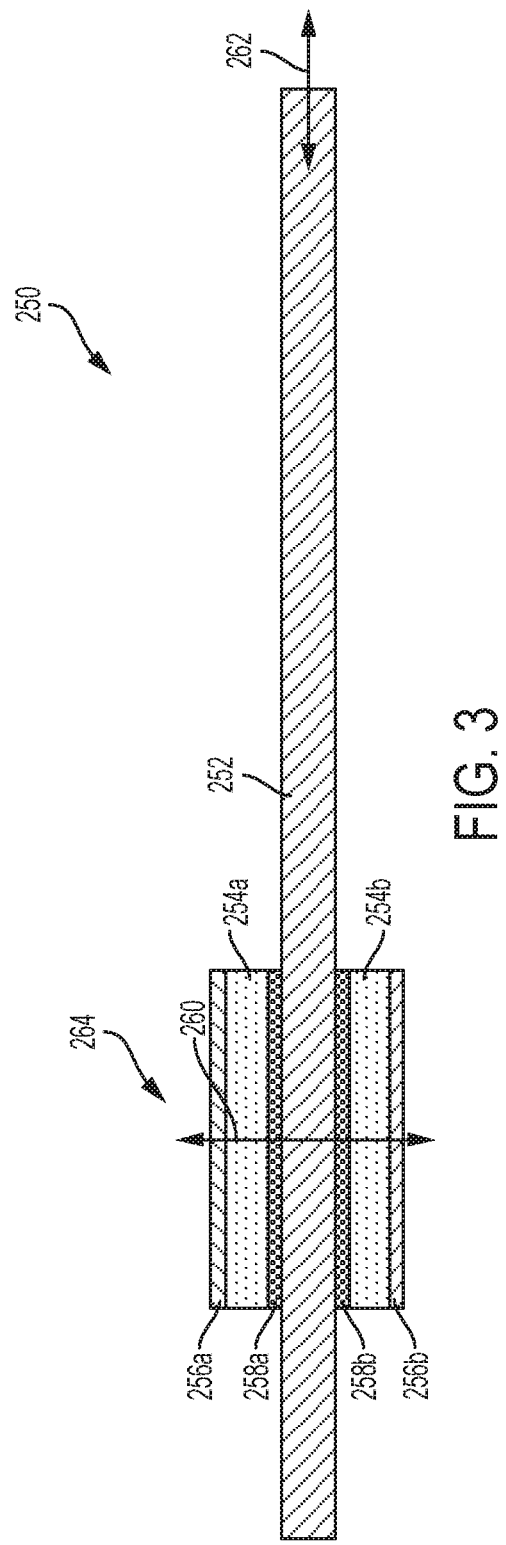

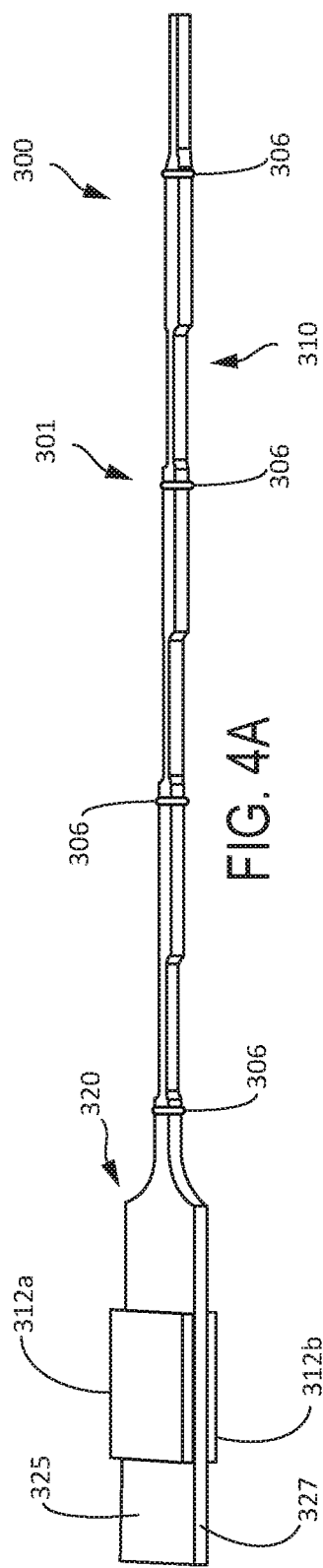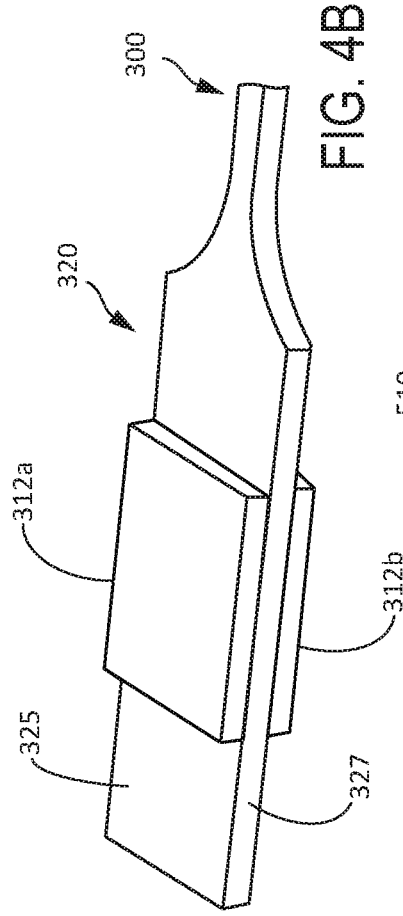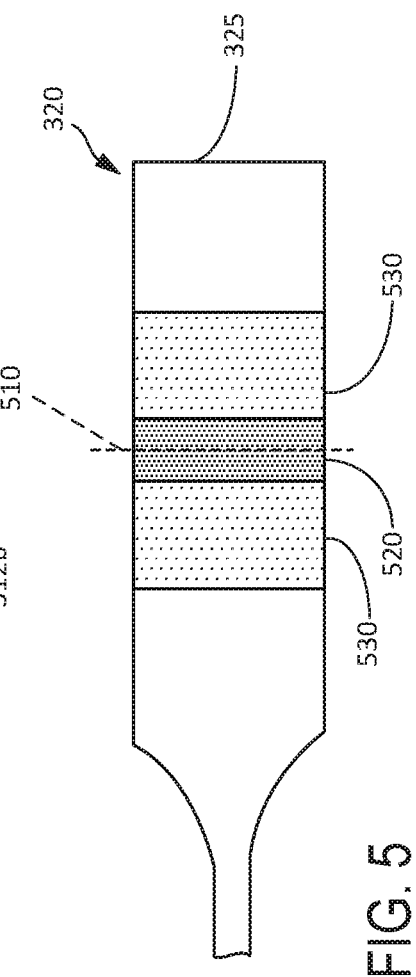

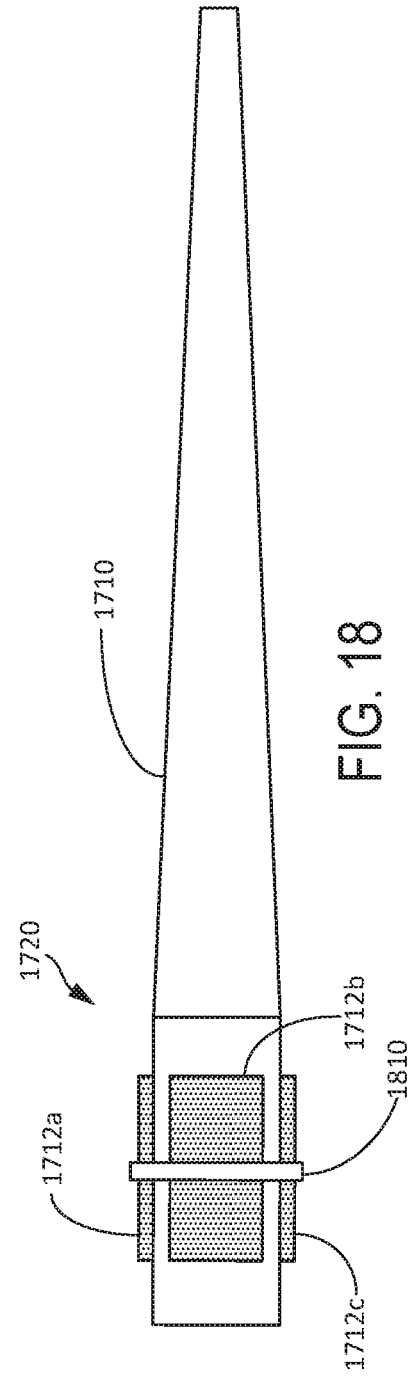

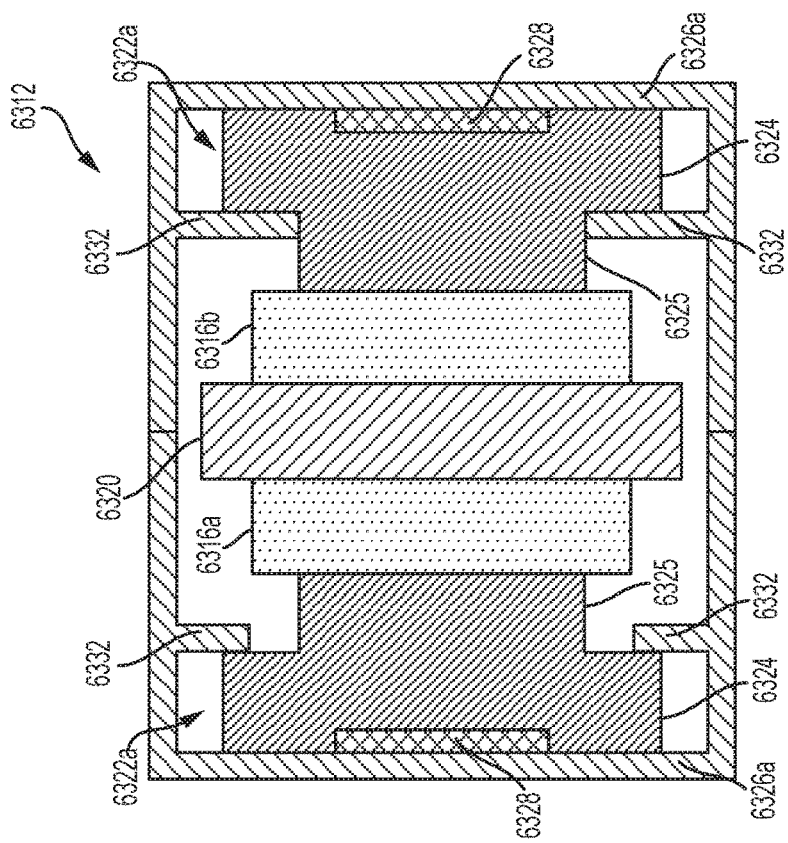
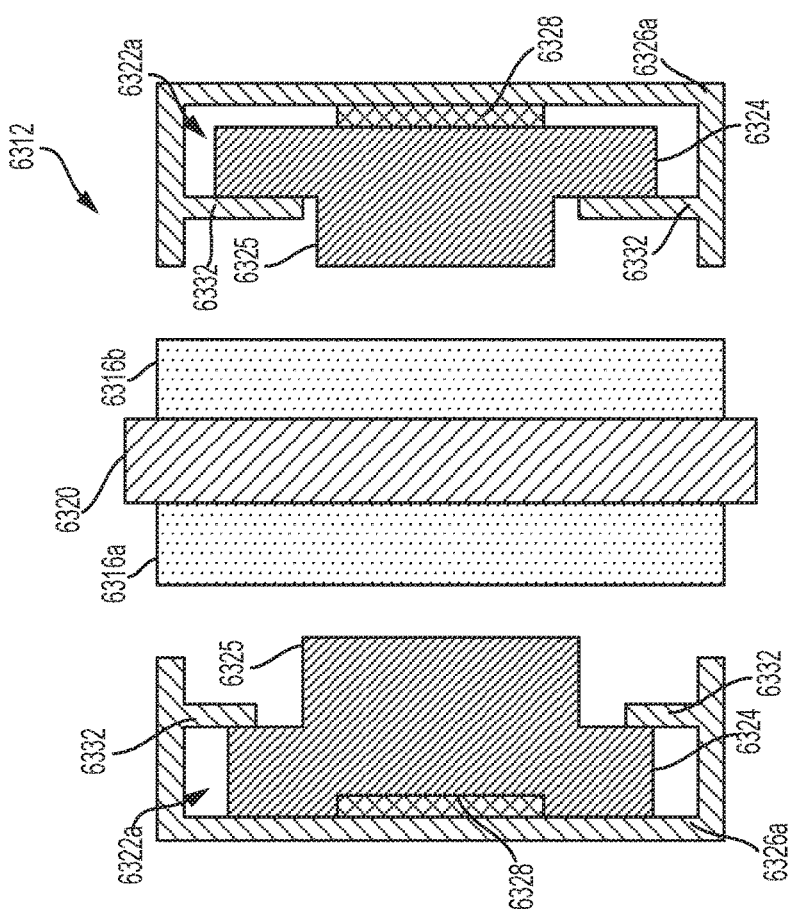
FIG. 86A
FIG. 86B

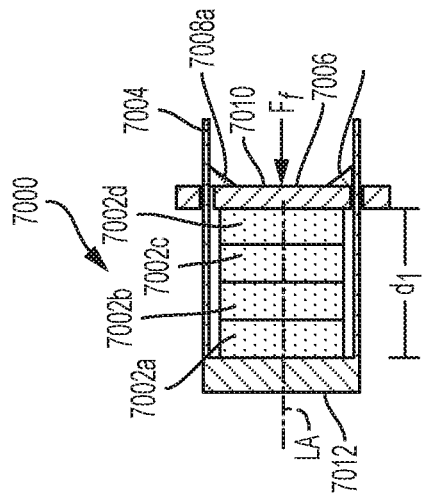
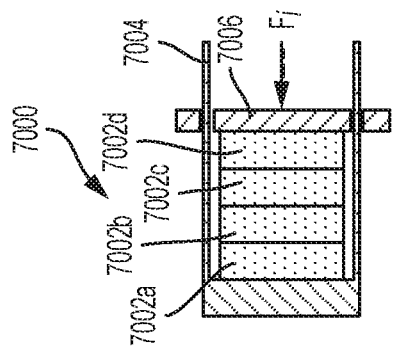
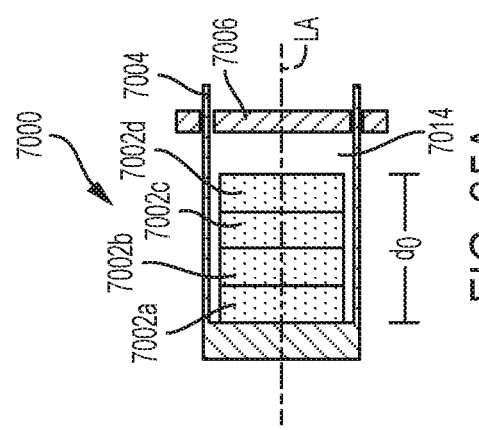

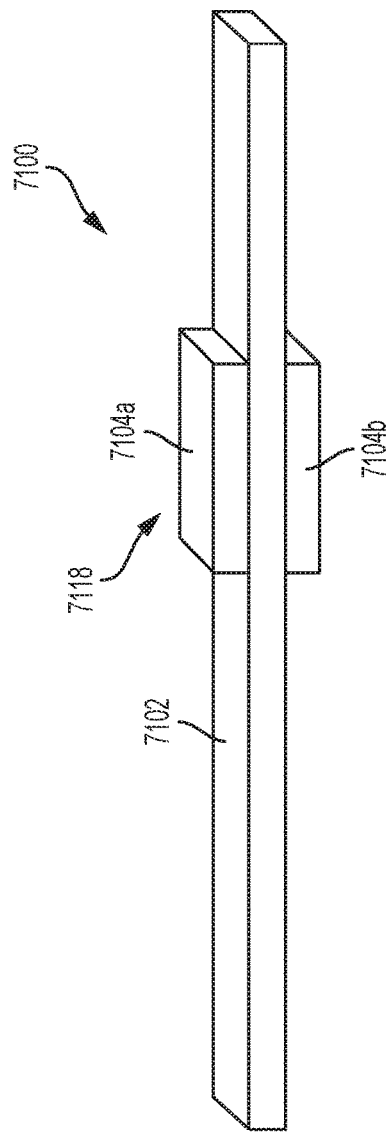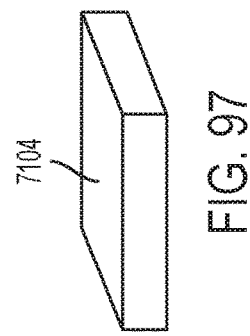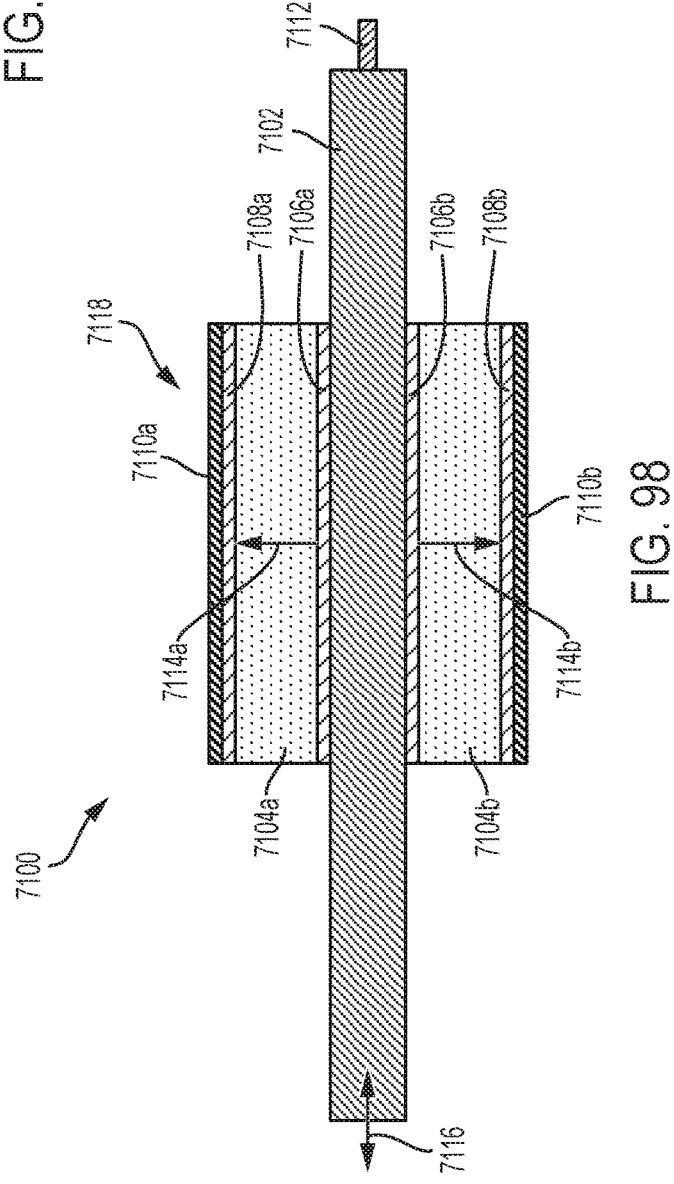

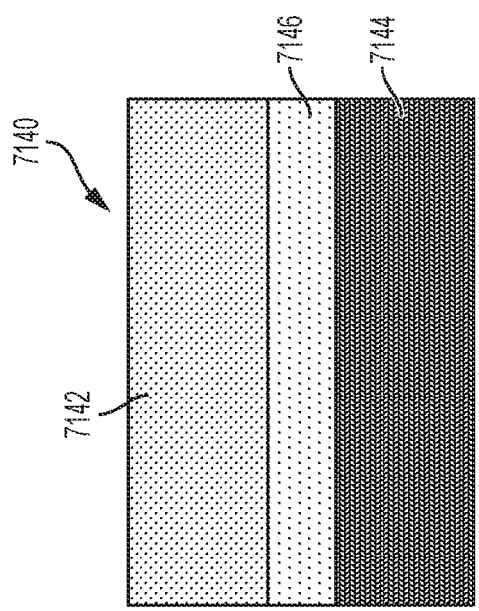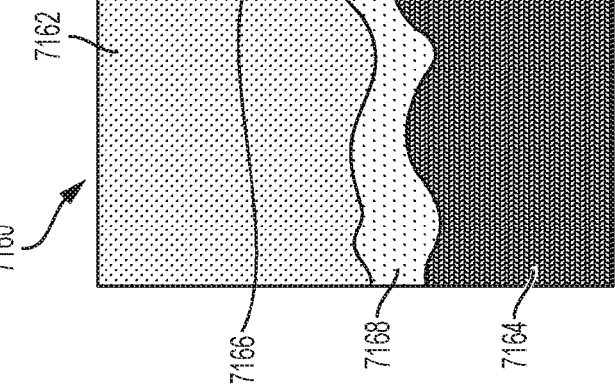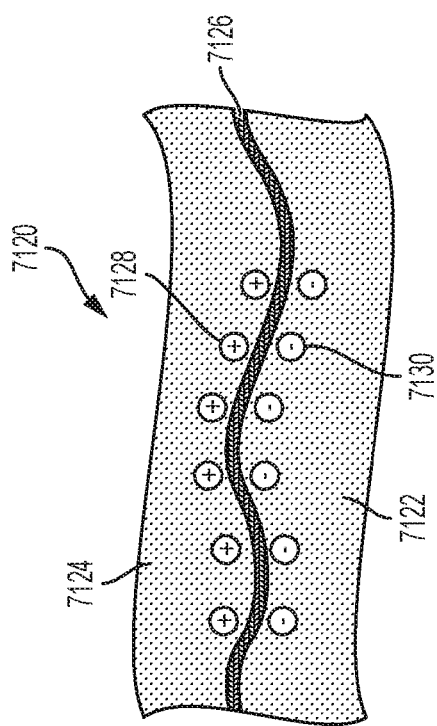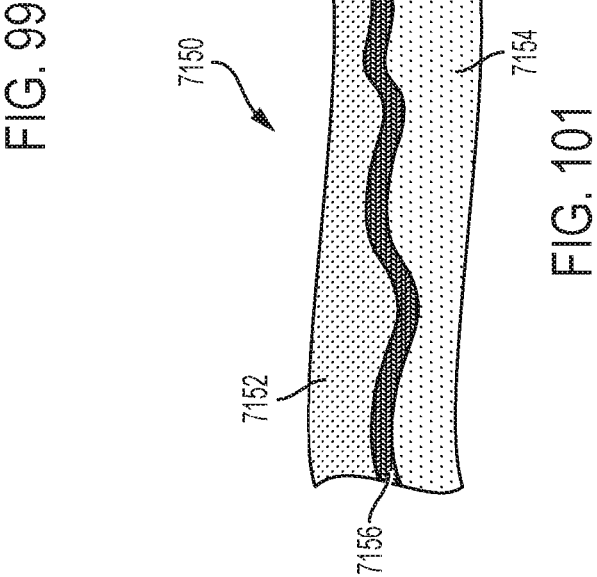

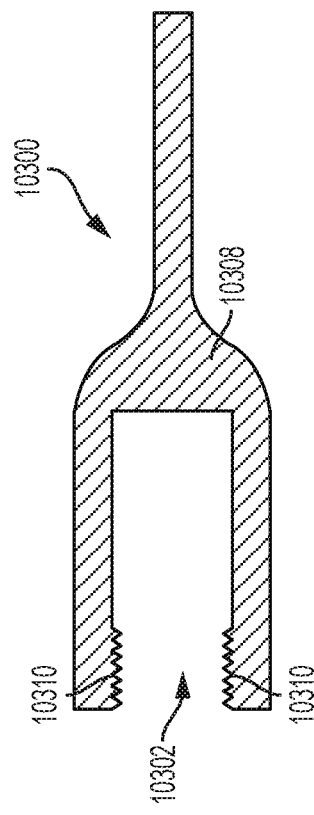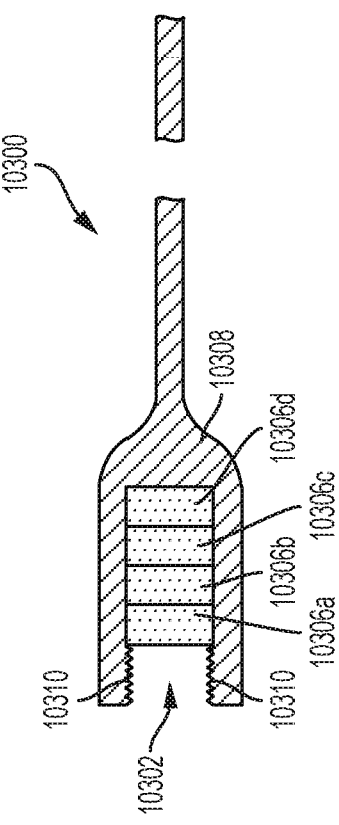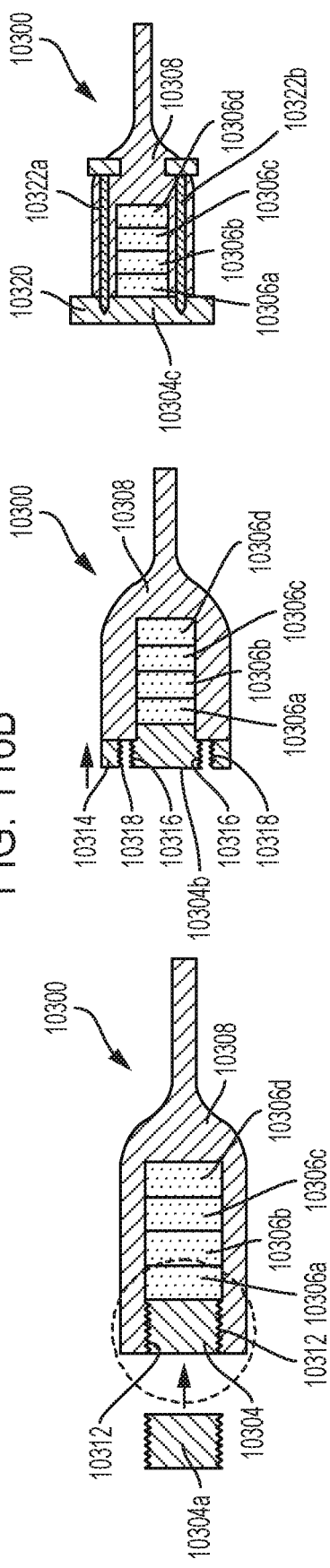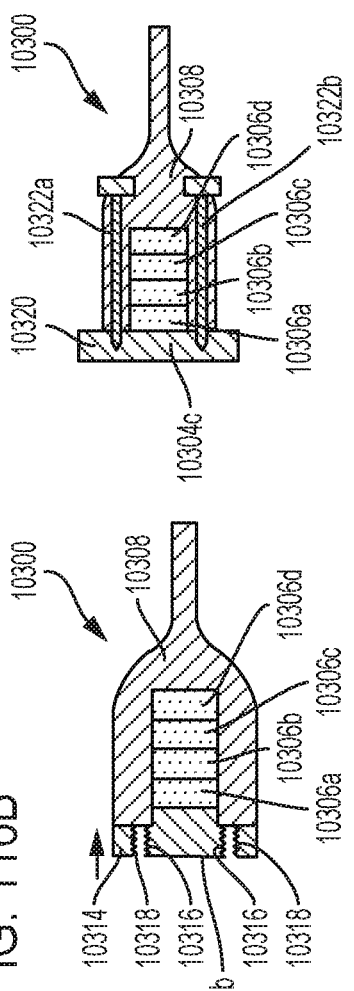

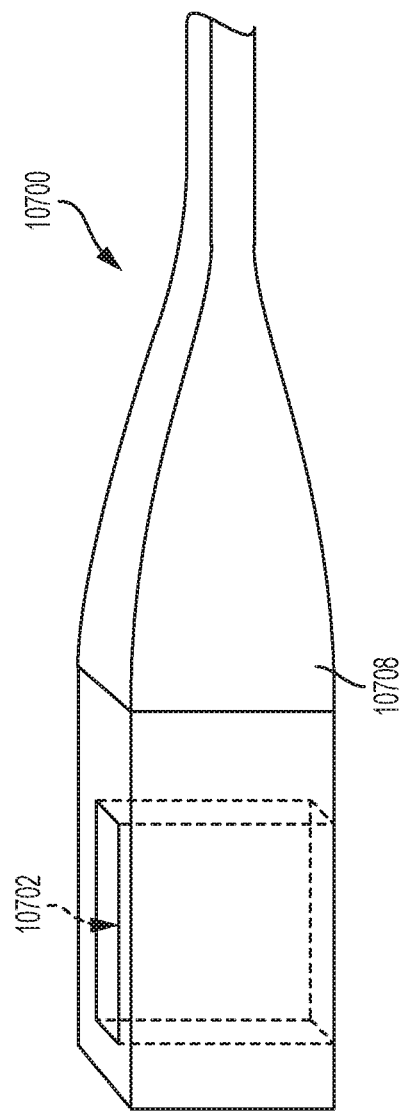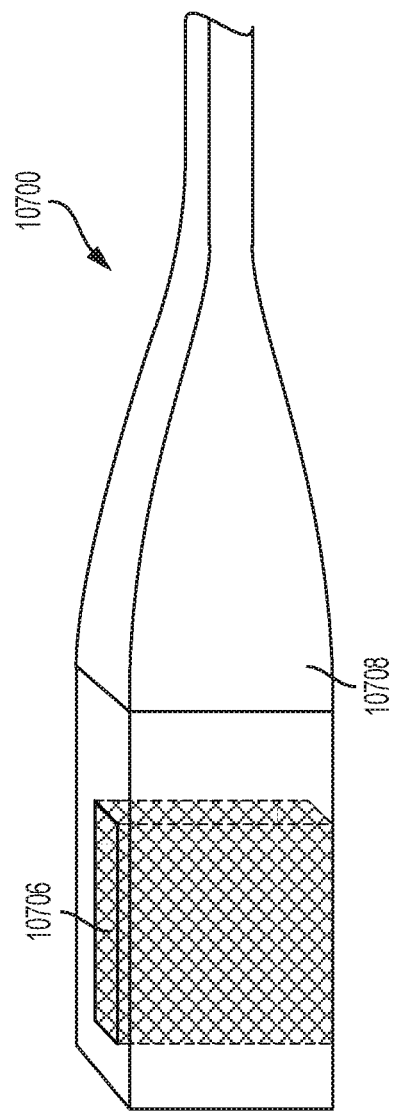

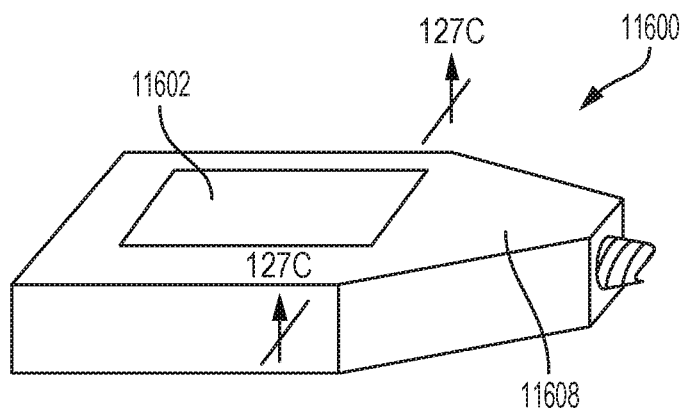
FIG. 127A
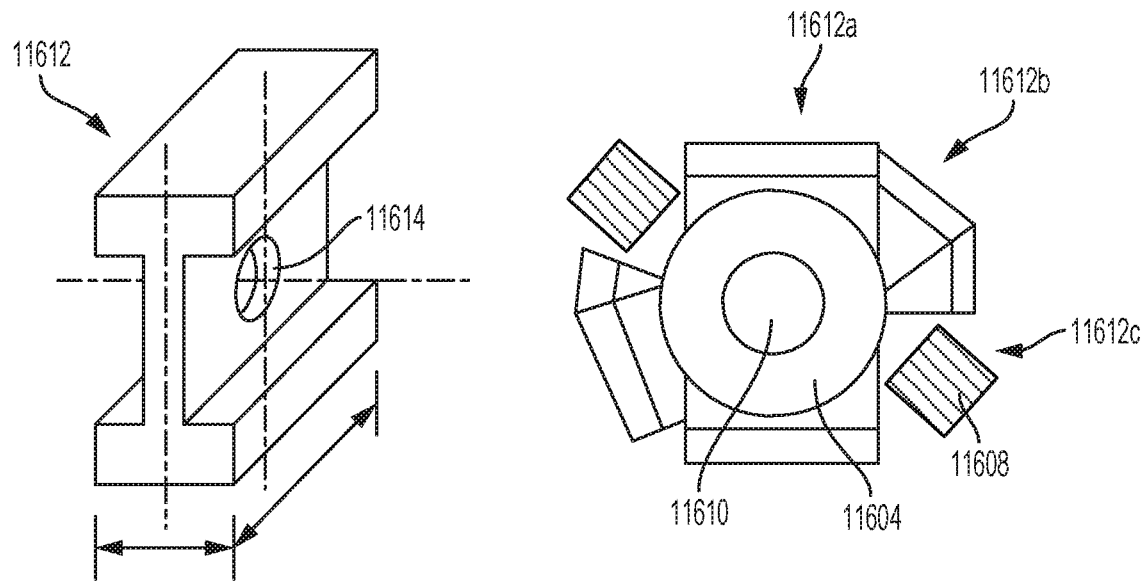
FIG. 127B
FIG. 127C
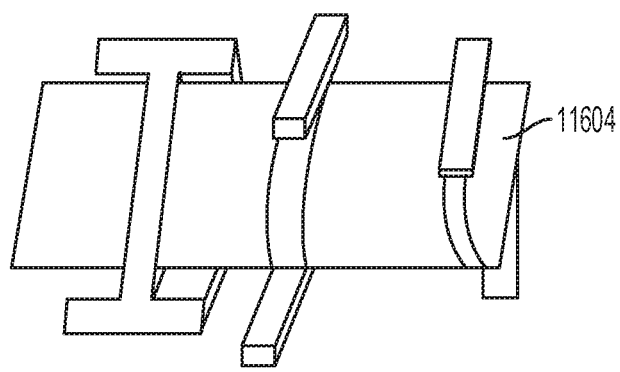
FIG. 127D

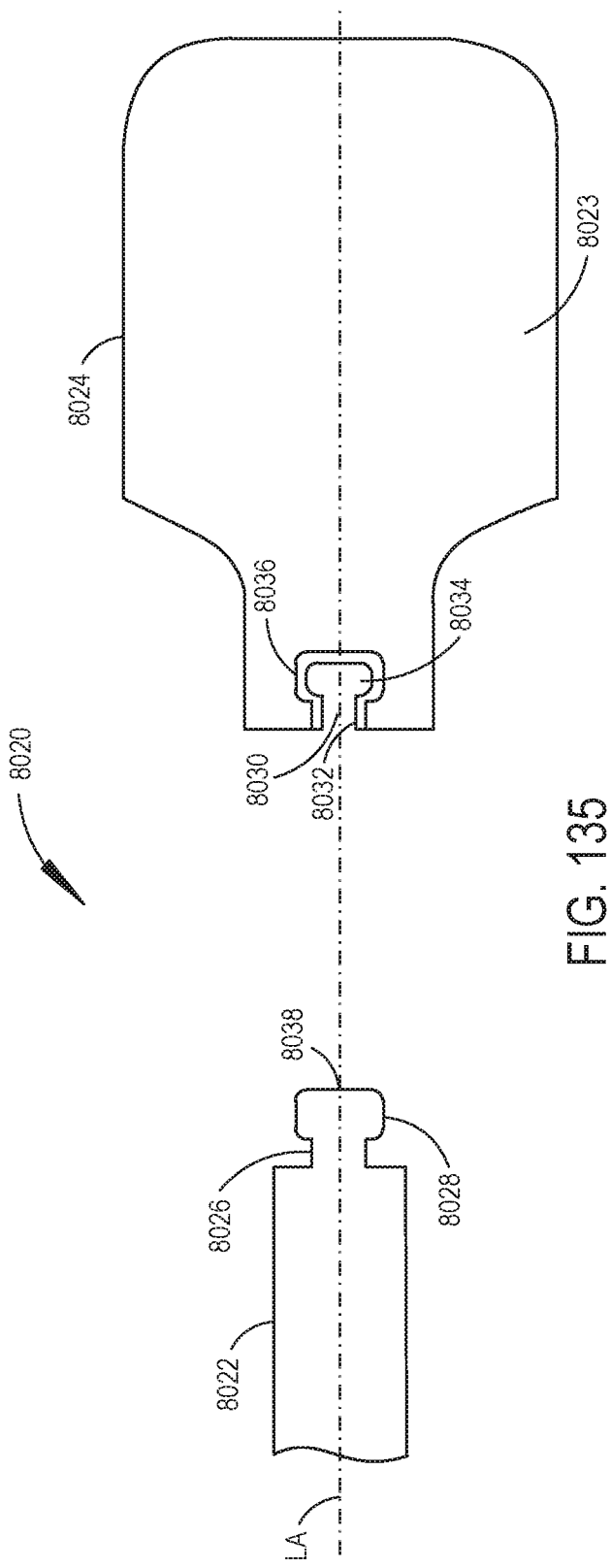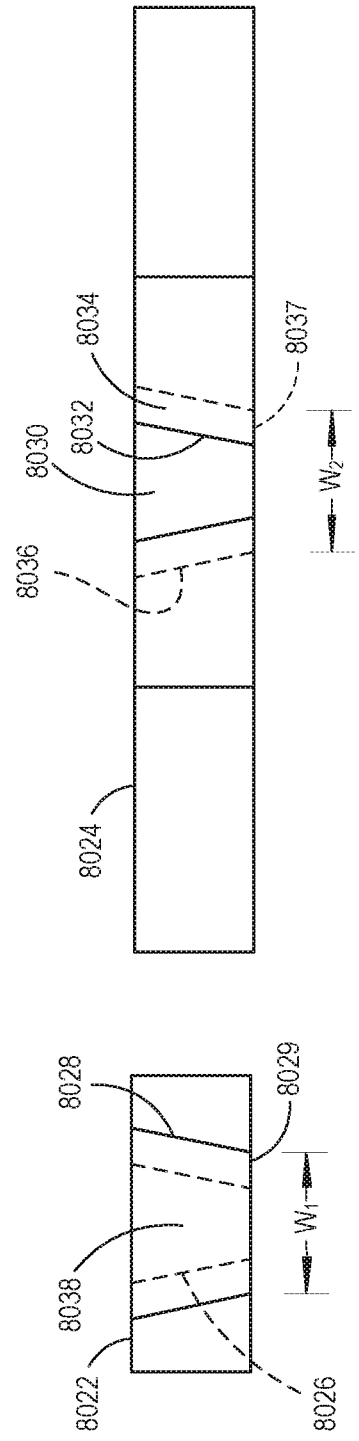
FIG. 135
FIG. 136
FIG. 137

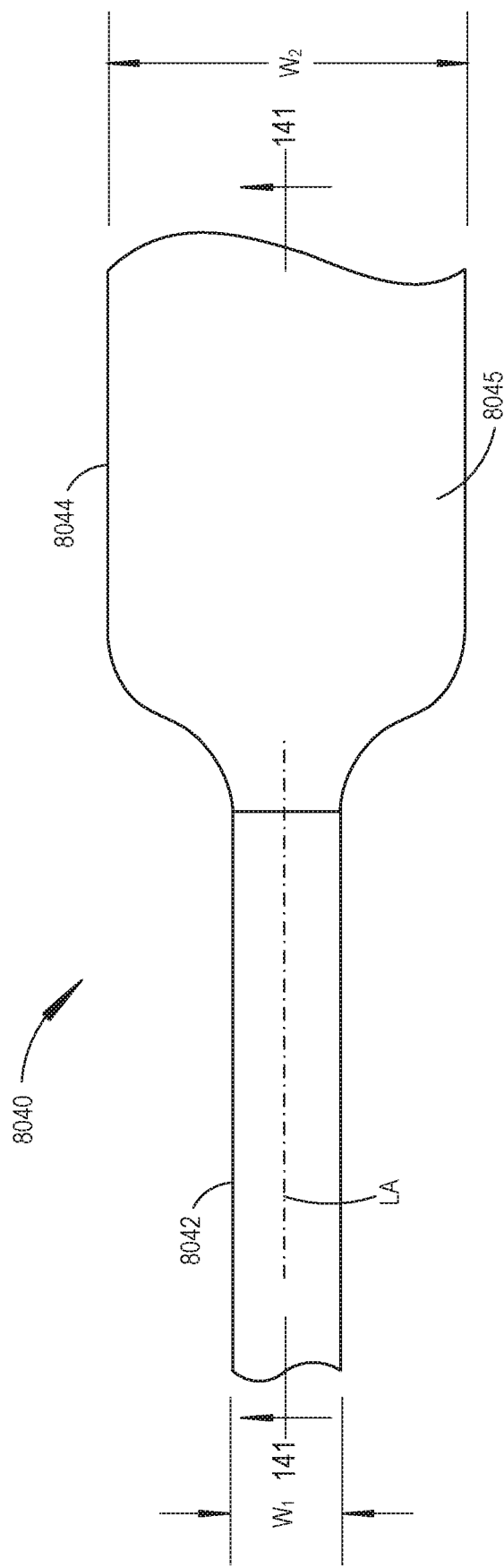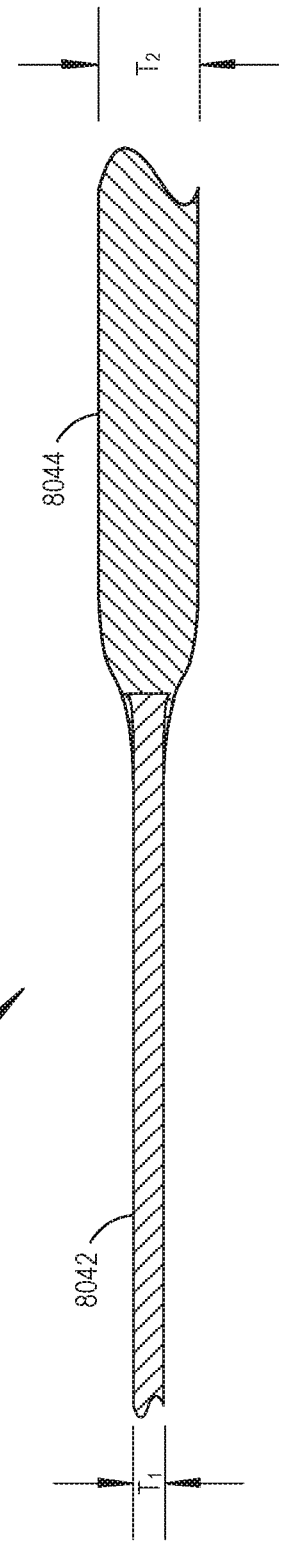

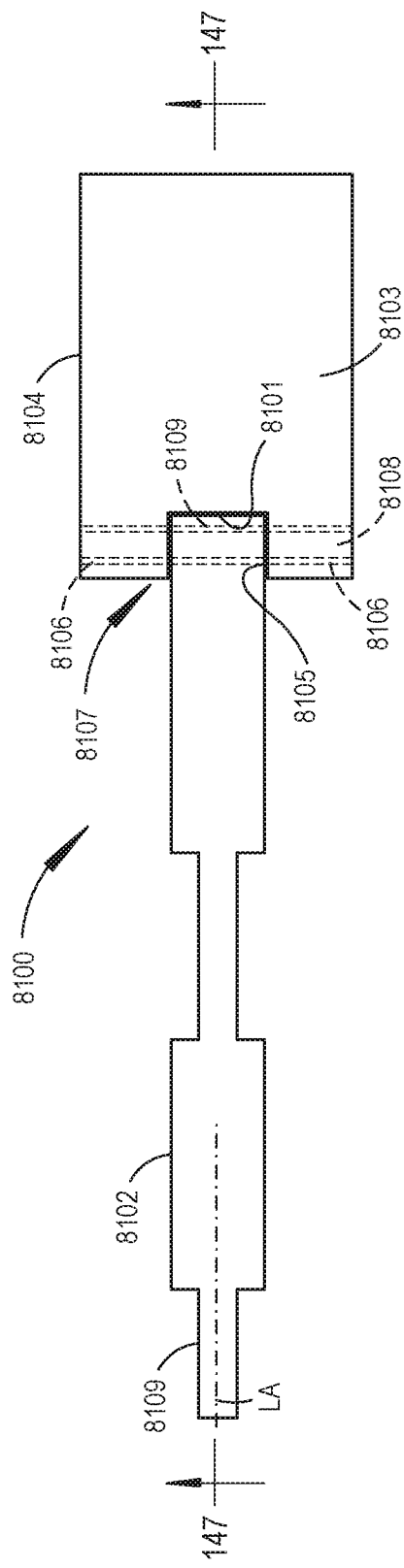
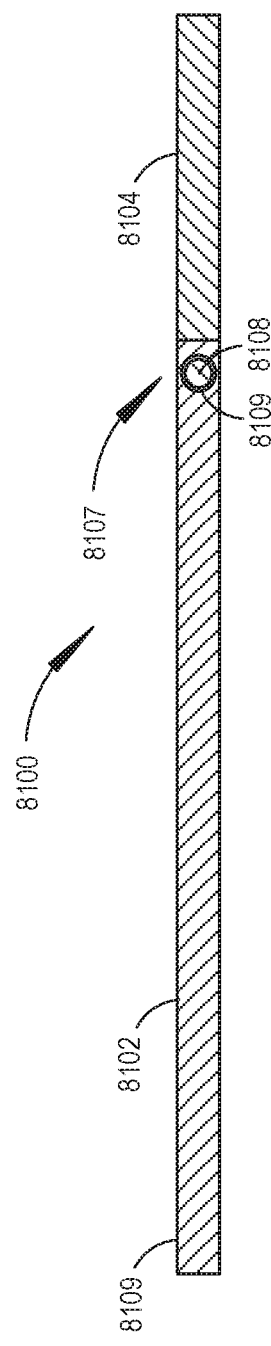
FIG. 146
FIG. 147

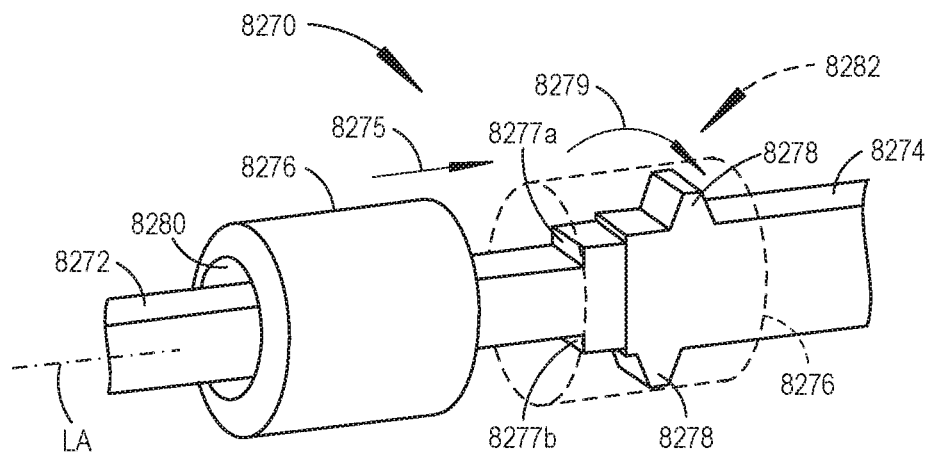
FIG. 173
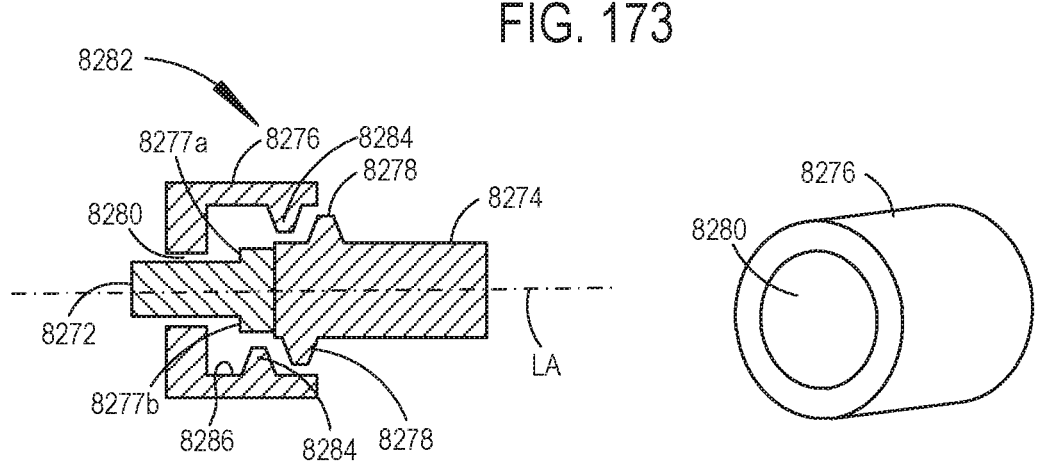
FIG. 174
FIG. 175
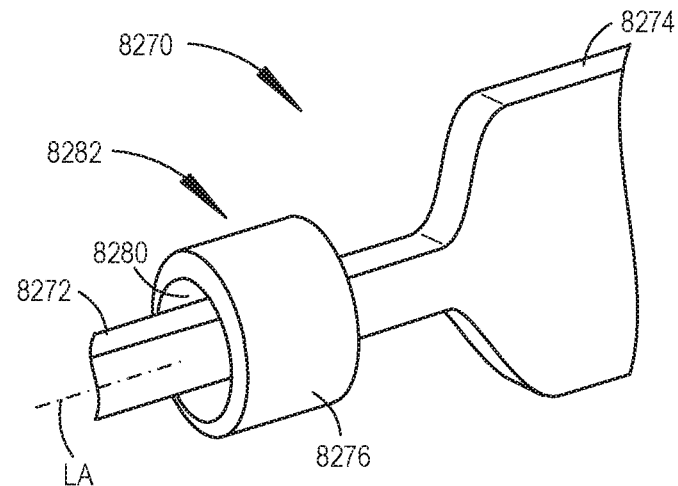
FIG. 176

ULTRASONIC TRANSDUCER TECHNIQUES FOR ULTRASONIC SURGICAL INSTRUMENT

PRIORITY

This application claims the benefit of U.S. Provisional Application Ser. No. 62/379,550 filed Aug. 25, 2016, which is incorporated herein by reference in its entirety.

BACKGROUND

The present disclosure relates, in general, to ultrasonic surgical instruments and more particularly to ultrasonic transducers to drive ultrasonic blades. Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue from bone. Ultrasonic instruments utilizing solid core technology are particularly advantageous because of the amount of ultrasonic energy that may be transmitted from the ultrasonic transducer, through a waveguide, and to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue. Because of the nature of ultrasonic instruments, a particular ultrasonically actuated end effector may be designed to perform numerous functions, including, for example, cutting and coagulation. Ultrasonic vibration is induced in the surgical end effector by electrically exciting a transducer, for example. The transducer may be constructed of one or more piezoelectric or magnetostrictive elements in the instrument hand piece. Vibrations generated by the transducer are transmitted to the surgical end effector via an ultrasonic waveguide extending from the transducer to the surgical end effector. The waveguide and end effector are designed to resonate at the same frequency as the transducer. Therefore, when an end effector is attached to a transducer, the overall system frequency is the same frequency as the transducer itself.

The amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals 27 times the cyclic frequency, f; and
A=the zero-to-peak amplitude.
The longitudinal excursion of the end effector tip is defined as the peak-to-peak (p-t-p) amplitude, which is just twice the amplitude of the sine wave or 2A. Often, the end effector can comprise a blade which, owing to the longitudinal excursion, can cut and/or coagulate tissue. U.S. Pat. No. 6,283,981, which issued on Sep. 4, 2001 and is entitled METHOD OF BALANCING ASYMMETRIC ULTRASONIC SURGICAL BLADES; U.S. Pat. No. 6,309,400, which issued on Oct. 30, 2001 and is entitled CURVED ULTRASONIC BLADE HAVING A TRAPEZOIDAL CROSS SECTION; and U.S. Pat. No. 6,436,115, which issued on Aug. 20, 2002 and is entitled BALANCED ULTRASONIC BLADE INCLUDING A PLURALITY OF BALANCE ASYMMETRIES, the entire disclosures of which are hereby incorporated by reference herein, disclose various ultrasonic surgical instruments.

SUMMARY

In one general aspect, various aspects are directed to an ultrasonic surgical instrument that comprises a transducer configured to produce vibrations along a longitudinal axis of a surgical tool at a predetermined frequency. In various aspects, the surgical tool may include an ultrasonic blade extends along the longitudinal axis and is coupled to the transducer. In various aspects, the surgical tool includes a body having a proximal end and a distal end, wherein the distal end is movable relative to the longitudinal axis by the vibrations produced by the transducer, and the proximal end is mechanically coupled to the transducer.

In another aspect, the present disclosure provides a method of fabricating an ultrasonic medical device comprising: machining a surgical tool from a portion of a flat metal stock, wherein the surgical tool comprises a proximal end, an end effector, and a longitudinal portion therebetween; contacting a face of a first transducer with a first face of the surgical tool, wherein the first transducer is configured to operate in a D31 mode with respect to the longitudinal portion of the surgical tool; and contacting a face of a second transducer with an opposing face of the surgical tool and opposite the first transducer, wherein the second transducer is configured to operate in a D31 mode with respect to the longitudinal portion of the surgical tool; wherein, upon activation, the first transducer and the second transducer are configured to induce a standing wave in the surgical tool; and wherein the induced standing wave comprises a node at a node location in the surgical tool and an antinode at an antinode location in the surgical tool.

In another aspect, the present disclosure provides a method of fabricating an ultrasonic medical device comprising: machining a surgical tool from a portion of a flat metal stock, wherein the surgical tool comprises a proximal end, an end effector, and a longitudinal portion therebetween; contacting a face of a first transducer with a first face of the surgical tool, wherein the first transducer is configured to operate in a D31 mode with respect to the longitudinal portion of the surgical tool; contacting a face of a second transducer with an opposing face of the surgical tool and opposite the first transducer, wherein the second transducer is configured to operate in a D31 mode with respect to the longitudinal portion of the surgical tool; and subjecting the surgical tool to one or more metalworking processes; wherein, upon activation, the first transducer and the second transducer are configured to induce a standing wave in the surgical tool; and wherein the induced standing wave comprises a node at a node location in the surgical tool and an antinode at an antinode location in the surgical tool.

In another aspect, the present disclosure provides a method of fabricating an ultrasonic medical device comprising: machining a surgical tool from a portion of a flat metal stock, wherein the surgical tool comprises a proximal end, an end effector, and a longitudinal portion therebetween; contacting a face of a first transducer with a first face of the surgical tool, wherein the first transducer is configured to operate in a D31 mode with respect to the longitudinal portion of the surgical tool; and contacting a face of a second transducer with an opposing face of the surgical tool and opposite the first transducer, wherein the second transducer is configured to operate in a D31 mode with respect to the longitudinal portion of the surgical tool; wherein, upon activation, the first transducer and the second transducer are configured to induce a standing wave in the surgical tool; wherein the induced standing wave comprises a node at a node location in the surgical tool and an antinode at an antinode location in the surgical tool; and wherein machining a surgical tool from a portion of a flat metal stock comprises laser machining, laser machining with a tilt degree of freedom, electrical discharge machining, milling, stamping, or fine blanking.

In another aspect, the present disclosure provides a method of fabricating an ultrasonic waveguide, comprising swaging an ultrasonic waveguide shaft made of a first metal to an ultrasonic blade made of a second metal.

In one aspect, the present disclosure provides an ultrasonic medical device comprising a surgical tool comprising a transducer mounting portion (e.g., a transducer base plate) at a proximal end, an end effector at a distal end, and a waveguide disposed therebetween, the waveguide extending along a longitudinal axis, the transducer mounting portion of the surgical tool comprising a first face and a second face at the proximal end, the second face positioned opposite the first face; a first transducer comprising a body defining a face; and a second transducer comprising a body defining a face; wherein the face of the first transducer is in mechanical communication with the first face of the surgical tool and the face of the second transducer is in mechanical communication with the second face of the surgical tool opposite the first transducer; wherein the first transducer and the second transducer are configured to operate in a D31 mode with respect to the longitudinal axis of the waveguide; wherein, upon activation by an electrical signal having a predetermined frequency component, the first and second transducers are configured to induce a standing wave in the surgical tool to cause the end effector to vibrate, the standing wave having a wavelength proportional to the predetermined frequency component of the electrical signal; and wherein the surgical tool defines nodes and antinodes corresponding to the nodes and antinodes of the induced standing wave, wherein the nodes correspond to locations of minimal displacement and the antinodes correspond to locations of maximum displacement.

In another aspect, the present disclosure provides an ultrasonic surgical device comprising a surgical tool comprising a proximal transducer mounting portion defining a surface, a distal end effector end, and a waveguide disposed therebetween, the waveguide extending along a longitudinal axis; and a transducer in mechanical communication with the surface of the transducer mounting portion; wherein the transducer is configured to operate in a D31 mode with respect to the longitudinal axis of the waveguide; and wherein, upon activation by an electrical signal having a predetermined frequency component, the transducer is configured to induce a standing wave in the surgical tool to cause the end effector to vibrate, the standing wave having a wavelength proportional to the predetermined frequency component of the electrical signal.

In another aspect, the present disclosure provides an ultrasonic medical device comprising: a surgical tool comprising a transducer mounting portion at a proximal end, an end effector at a distal end, and a waveguide disposed therebetween, the waveguide extending along a longitudinal axis, the transducer mounting portion of the surgical tool comprising a first face and a second face at the proximal end, the second face positioned opposite the first face; a first transducer comprising a body defining a face; and a second transducer comprising a body defining a face; a third transducer comprising a body defining a face; and a fourth transducer comprising a body defining a face; wherein the face of the first transducer is in mechanical communication with the first face of the surgical tool and the face of the second transducer is in mechanical communication with the second face of the surgical tool opposite the first transducer; wherein the first transducer and the second transducer are configured to operate in a D31 mode with respect to the longitudinal axis of the waveguide; wherein, upon activation by an electrical signal having a predetermined frequency component, the first and second transducers are configured to induce a standing wave in the surgical tool to cause the end effector to vibrate, the standing wave having a wavelength proportional to the predetermined frequency component of the electrical signal; and wherein the surgical tool defines nodes and antinodes corresponding to the nodes and antinodes of the induced standing wave, wherein the nodes correspond to locations of minimal displacement and the antinodes correspond to locations of maximum displacement.

In one general aspect, various aspects are directed to an ultrasonic surgical instrument that comprises a transducer configured to produce vibrations along a longitudinal axis of a surgical tool at a predetermined frequency. In various aspects, the surgical tool may include an ultrasonic waveguide that extends along the longitudinal axis and is coupled to the transducer. In various aspects, the surgical tool includes a body having a proximal end and a distal end, wherein the distal end is movable relative to the longitudinal axis by the vibrations produced by the transducer, and the proximal end is mechanically coupled to the transducer.

In one aspect, an ultrasonic surgical instrument is provided. The ultrasonic surgical instrument comprises a transducer base plate (e.g., a transducer mounting portion) comprising a first and second face; a first piezoelectric element positioned on the first face; a second piezoelectric element positioned on the second face, wherein the first and second piezoelectric element are each configured to operate in a D31 mode with respect to a longitudinal axis of a waveguide coupled to the transducer base plate, wherein the waveguide is electrically coupled to the first piezoelectric element and to the second piezoelectric element by a conductive adhesive; an electrode configured to electrically couple the first and second piezoelectric elements to an ultrasonic signal generator; and a thermal conductor configured to conduct thermal energy away from the first and second piezoelectric elements.

In another aspect, a method of fabricating an ultrasonic surgical instrument is provided. The method comprises machining a transducer base plate from a portion of a flat metal stock, wherein the transducer base plate comprises a first and second face; positioning a first piezoelectric element on the first face; positioning a second piezoelectric element on the second face, wherein the first and second piezoelectric element are each configured to operate in a D31 mode with respect to a longitudinal axis of a waveguide coupled to the transducer base plate; coupling, by a first electrically conductive adhesive, the waveguide to the first piezoelectric element and the second piezoelectric element; compressing, by an electrode, against the first and second piezoelectric elements to electrically couple the first and second piezoelectric elements to an ultrasonic signal generator; and conducting, by a thermal conductor, heat away from the first and second piezoelectric elements.

In another aspect, a transducer base plate is provided. The transducer base plate comprises a first and second face, wherein a first piezoelectric element is positioned on the first face and a second piezoelectric element is positioned on the second face, and wherein the first and second piezoelectric element are each configured to operate in a D31 mode with respect to a longitudinal axis of a waveguide coupled to the transducer base plate; a conductive adhesive to electrically couple the first and second piezoelectric elements to the waveguide; an electrode configured to electrically couple the first and second piezoelectric elements to an ultrasonic signal generator; and a thermal conductor configured to conduct heat away from the first and second piezoelectric elements.

In another aspect, an ultrasonic transducer assembly is provided. The ultrasonic transducer assembly comprises a stack of a plurality of piezoelectric elements, wherein the stack is configured to operate in a D33 mode with respect to a longitudinal axis of a waveguide coupled to the transducer base plate; a compression plate to compress the stack of the plurality of piezoelectric elements to couple the stack of piezoelectric elements to a waveguide; and a compressive element for applying a compressive force against the compression plate.

In one general aspect, various aspects are directed to an ultrasonic surgical instrument that comprises a transducer configured to produce vibrations along a longitudinal axis of a surgical tool at a predetermined frequency. In various aspects, the surgical tool may include an ultrasonic waveguide that extends along the longitudinal axis and is coupled to the transducer. In various aspects, the surgical tool includes a body having a proximal end and a distal end, wherein the distal end is movable relative to the longitudinal axis by the vibrations produced by the transducer, and the proximal end is mechanically coupled to the transducer.

In one aspect, a compressed ultrasonic transducer assembly is provided. The compressed ultrasonic transducer assembly comprises a metal housing defining an opening; at least two piezoelectric elements disposed within the opening and compressed by a compressive force, wherein the at least two piezoelectric elements are configured to work in a D33 mode; and a metal plug joined to the metal housing to close the opening and to maintain the at least two piezoelectric elements in a compressed state within the metal housing.

In another aspect, an ultrasonic surgical instrument is provided. The ultrasonic surgical instrument comprises an ultrasonic waveguide; an ultrasonic transducer mounted to the ultrasonic waveguide and configured to operated in a D31 mode, ultrasonic transducer comprising: a first ceramic piezoelectric element having a first side attached to a first side of the ultrasonic waveguide by a first bonding material; and a second ceramic piezoelectric element having a first side attached to a second side of the ultrasonic waveguide by the first bonding material, wherein the first side of the ultrasonic waveguide is opposite the second side of the ultrasonic waveguide.

In another aspect, an ultrasonic surgical instrument is provided. The ultrasonic surgical instrument comprises an ultrasonic waveguide comprising: a base portion; first and second walls extending from one side of the base portion; and first and second ledges projecting from the corresponding first and second walls, wherein a first space is defined between the first ledge and the base portion and wherein a second space is defined between the second ledge and the base portion; and an ultrasonic transducer attached to the ultrasonic waveguide, wherein the ultrasonic transducer comprises at least one piezoelectric element slidably disposed between the first and second spaces and fixed therein.

In another aspect, an ultrasonic surgical instrument is provided. The ultrasonic surgical instrument comprises an ultrasonic waveguide; and an ultrasonic transducer attached to the ultrasonic waveguide; wherein the ultrasonic waveguide comprises a tuning-fork-like frame comprising: an upper prong; and a lower prong defining a U-shaped aperture therebetween configured to receive the ultrasonic transducer therein.

In one general aspect, an ultrasonic surgical instrument is provided. The ultrasonic instrument comprises a waveguide comprising a distal end configured as a blade and a proximal end configured to couple to a transducer base plate; and the transducer base plate comprising a distal end coupled to the proximal end of the waveguide to define a joint at an interface between the waveguide and the transducer base plate, the transducer base plate comprising a first and second sides defining corresponding first and second flat faces, wherein the first flat face is configured to receive a first piezoelectric element and the second flat face is configured to receive a second piezoelectric element, wherein the first and second piezoelectric elements are configured to operate in a D31 mode.

In another aspect, an ultrasonic waveguide comprises a shaft comprising a proximal end and a distal end, wherein the proximal end is configured to couple to an ultrasonic transducer and the distal end defines cylindrical aperture with a flat perpendicular bottom configured to receive a proximal end of a blade; and a blade attached to the shaft, the blade comprising a distal end for treating tissue and a proximal end defining a conical male end defining a flat perpendicular bottom, wherein the conical male end defines a proximal diameter and a distal diameter, wherein the proximal diameter is larger than the distal diameter, and wherein the conical male end is received into the cylindrical aperture defined by the distal end of the shaft.

In another aspect, an ultrasonic surgical instrument comprises an ultrasonic waveguide defining a T-shaped male connector at a proximal end; and a symmetric two-piece clamshell housing comprising: first and second T-shaped pockets configured to receive the T-shaped male connector, wherein the T-shaped pockets are press fit to the T-shaped male connector; and first and second recessed pockets configured to support first and a second piezoelectric elements, wherein the first and second piezoelectric elements are configured to operate in a D31 mode.

In one general aspect, various aspects are directed to an ultrasonic surgical instrument that comprises a transducer configured to produce vibrations along a longitudinal axis of a surgical instrument at a predetermined frequency. In various aspects, the surgical instrument may include an ultrasonic waveguide that extends along the longitudinal axis and is coupled to the transducer. In various aspects, the surgical instrument includes a body having a proximal end and a distal end, wherein the distal end is movable relative to the longitudinal axis by the vibrations produced by the transducer, and the proximal end is mechanically coupled to the transducer.

In one aspect, an ultrasonic surgical instrument is provided. The ultrasonic surgical instrument comprises an end effector; a jaw movable relative to the end effector; a transducer assembly comprising at least two piezoelectric elements configured to ultrasonically oscillate the end effector; and an indicium coextensive with a portion of the jaw overlying the end effector.

In another aspect, an ultrasonic surgical instrument is provided. The ultrasonic surgical instrument comprises an end effector; a jaw movable relative to the end effector between an open position and a closed position; a transducer assembly comprising at least two piezoelectric elements configured to ultrasonically oscillate the end effector; and a cam movably connected to the jaw via a linkage; wherein in the jaw closed position, the cam is configured to extend towards a proximal end of the jaw; and wherein in the jaw open position, the cam is configured to retract.

In another aspect, an ultrasonic surgical instrument is provided. The ultrasonic surgical instrument comprises an end effector; a jaw movable relative to the end effector between an open position and a closed position; a transducer assembly comprising at least two piezoelectric elements configured to ultrasonically oscillate the end effector; a slidable member movable between a retracted position and an extended position, wherein in the slidable member extended position the slidable member is configured to contact a proximal end of the jaw; wherein the member is biased to the retracted position; and a projection, wherein in the jaw closed position the projection is configured to contact the spring-biased member, and wherein in the jaw closed position the projection is configured to move the slidable member to the extended position.

In another aspect, an ultrasonic surgical instrument is provided. The ultrasonic surgical instrument comprises a first arm; a second arm pivotably connected to the first arm; a jaw disposed at a distal end of the first arm; an end effector disposed at a distal end of the second arm; wherein the jaw is movable relative to the end effector between an open position and a closed position; a transducer assembly comprising at least two piezoelectric elements configured to ultrasonically oscillate the end effector; and a bar member extending from the second arm through the first arm at a position proximal to the jaw, the bar member comprising a curvature corresponding to a rotational arc of the first arm.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 3 illustrates a D31 ultrasonic transducer architecture that includes an ultrasonic waveguide and one or more piezoelectric elements fixed to the ultrasonic waveguide, according to one aspect of this disclosure.

FIG. 4A is another perspective view of an ultrasonic medical device having a single pair of piezoelectric transducers, according to one aspect of this disclosure.

FIG. 4B is a perspective view of a transducer mounting portion of an ultrasonic medical device depicted in FIG. 4A, according to one aspect of this disclosure.

FIG. 5 is a plan view of a transducer mounting portion of an ultrasonic medical device depicted in FIG. 4A, according to one aspect of this disclosure.

FIGS. 17 and 18 are plan views of an ultrasonic medical device having a transducer mounting portion having a form of a square or rectangular prism, according to one aspect of this disclosure.

FIGS. 86A-86B illustrate an assembly process of the transducer assembly shown in FIG. 83, with electrodes assembled from an initial uncompressed state to a final compressed state, according to one aspect of this disclosure.

FIGS. 95A-95C illustrate a compressed ultrasonic transducer assembly in a D33 configuration with tuned compression, according to one aspect of this disclosure.

FIG. 96 is a perspective view of an ultrasonic surgical instrument, according to one aspect of this disclosure.

FIG. 97 is perspective view of a piezoelectric element for use with the ultrasonic surgical instrument shown in FIG. 96, according to one aspect of this disclosure.

FIG. 98 is sectional view of the ultrasonic surgical instrument shown in FIG. 96, according to one aspect of this disclosure.

FIG. 99 illustrates an example of an adhesive bond between a metal and a metal alloy solder, according to one aspect of this disclosure.

FIG. 100 illustrates an adhesive bond between a ceramic and a metal formed by a metal alloy solder, according to one aspect of this disclosure.

FIG. 101 illustrates an example of a metallurgical/chemical bond, according to one aspect of this disclosure.

FIG. 102 is a microstructure illustration of a ceramic and metal alloy solder chemical bond, according to one aspect of this disclosure.

FIGS. 113A-D illustrate a D33 ultrasonic transducer configuration, according to one aspect of this disclosure.

Figure 114:
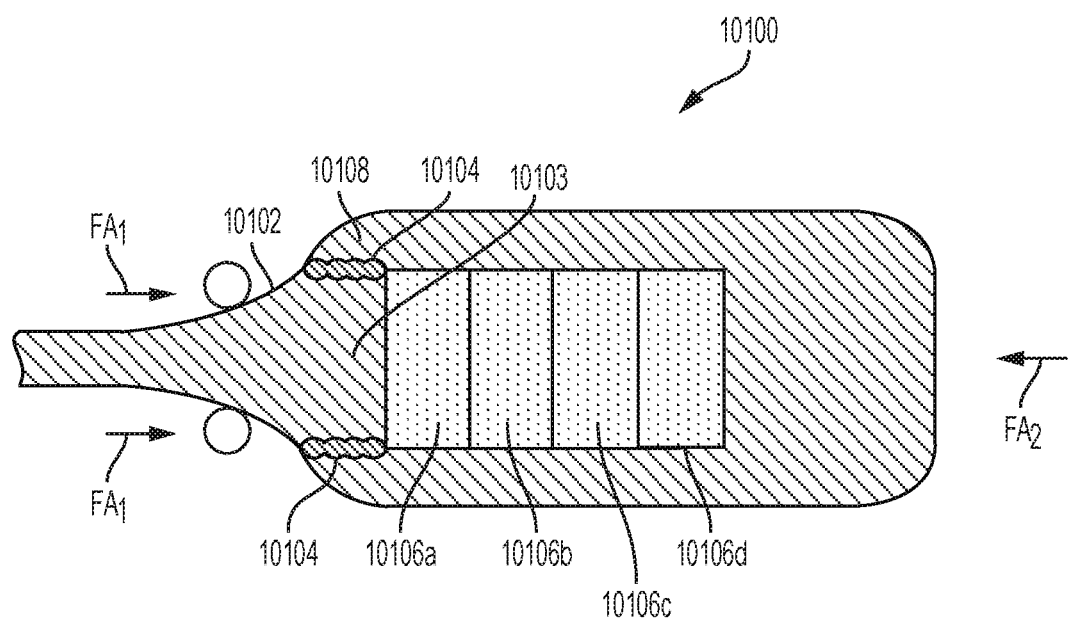

FIG. 114 illustrates a D33 ultrasonic transducer configuration, according to one aspect of this disclosure.

Figure 115A:
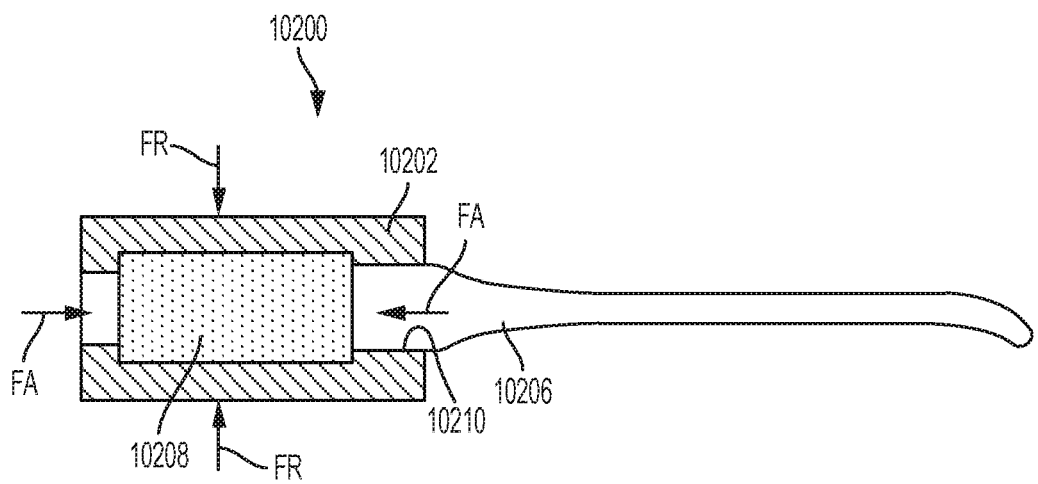

FIG. 115A illustrates a sectional view of a D31 ultrasonic transducer configuration along line 115A-115A, according to one aspect of this disclosure.

Figure 115B:
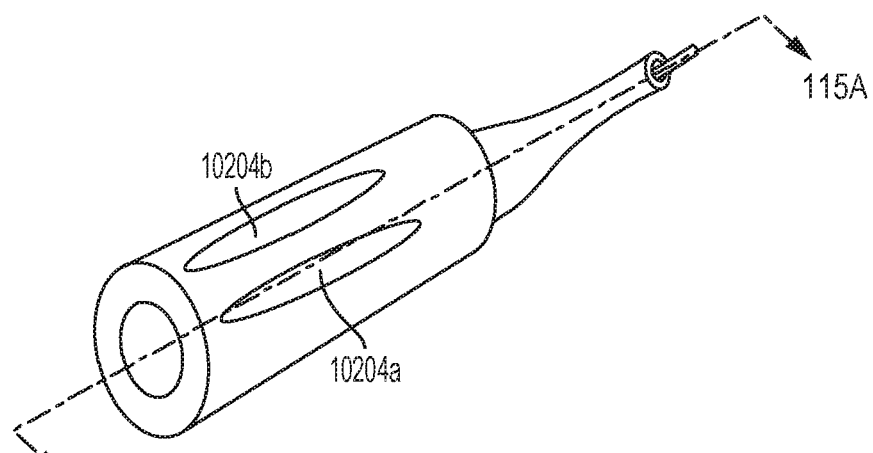

FIG. 115B illustrates a D31 ultrasonic transducer configuration, according to one aspect of this disclosure.

Figure 115C:
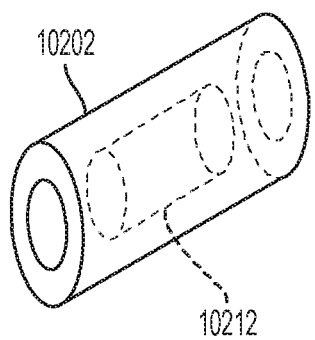

FIG. 115C illustrates the change in shape of the housing of the D31 ultrasonic transducer configuration shown in FIGS. 115A-B, according to one aspect of this disclosure.

FIGS. 116A-E illustrate a D33 ultrasonic transducer configuration, according to one aspect of this disclosure.

Figure 117A:
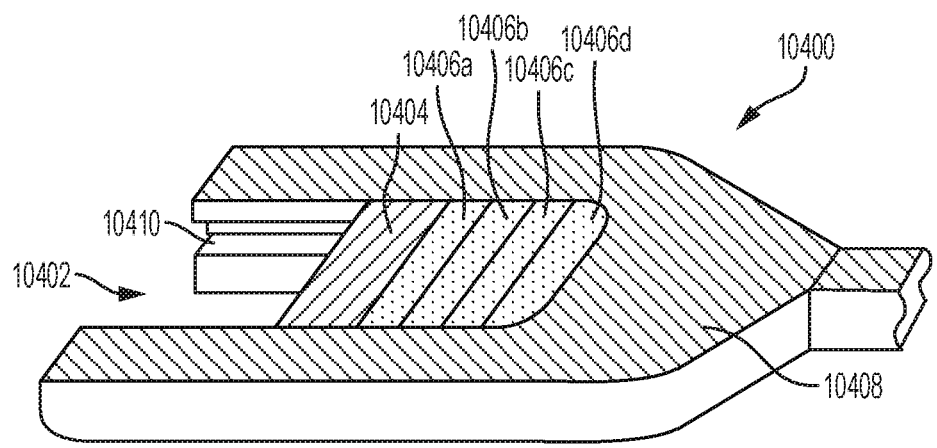

FIG. 117A illustrates a D33 ultrasonic transducer configuration, according to one aspect of this disclosure.

Figure 117B:
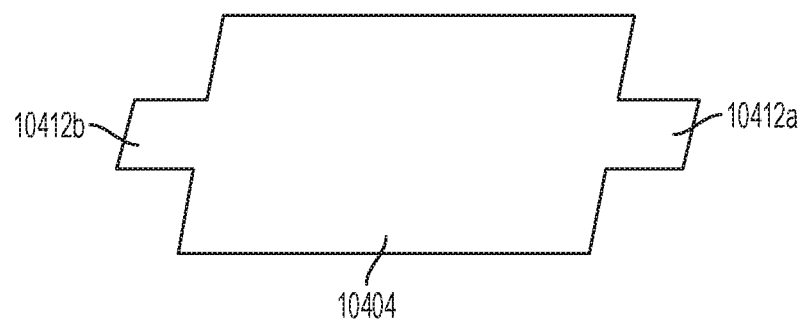

FIG. 117B illustrates the plug of the ultrasonic transducer configuration shown in FIG. 117A, according to one aspect of this disclosure.

Figure 117C:
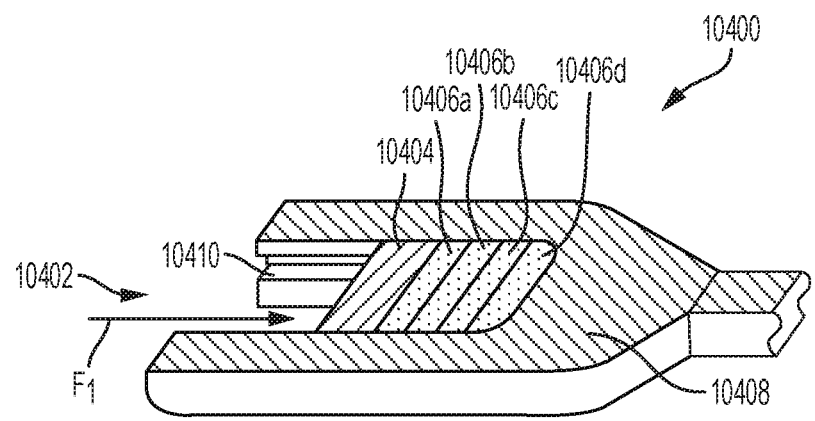
Figure 117D:
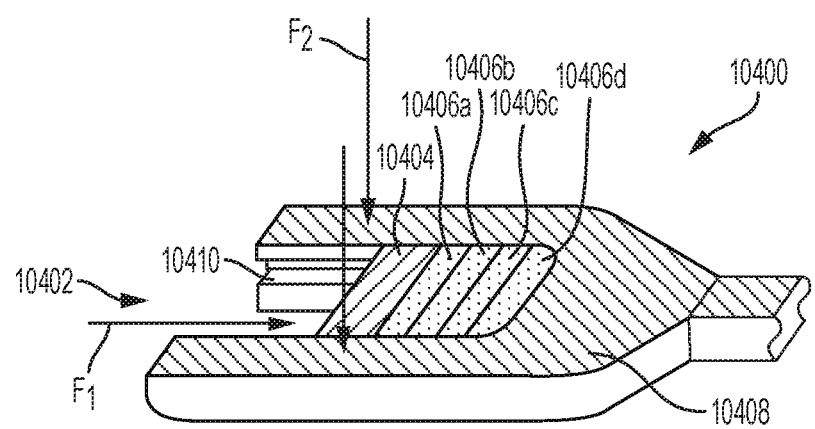

FIGS. 117C-D illustrate a method of installing the D33 ultrasonic transducer configuration shown in FIG. 117A, according to one aspect of this disclosure.

Figure 118:
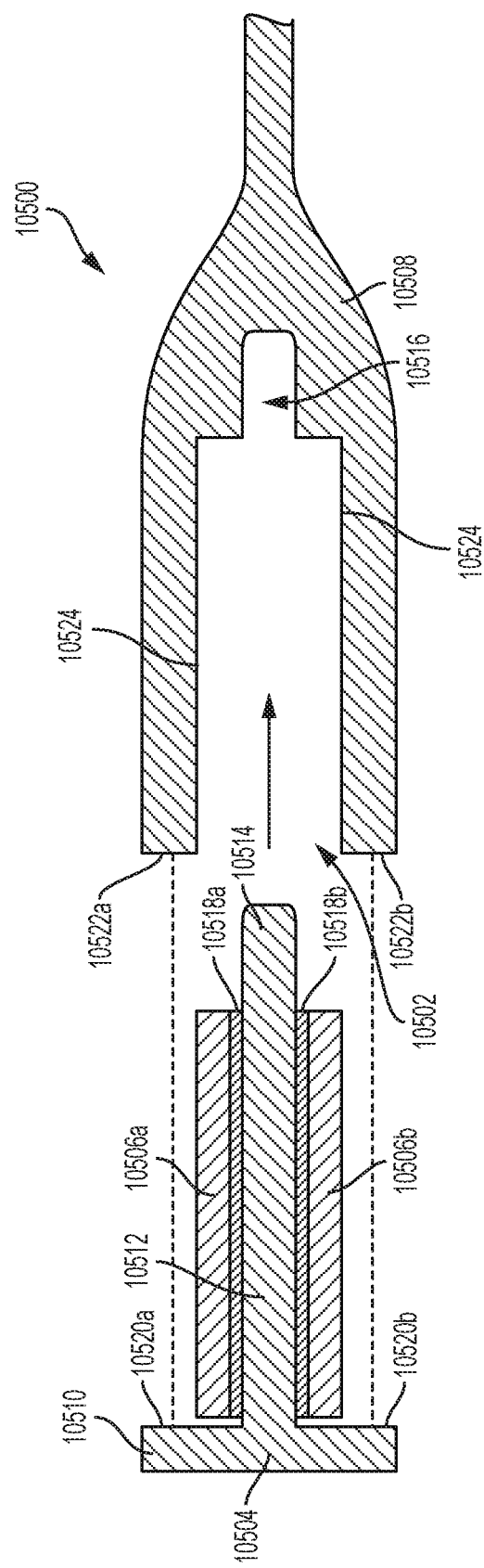

FIG. 118 illustrates a D31 ultrasonic transducer configuration, according to one aspect of this disclosure.

Figure 119:
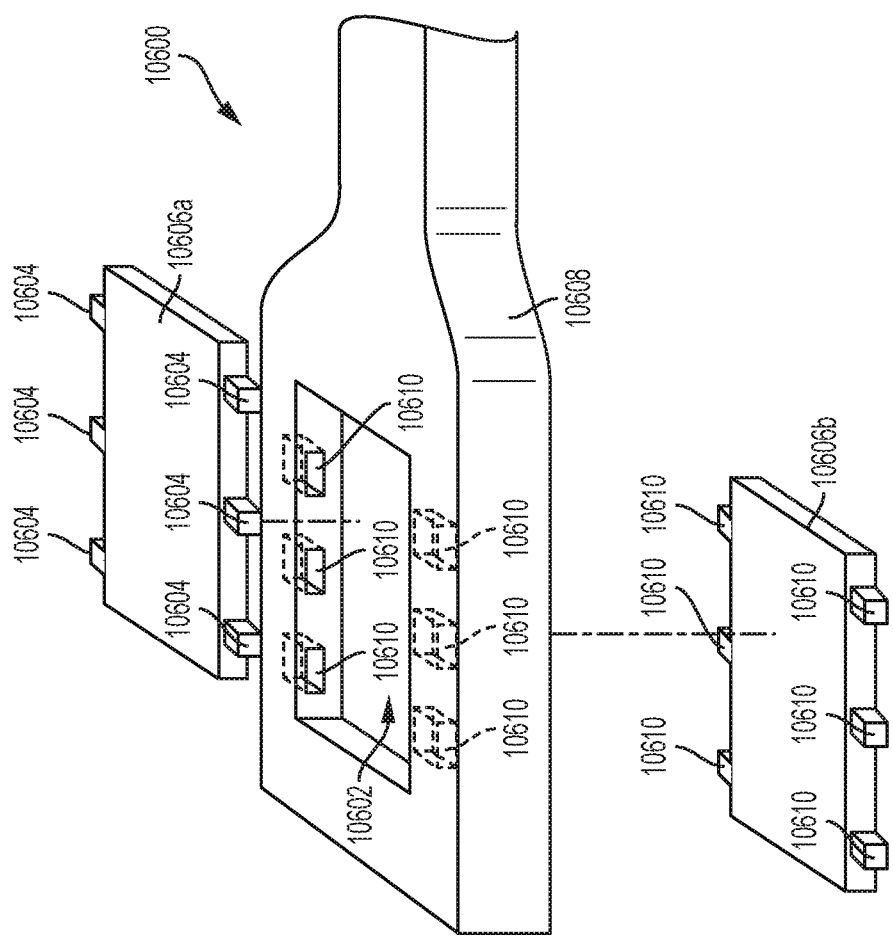

FIG. 119 illustrates a D31 ultrasonic transducer configuration, according to one aspect of this disclosure.

FIGS. 120A-B illustrate a D31 ultrasonic transducer configuration, according to one aspect of this disclosure.

Figure 121A:
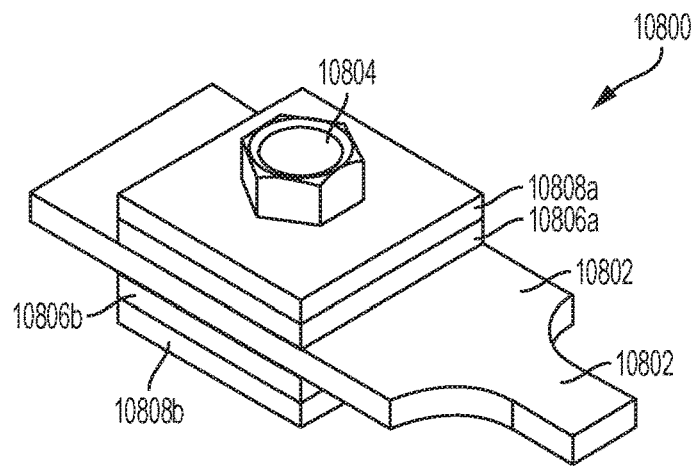

FIG. 121A illustrates a D31 ultrasonic transducer configuration, according to one aspect of this disclosure.

Figure 121B:
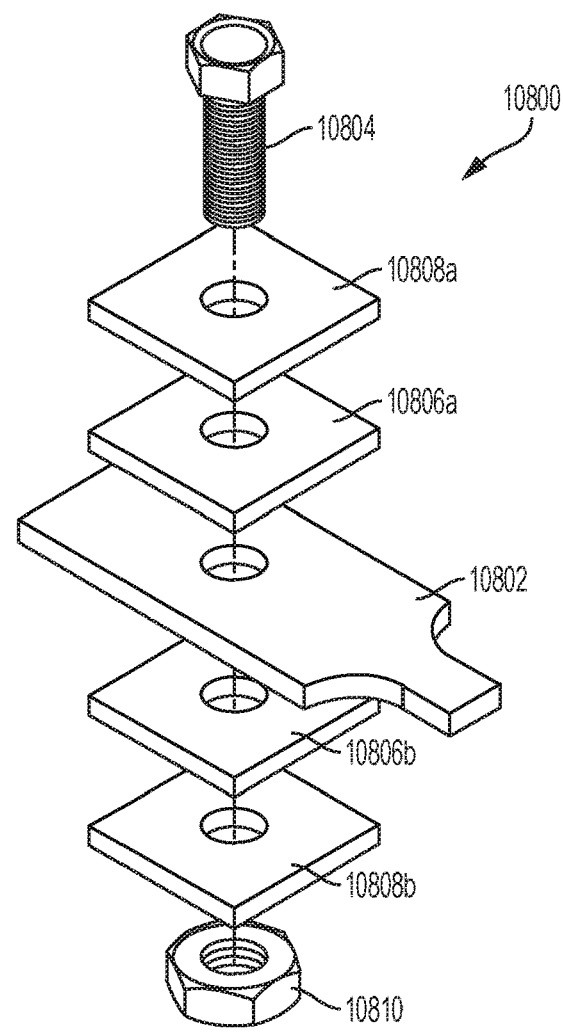

FIG. 121B illustrates an exploded view of the D31 ultrasonic transducer configuration shown in FIG. 121A, according to one aspect of this disclosure.

Figure 121C:
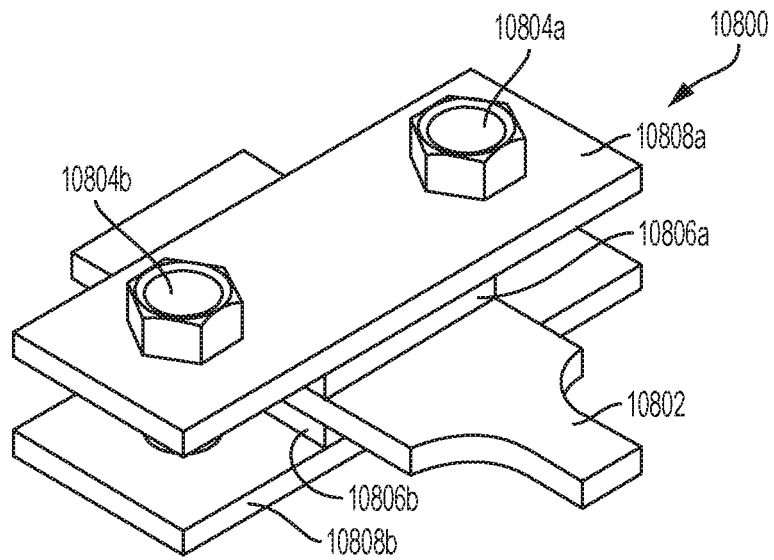

FIG. 121C illustrates a D31 ultrasonic transducer configuration, according to one aspect of this disclosure.

Figure 121D:
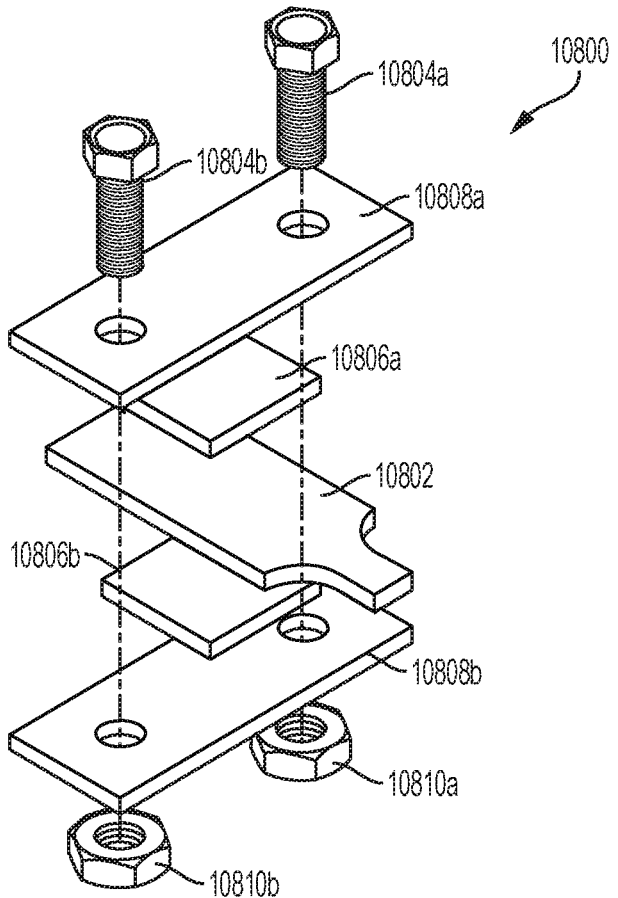

FIG. 121D illustrates an exploded view of the D31 ultrasonic transducer configuration shown in FIG. 121C, according to one aspect of this disclosure.

Figure 122:
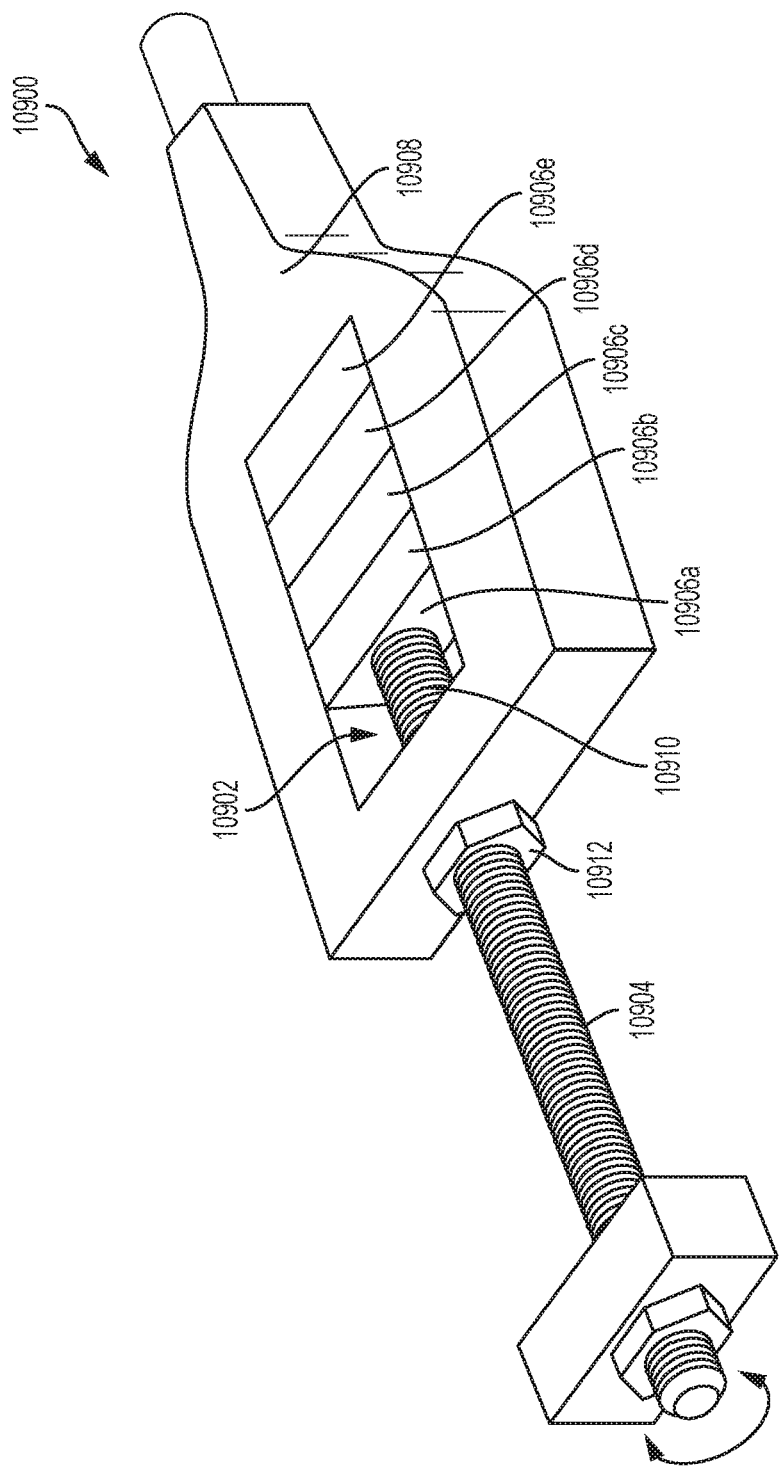

FIG. 122 illustrates a D33 ultrasonic transducer configuration, according to one aspect of this disclosure.

Figure 123A:
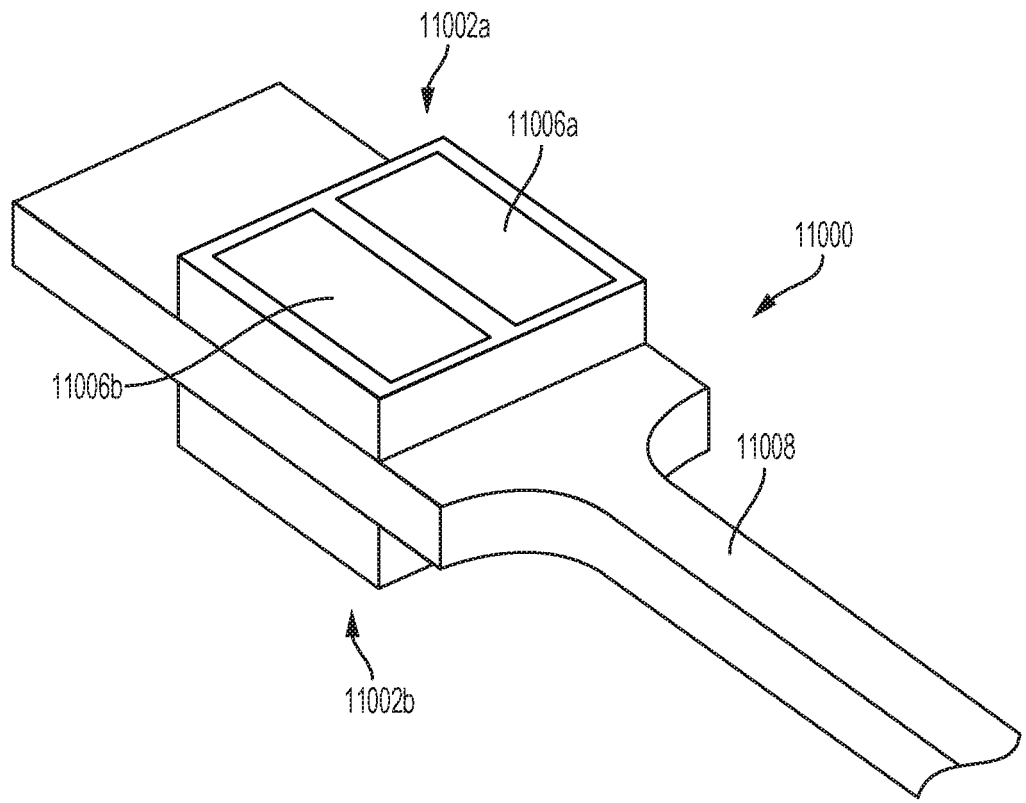
Figure 123B:
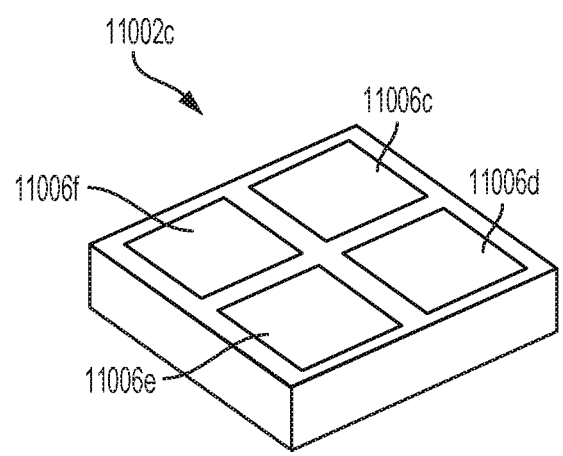

FIGS. 123A-B illustrate D31 ultrasonic transducer configurations having asymmetrically excitable piezoelectric transducer assemblies, according to one aspect of this disclosure.

Figure 124A:
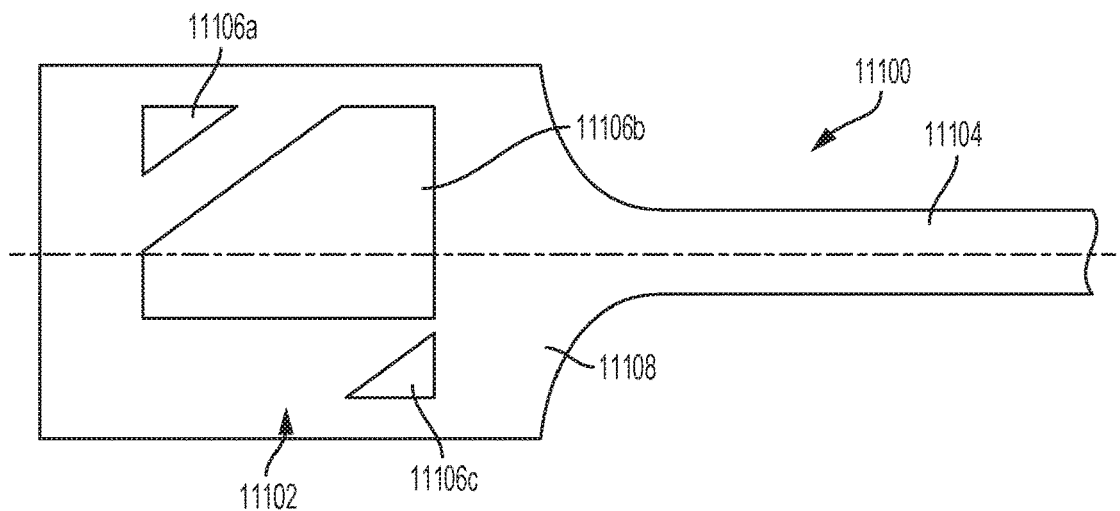
Figure 124B:
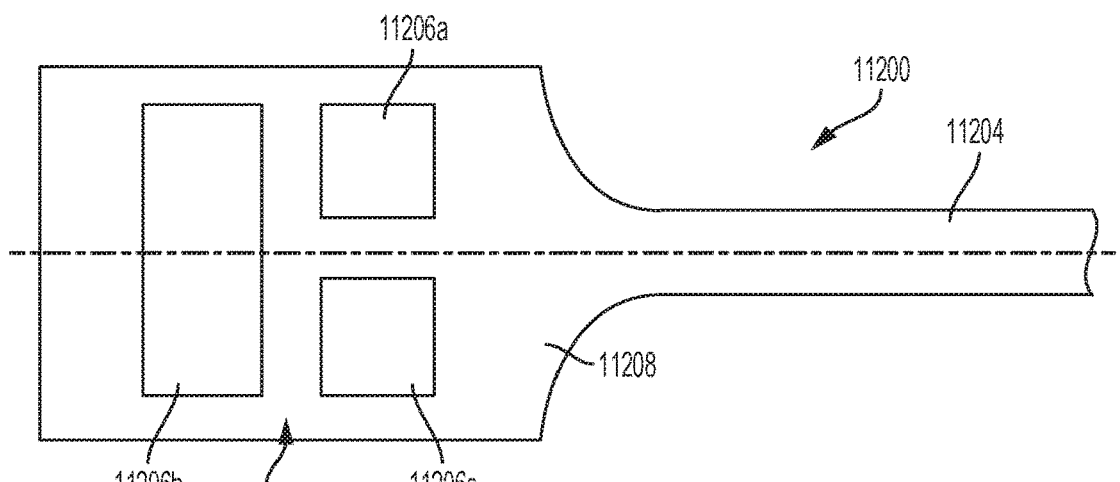
Figure 124C:
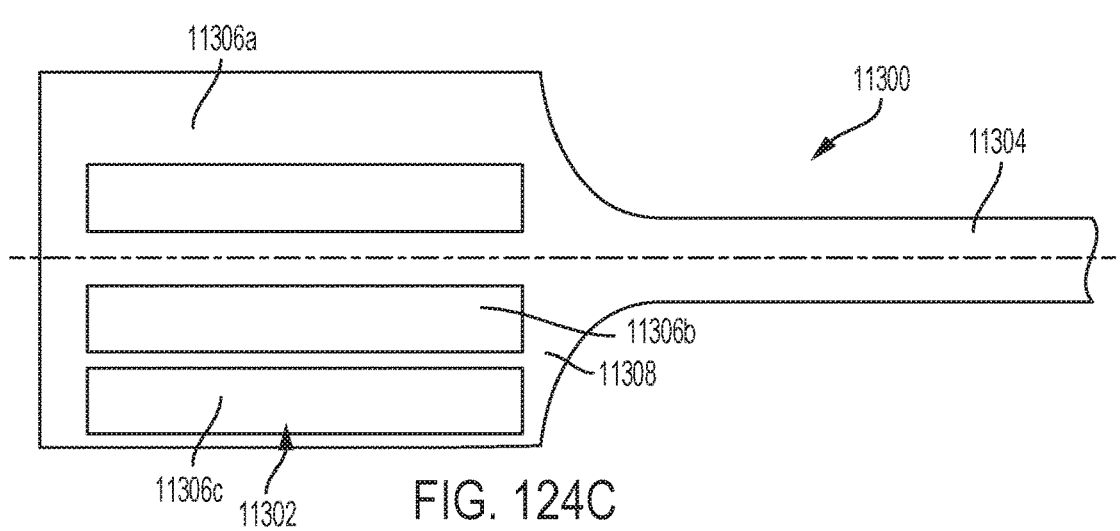

FIGS. 124A-C illustrate D31 ultrasonic transducer configurations having asymmetrically excitable piezoelectric transducer assemblies, according to one aspect of this disclosure.

Figure 125A:
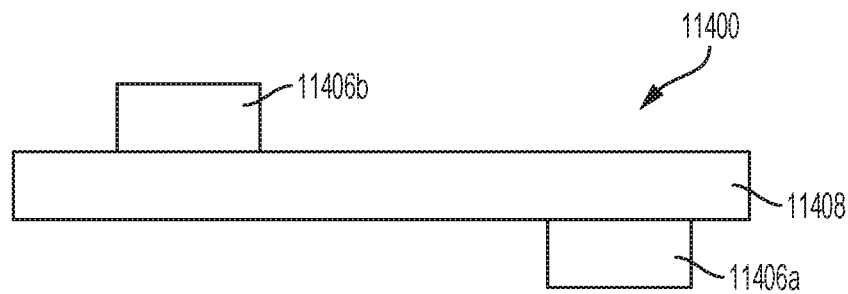
Figure 125B:
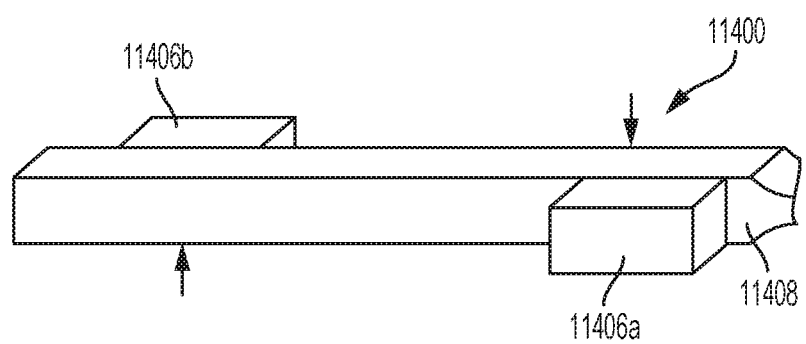

FIGS. 125A-B illustrate a D31 ultrasonic transducer configuration wherein the piezoelectric elements are offset relative to each other, according to one aspect of this disclosure.

Figure 125C:
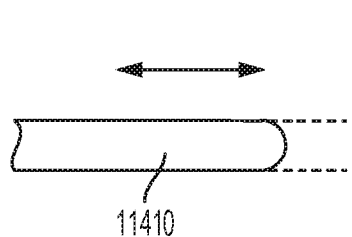
Figure 125D:
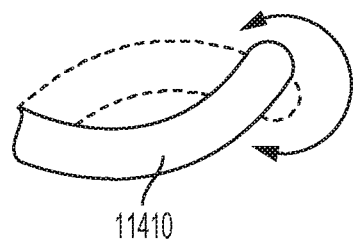

FIGS. 125C-D illustrate views of an end effector of a surgical instrument undergoing longitudinal and non-longitudinal motion, respectively, according to one aspect of this disclosure.

Figure 126A:
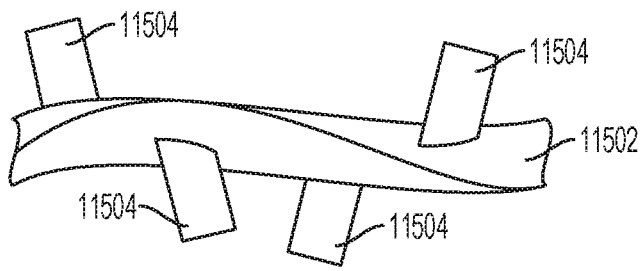

FIG. 126A illustrates a perspective view of a distal end of a waveguide of a surgical instrument having complex features, according to one aspect of this disclosure.

FIGS. 126B-E illustrate a process of fabricating the surgical instrument shown in FIG. 126A, according to one aspect of this disclosure.

FIG. 127A illustrates a perspective view of a D31 ultrasonic transducer configuration configured to generate non-longitudinal motion, according to one aspect of this disclosure.

FIG. 127B illustrates a perspective view of an electrode of the D31 ultrasonic transducer configuration shown in FIG. 127A, according to one aspect of this disclosure.

FIG. 127C illustrates a sectional view of the D31 ultrasonic transducer configuration shown in FIG. 127A along line 127C-127C, according to one aspect of this disclosure.

FIG. 127D illustrates a side view of the electrode and piezoelectric transducer assembly of the D31 ultrasonic transducer configuration shown in FIG. 127A, according to one aspect of this disclosure.

Figure 128:
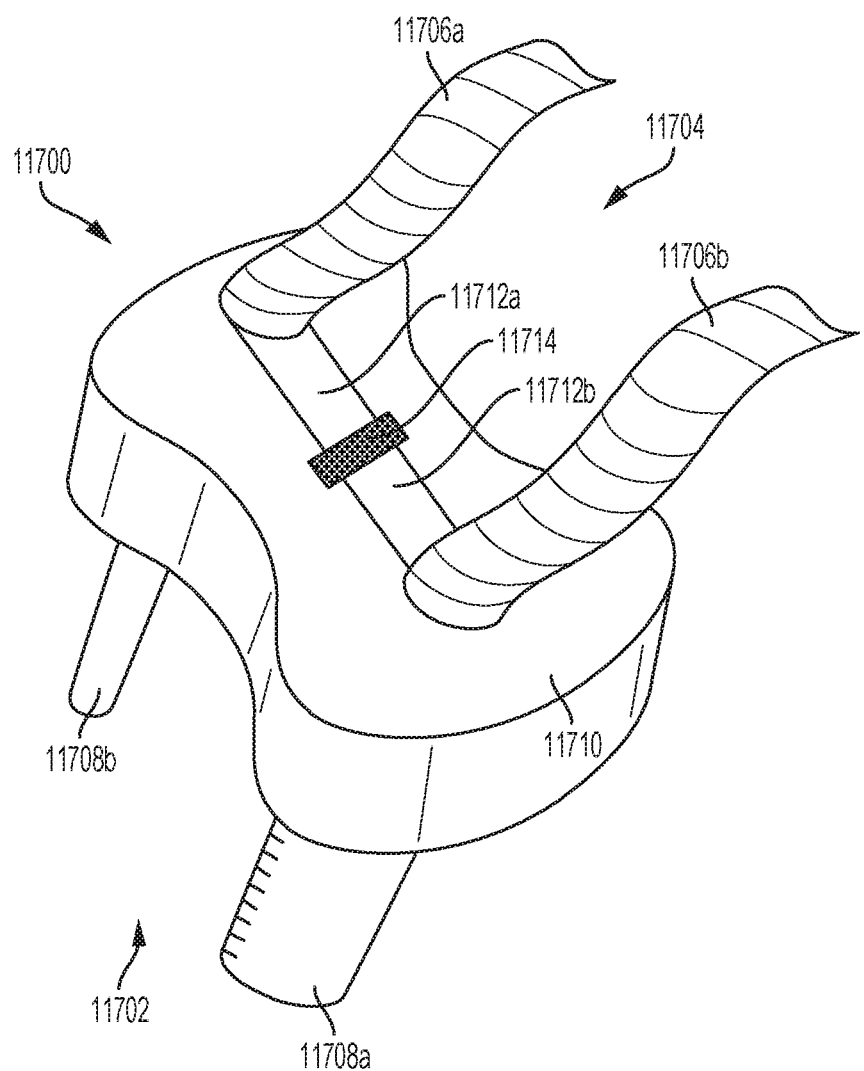

FIG. 128 illustrates a perspective view of an electrical connector to an ultrasonic signal generator for a surgical instrument, according to one aspect of this disclosure.

Figure 129:
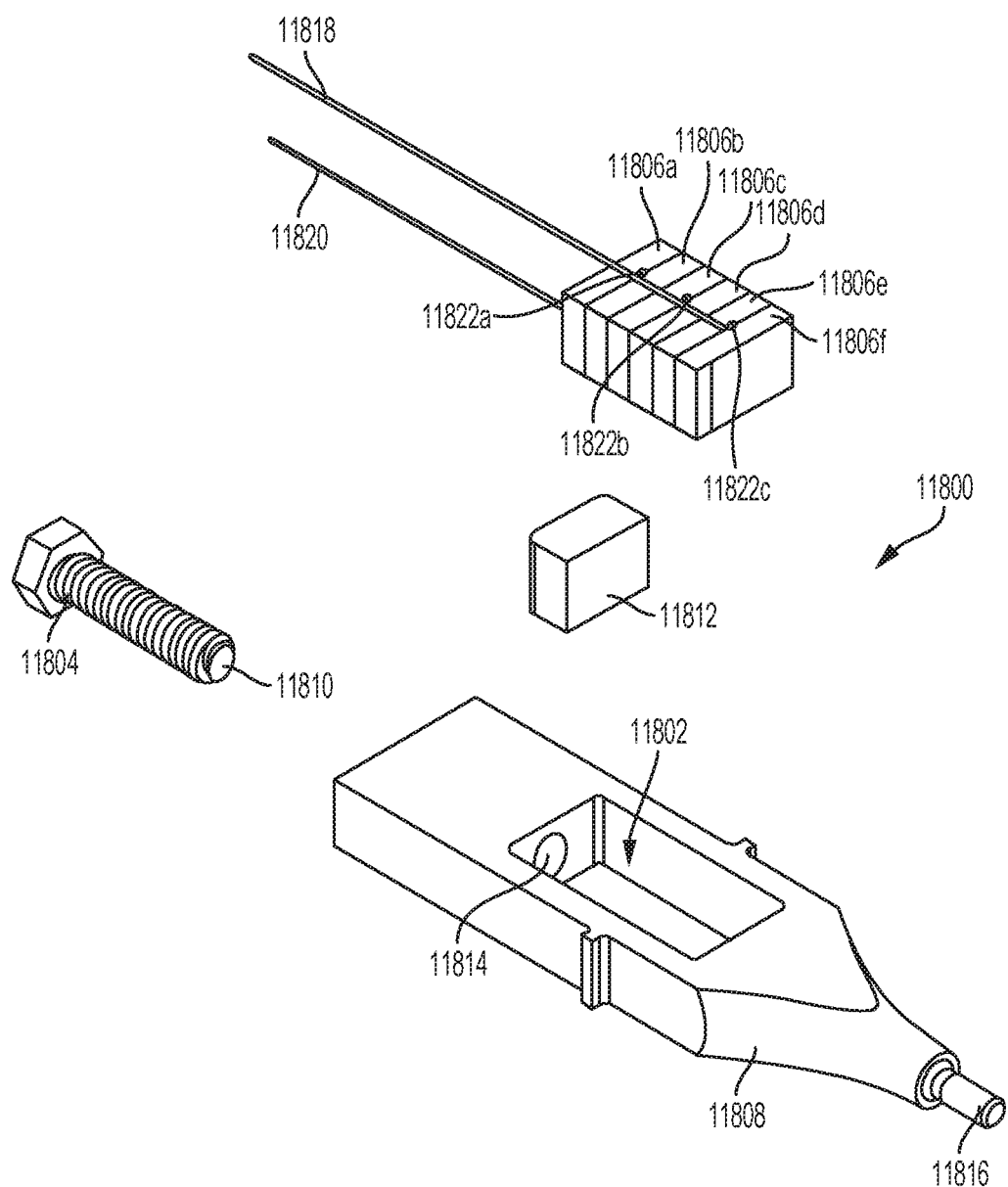

FIG. 129 illustrates an exploded view of a D33 ultrasonic transducer configuration, according to one aspect of this disclosure.

Figure 130:
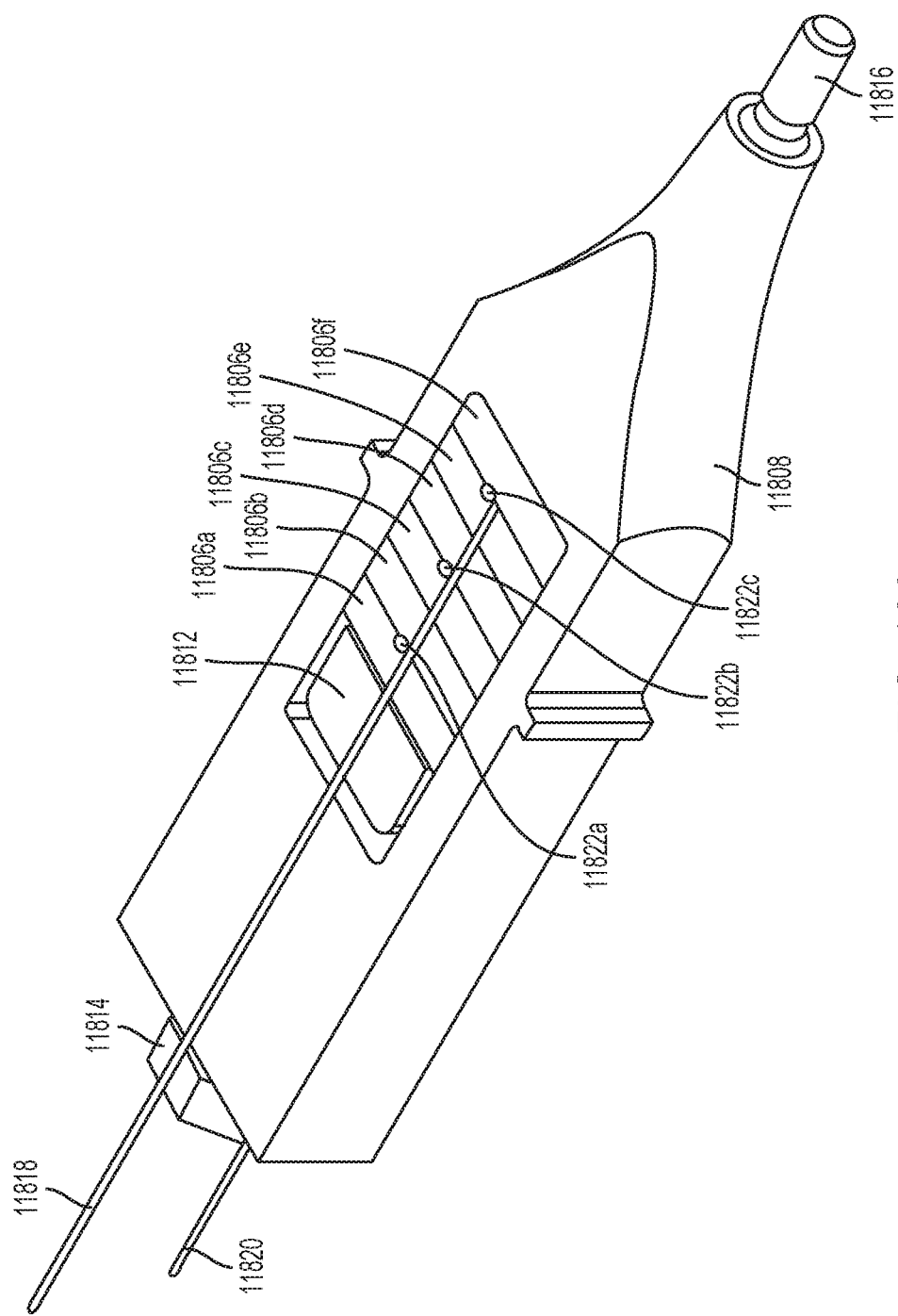

FIG. 130 illustrates a perspective view of the D33 ultrasonic transducer configuration of FIG. 129, according to one aspect of this disclosure.

Figure 131:
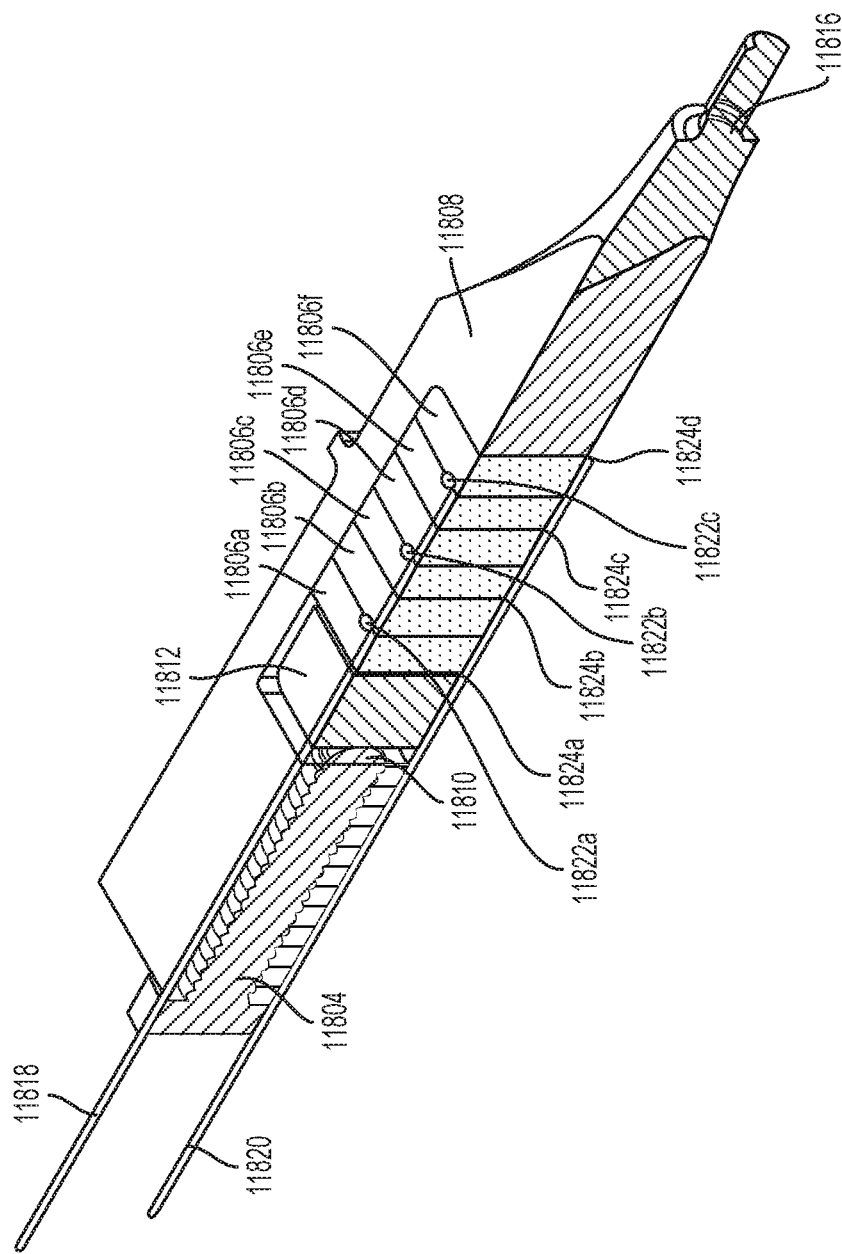

FIG. 131 illustrates a perspective sectional view of the D33 ultrasonic transducer configuration of FIG. 129, according to one aspect of this disclosure.

Figure 132:
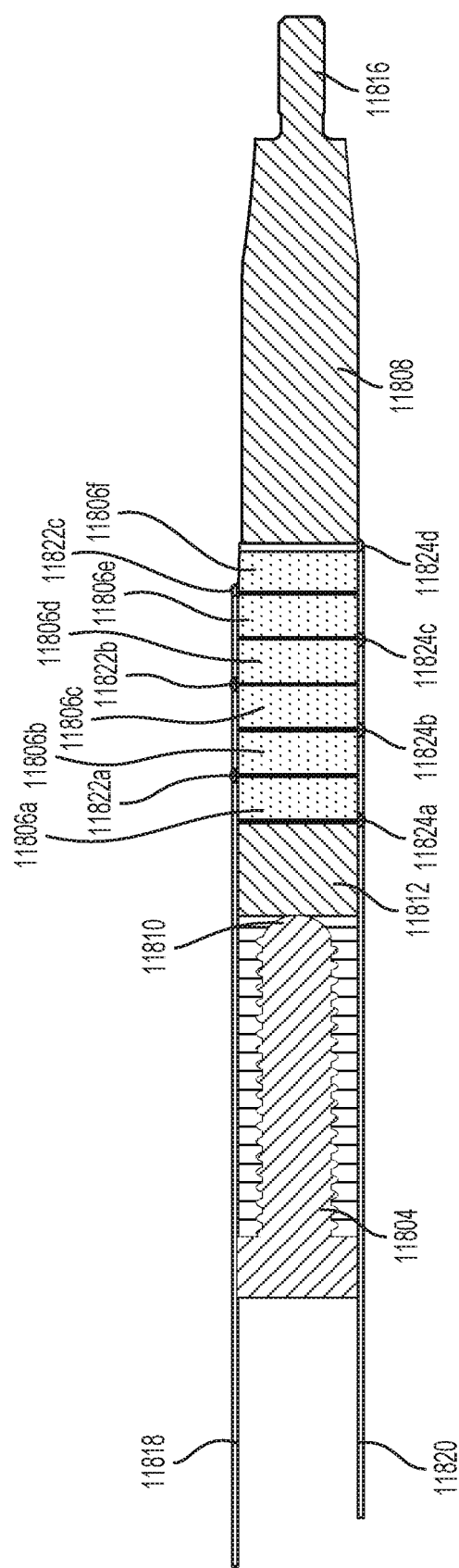

FIG. 132 illustrates a plan sectional view of the D33 ultrasonic transducer configuration of FIG. 129, according to one aspect of this disclosure.

Figure 133:
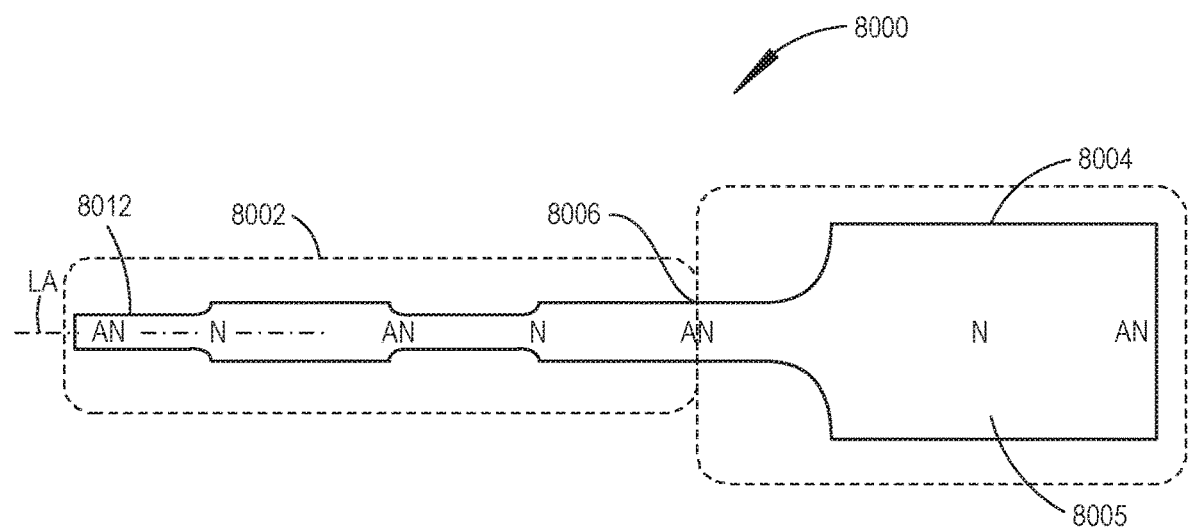

FIG. 133 is a side view of an ultrasonic surgical instrument configured in a D31 ultrasonic transducer architecture comprising separate ultrasonic waveguide and ultrasonic transducer base plate components shown in a coupled configuration, according to one aspect of this disclosure.

Figures 134A, 134B:
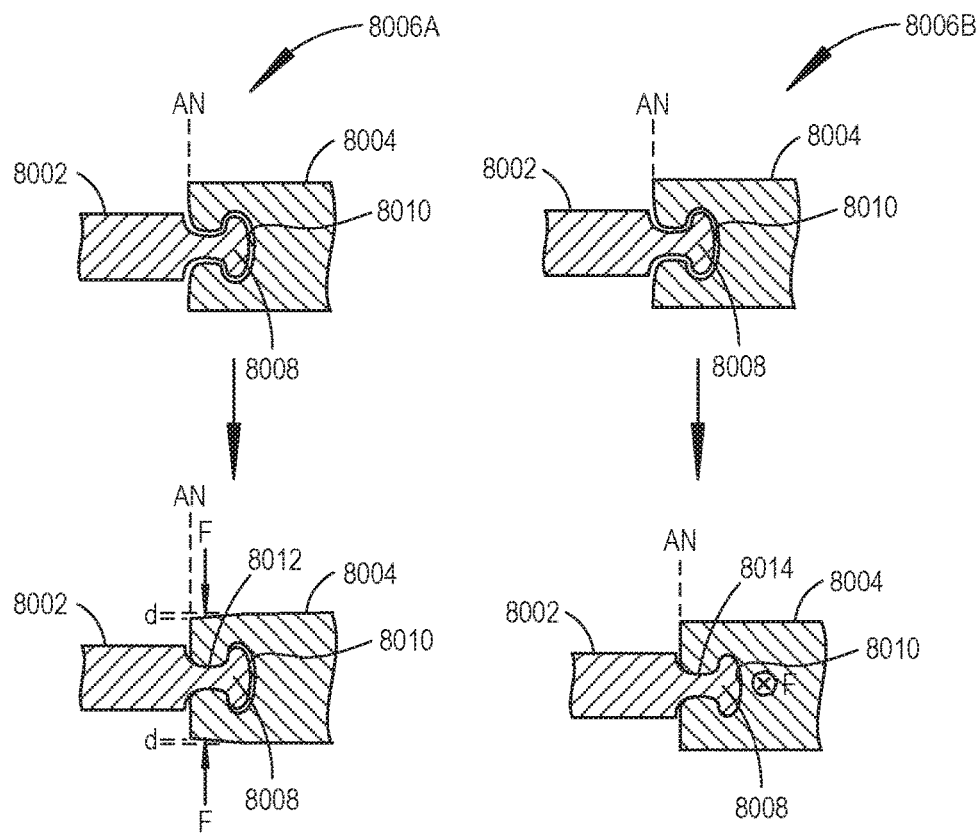

FIG. 134A is a section view of a jigsaw puzzle joint of the waveguide and transducer base plate components of the ultrasonic surgical instrument, according to one aspect of this disclosure.

FIG. 134B is a section view of a jigsaw puzzle joint of the waveguide and transducer base plate components of the ultrasonic surgical instrument, according to one aspect of this disclosure.

FIG. 135 is a side view of an ultrasonic surgical instrument configured in a D31 transducer architecture comprising separate ultrasonic waveguide and ultrasonic transducer base plate components shown in a decoupled configuration, according to one aspect of this disclosure.

FIG. 136 is an end view of the waveguide shown in FIG. 135, according to one aspect of this disclosure.

FIG. 137 is an end view of the transducer base plate shown in FIG. 135, according to one aspect of this disclosure.

Figure 138:
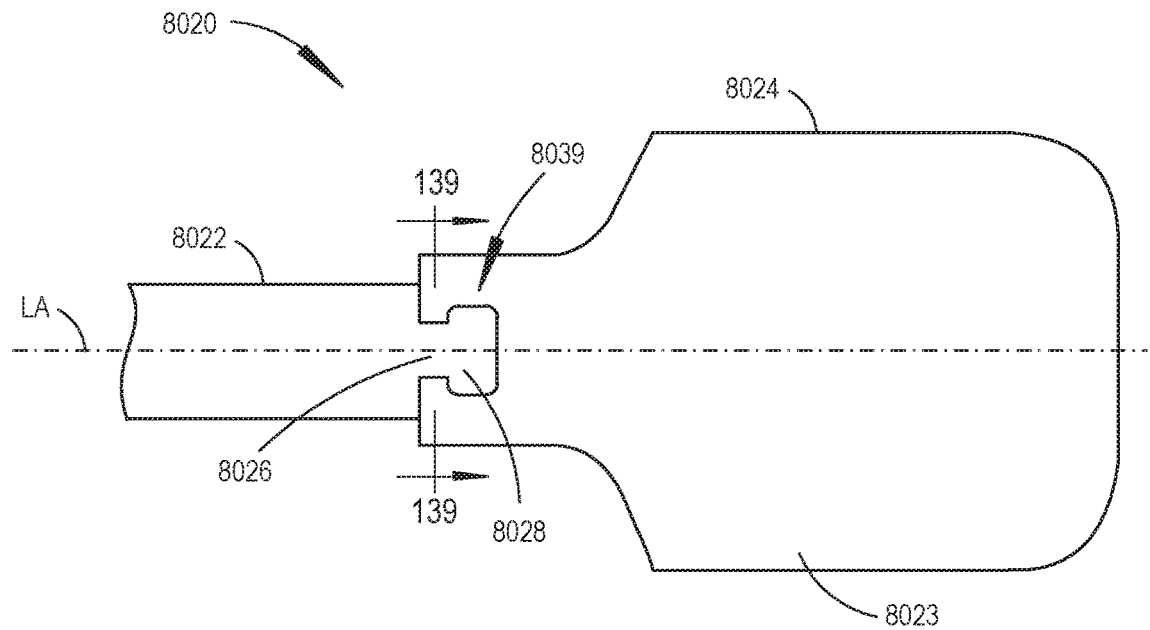

FIG. 138 is a side view of the ultrasonic instrument shown in FIG. 135 in a coupled configuration connected at the tapered joint, according to one aspect of this disclosure.

Figures 139A, 139B:
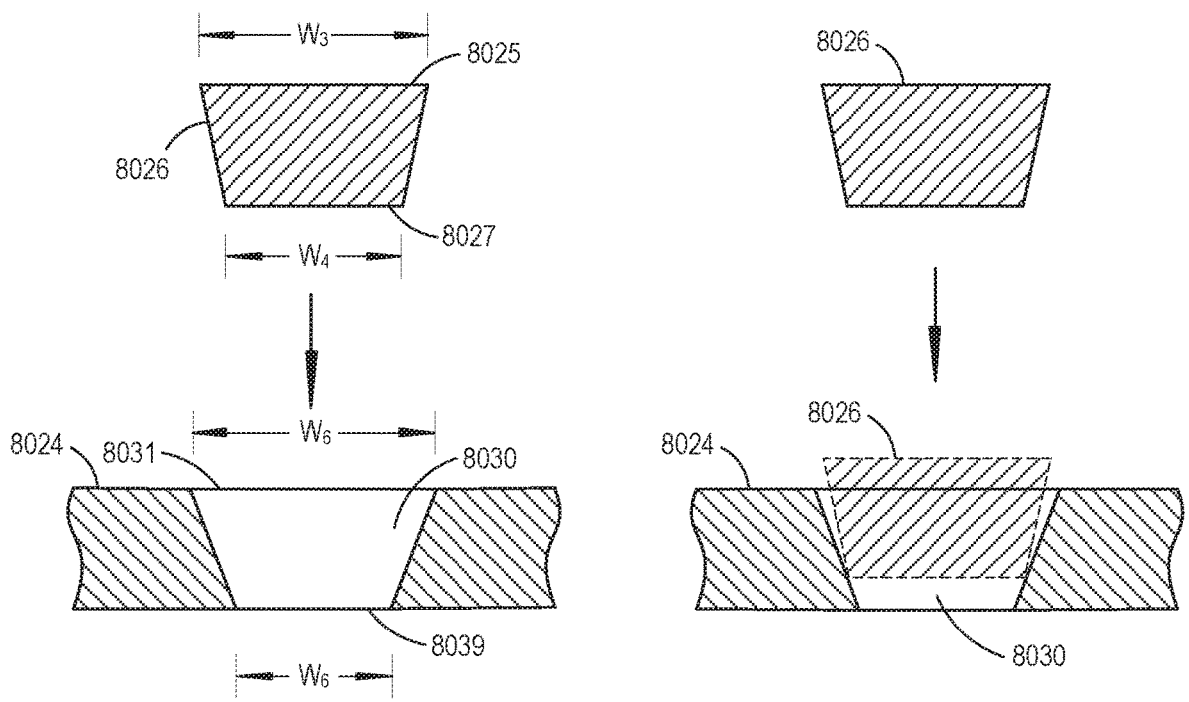

FIGS. 139A and 139B are section views taken along section line 139-139 shown in FIG. 138, where FIG. 139A is a section view taken prior to joining the waveguide to the transducer base plate and FIG. 139B is a section view taken after partially joining the waveguide to the transducer base plate.

FIG. 140 is a side view of an ultrasonic surgical instrument configured in a D31 transducer architecture comprising separate ultrasonic waveguide and ultrasonic transducer base plate components shown in a coupled configuration, according to one aspect of this disclosure.

FIG. 141 is a section view of the ultrasonic surgical instrument shown in FIG. 140 taken along section line 141-141 shown in FIG. 140, according to one aspect of this disclosure.

Figure 142:
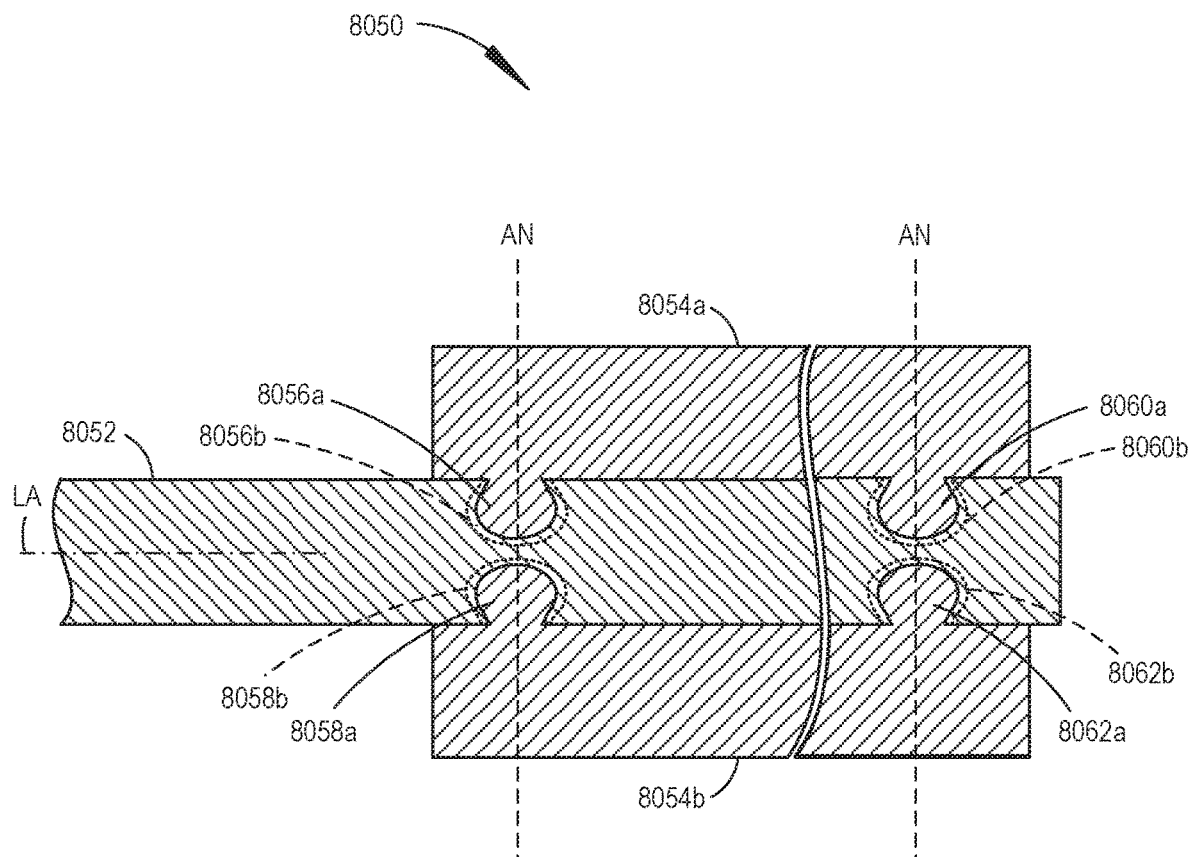

FIG. 142 is a section view of an ultrasonic surgical instrument configured in a D31 transducer architecture comprising multiple plates coupled by a thermal expansion joint, according to one aspect of this disclosure.

Figure 143:
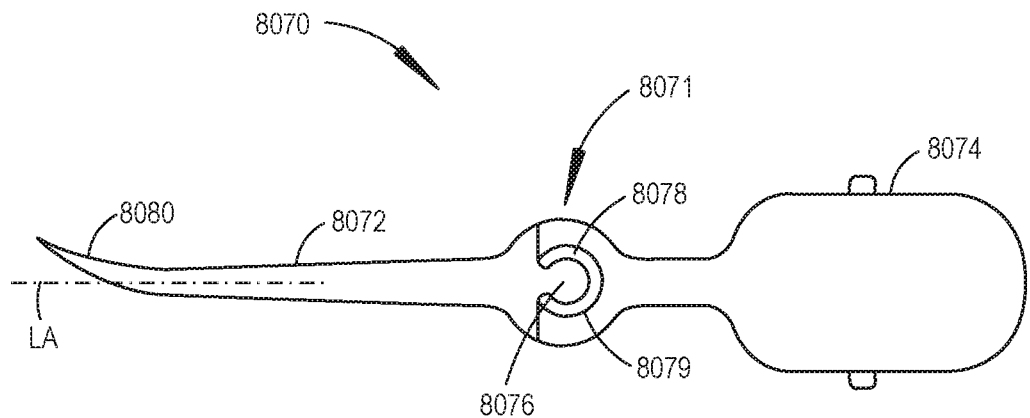

FIG. 143 is side view of an ultrasonic surgical instrument configured in a D31 transducer architecture comprising separate ultrasonic waveguide and ultrasonic transducer base plate shown in a coupled configuration, according to one aspect of this disclosure.

Figure 144:
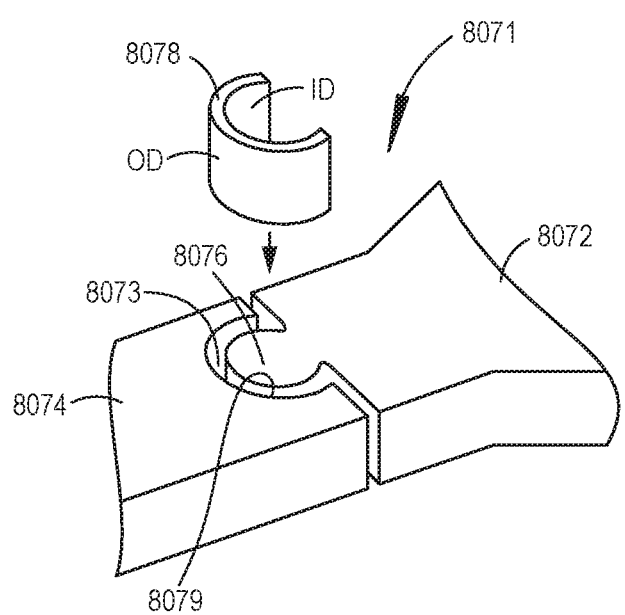

FIG. 144 is an exploded view of the C-shaped pin joint shown in FIG. 143, according to one aspect of this disclosure.

Figure 145:
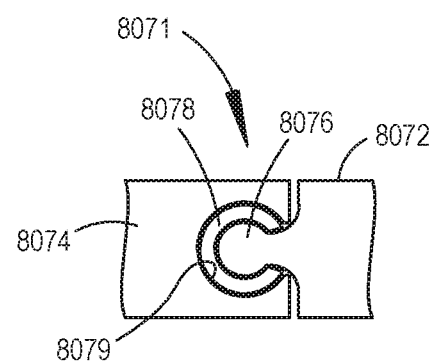

FIG. 145 is a plan view of the C-shaped pin joint shown in FIG. 143, according to one aspect of this disclosure.

FIG. 146 is a side view of an ultrasonic surgical instrument configured in a D31 transducer architecture comprising separate ultrasonic waveguide and ultrasonic transducer base plate components shown in a coupled configuration, according to one aspect of this disclosure.

FIG. 147 is a section view of the ultrasonic surgical instrument along section line 147-147 shown in FIG. 146, according to one aspect of this disclosure.

Figure 148:
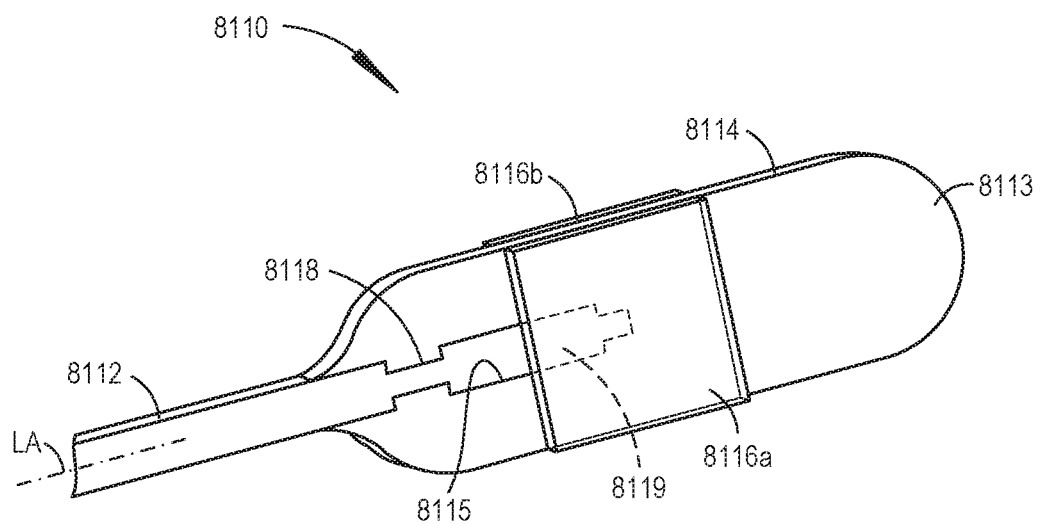

FIG. 148 is a perspective view an ultrasonic surgical instrument configured in a D31 transducer architecture comprising separate ultrasonic waveguide and ultrasonic transducer base plate components shown in a coupled configuration, according to one aspect of this disclosure.

Figure 149:
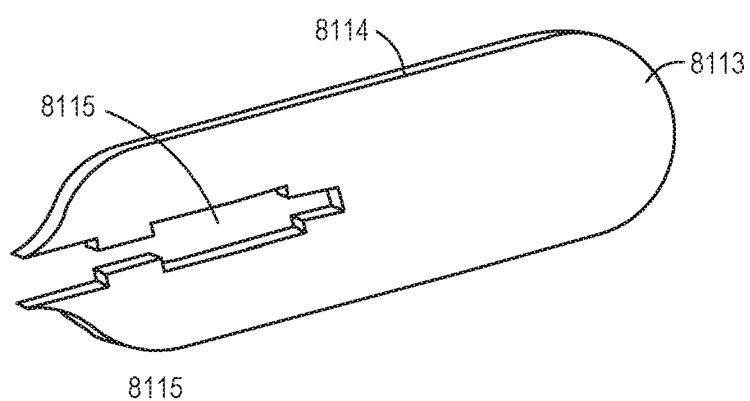

FIG. 149 is a perspective view the ultrasonic surgical instrument shown in FIG. 148 with the waveguide and the piezoelectric elements removed to show the cutout configured to receive a proximal portion of the waveguide, according to one aspect of this disclosure.

Figure 150:
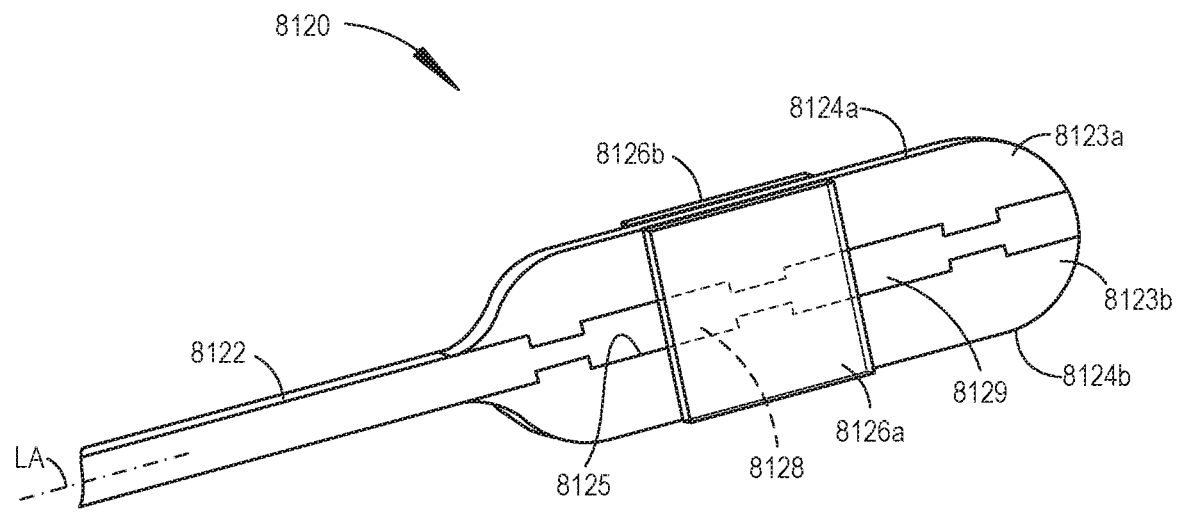

FIG. 150 is a perspective view of an ultrasonic surgical instrument configured in a D31 transducer architecture comprising ultrasonic waveguide and ultrasonic transducer base plate components shown in a coupled configuration, according to one aspect of this disclosure.

Figure 151:
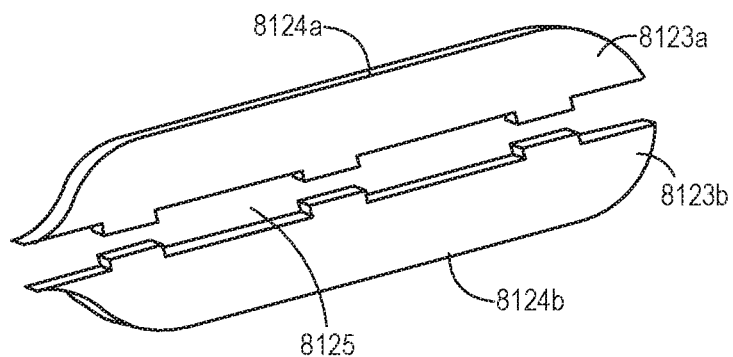

FIG. 151 is a perspective view of the ultrasonic surgical instrument shown in FIG. 150 with the waveguide and the piezoelectric elements removed to show the cutout configured to receive a proximal portion of the waveguide, according to one aspect of this disclosure.

Figure 152:
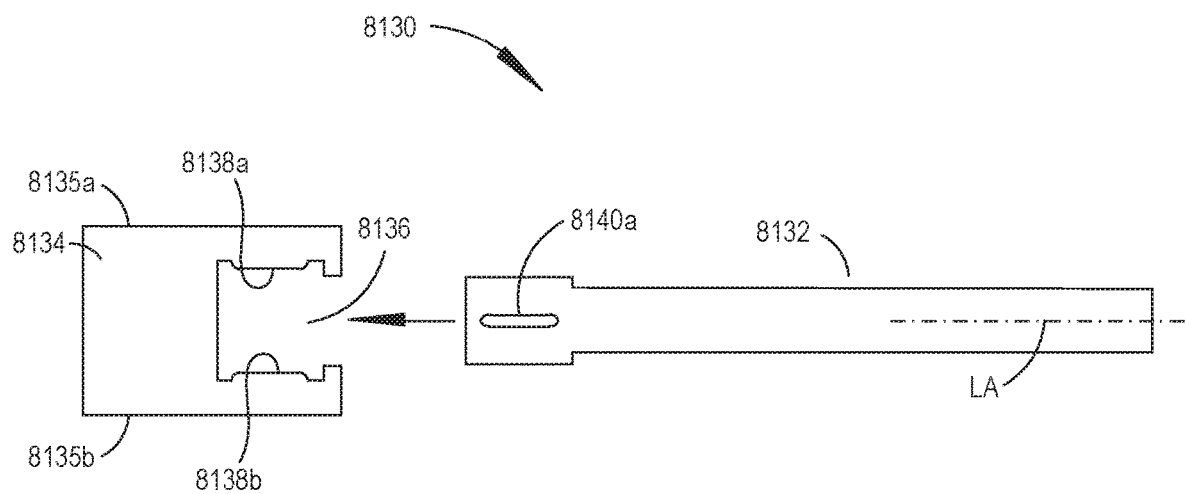

FIG. 152 is a side view of an ultrasonic surgical instrument configured in a D31 transducer architecture comprising separate ultrasonic waveguide and ultrasonic transducer base plate components shown in a decoupled configuration, according to one aspect of this disclosure.

Figure 153:
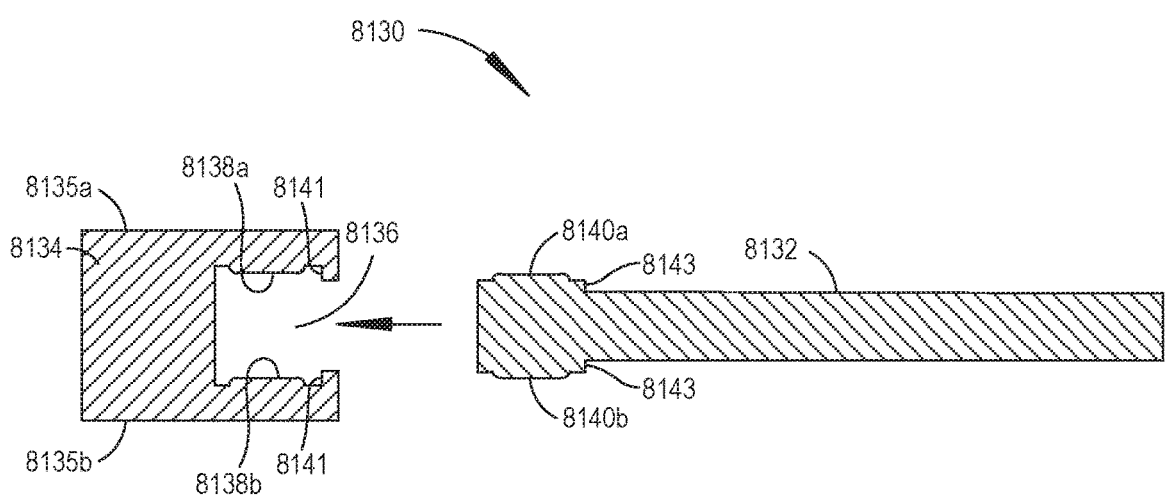

FIG. 153 is a section view of the ultrasonic surgical instrument shown in FIG. 152 with the ultrasonic waveguide rotated 90° in a decoupled configuration, according to one aspect of this disclosure.

Figure 154:
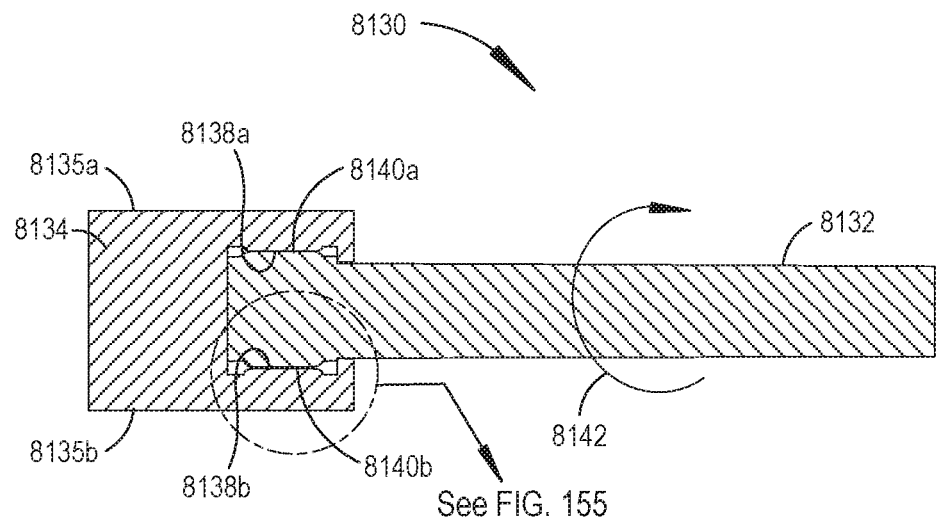

FIG. 154 is a section view of the ultrasonic surgical instrument shown in FIG. 152 with the ultrasonic waveguide rotated 90° in a coupled configuration, according to one aspect of this disclosure.

Figure 155:
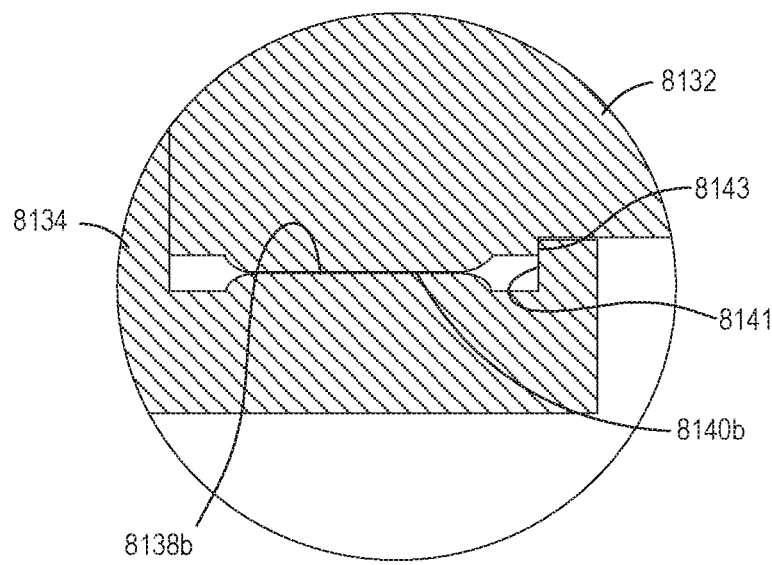

FIG. 155 is detail view of the joint between the waveguide and the transducer base plate, according to one aspect of this disclosure.

Figure 156:
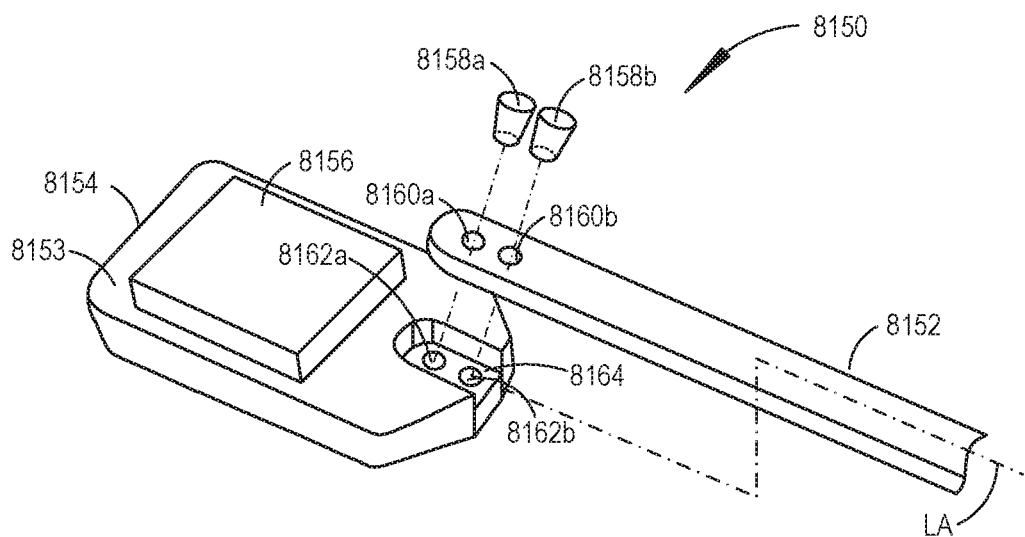

FIG. 156 is a perspective view of an ultrasonic surgical instrument configured in a D31 transducer architecture comprising separate ultrasonic waveguide and ultrasonic transducer base plate components shown in a decoupled configuration, according to one aspect of this disclosure.

Figure 157:
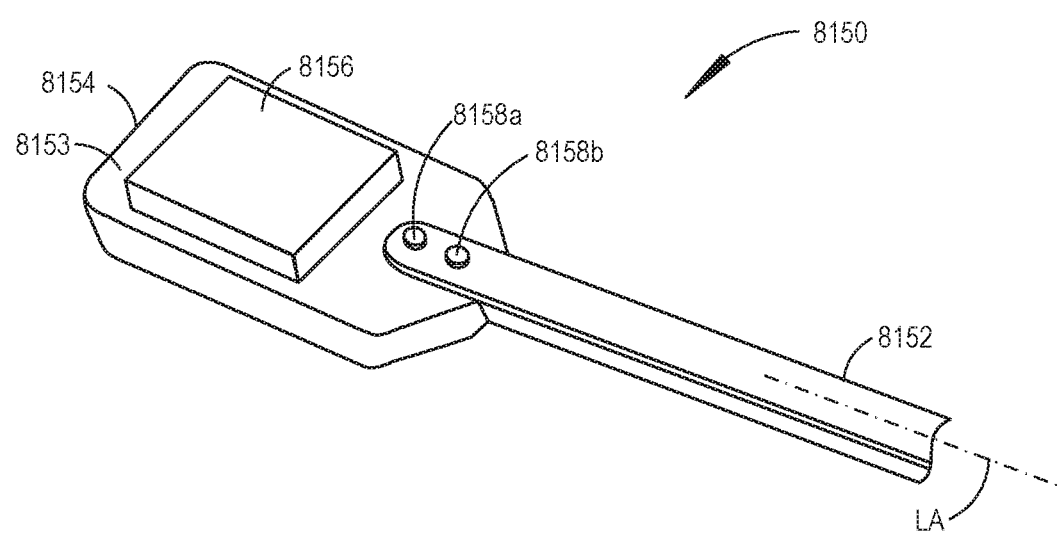

FIG. 157 is a perspective view of the ultrasonic surgical instrument shown in FIG. 156 in a coupled configuration, according to one aspect of this disclosure.

Figure 158:
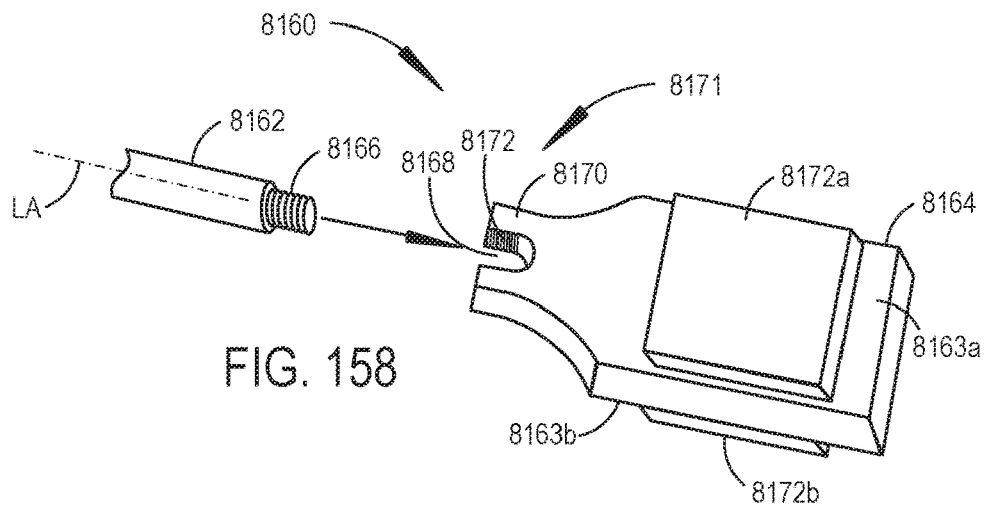

FIG. 158 is a perspective view of an ultrasonic surgical instrument configured in a D31 transducer architecture comprising separate ultrasonic waveguide and ultrasonic transducer base plate components shown in a decoupled configuration, according to one aspect of this disclosure.

Figure 159:
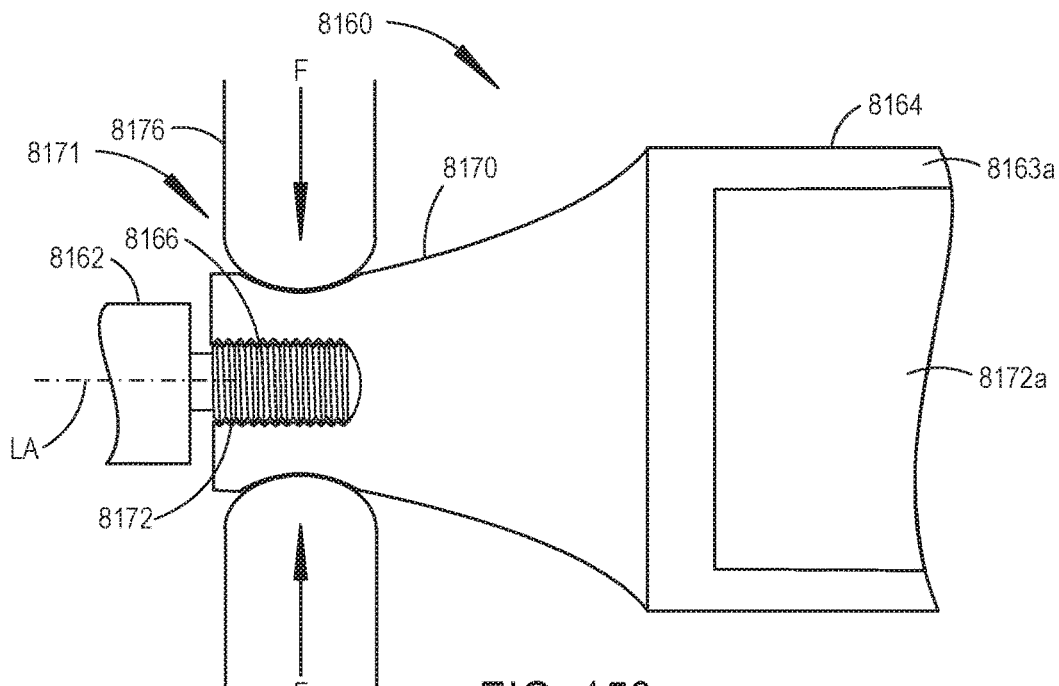

FIG. 159 is a side view of the threaded joint showing the threaded section of the waveguide threaded into the threaded section of the transducer base plate, according to one aspect of this disclosure.

Figure 160:
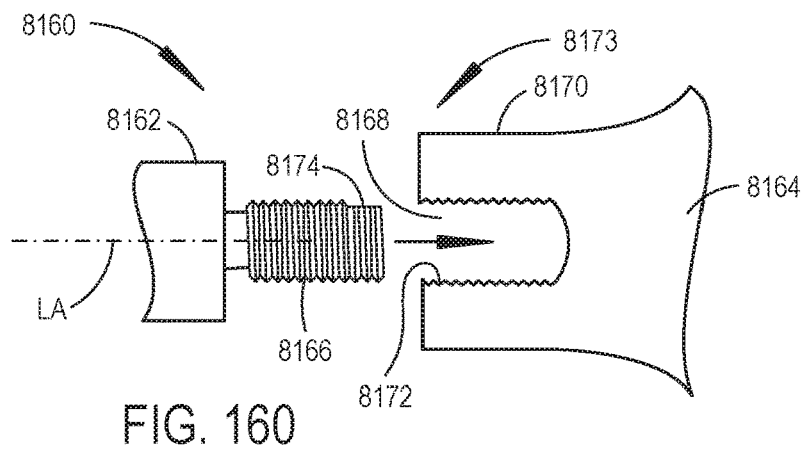

FIG. 160 is a side view of an alternate threaded joint where the threaded section includes a rotational orientation section to provide rotary alignment about the longitudinal axis LA of the threaded section of the waveguide, according to one aspect of this disclosure.

Figure 161:
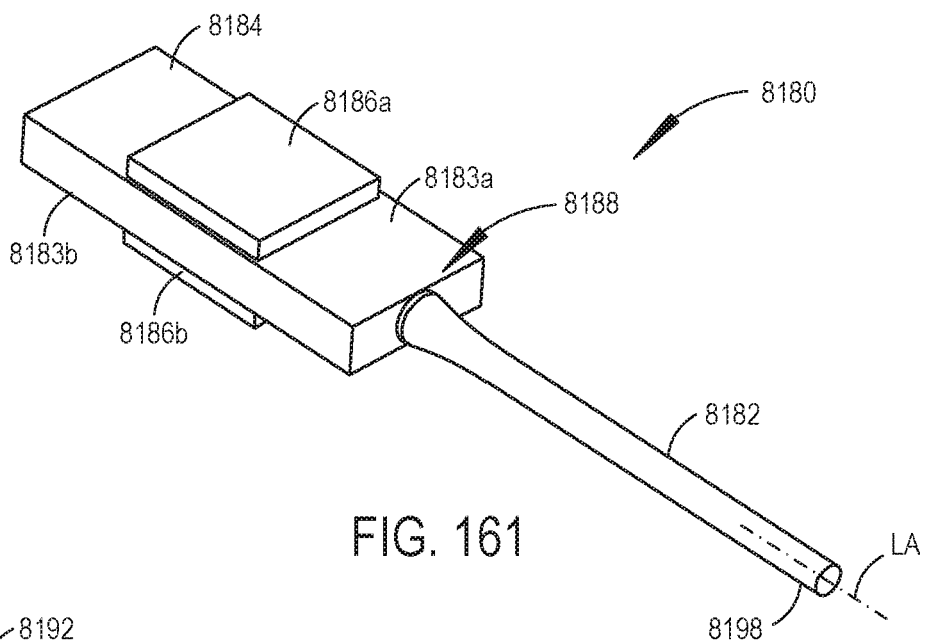

FIG. 161 is a perspective view of an ultrasonic surgical instrument configured in a D31 transducer architecture comprising separate ultrasonic waveguide and ultrasonic transducer base plate components shown in a coupled configuration, according to one aspect of this disclosure.

Figure 162:
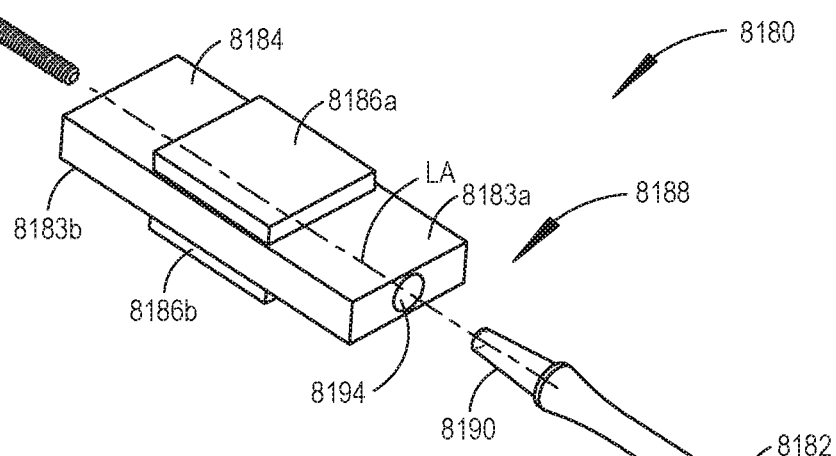

FIG. 162 is an exploded view of the ultrasonic surgical instrument shown in FIG. 161, according to one aspect of this disclosure.

Figure 163:
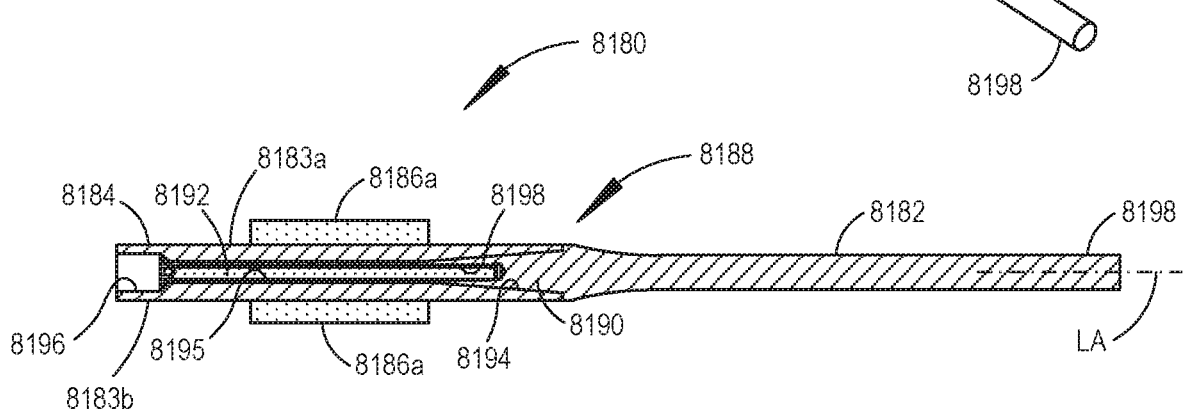

FIG. 163 is a section view of the ultrasonic surgical instrument shown in FIG. 161, according to one aspect of this disclosure.

Figure 164:
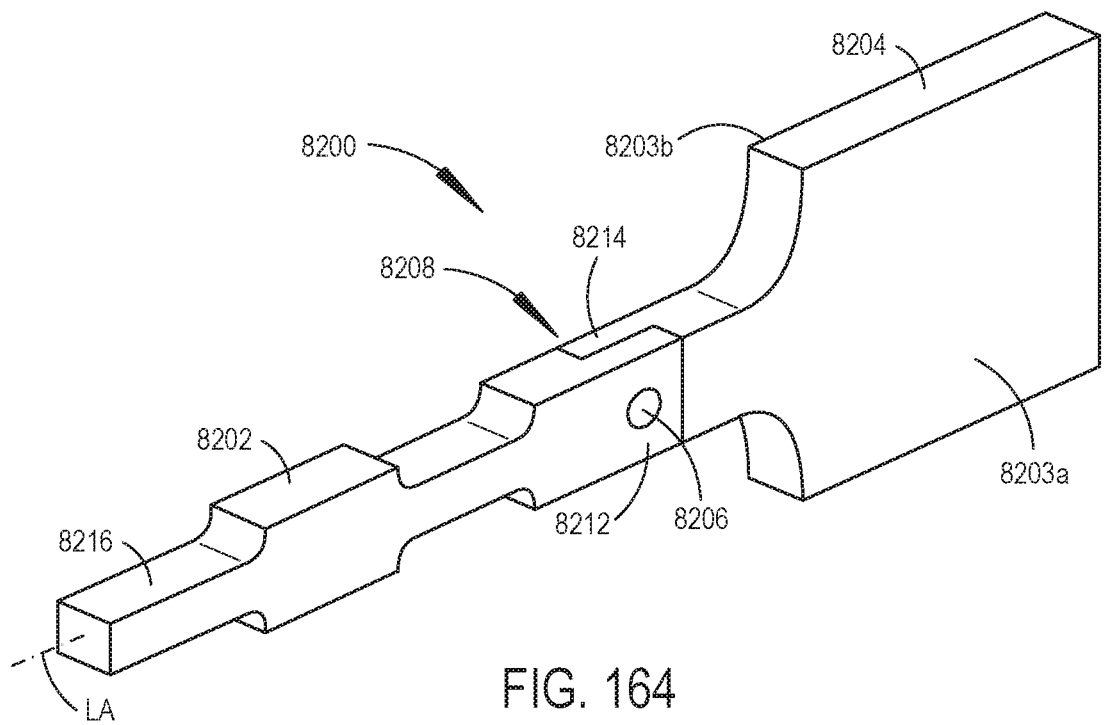

FIG. 164 is a perspective view of an ultrasonic surgical instrument configured in a D31 transducer architecture comprising separate ultrasonic waveguide and ultrasonic transducer base plate components shown in a coupled configuration, according to one aspect of this disclosure.

Figure 165:
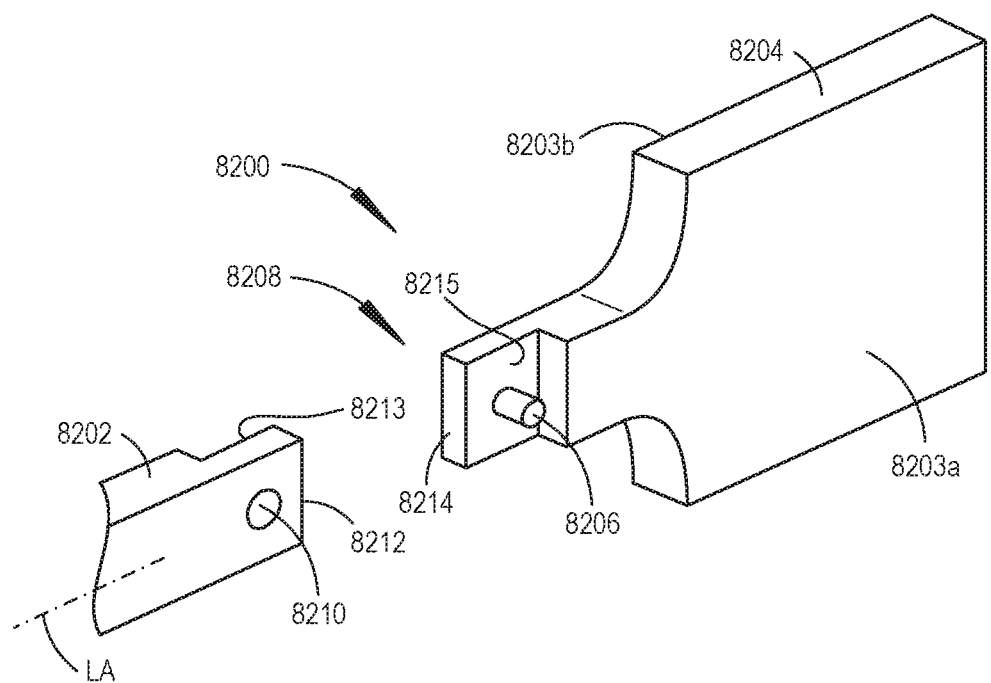

FIG. 165 is an exploded view of the ultrasonic surgical instrument shown in FIG. 164, according to one aspect of this disclosure.

Figure 166:
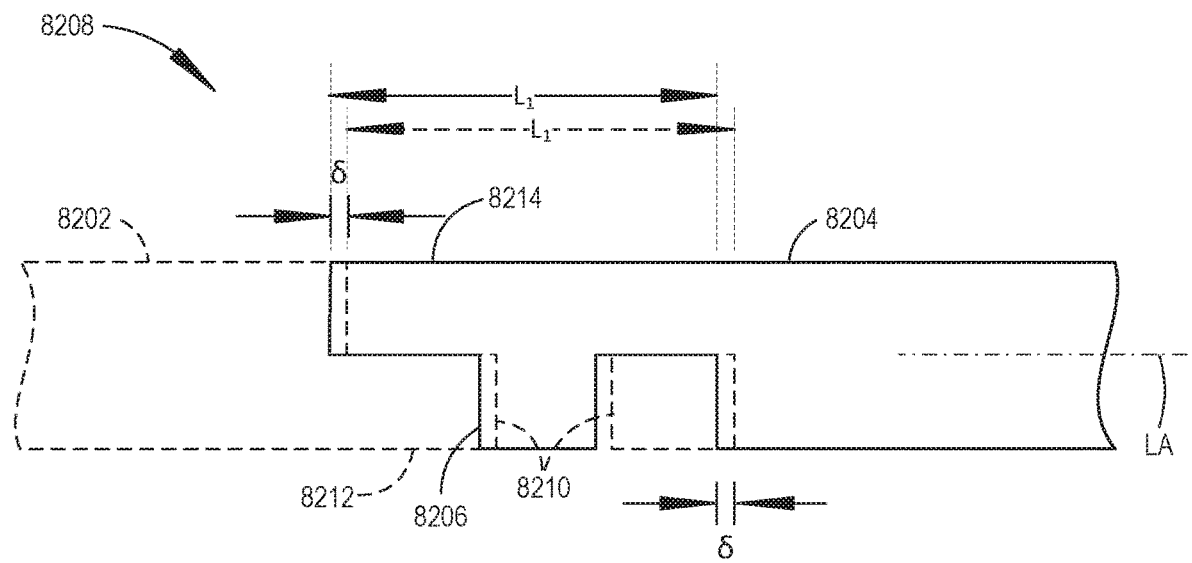

FIG. 166 illustrates the waveguide flange, shown in dashed line form, and the transducer base plate flange, shown in solid line form, superimposed in a decoupled configuration, according to one aspect of this disclosure.

Figure 167:
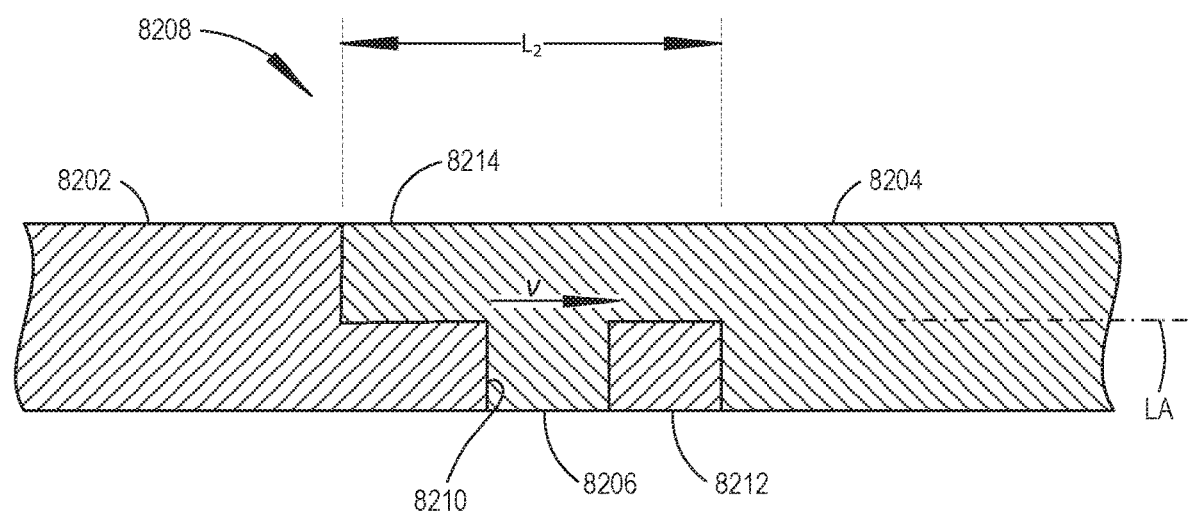

FIG. 167 illustrates the waveguide and the transducer base plate in a coupled configuration, according to one aspect of this disclosure.

Figure 168:
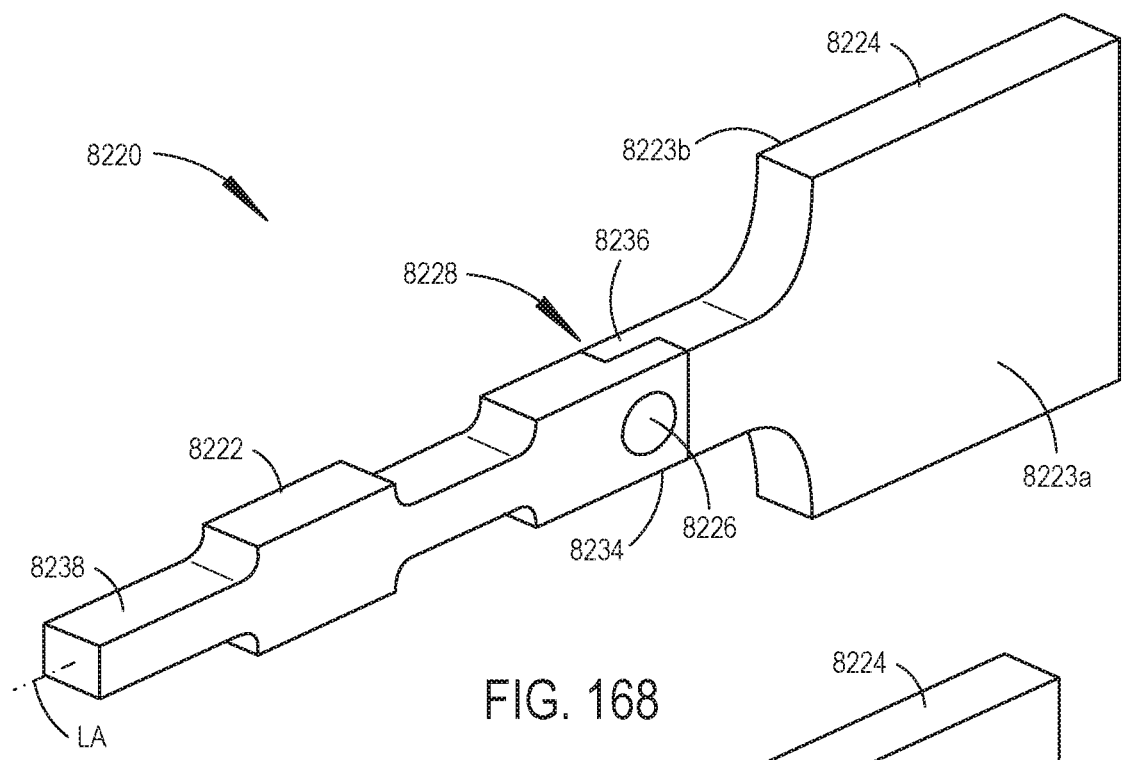

FIG. 168 is a perspective view of an ultrasonic surgical instrument configured in a D31 transducer architecture comprising separate ultrasonic waveguide and ultrasonic transducer base plate components shown in a coupled configuration, according to one aspect of this disclosure.

Figure 169:
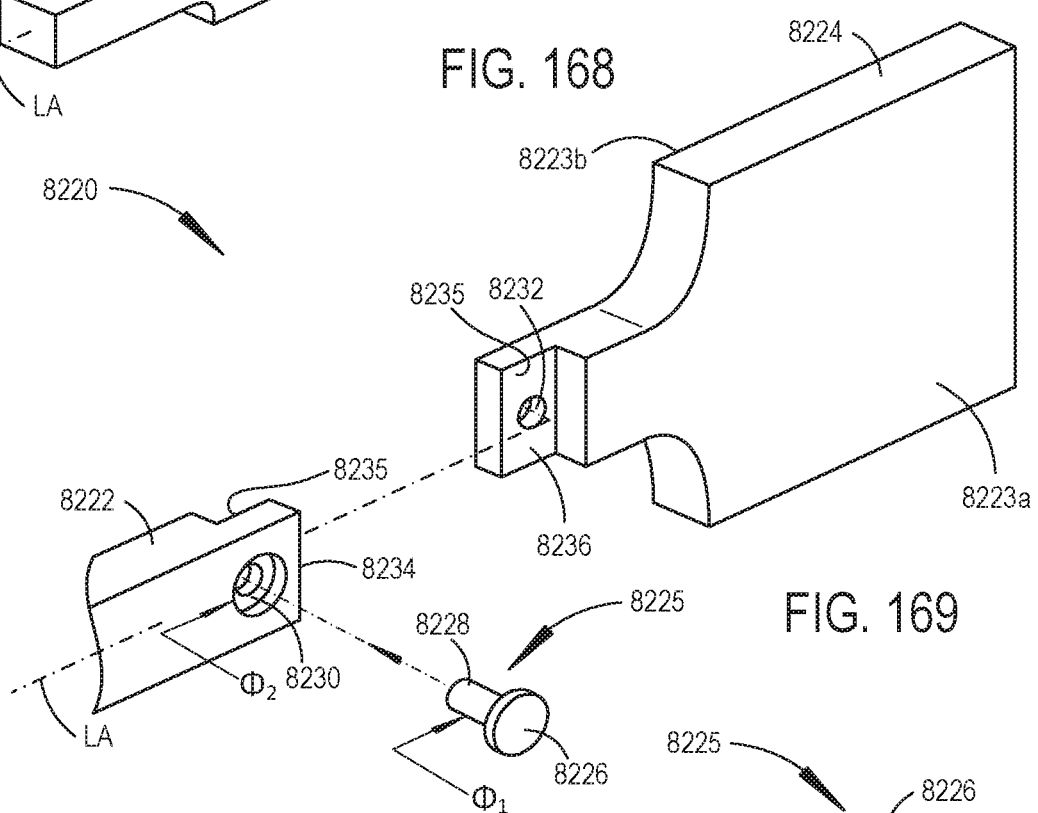

FIG. 169 is an exploded view of the ultrasonic surgical instrument shown in FIG. 168, according to one aspect of this disclosure.

Figure 170:
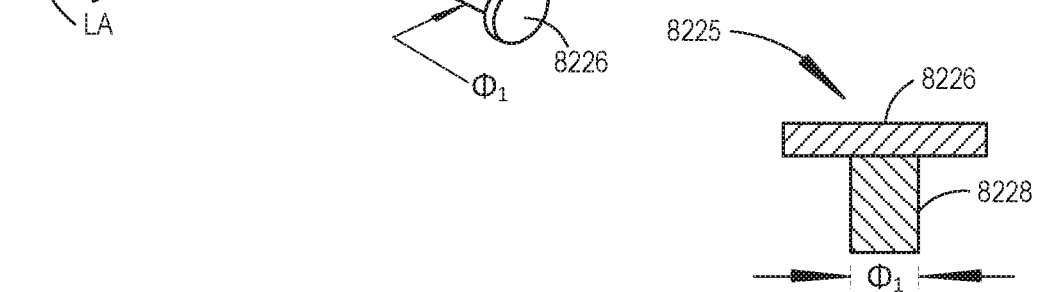

FIG. 170 is a section view of a pin, according to one aspect of this disclosure.

Figure 171:
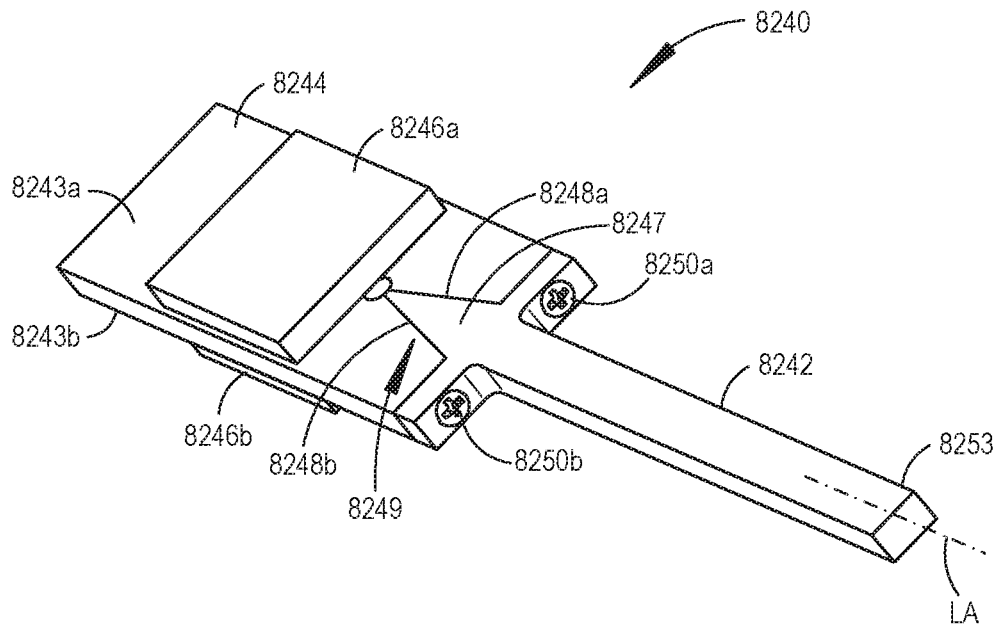

FIG. 171 is a perspective view of an ultrasonic surgical instrument configured in a D31 transducer architecture comprising separate ultrasonic waveguide and ultrasonic transducer base plate components shown in a coupled configuration, according to one aspect of this disclosure.

Figure 172:
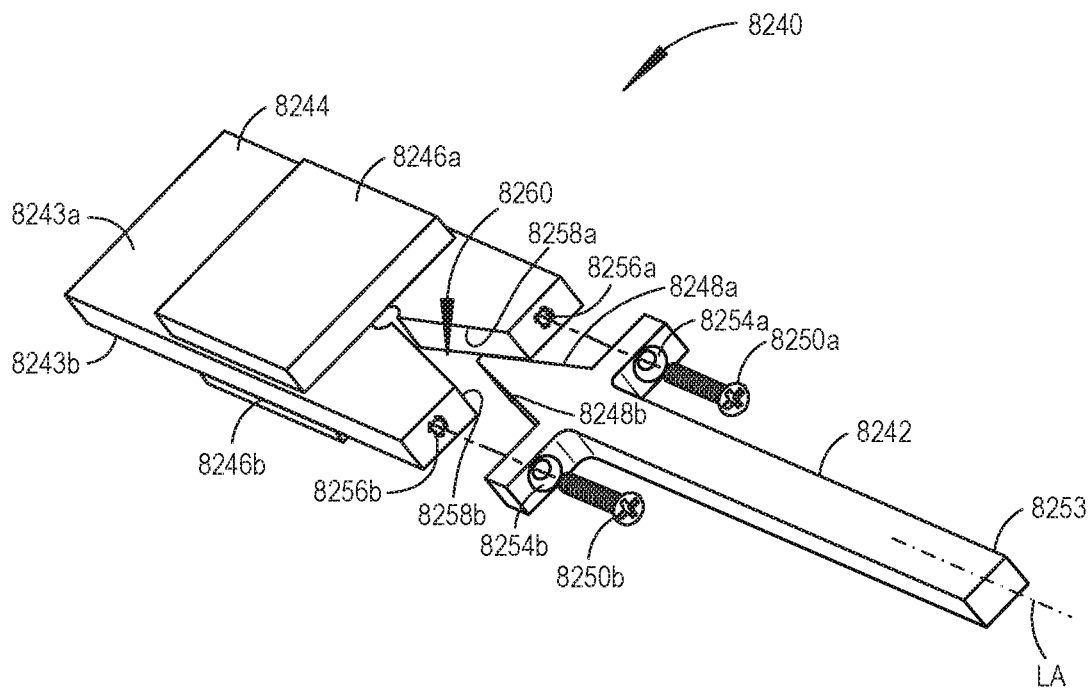

FIG. 172 is an exploded view of the ultrasonic surgical instrument shown in FIG. 171, according to one aspect of this disclosure.

FIG. 173 is a perspective view of a luer lock joint suitable for coupling ultrasonic waveguide and ultrasonic transducer base plate components of a two-piece ultrasonic surgical instrument, according to one aspect of this disclosure.

FIG. 174 is a section view of the luer lock joint in a coupled configuration, according to one aspect of this disclosure.

FIG. 175 is a luer nut component of the luer lock joint shown in FIG. 173, according to one aspect of this disclosure.

FIG. 176 is perspective view of the luer lock joint shown in FIG. 173 in a coupled configuration, according to one aspect of this disclosure.

Figures 177, 178:
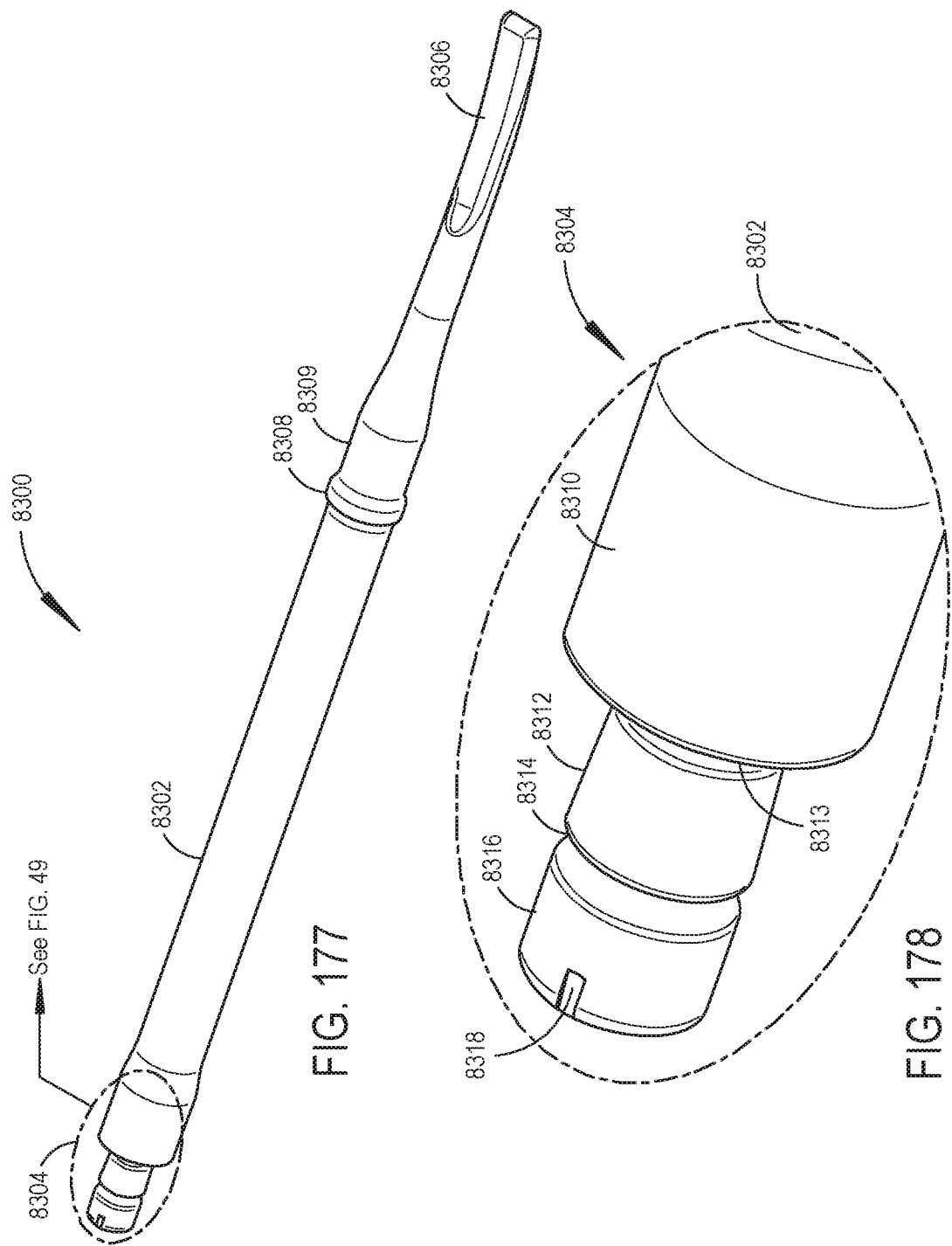

FIG. 177 is a perspective view of an ultrasonic waveguide for an ultrasonic surgical instrument comprising an ultrasonic waveguide shaft made of one metal and coupled to an ultrasonic blade made of a dissimilar metal, according to aspect of this disclosure.

FIG. 178 is a magnified view of the coupler, according to one aspect of this disclosure.

Figure 179:
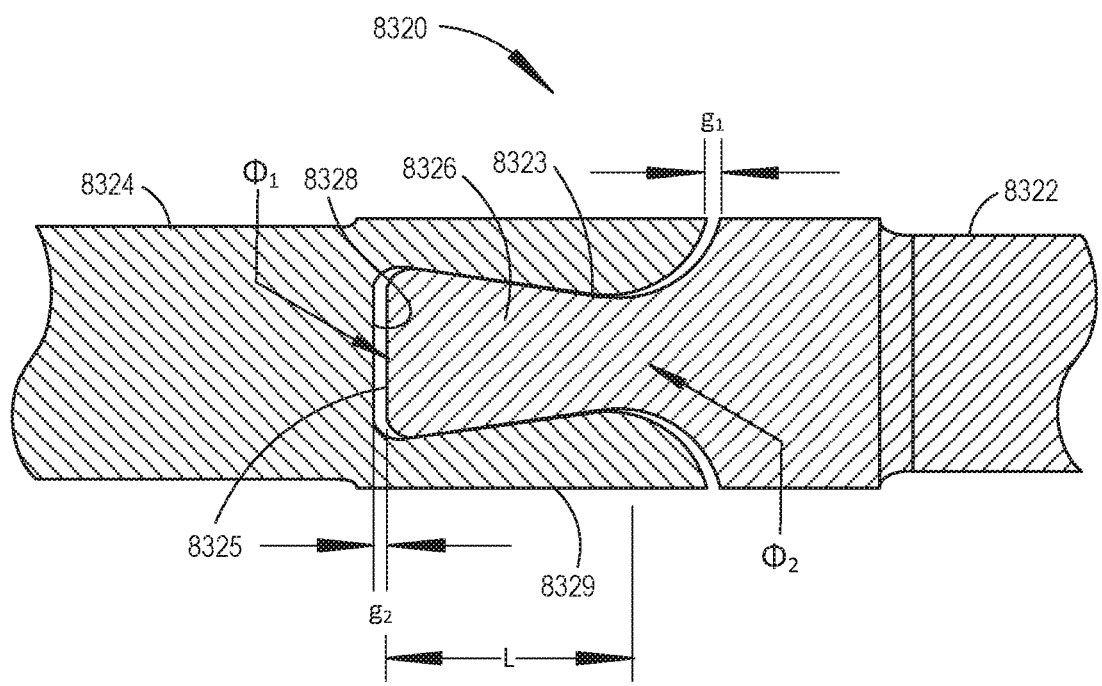

FIG. 179 is a section view of a swaged joint between a two-piece ultrasonic tool comprising an ultrasonic waveguide shaft made of one metal and an ultrasonic blade made of a different metal, according to one aspect of his disclosure.

Figure 180:
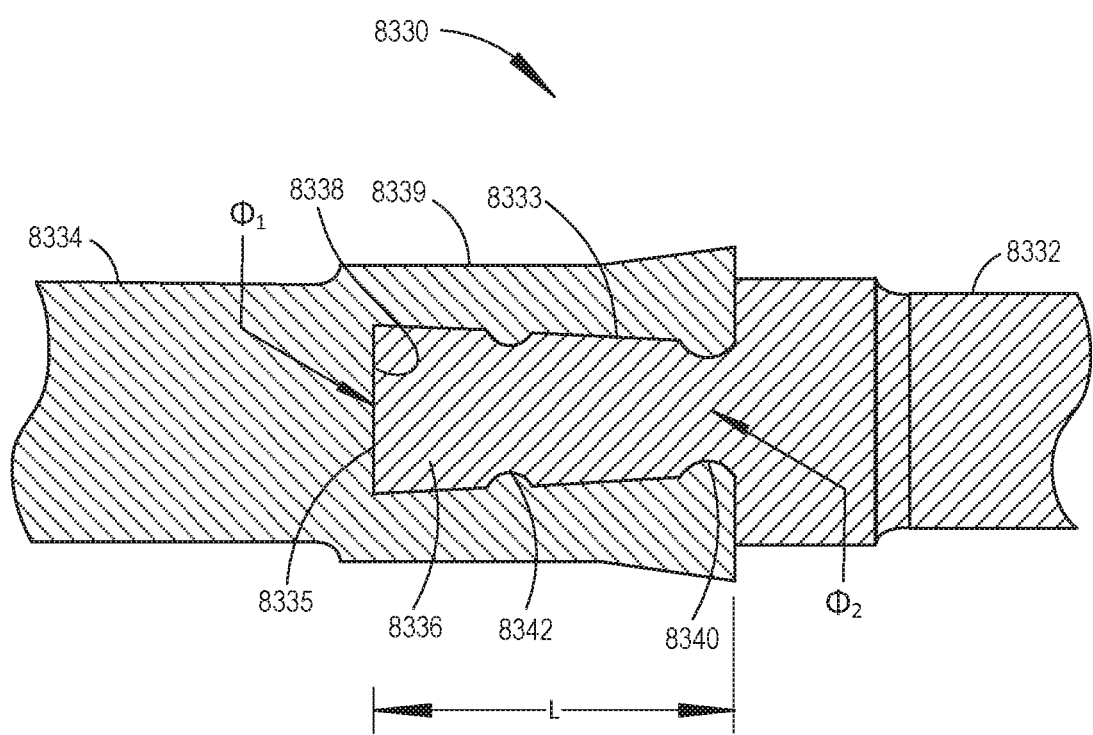

FIG. 180 is a section view of a swaged joint achieved between a two-piece ultrasonic waveguide comprising an ultrasonic waveguide shaft made of one metal and an ultrasonic blade made of a different metal, according to one aspect of his disclosure.

FIGS. 181-184 show the steps for producing the swaged joint shown in FIG. 180, according to one aspect of this disclosure.

Figure 181:
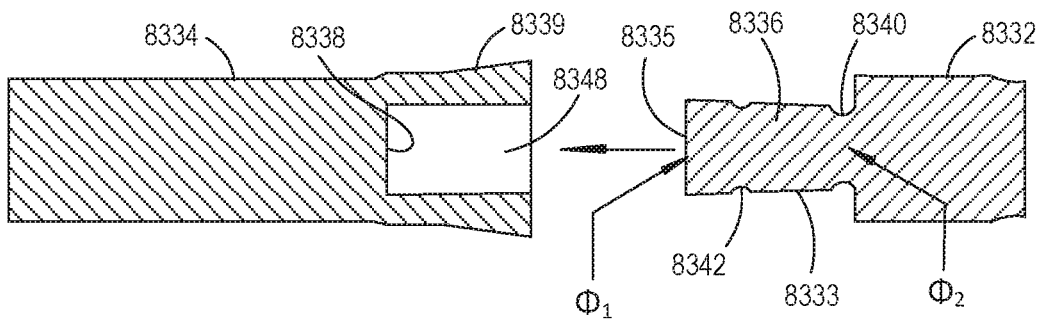

FIG. 181 a section view of the waveguide shaft and the ultrasonic blade shown in FIG. 180 a decoupled configuration, according to one aspect of this disclosure.

Figure 182:
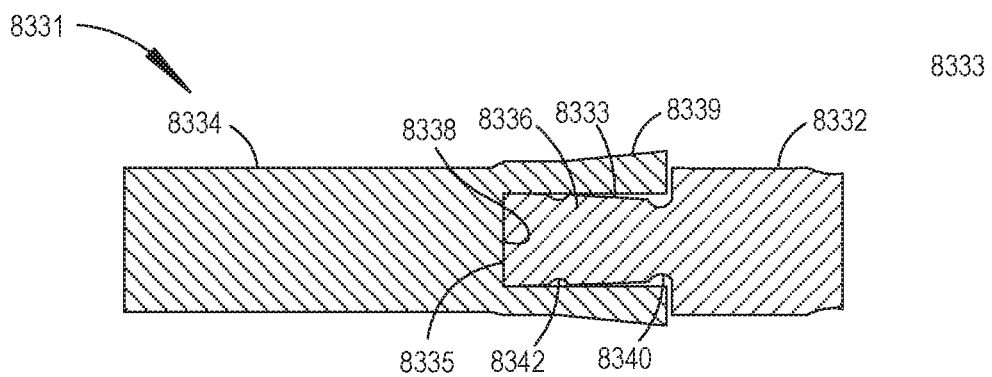

FIG. 182 a section view of a pre-assembly of the waveguide shaft and the ultrasonic blade shown in FIG. 18 in a coupled configuration prior to applying the swaging process, according to one aspect of this disclosure.

Figure 183:
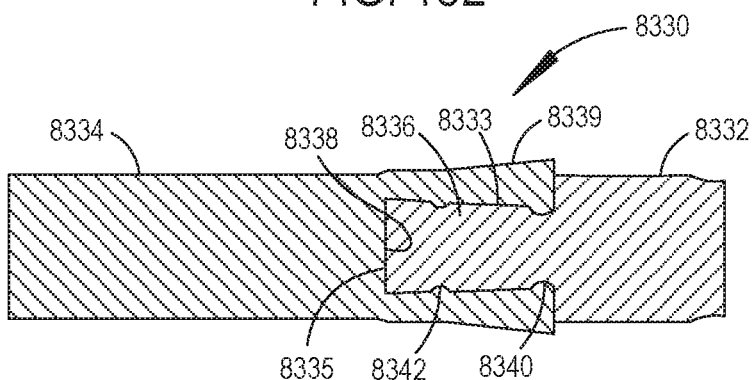

FIG. 183 a section view of the waveguide shaft and the ultrasonic blade shown in FIG. 182 a coupled after the application of the swaging process, according to one aspect of this disclosure.

Figure 184:
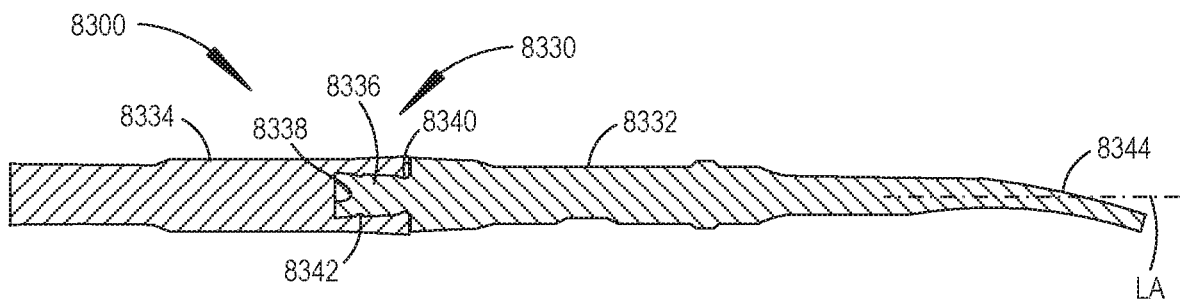

FIG. 184 is a section view of joined ultrasonic waveguide showing the waveguide shaft coupled to the ultrasonic blade shown in FIG. 180, according to one aspect of this disclosure.

Figure 185:
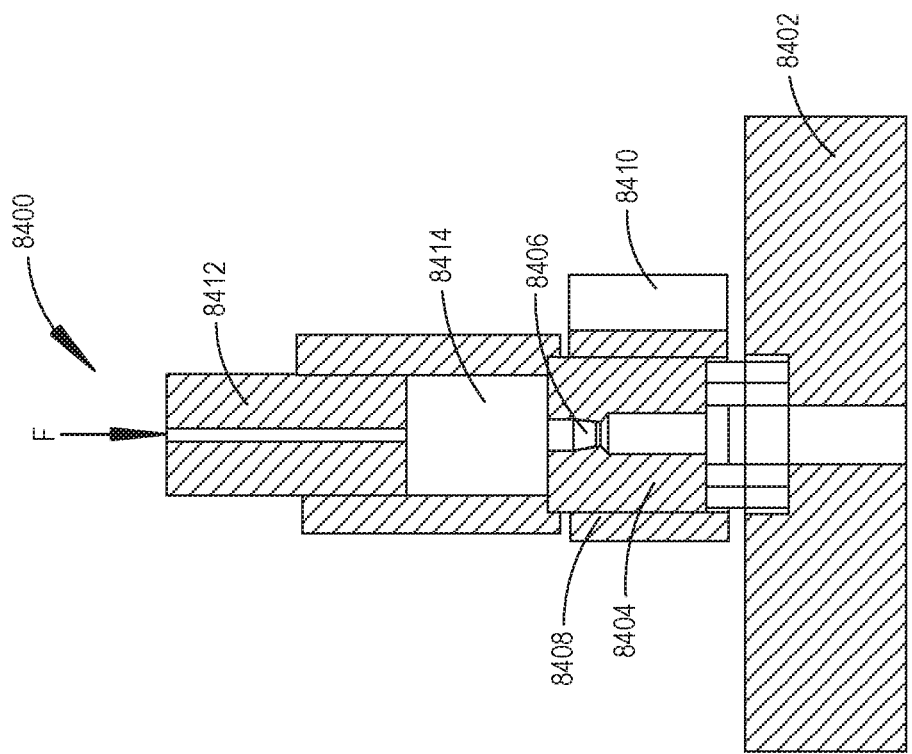

FIG. 185 is a section view of a heated draw die tool, according to one aspect of this disclosure.

Figure 186:
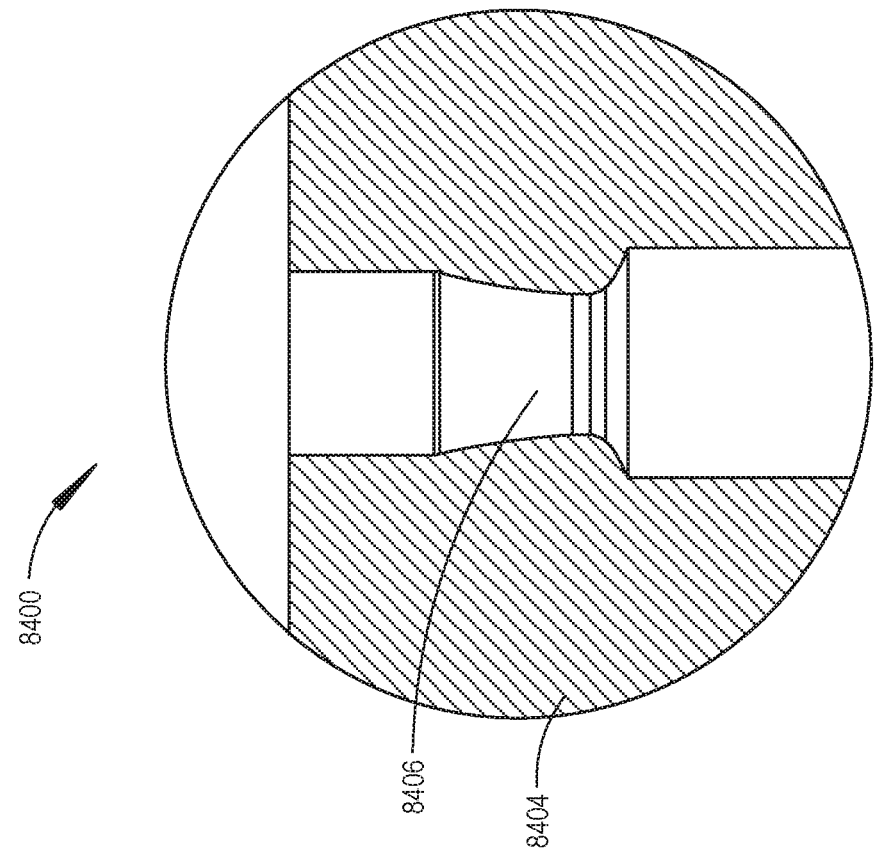

FIG. 186 is a detail section view of the draw die tool shown in FIG. 185, according to one aspect of this disclosure.

Figure 187:
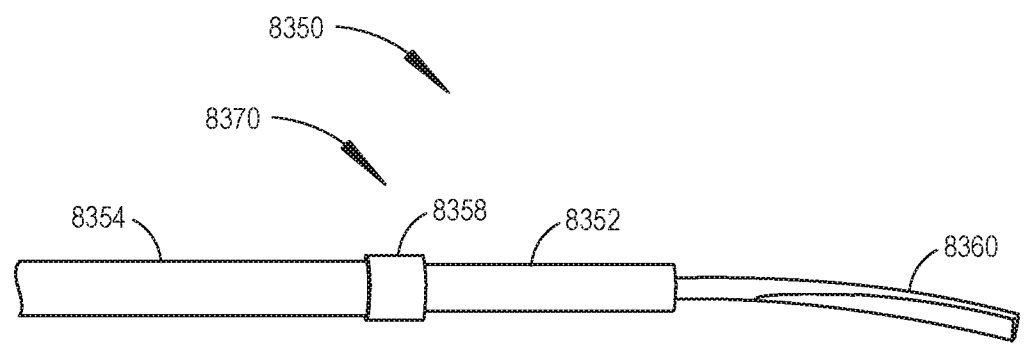

FIG. 187 is a side view of a two-piece ultrasonic waveguide comprising a waveguide shaft coupled to an ultrasonic blade by a swaged joint using the swaging process described in connection with FIGS. 177-186, according to one aspect of this disclosure.

Figure 188:
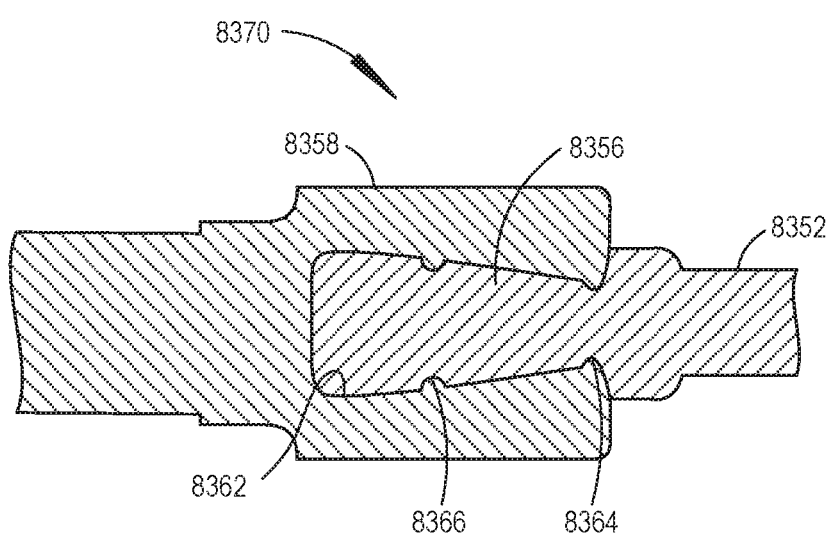

FIG. 188 is a section view of the swaged joint formed between the waveguide shaft and the ultrasonic blade, according to one aspect of this disclosure.

Figure 189:

FIG. 189 is a side view of the waveguide shaft shown in FIG. 188, according to one aspect of this disclosure.

Figure 190:
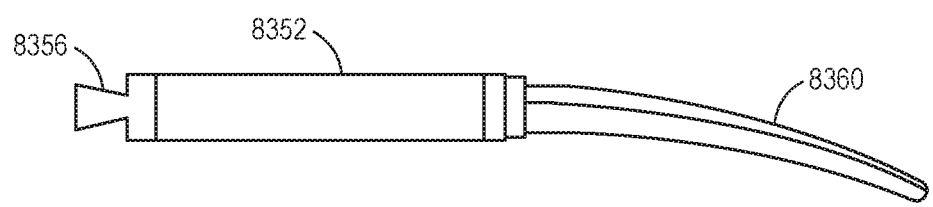

FIG. 190 is a side view of the ultrasonic blade is shown in FIG. 188, according to one aspect of this disclosure.

Figure 191:
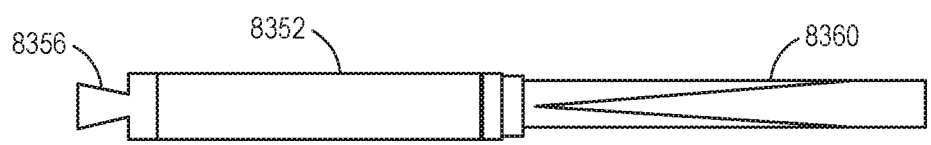

FIG. 191 is a plan view of the ultrasonic blade shown in FIG. 188, according to one aspect of this disclosure.

Figure 192:
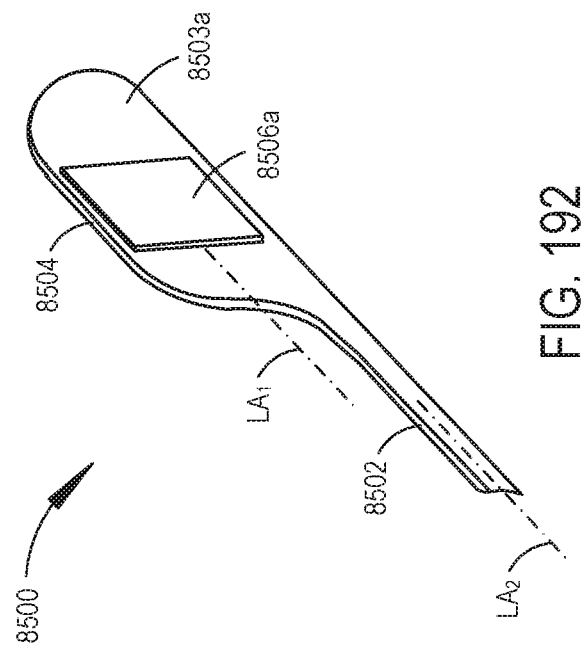

FIG. 192 illustrates an ultrasonic surgical instrument comprising an ultrasonic waveguide coupled to an offset ultrasonic transducer baseplate, according to one aspect of this disclosure.

Figure 193:
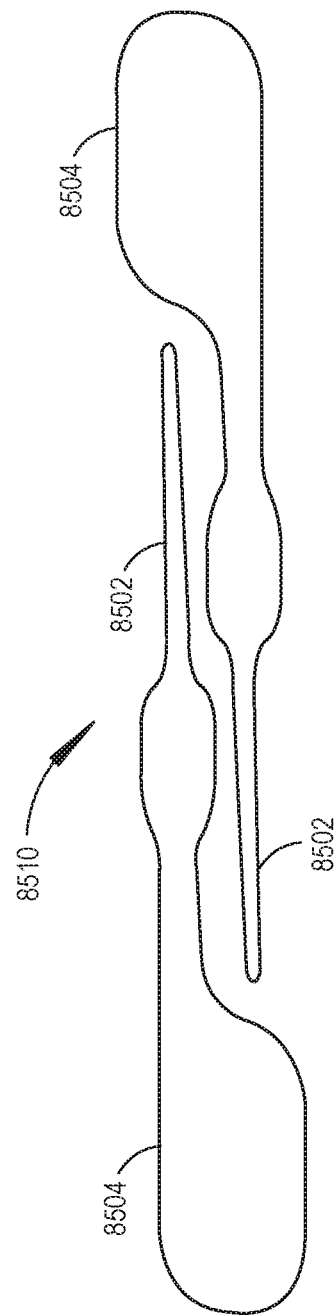

FIG. 193 illustrates two metal substrates components of the ultrasonic surgical instrument shown in FIG. 192 arranged in a complementary orientation for stamping or punching, according to one aspect of this disclosure.

Figure 194:
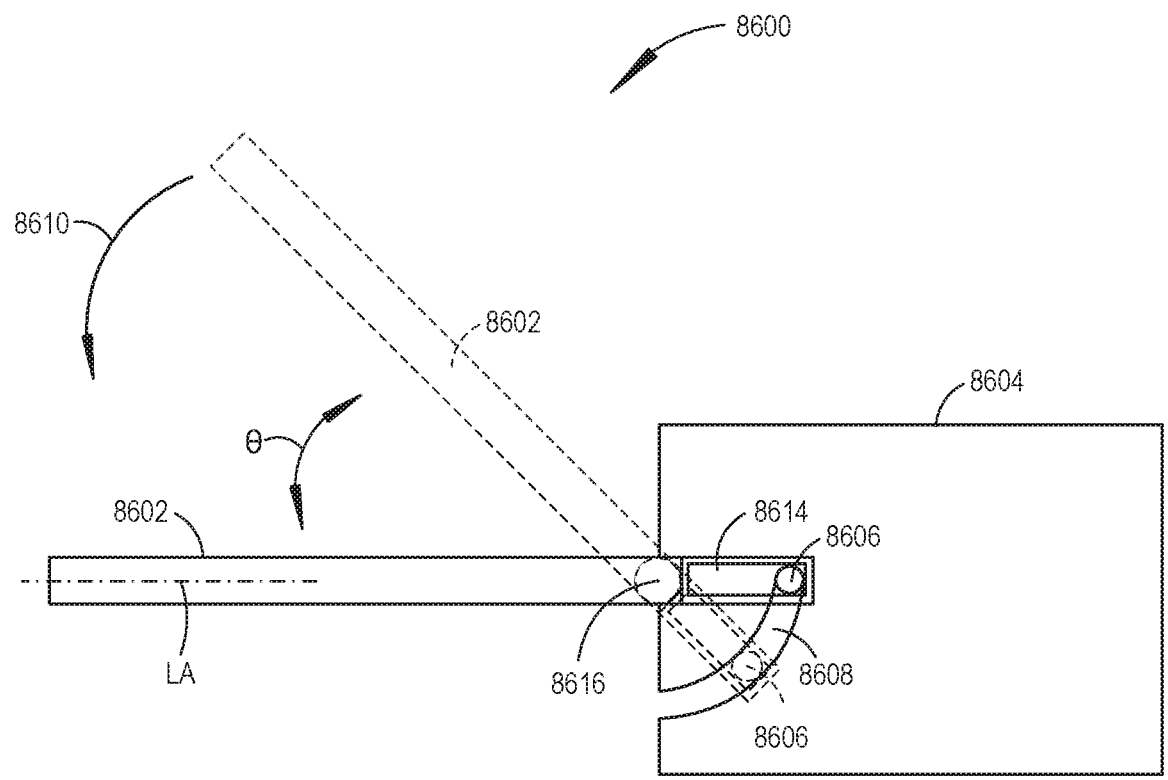

FIG. 194 is an ultrasonic surgical instrument configured in a D31 transducer architecture comprising separate ultrasonic waveguide and ultrasonic transducer base plate components shown in a coupled configuration, according to one aspect of this disclosure.

Figure 195:
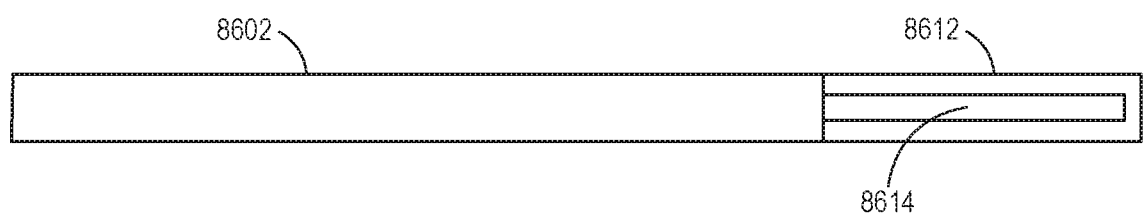

FIG. 195 is a side view of the ultrasonic blade, according to one aspect of this disclosure.

Figure 196:
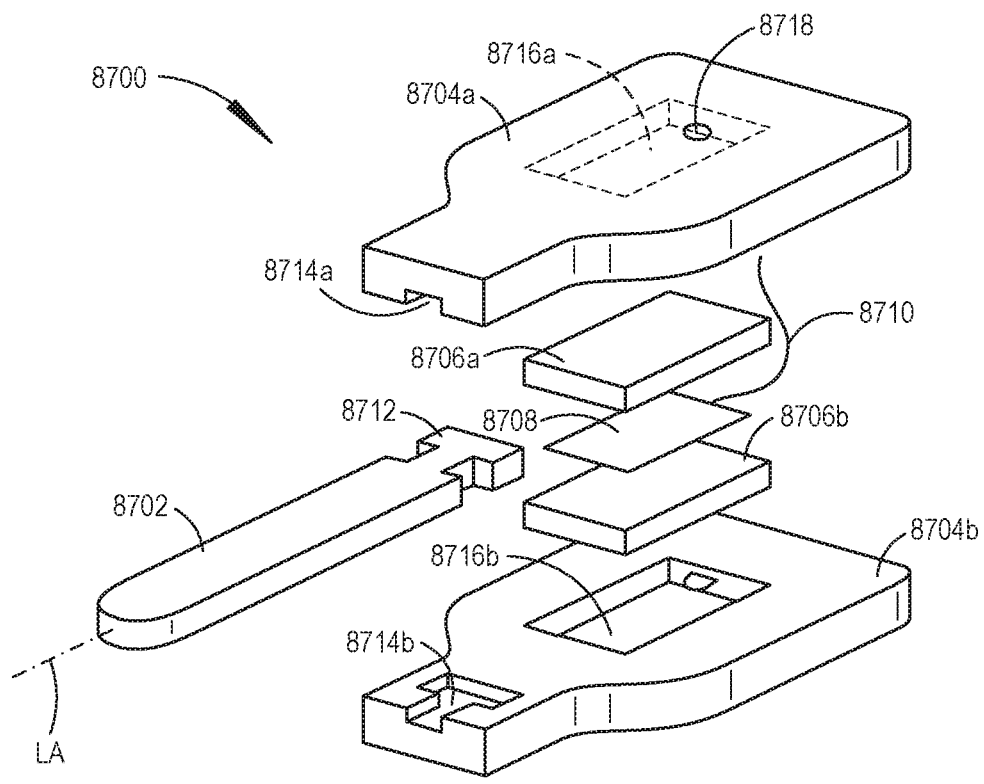

FIG. 196 is an exploded view of an ultrasonic surgical instrument configured in a D31 transducer architecture comprising separate ultrasonic waveguide and symmetric two-piece clamshell housing components to support ultrasonic transducer piezoelectric elements, according to one aspect of this disclosure.

Figure 197:
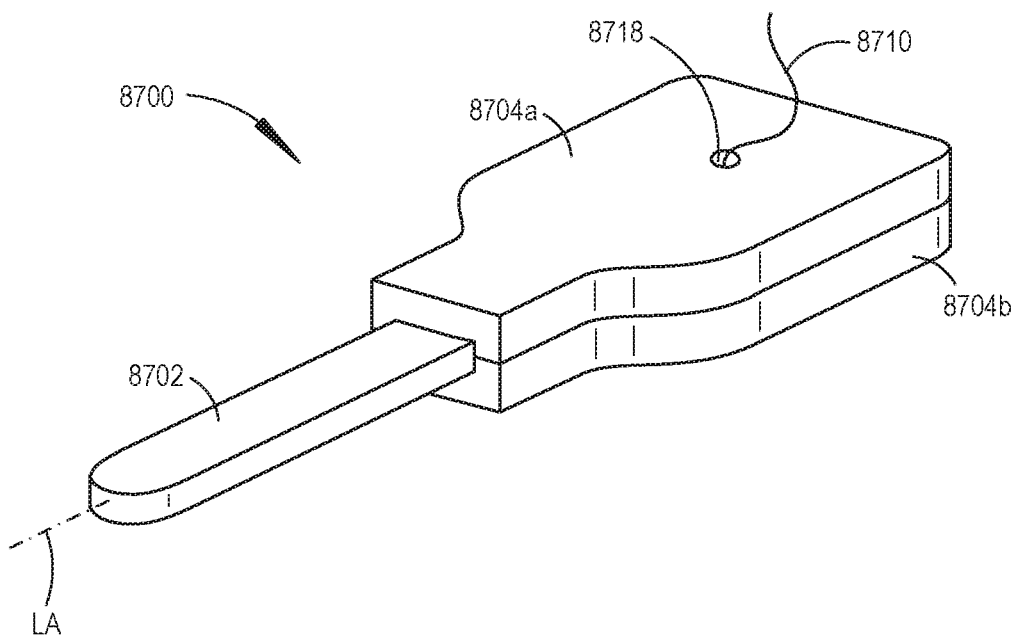

FIG. 197 is an assembled view of the ultrasonic surgical instrument shown in FIG. 196, according to one aspect of this disclosure.

Figure 198:
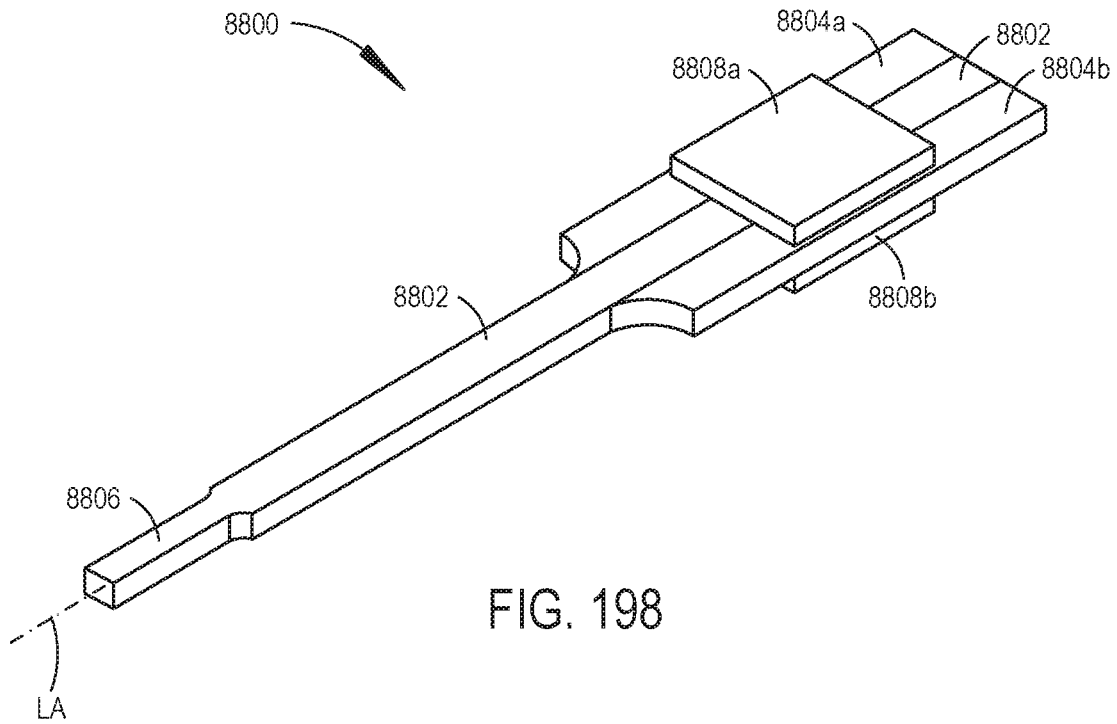

FIG. 198 is a perspective view of an ultrasonic surgical instrument configured in a D31 transducer architecture comprising separate ultrasonic waveguide and a two-piece ultrasonic transducer base plate to support PZT piezoelectric elements, according to one aspect of this disclosure.

Figure 199:
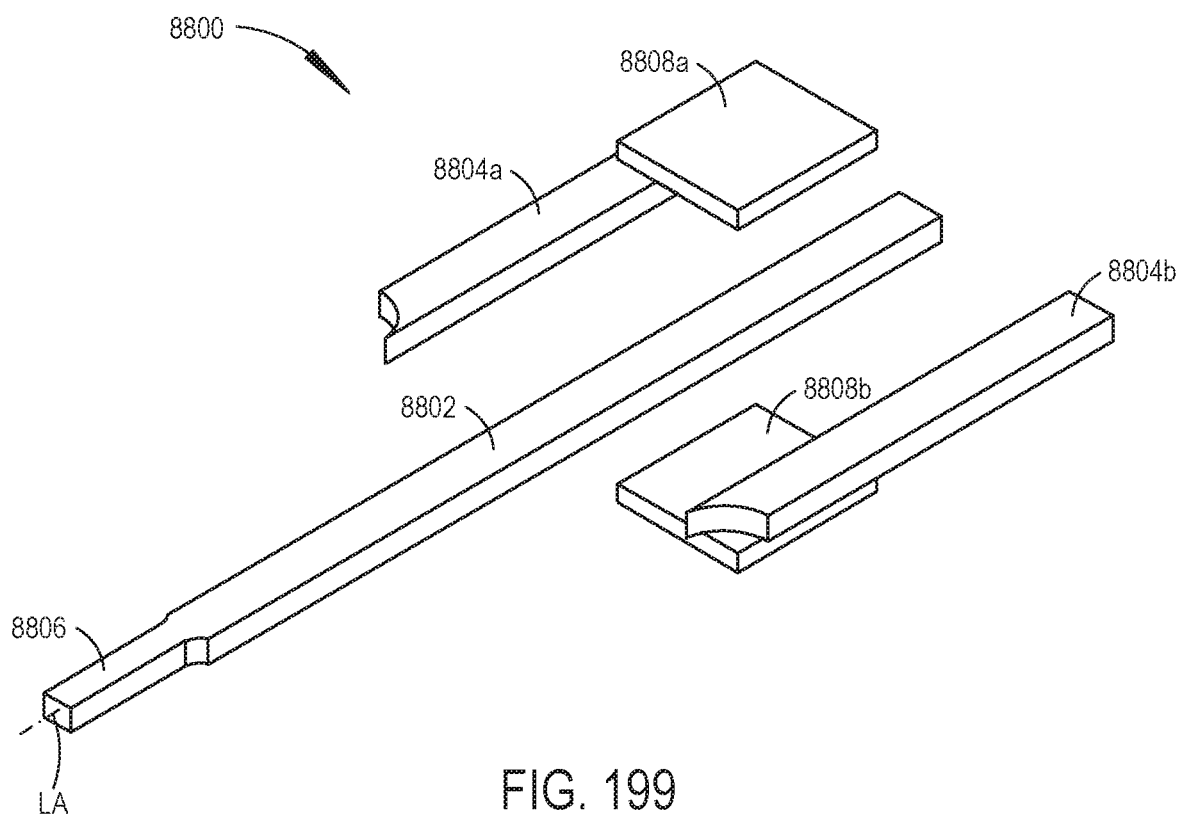

FIG. 199 is an exploded view of the ultrasonic surgical instrument shown in FIG. 198, according to one aspect of this disclosure.

Figure 200:
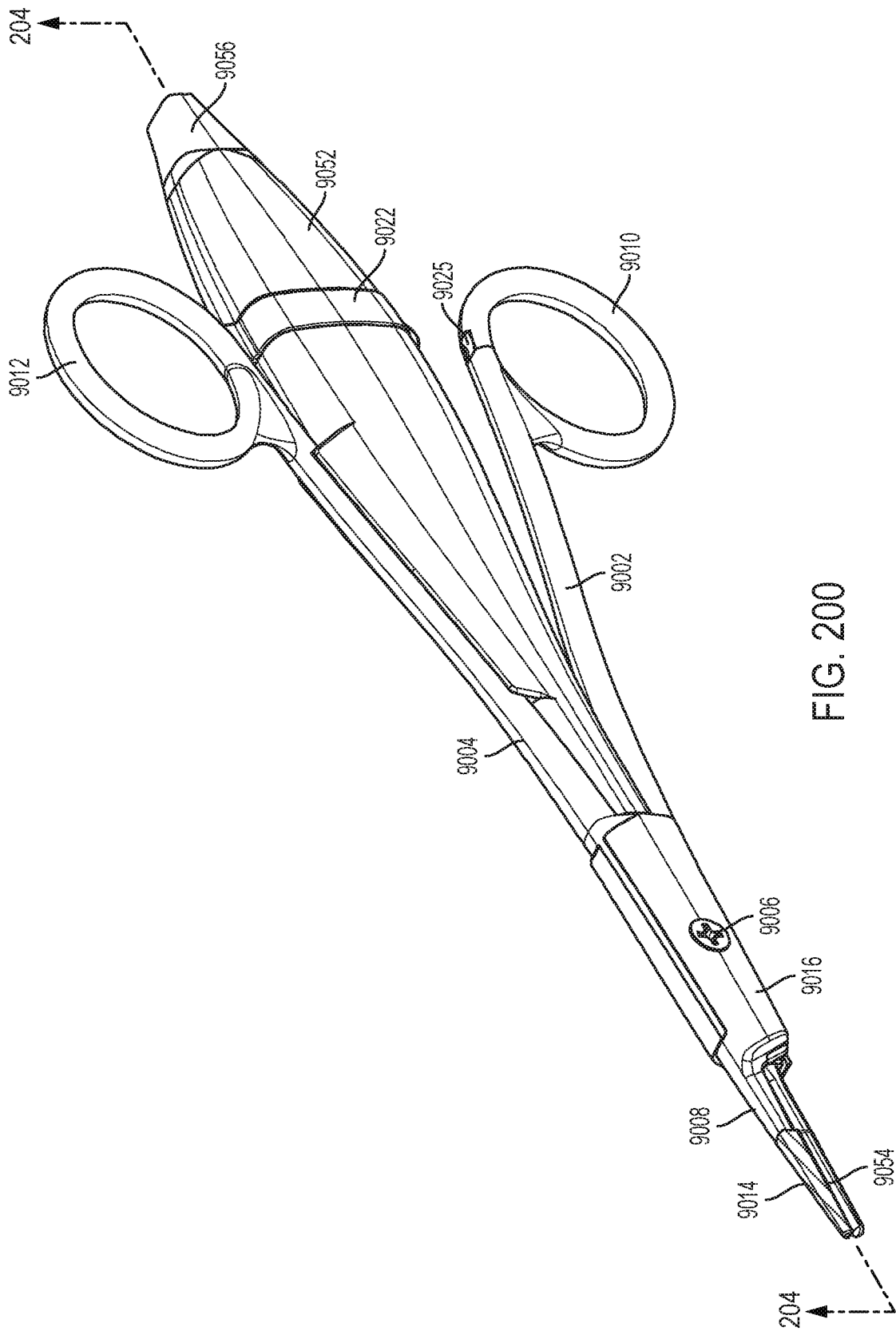

FIG. 200 illustrates a perspective view of an ultrasonic surgical instrument, according to one aspect of this disclosure.

Figure 201:
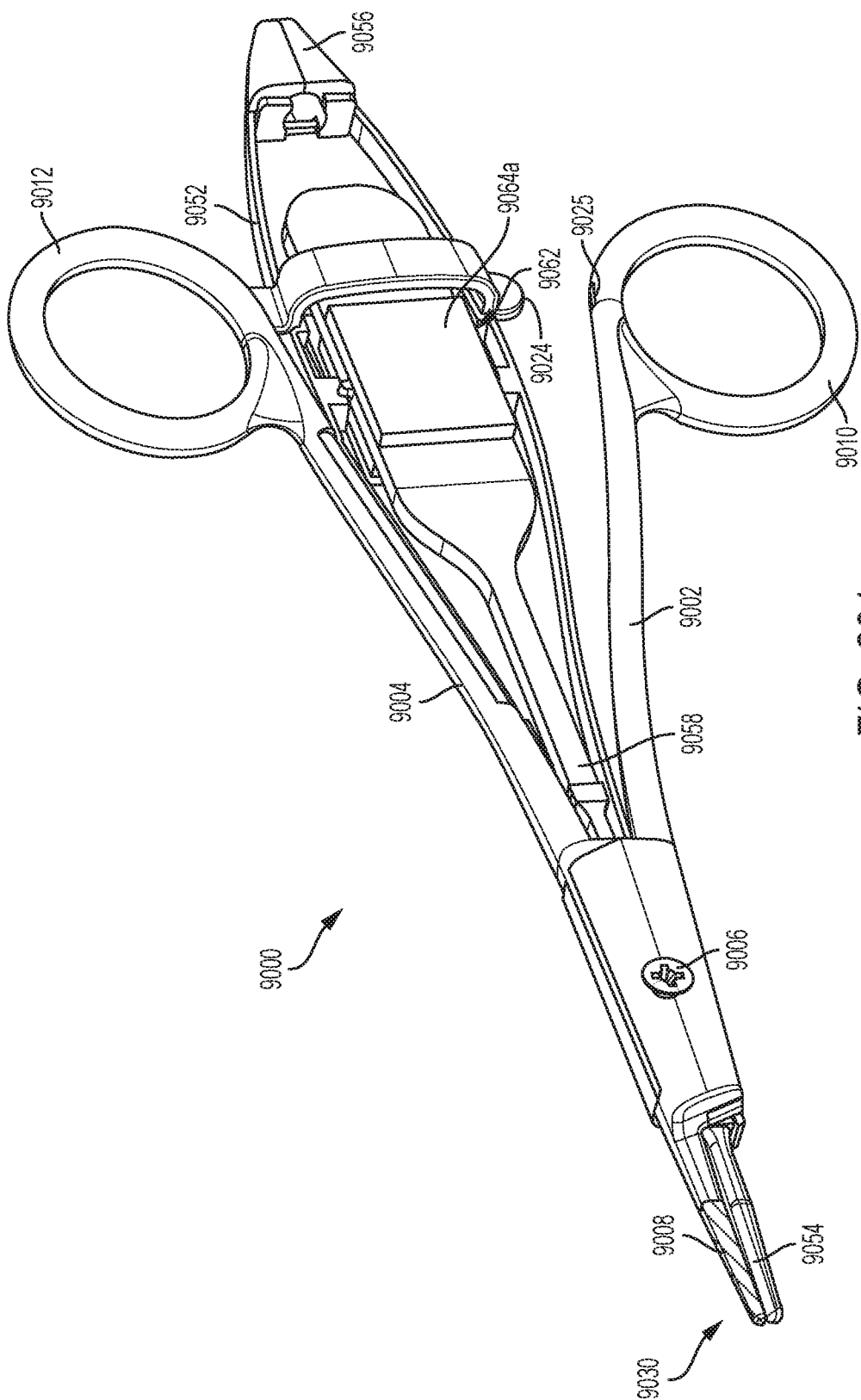

FIG. 201 illustrates a cutaway view of the ultrasonic surgical instrument in FIG. 200, according to one aspect of this disclosure.

Figure 202:
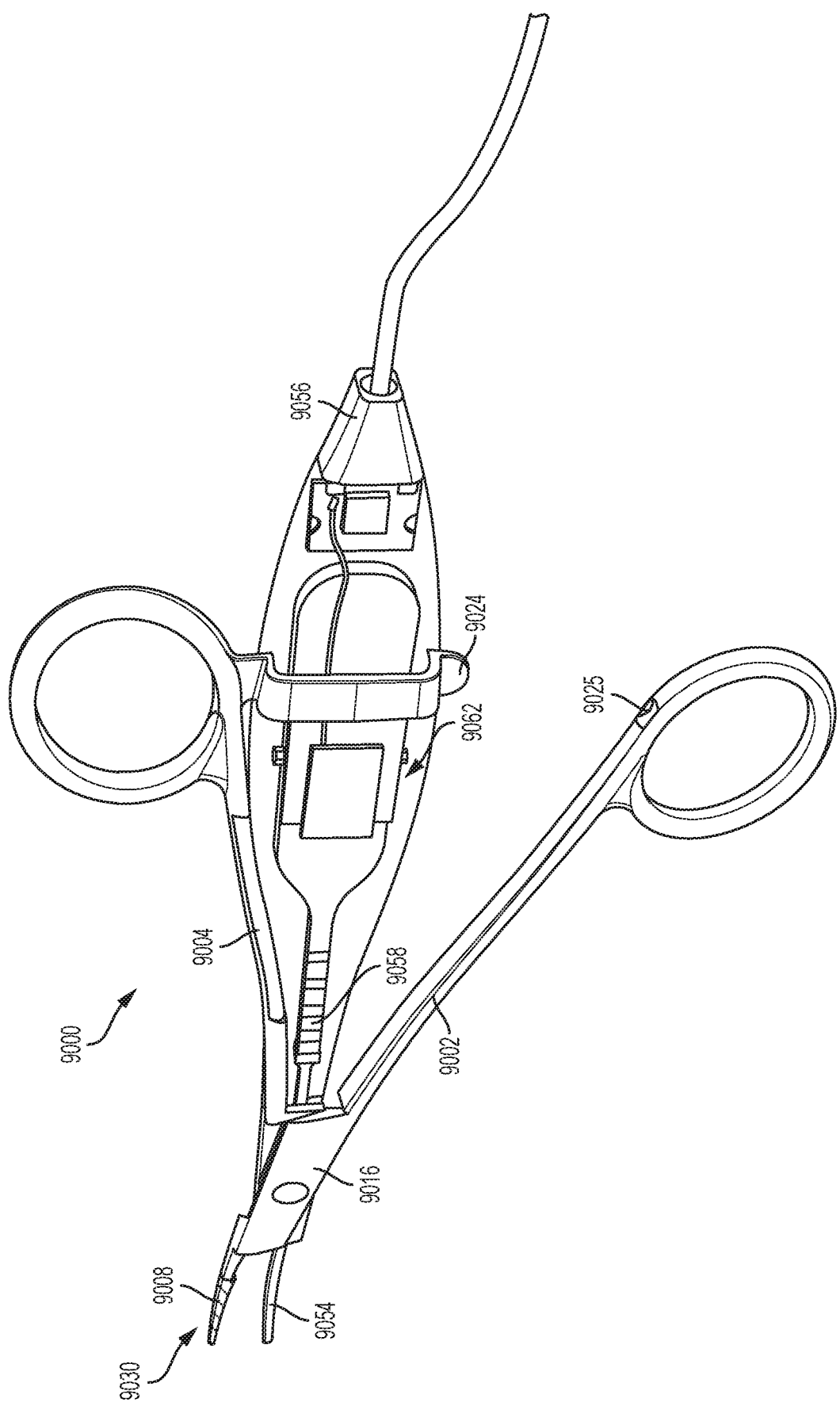

FIG. 202 illustrates a cutaway view of the ultrasonic surgical instrument in FIG. 200, wherein the ultrasonic surgical instrument is in an open position, according to one aspect of this disclosure.

Figure 203:
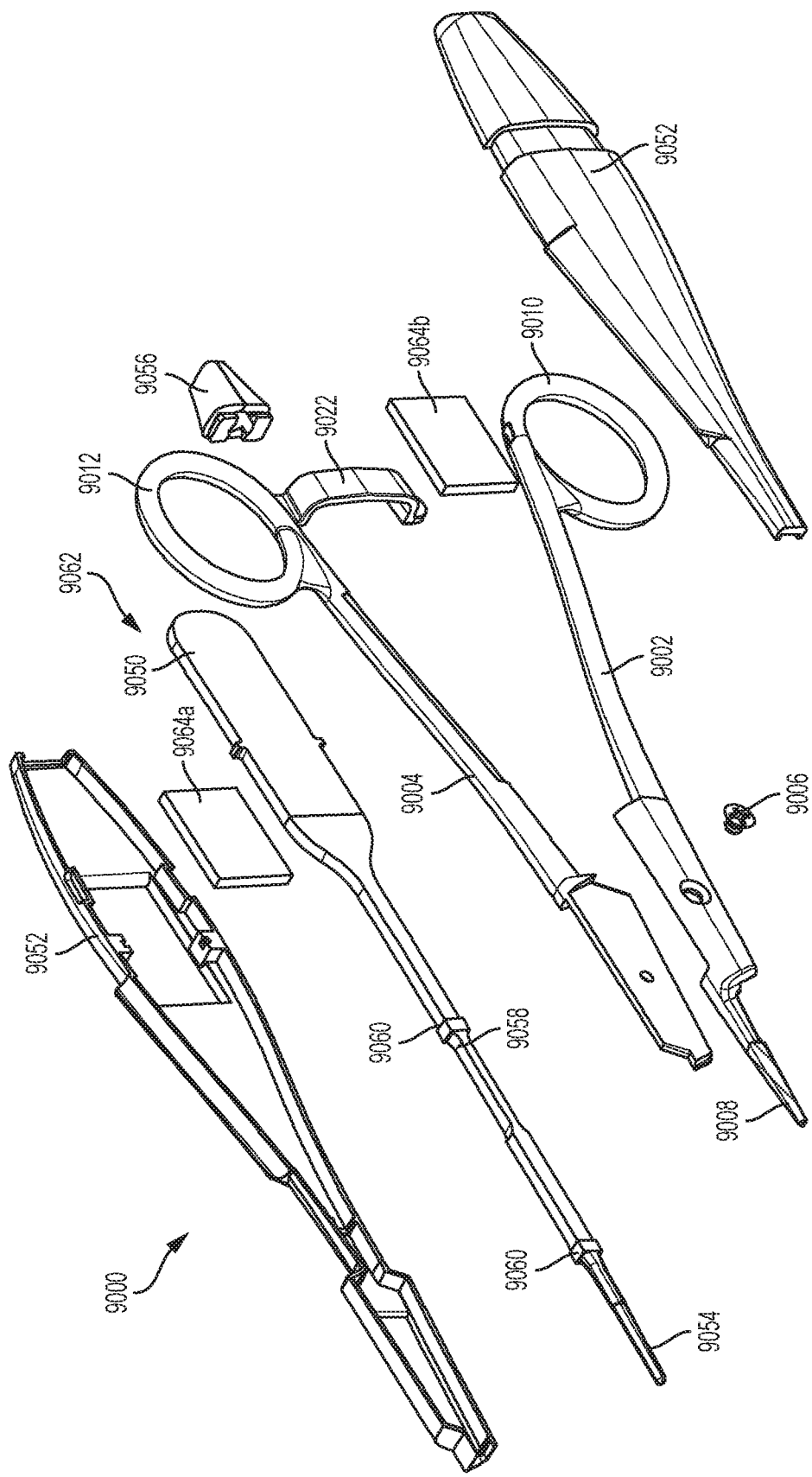

FIG. 203 illustrates an exploded view of the ultrasonic surgical instrument in FIG. 200, according to one aspect of this disclosure.

Figure 204:
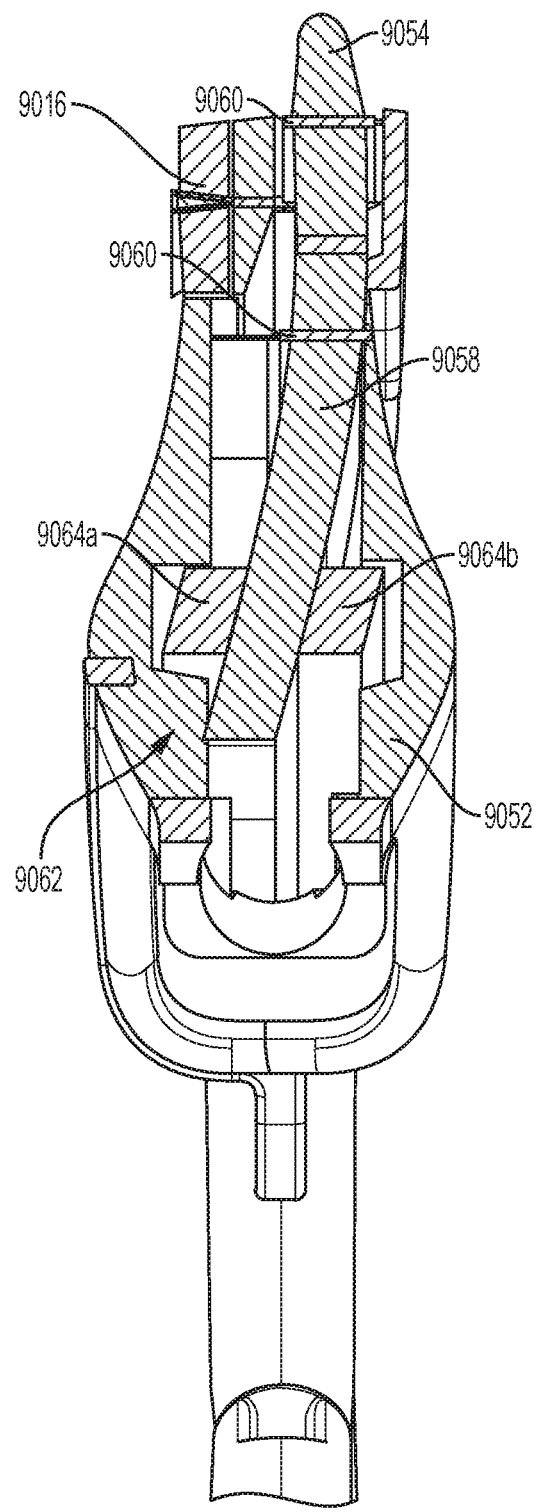

FIG. 204 illustrates a sectional view of the ultrasonic surgical instrument in FIG. 200 along line 204-204, according to one aspect of this disclosure.

Figure 205:
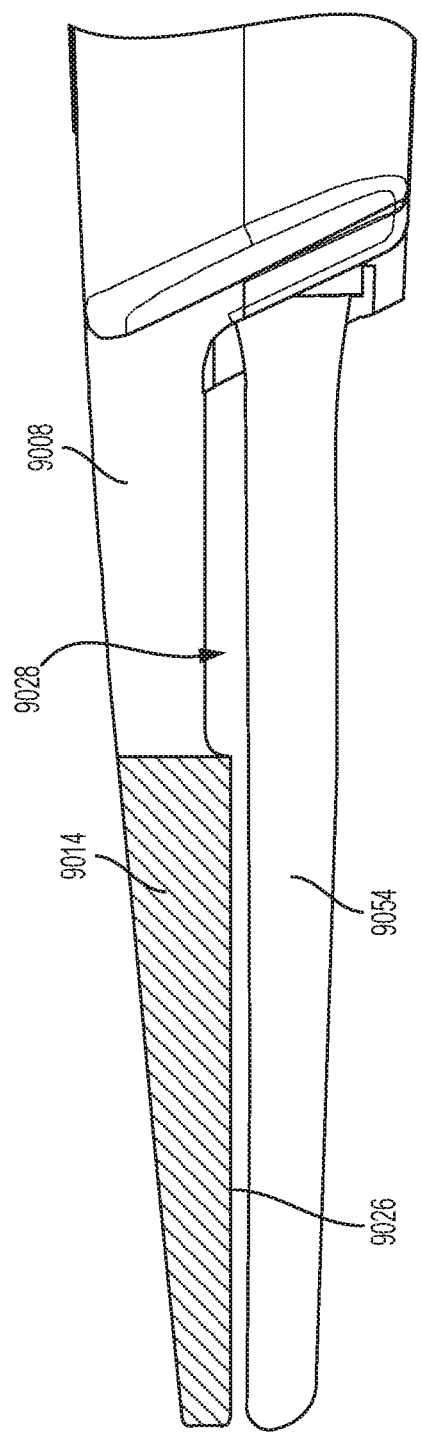

FIG. 205 illustrates a detail view of the jaw and end effector portions of the ultrasonic surgical instrument in FIG. 200, according to one aspect of this disclosure.

Figure 206:
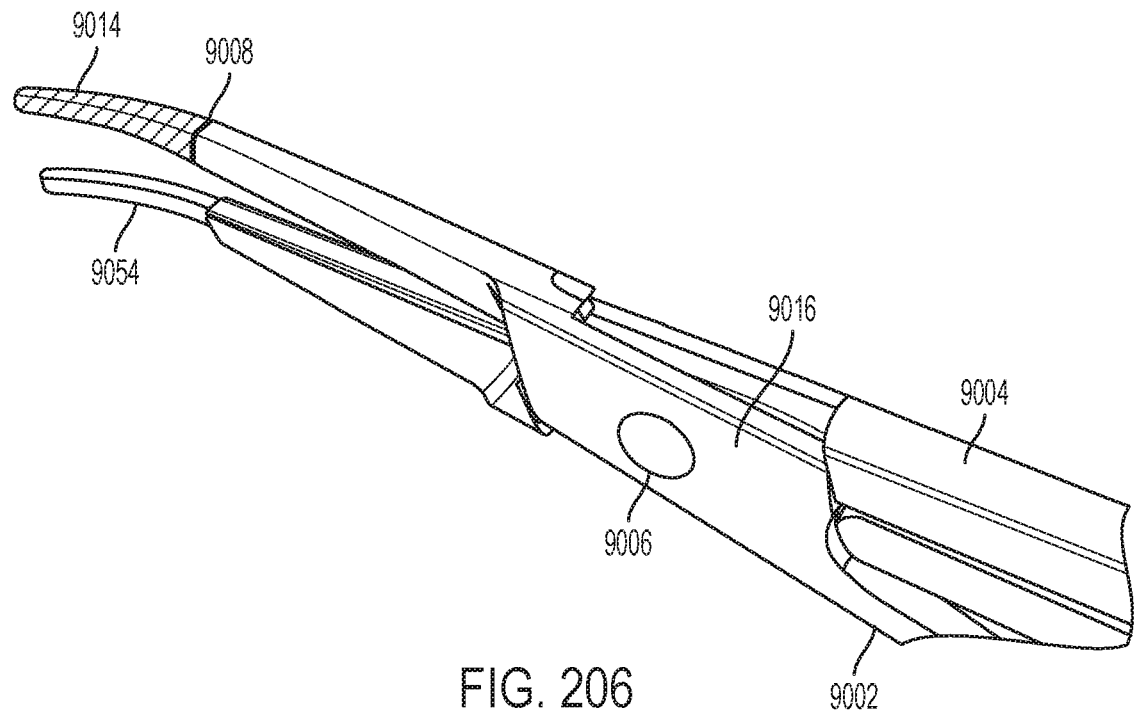

FIG. 206 illustrates a perspective view of the distal portion of an ultrasonic surgical instrument including a curved end effector, according to one aspect of this disclosure.

Figure 207:
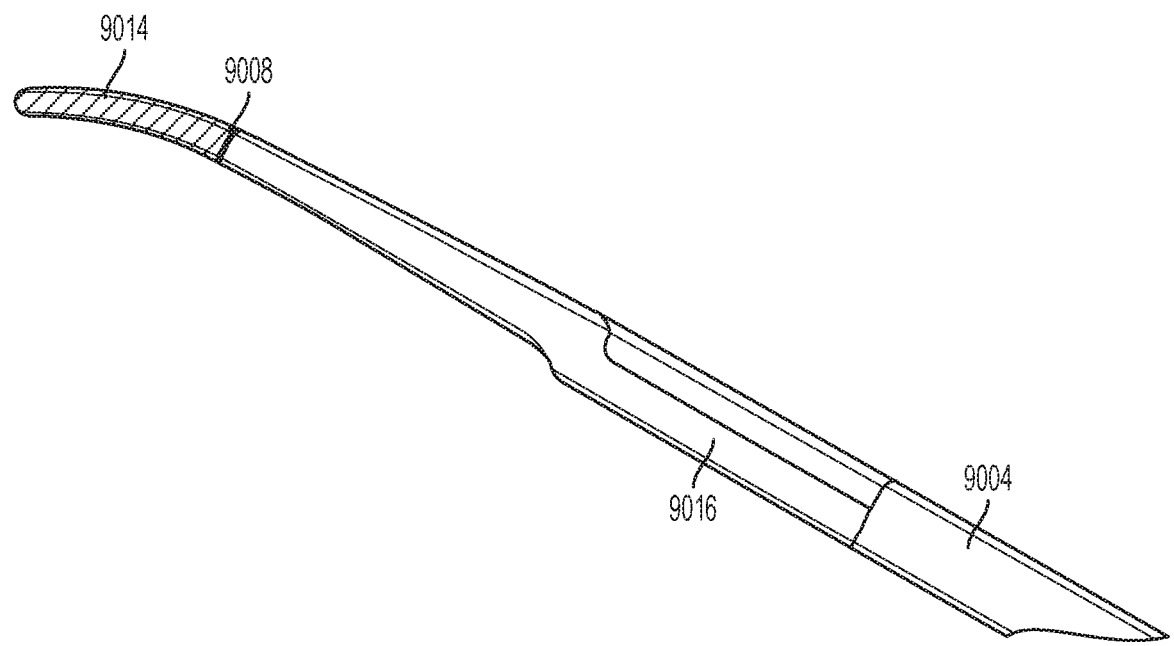

FIG. 207 illustrates a side view of the distal portion of the ultrasonic surgical instrument in FIG. 206, according to one aspect of this disclosure.

Figure 208:
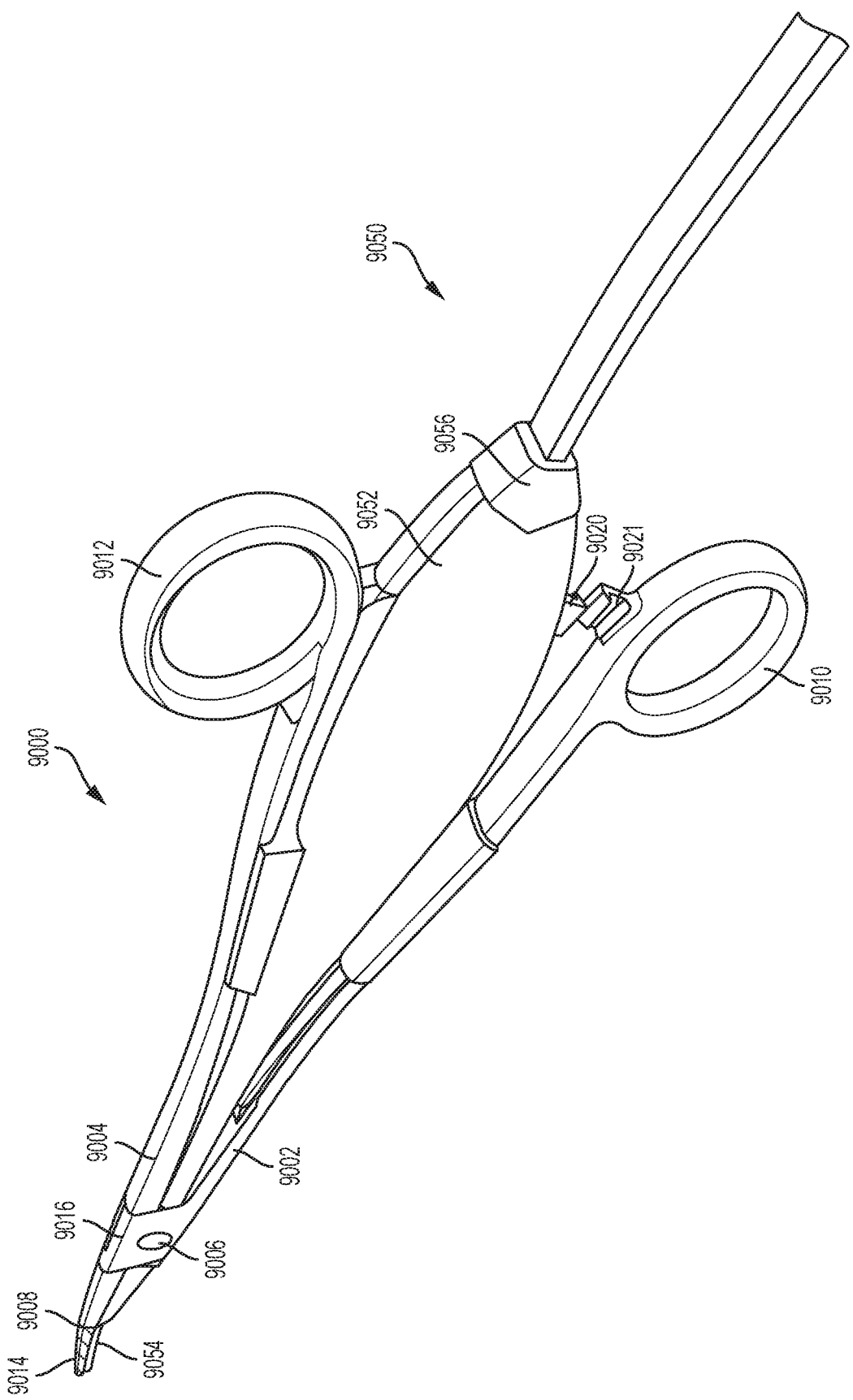

FIG. 208 illustrates a perspective view of an ultrasonic surgical instrument including a clip closure, according to one aspect of this disclosure.

Figure 209:
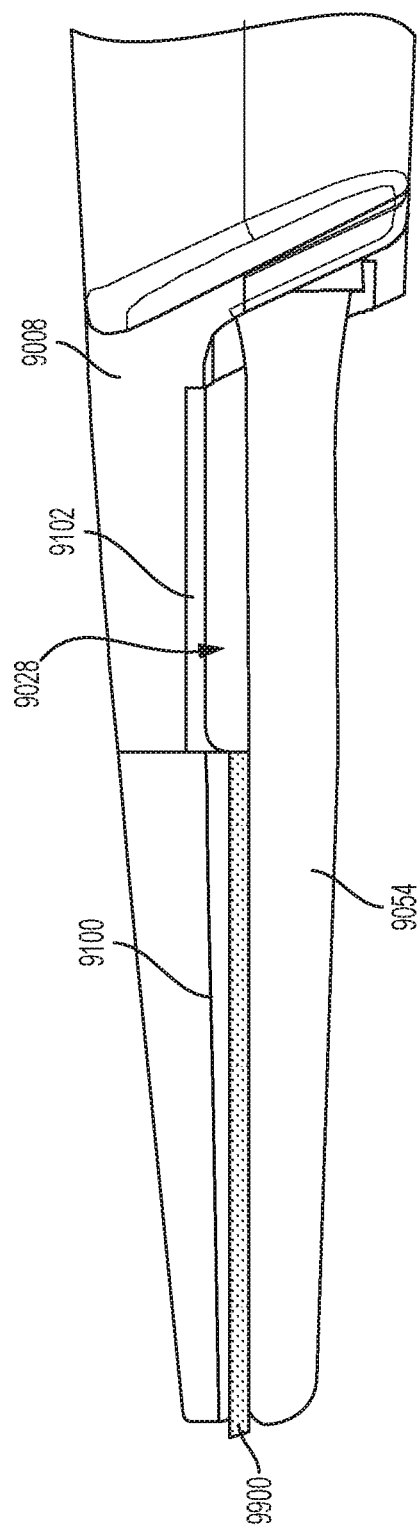

FIG. 209 illustrates an elevational view of the distal portion of an ultrasonic surgical instrument configured to detect improper tissue clamping, according to one aspect of this disclosure.

Figure 210:
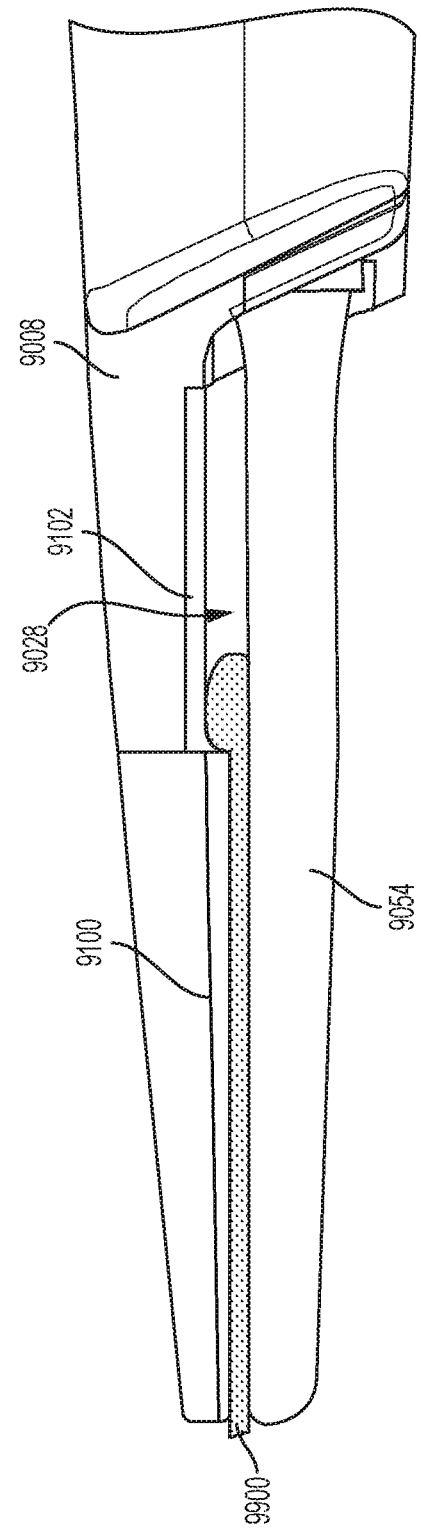

FIG. 210 illustrates a side view of the ultrasonic surgical instrument in FIG. 209, according to one aspect of this disclosure.

Figure 211:
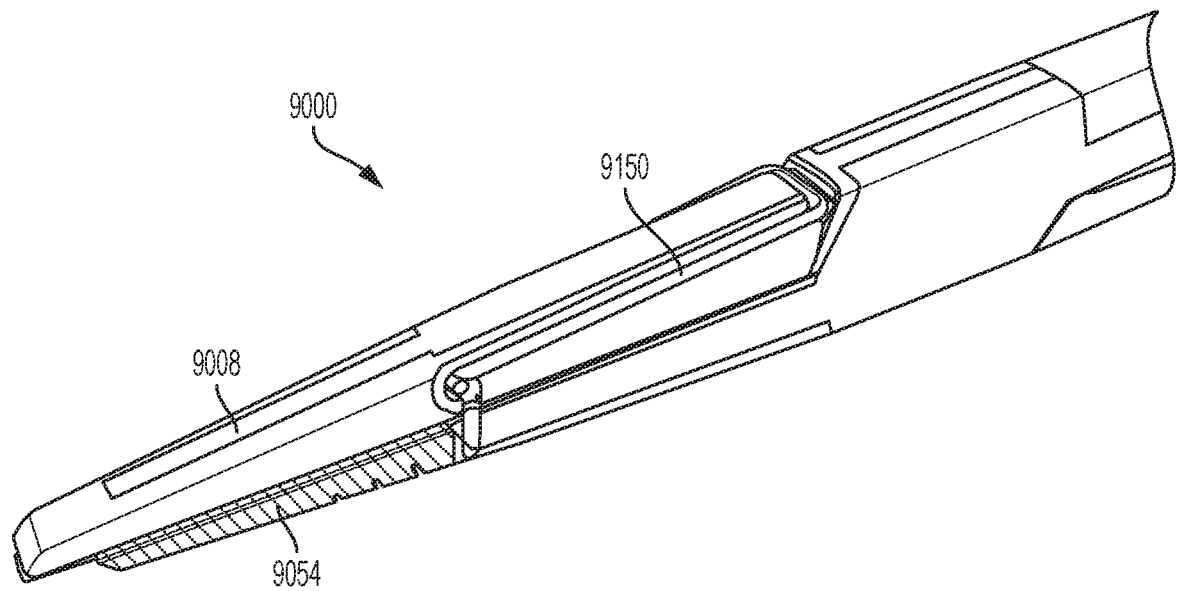

FIG. 211 illustrates a perspective view of an end portion of an ultrasonic surgical instrument incorporating a pivotable member tissue stop, wherein the pivotable member is in a stowed position, according to one aspect of this disclosure.

Figure 212:
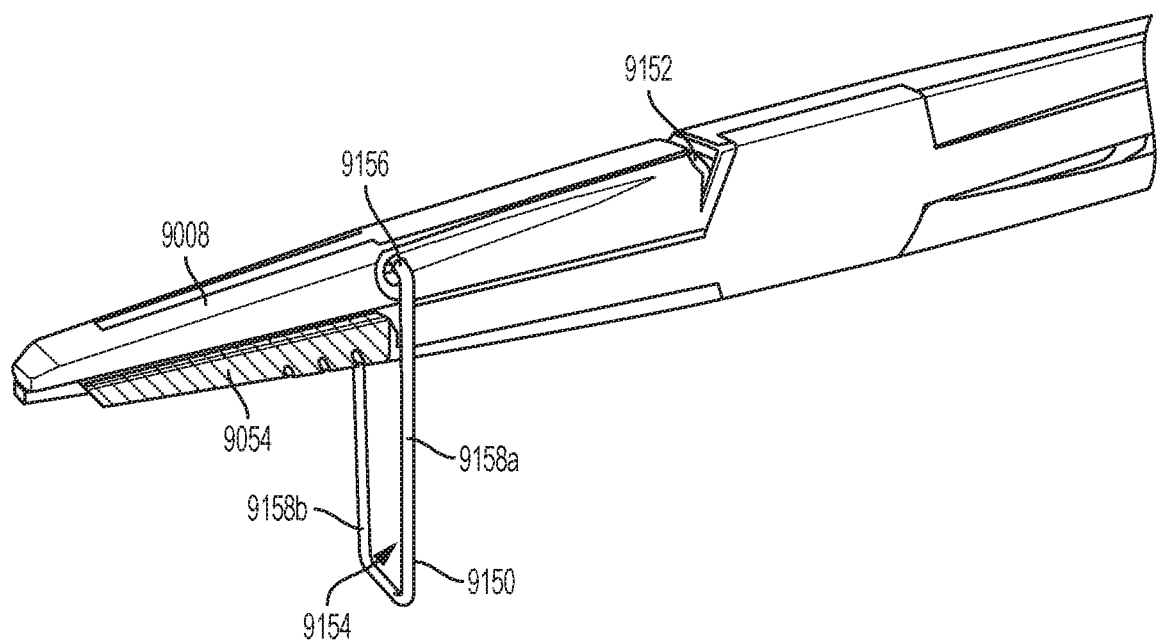

FIG. 212 illustrates a perspective view of the end portion of the ultrasonic surgical instrument in FIG. 211, wherein the pivotable member is in the deployed position, according to one aspect of this disclosure.

Figure 213:
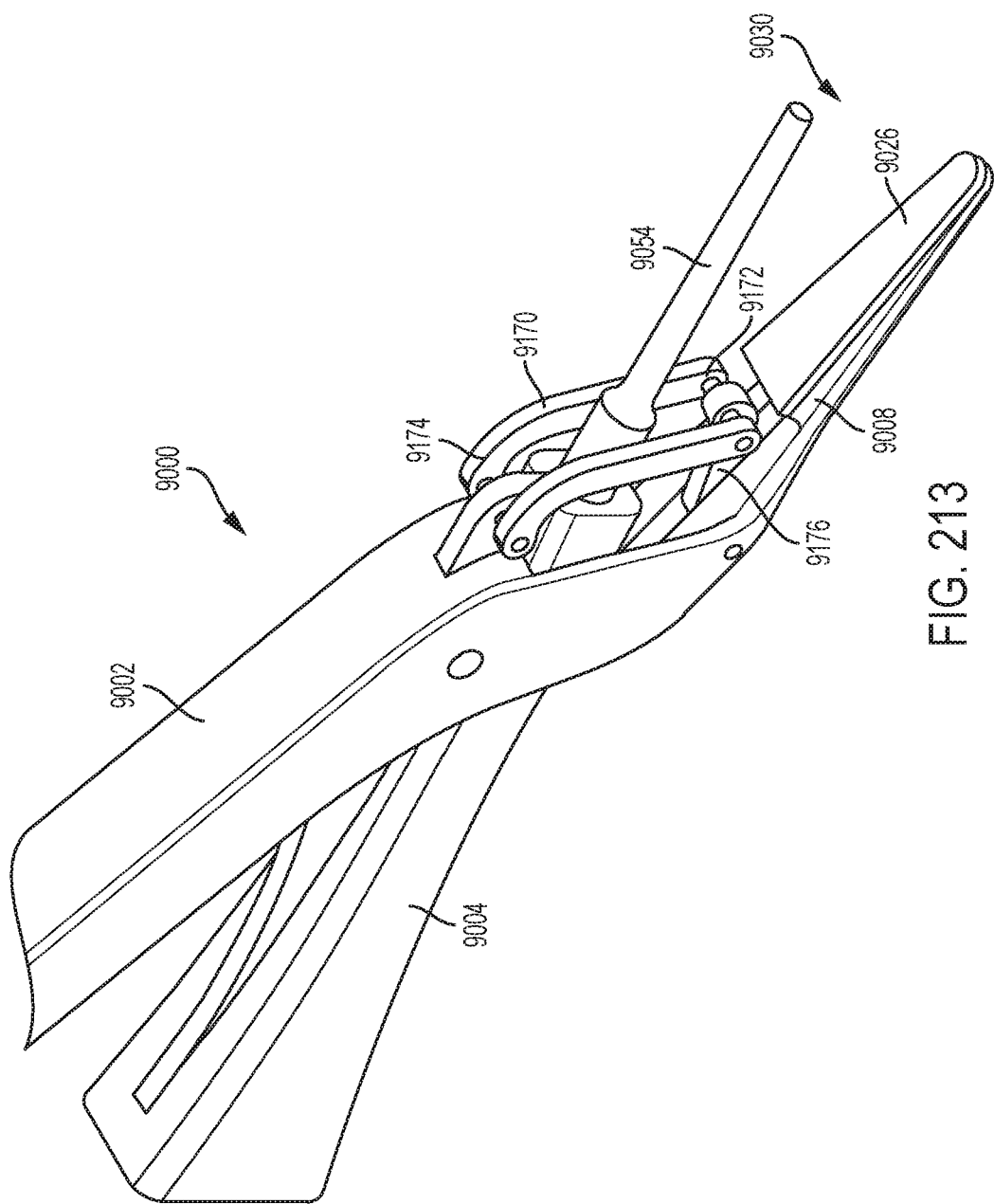

FIG. 213 illustrates a perspective view of an ultrasonic surgical instrument incorporating a mechanical linkage tissue stop, according to one aspect of this disclosure.

Figure 214:
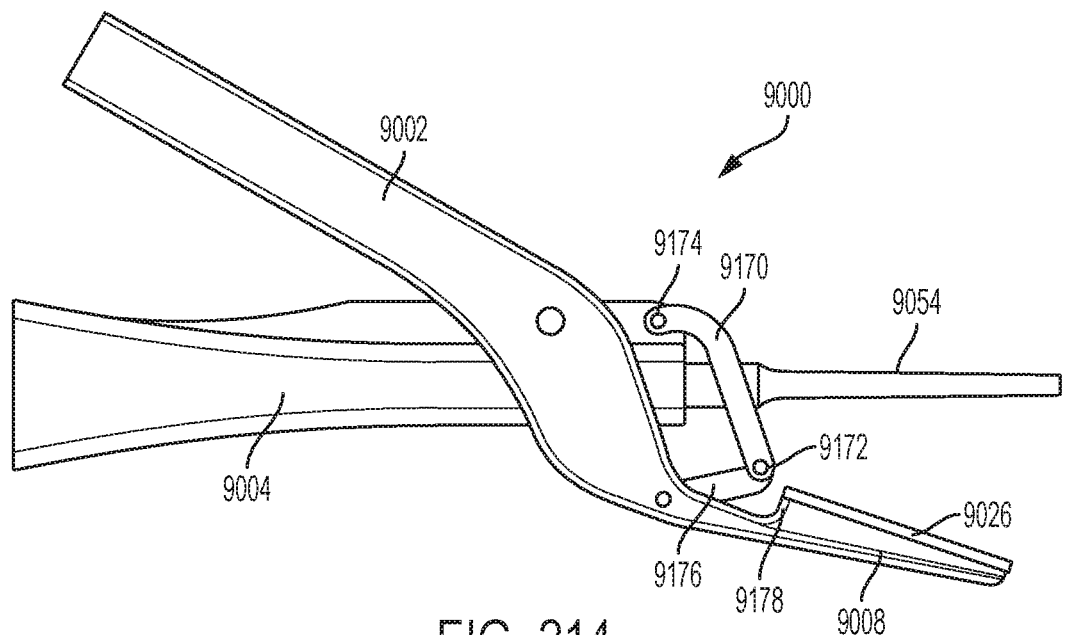

FIG. 214 illustrates a side view of the ultrasonic surgical instrument in FIG. 213 in an open position, according to one aspect of this disclosure.

Figure 215:
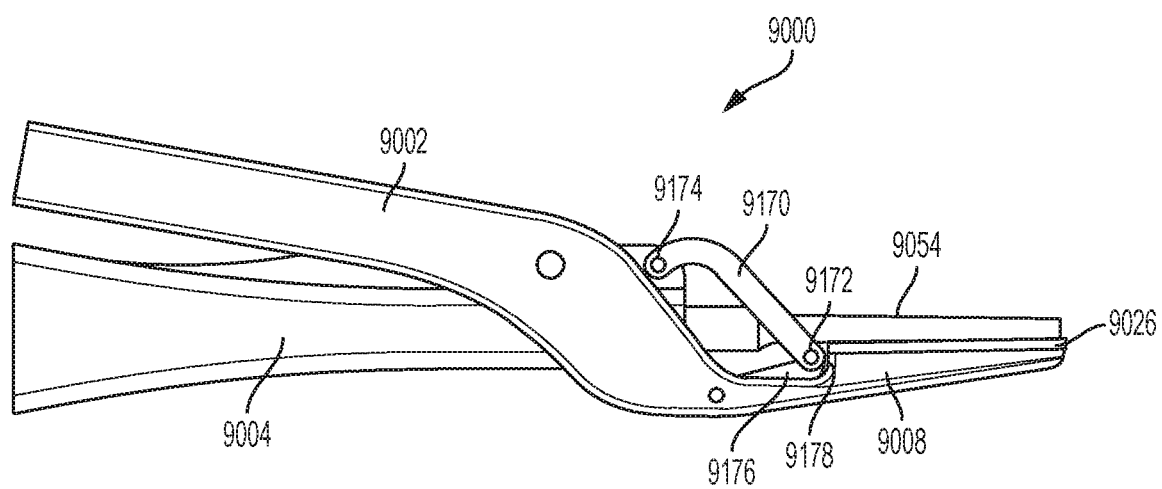

FIG. 215 illustrates a side view of the ultrasonic surgical instrument in FIG. 213 in a closed position, according to one aspect of this disclosure.

Figure 216:
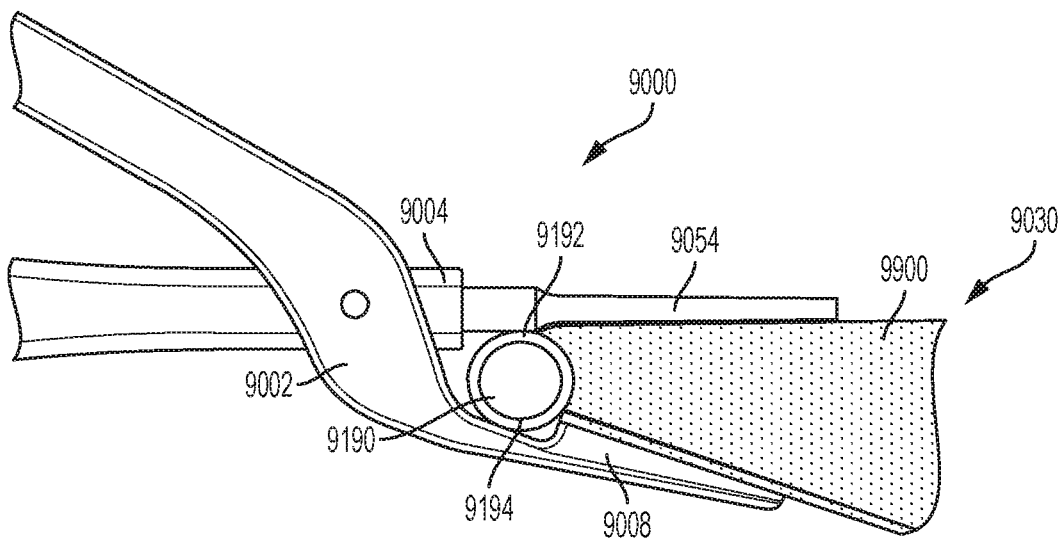

FIG. 216 illustrates a side view of an ultrasonic surgical instrument incorporating a deformable member tissue stop, according to one aspect of this disclosure.

Figure 217:
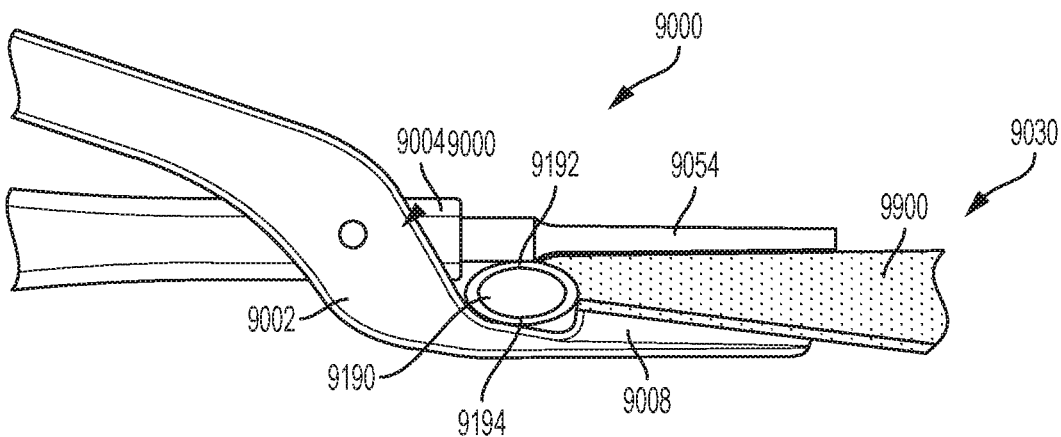

FIG. 217 illustrates a side view of the ultrasonic surgical instrument in FIG. 216 in a partially clamped position, according to one aspect of this disclosure.

Figure 218:
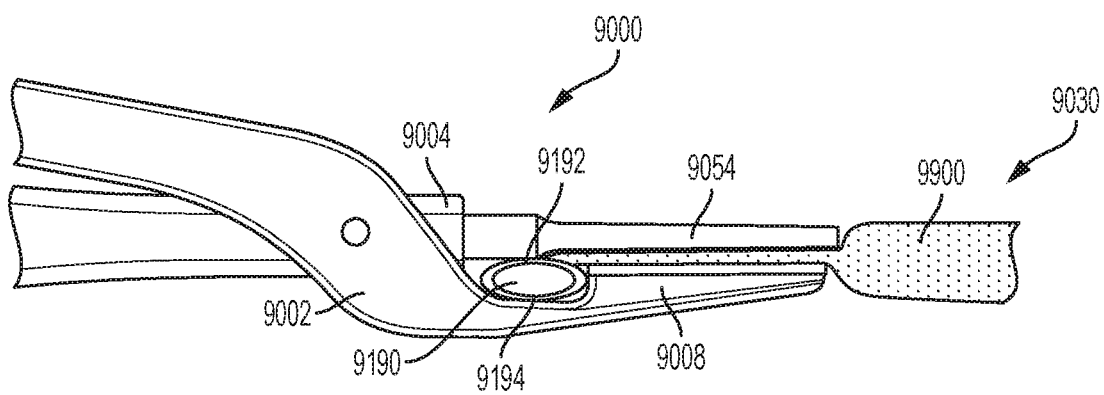

FIG. 218 illustrates a side view of the ultrasonic surgical instrument in FIG. 216 in a clamped position, according to one aspect of this disclosure.

Figure 219:
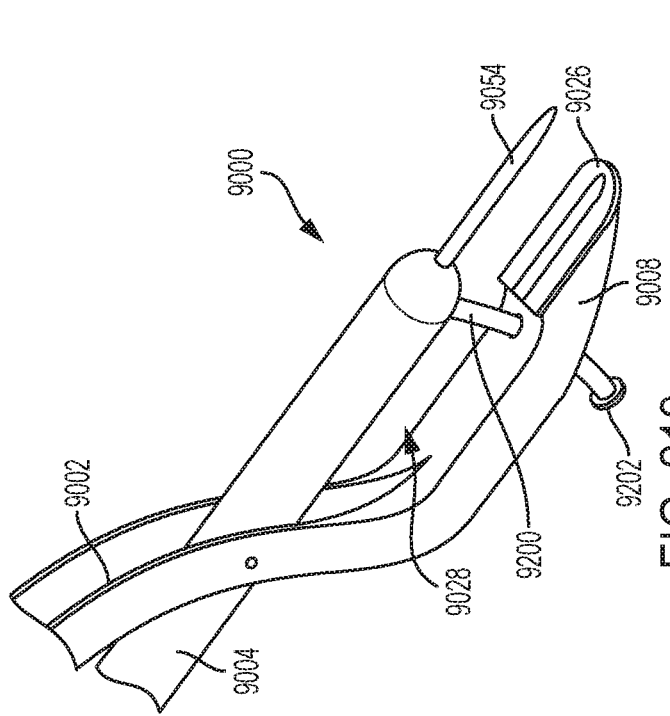

FIG. 219 illustrates a perspective view of an ultrasonic surgical instrument incorporating a curved bar tissue stop, according to one aspect of this disclosure.

Figure 220:
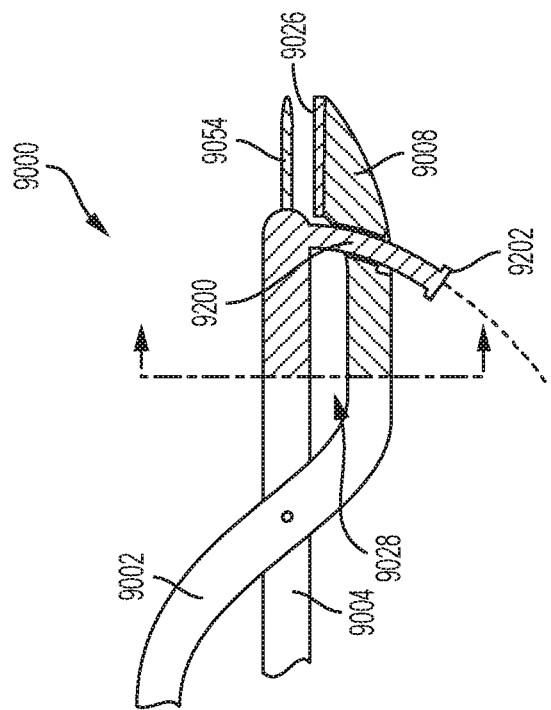

FIG. 220 illustrates a partial sectional view of the ultrasonic surgical instrument in FIG. 219, according to one aspect of this disclosure.

Figure 221:
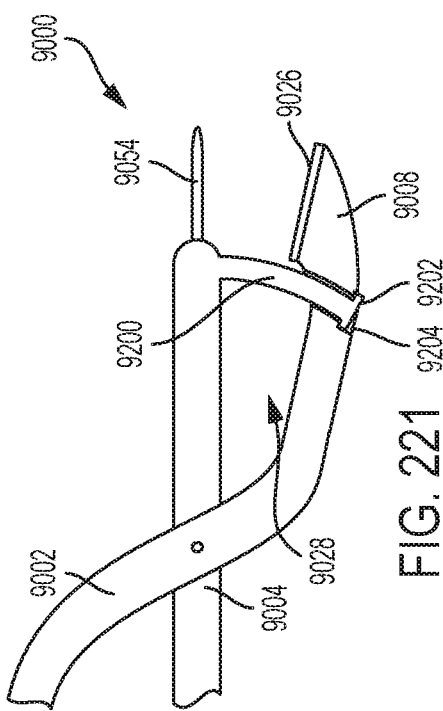

FIG. 221 illustrates a side view of the ultrasonic surgical instrument in FIG. 219 in an open position, according to one aspect of this disclosure.

Figure 222:
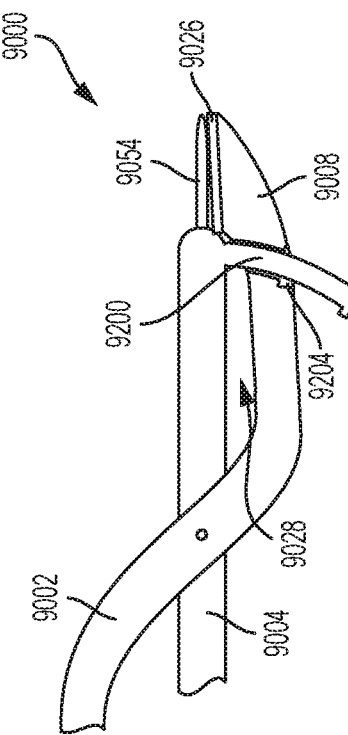

FIG. 222 illustrates a side view of the ultrasonic surgical instrument in FIG. 219 in a closed position, according to one aspect of this disclosure.

Figure 223:
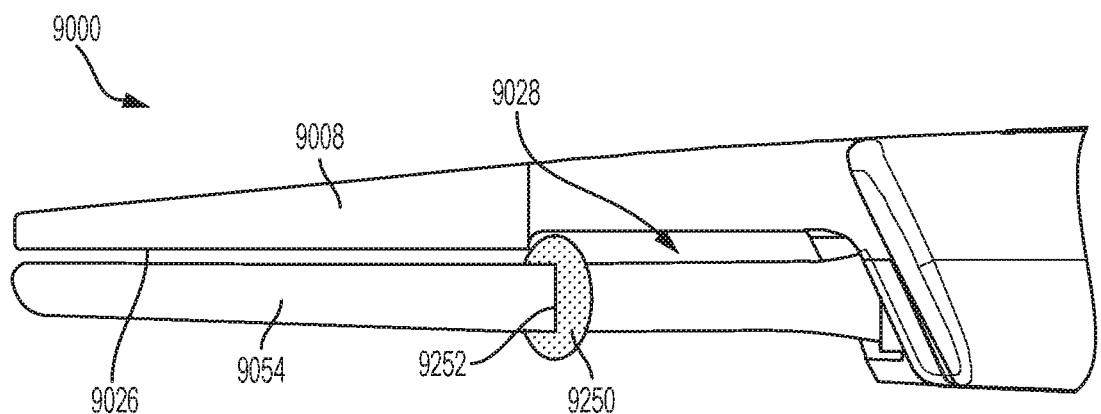

FIG. 223 illustrates a perspective view of an ultrasonic surgical instrument incorporating an end effector ring tissue stop, according to one aspect of this disclosure.

Figure 224:
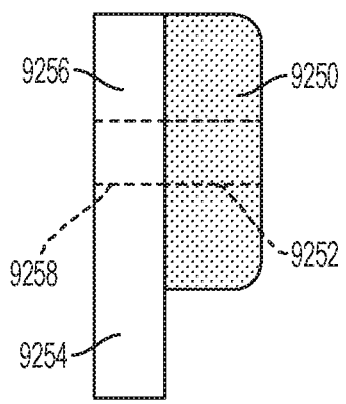

FIG. 224 illustrates a side view of one aspect of the tissue stop in FIG. 223, according to one aspect of this disclosure.

Figure 225:
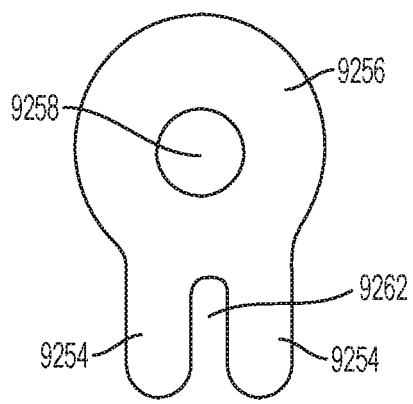

FIG. 225 illustrates a front view of the tissue stop in FIG. 223, according to one aspect of this disclosure.

Figure 226:
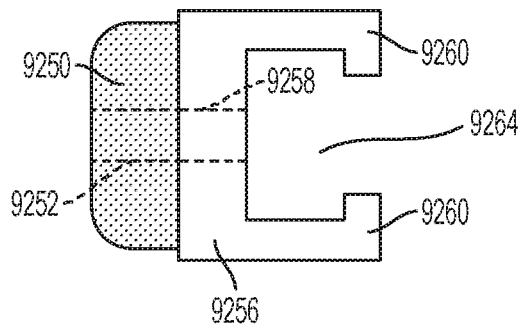

FIG. 226 illustrates a top view of one aspect of the tissue stop in FIG. 223, according to one aspect of this disclosure.

Figure 227:
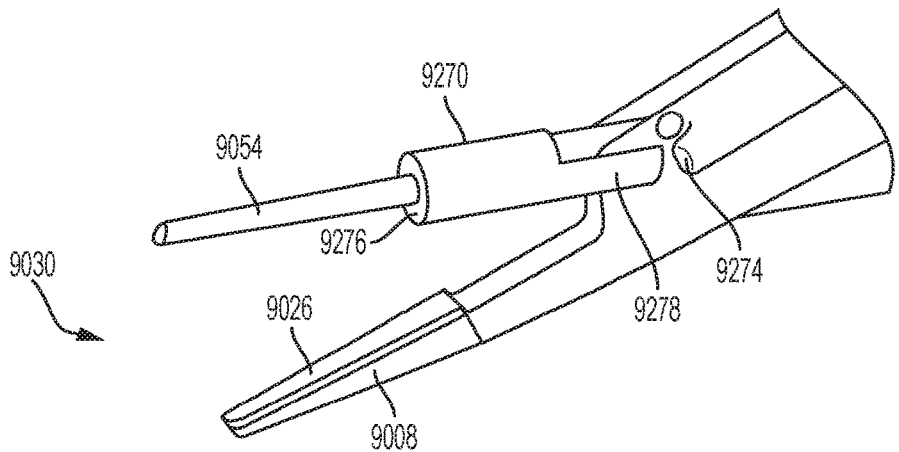

FIG. 227 illustrates a perspective view of an ultrasonic surgical instrument incorporating a longitudinally slidable member tissue stop, wherein the ultrasonic surgical instrument is in an open position, according to one aspect of this disclosure.

Figure 228:
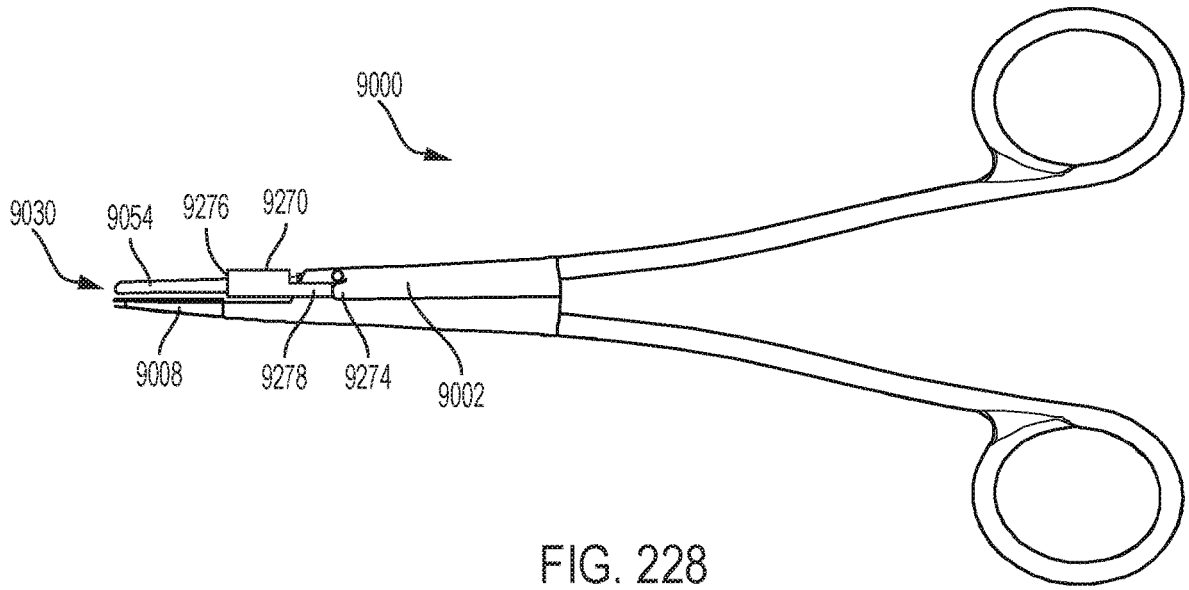

FIG. 228 illustrates a perspective view of the ultrasonic surgical instrument in FIG. 227 in a closed position, according to one aspect of this disclosure.

Figure 229:
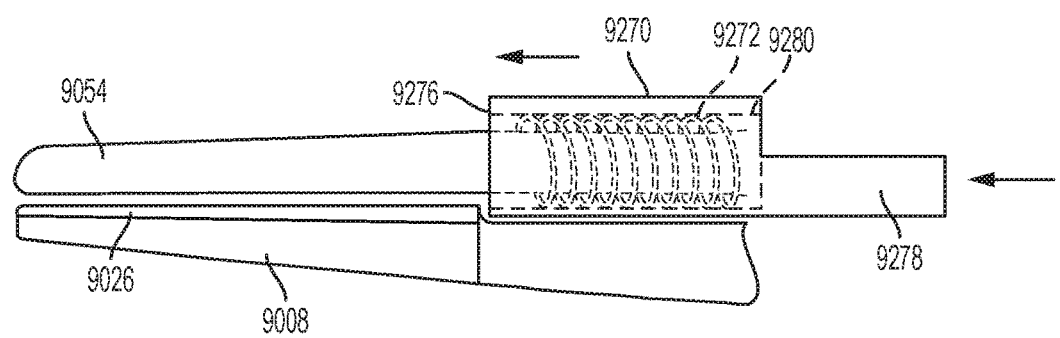

FIG. 229 illustrates a cutaway view of the longitudinally slidable member tissue stop in FIG. 227, according to one aspect of this disclosure.

Figure 230:
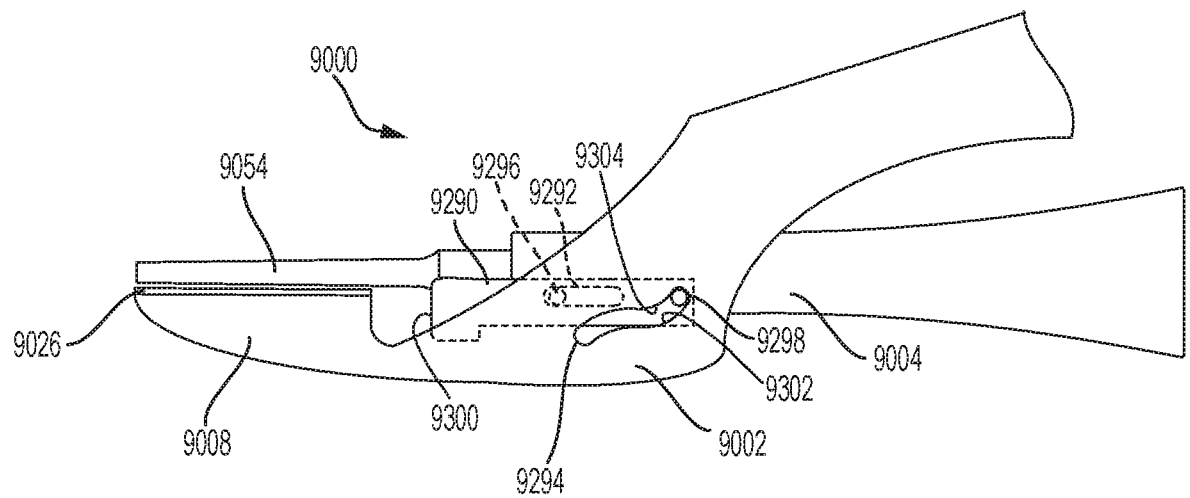

FIG. 230 illustrates a side view of an ultrasonic surgical instrument incorporating a cam-actuated member tissue stop in an open position, according to one aspect of this disclosure.

Figure 231:
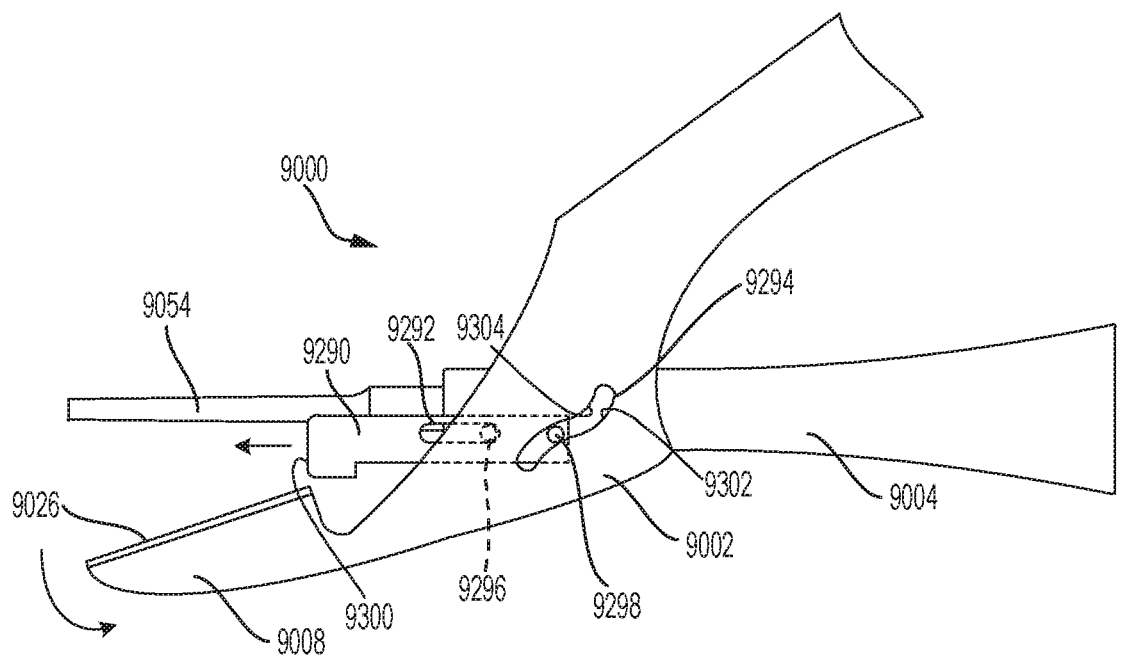
Figure 233:
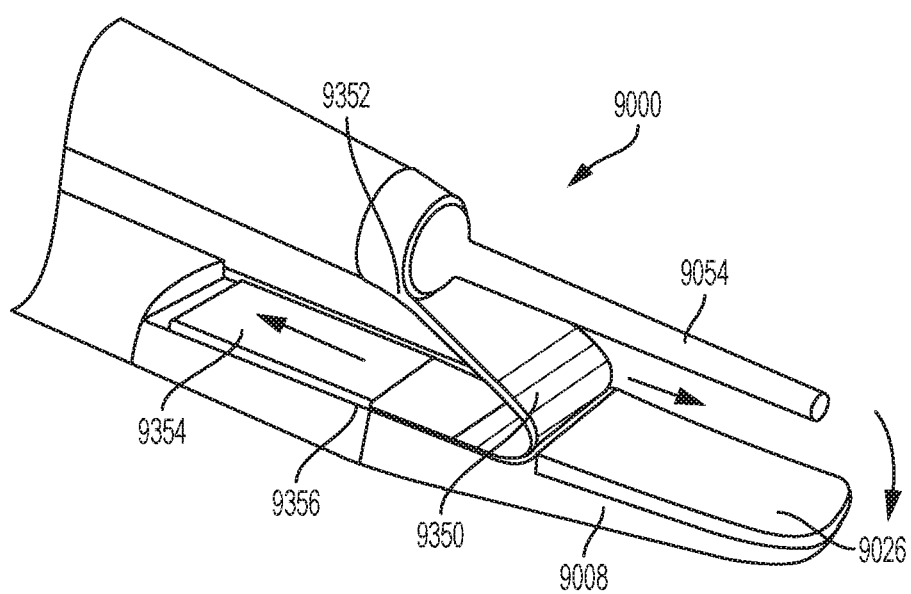

FIG. 231 illustrates a side view of the ultrasonic surgical instrument in FIG. 233 in a closed position, according to one aspect of this disclosure.

Figure 232:
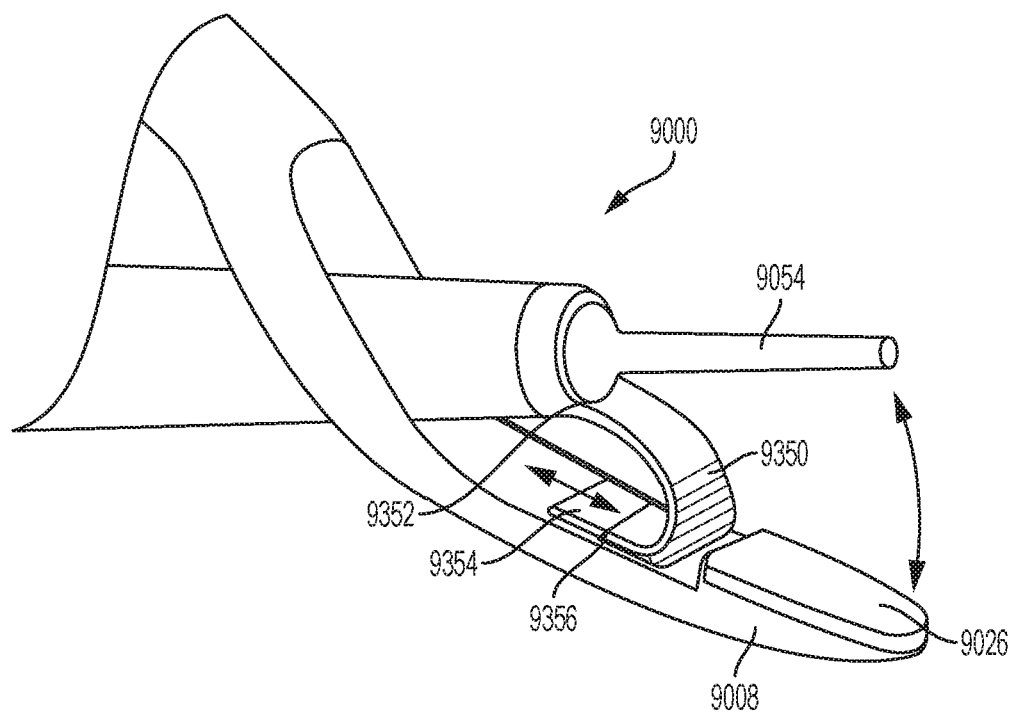

FIG. 232 illustrates a side view of an ultrasonic surgical instrument incorporating a flexible strip tissue stop, according to one aspect of this disclosure.

FIG. 233 illustrates a perspective view of the ultrasonic surgical instrument in FIG. 232 in a closed position, according to one aspect of this disclosure.

Figure 234:
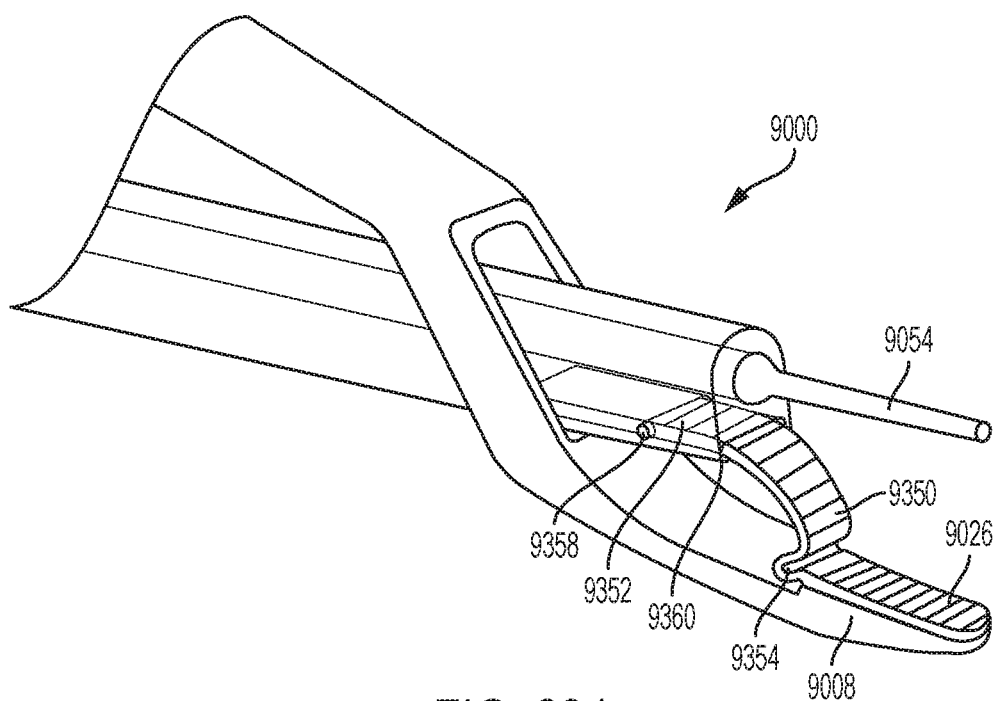

FIG. 234 illustrates a perspective view of an ultrasonic surgical instrument incorporating a flexible strip tissue stop, according to one aspect of this disclosure.

Figure 235:
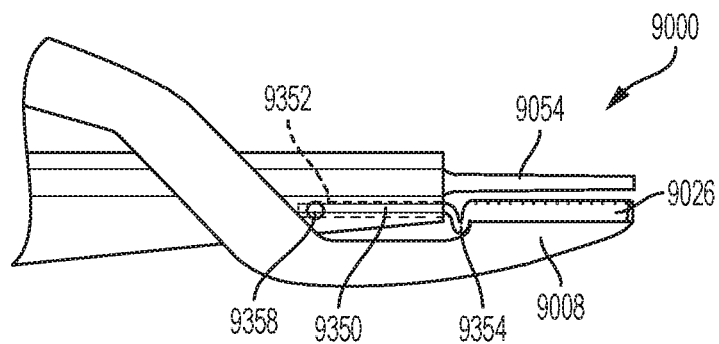

FIG. 235 illustrates a side view of the ultrasonic surgical instrument in FIG. 234 in a closed position, according to one aspect of this disclosure.

Figure 236:
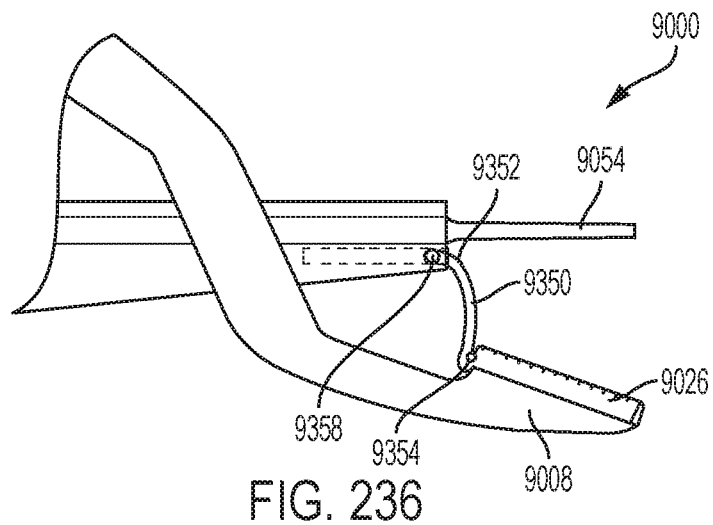

FIG. 236 illustrates a side view of the ultrasonic surgical instrument in FIG. 234 in an open position, according to one aspect of this disclosure.

Figure 237:
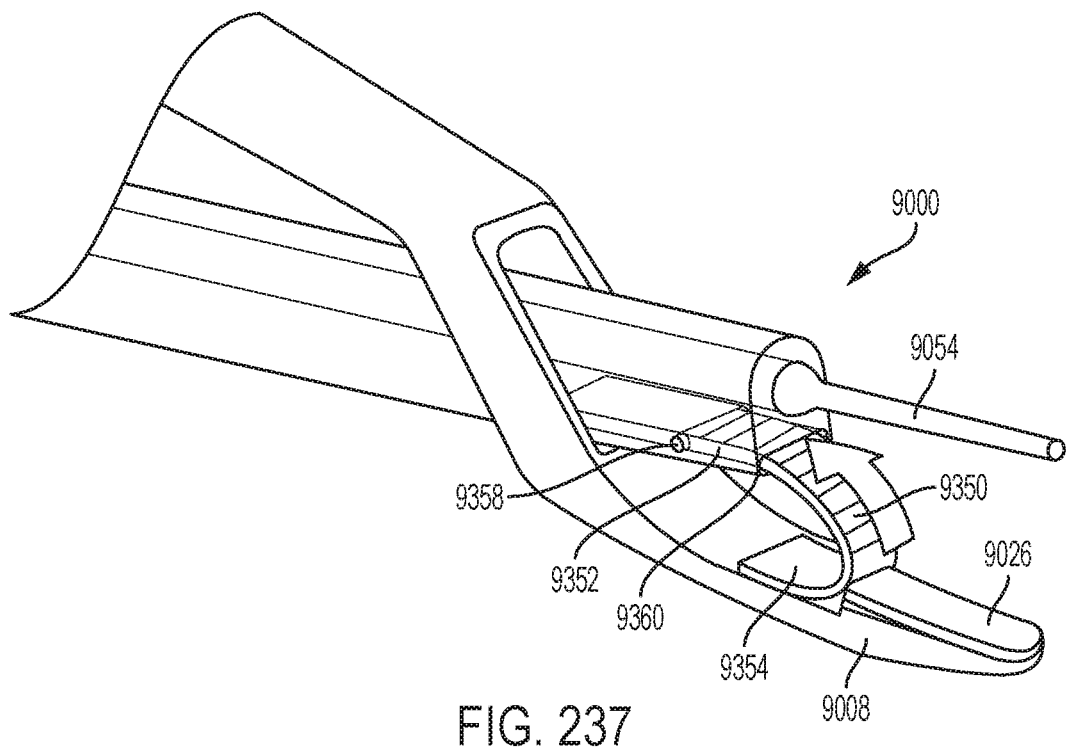

FIG. 237 illustrates a perspective view of an ultrasonic surgical instrument incorporating a flexible strip tissue stop, according to one aspect of this disclosure.

Figure 238:
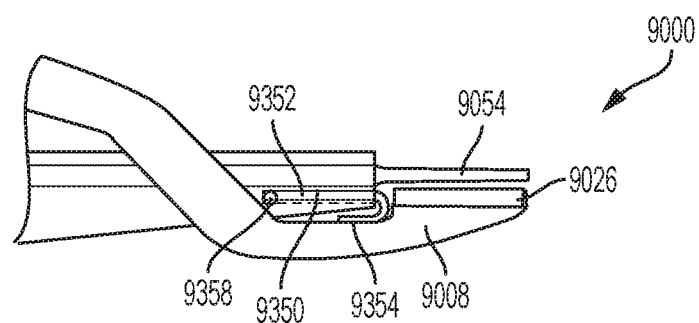

FIG. 238 illustrates a side view of the ultrasonic surgical instrument in FIG. 237 in a closed position, according to one aspect of this disclosure.

Figure 239:
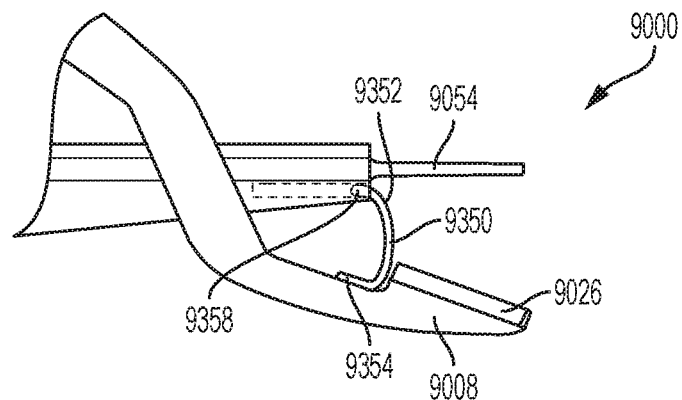

FIG. 239 illustrates a side view of the ultrasonic surgical instrument in FIG. 237 in an open position, according to one aspect of this disclosure.

DESCRIPTION

Ultrasonic Transducer for Surgical Instrument

Applicant of the present application owns the following patent applications filed on Aug. 17, 2017 and which are each herein incorporated by reference in their respective entireties:

U.S. patent application Ser. No. 15/679,948, entitled "Ultrasonic Transducer For Surgical Instrument" by inventors Jeffrey Messerly et al. filed Aug. 17, 2017, now U.S. Pat. No. 10,420,580;

U.S. patent application Ser. No. 15/679,959, entitled "Electrical And Thermal Connections For Ultrasonic Transducer" by inventors Jeffrey Messerly et al. filed Aug. 17, 2017, now U.S. Pat. No. 10,736,649;

U.S. patent application Ser. No. 15/679,960, entitled "Ultrasonic Transducer to Waveguide Acoustic Coupling, Connections, and Configurations" by inventors Jeffrey Messerly et al. filed Aug. 17, 2017, now U.S. Pat. No. 10,828,056;

U.S. patent application Ser. No. 15/679,960, entitled "Ultrasonic Transducer to Waveguide Joining" by inventors Jeffrey Messerly et al. filed Aug. 17, 2017, now U.S. Pat. No. 10,779,847;

U.S. patent application Ser. No. 15/679,967, "Tissue Loading of a Surgical Instrument" by inventors Jeffrey Messerly et al. filed Aug. 17, 2017, now U.S. Pat. No. 10,952,759.

Before explaining various aspects in detail, it should be noted that such aspects are not limited in their application or use to the details of construction and arrangement of parts illustrated in the accompanying drawings and description. The illustrative aspects may be implemented or incorporated in other aspects, variations and modifications, and may be practiced or carried out in various ways. For example, the surgical instruments disclosed below are illustrative only and not meant to limit the scope or application thereof. Furthermore, unless otherwise indicated, the terms and expressions employed herein have been chosen for the purpose of describing the illustrative aspects for the convenience of the reader and are not to limit the scope thereof.

Certain exemplary aspects will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various aspects is defined solely by the claims. The features illustrated or described in connection with one exemplary aspect may be combined with the features of other aspects. Such modifications and variations are intended to be included within the scope of the claims.

Various aspects described herein relate, in general, to ultrasonic surgical instruments and blades for use therewith. Examples of ultrasonic surgical instruments and blades are disclosed in U.S. Pat. Nos. 5,322,055; 5,954,736; 6,309,400; 6,278,218; 6,283,981; 6,325,811; and 8,319,400, wherein the entire disclosures of which are incorporated by reference herein.

According to various aspects, an ultrasonic instrument comprising a surgical tool having an end effector such as a blade can yield a particular benefit or benefits in orthopedic procedures where it is desirable to remove cortical bone and/or tissue while controlling bleeding. Due to its cutting and coagulation characteristics, a blade of an ultrasonic surgical instrument may be useful for general soft tissue cutting and coagulation. In certain circumstances, a blade according to various aspects may be useful to simultaneously cut and hemostatically seal or cauterize tissue. A blade may be straight or curved, and useful for either open or laparoscopic applications. A blade according to various aspects may be useful in spine surgery, especially to assist in posterior access in removing muscle from bone.

Figure 1:
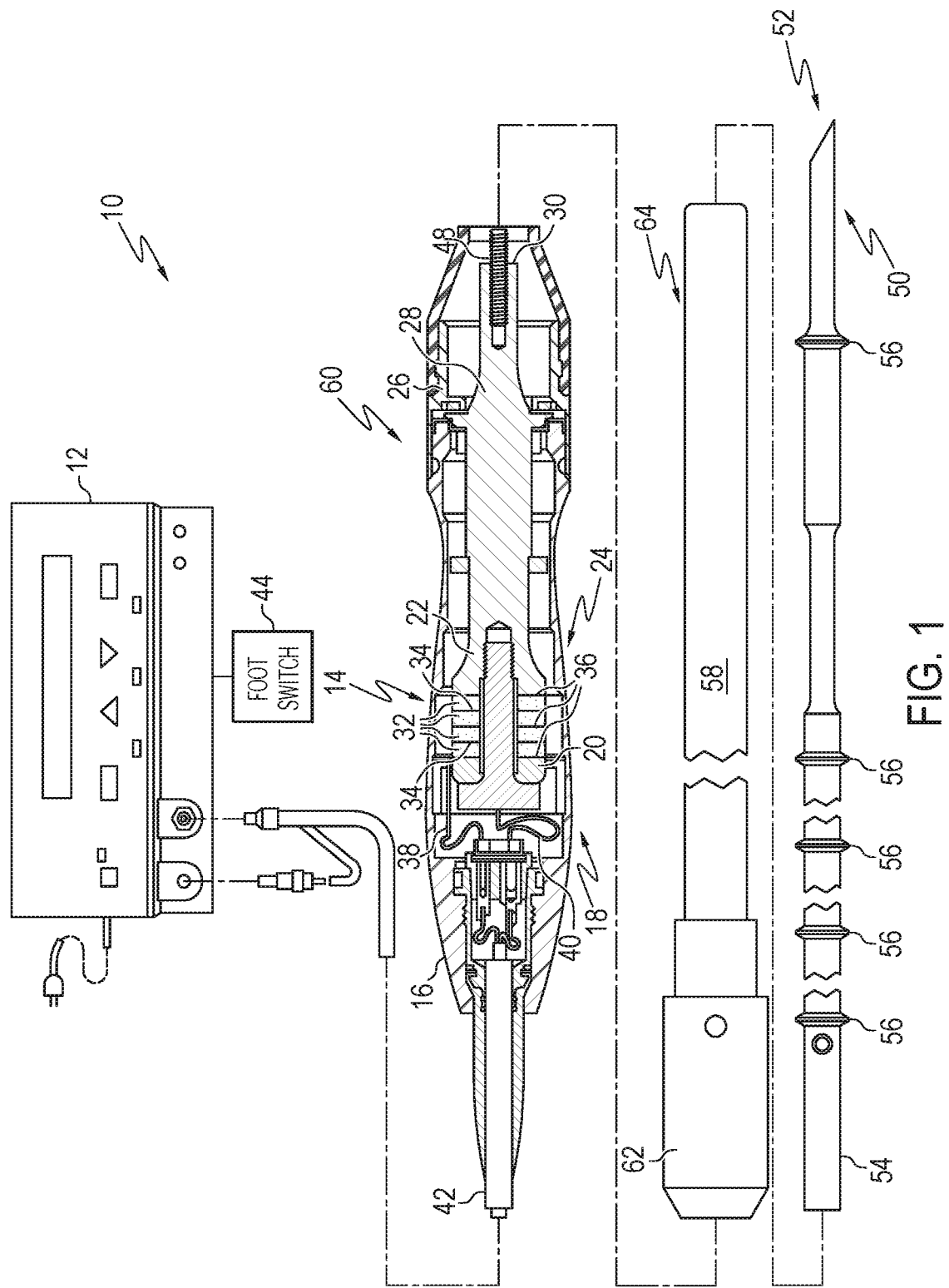
FIG. 1 illustrates an ultrasonic surgical instrument system, according to one aspect of this disclosure.

FIG. 1 illustrates one aspect of an ultrasonic system 10. One aspect of the ultrasonic system 10 comprises an ultrasonic signal generator 12 coupled to an ultrasonic transducer 14, a hand piece assembly 60 comprising a hand piece housing 16, and an end effector 50. The ultrasonic transducer 14, which is known as a "Langevin stack," generally includes a transduction portion 18, a first resonator or end-bell 20, and a second resonator or fore-bell 22, and ancillary components. In various aspects, the ultrasonic transducer 14 is preferably an integral number of one-half system wavelengths (n$\lambda$/2) in length as will be described in more detail below. An acoustic assembly 24 can include the ultrasonic transducer 14, a mount 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude of the velocity transformer 28, or, alternately, fore-bell 22 may have no tapering.

Referring again to FIG. 1, end-bell 20 can include a threaded member extending therefrom which can be configured to be threadably engaged with a threaded aperture in fore-bell 22. In various aspects, piezoelectric elements, such as piezoelectric elements 32, for example, can be compressed between end-bell 20 and fore-bell 22 when end-bell 20 and fore-bell 22 are assembled together. Piezoelectric elements 32 may be fabricated from any suitable material, such as, for example, lead zirconate-titanate, lead metaniobate, lead titanate, and/or any suitable piezoelectric crystal material, for example.

In various aspects, as discussed in greater detail below, transducer 14 can further comprise electrodes, such as positive electrodes 34 and negative electrodes 36, for example, which can be configured to create a voltage potential across one or more piezoelectric elements 32. Each of the positive electrodes 34, negative electrodes 36, and the piezoelectric elements 32 can comprise a bore extending through the center which can be configured to receive the threaded member of end-bell 20. In various aspects, the positive and negative electrodes 34 and 36 are electrically coupled to wires 38 and 40, respectively, wherein the wires 38 and 40 can be encased within a cable 42 and electrically connectable to the ultrasonic signal generator 12 of the ultrasonic system 10.

In various aspects, the ultrasonic transducer 14 of the acoustic assembly 24 converts the electrical signal from the ultrasonic signal generator 12 into mechanical energy that results in primarily longitudinal vibratory motion of the ultrasonic transducer 24 and the end effector 50 at ultrasonic frequencies. A suitable generator is available as model number GEN11, from Ethicon Endo-Surgery, Inc., Cincinnati, Ohio. When the acoustic assembly 24 is energized, a vibratory motion standing wave is generated through the acoustic assembly 24. A suitable vibrational frequency range may be about 20 Hz to 120 kHz and a well-suited vibrational frequency range may be about 30-70 kHz and one example operational vibrational frequency may be approximately 55.5 kHz.

The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength ($\lambda$/4).

As outlined above, the wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a foot switch 44, for example, to produce an acoustic standing wave in the acoustic assembly 24. The electrical signal causes disturbances in the piezoelectric elements 32 in the form of repeated small displacements resulting in large compression forces within the material. The repeated small displacements cause the piezoelectric elements 32 to expand and contract in a continuous manner along the axis of the voltage gradient, producing longitudinal waves of ultrasonic energy.

In various aspects, the ultrasonic energy produced by transducer 14 can be transmitted through the acoustic assembly 24 to the end effector 50 via an ultrasonic transmission waveguide 46. In order for the acoustic assembly 24 to deliver energy to the end effector 50, the components of the acoustic assembly 24 are acoustically coupled to the end effector 50. For example, the distal end of the ultrasonic transducer 14 may be acoustically coupled at the surface 30 to the proximal end of the ultrasonic transmission waveguide 46 by a threaded connection such as a stud 48.

The components of the acoustic assembly 24 can be acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths ($\lambda/2$). A distal end 52 of the ultrasonic end effector 50 may be disposed at, or at least near, an antinode in order to provide the maximum, or at least nearly maximum, longitudinal excursion of the distal end. When the transducer assembly is energized, in various aspects, the distal end 52 of the ultrasonic end effector 50 may be configured to move in the range of, for example, approximately 10 to 500 microns peak-to-peak and preferably in the range of approximately 30 to 150 microns at a predetermined vibrational frequency.

As outlined above, the ultrasonic end effector 50 may be coupled to the ultrasonic transmission waveguide 46. In various aspects, the ultrasonic end effector 50 and the ultrasonic transmission guide 46 as illustrated are formed as a single unit construction from a material suitable for transmission of ultrasonic energy such as, for example, Ti6Al4V (an alloy of titanium including aluminum and vanadium), aluminum, stainless steel, and/or any other suitable material. Alternately, the ultrasonic end effector 50 may be separable (and of differing composition) from the ultrasonic transmission waveguide 46, and coupled by, for example, a stud, weld, glue, quick connect, or other suitable known methods. The ultrasonic transmission waveguide 46 may have a length substantially equal to an integral number of one-half system wavelengths ($\lambda/2$), for example. The ultrasonic transmission waveguide 46 may be preferably fabricated from a solid core shaft constructed out of material that propagates ultrasonic energy efficiently, such as titanium alloy (i.e., Ti6Al4V) or an aluminum alloy, for example.

In the aspect illustrated in FIG. 1, the ultrasonic transmission waveguide 46 comprises a proximal portion 54 and a plurality of stabilizing silicone rings or compliant supports 56 positioned at, or at least near, a plurality of nodes. The silicone rings 56 can dampen undesirable vibration and isolate the ultrasonic energy from a sheath 58 at least partially surrounding waveguide 46, thereby assuring the flow of ultrasonic energy in a longitudinal direction to the distal end 52 of the end effector 50 with maximum efficiency.

As shown in FIG. 1, the sheath 58 can be coupled to the distal end of the handpiece assembly 60. The sheath 58 generally includes an adapter or nose cone 62 and an elongated tubular member 64. The tubular member 64 is attached to and/or extends from the adapter 62 and has an opening extending longitudinally therethrough. In various aspects, the sheath 58 may be threaded or snapped onto the distal end of the housing 16. In at least one aspect, the ultrasonic transmission waveguide 46 extends through the opening of the tubular member 64 and the silicone rings 56 can contact the sidewalls of the opening and isolate the ultrasonic transmission waveguide 46 therein. In various aspects, the adapter 62 of the sheath 58 is preferably constructed from Ultem®, for example, and the tubular member 64 is fabricated from stainless steel, for example. In at least one aspect, the ultrasonic transmission waveguide 46 may have polymeric material, for example, surrounding it in order to isolate it from outside contact.

As described above, a voltage, or power source can be operably coupled with one or more of the piezoelectric elements of a transducer, wherein a voltage potential applied to each of the piezoelectric elements can cause the piezoelectric elements to expand and contract, or vibrate, in a longitudinal direction. As also described above, the voltage potential can be cyclical and, in various aspects, the voltage potential can be cycled at a frequency which is the same as, or nearly the same as, the resonant frequency of the system of components comprising transducer 14, wave guide 46, and end effector 50, for example. In various aspects, however, certain of the piezoelectric elements within the transducer may contribute more to the standing wave of longitudinal vibrations than other piezoelectric elements within the transducer. More particularly, a longitudinal strain profile may develop within a transducer wherein the strain profile may control, or limit, the longitudinal displacements that some of the piezoelectric elements can contribute to the standing wave of vibrations, especially when the system is being vibrated at or near its resonant frequency.

It may be recognized, in reference to the ultrasonic surgical instrument system 10 of FIG. 1, that multiple components may be required to couple the mechanical vibrations from the piezoelectric elements 32 through the wave guide 46 to the end effector 50. The additional acoustic elements comprising the acoustic assembly 24 may add additional manufacturing costs, fabrication steps, and complexity to the system. Disclosed below are aspects of an ultrasonic medical device that may require fewer components, manufacturing steps, and costs than the equivalent device illustrated in FIG. 1 and as disclosed above.

Again, referring to FIG. 1, the piezoelectric elements 32 are configured into a "Langevin" stack, in which the piezoelectric elements 32 and their activating electrodes 34 and 36 (together, transducer 14) are interleaved. The mechanical vibrations of the activated piezoelectric elements 32 propagate along the longitudinal axis of the transducer 14, and are coupled via the acoustic assembly 24 to the end of the waveguide 46. Such a mode of operation of a piezoelectric element is frequently described as the D33 mode of the element, especially for ceramic piezoelectric elements comprising, for example, lead zirconate-titanate, lead metaniobate, or lead titanate. The D33 mode of operation of a ceramic piezoelectric element is illustrated in FIGS. 2A-2C.

Figure 2A:
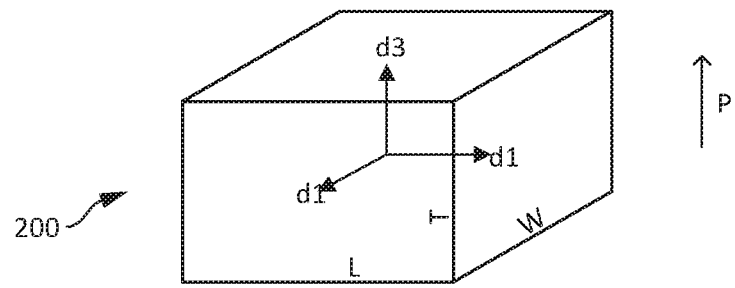
FIGS. 2A-2C illustrate a piezoelectric transducer, according to one aspect of this disclosure.

FIG. 2A depicts an exemplary piezoelectric element 200 fabricated from a ceramic piezoelectric material. A piezoelectric ceramic material is a polycrystalline material comprising a plurality of individual microcrystalline domains. Each microcrystalline domain possesses a polarization axis along which the domain may expand or contract in response to an imposed electric field. However, in a native ceramic, the polarization axes of the microcrystalline domains are arranged randomly, so there is no net piezoelectric effect in the bulk ceramic. A net re-orientation of the polarization axes may be induced by subjecting the ceramic to a temperature above the Currie temperature of the material and placing the material in a strong electrical field. Once the temperature of the sample is dropped below the Currie temperature, a majority of the individual polarization axes will be re-oriented and fixed in a bulk polarization direction. FIG. 2A illustrates such a piezoelectric element 200 after being polarized along the inducing electric field axis P. While the un-polarized piezoelectric element 200 lacks any net piezoelectric axis, the polarized element 200 can be described as possessing a polarization axis, d3, parallel to the inducing field axis P direction. For completeness, an axis orthogonal to the d3 axis may be termed a d1 axis. The dimensions of the piezoelectric element 200 are labeled as length (L), width (W), and thickness (T).

Figure 2B:
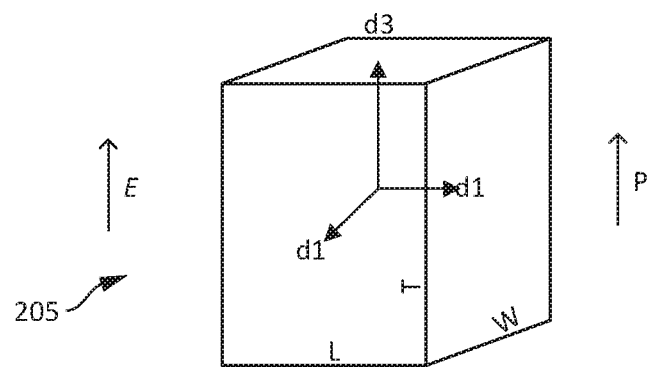
Figure 2C:
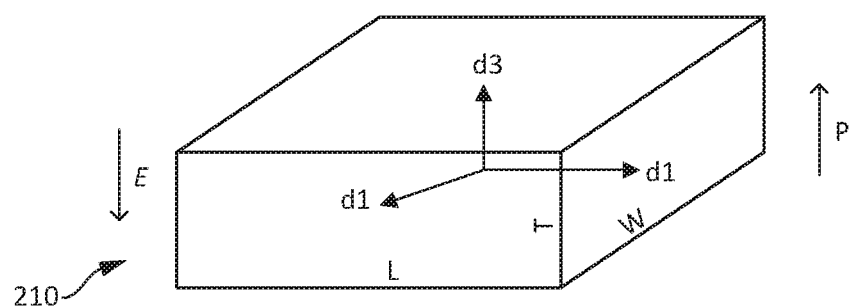

FIGS. 2B and 2C illustrate the mechanical deformations of a piezoelectric element 200 that may be induced by subjecting the piezoelectric element 200 to an actuating electrical field E oriented along the d3 (or P) axis. FIG. 2B illustrates the effect of an electric field E having the same direction as the polarization field P along the d3 axis on a piezoelectric element 205. As illustrated in FIG. 2B, the piezoelectric element 205 may deform by expanding along the d3 axis while compressing along the d1 axis. FIG. 2C illustrates the effect of an electric field E having the opposing direction to the polarization field P along the d3 axis on a piezoelectric element 210. As illustrated in FIG. 2C, the piezoelectric element 210 may deform by compressing along the d3 axis, while expanding along the d1 axis. Vibrational coupling along the d3 axis during the application of an electric field along the d3 axis may be termed D33 coupling or activation using a D33 mode of a piezoelectric element. The transducer 14 illustrated in FIG. 1 uses the D33 mode of the piezoelectric elements 32 for transmitting mechanical vibrations along the wave guide 46 to the end effector 50.

Because the piezoelectric elements 32 also deform along the d1 axis, vibrational coupling along the d1 axis during the application of an electric field along the d3 axis may also be an effective source of mechanical vibrations. Such coupling may be termed D31 coupling or activation using a D31 mode of a piezoelectric element. As illustrated by FIGS. 2A-2C, during operation in the D31 mode, transverse expansion of piezoelectric elements 200, 205, 210 may be mathematically modeled by the following equation:

$$\frac{\Delta L}{L} = \frac{\Delta W}{W} = \frac{V_{d31}}{T}$$

In the equation, L, W, and T refer to the length, width and thickness dimensions of a piezoelectric element, respectively. $V_{d31}$ denotes the voltage applied to a piezoelectric element operating in the D31 mode. The quantity of transverse expansion resulting from the D31 coupling described above is represented by $\Delta L$ (i.e., expansion of the piezoelectric element along the length dimension) and $\Delta W$ (i.e., expansion of the piezoelectric element along the width dimension). Additionally, the transverse expansion equation models the relationship between $\Delta L$ and $\Delta W$ and the applied voltage $V_{d31}$. Disclosed below are aspects of ultrasonic medical devices based on D31 activation by a piezoelectric element.

In various aspects, as described below, a ultrasonic medical device can comprise a transducer configured to produce longitudinal vibrations, and a surgical tool having a transducer mounting portion operably coupled to the transducer, an end effector, and wave guide therebetween. In certain aspects, as also described below, the transducer can produce vibrations which can be transmitted to the end effector, wherein the vibrations can drive the transducer mounting portion, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer mounting portion, wave guide, and/or end effector, in a sinusoidal, or at least substantially sinusoidal, manner. In at least one aspect, for example, the longitudinal strain pattern can have maximum peaks and zero points, wherein the strain values can vary in a nonlinear manner between such peaks and zero points.

FIG. 3 illustrates an ultrasonic surgical instrument 250 that includes an ultrasonic waveguide 252 attached to an ultrasonic transducer 264 by a bonding material, where the ultrasonic surgical instrument 250 is configured to operate in a D31 mode, according to one aspect of the present disclosure. The ultrasonic transducer 264 includes first and second piezoelectric elements 254a, 254b attached to the ultrasonic waveguide 252 by a bonding material. The piezoelectric elements 254a, 254b include electrically conductive plates 256a, 256b to electrically couple one pole of a voltage source suitable to drive the piezoelectric elements 254a, 254b (e.g., usually a high voltage). The opposite pole of the voltage source is electrically coupled to the ultrasonic waveguide 252 by electrically conductive joints 258a, 258b. In one aspect, the electrically conductive plates 256a, 256b are coupled to a positive pole of the voltage source and the electrically conductive joints 258a, 258b are electrically coupled to ground potential through the metal ultrasonic waveguide 252. In one aspect, the ultrasonic waveguide 252 is made of titanium or titanium alloy (i.e., Ti6Al4V) and the piezoelectric elements 254a, 254b are made of a lead zirconate titanate intermetallic inorganic compound with the chemical formula $Pb[Zr_xTi_{1-x}]O_3$ ($0 \leq x \leq 1$). Also called PZT, it is a ceramic perovskite material that shows a marked piezoelectric effect, meaning that the compound changes shape when an electric field is applied. It is used in a number of practical applications such as ultrasonic transducers and piezoelectric resonators PZT. The poling axis (P) of the piezoelectric elements 254a, 254b is indicated by the direction arrow 260. The motion axis of the ultrasonic waveguide 252 in response to excitation of the piezoelectric elements 254a, 245b is shown by a motion arrow 262 at the distal end of the ultrasonic waveguide 252 generally referred to as the ultrasonic blade portion of the ultrasonic waveguide 252. The motion axis 262 is orthogonal to the poling axis (P) 260.

In conventional D33 ultrasonic transducer architectures as shown in FIG. 1, the bolted piezoelectric elements 32 utilize electrodes 34, 36 to create electrical contact to both sides of each piezoelectric element 34. The D31 architecture 250 according to one aspect of the present disclosure, however, employs a different technique to create electrical contact to both sides of each piezoelectric element 254a, 254b. Various techniques for providing electrical contact to the piezoelectric elements 254a, 254b include bonding electrical conductive elements (e.g., wires) to the free surface of each piezoelectric element 254a, 254b for the high potential connection and bonding each piezoelectric element 254a, 254b the to the ultrasonic waveguide 252 for the ground connection using solder, conductive epoxy, or other techniques described herein. Compression can be used to maintain electrical contact to the acoustic train without making a permanent connection. This can cause an increase in device thickness and should be controlled to avoid damaging the piezoelectric elements 254a, 254b. Low compression can damage the piezoelectric element 254a, 254b by a spark gap and high compression can damage the piezoelectric elements 254a, 254b by local mechanical wear. In other techniques, metallic spring contacts may be employed to create electrical contact with the piezoelectric elements 254a, 254b. Other techniques may include foil-over-foam gaskets, conductive foam, solder. Electrical connection to both sides of the piezoelectric elements 254a, 254b the D31 acoustic train configuration. The electrical ground connection can be made to the metal ultrasonic waveguide 252, which is electrically conductive, if there is electrical contact between the piezoelectric elements 254a, 254b and the ultrasonic waveguide 252.

In various aspects, as described below, an ultrasonic medical device may comprise a transducer configured to produce longitudinal vibrations, and a surgical instrument having a transducer mounting portion operably coupled to the transducer, an end effector, and wave guide therebetween. In certain aspects, as also described below, the transducer can produce vibrations which can be transmitted to the end effector, wherein the vibrations can drive the transducer mounting portion, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer mounting portion, wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points.

In conventional D33 ultrasonic transducer architectures as shown in FIG. 1, a bolt provides compression that acoustically couples the piezoelectric elements rings to the ultrasonic waveguide. The D31 architecture 250 according to one aspect of the present disclosure employs a variety of different techniques to acoustically couple the piezoelectric elements 254a, 254b to the ultrasonic waveguide 252. These techniques are disclosed hereinbelow.

FIG. 4A illustrates an aspect of an ultrasonic medical device 300 that incorporates one or more piezoelectric transducers 312a,b configured to operate in a D31 mode. The ultrasonic medical device 300 may include a surgical tool 301 having a waveguide 310 and a transducer mounting portion 320 (e.g., a transducer base plate). In some aspects, the surgical tool 301 may be fabricated from sheet stock and have essentially flat faces 325 and side edges 327 orthogonal to the flat faces 325. The waveguide 310 may include an end effector at a distal end and a longitudinal portion connecting the end effector with the transducer mounting portion 320 (located at a proximal end of the surgical tool 301). One or more piezoelectric transducers 312a,b may be affixed to the transducer mounting portion 320 of the surgical tool 301. In certain aspects, the waveguide 310 may also include one or more stabilizing silicone rings or compliant supports 306 positioned at, or at least near, a plurality of vibration nodes, which may dampen undesirable vibration and isolate the ultrasonic energy from a sheath at least partially surrounding the surgical tool 301. In order for the piezoelectric transducers 312a,b to operate in a D31 mode, a first electrode may be electrically coupled to an exposed face of a transducer (for example 312a) that is opposite to the face of the transducer in mechanical communication with a face 325 of the surgical tool 301. In some aspects, a conductive electrode (for example, a silver electrode) may be painted or screen printed on an exposed face of the piezoelectric transducers 312a,b and conducting wires may then be soldered onto the conductive electrodes. Alternatively, the wires may be affixed to the exposed faces of the piezoelectric transducers 312a,b by means of a conductive epoxy. The surgical tool may be electrically coupled to a second electrode, thereby permitting an electric field to be imposed on the piezoelectric transducer orthogonal to a longitudinal axis of the surgical tool 301.

FIG. 4B is a close-up view of the transducer mounting portion 320 of the ultrasonic medical device of FIG. 4A, illustrating the mechanical contacts that may be made between a face of each of the piezoelectric transducers 312a,b and a face 325 of the surgical tool 301. In the aspect illustrated in FIG. 4B, a single pair of piezoelectric transducers 312a,b contact the surgical tool 301 based on a face of each transducer 312a,b contacting an opposing face of the surgical tool. It may be observed that each of the pair of piezoelectric transducers 312a,b is positioned opposite the other. As disclosed above with respect to FIG. 1, the piezoelectric transducers 312a,b may be activated by a power source at a predetermined frequency to induce a standing mechanical wave along the body of the surgical tool 301. The standing wave may be proportional to the predetermined frequency component of the electrical signal. The standing wave induced along the body of the surgical tool 301 may be characterized by one or more nodes and anti-nodes. The standing wave nodes may be effectively centered at one or more node locations on the surgical tool 301, and the standing wave anti-nodes may be effectively centered at one or more anti-node locations on the surgical tool 301. Each piezoelectric transducer 312a,b may be symmetrically disposed about a node location in the transducer mounting portion 320 of the surgical tool 301. Such a disposition may result in each transducer 312a, b contacting a portion of the surgical tool 301 at a location having minimal mechanical displacement during the activation of the transducers 312a,b.

FIG. 5 illustrates a mechanism for attaching a piezoelectric transducer to the transducer mounting portion 320 of a surgical tool. A node location 510 of the surgical tool at the transducer mounting portion 320 may be identified based on the wavelength of the standing wave induced in the surgical tool. An electrically conductive adhesive 520 may be applied to the face 325 of the transducer mounting portion 320 centered around the node location 510 of the surgical tool. Additionally, a high strength adhesive 530 may be applied to the face 325 of the transducer mounting portion 320 near the electrically conductive adhesive 520 and somewhat distant from the node location 510. In some aspects, the electrically conductive adhesive 520 may include an electrically conductive epoxy adhesive. In some aspects, the high strength adhesive 530 may include a high strength epoxy adhesive. As disclosed above, the piezoelectric transducers may operate in a D31 mode if the activating electric field is oriented orthogonal to the axis of the surgical tool. Thus, a first electrode may contact the piezoelectric transducer on one face opposing the face of the transducer in contact with the surgical tool. The surgical tool may form the second electrode. The electrically conductive adhesive 520 may thus provide the piezoelectric transducer with an electrical contact with the surgical tool, while the high strength adhesive 530 may form a mechanically stable contact between the piezoelectric transducer and the surgical tool.

Figure 6:
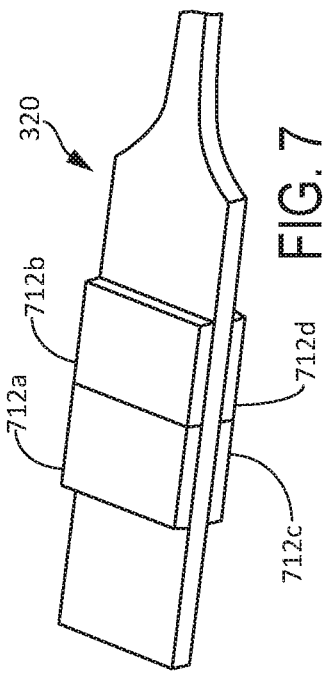
FIGS. 6-9 are perspective views of a transducer mounting portion of an ultrasonic medical device having multiple pairs of piezoelectric transducers, according to one aspect of this disclosure.

FIGS. 6-9 depict alternative aspects of an ultrasonic medical device including multiple pairs of piezoelectric transducers. FIG. 6 illustrates the transducer mounting portion 320 of a surgical tool having a first pair of piezoelectric transducers 312*a,b* contacting the surgical tool and each of a second pair of piezoelectric transducers 612*a,b* may contact an exposed face of one of the first pair of transducer 312*a,b*. The second pair of piezoelectric transducers 612*a,b* may have the same or smaller dimensions as the first pair 312*a,b*.

Figure 7:
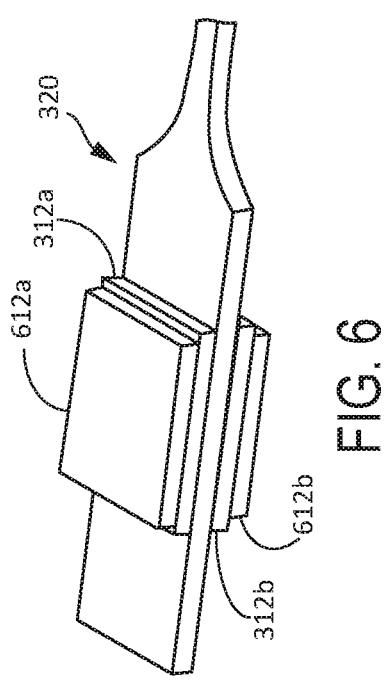

FIG. 7 depicts a total of four piezoelectric transducers 712*a-d* disposed as a pair of transducers 712*a,b* contacting a first face of the transducer mounting portion 320 of the surgical tool and a second pair of transducer 712*c,d* disposed opposite to the first pair of transducers 712*a,b* and contacting an opposing face of the surgical tool. In some aspects, piezoelectric transducers 712*a* and 712*c* may be disposed on one side of a node location of the transducer mounting portion 320, while piezoelectric transducers 712*b* and 712*d* may be disposed adjacent to piezoelectric transducers 712*a* and 712*c*, respectively, and on a second side of the node location.

Figure 8:
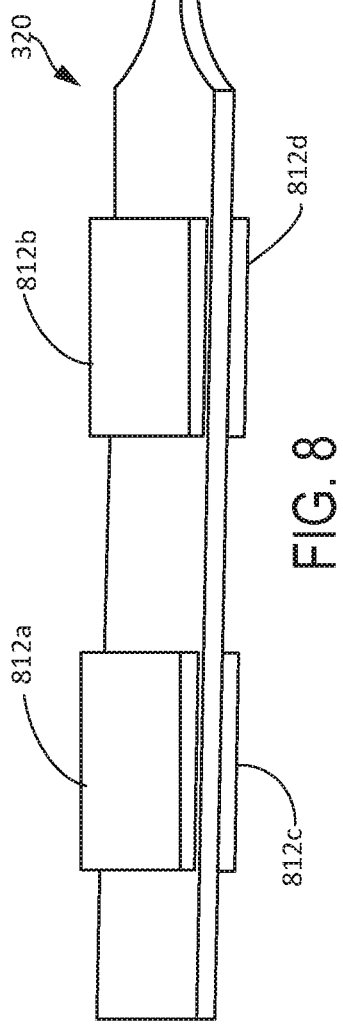

In another aspect, illustrated in FIG. 8, a total of four piezoelectric transducers 812*a-d* disposed as a pair of transducers 812*a,b* contacting a first face of the transducer mounting portion 320 of the surgical tool and a second pair of transducer 812*c,d* disposed opposite to the first pair of transducers 812*a,b* and contacting an opposing face of the surgical tool. In some aspects, piezoelectric transducers 812*a* and 812*c* may be disposed at some distance from a node location of the transducer mounting portion 320, while piezoelectric transducers 812*b* and 812*d* may be disposed symmetrically about the node location with respect to piezoelectric transducers 812*a* and 812*c* and at the same distance from the node location. Alternatively, piezoelectric transducers 812*a* and 812*c* may be centered about a first node location of the transducer mounting portion 320, while piezoelectric transducers 812*b* and 812*d* may be centered about a second node location.

Figure 9:
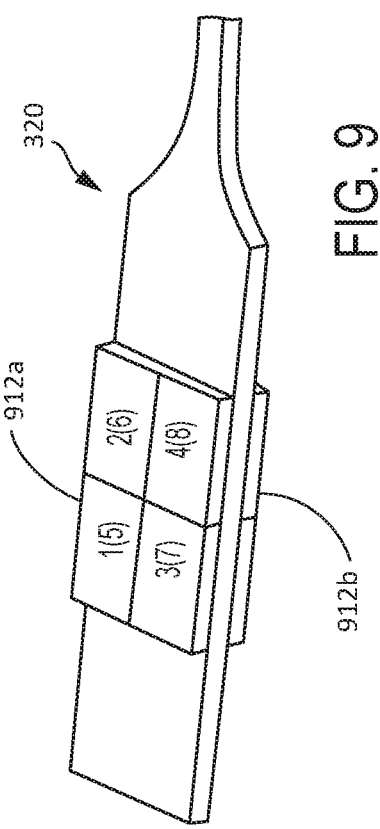

FIG. 9 illustrates an aspect in which a first transducer 912*a* comprises a first planar array of first transducer plates and the second transducer 912*b* comprises a second planar array of second transducer plates. As illustrated in FIG. 9, the first transducer 912*a* comprises a first planar array of first transducer plates indicated by numbers 1, 2, 3, and 4. The second transducer 912*b* comprises a second planar array of second transducer plates (not visible in the perspective view of FIG. 9) indicated by numbers in parentheses (5), (6), (7), and (8). It may be understood that second transducer plate (5) is disposed on an opposing side of the transducer mounting portion 320 with respect to first transducer plate 1, second transducer plate (6) is disposed on an opposing side of the transducer mounting portion 320 with respect to first transducer plate 2, second transducer plate (7) is disposed on an opposing side of the transducer mounting portion 320 with respect to first transducer plate 3, and second transducer plate (8) is disposed on an opposing side of the transducer mounting portion 320 with respect to first transducer plate 4. Transducer plates 1, (5), 3, and (7) may be disposed about one side of a node location and transducer plates 2, (6), 4, and (8) may be disposed about an opposing side of the node location.

It may be understood that the transducers or transducer plates depicted in the aspects in FIGS. 1, 3-4, 6-9 may all be made of the same material. Alternatively, the transducers or transducer plates depicted in the aspects in FIGS. 1, 3-4, 6-9 may be made of different materials. For example the transducers or transducer plates may be fabricated from piezoelectric materials that differ in their respective strain constants, dielectric dissipation or dampening properties, dielectric constants, voltage sensitivities, or Currie temperatures. Similarly, the transducers or transducer plates may all have the same shape and size. Alternatively, transducers or transducer plates may differ in shape, size, or both shape and size depending on their respective placements on the surgical tool or on each other.

Each transducer or transducer plate illustrated in FIGS. 1, 3-4, 6-9 may be individually activated. In some aspects, each transducer or transducer plate may be activated by a separate ultrasonic signal generator in which the individual ultrasonic signal generators have a common ground in electrical communication with the surgical tool. In such an aspect, each transducer or transducer plate may be activated by a separate electric signal. In some examples, the electrical characteristics of the separate electrical signals may be the same, for example having the same amplitude, frequency, and phase. In alternative examples, the electrical characteristics of the separate electrical signals may differ in one or more of amplitude, frequency, and phase. In alternative aspects, each transducer or transducer plate may be activated by the same ultrasonic signal generator, but may be separately activatable by one or more transducer activation switches. Such switches may direct a first polarity of an ultrasonic signal to one set of transducers or transducer plates and a second polarity of the ultrasonic signal to a second set of transducers or transducer plates. It may be understood that such switches may also be used to disconnect one or more transducers or transducer plates from the ultrasonic signal generator while allowing other transducers or transducer plates to receive an ultrasonic signal from the ultrasonic signal generator.

In at least one such aspect, the surgical instrument can comprise a handle which can comprise one or more switches which can be configured to selectively actuate the transducers or transducer plates. For example, a switch can be moved from an off position to a first position in order to actuate a first transducer or set of transducer plates, to a second position to actuate the second transducer or set of transducer plates. It may be recognized that in an aspect such as depicted in FIG. 9, such a switch may have multiple positions, each position configured to actuate a specified group of transducer plates. In certain other aspects, a handle can comprise a first switch configured to selectively actuate a first transducer or set of transducer plates, and, in addition, a second switch configured to selectively actuate the second transducer or set of transducer plates. In such aspects, the surgeon can select the power to be supplied to the surgical tool and/or end effector.

It may be recognized that switched activation of the transducers or transducer plates may result in vibrational patterns of the surgical tool that are more complex than a single longitudinal standing mechanical wave. Such complex mechanical waves may be used to impart complex movement to the end effector of the surgical tool. For example, with respect to the aspect illustrated in FIG. 9, a predominantly transverse flapping motion may be induced in the end effector if transducer plates 1, 2, (5), and (6) are activated with a first polarity ultrasonic signal while transducer plates 3, 4, (7), and (8) are activated with a second and opposing polarity ultrasonic signal. A predominantly transverse hooking motion may be induced in the end effector if transducer plates 1, (5), 3, and (7) are activated with a first polarity ultrasonic signal while transducer plates 2, (6), 4, and (8) are activated with a second and opposing polarity ultrasonic signal. A predominantly torsional motion may be induced in the end effector if transducer plates 1, (7), 2, and (8) are activated with a first polarity ultrasonic signal while transducer plates 3, (5), 4, and (6) are activated with a second and opposing polarity ultrasonic signal. A combination of torsional and transverse motions may be induced in the end effector if transducer plates 1, (7), 4, and (6) are activated with a first polarity ultrasonic signal while transducer plates (5), 3, 2, and (8) are activated with a second and opposing polarity ultrasonic signal. Additional motions may be achieved through the activation of other groups of transducer plates.

Figure 10:
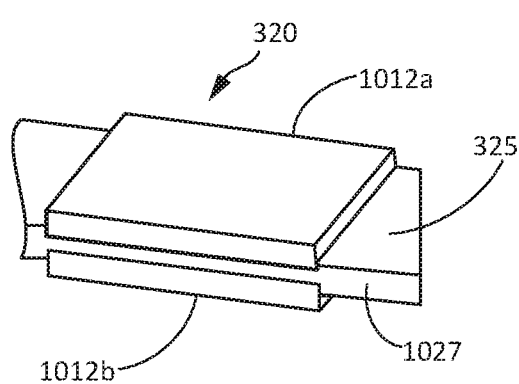
FIGS. 10 and 11 are perspective views of a transducer mounting portion of an ultrasonic medical device having a pair of piezoelectric transducers imbedded in a surgical tool, according to one aspect of this disclosure.
Figure 11:
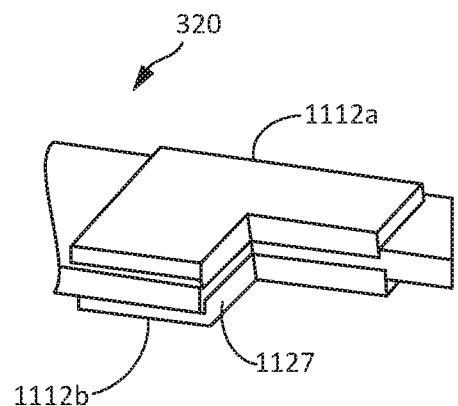

FIGS. 10 and 11 illustrate additional mechanisms by which the transducers may be affixed onto the surgical tool. The piezoelectric transducers may be mounted on the transducer mounting portion 320 of a surgical tool. The face 325 of the surgical tool may be machined to form a pocket in which the piezoelectric transducers may be mounted. As illustrated in FIG. 10, the piezoelectric transducers 1012*a,b* may have a width approximately equal to the width of the surgical tool, so the pocket may be fabricated across the width of the surgical tool and may extend to the edges 1027 of the surgical tool. As illustrated in FIG. 11, the piezoelectric transducers 1112*a,b* may have a width less than the width of the surgical tool, so the pocket may be fabricated within the width of the surgical tool but may not extent to the edges 1127 of the surgical tool. As illustrated in FIGS. 10 and 11, the thickness of the surgical tool within the pocket may be less than the overall thickness of the surgical tool. The piezoelectric transducers (1012*a,b* in FIGS. 10 and 1112*a,b* in FIG. 11) may be fixed within the respective pockets through the use of one or more adhesives, such as electrically conductive adhesives and/or high strength adhesives. Alternatively, the piezoelectric transducers (1012*a,b* in FIGS. 10 and 1112*a,b* in FIG. 11) may be fixed within the respective pockets by means of an interference fit. The interference fits may be accomplished by heating and cooling the surgical tool, thereby causing thermal expansion and contraction of the pocket of the surgical tool. The interference fits may also be accomplished by activating and deactivating the piezoelectric transducers, thereby causing piezoelectric expansion and contraction of the piezoelectric transducers.

Figure 12:
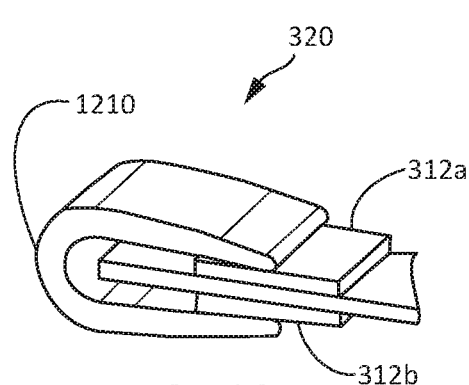
FIGS. 12 and 13 are perspective views of a transducer mounting portion of an ultrasonic medical device having a pair of piezoelectric transducers held by one or more securing clips, according to one aspect of this disclosure.
Figure 13:
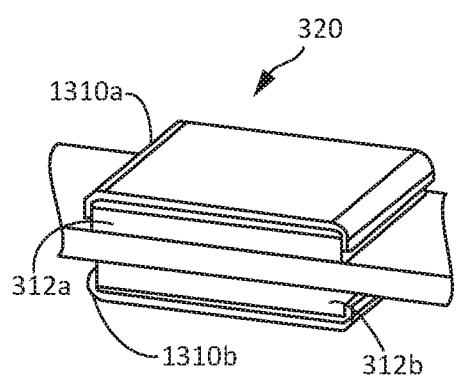

FIGS. 12 and 13 illustrate further mechanisms by which the transducers may be affixed onto the surgical tool by the use of one or more clips. FIG. 12 illustrates the use of a single clip 1210, such as a C-clip that may compress each of the piezoelectric transducers 312*a,b* against their respective faces of the transducer mounting portion 320 of the surgical tool. FIG. 13 depicts clips 1310*a,b* that may be used to apply a pre-loading compression across a longitudinal direction of the piezoelectric transducers 312*a,b*. The piezoelectric transducers 312*a,b* illustrated in FIG. 13 may be affixed to the surgical tool through one or more adhesives as disclosed above (for example in FIG. 5).

Figure 14:
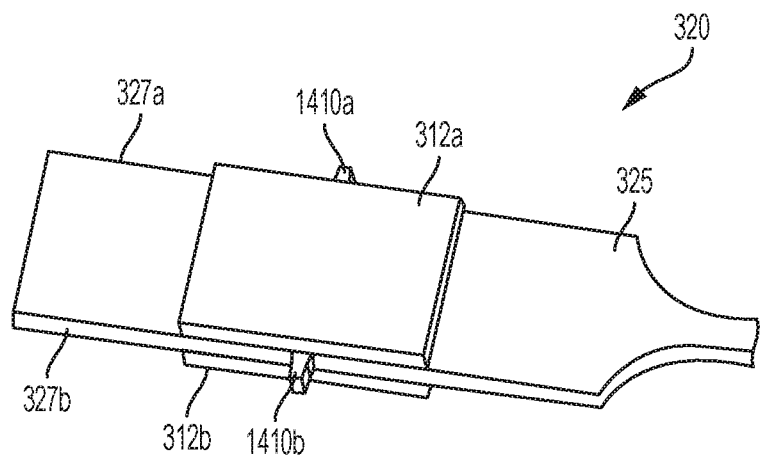
FIG. 14 is a perspective view of a transducer mounting portion of an ultrasonic medical device including mounting flanges, according to one aspect of this disclosure.

The ultrasonic medical device depicted in FIG. 3 may also incorporate features for mounting in an ultrasound system. FIG. 14 illustrates an aspect of an ultrasonic medical device adapted for mounting in a housing. As depicted in FIG. 14, the ultrasonic medical device may include a surgical tool having a transducer mounting portion 320 comprising faces (such as face 325) and edges such as edge 327). Piezoelectric transducers 312*a,b* may be mounted on the transducer mounting portion 320 and disposed symmetrically about a node location in the surgical tool. The surgical tool may be fabricated to incorporate flanges 1410*a,b* located at the node location on opposing edges 327*a,b* of the surgical tool. As depicted in FIG. 14, the first flange (for example 1410*a*) may extend from a first side edge 327*a* of the surgical tool and the second flange (for example 1410*b*) may extend from an opposing side edge 327*b* of the surgical tool, so that each of the first flange 1410*a* and the second flange 1410*b* may be symmetrically disposed about the node location in the surgical tool.

In various aspects, further to the above, an ultrasonic medical device may comprise a surgical tool comprising a transducer mounting portion, a waveguide, and an end effector, along with one or more piezoelectric transducers affixed thereon. The ultrasonic medical device may further comprise a housing at least partially surrounding the transducer mounting portion of the surgical tool and a sheath at least partially surrounding the waveguide and/or end effector. In at least one aspect, an ultrasonic medical device can comprise one or more piezoelectric transducers, a housing encompassing transducer mounting portion, waveguide, a sheath encompassing the waveguide, and an end effector. In certain aspects, the ultrasonic medical device can further comprise one or more stabilizing supports which can be configured to support the waveguide and/or end effector within the sheath. In at least one such aspect, the sheath can comprise a handle portion and/or can be configured to be grasped, or gripped, by a surgeon such that the surgeon can accurately manipulate the ultrasonic medical device and, in particular, accurately manipulate a distal end of the end effector. In at least one aspect, at least a portion of the outer surface of the sheath can comprise a roughened and/or textured surface. In certain aspects, the outer surface of the sheath can comprise a round, or at least substantially round, cross-section having a diameter of approximately 5 millimeters, approximately 10 millimeters, approximately 15 millimeters, and/or a diameter between approximately 4 millimeters and approximately 16 millimeters.

Figure 15:
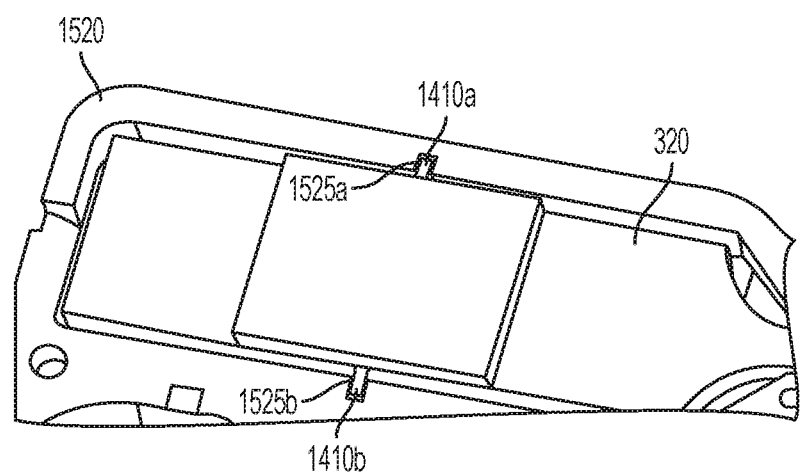
FIG. 15 is a perspective view of a transducer mounting portion of the ultrasonic medical device of FIG. 14 mounted in a housing, according to one aspect of this disclosure.
Figure 16:
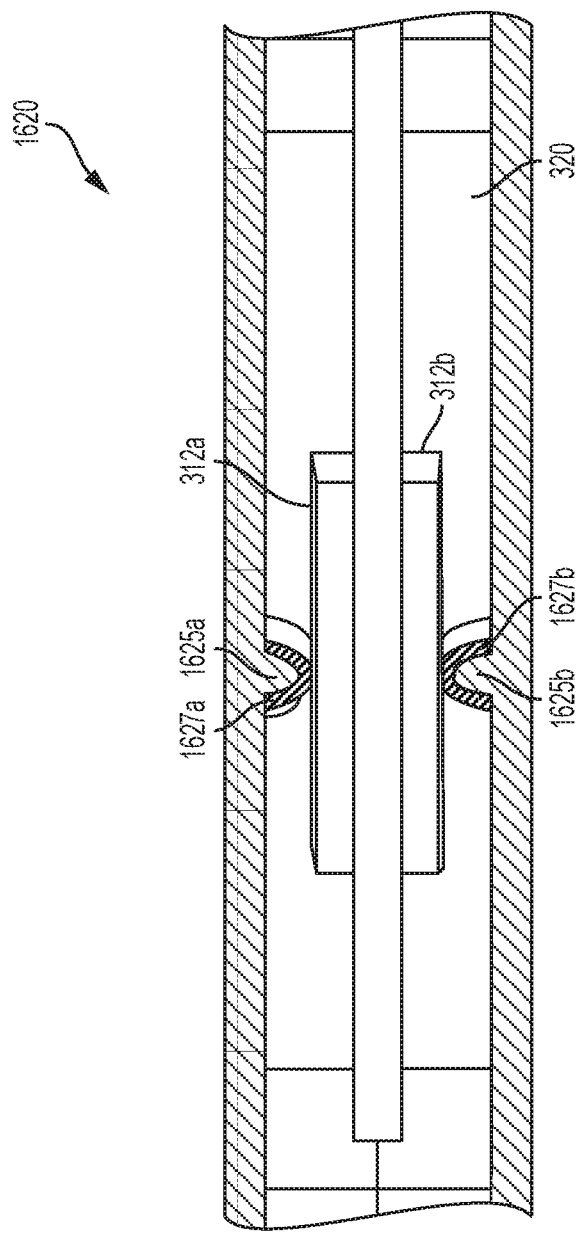
FIG. 16 is a side view the transducer mounting portion of the ultrasonic medical device of FIG. 1 mounted in a housing, according to one aspect of this disclosure, according to one aspect of this disclosure.

The ultrasonic medical device of FIG. 14 may be mounted in a housing as depicted in FIG. 15. The transducer mounting portion 320 may be mounted within a housing 1520 that includes retainers 1525*a,b*, in which each retainer 1525*a,b* is configured to receive one of the flanges 1410*a,b*. Such an arrangement may allow the surgical tool to move according to the standing wave induced therein, while being held securely in the housing 1520 at a node point that generally does not move while the piezoelectric transducers are activated. FIG. 16 illustrates an additional aspect for securing an ultrasonic medical device within a housing. FIG. 16 depicts the transducer mounting portion 320 of a surgical tool having a pair of piezoelectric transducers 312*a,b* mounted thereon. The housing may include a shroud 1620 that may surround the surgical tool. The shroud 1620 may include one or more contacts 1625a,b configured to apply a compressive force to the piezoelectric transducers 312a,b. The contacts 1625a,b may be designed to apply the compressive force to the piezoelectric transducers 312a,b approximately at a node location of the surgical tool when the piezoelectric transducers 312a,b are activated by an ultrasound generator. The contacts 1625a,b may be electrically conductive to permit power from the ultrasound generator to activate the piezoelectric transducers 312a,b. Alternatively, the contacts 1625a,b may include electrically conducting surfaces 1627a,b that directly contact the exposed surfaces of the piezoelectric transducers 312a,b. The electrically conducting surfaces 1627a,b that may be placed in electrical communication with the ultrasound generator to conduct energy from the ultrasound generator to the piezoelectric transducers 312a,b. Aspects of the ultrasonic medical device, as disclosed above, incorporate a surgical tool generally described as being manufactured from flat stock. However, additional aspects may include a surgical tool that may be manufactured from round stock or square stock (such as a long bar). FIGS. 17 and 18 depict aspects of an ultrasonic medical device manufactured from either round or square stock. Such an ultrasonic medical device may have a waveguide 1710 having a cylindrical or truncated conical cross section and a transducer mounting portion 1720 having a square or rectangular cross section. Alternatively, the waveguide 1710 may have the form of a double wedge with appropriate tips to achieve desired tissue effect. Double-wedge horns are well known in ultrasonic welding.

The transducer mounting portion 1720 of such an ultrasonic device may be described as having the form of a square or rectangular prism. While a surgical tool manufactured from flat stock may have a single pair of surfaces (see 325 of FIG. 3) on which the piezoelectric transducers may be mounted, a surgical tool having a transducer mounting portion 1720 having the form of a square or rectangular prism may have four surfaces on which the piezoelectric transducers 1712a-c may be mounted (note that a fourth piezoelectric transducer, in addition to the three piezoelectric transducers 1712a-c illustrated in FIG. 17, may be affixed to a fourth side of the transducer mounting portion 1720 that is not shown in the view). The multiple piezoelectric transducers may be affixed to the surfaces of the transducer mounting portion 1720 using adhesives as disclosed above with respect to FIG. 5. Alternatively, a clip or band 1810 may be used to secure the multiple piezoelectric transducers. It may be understood that the clip or band 1810 may be designed to incorporate electrodes to supply an electrical signal to activate the multiple piezoelectric transducers.

FIGS. 17 and 18 depict a surgical tool with a transducer mounting portion 1720 having the form of a square or rectangular prism on which each of the piezoelectric transducers 1712a-c (including the transducer not depicted in the figures) may be mounted. It may be recognized that a piezoelectric transducer may be mounted on each of the four sides of the transducer mounting portion 1720 or only on a pair of opposing sides. Further, each of the piezoelectric transducers 1712a-c may comprise one or more transducer plates (similar in structure as depicted in FIG. 9). In some examples, the width of piezoelectric transducers 1712a-c may be half that of the piezoelectric transducers 312a,b (see FIG. 3) that may be used on surgical tools fabricated from flat stock to preserve the total volume. In some fabricated examples, a piezoelectric transducer, such as 1712a, was able to deliver 35 watts.

As disclosed above with respect to FIGS. 7-9, each of the piezoelectric transducers 1712a-c (including the hidden fourth transducer) may be activated by the same or different power supplied. If all four transducers are driven in parallel, the motion of the end effector of the surgical tool may be longitudinal (similar to the motion of a flat ultrasonic medical device comprising a surgical tool fabricated from sheet stock, as depicted in FIG. 3). However, if two transducers, located on opposing faces of the transducer mounting portion 1720 are driven out of phase, then a transverse motion may be produced in the end effector. If the two transducers on the other faces are driven out phase, then a transverse motion of the end effector may be produced in the opposite direction. Further, if each of a first pair of opposing transducers is driven at 180 degrees apart, and each of a second pair of opposing transducers is driven at 180 degrees apart and further are driven 90 degrees apart from the first pair, then an orbital motions may be produced at the end effector. It may be recognized that the geometry of the waveguide 1710 and driving frequency of the transducers may be designed to achieve a longitudinal, transverse, and orbital motion in one device.

Aspects depicted in FIGS. 17 and 18 may benefit from low-cost fabrication methods to produce a square/rectangular transducer with a relatively small cross section. As disclosed above, the use of independent activation signals to the transducers having appropriate driving characteristics in frequency and phase, may result in longitudinal, transverse (in two directions) and orbital motions. Such an orbital motion with a hollow blade may provide improved fragmentation and skeltonization of tissue. Additionally, such multiple controllable motions may form the basis for dynamic steering of an end effector, which may include a light source or sensor.

Figure 20:
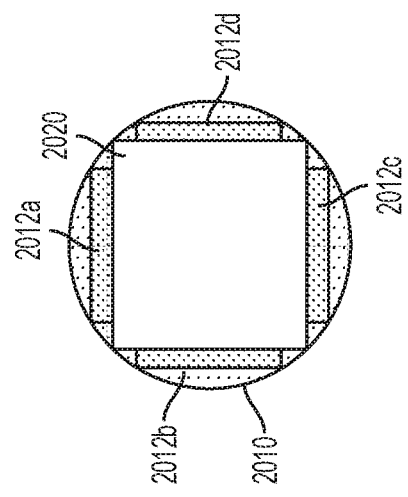
FIG. 20 is a cross-sectional view of an ultrasonic medical device fabricated from round stock, according to one aspect of this disclosure.
Figure 19:
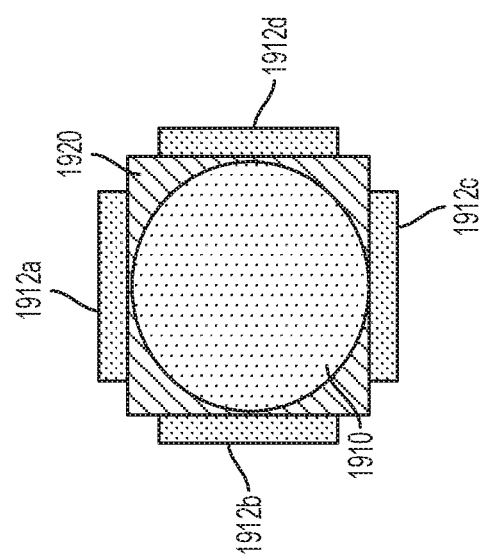
FIG. 19 is a cross-sectional view of an ultrasonic medical device fabricated from square stock, according to one aspect of this disclosure.

FIGS. 19 and 20 depict a cross section of an ultrasonic medical device manufactured from bar stock and round stock, respectively. FIG. 19 illustrates a medical device having a cylindrical waveguide 1910 machined from a bar stock, for example on a lathe. The un-machined portion, having a square cross-section, is retained at the transducer mounting portion 1920 of the medical device. A piezoelectric transducer (1912a-d) may be mounted on each surface of the transducer mounting portion 1920 of the device. FIG. 20 illustrates a medical device, comprising a transducer mounting portion 2020 having a square cross section, machined from round stock, for example by a milling machine. The un-machined portion, having a circular cross-section, is retained for the waveguide 2010. A piezoelectric transducer (2012a-d) may be mounted on each surface of the transducer mounting portion 2020 of the device.

Figure 21:
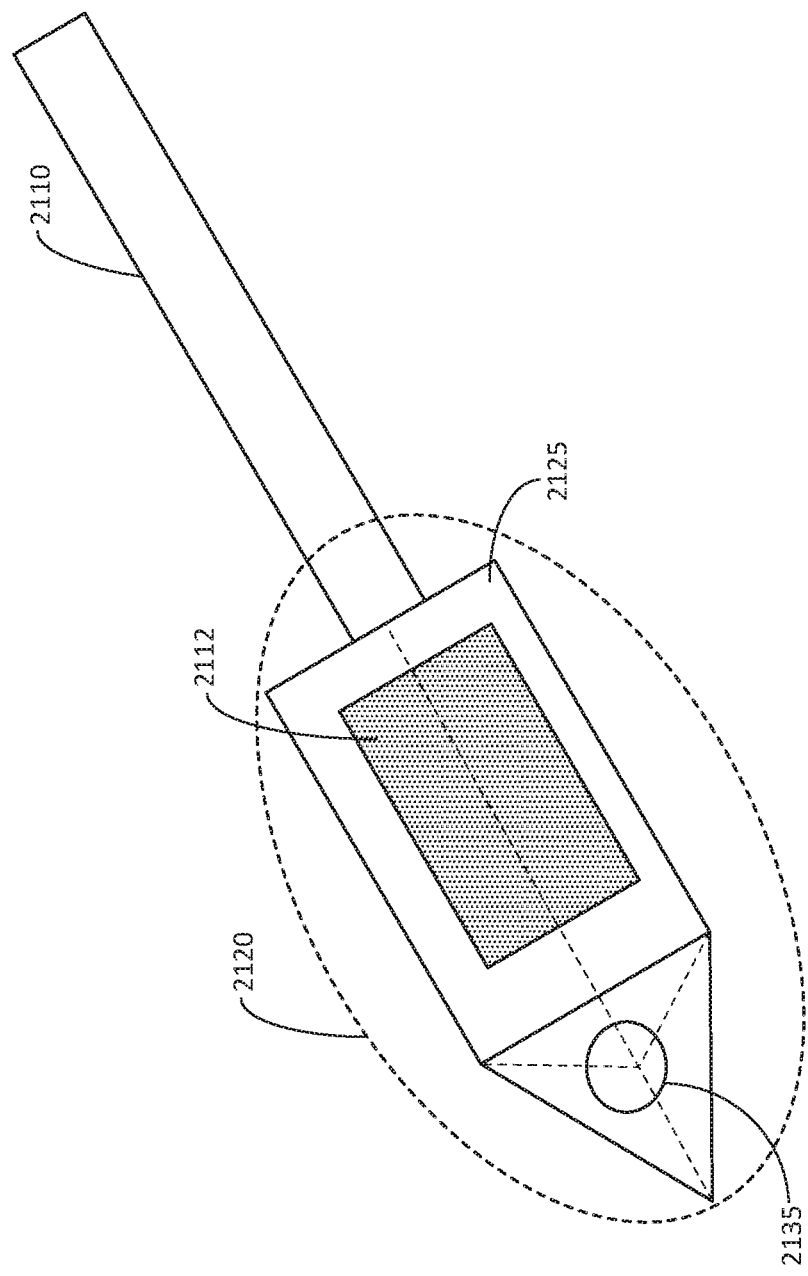
FIG. 21 is a perspective view of an ultrasonic medical device having a transducer mounting portion having a form of a triangular prism, according to one aspect of this disclosure.

FIG. 21 depicts another aspect of an ultrasonic medical device having a transducer mounting portion 2120 fabricated in the form of a triangular prism. Such a medical device may also include a waveguide 2110 having a round, flat, square, or other cross section as disclosed above. In one aspect, a piezoelectric transducer 2112 may be affixed to each of the faces (such as face 2125, as illustrated in FIG. 21). As disclosed above with respect to aspects having more than two transducers, each transducer may be activated from a common power supply or from individual power supplies. The transducers may also be activated in phase or out of phase. In one example, if all three transducers are driven in parallel, the motion of the end effector may be primarily longitudinal. In another example, in an aspect having a transducer mounting portion 2120 fabricated in the form of a triangular prism, the transducers may be activated 120 degrees apart from each other. Such an activation may result in a rotational or torsional motion at the end effector. If two of the transducers are driven with a greater amplitude than the third (including not driving the third at all), then a mainly lateral motion may be induced in the end effector.

Additionally, each of the transducers may be operated at a different frequency, which may result in more complex motions of the end effector. In another example, the current delivered to each transducer may be modulated so that one or two transducers may be activated with the other(s) off (inactivated for a period of time, and then one or two other transducers may be activated (with the first one or two transducers remaining in an off or inactivated state) after a brief rest period. The rest period may be long enough for transients to die down and drive at resonance for some time. For example, the rest period may be between about 0.1 and 1 msec. The use of such a rest period between successive activations of the transducers may be useful for "soft" start-ups and shut downs. As disclosed above with respect to FIG. 17, it may be recognized that the geometry of the waveguide 2110 and driving frequency of the transducers may be designed to achieve a longitudinal, transverse, and orbital motion in one device. It may be recognized that one-phase to three-phase converters are well known in industrial electrical systems to power motors, for example. It may also be possible to have a small converter on a circuit board that is contained in the transducer body. The 120 phase difference between the transducers may be achieved with lead- and lag-circuits from passive components.

The ultrasonic medical device depicted in FIG. 21 may be fabricated from a surgical tool having a triangular prismatic transducer mounting portion 2120. A piezoelectric transducer, such as transducer 2112, may be affixed to each of the faces 2125 of the surgical tool. In an alternative aspect, the ultrasonic medical device may lack a triangular prismatic transducer mounting portion 2120, but rather incorporate three piezoelectric transducers attached directly to each other along their neighboring length-wise edges. The waveguide 2110 may terminate at a proximal end with a triangular frame or plate to which the three piezoelectric transducers may be affixed at their respective distal edges.

Additionally, the ultrasonic medical device may include a lumen 2135 disposed within the device and fabricated along a central longitudinal axis thereof. The lumen 2135 may be used to transport a fluid, such as a cooling fluid, through the device. If the lumen 2135 extends throughout the entire length of the device, having a distal portal at a distal end of the end effector, the cooling fluid may be used to cool tissue contacting the end effector. Alternatively, the lumen 2135 may be in fluid communication with a proximal vacuum source that may be used to remove fluids from the tissue at the distal end of the end effector.

Figure 25:
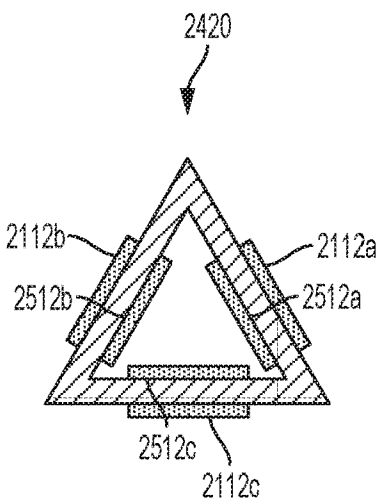
FIGS. 22-25 are cross-sectional views of a transducer mounting portion of an ultrasonic medical device in which the transducer mounting portion has a form of a triangular prism, according to one aspect of this disclosure.
Figure 24:
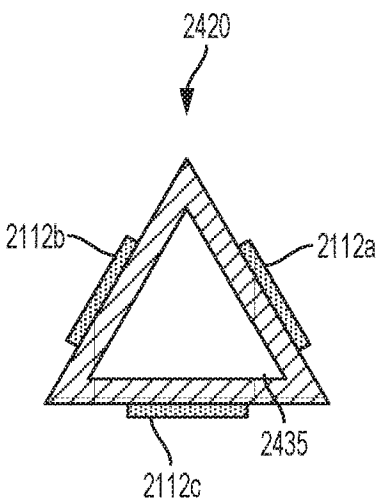
Figure 23:
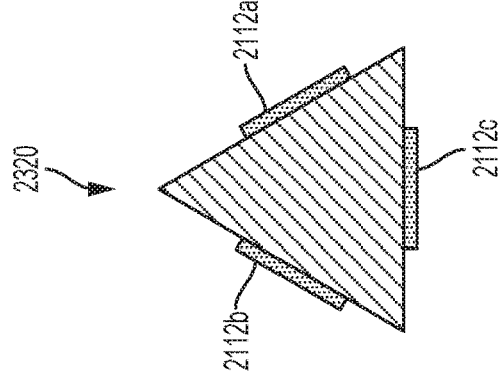
Figure 22:
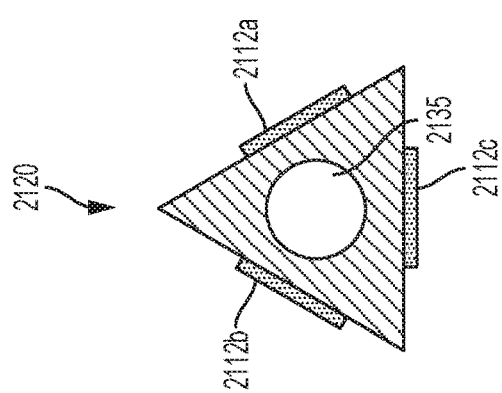

FIGS. 22-25 depict a variety of aspects of an ultrasonic medical device having a triangular prismatic transducer mounting portion. FIG. 22, for example, is a cross-sectional view of the ultrasonic medical device illustrated in FIG. 21. It may be observed that the transducer mounting portion 2120 has a piezoelectric transducer 2112a-c affixed to each of the faces of the transducer mounting portion 2120, and a central, cylindrical lumen 2135 disposed therein. FIG. 23, for example, is a cross-sectional view of the ultrasonic medical device having a transducer mounting portion 2320 that lacks a central lumen. FIG. 24, for example, is a cross-sectional view of the ultrasonic medical device having a hollow triangular prismatic transducer mounting portion 2420 that has a triangular lumen 2435. FIG. 25, for example, is a cross-sectional view of the ultrasonic medical device of FIG. 24, having a hollow triangular prismatic transducer mounting portion 2420 that has a triangular lumen 2435. FIG. 25 also illustrates that piezoelectric transducers 2512a-c may be mounted on the inner faces of the triangular lumen.

Generalizing from FIGS. 3-25, a surgical tool may include a transducer mounting portion fabricated in the form of a polygonal prism (the transducer mounting portion of the surgical tools disclosed in FIGS. 3-16 may be considered to have the form of a rectangular prism in which one set of opposing sides is much longer than the second set of opposing sides). It may be recognized that additional aspects of a surgical tool may include a transducer mounting portion having the form of a cylindrical or partially cylindrical prism.

Figure 26:
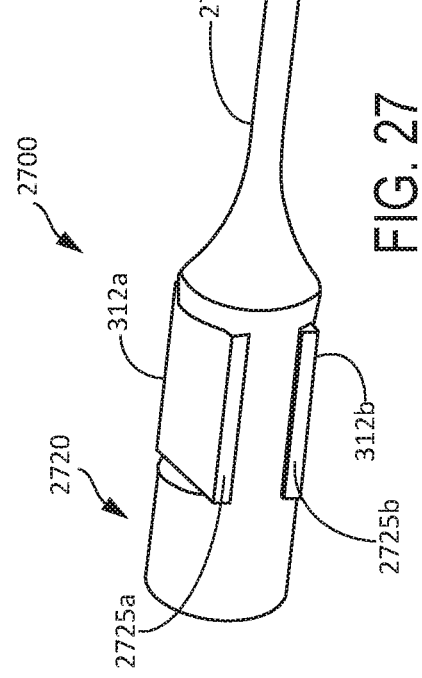
FIGS. 26-28 are perspective views of an ultrasonic medical device fabricated from round stock, according to one aspect of this disclosure.

FIGS. 26-31 are directed to aspects of an ultrasonic medical device comprising a surgical tool having a cylindrical, or partially cylindrical, transducer mounting portion. FIG. 26 illustrates an ultrasonic medical device 2600 comprising surgical tool having a cylindrical waveguide 2610 and a transducer mounting portion 2620 having the form of a horizontal cylindrical segment formed from a pair of sectional planes parallel to the long axis of the cylinder. The transducer mounting portion 2620 may further include a pair of parallel and opposing flat surfaces 2625 on which the piezoelectric transducers 312a,b may be mounted as disclosed above with respect to FIG. 5, for example.

Figure 27:
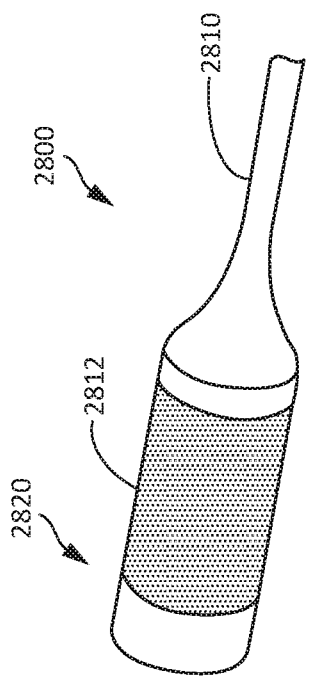

FIG. 27 illustrates an ultrasonic medical device 2700 comprising a surgical tool having a cylindrical waveguide 2710 and a transducer mounting portion 2720 having the form of a cylindrical prism in which a pair of opposing flats 2725a,b may be fabricated to receive the piezoelectric transducers 312a,b. As disclosed with respect to FIGS. 10 and 11, the piezoelectric transducers 312a,b may be affixed to the flats 2725a,b by means of one or more types of adhesives. Alternatively, the piezoelectric transducers 312a,b may be affixed to the flats 2725a,b by means of an interference fit. The interference fits may be accomplished by heating and cooling the surgical tool, thereby causing thermal expansion and contraction of the transducer mounting portion 2720 surrounding the flats 2725a,b. The interference fits may also be accomplished by activating and deactivating the piezoelectric transducers, thereby causing piezoelectric expansion and contraction of the piezoelectric transducers.

Figure 28:
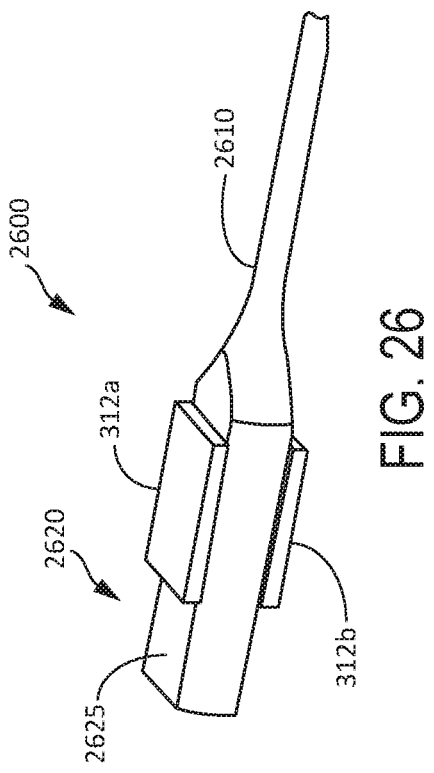

FIG. 28 illustrates an ultrasonic medical device 2800 comprising a surgical tool having a cylindrical waveguide 2810 and a transducer mounting portion 2820 having the form of a cylindrical prism. The piezoelectric transducer 2812 may have the form of a ring or a tube. In one aspect, the surgical tool 2800 may be fabricated from a separate waveguide 2810 and a transducer mounting portion 2820. The transducer mounting portion 2820 may include a machined portion having a smaller diameter than the remaining transducer mounting portion 2820 to receive the piezoelectric transducer 2812 (see FIG. 29). An ultrasonic medical device comprising the surgical tool 2800 and the piezoelectric transducer 2812, may be assembled from the waveguide 2810, the transducer mounting portion 2820, and the piezoelectric transducer 2812. During fabrication, a flange portion of the waveguide 2810 may be secured against an edge of the piezoelectric transducer 2812, thereby applying longitudinal compression against the transducer. In one example, the waveguide 2810 may include a threaded portion that may be threaded into a mating portion of the transducer mounting portion 2820 to assemble the ultrasonic medical device.

Figure 29:
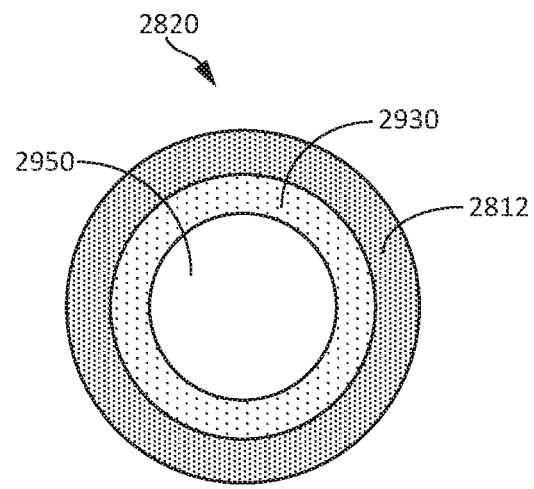
FIG. 29 is a cross-sectional view of the transducer mounting portion of the ultrasonic medical device of FIG. 28, according to one aspect of this disclosure.

FIG. 29 illustrates a cross-sectional view of the transducer mounting portion 2820 of the ultrasonic medical device depicted in FIG. 28, illustrating the piezoelectric transducer 2812 placed over smaller diameter machined portion 2950 of the transducer mounting portion 2820. It may be recognized that good conduction of the mechanical vibrations created by an energized cylindrical piezoelectric transducer 2812 into the waveguide may require tight mechanical coupling between the piezoelectric transducer 2812 and the waveguide 2810. Further, for the piezoelectric transducer 2812 to operate in a D31 mode, electrodes must form electrical contacts with the outer surface and the inner surface of the piezoelectric transducer 2812. In some aspects, an electrode connected to a hot conductor of an ultrasound power generator may contact an exposed surface of a transducer, while the surgical tool, contacting the opposing face of the transducer, may be in electrical contact with the neutral conductor of the ultrasound power supply. Because the piezoelectric transducer 2812 may be formed from a ceramic, it may be difficult to assure that the inner surface of the piezoelectric transducer 2812 forms a good electrical contact with the machined portion 2950 of the transducer mounting portion 2820. If a gap between the machined portion 2950 and the inner surface of the piezoelectric transducer 2812 is small (for example about 0.005 inches), the gap may be filled with a conductive epoxy 2930 and still deliver the needed power. Alternatively, a "green" (or un-fired) piezoelectric ceramic material may be assembled on the surgical tool and co-fired along with the surgical tool. In another alternative method of fabrication, the metallic portions of the ultrasonic medical device may be assembled with a piezoelectric ceramic that is between the green state and the fully fired state.

Figure 30:
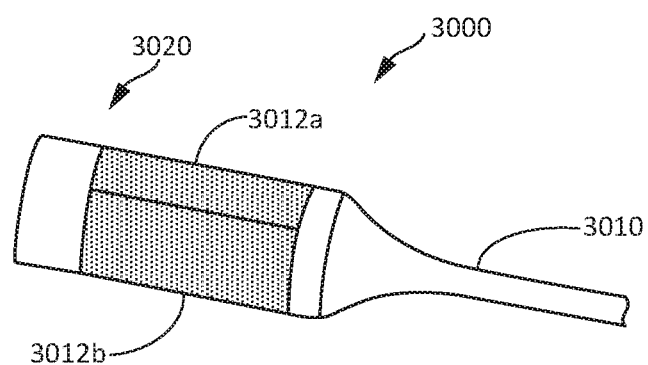
FIG. 30 is a side view of an ultrasonic medical device fabricated from round stock, according to one aspect of this disclosure.

FIG. 30 illustrates yet another aspect of an ultrasonic medical device 3000 composed of a surgical tool having a cylindrical waveguide 3010 and a cylindrical prismatic transducer mounting portion 3020. The ultrasonic medical device 3000 may be distinguished from the ultrasonic medical device 2800 in that the transducer comprises a plurality of cylindrical piezoelectric plates 3012a,b. Such cylindrical piezoelectric plates 3012a,b may be considered as being formed from longitudinal sections of a single tubular piezoelectric transducer 2812 as illustrated in FIG. 28. There may be two, three, or more cylindrical piezoelectric plates 3012; two such cylindrical piezoelectric plates 3012a,b are depicted in FIG. 30.

Figure 31:
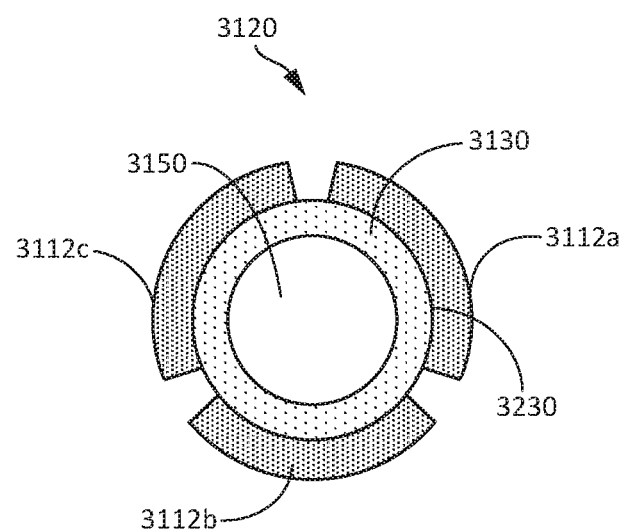
FIG. 31 is a cross-sectional view of the transducer mounting portion of the ultrasonic medical device of FIG. 30, according to one aspect of this disclosure.

FIG. 31 is a cross-sectional view 3120 of the transducer mounting portion 3020 of the ultrasonic medical device 3000 illustrated in FIG. 30. It may be recognized that the cylindrical piezoelectric plates 3012a,b depicted in FIG. 30 comprise a ceramic material that may be difficult to machine to permit a close fit, both to each other (along their respective length-wise edges) and to the machined portion 3150 of the transducer mounting portion 3120. As depicted in FIG. 31, the ultrasonic medical device (3000 of FIG. 30) may include cylindrical piezoelectric plates 3112a-c that do not contact each other along their respective length-wise edges, but may be fabricated so that their inner surfaces may conform more closely to the machined portion 3150 of the transducer mounting portion 3120. The cylindrical piezoelectric plates 3112a-c may then be affixed to the machined portion 3150 of the transducer mounting portion 3120 using a conductive epoxy 3230. As disclosed above with respect to other aspects of ultrasonic medical devices, for example the device depicted in FIG. 21, each of the individual cylindrical piezoelectric plates 3112a-c may be activated independently. For example, in the aspect depicted in FIG. 31, the three cylindrical piezoelectric plates 3112a-c may be activated by piezoelectric driving signals that are 120 degrees out of phase. Other examples of methods for activating three cylindrical piezoelectric plates 3112a-c may include those disclosed above with respect to FIG. 21. As noted above, other examples of an ultrasonic medical device 3000 may include 2, 3, 4, or more piezoelectric transducers that may be activated synchronously, asynchronously, or with a variety of ultrasound activation signals that may differ in frequency, phase, or amplitude.

Although the aspects disclosed above in FIGS. 3-31 are directed to a plurality of piezoelectric transducers positioned relative to the location of a single (for example proximal) vibrational node induced in a surgical tool, it may be recognized that transducers may similarly be positioned relative to more than one vibrational node. As disclosed above, the plurality of piezoelectric transducers may be activated by a single source of ultrasonic power or multiple sources of ultrasonic power, and may be operated synchronously or asynchronously. The electrical characteristics, such as frequency, amplitude, and phase, of the ultrasonic power may be the same or may differ among all of the plurality of piezoelectric transducers.

Figure 32:
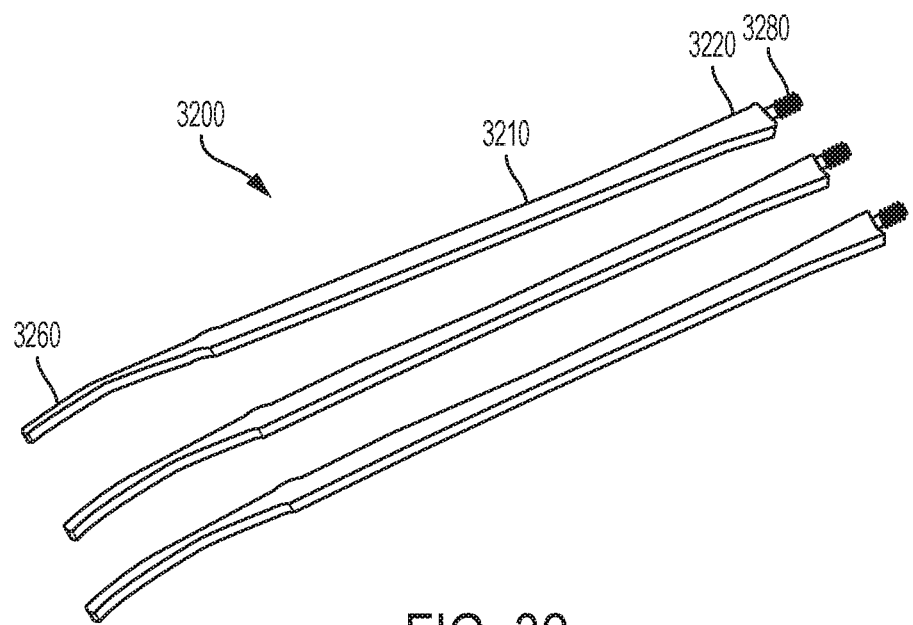
FIG. 32 is a perspective view of surgical tools for an ultrasonic medical device, according to one aspect of this disclosure.

FIG. 32 illustrates aspects of a surgical tool 3200. In some aspects, the surgical tool 3200 may be used as part of an ultrasonic system 10 as depicted in FIG. 1. Alternatively, one or more piezoelectric transducers may be mounted on the surgical tool 3200 to form an ultrasonic medical device, for example 300 as depicted in FIG. 3. The surgical tool 3200 may comprise a proximal transducer mounting portion 3220, a distal end effector 3260 and a longitudinal portion or waveguide 3210 therebetween. The surgical tool 3200 may also comprise an attachment boss 3280 that may permit the surgical tool 3200 to be mounted in a housing or other ultrasonic system. Such a surgical tool 3200 may be manufactured from titanium stock or from aluminum stock although any material having appropriate mechanical and/or electrical characteristics may be used.

Figure 33:
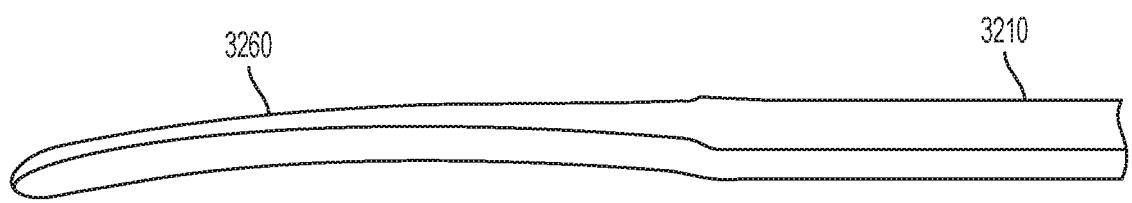
FIG. 33 is a perspective view of an end effector of a surgical tools depicted in FIG. 32, according to one aspect of this disclosure.

FIG. 33 illustrates a close-up view of the end effector 3260 and the distal end of the waveguide 3210. The waveguide 3210 may have a rectangular cross section as depicted in FIG. 33 although the cross section may of any polygon as may be appropriate for its use. Alternatively, the cross section may be elliptical or circular. The end effector 3260 may be fabricated as an integral part of the surgical tool, or may comprise a separate component affixed onto the waveguide 3210. The end effector 3260 may have a curved shape and may curve either in a vertical or horizontal direction with respect to the longitudinal axis of the surgical tool as may be appropriate for its use. Alternatively, the end effector 3260 may comprise a straight section that is bent at some angle, either vertically or horizontally, from the longitudinal axis of the surgical tool. In other examples, the end effector 3260 may comprise a more complex geometry including straight sections and curved sections, or multiple curved sections that differ in their respective radii of curvature. The end effector 3260 may extend directly from the waveguide 3210 or the waveguide 3210 may include shoulders from which the end effector 3260 extends.

In various aspects, the length and mass of a surgical tool comprising a transducer mounting portion, a wave guide, and/or an end effector can dictate the resonant frequency of the surgical tool. In various circumstances, the length of the surgical tool can be selected such that the resonant frequency of the surgical tool is within a range of frequencies that a voltage or current source can supply to a piezoelectric transducer coupled thereto. In certain aspects, a given transducer, wave guide, and/or end effector may be required to be used together and, in the event that a different length wave guide or different end effector is needed, a different surgical tool altogether may be required.

Figure 34:
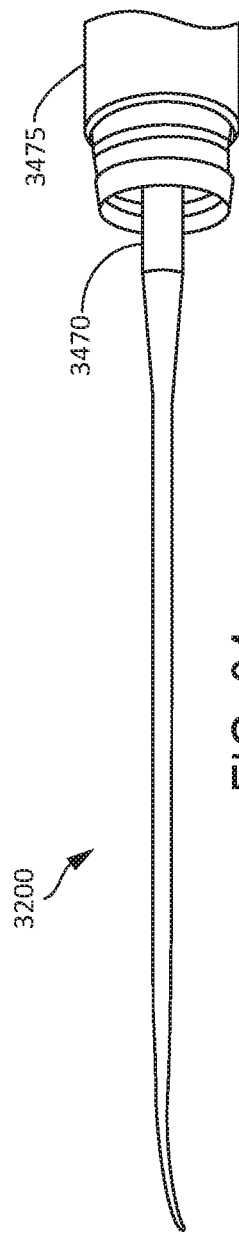
FIG. 34 is a perspective view of an ultrasonic medical device incorporating a surgical tool depicted in FIG. 32, according to one aspect of this disclosure.

FIG. 34 illustrates an example of a surgical tool 3200 mounted within an ultrasound medical system comprising a housing 3475 or a handle. The surgical tool 3200 may be secured to or within the housing 3475 according to any means consistent with its function and use. For example, the surgical tool 3200 may be secured to the housing 3475 by means of a clamp, clip, or collet 3470. For example, such an ultrasound medical system may use the surgical tool 3200 alone to contact a tissue for therapeutic means.

Figure 35:
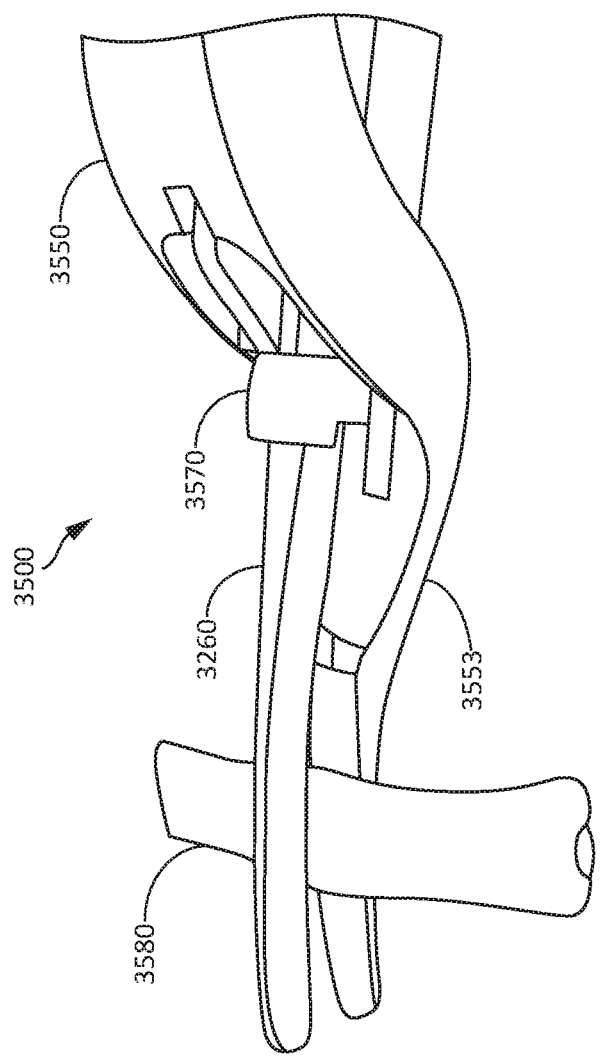
FIG. 35 is a perspective view of an ultrasonic medical device incorporating a surgical tool depicted in FIG. 32, according to one aspect of this disclosure.

FIG. 35 illustrates a more complex ultrasound medical system, such as an ultrasound shear 3500, in which a surgical tool may be incorporated. The ultrasound shear 3500 may include a surgical tool (the end effector 3260 of the surgical tool being illustrated) which may operate against an anvil 3553. The anvil 3553 may be moved by a movable handle 3550. The movable handle 3550 may be manipulated so that a tissue 3580 contacted by the anvil 3553 may be brought into contact with the end effector 3260. The surgical tool may be affixed to the ultrasound shear 3500 by means of a clamp, clip, or collet 3570.

It may be recognized that the utility of an ultrasound surgical tool is based on the standing mechanical vibrational waves that may be induced therein by an associated piezoelectric transducer. Owing to various manufacturing differences, however, each surgical tool may have a slightly different resonant frequency and, as a result, each surgical tool may be tested in order to find its resonant frequency. If it is determined that the natural frequency of the surgical tool needs to be adjusted, the transducer mounting portion of the surgical tool and/or the end effector may be ground in order to adjust their length and, as a result, adjust the resonant frequency of the surgical tool. Although such manufacturing methods may be useful for their intended purposes, the process may be time consuming and/or may not provide adequate adjustability of the surgical tool. For example, in the event that too much length is ground off of a surgical tool transducer mounting portion, for example, the surgical tool typically may be thrown out and the adjustment process must be repeated with a new surgical tool. More efficient processes for fabrication of surgical tools is therefore useful.

Figure 36:
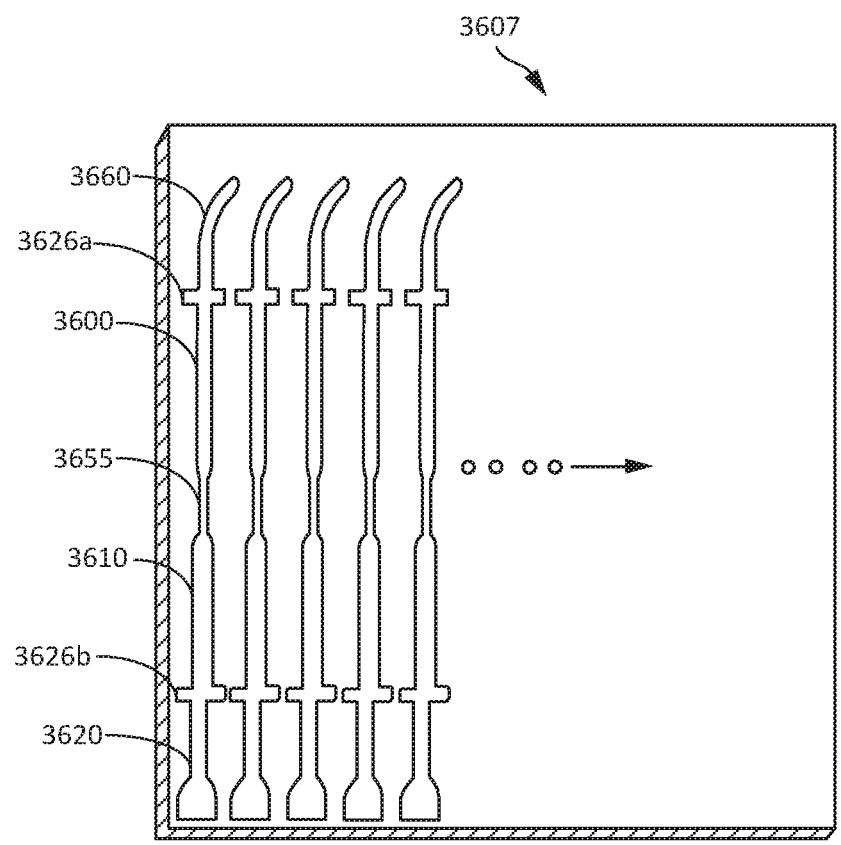
FIG. 36 is a perspective view of surgical tools during a fabrication step from flat stock, according to one aspect of this disclosure.

FIG. 36 illustrates a portion of a method of fabrication of one or more surgical tools, such as surgical tool 3600. Each surgical tool 3600 may comprise a transducer mounting portion 3620, an end effector 3660, and an elongated portion or waveguide 3610 therebetween. The surgical tool 3600 may also incorporate additional features such as a gain feature 3655 to modify the amplitude of the mechanical wave induced in the surgical tool 3600 by the activated piezoelectric transducers driving it. Additional features may include one or more blade attachment features 3626a,b that may be used for attaching the surgical tool to a housing or ultrasound medical system. In some examples, the attachment features 3626a,b may be fabricated at one or more node locations of the surgical tool 3600 where mechanical displacement during piezoelectric activation may be minimized.

The surgical tool 3600 may be fabricated from sheet stock 3607 comprising titanium or aluminum. Titanium or other surgical tool 3600 material may be rolled, pressed, molded, or cast into sheets 3607 in a manner that creates the best material microstructure and orientation (grain) to produce efficient surgical tools 3600. The surgical tools 3600 may be "blanked" by way of laser machining, laser machining with tilt degree of freedom, wire EDM, conventional milling, stamping, fine blanking, or other two dimensional cutting method from the sheet 3607. In some aspects, the surgical tools 3600 may be bulk finished to round edges by way of tumbling, sand blasting, bead blasting, electropolishing, forging, coining, or other finishing methods. In alternative aspects, only those areas or features on the surgical tool 3600 that require further shape refinement may be machined to their final dimensions. Such portions of the surgical tool 3600 may include, for example, the exposed portion of the end effector 3660, the proximal transducer mounting portion 3620, surfaces or other features. Other surfaces may be untouched, or at most rough-shaped. Examples of such unfinished portions may include a portion of the surgical tool 3600 that may be contained inside a housing of a ultrasound medical system incorporating the surgical tool 3600.

Further fabrication steps may include removing material from the thickness of the part by machining, skiving, forming, coining, forging, or other methods known in the art. This additional machining may be performed on only one side or the surgical tool 3600 or on opposing sides of the surgical tool 3600. Such additional machining to adjust the thickness of the surgical tool 3600 may be used to form a gain feature 3655 to modify the amplitude of the mechanical wave induced in the surgical tool 3600 by the activated piezoelectric transducers driving with it. In some aspects, the gain features 3655 may be fabricated starting at a location proximal to an antinode and ending at a location distal to the antinode. The fabricated gain features 3655 may incorporate regions of high mechanical gain of the waveguide 3610 thereby minimizing the part-to-part variation in gain. The resulting thickness of the part by removal or reduction may yield a section of the surgical tool 3600 that is at or near the lower end of the standard sheet thickness tolerance.

Typical thickness tolerance on sheet stock materials such as sheet titanium or aluminum may be about +/−0.0080 inches or +/−0.203 mm. This tolerance is roughly four to eight times that which may be found in ultrasonic surgical tools machined via precise turning operations (e.g., lathe, Swiss screw machine, etc.). The displacement gain through a waveguide 3610 is related to changes in cross sectional area of the member. Therefore, large variation in the lateral aspects of a transmission member (such as thickness variation) may result in large part-to-part variation in displacement gain. Therefore, precision tuning of the displacement gain between surgical tools may be accomplished through such additional machining. It may be recognized that changes in area at or near antinodes of vibration have little to no effect on displacement gain, while changes in area at or near nodes of vibration have maximal effect on displacement gain.

Figure 37:
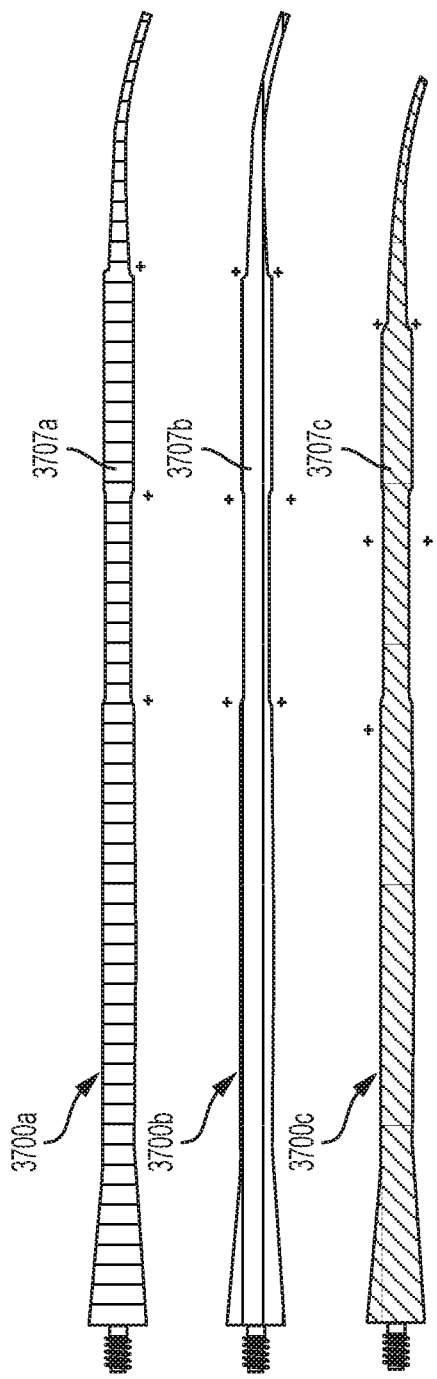
FIG. 37 is a plan view of surgical tools depicting the metal grain orientation of the surgical tools, according to one aspect of this disclosure.

As disclosed above, precision tuning of the displacement gain between surgical tools may be accomplished through appropriate precision machining of a surgical tool. An additional manner to tune the vibrational characteristics of a surgical tool may be to fabricate the surgical tool in a specified direction with respect to the grain orientation of the sheet stock from which it is manufactured, specifically orienting a longitudinal axis of the tool with respect to the grain orientation of the sheet stock. FIG. 37 illustrates surgical tools 3700a-c that may be machined according to the grain pattern of the sheet stock from which they are manufactured. Thus, surgical tool 3700a is fabricated having a transverse grain pattern 3707a, in which the longitudinal axis of the surgical tool 3700a is oriented orthogonal to the grain direction. Surgical tool 3700b is fabricated to have a longitudinal grain pattern 3707b, in which the longitudinal axis of the surgical tool 3700b is oriented parallel to the grain direction. Surgical tool 3700c is fabricated to have the longitudinal axis of the surgical tool 3700c oriented in another direction with respect to the grain orientation. In some applications, the longitudinal axis of the surgical tool is oriented at an angle with respect to the grain direction to minimize stress in at least a portion of the surgical tool upon activation. In other applications, the longitudinal axis of the surgical tool is oriented at an angle with respect to the grain direction to maximize a longitudinal deflection of the surgical tool upon activation.

The properties of such surgical tools, based on samples fabricated from titanium alloy Ti 6Al4V ELI have been determined as follows. A surgical tool 3700a, having a transverse grain 3707a may have a stiffness, E=18,520,000 PSI 55.5 and a quarter-wave length (at 55.5 kHz)=0.952 inches. A surgical tool 3700b, having a longitudinal grain 3707b may have a stiffness, E=16,310,000 PSI, and a quarter-wave length (at 55.5 kHz)=0.894 inches. These values may be compared to un-oriented rod stock which may have a stiffness, E=15,680,000 PSI a quarter-wave length (at 55.5 kHz)=0.876 inches. The choice of grain orientation for a surgical tool may help maximize the end effector length by minimizing the error in perpendicularity from the centerline of the end effector to the grain direction. For example, a transverse grain orientation 3707a may result in a minimal error (theoretically zero) and maximum length for a surgical tool having a straight end effector (i.e., no curve). Alternatively, a choice of grain orientation for a surgical tool may help minimize the end effector length by maximizing the error in perpendicularity from the centerline of end effector to the grain direction Additionally, the choice of grain orientation may help reduce stress if the grain orient permits increased wavelength in high stress areas In some fabricated samples, surgical tools fabricated having longitudinal and transverse grain orientations have demonstrated acoustic function. In some fabricated samples, surgical tools having curved end effectors with transverse grains have demonstrated acoustic and vessel sealing function.

Figure 38:
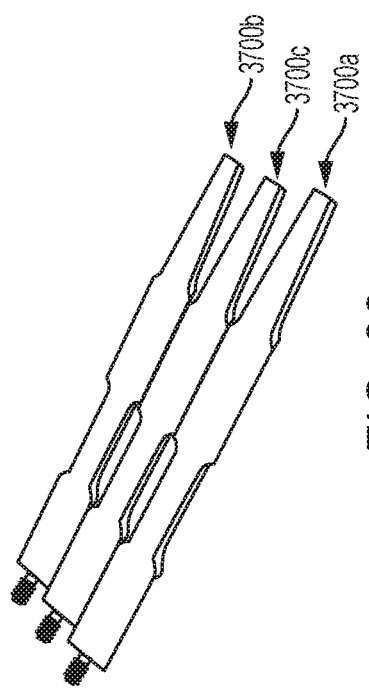
FIG. 38 is a perspective view of the surgical tools depicted in FIG. 37, according to one aspect of this disclosure.

FIG. 38 depicts the surgical tools 3700a-c of FIG. 37 illustrating that the length of a surgical tool may be optimized based on the grain orientation of the metal comprising the surgical tools. As disclosed above, a surgical tool 3700a having a transverse grain 3707a may have a longer resonance quarter wavelength by about 0.06 inches than a surgical tool 3700b having a longitudinal grain 3707b (when activated at 55.5 kHz). It may be understood that more precise tuning of a surgical tool may be accomplished in this manner.

Figure 39:
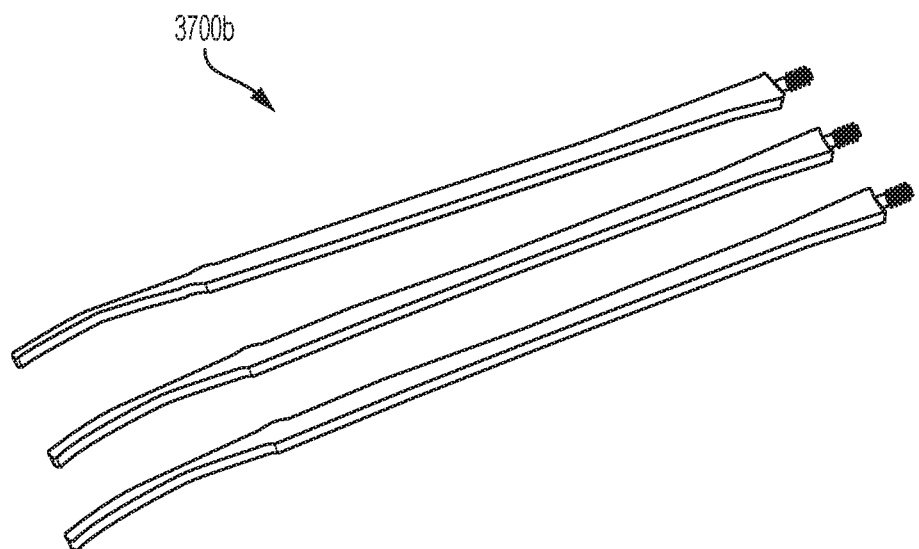
FIG. 39 is a perspective view of additional surgical tools depicted in FIG. 37, according to one aspect of this disclosure.
Figure 40:
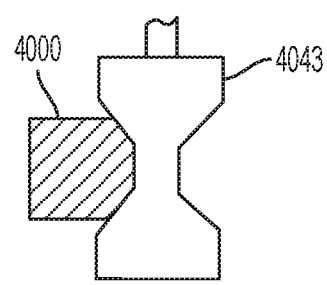
FIG. 40 is a side view of an additional fabrication step of a surgical tool, according to one aspect of this disclosure.

FIG. 39 illustrates a surgical tool 3700b having a longitudinal grain. Additional performance tuning may be provided by additional machining of a face of the surgical tool (as opposed to machining the edges of the tool as indicated in FIG. 36). Further performance tuning, for example of the displacement amplitude of the surgical tool, is depicted in FIG. 40. In FIG. 40, the cross-section of the waveguide 4000 optionally may be routed (milled), using a side or end mill 4043, into an octagonal or more rounded shape using a single pass on each of two opposite sides, possibly at the same time, in order to reduce the required instrument shaft diameter.

As disclosed above with respect to FIGS. 36-40, a variety of mechanical fabrication steps may be considered for optimizing the price and performance of a surgical tool. Thus, minimizing the number of finishing steps may result in well-performing surgical tools without resorting to costly, but unnecessary, additional steps added for purely aesthetic reasons. The surgical tool may be manufactured at a predetermined angle with respect to the flat stock grain, thereby optimizing the length or stiffness of the resultant tool. Reproducibility of performance between multiple surgical tools fabricated from flat stock may be accomplished through machining ("shaving") small amounts of mass from the tools to overcome variability in flat stock thickness and to improve inter-tool tolerance. Additionally, fabrication steps may be included to tune the mechanical displacement (or gain) of the surgical tool.

Figure 41:
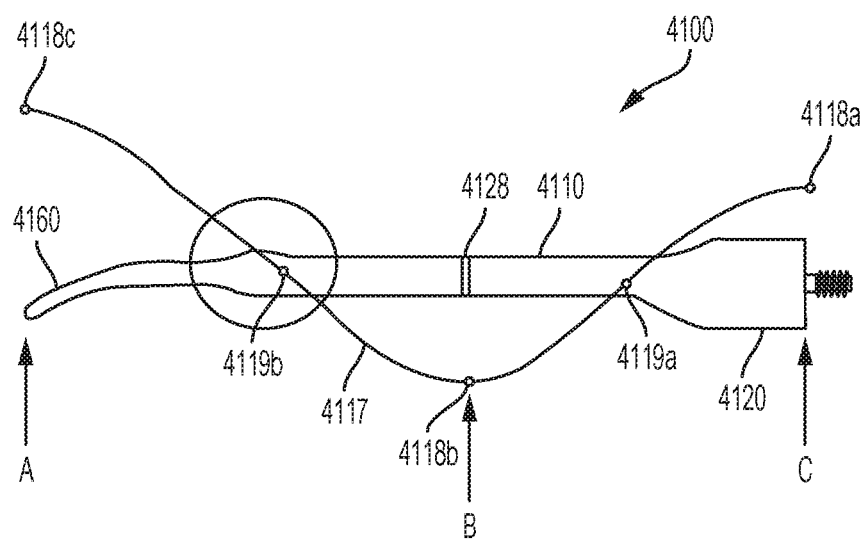
FIG. 41 is a plan view of the surgical tool depicted in FIG. 32 with a superimposed illustration of a mechanical standing wave imparted to it by an activated piezoelectric transducer, according to one aspect of this disclosure.
Figure 42:
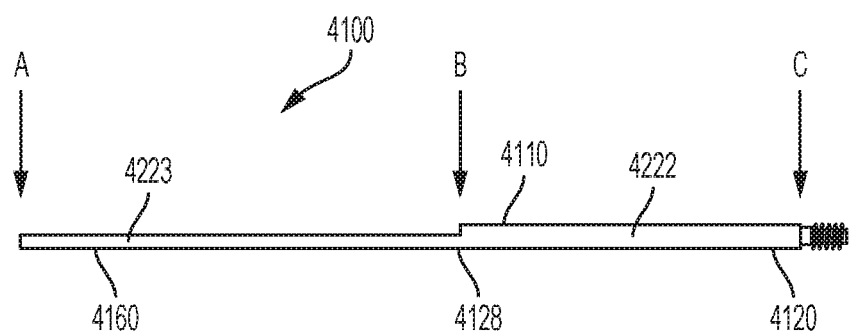
FIG. 42 is a side view of the surgical tool depicted in FIG. 41, according to one aspect of this disclosure.

FIGS. 41 and 42 illustrate a plan (FIG. 41) and edge (FIG. 42) view, respectively, of a surgical tool 4100 machined to preferentially increase the mechanical displacement of an end effector 4160. Surgical tool 4100, as illustrated, comprises a transducer mounting portion 4120, and end effector 4160, and a waveguide 4110 disposed therebetween. For comparisons between FIGS. 41 and 42, indicia A and C correspond to the most distal end of the end effector 4160 and the most proximal terminal end of the transducer mounting portion 4120, respectively. Overlaid on the image of the surgical tool 4100 is a mechanical standing wave 4117 that may be induced in the surgical tool 4100 when it vibrates due to an induced mechanical wave from a piezoelectric transducer contacting the transducer mounting portion 4120 of the surgical tool 4100. The standing wave 4117 may be induced in the surgical tool 4100 through the activation of one or more transducers in mechanical communication with the surgical tool 4100 by an electrical signal having a predetermined frequency component. The standing wave 4117 may have a wavelength proportional to the predetermined frequency component of the electrical signal. The standing wave 4117 may be effectively sinusoidal, and characterized by nodes 4119a,b and antinodes 4118a,b,c. Without being bound by theory, the nodes 4119a,b may represent locations of the surgical tool that undergo minimal mechanical displacement, and the antinodes 4118a,b,c may represent locations demonstrating a maximal absolute mechanical displacement of the surgical tool 4100. Solely for descriptive purposes with respect to FIG. 41, antinode 4118a may be termed the proximal antinode, antinode 4118b may be termed the medial antinode, and antinode 4118c may refer to the distal antinode. Again, for purposes of comparison between FIGS. 41 and 42, indicium B may correspond to the location of the medial antinode 4118b. The medial antinode 4118b may be located in the surgical tool 4100 at medial antinode location 4128.

The amount of mechanical displacement of any portion of an activated surgical tool 4100 may depend on a number of factors including the amount of power supplied to the piezoelectric transducers, the local geometry at the portion of the surgical tool 4100 and the local mass of the portion of the surgical tool 4100. Again, without being bound by theory, the mechanical displacement of a portion of an activated surgical tool may vary inversely with mass (controlling for piezoelectric transducer power and local geometry). In FIG. 41, the thickness of the surgical tool 4100 is decreased, thereby reducing the mass, distal to the medial antinode location 4128. This is made clear in FIG. 42, in which the thickness 4222 of the proximal end of the surgical tool 4100 (corresponding to the tool from the medial antinode location 4128 to the proximal end of the tool at indicium C) is greater than the thickness 4223 of the distal end of the surgical tool 4100 (corresponding to the tool from the medial antinode location 4128 to the distal end of the tool at indicium A). As a result, the mechanical displacement of the end effector 4160 corresponding to the distal antinode 4118*c* may be greater than the displacement of the surgical tool 4100 at other antinodes, such as at antinodes 4118*a,b*. Such a fabrication technique may be useful to create a surgical tool 4100 with a greater amount of mechanical displacement at the end effector 4160 than at the locations of other anti-node 4118*a,b* throughout the surgical tool. 4100.

In general, additional fabrication steps of a surgical tool may include lateral or side machining, or surface machining (or a combination of the two). Fabrication methods that may be directed to machining the lateral or side surfaces of a surgical tool may result in a short and wide blade design. The lateral machining processes may be used to create a curved blade tip of an end effector. The face of the surgical tool, derived from the surface of the flat stock from which it is fabricated, may then become a clamping surface for a shear-type device. After such lateral machining steps, changes to vertical dimensions (for example, vertical tapering) may be created using additional process (for example, coining). Additional features in the surgical tool that may be created by lateral machining processes may include a vertical ribbon section to allow horizontal articulation, lateral steps in the waveguide to adjust the gain in mechanical deflection, and lateral offsets that may be used to create clearance of vertical structures. Fabrication methods that may be directed to machining the face or transverse surface may result in a long and skinny blade design. The transverse surface machining processes may be used to create a vertical profile of the blade tip (for example, a vertically tapered tip). The machined transverse faces may become a clamping surface for a shear-type device and the vertical machined profiles may result in an end effector having improved clamping pressure profile or any improved gripping capability, useful for clamping wet tissue. After such surface machining steps, changes to the lateral dimension (for example, curve, lateral tapering) may be created using additional process (for example, forming). Additional features in the surgical tool that may be created by transverse surface machining processes may include a horizontal ribbon section to allow vertical articulation, vertical steps in the waveguide to adjust the gain in mechanical deflection, and vertical offsets that may be used to create clearance of horizontal structures such as a waveguide that terminates with straight lateral structures, such as clamp arm pivot pins. Combinations of both lateral and transverse machining steps may be used to create a surgical tool having more complex geometries, for example one having a waveguide and/or end effector consisting of curve(s), or any number of centerlines.

Figure 43:
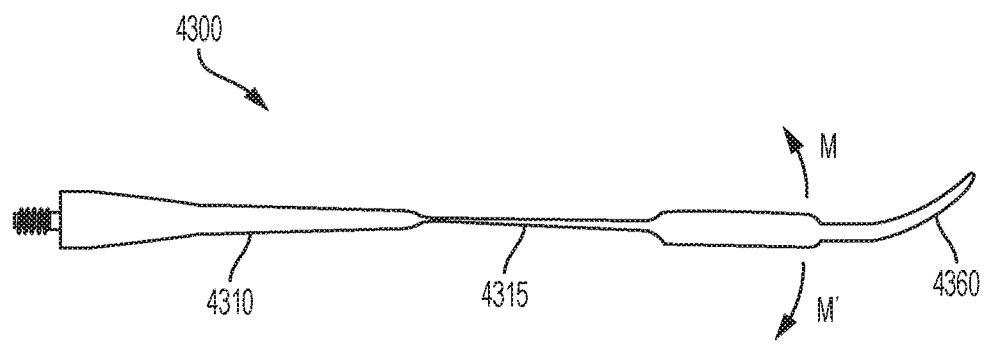
FIG. 43 is a plan view of a surgical tool configured to be displaced in a side-way manner, according to one aspect of this disclosure.
Figure 44:
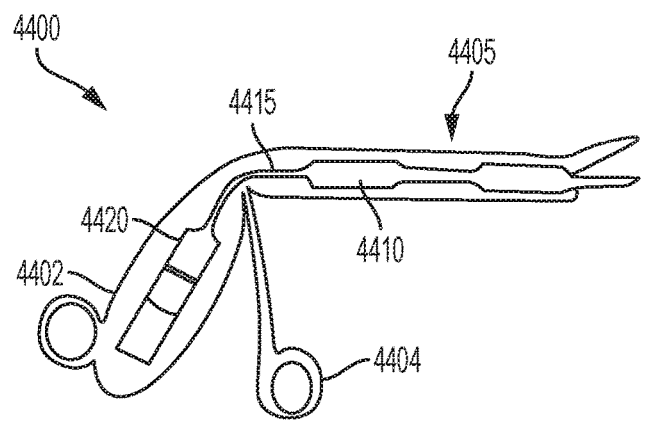
FIGS. 44 and 45 illustrate hand actuated ultrasonic medical devices, according to one aspect of this disclosure.

FIG. 43 illustrates a side view of a surgical device 4300 having a waveguide 4310 and an end effector 4360. As depicted, the waveguide 4310 may include horizontal ribbon section 4315 that may be machined using transverse machining processes as disclosed above. The resulting surgical device 4300 is thereby configured to articulate in directions M and M' about the horizontal ribbon section 4315 in the vertical cutting plane. Additional lateral machining may impart a vertical taper to the end effector 4360. FIG. 44 illustrates a hand-held ultrasound medical system 4400 incorporating a surgical tool 4405 (shown in plan view) having a transducer mounting portion 4420, and end effector, and a waveguide 4410 therebetween. In the aspect of FIG. 44, the ultrasound medical system 4400 may include a housing 4402 and a clamping actuator 4404. The hand-held ultrasound medical system 4400 may incorporate such electronics and power sources (such as one or more batteries) to control the activation of the surgical tool 4405 thereby allowing the ultrasound medical system 4400 to operate without requiring an external ultrasound power source. The waveguide 4410 may include a vertical ribbon section 4415 that may be machined using lateral machining processes as disclosed above. The surgical tool 4405 may be fabricated using lateral machining methods to form the upper and lower surface of the end effector. Vertical tapering of the end effector may require one or more additional transverse surface machining processes. The surgical tool 4405 is thus configured to articulate about the vertical ribbon section 4415 orthogonal to the vertical cutting plane.

Figure 45:
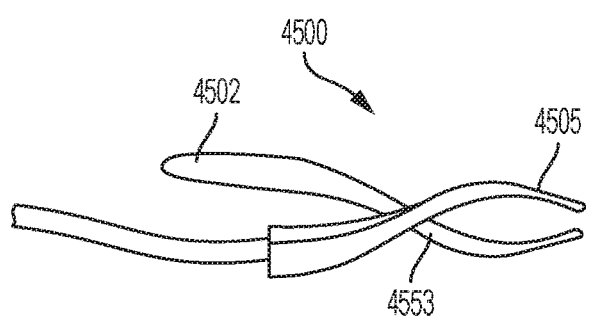
Figure 46:
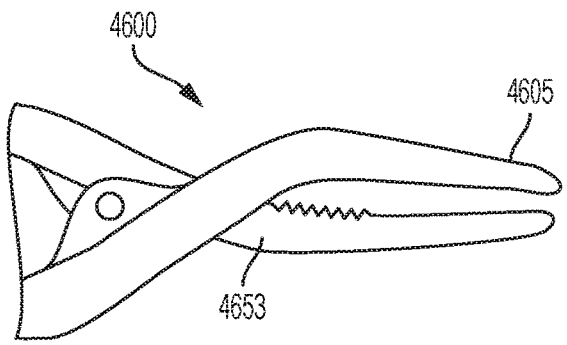
FIG. 46 illustrates the effector end of the hand actuated ultrasonic medical device of FIG. 45, according to one aspect of this disclosure.

In many of the aspects disclosed above, a surgical tool may be a cutting tool in which the end effector comprises a blade designed for cutting a tissue. However, with additional or alternative fabrication steps, the surgical tool may become a clamping or clamping-plus-cutting tool. FIGS. 45 and 46 illustrate hand-held ultrasound medical systems that may incorporate clamping functions. The ultrasound medical system 4500 depicted in FIG. 45 may be a clamping device including a clamping actuator 4502 that may control the position of a clamp jaw 4553 with respect to the distal end 4505 of the surgical tool. The distal end 4505 of the surgical tool may be fabricated to have a complementary shape to the clamp jaw 4553. For example, the distal end 4505 may have a waveguide including an angled portion immediately proximal to a straight end effector, thereby allowing precision working at the end effector. FIG. 46 depicts another example of an ultrasound medical system 4600 that is similarly configured for tissue clamping as opposed to tissue cutting. In the example of FIG. 46, the clamp jaw 4653 may have a complementary shape to the distal end 4605 of the surgical tool. Thus, the distal end 4605 may have a curved waveguide portion immediately proximal to a straight end effector having a flat clamping surface to mate with the end of the clamp jaw 4653.

FIGS. 47-57 are directed to mechanisms by which a surgical tool may be attached to an ultrasonic system (such as depicted in FIG. 1) or ultrasound medical system (such as depicted in FIGS. 34, 35, and 44-46), or any other medical device configured to use ultrasonic vibration to effect a therapeutic result. Such a surgical tool, for example, may be fabricated from sheet stock, although alternative examples of such a surgical tool may be fabricated from round stock or bar stock. Such a surgical tool may also be a component of an ultrasonic medical device that includes one or more piezoelectric transducers affixed onto a transducer mounting portion of the surgical tool.

Figure 47:
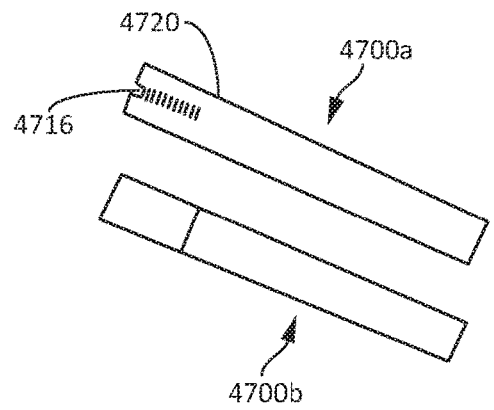
FIG. 47 illustrates a plan view of two surgical tools having female threads machined in the transducer mounting portion, according to one aspect of this disclosure.
Figure 48:
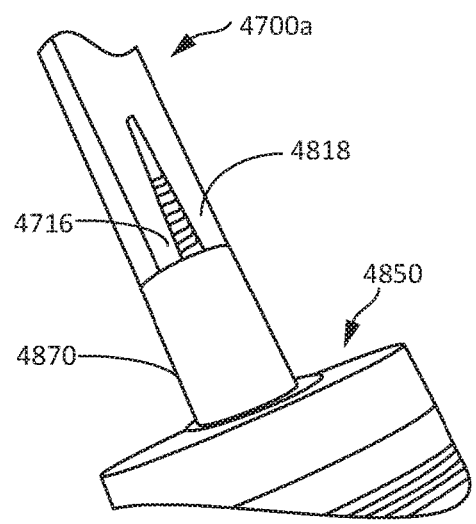
FIG. 48 is a perspective view of a transducer mounting portion of the surgical tool of FIG. 47 mounted in an ultrasonic medical device, according to one aspect of this disclosure.
Figure 49:
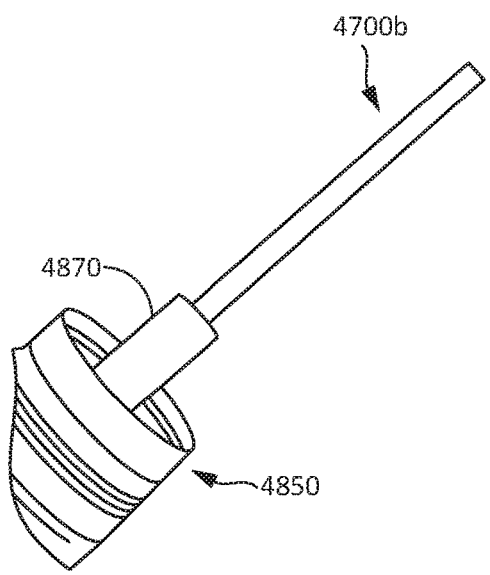
FIGS. 49 and 50 are a side view and a perspective view, respectively, of the two surgical tools of FIG. 47 mounted in the ultrasonic medical device of FIG. 48, according to one aspect of this disclosure.
Figure 50:
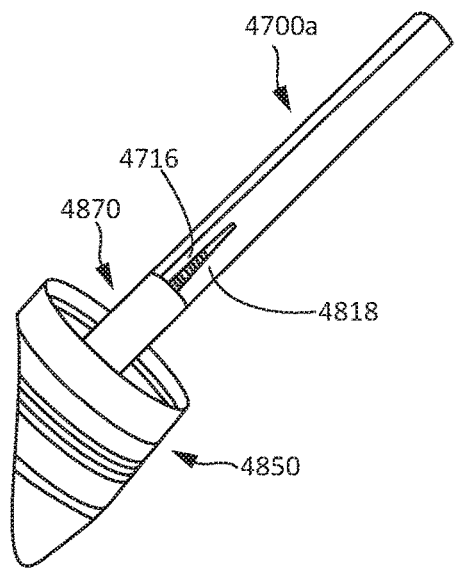

FIGS. 47-53 depict a surgical tool 4700 having female threads 4716 machined into a transducer mounting portion 4720. FIG. 47 depicts a surgical tool 4700*a* fabricated from sheet stock having a thickness of about 0.100" and a surgical tool 4700*b* fabricated from sheet stock having a thickness of about 0.125". Both surgical tools 4700*a,b* have a 4-40 threaded hole tapped along a longitudinal axis of the surgical tools 4700*a,b*. It may be noted that a component having a male thread configured to mate with the 4-40 threaded hole may have a major dimension of about 0.110". Thus, the female threads 4716 extend beyond the surfaces of the surgical tool 4700*a* because the male threads may extend laterally beyond the surfaces of the surgical tool 4700*a*. FIG. 48 illustrates an assembled ultrasonic medical device 4850 including the surgical tool 4700*a*, a collet, clamp or collar 4870 configured to secure the surgical tool 4700*a*, and a threaded male component 4818 inserted into the female threads 4716 of the surgical tool 4700*a*. FIG. 49 illustrates a side view of an assembled ultrasonic medical device 4850 including the surgical tool 4700b, and a collet, clamp or collar 4870 configured to secure the surgical tool 4700b. In FIG. 49, the threaded male component 4818 is not visible since the surgical tool 4700b has a thickness greater than the major dimension of the threaded male component. FIG. 50 depicts another view of the assembled ultrasonic medical device 4850 of FIG. 48 in which the entirety of the surgical tool 4700a is illustrated.

Figure 51:
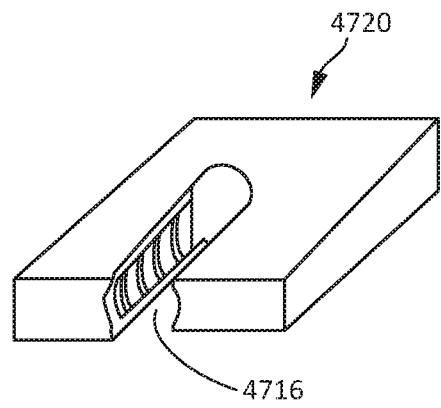
FIG. 51 is an end perspective view of the surgical device of FIG. 47, illustrating the female threads tapped into the transducer mounting portion, according to one aspect of this disclosure.
Figure 52:
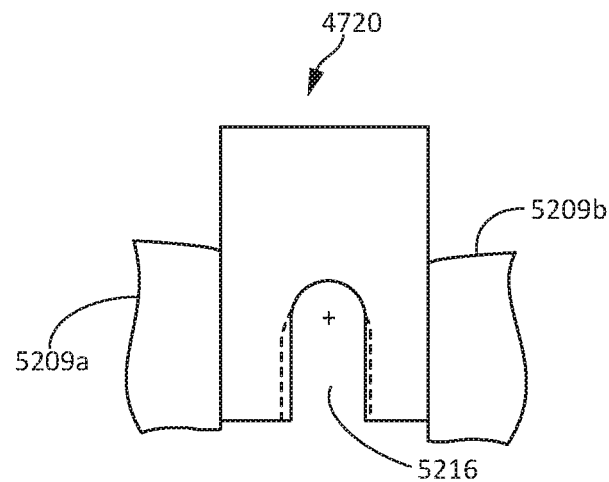
FIG. 52 is a plan view of fabricating female threads into the transducer mounting portion of the surgical tool of FIG. 47, according to one aspect of this disclosure.
Figure 53:
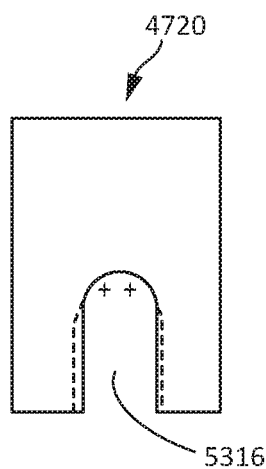
FIG. 53 is a plan view of the female threads tapped into the transducer mounting portion of the surgical tool of FIG. 47, according to one aspect of this disclosure.

FIG. 51 depicts a close-up view of the transducer mounting portion 4720 of the surgical tool 4700a illustrated in FIG. 47. The female threads 5216 are depicted as being formed along the inner surface of a hole tapped along a longitudinal axis of the surgical tool 4700a. FIG. 52 illustrates a method by which the female threads 5216 may be fabricated into the transducer mounting portion 4720 of a surgical tool such as 4700a in which the major dimension of the corresponding male thread is larger than the thickness of the surgical tool 4700a. In one method, supports 5209a,b may be braced against the lateral edges of the surgical tool 4700a. A slot may then be machined along the longitudinal axis of the surgical tool 4700a in the transducer mounting portion and the female threads 5216 may be tapped. In this manner, the transducer mounting portion of the surgical tool 4700a is not deformed during the tapping process. The slot may terminate with a radius or radii at its distal termination for reducing acoustic stresses. The radius may comprise a single radius (+ in FIG. 52) or a double radius (++ in FIG. 53).

Figure 54:
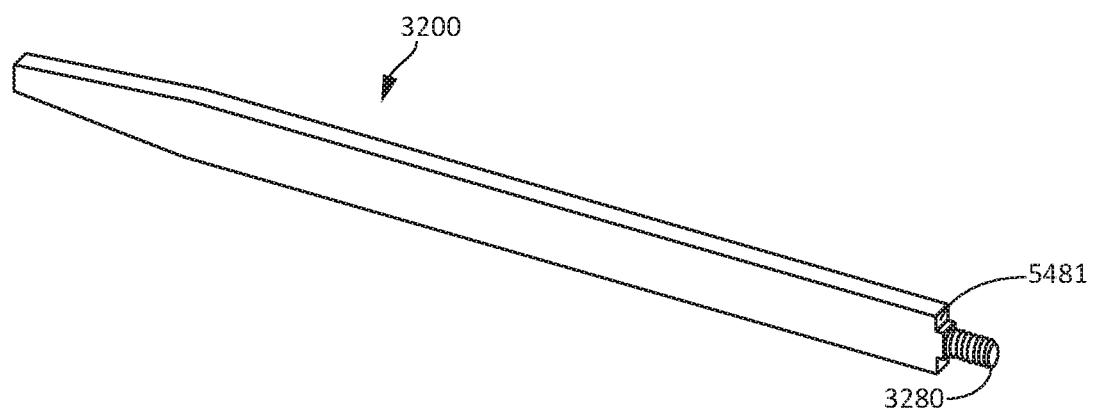
FIG. 54 is a perspective view of a surgical tool including a threaded stub at the transducer mounting portion, according to one aspect of this disclosure.

FIGS. 54-57 depict aspects of a male threaded stud or boss 3280 attached at the proximal end of a surgical tool 3200, in which the stud or boss 3280 is coaxial with a longitudinal axis of the surgical tool 3200. FIG. 54 illustrates a threaded boss 3280 having male threads having a major dimension less than or equal to the width of the surgical tool 3200. Also illustrated is a portion of a proximal surface of the surgical tool 3200 that is faced 5481 from the threaded boss. The portion of the proximal surface may be faced 5481 using a turning operation so that the faced portion 5481 is normal with respect to the longitudinal aspect of the surgical tool 3200.

Figure 55:
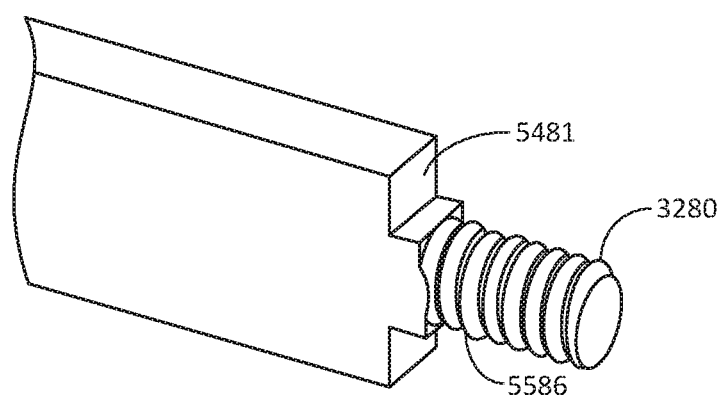
FIG. 55 is a close-up perspective view of the transducer mounting portion of the surgical tool of FIG. 54, according to one aspect of this disclosure.

FIG. 55 is a close-up view of the proximal end of the surgical tool 3200 depicted in FIG. 54. As can be observed, the threaded boss 3280 is affixed to a stand-off portion of the proximal surface and raised above the faced portion 5481 of the proximal surface. FIG. 55 also depicts the threaded boss 3280 having a male thread 5586 that possesses a major dimension greater than the width of the surgical tool 3200. The male thread may also be faced so that the portion of the male thread 5586 is reduced to the thickness of the surgical tool 3200. Such faced or machined male threads 5586 may be used to lock the threads during manufacturing for non-field-attachable/detachable products.

Figure 56:
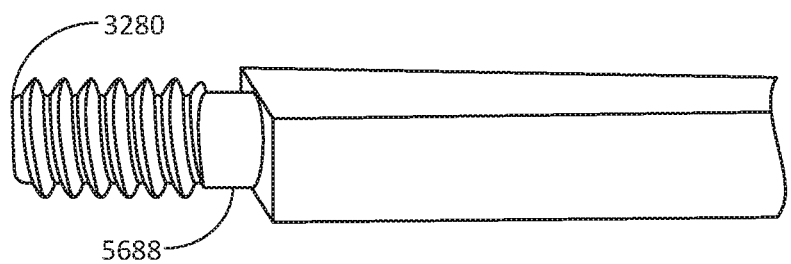
FIG. 56 is a close-up perspective view of the transducer mounting portion of a surgical tool including a threaded stub, according to one aspect of this disclosure.
Figure 57:
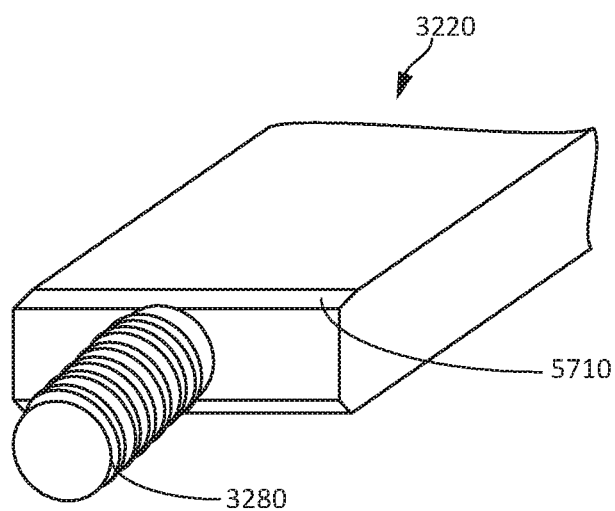
FIG. 57 is a close-up perspective view of the transducer mounting portion of a surgical tool including a threaded stub and chamfers, according to one aspect of this disclosure.

FIG. 56 depicts the proximal end of a surgical tool 3200 in which the male threads are fabricated on a boss 3280 that includes a stand-off portion 5688 that is unthreaded. FIG. 57 depicts another example of the proximal end of a surgical tool 3200 having a threaded boss 3280. In the aspect of FIG. 57, edges of proximal face include chamfers 5710 that may be fabricated by filleted, cutting, tumbling, or other appropriate methods. The use of such chamfers 5710 may be useful to prevent the edges of the proximal end of the surgical tool 3200 from "kick up a burr" on the face a mating portion of an ultrasonic medical system.

Figure 58:
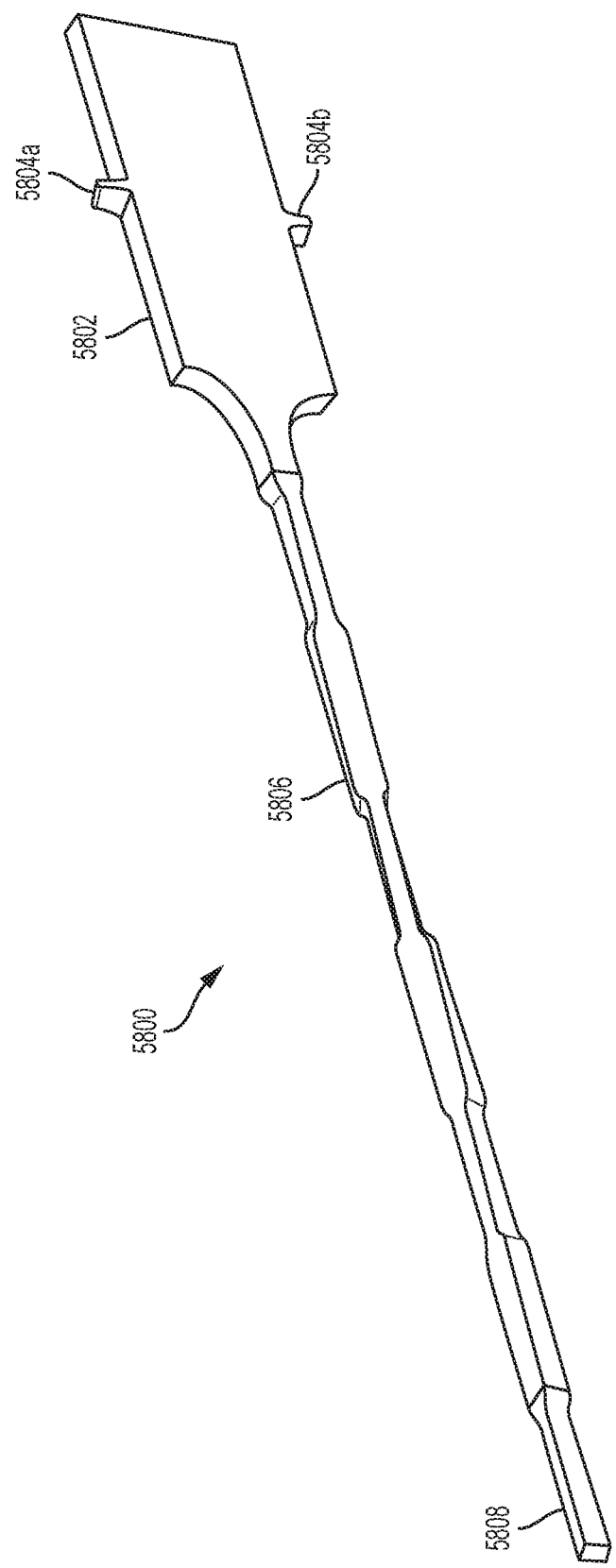
FIG. 58 is a perspective view of a surgical tool having a flat blade with a straight tip, according to one aspect of this disclosure.
Figure 59:
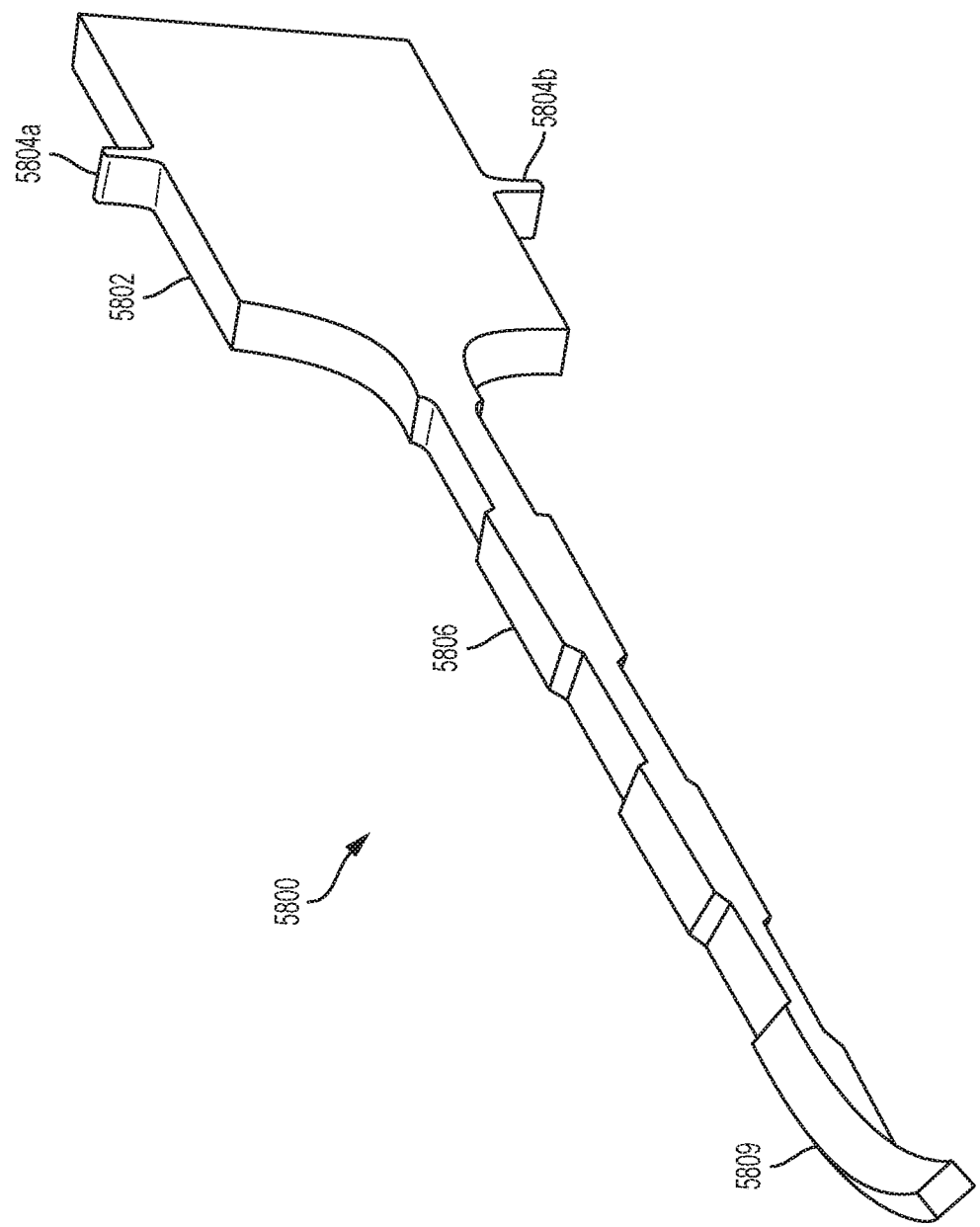
FIG. 59 is a perspective view of a surgical tool having a twisted flat blade with a curved and tapered tip, according to one aspect of this disclosure.

FIG. 58 depicts a surgical tool 5800 comprising a proximal transducer mounting portion 5802, a distal flat blade 5808 and a longitudinal portion or waveguide 5806 therebetween. The distal flat blade 5808 may comprise an end effector 5808 of the surgical tool 5800. In various aspects, referencing FIG. 36, a fabricated surgical tool 3600 or some component thereof such as the end effector 3660, may have a undesired thickness and orientation. To adjust the thickness and orientation, one or more additional manufacturing steps such as forming, machining, cutting, forging, grinding, polishing, de-burring, or tumbling may be implemented. These additional manufacturing steps may also be useful for adjusting the shape, edge quality, curvature and offset of an end effector such as the flat blade 5808. Alternatively, after using a two dimensional cutting method to form the geometry of the flat blade 5808, the flat blade 5808 may be twisted to adjust the orientation relative to a proximal feature, such as the transducer mounting portion assembly 5802. The twisting may also be used to adjust other features of the flat blade 5808, such as curvature, offset, flex section, and thin or tapered tissue clamping sections. The flat blade 5808 can be twisted at any point along its length. FIG. 59 illustrates one example of a twisted flat blade 5809 with a curved and tapered tip. The twisted flat blade 5809 is twisted for a suitable degree of rotation, such as 90 degrees, along a section of the surgical tool 5800 located between the twisted flat blade 5809 and a proximal section of the tool 5800. In some aspects, the twisted flat blade 5809 with the curved and tapered tip does not require an additional manufacturing step to adjust thickness and orientation. For example, no machining operation to form the curved and tapered tip and no forming operation to form the curvature of the twisted flat blade 5809 is necessary.

Figure 60:
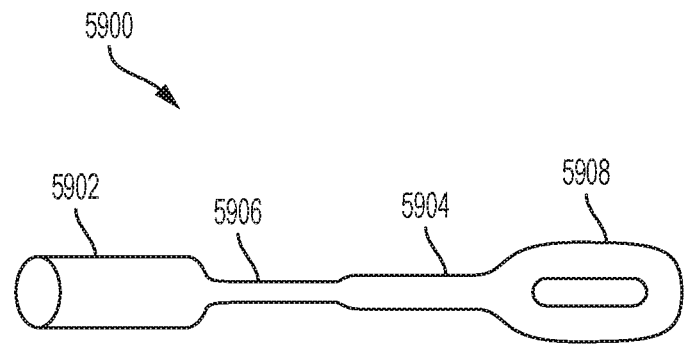
FIGS. 60-62 are plan views of surgical tools having blades with complex features, according to one aspect of this disclosure.

FIGS. 60-66 show surgical tools 5900 each comprising a proximal transducer mounting portion 5902, an ultrasonic blade 5904 with complex features 5908, 5909, 5910, 5911, 5912, 5913, 5914, 5915 and a longitudinal portion or waveguide 5906 therebetween. The blade 5904 may comprise an end effector 5904 of the surgical tool 5900. The surgical tools 5900 may be fabricated from titanium material using a metal injection molding (MIM). MIM is a net shape process for creating surgical tools with a reduction in the amount of machining required. Additionally, MIM fabricated titanium material may have similar properties to wrought titanium, such as similar stiffness, density (e.g., within 4%), and speed of sound (e.g., within 3.5%). In various aspects, MIM may be useful for fabricating ultrasonic blades with complex features. Fabricating blades with such complex features with MIM may reduce waste and cost compared to fabricating such complex blades with a conventional machining process. For example, FIG. 60 depicts a surgical tool 5900 comprising a MIM blade 5904 with a complex feature 5908 (i.e., internal hole 5908 in the ultrasonic blade 5904). The internal hole 5908 may be useful for particular surgical procedures.

Figure 61:
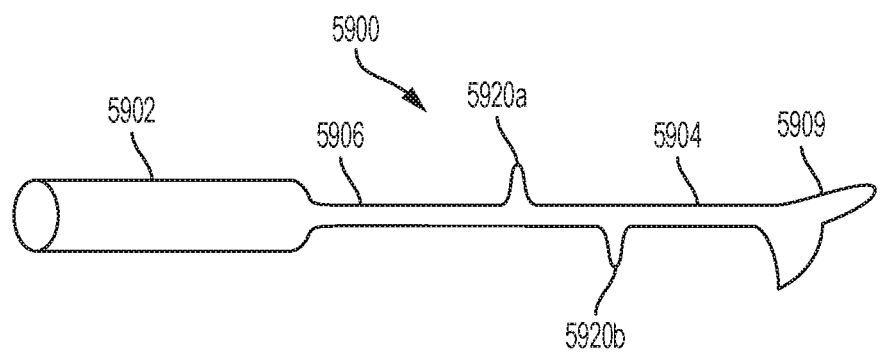
Figure 62:
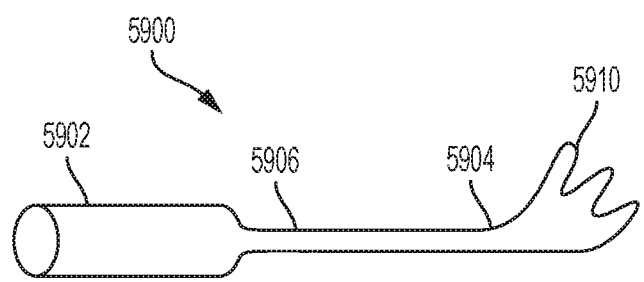
Figure 63:
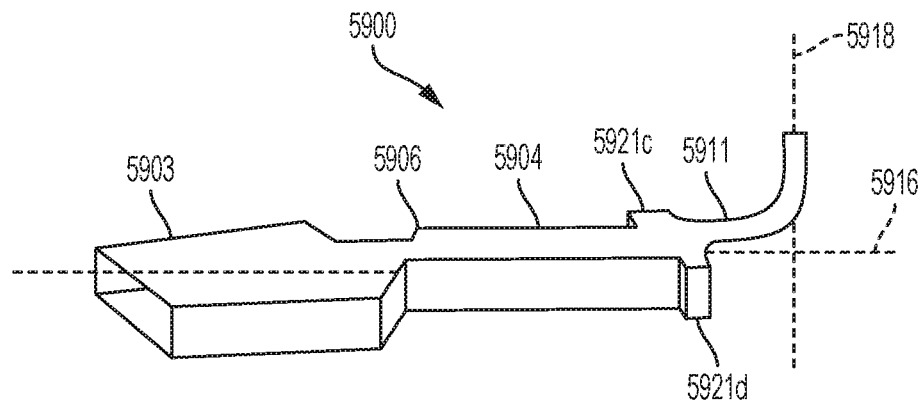
FIG. 63 is a perspective view of a surgical tool having a blade with a curved tip of large curvature, according to one aspect of this disclosure.

FIG. 61 depicts a surgical tool 5900 comprising a MIM blade 5904 with another complex feature 5909. The complex feature 5909 comprises an asymmetric design, as can be seen in FIG. 61. Specifically, the protrusions 5920a,b are disposed on opposing surface of the surgical tool 5900. For example, protrusion 5920a may be disposed on a top surface of the tool 5900 and protrusion 5920b may be disposed on a bottom surface of the tool 5900. The distal end of the MIM blade 5904 comprising the asymmetric complex feature 5909 can have a teeth type configuration. Such teeth type configurations may be particularly advantageous for cutting tissue in a surgical procedure. FIG. 62 depicts a surgical tool 5900 comprising a MIM blade 5904 with a third complex feature 5910. The complex feature 5910 comprises a finger type configuration. As can be seen in FIG. 62, the complex feature 5910 includes three fingers or prongs and can be similar to a three pronged fork. Such finger type configurations may be particularly advantageous for gripping tissue for cutting in a surgical procedure. FIG. 63 shows a surgical tool 5900 comprising a MIM blade 5904 with a large curved tip 5911. The large curvature of the blade tip 5911 protrudes in two dimensions. For example, the curved blade tip 5911 extends along both the x axis 5916 and they axis 5918. The protrusions 5921c,d may form attachment features of the MIM blade 5904. Using MIM to fabricate a blade tip with such a large curvature can result in reduced manufacturing costs and waste. In contrast to MIM, two alternative approaches of using a larger stock to machine the large curvature into a blade or forming the curvature after fabricating a curved blade both generate waste compared to a MIM fabrication process.

Figure 64:
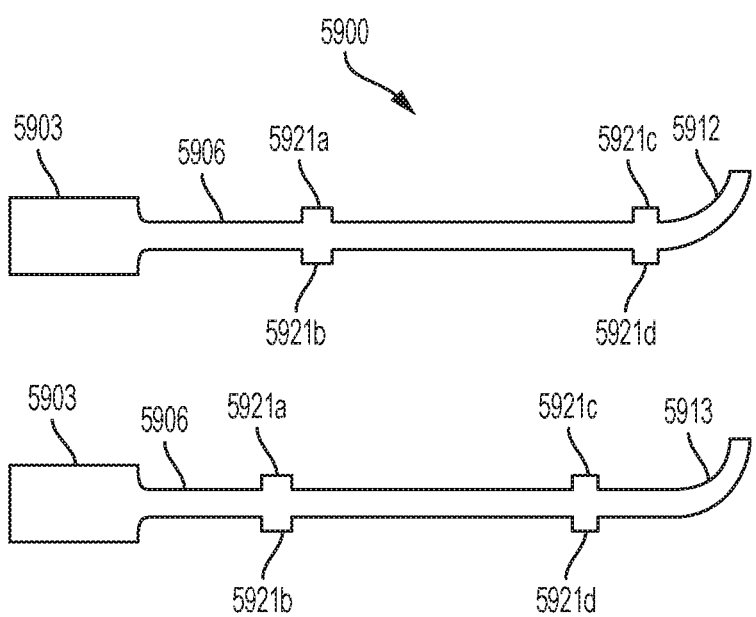
FIG. 64 is a plan view of surgical tools having blades with curved tips, according to one aspect of this disclosure.
Figure 65:
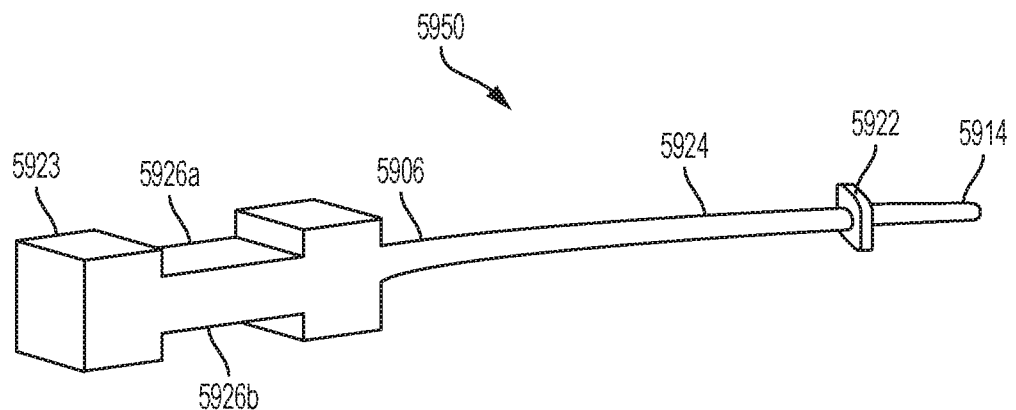
FIG. 65 is a perspective view of a surgical tool having a transducer mounting portion with a wide and flat surface, according to one aspect of this disclosure.
Figure 66:
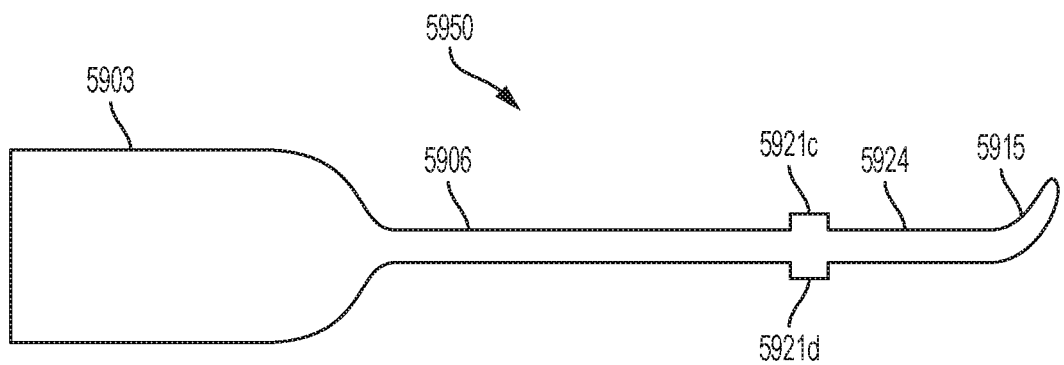
FIG. 66 is a plan view of a surgical tool having a transducer mounting portion with a wide and flat surface, according to one aspect of this disclosure.

FIG. 64 shows two surgical tools 5900 comprising blades 5904 with curved tips of varying curvatures. As can be seen in FIG. 64, the curvature of the curved blade tip 5913 is greater than the curvature of the curved blade tip 5912. The curved blade tip 5913 with greater curvature corresponds to an MIM fabricated blade 5904 while the curved blade tip 5912 with lesser curvature corresponds to a non-MIM fabricated blade 5904. The blades 5904 each have protrusions 5921c,d, which may form attachment features of the blades 5904. The tool 5900 also has attachment features 5921a,b. FIG. 65 shows a surgical tool 5950 with a MIM fabricated blade 5924 that is configured for use in a D31 mode, as described previously. The surgical tool 5950 may be particularly advantageous for D31 use because the proximal transducer mounting portion 5923 comprises a square geometry with a wide and large flat surface while the blade 5924 comprises a round geometry. The transducer mounting portion 5923 also comprises grooves 5924a,b for receiving transducers such as transducers 312a,b, in an interference fit. The interference fit may comprise a heating process to press fit the transducers into the grooves 5924a,b, which may be undersized. Additionally, the MIM fabricated blade 5924 has a small round blade tip 5914 for effecting cutting of tissue. The blade 5924 also comprises a square guard 5922. FIG. 66 depicts a surgical tool 5950 comprising a proximal transducer mounting portion 5923 with a wide and flat surface. The MIM fabricated blade 5924 of the surgical tool 5950 comprises a curved small round blade tip 5915 for effecting cutting of tissue. The blade 5924 also comprises protrusions 5921c,d, which may form attachment features of the blade 5924.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

An ultrasonic medical device comprising: a surgical tool comprising a transducer mounting portion at a proximal end, an end effector at a distal end, and a waveguide disposed therebetween, the waveguide extending along a longitudinal axis, the transducer mounting portion of the surgical tool comprising a first face and a second face at the proximal end, the second face positioned opposite the first face; a first transducer comprising a body defining a face; and a second transducer comprising a body defining a face; wherein the face of the first transducer is in mechanical communication with the first face of the surgical tool and the face of the second transducer is in mechanical communication with the second face of the surgical tool opposite the first transducer; wherein the first transducer and the second transducer are configured to operate in a D31 mode with respect to the longitudinal axis of the waveguide; wherein, upon activation by an electrical signal having a predetermined frequency component, the first and second transducers are configured to induce a standing wave in the surgical tool to cause the end effector to vibrate, the standing wave having a wavelength proportional to the predetermined frequency component of the electrical signal; and wherein the surgical tool defines nodes and antinodes corresponding to the nodes and antinodes of the induced standing wave, wherein the nodes correspond to locations of minimal displacement and the antinodes correspond to locations of maximum displacement.

Example 2

The ultrasonic medical device of Example 1, wherein the surgical tool comprises a metal having a grain direction oriented at an angle with respect to the longitudinal axis.

Example 3

The ultrasonic medical device of Example 1 or Example 2, wherein the longitudinal axis of the surgical tool is oriented parallel to the grain direction.

Example 4

The ultrasonic medical device of one or more of Example 2 through Example 3, wherein the longitudinal axis of the surgical tool is oriented orthogonal to the grain direction.

Example 5

The ultrasonic medical device of one or more of Example 2 through Example 4, wherein the longitudinal axis of the surgical tool is oriented at an angle with respect to the grain direction to minimize stress in at least a portion of the surgical tool upon activation.

Example 6

The ultrasonic medical device of one or more of Example 2 through Example 5, wherein the longitudinal axis of the surgical tool is oriented at an angle with respect to the grain direction to maximize a longitudinal deflection of the surgical tool upon activation.

Example 7

The ultrasonic medical device of one or more of Example 1 through Example 6, wherein the body of the first transducer is disposed symmetrically about a node location of the surgical tool.

Example 8

The ultrasonic medical device of Example 7, wherein a body of the second transducer is disposed symmetrically about the node location in the surgical tool.

Example 9

The ultrasonic medical device of Example 8, wherein the face of the second transducer is fixed to the second face of the surgical tool with the conductive adhesive at the node location in the surgical tool and with a high strength adhesive at a location distant from the node location in the surgical tool.

Example 10

The ultrasonic medical device of one or more of Example 7 through Example 9, wherein the face of the first transducer is fixed to the first face of the surgical tool with an electrically conductive adhesive at the node location and wherein the face of the first transducer is fixed to the first face of the surgical tool with a high strength adhesive at a location away from the node location.

Example 11

The ultrasonic medical device of one or more of Example 1 through Example 10, further comprising a third transducer and a fourth transducer, each of the third and fourth transducer comprising a body defining a face.

Example 12

The ultrasonic medical device of Example 11, wherein the third transducer is in mechanical communication with a second face of the first transducer and the fourth transducer is in mechanical communication with a second face of the second transducer.

Example 13

The ultrasonic medical device of Example 12, wherein the third transducer is smaller than the first transducer.

Example 14

The ultrasonic medical device of Example 13, wherein the fourth transducer is smaller than the second transducer.

Example 15

The ultrasonic medical device of one or more of Example 11 through Example 14, wherein a face of the third transducer is in mechanical communication with the first face of the surgical tool and a face of the fourth transducer is in mechanical communication with the opposing face of the surgical tool and opposite the third transducer, and wherein the third transducer is disposed along the waveguide of the surgical tool relative to the first transducer and the fourth transducer is disposed along the waveguide of the surgical tool relative to the second transducer.

Example 16

The ultrasonic medical device of Example 15, wherein the first transducer and the third transducer are disposed longitudinally symmetrically about the node location in the surgical tool and the second transducer and the fourth transducer are disposed longitudinally symmetrically about the node location in the surgical too.

Example 17

The ultrasonic medical device of Example 16, wherein the first transducer is disposed proximate to the third transducer along the waveguide and the second transducer is disposed proximate to the fourth transducer along the waveguide.

Example 18

The ultrasonic medical device of one or more of Example 1 through Example 17, wherein the first transducer comprises a first planar array of first transducer plates and the second transducer comprises a second planar array of second transducer plates, wherein each of the first transducer plates and each of the second transducer plates is independently activatable by an electrical signal having a predetermined frequency component.

Example 19

The ultrasonic medical device of one or more of Example 1 through Example 18, further comprising a clip configured to apply a compression force to each of the first transducer and the second transducer against the surgical tool.

Example 20

The ultrasonic medical device of one or more of Example 1 through Example 19, further comprising a clip configured to apply a longitudinal compression force to the first transducer.

Example 21

The ultrasonic medical device of one or more of Example 1 through Example 20, wherein at least a portion of the waveguide of the surgical tool distal to the first transducer and the second transducer has a rectangular cross section.

Example 22

The ultrasonic medical device of one or more of Example 1 through Example 21, wherein the rectangular cross-section is a square cross-section.

Example 23

The ultrasonic medical device of one or more of Example 1 through Example 22, wherein at least a portion of the waveguide of the surgical tool distal to the first transducer and the second transducer has an elliptical cross section.

Example 24

The ultrasonic medical device of one or more of Example 1 through Example 23, wherein the elliptical cross section is a circular cross section.

Example 25

The ultrasonic medical device of one or more of Example 1 through Example 24, further comprising a housing, wherein at least a portion of the surgical tool is disposed within the housing.

Example 26

The ultrasonic medical device of Example 25, wherein the surgical tool further comprises a first flange and a second flange, wherein the first flange extends from a first side of the surgical tool and the second flange extends from an opposing side of the surgical tool, wherein each of the first flange and the second flange is symmetrically disposed about a node location in the surgical tool, wherein the housing comprises a first retainer and a second retainer, and wherein the first retainer is configured to receive the first flange and the second retainer is configured to receive the second flange.

Example 27

The ultrasonic medical device of one or more of Example 25 through Example 26, wherein the housing comprises a pair of electrical contacts, wherein a first electrical contact of the pair of electrical contacts is configured to contact an electrically conductive portion of the first transducer and a second electrical contact of the pair of electrical contacts is configured to contact an electrically conductive portion of the second transducer.

Example 28

The ultrasonic medical device of Example 27, wherein the first contact is configured to provide a compression force to the first transducer against the surgical tool and the second contact is configured to provide a compression force to the second transducer against the surgical tool.

Example 29

The ultrasonic medical device of one or more of Example 27 through Example 28, wherein the first contact is configured to provide an electrical contact with the first transducer and the second contact is configured to provide an electrical contact with the second transducer.

Example 30

The ultrasonic medical device of one or more of Example 1 through Example 29, further comprising a plurality of female screw threads fabricated into the proximal end of the surgical tool and oriented along a longitudinal axis thereof.

Example 31

The ultrasonic medical device of Example 30, wherein the plurality of female screw threads are configured to receive a component having mating male threads that have a major dimension less than or equal to a thickness of the surgical tool, wherein the thickness comprises a distance between the first face of the surgical tool and the second face of the surgical tool.

Example 32

The ultrasonic medical device of one or more of Example 30 through Example 31, wherein the plurality of female screw threads are configured to receive a component having mating male threads that have a major dimension greater than a thickness of the surgical tool, wherein the thickness comprises a distance between the first face of the surgical tool and the second face of the surgical tool.

Example 33

The ultrasonic medical device of one or more of Example 1 through Example 32, further comprising a boss extending in a proximal direction from the proximal end of the surgical tool and oriented along a longitudinal axis thereof, and wherein the boss comprises a plurality of male screw threads.

Example 34

The ultrasonic medical device of Example 33, wherein a portion of the plurality of male screw threads have a major dimension less than or equal to a thickness of the surgical tool, wherein the thickness comprises a distance between the first face of the surgical tool and the second face of the surgical tool.

Example 35

A method of fabricating an ultrasonic medical device comprising: machining a surgical tool from a portion of a flat metal stock, wherein the surgical tool comprises a transducer mounting portion at a proximal end, an end effector at a distal end, and a waveguide disposed therebetween, the waveguide extending along a longitudinal axis, the transducer mounting portion of the surgical tool comprising a first face and a second face at the proximal end, the second face positioned opposite the first face; contacting a face of a first transducer with the first face of the surgical tool wherein the first transducer is configured to operate in a D31 mode with respect to the longitudinal axis of the waveguide; and contacting a face of a second transducer with the second face of the surgical tool opposite the first transduce, wherein the second transducer is configured to operate in a D31 mode with respect to the longitudinal axis of the waveguide; wherein, upon activation by an electrical signal having a predetermined frequency component, the first and second transducers are configured to induce a standing wave in the surgical tool to cause the end effector to vibrate, the standing wave having a wavelength proportional to the predetermined frequency component of the electrical signal; and wherein the surgical tool defines nodes and antinodes corresponding to the nodes and antinodes of the induced standing wave, wherein the nodes correspond to locations of minimal displacement and the antinodes correspond to locations of maximum displacement.

Example 36

The method of Example 35, wherein machining a surgical tool from a portion of a flat metal stock comprises machining a surgical tool comprising a metal having a grain direction oriented at an angle with respect to the longitudinal axis of the surgical tool thereby optimizing an operational characteristic of the surgical tool.

Example 37

The method of Example 35 or Example 36, wherein machining a surgical tool having a longitudinal axis oriented at an angle with respect to a grain direction of the flat metal stock comprises machining a surgical tool having a longitudinal axis oriented parallel to the grain direction of the flat metal stock.

Example 38

The method of one or more of Example 36 through Example 37, wherein machining a surgical tool having a longitudinal axis oriented at an angle with respect to a grain direction of the flat metal stock comprises machining a surgical tool having a longitudinal axis oriented orthogonal to the grain direction of the flat metal stock.

Example 39

The method of one or more of Example 36 through Example 38, wherein optimizing an operational characteristic of the surgical tool comprises: maximizing a length of the end effector; minimizing the length of the end effector; or reducing a stress in at least a portion of the surgical tool.

Example 40

The method of one or more of Example 35 through Example 39, further comprising subjecting the surgical tool to one or more metalworking processes.

Example 41

The method of Example 40, wherein subjecting the surgical tool to one or more metalworking processes comprises applying a metalworking process to a portion of the surgical tool proximal to the anti-node location in the surgical tool.

Example 42

The method of one or more of Example 40 through Example 41, wherein subjecting the surgical tool to one or more metalworking processes comprises removing a portion of mass of the surgical tool in a region bounded by a first anti-node location in the surgical tool and a second anti-node location in the surgical tool.

Example 43

The method of one or more of Example 40 through Example 42, wherein subjecting the surgical tool to one or more metalworking processes comprises subjecting the surgical tool to machining, skiving, coining, forming, forging, milling, end milling, chamfering, tumbling, sand blasting, bead blasting, or electropolishing, or any combination or combinations thereof.

Example 44

The method of one or more of Example 40 through Example 43, wherein subjecting the surgical tool to one or more metalworking processes comprises removing a portion of mass of the surgical tool in a section of the waveguide and bending the surgical tool in the section of the waveguide.

Example 45

The method of one or more of Example 40 through Example 44, wherein subjecting the surgical tool to one or more metalworking processes comprises machining a plurality of female screw threads into the proximal end of the surgical tool, wherein the female screw threads are oriented along a longitudinal axis thereof.

Example 46

The method of Example 45, wherein machining a plurality of female screw threads into the proximal end of the surgical tool comprises machining a plurality of female screw threads configured to receive a component having mating male threads that have a major dimension less than or equal to a thickness of the surgical tool, wherein the thickness comprises a distance between the first face of the surgical tool and the second face of the surgical tool.

Example 47

The method of one or more of Example 45 through Example 46, wherein machining a plurality of female screw threads into the proximal end of the surgical tool comprises machining a plurality of female screw threads configured to receive a component having mating male threads that have a major dimension greater than a thickness of the surgical tool, wherein the thickness comprises a distance between the first face of the surgical tool and the second face of the surgical tool.

Example 48

The method of one or more of Example 35 through Example 47, wherein machining a surgical tool from a portion of a flat metal stock comprises laser machining, laser machining with a tilt degree of freedom, electrical discharge machining, milling, stamping, or fine blanking.

Example 49

The method of one or more of Example 35 through Example 48, wherein machining a surgical tool from a portion of a flat metal stock comprises machining a surgical tool further comprising a first flange and a second flange, wherein the first flange extends from a first side of the surgical tool and the second flange extends from an opposing side of the surgical tool.

Example 50

The method of Example 49, wherein machining a surgical tool from a portion of a flat metal stock comprises machining a surgical tool further comprising a first flange and a second flange wherein each of the first flange and the second flange is symmetrically disposed about the node location in the surgical device.

Example 51

The method of one or more of Example 35 through Example 50, wherein machining a surgical tool from a portion of a flat metal stock comprises machining a surgical tool from a flat metal stock comprising aluminum or titanium.

Example 52

The method of one or more of Example 35 through Example 51, wherein contacting a face of a first transducer with the first face of the surgical tool comprises fixing the face of the first transducer to the first face of the surgical tool with an electrically conductive adhesive at a node location and wherein the face of the first transducer is fixed to the first face of the surgical tool with a high strength adhesive at a location away from the node location.

Example 53

The method of Example 52, wherein contacting a face of a second transducer with an opposing face of the surgical tool and opposite the first transducer comprises fixing a face of a second transducer to an opposing face of the surgical tool and opposite the first transducer with a conductive adhesive at the node location in the surgical tool and with a high strength adhesive at a location away from the node location in the surgical tool.

Example 54

An ultrasonic surgical device comprising: a surgical tool comprising a proximal transducer mounting portion defining a surface, a distal end effector end, and a waveguide disposed therebetween, the waveguide extending along a longitudinal axis; and a transducer in mechanical communication with the surface of the transducer mounting portion; wherein the transducer is configured to operate in a D31 mode with respect to the longitudinal axis of the waveguide; and wherein, upon activation by an electrical signal having a predetermined frequency component, the transducer is configured to induce a standing wave in the surgical tool to cause the end effector to vibrate, the standing wave having a wavelength proportional to the predetermined frequency component of the electrical signal.

Example 55

The ultrasonic surgical device of Example 54, wherein the surgical tool defines a lumen extending along the longitudinal axis.

Example 56

The ultrasonic surgical device of Example 54 or Example 55, wherein the proximal transducer mounting portion comprises a cylindrical prism.

Example 57

The ultrasonic surgical device of Example 56, wherein the waveguide has a circular cross-section

Example 58

The ultrasonic surgical device of one or more of Example 56 through Example 57, wherein the waveguide has a rectangular cross-section.

Example 59

The ultrasonic surgical device of one or more of Example 56 through Example 58, wherein the transducer defines a hollow cylindrical portion in mechanical communication with the proximal transducer mounting portion.

Example 60

The ultrasonic surgical device of one or more of Example 56 through Example 59, wherein the transducer comprises a plurality of partial cylindrical plates and wherein each of the plurality of partial cylindrical plates is in mechanical communication with the proximal transducer mounting portion.

Example 61

The ultrasonic surgical device of Example 60, wherein each of the plurality of partial cylindrical plates is independently actuatable.

Example 62

The ultrasonic surgical device of one or more of Example 54 through Example 61, wherein the proximal transducer mounting portion comprises a prism having a plurality of flat surfaces.

Example 63

The ultrasonic surgical device of one or more of Example 56 through Example 62, wherein the transducer mounting portion further comprises a flat surface in the cylindrical prism.

Example 64

The ultrasonic surgical device of Example 63, wherein the transducer is in mechanical communication with the flat surface.

Example 65

The ultrasonic surgical device of one or more of Example 62 through Example 64, wherein the waveguide has a circular cross-section

Example 66

The ultrasonic surgical device of one or more of Example 62 through Example 65, wherein the waveguide has a rectangular cross-section.

Example 67

The ultrasonic surgical device of one or more of Example 62 through Example 66, wherein the transducer comprises a plurality of plates wherein each of the plurality of plates is in mechanical communication with one of the plurality of side surfaces.

Example 68

The ultrasonic surgical device of one or more of Example 65 through Example 67, wherein each of the plurality of plates is independently actuatable by an electrical signal having a predetermined frequency component.

Example 69

The ultrasonic surgical device of one or more of Example 62 through Example 68, wherein the prism is a quadrilateral prism.

Example 70

The ultrasonic surgical device of one or more of Example 62 through Example 69, wherein the prism is a triangular prism.

Example 71

The ultrasonic surgical device of Example 70, wherein the prism is a hollow triangular prism having a plurality of inner side surfaces.

Example 72

The ultrasonic surgical device of Example 71, wherein the transducer comprises a plurality of rectangular plates wherein each of the plurality of rectangular plates is in mechanical communication with one of the plurality of inner side surfaces.

Electrical and Thermal Connections for Ultrasonic Transducer

Figure 67:
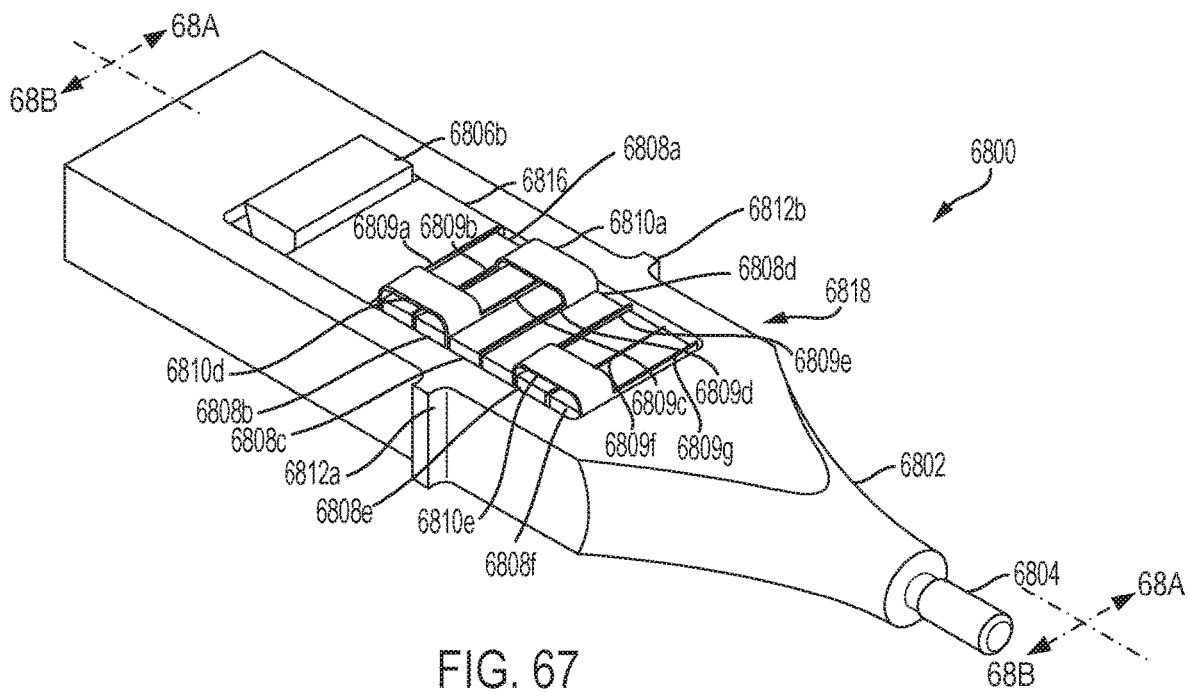
FIG. 67 is a perspective view of a transducer assembly employing a wedge configuration and configured to operate in a D33 mode of operation, according to one aspect of this disclosure.

FIG. 67 is a perspective view of a transducer assembly 6800 configured to operate in a D33 mode of operation, according to one aspect of this disclosure. The transducer assembly 6800 comprises transducer 6818, piezoelectric elements 6808a-6808f, a horn shaped portion 6802, and a threaded connection such as a stud 6804 to connect to an ultrasonic waveguide. The transducer 6818 includes piezoelectric elements 6808a-6808f. As described above, the transducer 6800 is configurable as a "Langevin" stack (e.g., with a rectangular cross section), in which the piezoelectric elements 6808a-6800f and corresponding activating electrodes 6810a-c are interleaved. In one aspect, the activating electrodes 6809a-6809g can be thin sheets of an electrically conductive metal such as, for example, aluminum, silver, gold, copper, and/or alloys thereof. The activating electrodes 6809a-g are each electrically connected to an ultrasonic signal generator via the electrically conductive elements 6810a-6810f. The electrically conductive elements 6810a, 6810b, 6810c may form a path to a pole (e.g., the positive pole) of the generator. The electrically conductive elements 6810d, 6810e, 6810f, 6810g may form another path to an opposing pole (e.g., the negative pole) of the generator. The electrically conductive elements 6810a-6810g may be U-shaped shorting caps that appear similar to brackets. As shown in FIG. 67, shorting caps 6810a-6810c are positioned over the piezoelectric elements 6808a-f. In various aspects, rather than employing a bolt to compress and acoustically couple the piezoelectric elements 6808a-6808f to an ultrasonic waveguide, the transducer assembly 6800 instead employs wedges 6806a-6806b to compress against a compressing plate 6816. In turn, the compressing plate 6816 compresses and acoustically couples the piezoelectric elements 6808 to an ultrasonic waveguide. Such compression of the piezoelectric elements 6808a-6808f can be useful for operation of the transducer 6800 stack. The compressing plate 6816 may be made of an electrically conductive metal such as steel, for example. The wedges 6806a, 6806b also may be made of an electrically conductive metal such as steel, for example.

In one aspect, the wedges 6806a, 6806b (not shown) can be machined and inserted by a suitable forming press. Additionally, the wedges 6806a, 6806b may be secured by a conductive bonding material or adhesive. In addition to the piezoelectric elements 6808, wedges 6806a, 6806b, electrodes 6809a-6809g, and shorting caps 6810a-6810g, the transducer assembly 6800 includes flanges 6812a, 6812b located on opposing sides of the transducer assembly 6800, such as a node location of the transducer assembly 6800. The flanges 6812a, 6812b may be configured to be received within a retainer of a housing (not shown) of an ultrasonic surgical instrument for secure attachment of the transducer assembly 6800 to the housing. Replacing the bolt with the wedges 6806a, 6806b can be advantageous because of easier machining and assembling of the transducer 6800 stack. Additional advantages of the wedge configuration include the ability to tune the acoustic assembly of the transducer assembly 6800 by modulating the tension in the transducer 6800 with the wedges 6806a, 6806b and the relatively inexpensive, simple geometric shape of the piezoelectric elements 6808a-6808f.

Figure 68A:
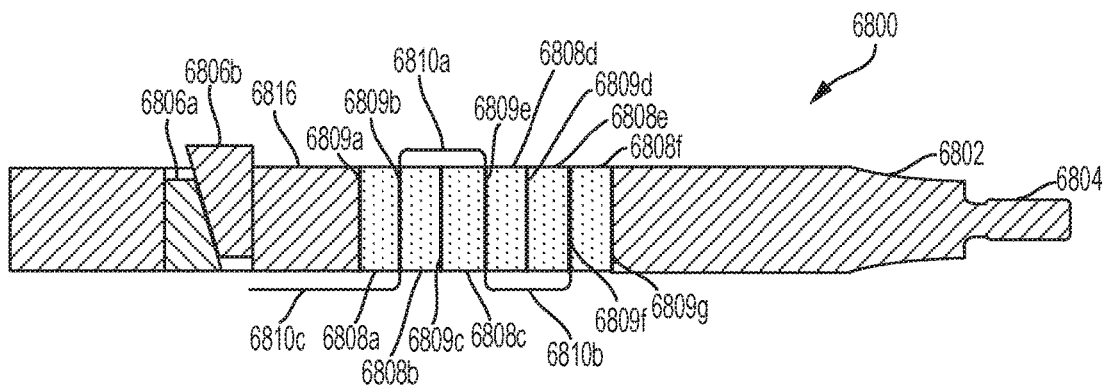
FIG. 68A is a section view of the ultrasonic transducer assembly shown in FIG. 67 taken along section line 68A-68A shown in FIG. 67, according to one aspect of this disclosure.
Figure 68B:
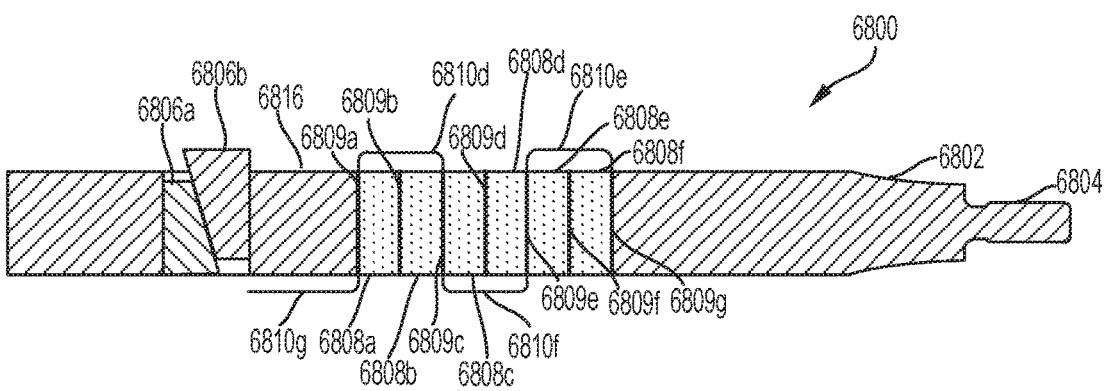
FIG. 68B is a section view of the ultrasonic transducer assembly shown in FIG. 67 taken along section line 68B-68B shown in FIG. 67, according to one aspect of this disclosure.

FIGS. 68A-68B illustrate cross section views of the ultrasonic transducer assembly 6800 employing the wedge configuration, according to one aspect of this disclosure, where FIG. 68A is a section view taken along section line 68A-68A as shown in FIG. 67 and FIG. 68B is a section view taken along section line 68B-68B as shown in FIG. 67. In FIGS. 68A-68B, the wedges 6806a, 6806b each have an irregular quadrilateral or tetragon shape. If the individual shapes of the wedges 6806a, 6806b are laterally combined, the combination has a square shape. As described above, the wedges 6806a, 6806b are configured to compress and acoustically couple the piezoelectric elements 6808a-6808f to an ultrasonic waveguide through the stud 6804.

The rightward facing sectional view of FIG. 68A is obtained by starting from the longitudinal axis passing through the center of the transducer assembly 6800 and continuing right in the direction of the corresponding arrow 68A, as depicted in FIG. 67. As can be seen in FIG. 68A, in one aspect, the first pair of shorting caps 6810a-6810c may be connected in an offset manner. Specifically, shorting cap 6810c may be connected to a pole of the ultrasonic signal generator on one end and to the activating electrode 6809b on the other end. Similarly, shorting cap 6810a may be connected to the activating electrode 6809b on one end and to the activating electrode 6809d on the other end. Shorting cap 6810b may be connected to the activating electrode 6809d on one end and to activating electrode 6809f on the other end. Accordingly, the shorting caps 6810a-6810c are configured to provide a safe means of closing the electrical circuit connecting the generator to the piezoelectric elements 6808a-6808f and electrodes 6809a-6809g. As can be seen in FIG. 68A, the shorting cap 6810a is positioned on the upper side of the transducer assembly 6800 while the shorting caps 6810b-6810c are positioned on the lower side of the transducer assembly 6800.

The leftward facing sectional view of FIG. 68B is obtained by starting from the longitudinal axis passing through the center of the transducer assembly 6800 and continuing left in the direction of the corresponding arrow 5B, as depicted in FIG. 67. In another aspect, as can be seen in FIG. 68B, the second pair of shorting caps 6810a-6810c may be connected in an opposing offset manner. Specifically, shorting cap 6810g may be connected to a pole of the ultrasonic signal generator on one end (opposing the pole that shorting cap 6810c is connected to) and to activating electrode 6809a on the other end. Similarly, shorting cap 6810d may be connected to the activating electrode 6809a on one end and to activating electrode 6809c on the other end. Shorting cap 6810f may be connected to activating electrode 6809c on one end and to activating electrode 6809e on the other end. Shorting cap 6810e may be connected to activating electrode 6809e on one end and to activating electrode 6809g on the other end. Accordingly, the shorting caps 6810d-6810g also are configured to provide a safe means of closing the electrical circuit connecting the generator to the piezoelectric elements 6808a-6808f and electrodes 6809a-6809g. As can be seen in FIG. 68B, the shorting caps 6810g and 6810f are positioned on the lower side of the transducer assembly 6800 while the shorting caps 6810d-6810e are positioned on the upper side of the transducer assembly 6800.

Figure 68C:
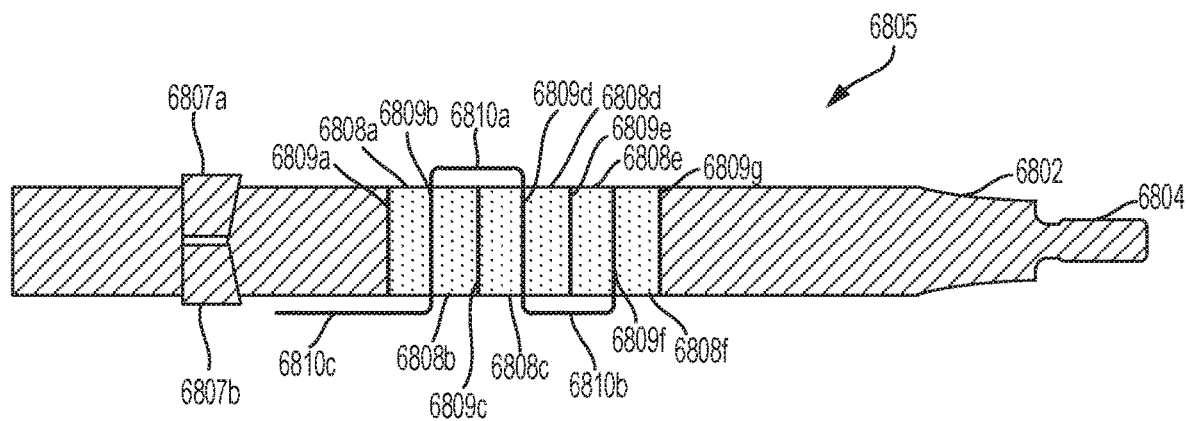
FIGS. 68C-68D illustrate cross section views of the ultrasonic transducer assembly 6805 employing another wedge configuration taken along similar section lines as shown in FIGS. 68A and 68B, according to one aspect of this disclosure.
Figure 68D:
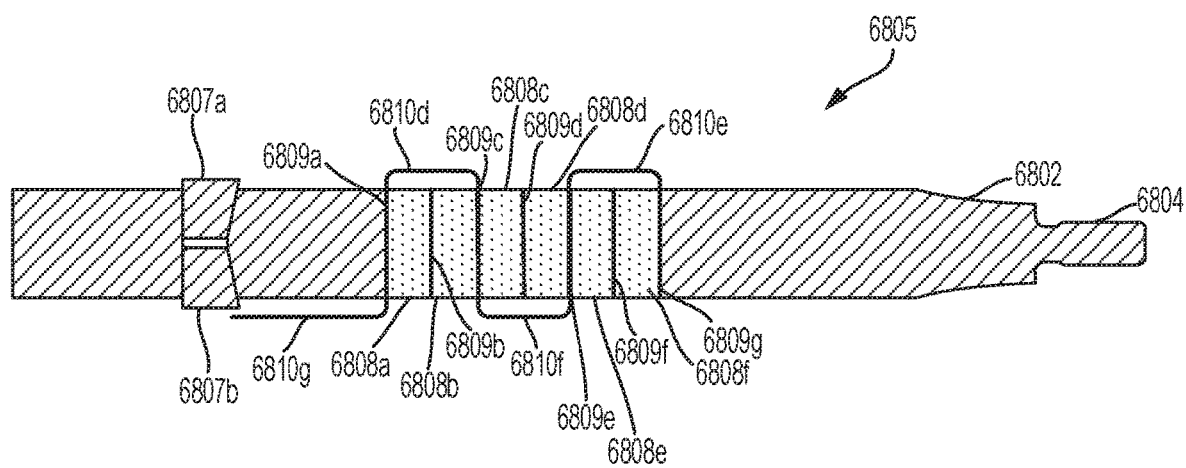

FIGS. 68C-68D illustrate cross section views of the ultrasonic transducer assembly 6805 employing another wedge configuration taken along similar section lines as shown in FIGS. 68A and 68B, according to one aspect of this disclosure. In FIGS. 68C-68D, the wedges 6807a, 6807b have a different irregular quadrilateral or tetragon shape than the shape of the wedges 6806a, 6806b in FIGS. 68A-68B. If the individual shapes of the wedges 6807a, 6807b are longitudinally combined, the combination has a square shape. As described above, the wedges 6807a, 6807b are configured to compress and acoustically couple the piezoelectric elements 6808a-6808f to an ultrasonic waveguide through the stud 6804. FIG. 68C depicts the same configuration of shorting caps 6810a-6810c as described in connection with FIG. 68A. Similarly, FIG. 68D depicts the same configuration of shorting caps 6810d-6810g as described in connection with FIG. 68B.

Figure 69:
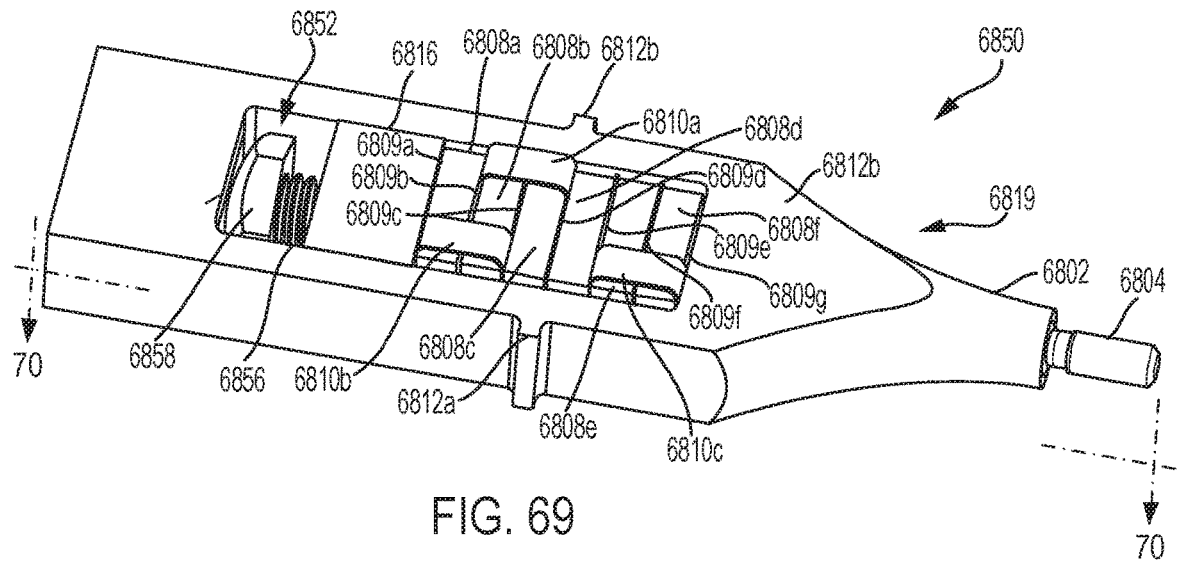
FIG. 69 is perspective view of an ultrasonic transducer assembly employing a screw to compress against the compression plate to compress and acoustically couple piezoelectric elements to an ultrasonic waveguide, according to one aspect of this disclosure.
Figure 70:
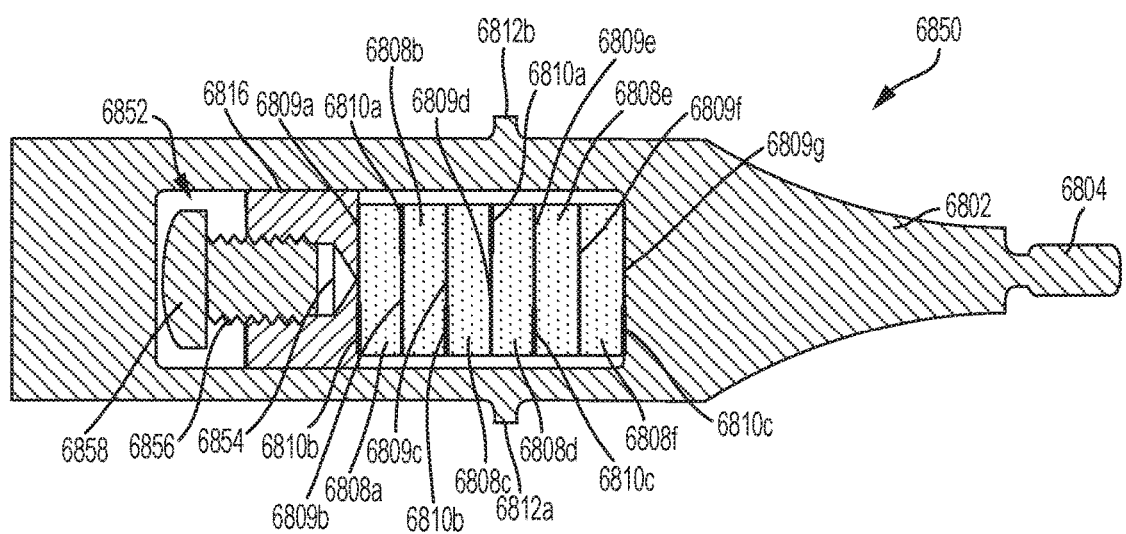
FIG. 70 is a section view of the of the ultrasonic transducer assembly shown in FIG. 69 taken along section 70-70 as shown in FIG. 69.
Figure 71:
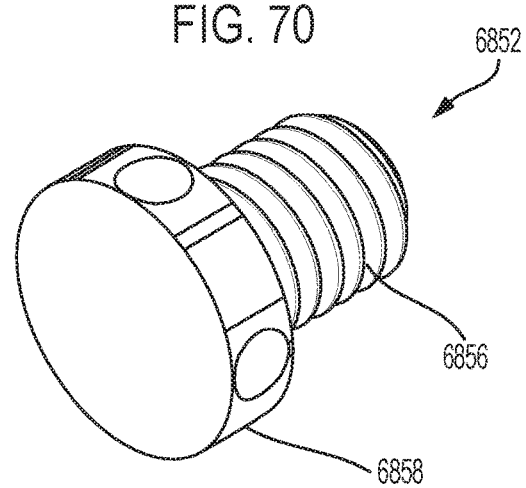
FIG. 71 is a perspective view of the screw, according to one aspect of this disclosure.

FIG. 69 is a perspective view of an ultrasonic transducer assembly 6850 similar to the ultrasonic surgical instrument 6800 according to one aspect of this disclosure, except that the transducer assembly 6850 comprises a transducer 6819 employing a screw 6852 to compress against the compression plate 6816 to compress and acoustically couple the piezoelectric elements 6808a-6808f to an ultrasonic waveguide. FIG. 70 is a section view of the ultrasonic transducer assembly 6850 taken along section line 70-70 as shown in FIG. 69, according to one aspect of this disclosure. With reference now to FIGS. 69-70, in one aspect, no wedges are used in the ultrasonic surgical instrument 6850, as shown in the perspective view of FIG. 69. Instead, the screw 6852 may be fastened into the compression plate 6816, such as by threading the pointed point or tip 6854 (and a proximal portion of the thread) of the screw 6852 distally into the compression plate 6816. As can be seen in the sectional view of FIG. 70, the pointed tip 6854 of the screw 6852 is in contact with the most proximal of the piezoelectric elements 6808. A distal portion of the thread 6856 and the head 6858 of the screw 6852 extend distally from the compression plate 6816. Advantages of this screw configuration include avoiding the use of a central bolt for compression and coupling and the ability to tune the acoustic assembly of the transducer assembly 6850 by modulating the tension in the transducer 6819 with the screw 6852. Compared to a transducer assembly with a central bolt, the transducer assembly 6850 with the screw 6852 is easier to machine because the distal portion of the thread 6856 of the screw 6852 is simply fastened into the compression plate 6816. FIG. 71 is a perspective view of the screw 6852, according to one aspect of this disclosure.

Figure 72:
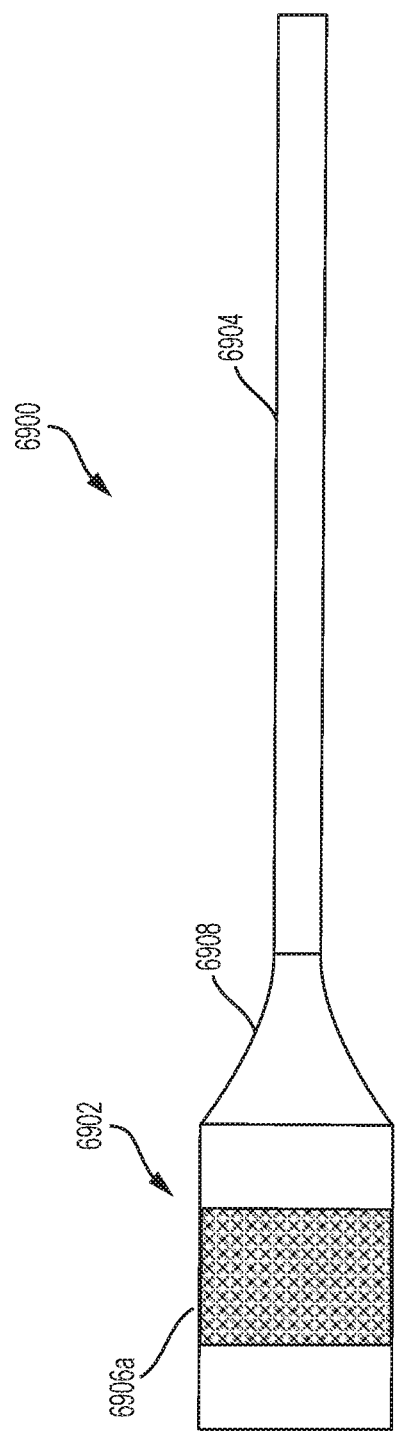
FIG. 72 illustrates an ultrasonic surgical instrument configured to operate in a D31 mode of operation, according to one aspect of this disclosure.
Figure 73:
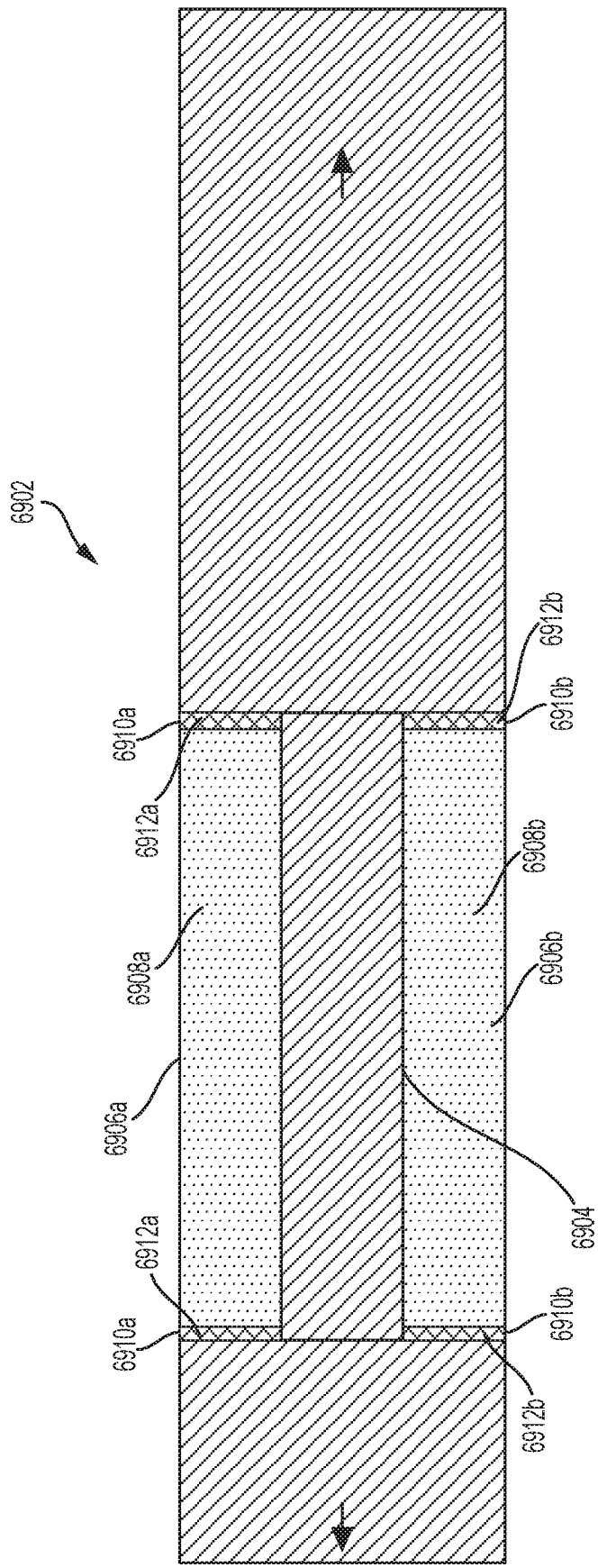
FIG. 73 is a section view of the transducer assembly comprising a first piezoelectric element positioned on a first side of the waveguide and a second piezoelectric element positioned on a second opposing side of the waveguide, according to one aspect of this disclosure.

FIG. 72 illustrates an ultrasonic surgical instrument 6900 configured to operate in a D31 mode of operation, according to one aspect of this disclosure. The ultrasonic surgical instrument 6900 comprises a transducer assembly 6902 and an ultrasonic waveguide 6904. The transducer assembly 6902 includes a horn shaped portion 6908, piezoelectric elements 6906a, 6906b, and a threaded connection such as a stud 6804 to connect to the ultrasonic waveguide 6904. As illustrated in FIG. 73, the transducer assembly 6902 is configured to create a strong mechanical bond between each of the piezoelectric elements 6906a, 6906b and the waveguide 6904. FIG. 73 is a section view of the transducer assembly 6902 comprising a first piezoelectric element 6906a positioned on a first side of the waveguide 6904 and a second piezoelectric element 6906b positioned on a second opposing side (opposing the first side) of the waveguide 6904, according to one aspect of this disclosure. In one aspect, the waveguide 6904 includes a first and second interior recess 6908a, 6908b for insertion of the piezoelectric elements 6906a, 6906b, respectively. As illustrated in FIG. 73, the first interior recess 6908a may extend from an interior top surface into and the second interior recess 6908a may extend from an interior bottom surface into the waveguide 6904, respectively. The depths of the first and second recess 6908a, 6908b may each equal or substantially equal the heights of the piezoelectric elements 6906a, 6906b, respectively.

Accordingly, when the piezoelectric elements 6906a, 6906b are inserted into the recesses 6908a, 6908b, the piezoelectric elements 6906a, 6906b can be flush (i.e., level or substantially level) with the waveguide 6904. In other words, the highest point or portion of the piezoelectric element 6906a is aligned with the exterior top surface of the waveguide 6904. Similarly, the lowest point or portion of the piezoelectric elements 6906b is aligned with the exterior bottom surface of the waveguide 6904. Thus, neither of the piezoelectric elements 6906a, 6906b protrudes beyond the exterior top or bottom surface of the waveguide 6904. In another aspect, the length of each interior recess 6908a, 6908b is greater than the respective length of each of the piezoelectric elements 6906a, 6906b. Consequently, when the piezoelectric elements 6906a, 6906b are inserted into the respective interior recesses 6908a, 6908b, there are proximal and distal gap portions 6910a, 6910b of the recesses 6908a, 6908b. Bonding material (e.g., conductive adhesive) such as cured epoxy adhesive 6912a, 6912b is applied to each of the gap portions 6910a, 6910b.

Consequently, a strong and durable mechanical bond between each of the piezoelectric elements 6906a, 6906b and the waveguide 6904 is created because of a lower risk of epoxy adhesive 6912a, 6912b bond failure during operation of the transducer 6902. Specifically, the tensile strength of epoxy may be substantially greater than the shear strength of epoxy. During operation of the transducer 6902, the epoxy adhesive 6912a, 6912b may experience a high extent of shear loading which can cause the bonds of the epoxy adhesive 6912a, 6912b to fail via delamination, for example. However, as shown in the transducer assembly 6902 of FIG. 73, the epoxy adhesive 6912a, 6912b is loaded in a tensile configuration, which may result in a lower rate of bond failure. Therefore, advantages of the transducer configuration of FIG. 73 include a strong mechanical coupling between each of the piezoelectric elements 6906a, 6906b and the waveguide 6904. In another aspect, no bonding material might be applied to the surfaces of the piezoelectric elements 6906a, 6906b that contact the waveguide 6904.

Figure 74:
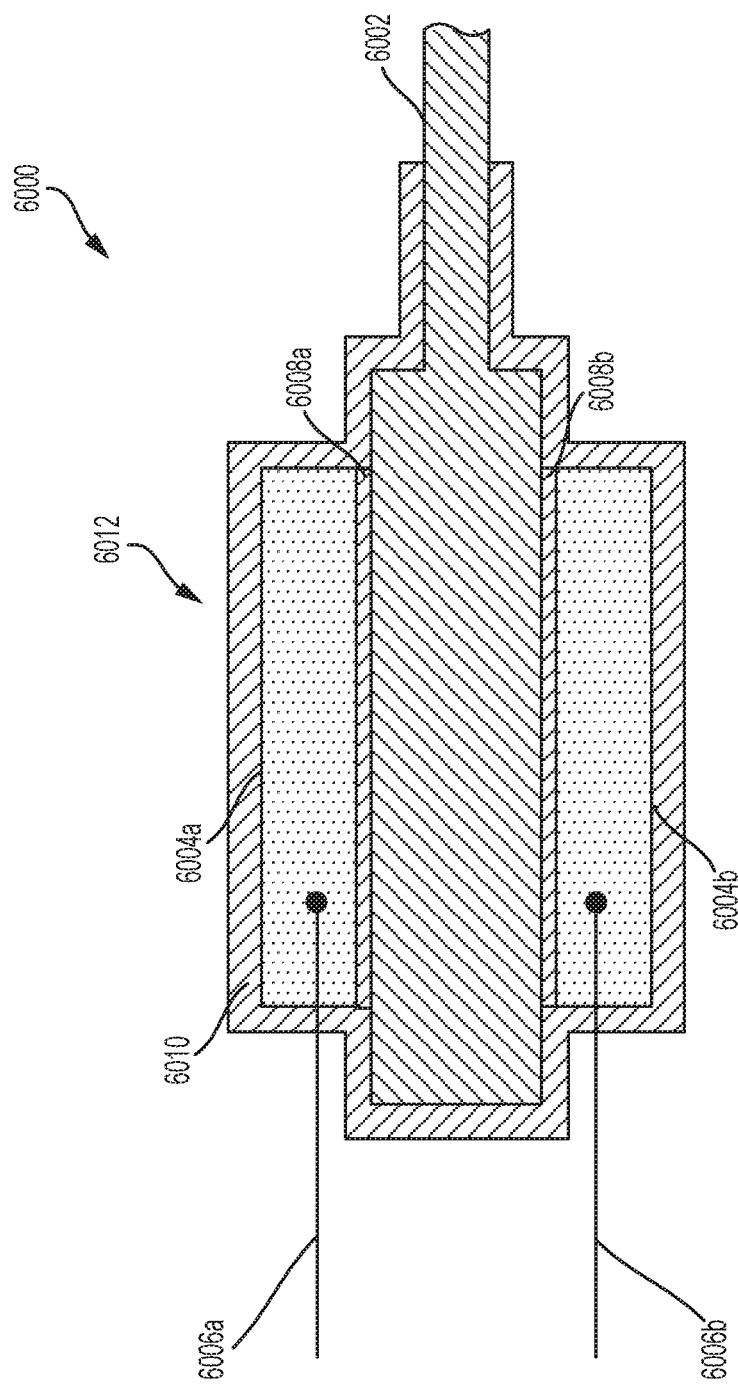
FIG. 74 is a section view of an ultrasonic surgical instrument configured to operate in a D31 mode of operation, according to one aspect of this disclosure.

The D31 architecture 250 according to one aspect of this disclosure employs a variety of different techniques to electrically and thermally couple the piezoelectric elements 254a, 254b to the ultrasonic waveguide 252. These techniques are disclosed hereinbelow. FIG. 74 is a section view of an ultrasonic surgical instrument 6000 configured to operate in a D31 mode of operation, according to one aspect of this disclosure. The ultrasonic surgical instrument 6000 includes an ultrasonic transducer 6012 attached to an ultrasonic waveguide 6014 by a bonding material. The ultrasonic surgical instrument 6000 comprises the waveguide 6014, first and second piezoelectric elements 6004a, 6004b, first and second electrically conductive elements 6006a, 6006b, and an overmolded housing 6010. Components of the transducer 6012 include the first and second piezoelectric elements 6004a, 6004b attached to opposing sides of the waveguide 6014 by a bonding material, such as first and second conductive adhesive 6008a, 6008b. The first and second conductive adhesive 6008a, 6008b can be a conductive epoxy adhesive, for example.

As shown in FIG. 74, the lower surface of the piezoelectric element 6004a is coupled to waveguide 6014 by the conductive adhesive 6008a and the upper surface of the piezoelectric element 6004b is coupled to waveguide 6014 by the conductive adhesive 6008b. The lower and upper surface may be opposing. The overmolded housing 6010 can be formed by a suitable overmolding process such a low pressure, hot melt adhesive molding process. For example, the TECHNOMELT® molding process of Henkel Electronic Materials LLC of Irvine, Calif., can be used with a suitable polyamide or polyolefin to form the overmolded housing 6010. The overmolded housing 6010 is configured to encompass at least a portion of the ultrasonic surgical instrument 6000. In one aspect, the overmolded housing 6010 encompasses the transducer 6012 and a proximal portion of the waveguide 6014. By encompassing the first and second piezoelectric elements 6004a, 6004b and a proximal portion of the waveguide 6014, the overmolded housing 6010 can ensure a durable and consistent attachment or coupling between the piezoelectric elements 6004a, 6004b and waveguide 6014.

Specifically, the overmolded housing 6010 may be configured to compress the first and second piezoelectric elements 6004a, 6004b against the waveguide 6014 or retain the elements 6004a, 6004b and waveguide 6014 in a friction fit. Additionally, the overmolded housing 6010 may be formed to include nonmolded portions for electrically conductive elements 6006a, 6006b to protrude from the overmolded housing 6010. As illustrated in FIG. 74, the leads 6006a, 6006b protrude proximally from the housing 6014 to electrically couple the first and second piezoelectric elements 6004a, 6004b to an ultrasonic signal generator. In one aspect, the first and second piezoelectric elements 6004a, 6004b are electrically coupled to a positive pole of an ultrasonic signal generator. As shown in FIG. 74, the waveguide 6002 may taper distally. The piezoelectric elements 6004a, 6004b may be constructed of ceramic material, such as PZT. The electrically conductive elements 6006a, 6006b may be electrical connectors such as wires, leads, metal electrically conductive pads (e.g., Solder Mask Defined pad (SMD) or Non-Solder Mask Defined pad (NSMD)), or other suitable electrical connectors.

Figure 75:
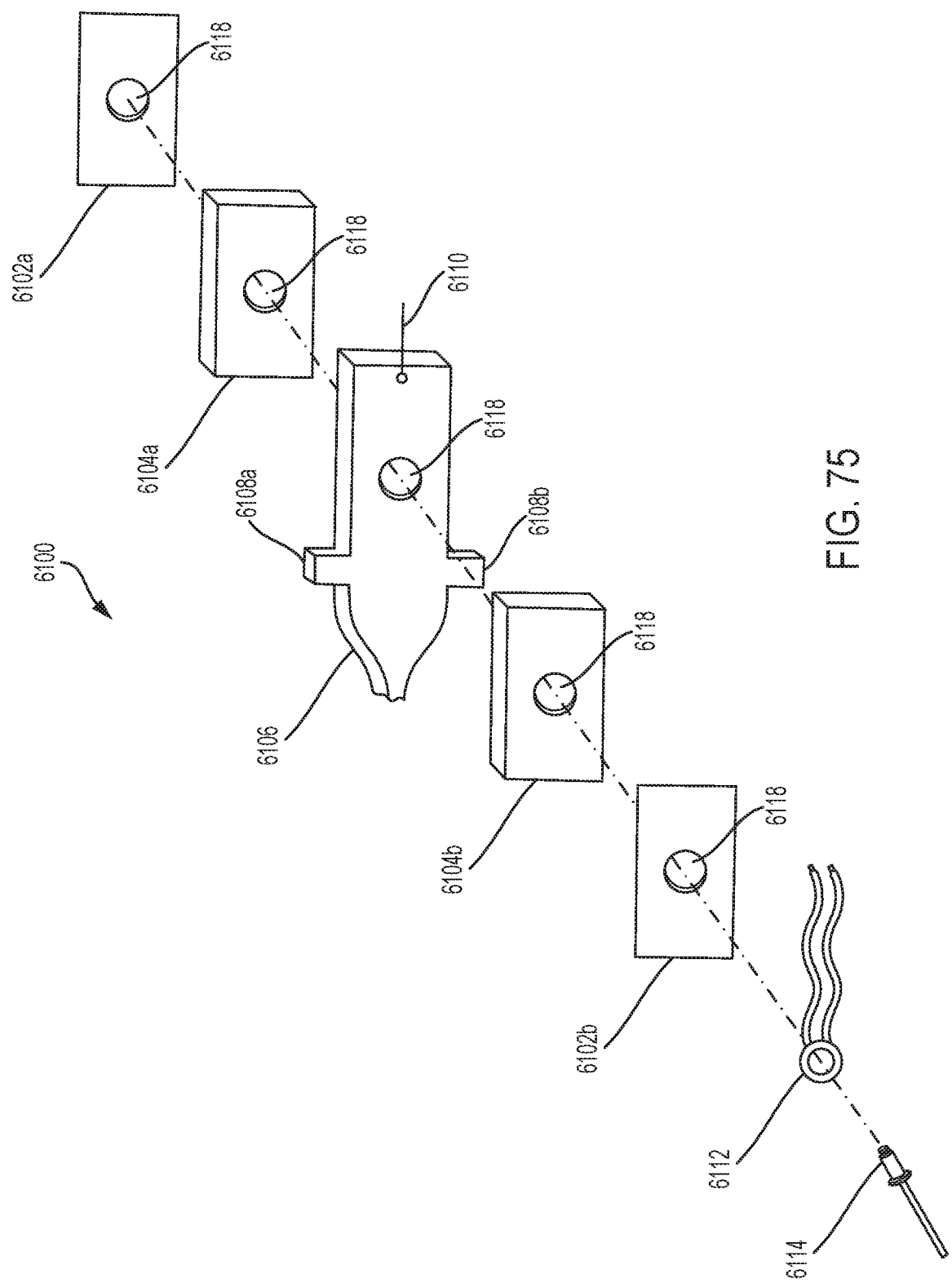
FIG. 75 is an exploded view of an ultrasonic surgical instrument configured to operate in a D31 mode of operation, according to one aspect of this disclosure.

FIG. 75 is an exploded view of an ultrasonic surgical instrument 6100 configured to operate in a D31 mode of operation, according to one aspect of this disclosure. The ultrasonic surgical instrument 6100 comprises a plurality of plate components, including first and second electrode plates 6102a, 6102b, first and second piezoelectric plates 6104a, 6104b, transducer base plate 6106 (e.g., a transducer mounting portion), electrically conductive element such as wire loop 6112, and a pop rivet 6114 In one aspect, each of the plates 6102a, 6102b, 6104a, 6104b, 6106 each comprise a grooved receiving aperture 6118, which may be formed by a suitable machining process. Each of the grooved receiving apertures 6118 may be configured to receive wire loop 6112 in order to electrically couple the plates 6102a, 6102b, 6104a, 6104b, 6106. In particular, when combined with the pop rivet 6114, the wire loop 6112 may be coupled to a positive pole of a voltage or energy source (e.g., an ultrasonic signal generator). The transducer base plate 6106 may act as electrical ground for the current flowing through the wire loop 6112. A connection to electrical ground can be made through a ground wire 6110 of the transducer base plate 6106.

In another aspect, the ground wire 6110 is soldered, mechanically looped, or otherwise coupled via a suitable means to the transducer base plate 6106. Aside from the grooved receiving aperture 6118 and ground wire 6118, the transducer base plate 6106 comprises flanges 6108a, 6108b, which may be configured to be received within a retainer of a housing (not shown) of the ultrasonic surgical instrument 6100 for secure attachment of the transducer base plate 6106 to the housing. In another aspect, the pop rivet 6114 is configured to be inserted through the wire loop 6112 and each of the 6102a, 6102b, 6104a, 6104b, 6106 such that the pop rivet 6114 compresses the electrode plates 6102a, 6102b, which in turn compress the piezoelectric plates 6104a, 6104b. Unlike the aspect illustrated by FIG. 74, for example, the ultrasonic surgical instrument 6100 may not require the use of epoxy for electrical coupling. Instead, the pop rivet 6114 provides compression through the electrode plates 6102a, 6102b to electrically couple the piezoelectric plates 6104a, 6104b to a waveguide of the ultrasonic surgical instrument 6100. Advantages of the pop rivet 6114 configuration may include decreased assembly time, improved electrical coupling (based on the provided compression), and reduced cost (e.g., no epoxy is necessary).

Figure 76A:
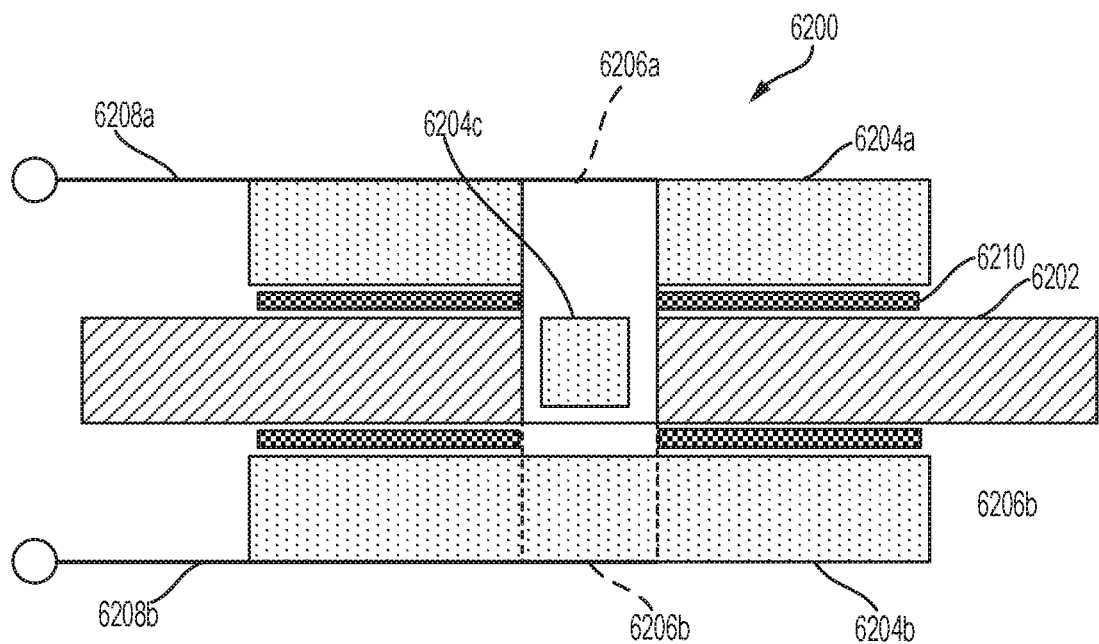
FIG. 76A is a side view of an ultrasonic surgical instrument configured to operate in a D31 mode of operation, according to one aspect of this disclosure.

FIG. 76A is a side view of an ultrasonic surgical instrument 6200 configured to operate in a D31 mode of operation, according to one aspect of this disclosure. The ultrasonic surgical instrument 6200 comprises an ultrasonic waveguide 6202, piezoelectric elements 6204a, 6204b, 6204c (shown in phantom), and electrode shims 6206a, 6206b. The ultrasonic waveguide 6202 comprises a recessed or "cut out" portion in which the piezoelectric element 6204c may be inserted. Piezoelectric element 6204c can have a smaller surface area than piezoelectric elements 6204a, 6204b. In one aspect, the electrode shims 6206a, 6206b are flat electrodes which are configured to electrically couple piezoelectric elements 6204a, 6204b, 6204c to each other and to a voltage or energy source (e.g., an ultrasonic signal generator). The electrode shim 6206a may include three portions which each compress against a surface of the piezoelectric element 6204a. For example, as shown in FIG. 76A, a portion of the electrode shim 6206a is wrapped into (i.e., extends in a sideways direction toward an interior portion of the ultrasonic surgical instrument 6200 to contact) the piezoelectric element 6204c inserted inside the recessed portion of the waveguide 6202 for electrical coupling of the piezoelectric elements 6204a, 6204b, 6204c.

Additionally, as shown in phantom in FIG. 76A, the electrode shim 6206b is also wrapped into (i.e., extends in a sideways direction toward an interior portion of the ultrasonic surgical instrument 6200 to contact) the piezoelectric element 6204c or electrical coupling of the piezoelectric elements 6204a, 6204b, 6204c. The electrode shims 6206a, 6206b may be wrapped into the piezoelectric element 6204c in opposing directions. In another aspect, the piezoelectric element 6204a comprises a connection portion 6208a to electrically couple to a positive pole of the energy source and the piezoelectric element 6204b comprises a connection portion 6208b to electrically couple to a negative pole of the energy source. Accordingly, current may flow through the electrical connection portions 6208a, 6208b through the piezoelectric elements 6204a, 6204b, 6204c and the ultrasonic waveguide 6202, with the ultrasonic waveguide 6202 as electrical ground.

Figure 76B:
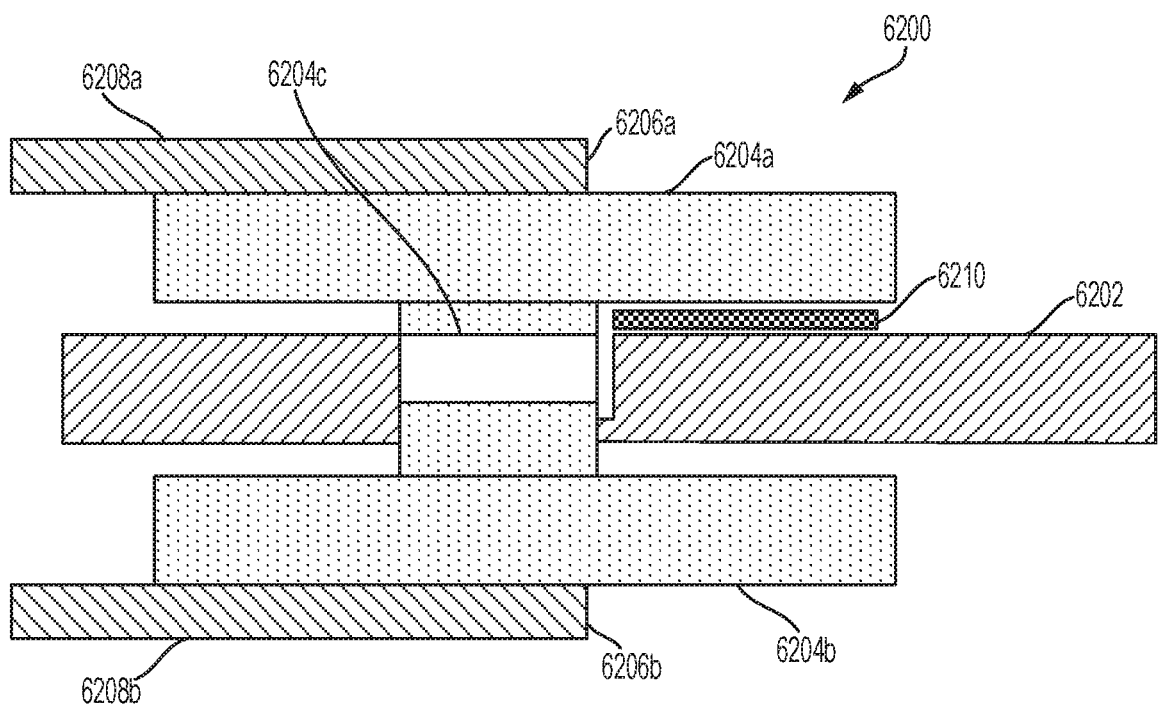
FIG. 76B is a cross sectional view of a side of the ultrasonic surgical instrument shown in FIG. 76A, according to one aspect of this disclosure.
Figure 77:
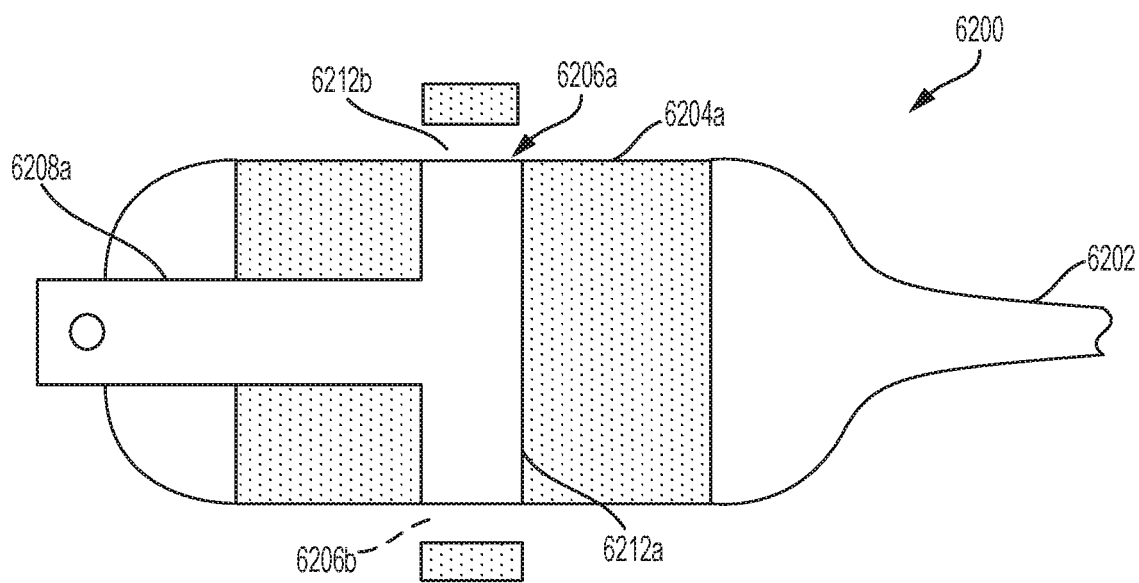
FIG. 77 is a top view of the ultrasonic surgical instrument shown in FIG. 76A, according to one aspect of this disclosure.

FIG. 76B is a cross sectional view of a side of the ultrasonic surgical instrument 6200, according to one aspect of this disclosure. As can be seen in FIG. 76, an end of each of the electrode shims 6206a, 6206b is in contact with the piezoelectric element 6204c. Referring now to both FIGS. 76A and 76B, electrical insulation such as plastic or polyamide insulators 6210a, 6210b may be used to reduce or prevent the risk of electrical shorting. The insulator 6210a, 6210b may be positioned on either the electrode shims 6206a, 6206b or the waveguide 6202 such that current may flow through only a portion of the area located between one of the piezoelectric elements 6204a, 6204b and the waveguide 6202. In another aspect, similar to the piezoelectric elements 6004a, 6004b, the piezoelectric elements 6204a, 6204b can be attached to opposing sides of the waveguide 6202 by a bonding material, such as conductive epoxy adhesive. FIG. 77 is a top view of the ultrasonic surgical instrument 6200, according to one aspect of this disclosure.

Figure 78:
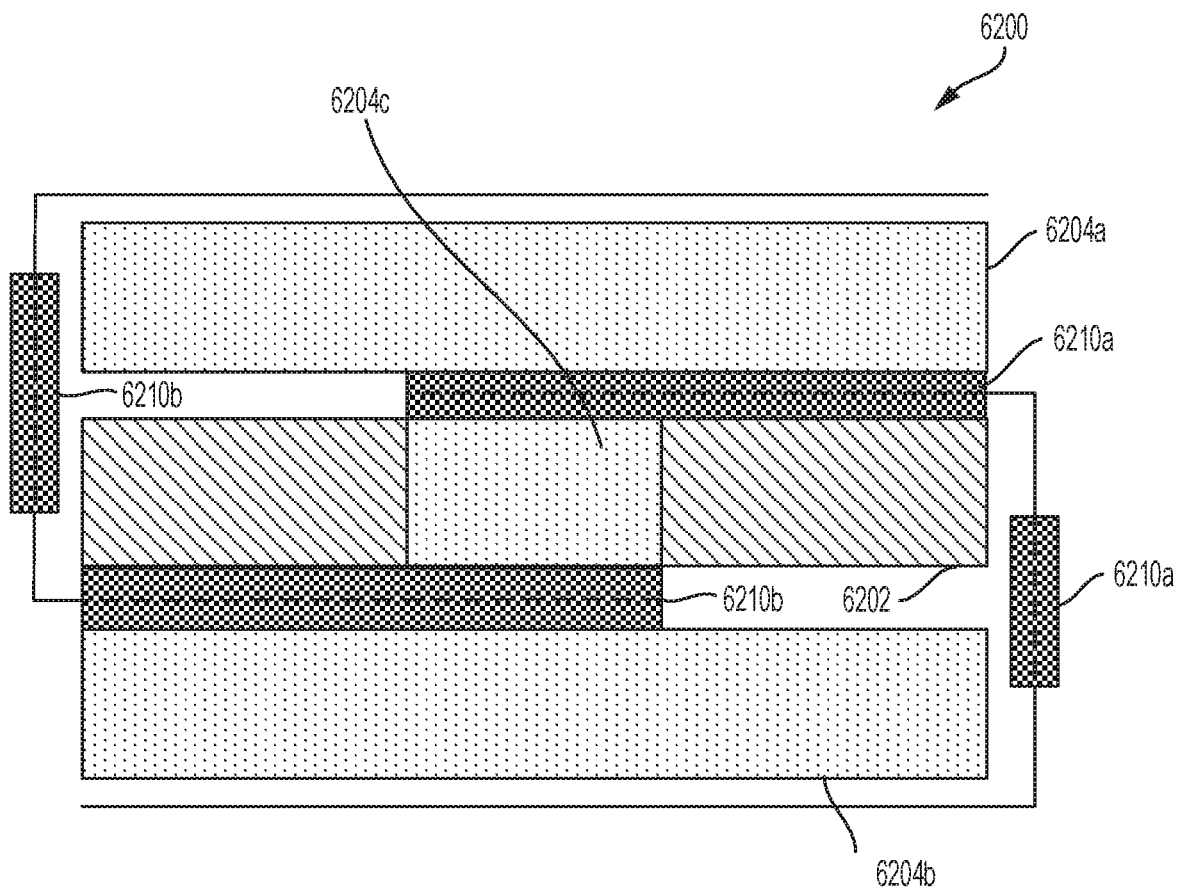
FIG. 78 is a rear cross sectional view of the ultrasonic surgical instrument shown in FIG. 76A, according to one aspect of this disclosure.

In FIG. 77, only the piezoelectric element 6204a is visible. As shown in FIG. 77, the first portion 6212a of the electrode shim 6206a is positioned on or wrapped into the top surface of the piezoelectric element 6204a. The second portion 6212b of the electrode shim 6206a is positioned on a first side surface of the piezoelectric element 6204a. In one aspect, the second portion of the other electrode shim 6206b is positioned on a second side surface of the piezoelectric element 6204a. The first and second side surfaces of the piezoelectric element 6204a are opposing. The third portion (not shown) of the electrode shim 6206a extends sideways toward the interior of the ultrasonic surgical instrument 6200 such that the third portion contacts the piezoelectric element 6204c. A portion of each of the electrical insulators 6210a, 6210b located on opposing surfaces of the ultrasonic surgical instrument 6200 may be seen in the view of FIG. 77. FIG. 78 is a rear cross sectional view of the ultrasonic surgical instrument 6200, according to one aspect of this disclosure. As can be seen in FIG. 78, insulator 6210a may extend from a side surface of the piezoelectric elements 6204a, 6204b into an area between the waveguide 6202 and the piezoelectric element 6204b. Similarly, insulator 6210b may extend from a side surface of the piezoelectric elements 6204a, 6204b into an area between the waveguide 6202 and the piezoelectric element 6204a.

Figure 79A:
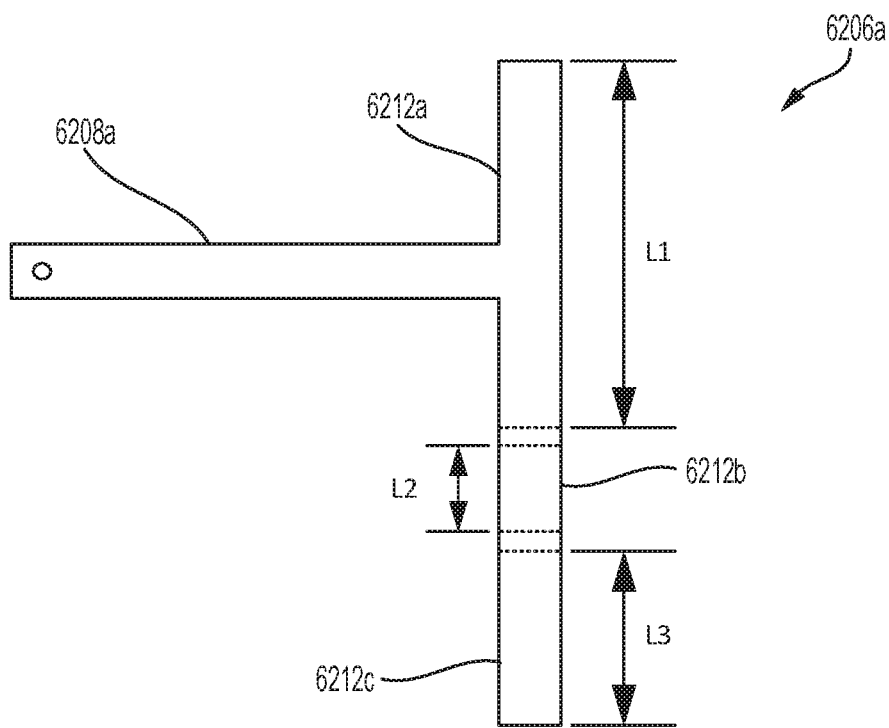
FIG. 79A is a plan view of an electrode shim in a flat configuration, according to one aspect of this disclosure.
Figure 79B:
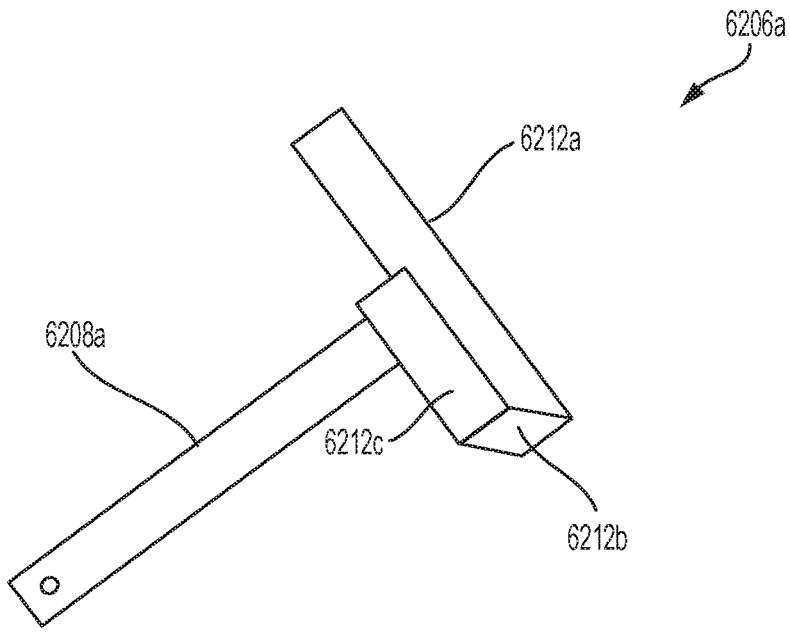
FIG. 79B is a perspective view of the electrode shim shown in FIG. 79A in a folded configuration, according to one aspect of this disclosure.

FIG. 79A is a plan view of an electrode shim 6206a in a flat configuration, according to one aspect of this disclosure. FIG. 79B is a perspective view of the electrode shim 6206a shown in FIG. 79A in a folded configuration, according to one aspect of this disclosure. As described above, the electrode shim 6206a comprises first, second and third portions 6212a, 6212b, 6212c. In addition, the electrode shim 6206a comprises the connection portion 6208a to connect to, for example, the positive pole of the energy source. According to one aspect of this disclosure, FIG. 79A illustrates the electrode shim 6206a, which may be manufactured as a flat electrode from a copper sheet and may be bent into three portions. The first portion 6212a can have the same or substantially the same length L1 as the waveguide 6202. The second portion 6212a can have the same or substantially the same length L2 as the waveguide 6202. The third portion 6212a can have two thirds the length L3 of the waveguide 6202. The electrode shim 6206b may be identical or substantially similar to the electrode shim 6206a, except that the electrode shim 6206b is oriented in an opposing direction. FIG. 79B is a perspective view of the electrode shim 6206a in a bent configuration, according to one aspect of this disclosure.

Figure 80A:
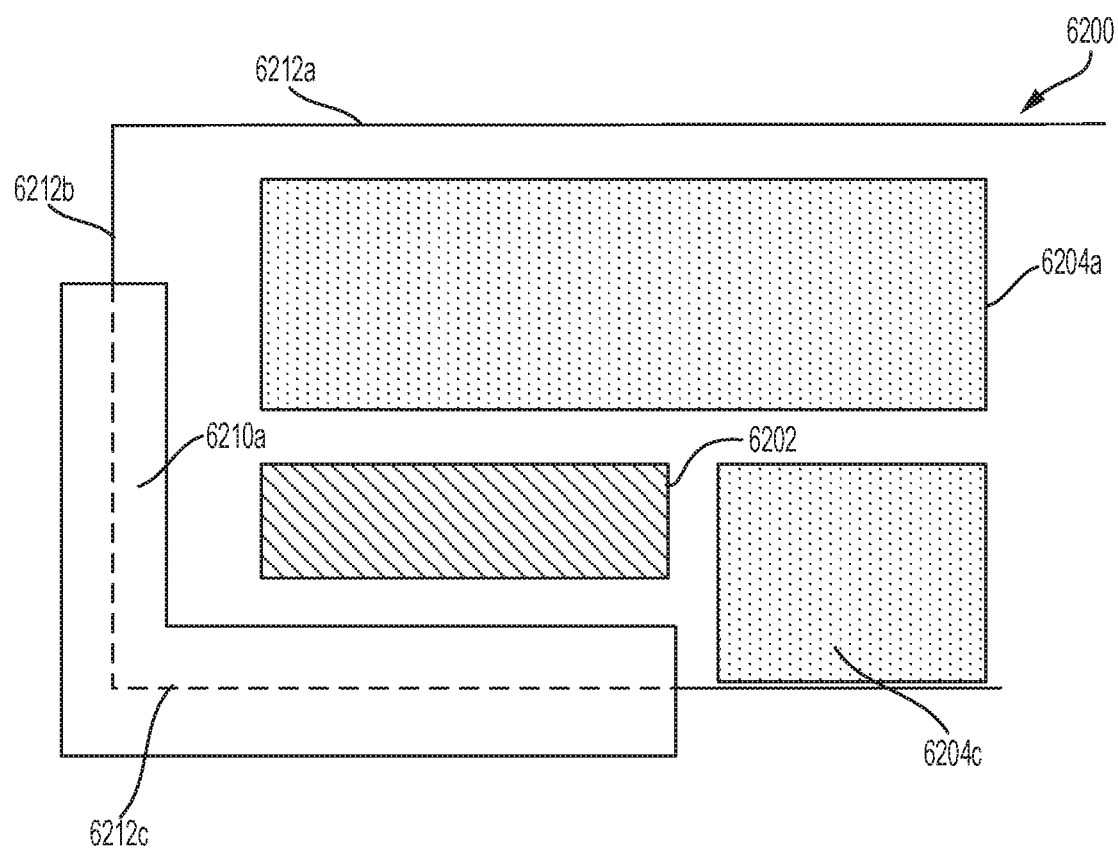
FIGS. 80A-80B are views of a portion of the ultrasonic surgical instrument shown in FIG. 76A with polyimide film material coating as an insulator positioned on the electrode shim, according to one aspect of this disclosure.
Figure 80B:
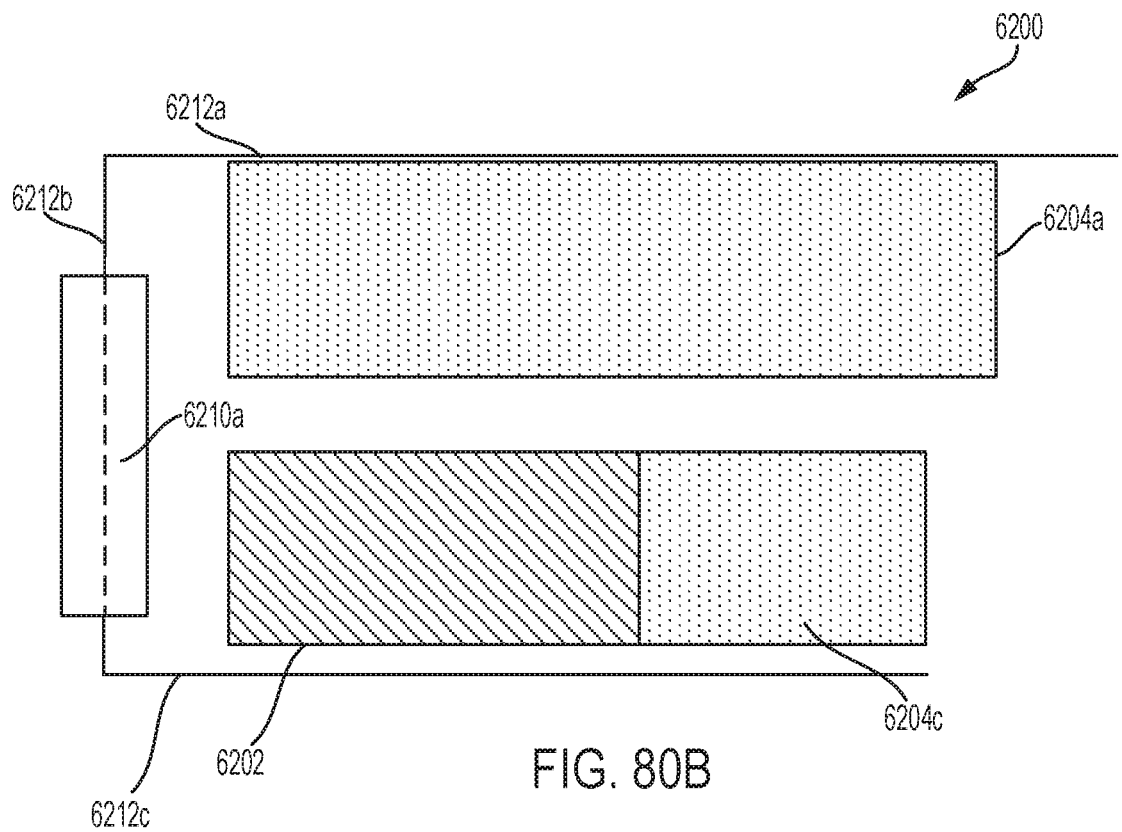

FIGS. 80A-80B are views of a portion of the ultrasonic surgical instrument 6200 with polyimide film material coating, such as Kapton® polyimide film available from E. I. du Pont de Nemours and Company of Wilmington, Del., as the insulator 6210a positioned on the electrode shim 6206a, according to one aspect of this disclosure. As shown in FIG. 80A, in one aspect, the Kapton insulator 6210a may be coated onto the bend between second and third portions 6212b, 6212c such that the Kapton insulator 6210a is positioned between the electrode shim 6206a and the waveguide 1602. In another aspect, as shown in FIG. 80B, the Kapton insulator 6210a may be applied on the second portion 6212b such that the Kapton insulator 6210a extends along the piezoelectric element 6204a and waveguide 6202.

Figure 81:
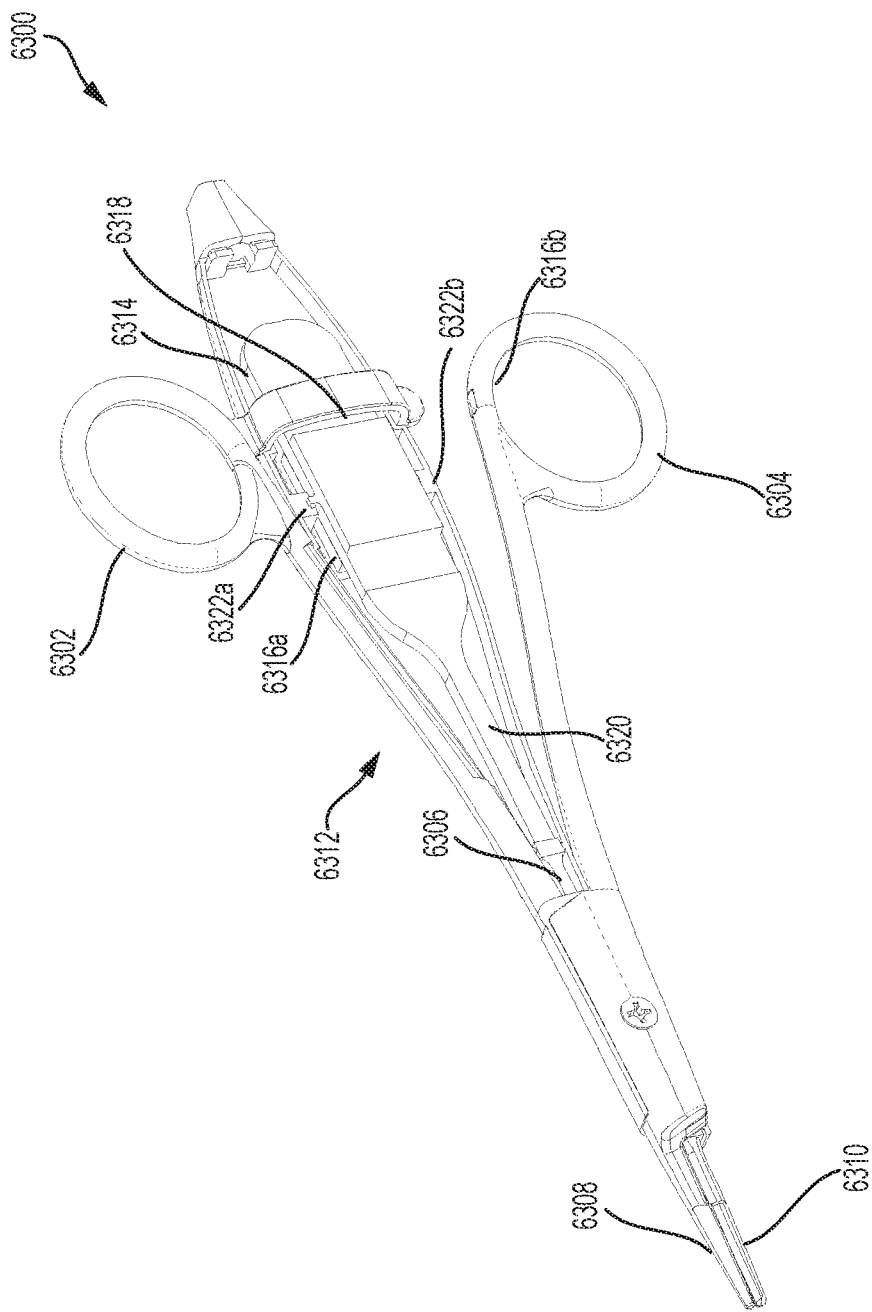
FIG. 81 is a perspective view of an ultrasonic surgical instrument, which is configured to operate in a D31 mode of operation, according to one aspect of this disclosure.

FIG. 81 is a perspective view of an ultrasonic surgical instrument 6300 (may be referred to as a pair of ultrasonic shears or forceps), which is configured to operate in a D31 mode of operation, according to one aspect of this disclosure. The shears 6300 comprise a first arm 6302 pivotably connected to a second arm 6304 by a fastener 6306. The first arm 6302 includes a jaw 6008 or clamp positioned at its distal end that is configured to cooperate with an end effector 9054 extending distally from the second arm 6304. Actuating the first arm 6302 in a first direction causes the jaw 6308 to pivot towards the end effector 6310 and actuating the first arm 6302 in a second direction causes the jaw 6308 to pivot away from the end effector 6310. In one aspect, the ultrasonic surgical instrument 6300 includes a transducer assembly 6312, such as the transducer assembly 6902. The transducer assembly 6312 comprises a housing 6314 enclosing the first and second piezoelectric elements 6316a, 6316b and an ultrasonic waveguide 6320. The first and second piezoelectric elements 6316a, 6316b are attached to opposite sides of the waveguide 6320 by a bonding material. The transducer 6318 includes the first and second piezoelectric elements 6316a, 6316b. The transducer assembly 6312 includes flanges 6322a, 6322b, which may be configured to be received within a retainer of the housing 6314 for secure attachment of the transducer 6318 to the housing 6314. The transducer assembly 6312 comprises a recessed receiving portion configured to receive an electrode for compressing the piezoelectric elements 6316a, 6316b.

Figure 82:
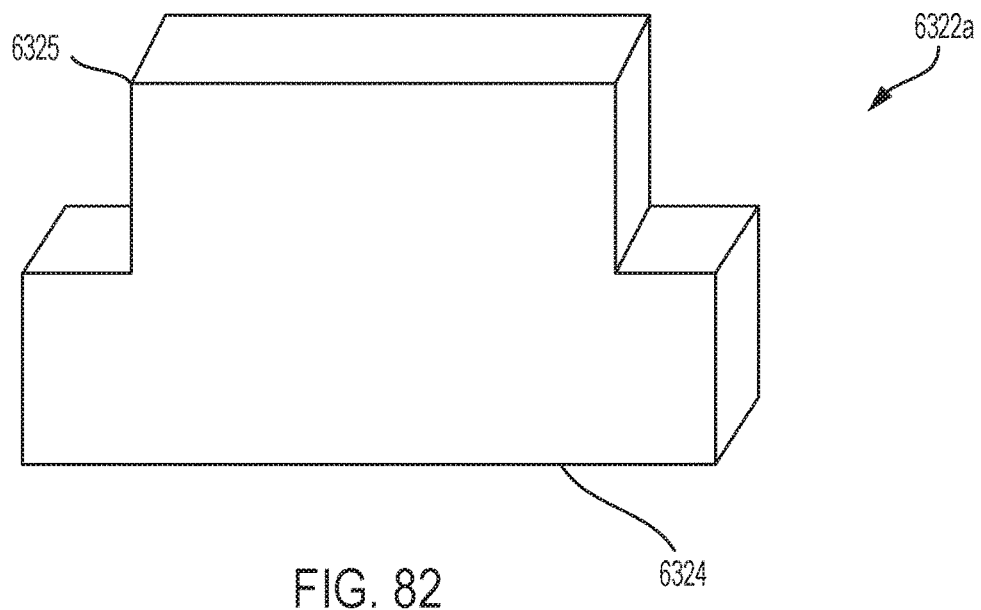
FIG. 82 is a perspective view of an electrode of the ultrasonic surgical instrument shown in FIG. 81, according to one aspect of this disclosure.
Figure 83:
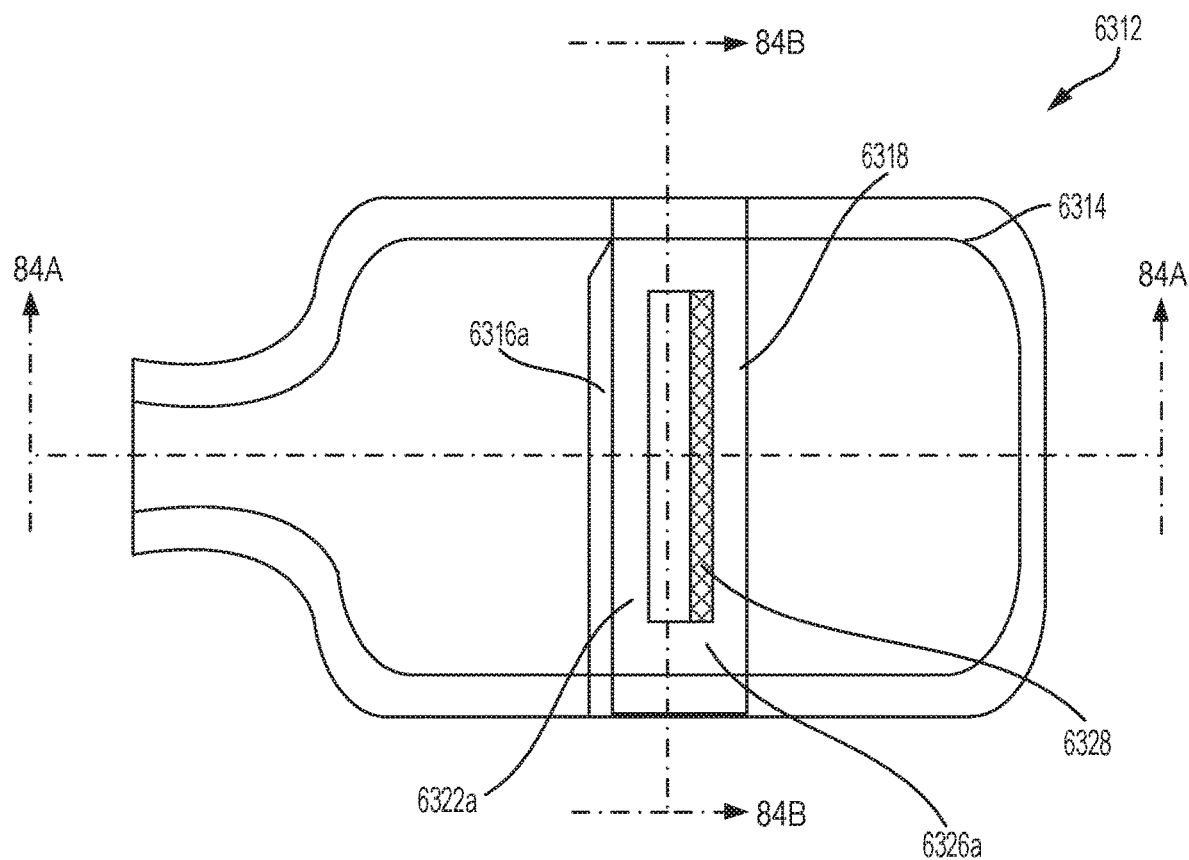
FIG. 83 is a plan view of the transducer assembly of the ultrasonic surgical instrument shown in FIG. 81 including a recessed receiving portion configured to receive an electrode, according to one aspect of this disclosure.

FIG. 82 is a perspective view of such an electrode 6322a of the ultrasonic surgical instrument 6300, according to one aspect of this disclosure. The electrode 6322a comprises a base portion 6324 and a protruding portion 6325. FIG. 83 is a plan view of the transducer assembly 6312 including a recessed receiving portion 6326a configured to receive an electrode such as the electrode 6322a, according to one aspect of this disclosure. The base of the recessed receiving portion 6326a and the electrode 6322a are visible in FIG. 83. As described below in further detail, the electrode 6322a may be positioned into a receiving area defined by the base via an interference or a geometrical fit. The electrode (e.g., conductive foam) 6322 is configured to compress the piezoelectric element 6316a to maintain electrical contact between the piezoelectric element 6316a and the waveguide 6320. In one aspect, a molded interconnect pad 6328 is used to electrically couple to an electrical connector (e.g., a wire) which is connected to an ultrasonic signal generator. In another aspect, conductive bonding material such as conductive grease adhesive is applied between the electrode 6322a and piezoelectric element 6316a for a stronger electrical connection.

Figure 84A:
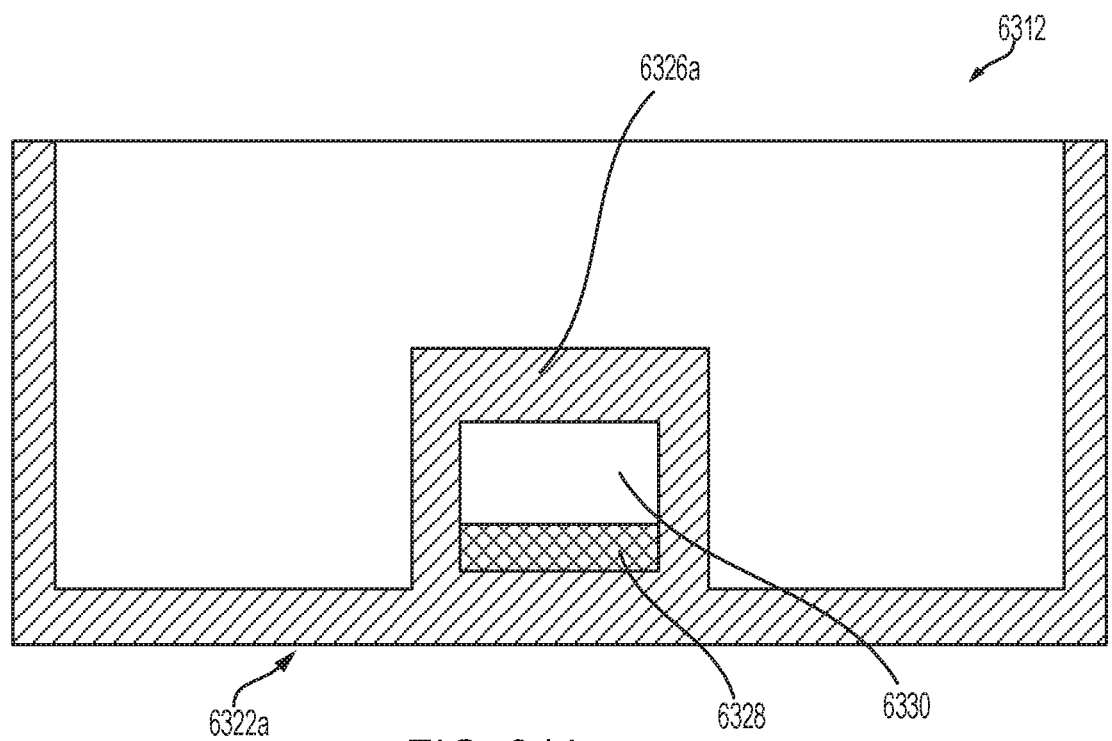
FIG. 84A is a longitudinal sectional view of the transducer assembly shown in FIG. 83, with a portion of the electrode, the molded interconnect pad, the receiving area, and a portion of the recessed receiving portion, according to one aspect of this disclosure.
Figure 84B:
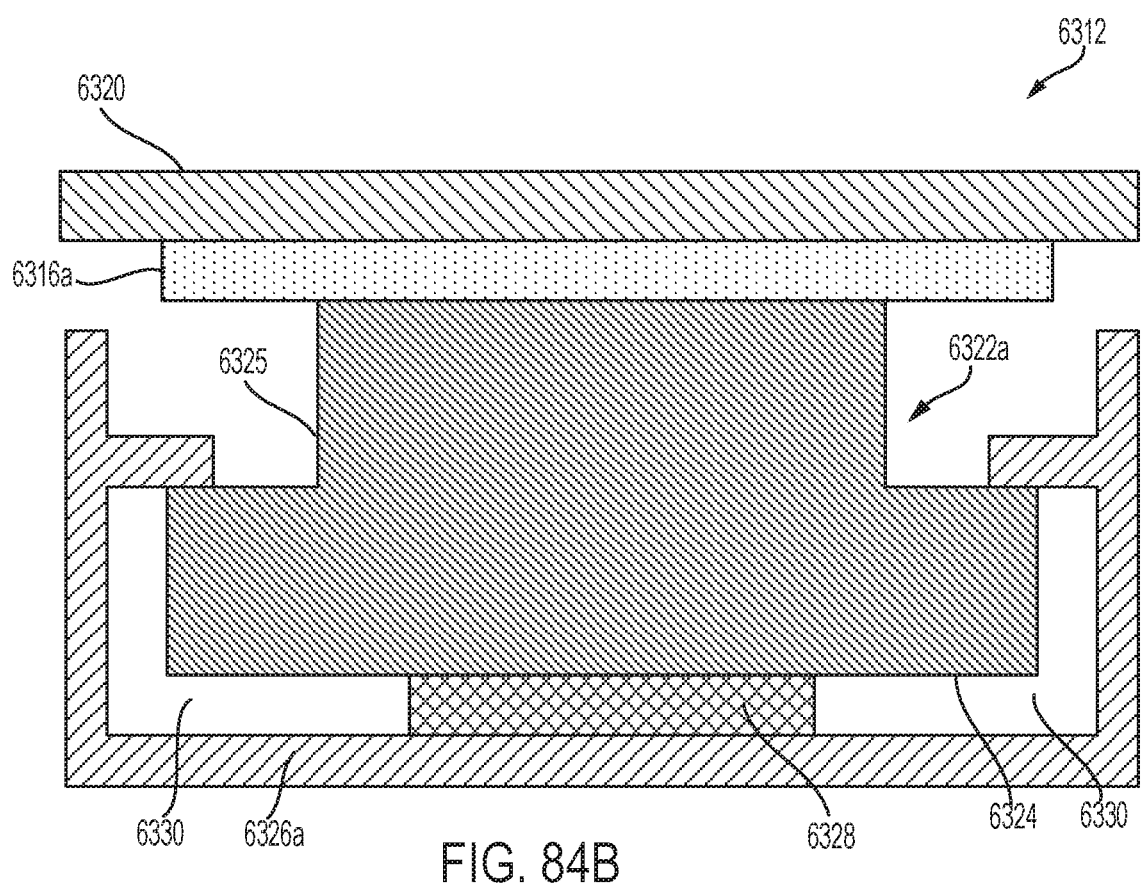
FIG. 84B is a lateral sectional view of the transducer assembly shown in FIG. 83, with a portion of the electrode, the molded interconnect pad, the receiving area, and the recessed receiving portion, according to one aspect of this disclosure.

FIG. 84A is a longitudinal sectional view of the transducer assembly 6312 which shows a portion of the electrode 6322a, the molded interconnect pad 6328, the receiving area 6330, and a portion of the recessed receiving portion 6326a, according to one aspect of this disclosure. The longitudinal sectional view is obtained based on a section starting from the axis AA and continuing in the direction of the depicted corresponding arrow. FIG. 84B is a lateral sectional view of the transducer assembly 6312 which shows a portion of the electrode 6322a, the molded interconnect pad 6328, the receiving area 6330, and the recessed receiving portion 6326a, according to one aspect of this disclosure. The lateral sectional view is obtained based on a section starting from the axis BB and continuing in the direction of the depicted corresponding arrow.

Figure 85A:
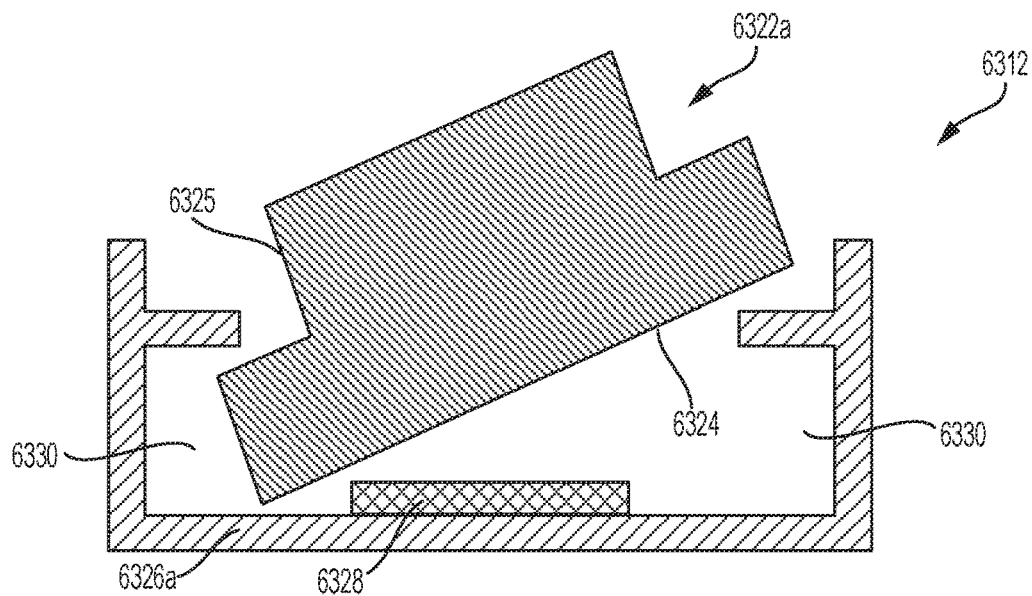
FIGS. 85A-85C illustrate an assembly process of an electrode of the ultrasonic surgical instrument shown in FIG. 81, into the recessed receiving portion, according to one aspect of this disclosure.
Figure 85B:
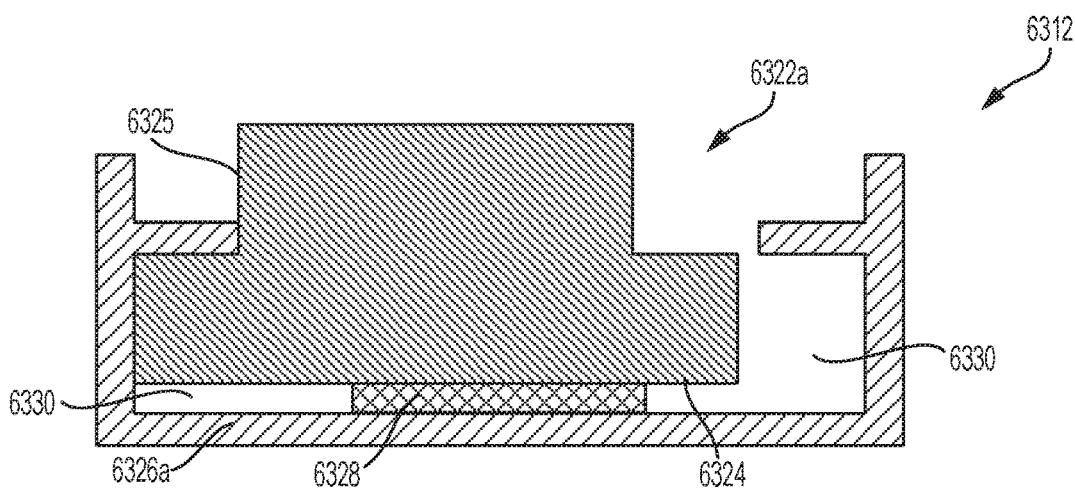
Figure 85C:
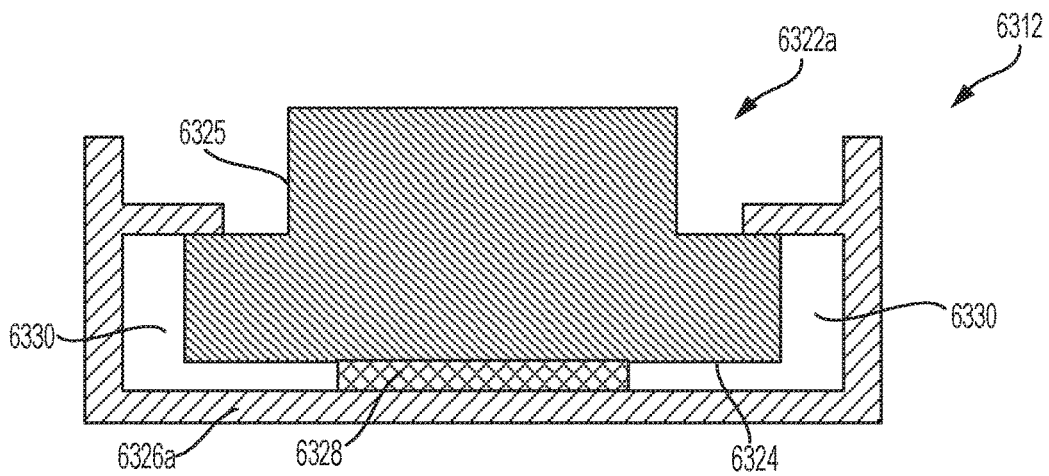

FIGS. 85A-85C illustrate an assembly process of the electrode 6322a into the recessed receiving portion 6326a, according to one aspect of this disclosure. FIG. 85A shows a side view of the electrode 6322a positioned at an angle such that one end of the base portion 6324 is located within the receiving area 6330 and the other end of the base portion 6324 is located outside of the receiving area 6330. As shown in FIG. 85A, the other end and the protruding portion 6325 both protrude away from the recessed receiving portion 6326a. Additionally, the electrode 6322a is not in contact with the molded interconnect pad 6328. FIG. 85B shows the one end of the base portion 6324 positioned into the receiving area 6330 such that the one end engages a first side wall and an arm 6332 (proximal to the first wall) of the recessed receiving portion 6326a in a slight interference fit. As can be seen in FIG. 85B, the electrode 6322a transitions from the initial angled position to a substantially flat or level position and moves in a direction towards the first side wall. The other end of the base portion 6324 is positioned away from a second side wall and another arm 6332 (proximal to the second side wall). The protruding portion 6325 remains protruding away from the recessed receiving portion 6326a. In one aspect, the arms 6332 extend from opposing side walls of the recessed receiving portion 6326a. FIG. 85C shows the electrode 6322a in a final position for compressing the piezoelectric element 6316a based on moving in an opposing direction towards the second side wall. In the final position, portions of the top sides of both ends of the base portion 6324 engage respective arms 6332. The remaining portions of the top sides of both ends of the base portion 6324 are uncontacted. Moreover, neither end of the base portion 6324 is in contact with either of the first or second side wall. The protruding portion 6325 remains protruding away from the recessed receiving portion 6326a. As shown in the aspects of FIGS. 85B-85C, the molded interconnect pad 6328 is electrically coupled to the electrode 6322a.

FIGS. 86A-86B illustrate an assembly process of the transducer assembly 6312 with electrodes 6322a, 6322b assembled from an initial uncompressed state to a final compressed state, relative to the piezoelectric elements 6316a, 6316b, according to one aspect of this disclosure. As shown in FIG. 86A, in one aspect, the transducer assembly 6312 includes two electrodes 6322a, 6322b configured to compress the piezoelectric elements 6316a, 6316b, respectively. Each of the two electrodes 6322a, 6322b is inserted in the receiving areas 6330 of the recessed receiving portions 6326a, 6326b, as described in connection with FIGS. 85A-85C. The two recessed receiving portions 6326a, 6326b in the initial uncompressed state as shown in FIG. 86A may be combined to form a unitary assembled component in the final compressed state. Specifically, the side walls of the recessed receiving portion 6326a are pressed against or combined with the side walls of the recessed receiving portion 6326b. The recessed receiving portion 6326a is transitioned in a direction towards the piezoelectric element 6316a and the recessed receiving portion 6326b is transitioned in a direction towards the piezoelectric element 6316b. FIG. 86B shows the transducer assembly 6312 with the unitary assembled component.

As can be seen in FIG. 86B, the first side walls of the two recessed receiving portions 6326a, 6326b combine to form one connected side wall of the unitary assembled component. Similarly, the second side walls of the two recessed receiving portions 6326a, 6326b combine to form another connected side wall of the unitary assembled component. In the final compressed state depicted in FIG. 86B, a top surface of each protruding portion 6325 of the electrodes 6322a, 6322b compresses against a corresponding surface of the piezoelectric elements 6316a, 6316b, respectively. Advantages of the compressed electrode configuration of the transducer assembly 6312 may include reduced assembly time, steps, and costs. Additionally, the configuration may result in an improved electrical connection between the piezoelectric elements 6316a, 6316b and waveguide 6320.

Figure 87:
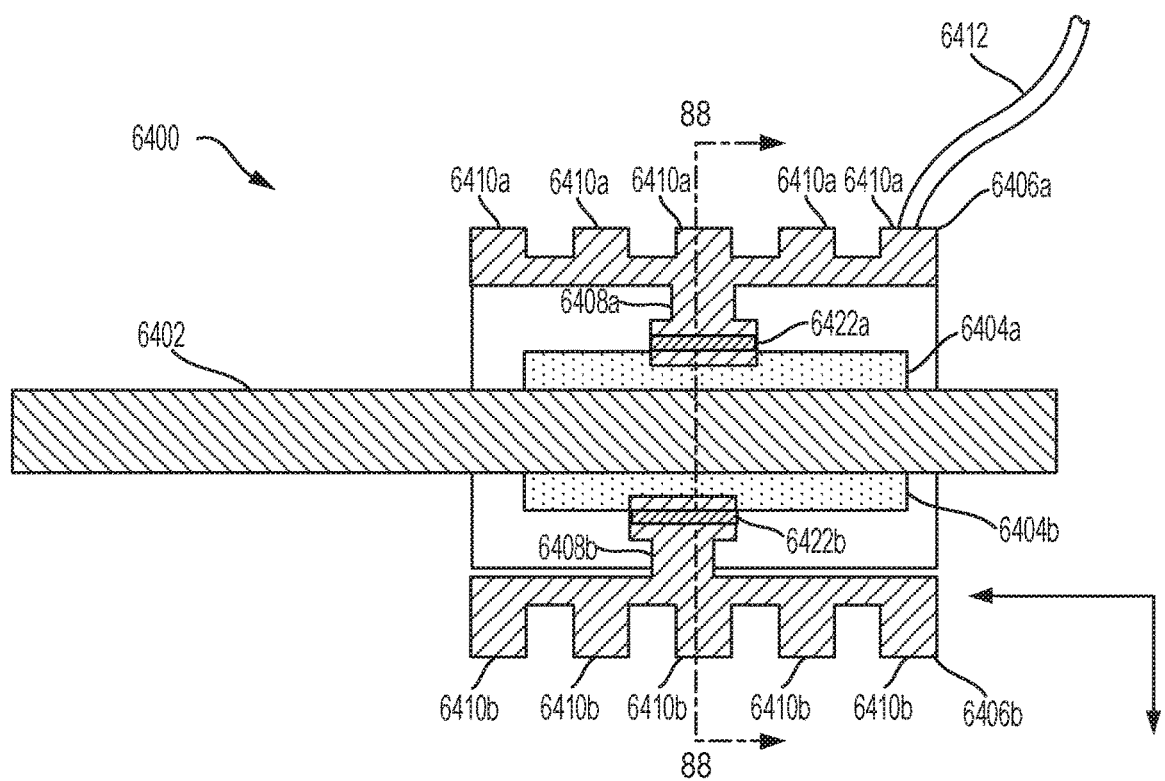
FIG. 87 shows aspects of an ultrasonic surgical instrument, which is configured to operate in a D31 mode of operation, according to one aspect of this disclosure.

FIG. 87 shows aspects of an ultrasonic surgical instrument 6400, which is configured to operate in a D31 mode of operation, according to one aspect of this disclosure. The ultrasonic surgical instrument 6400 may be the same as or substantially similar to the ultrasonic surgical instrument 6300. As seen in the side sectional view of FIG. 87, the ultrasonic surgical instrument 6400 includes a waveguide 6402, piezoelectric elements 6404a, 6404b, heat sink 6406a, 6406b, and an electrical connector such as a wire 6412. In one aspect, the heat sink 6406a, 6406b comprises a metal housing with two heat sink component halves. The upper heat sink half 6406a may be positioned on a top surface of the waveguide 6402 while the lower heat sink half 6406b may be positioned on a bottom surface of the waveguide 6402. The metal housing can be made of a suitable metal, such as aluminum or steel. Each of the heat sink halves 6406a, 6406b comprises a rib 6408a, 6408b, and a plurality of fins 6410a, 6410b. Suitable bonding material, such as conductive foam or grease 6422a, 6422b, may be used to thermally and electrically couple each of the ribs 6408a, 6408b to the piezoelectric elements 6404a, 6404b, respectively. Additionally, the conductive foam or grease 6422a, 6422b are adhesives to securely adhere the ribs 6408a, 6408b to the piezoelectric elements 6404a, 6404b. In another aspect, thermal energy or heat generated during operation of the piezoelectric elements 6404a, 6404b may be dissipated through the plurality of fins 6410a, 6410b. In particular, the heat sink 6406a, 6406b functions based on conducting heat generated from either of the piezoelectric elements 6404a through the corresponding rib 6408a, 6408b and away from the ultrasonic surgical instrument 6400 via one or more of the corresponding fins 6410a, 6410b. Each of the plurality of fins 6410a, 6410b may be spaced at a predetermined interval apart. Specifically, there may be a recessed space between adjacent fins 6410a, 6410b, except for the fins 6410a, 6410b located at an end of the heat sink halves 6406a, 6406b.

Figure 88:
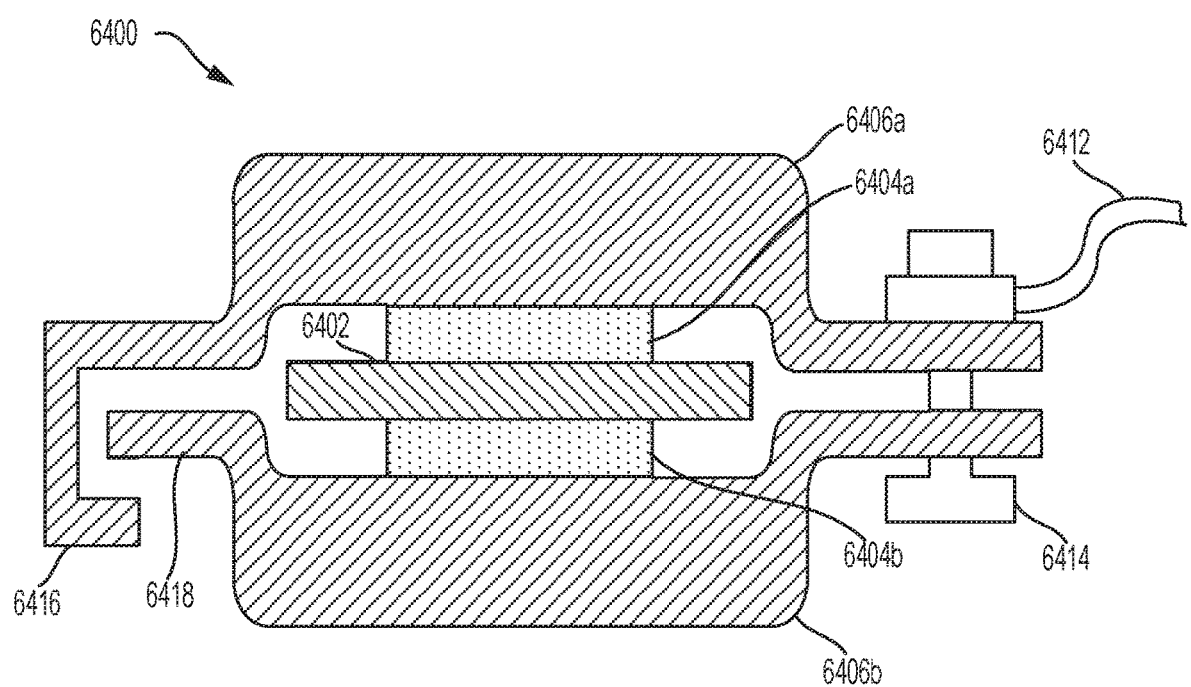
FIG. 88 is a sectional view of the ultrasonic surgical instrument shown in FIG. 24 taken along section line 88-88 as shown in FIG. 87, according to one aspect of this disclosure.

In yet another aspect, as shown in FIG. 87, the wire 6412 is positioned or wedged between the heat sink halves 6406a, 6406b and is configured to be electrically connected to an ultrasonic signal generator. FIG. 88 is a sectional view of the ultrasonic surgical instrument 6400 taken along section line 88-88 as shown in FIG. 87, according to one aspect of this disclosure. As shown in FIG. 88, in one aspect, the upper heat sink half 6406a comprises a receiving portion 6416 at a proximal end. The lower heat sink half 6406b comprises an inserting portion 6418 at a proximal end. The inserting portion 6418 is configured to engage or be inserted into the receiving portion 6416 in an interference fit for coupling the lower and upper heat sink halves 6406a, 6406b to each other. In another aspect, a fastener device 6414, such as a locking screw or pop rivet, for example, is used to secure the two heat sink halves 6406a, 6406b together such that the halves 6406a, 6406b form the unitary metal housing of the heat sink 6406a, 6406b.

Figure 89:
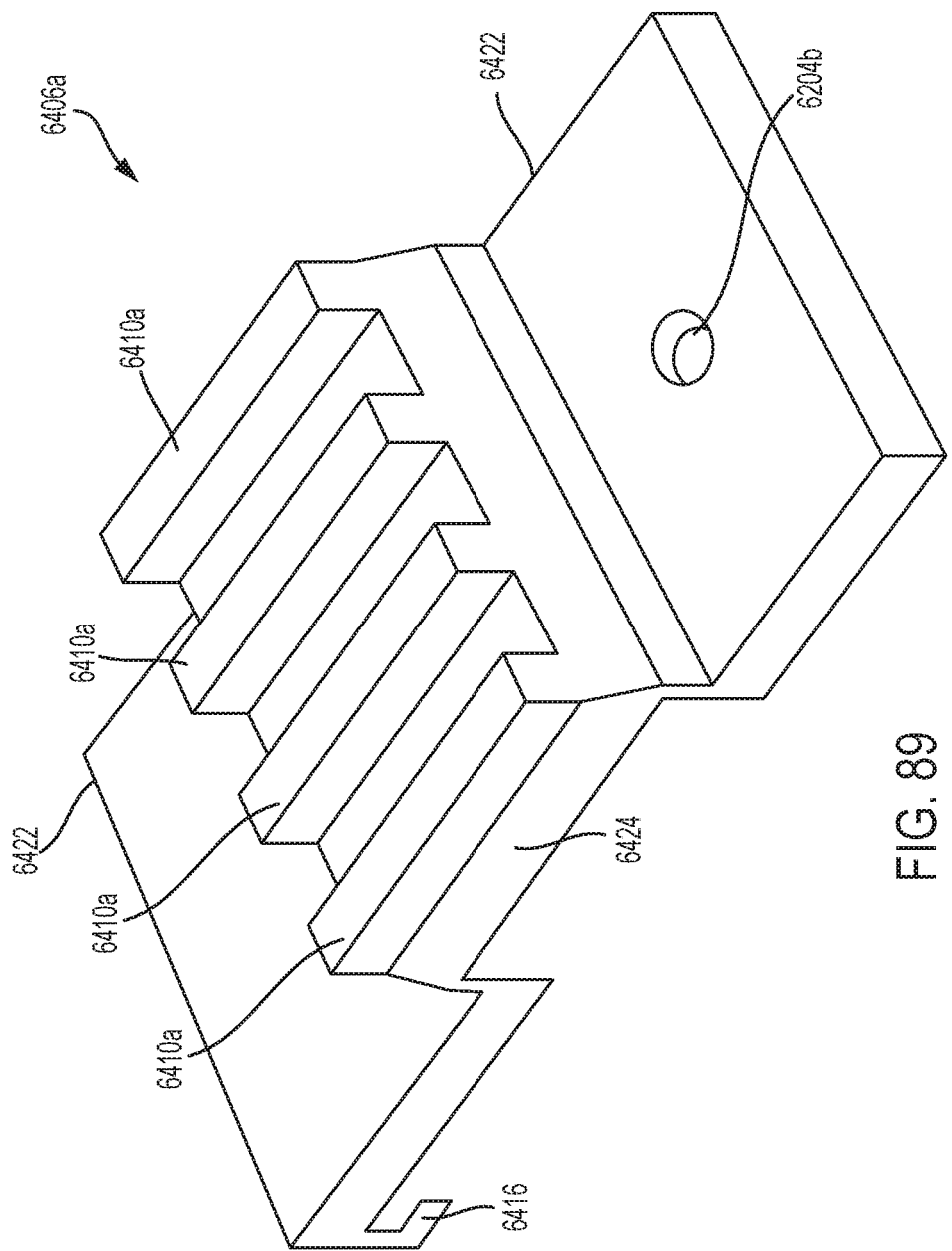
FIG. 89 is a perspective view of an upper heat sink half of the ultrasonic surgical instrument shown in FIG. 87, according to one aspect of this disclosure.

FIG. 89 is a perspective view of the upper heat sink half 6406a, according to one aspect of this disclosure. In one aspect, as shown in FIG. 89, the receiving portion 6416 extends in a direction towards the waveguide 6402 such that the receiving portion 6416 defines a space for the inserting portion 6418. As can be seen in FIG. 89, the upper heat sink half 6406a comprises a base portion 6422, which is interrupted by a protruding portion 6424 extending away (i.e., upwards) from the piezoelectric element 6404a. The protruding portion 6424 comprises the plurality of fins 6410a, which may be mounted to or extend from the top surface of the protruding portion 6424. As described above, the plurality of fins 6410a may be spaced at a predetermined interval apart. As shown in FIG. 89, the base portion 6422 and the protruding portion 6424 form an interconnected component of the upper heat sink half 6406a via an interconnecting portion. The rib 6408a (not shown in FIG. 89) can be coupled to the bottom surface of the protruding portion and connected to the piezoelectric element 6404a through the conductive foam or grease 6422a, as described above. In another aspect, the lower heat sink half 6406b may be similar to upper heat sink half 6406a except that the base portion of the lower heat sink half 6406b can be interrupted by a protruding portion extending away (i.e., downwards) from the piezoelectric element 6404b. The protruding portion may comprise the plurality of fins 6410b.

Figure 90:
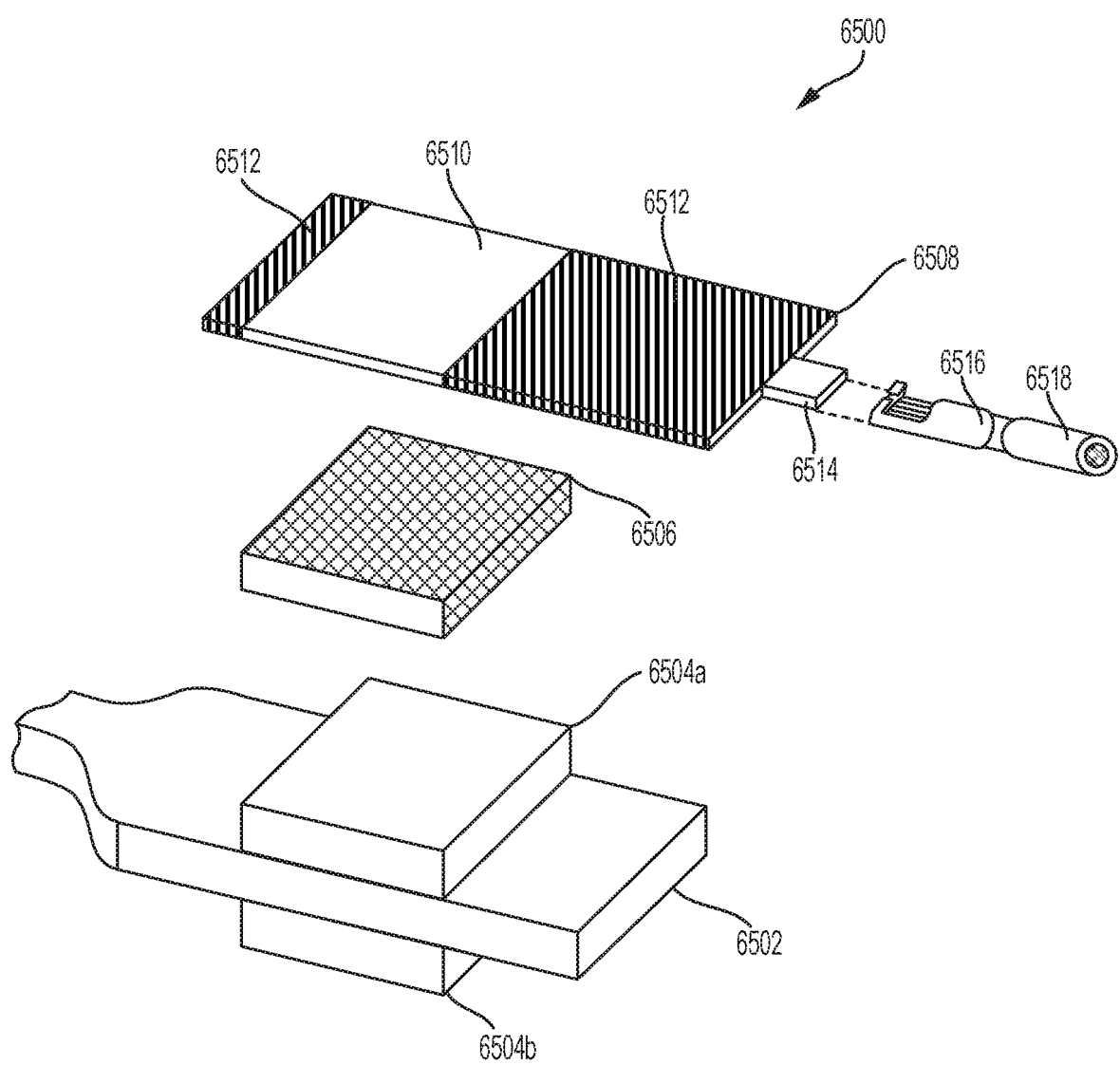
FIG. 90 is a perspective view of an ultrasonic surgical instrument, which is configured to operate in a D31 mode of operation, according to one aspect of this disclosure.

FIG. 90 is a perspective view of an ultrasonic surgical instrument 6500, which is configured to operate in a D31 mode of operation, according to one aspect of this disclosure. The ultrasonic surgical instrument 6500 comprises a waveguide 6502, piezoelectric elements 6504a, 6504b, a conductive bridge 6506, a heat sink 6508, a crimp connector 6516, and a wire 6518. The piezoelectric elements 6504a, 6504b are positioned on opposite surfaces of the waveguide 6502. In one aspect, the conductive bridge 6506 is both thermally and electrically conductive. The conductive bridge 6506 can be a thermal foam gasket (TFG), which is constructed from a graphite sheet over a foam core. For example, the graphite sheet could be formed from suitable graphite material such as eGRAF® SPREADERSHIELD™ or eGRAF® HITHERM™ flexible graphite thermal interface materials (TIMs), both available from GrafTech International Holdings Inc. of Brooklyn Heights, Ohio. The graphite sheet may be wrapped or positioned over a plurality of the surfaces of the foam core. The SPREADERSHIELD™ flexible graphite has an in-plane thermal conductivity range of, for example, 300 to 1500 watts per meter Kelvin (W/mK). In contrast, aluminum has a thermal conductivity range of about 200 to 250 W/mK. The foam core can be formed from suitable thermoplastic elastomers (TPEs), such as thermoplastic polyurethanes or thermally conductive silicone gap fillers available from Stockwell Elastomerics, Inc. of Philadelphia, Pa. The foam core may also be made of nickel & copper (Ni/Cu) metallized urethane conductive foam. Similarly, the top and bottom surfaces of the conductive foam can be made of Ni/Cu knit polyester mesh.

In other aspects, the conductive bridge 6506 could be a foil over foam gasket such as the SOFT-SHIELD 4000 Series electromagnetic interference (EMI) gasket (comprising a PORON1 Urethane Foam core) available from Parker Hannifin Corporation of Cleveland, Ohio, or a suitable metallized fabric over foam gasket available from Laird Technologies of Warren, Ohio. In another aspect, the conductive bridge 6506 is configured be electrically coupled to a metal electrode shim 6508, such as to electrically bridge or conduct signals (e.g generated by an ultrasonic signal generator) passing from the shim 6508 through the bridge 6506 to the piezoelectric element 6504a. The shim 6508 is configured to compress the piezoelectric element 6504a against the waveguide 6502. As shown in FIG. 90, the shim 6508 comprises two coated, electrically non-conductive portions 6512 that are interrupted by a conductive portion 6510. The conductive portion 6510 of the shim 6508 is configured to be positioned over the conductive bridge 6506 such that the bottom surface of the conductive portion 6510 is in electrical and thermal contact with the top surface of the conductive bridge 6506. Moreover, the bottom surface of the conductive bridge 6506 can be positioned over piezoelectric element 6504a. Thus, piezoelectric element 6504a, conductive bridge 6506 and shim 6508 are all thermally and electrically coupled to each other.

Accordingly, the shim 6508 operates as a heat sink and a compressive electrode for the ultrasonic surgical instrument 6500. In particular, thermal energy or heat generated during operation of the piezoelectric element 6504a may be conducted through the conductive bridge 6506 to be absorbed and dissipated by the shim 6508 heat sink. Additionally, electrical energy may be conducted from a generator through the conductive portion 6510 of the shim 6508 and the conductive bridge 6506 to the piezoelectric element 6504a. In one aspect, the safe operating temperature of the piezoelectric elements 6504a, 6504b is below 150 degrees Celsius (i.e., temperature to ensure against damage to the piezoelectric elements 6504a, 6504b). A flange or attachment component 6514 may be configured to be received within a receiving portion of the crimp connector 6516. The crimp connector 6516 can be electrically coupled to the wire 6518, which can be connected to the generator. In various aspects, a second conductive bridge 6506 and shim 6508 may be located below the bottom surface of the piezoelectric element 6504b in a similar but symmetrical configuration to the configuration described above (i.e., the conductive bridge 6506 and shim 6508 located above the piezoelectric element 6504a). Specifically, the top surface of the second conductive bridge 6506 may be positioned below the bottom surface of the piezoelectric element 6504b and the top surface of the second conductive portion 6510 of the second shim 6508 may be positioned below the bottom surface of the second conductive bridge 6506. Advantages of the bridge and shim configuration of the ultrasonic surgical instrument 6500 may include reduced costs, easier manufacture and assembly, and efficiency based on using the shim 6508 heat sink as an electrical connection.

Figure 91:
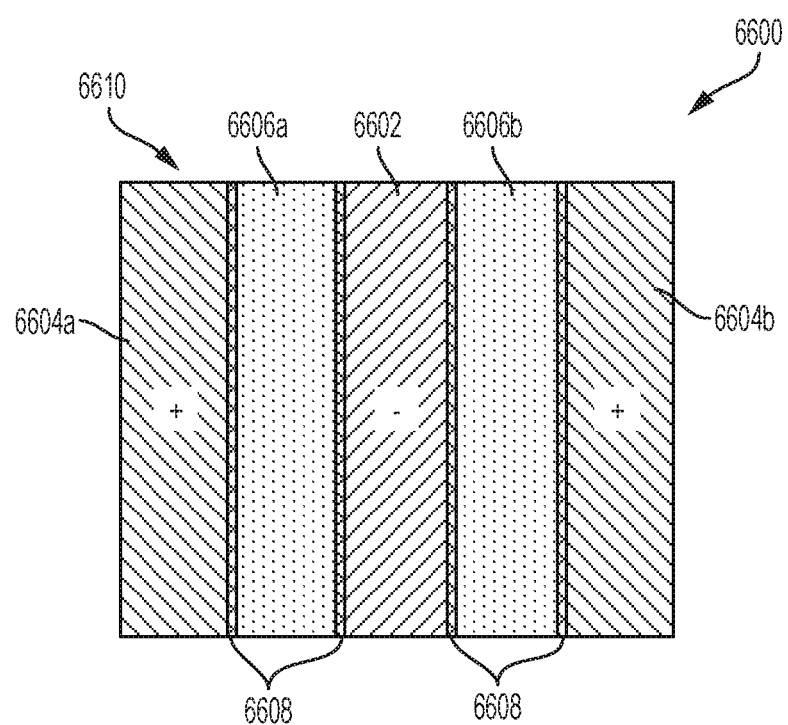
FIG. 91 illustrates a D31 ultrasonic surgical instrument that includes piezoelectric elements attached on one side to an ultrasonic waveguide by a conductive adhesive and attached on another side to electrically conductive plates by a conductive adhesive, according to one aspect of this disclosure.

FIG. 91 illustrates an ultrasonic surgical instrument 6600 including an ultrasonic transducer 6610 attached to an ultrasonic waveguide 6602, by a bonding material, where the ultrasonic surgical instrument 6600 is configured to operate in a D31 mode, according to one aspect of this disclosure. The ultrasonic transducer 6610 includes piezoelectric elements 6606a, 6606b attached on opposite sides of the ultrasonic waveguide 6602 by a bonding material. In one aspect, the bonding material is a conductive adhesive 6608. Conductive plates 6604a, 6604b are attached to the piezoelectric elements 6606a, 6606b, respectively, by a bonding material such as a conductive adhesive 6608, according to one aspect of this disclosure. An electrical connection method includes soldering the piezoelectric elements 6606a, 6606b on one side directly to the inside surfaces of the electrically conductive plates 6604a, 6604b (e.g., copper plates or sheets) and on the other side to the ultrasonic waveguide 6602. A conductive epoxy 6608 is applied between the electrically conductive plates 6604a, 6604b and the free ends of the piezoelectric elements 6606a, 6606b. A conductive epoxy 6608 also is applied between the fixed ends of the piezoelectric elements 6606a, 6606b and the ultrasonic waveguide 6602. Electrically conductive elements such as wires may be connected to the electrically conductive plates 6606a, 6606b and to the ultrasonic waveguide 6602. In one aspect, the ultrasonic waveguide 6602 may be formed by stamping and electrical connection features may be added to the ultrasonic waveguide 6602. The electrically conductive plates 6606a, 6606b may be formed of copper sheets and assembled to female electrical connectors on a cable. Crimp connections may be stamped or formed on the ultrasonic waveguide 6602 and the electrically conductive plates 6606a, 6606b (e.g., copper sheets). The connections to wires may be crimped during assembly. In various aspects, the electrical connection process may include any combination of the above.

Figure 92:
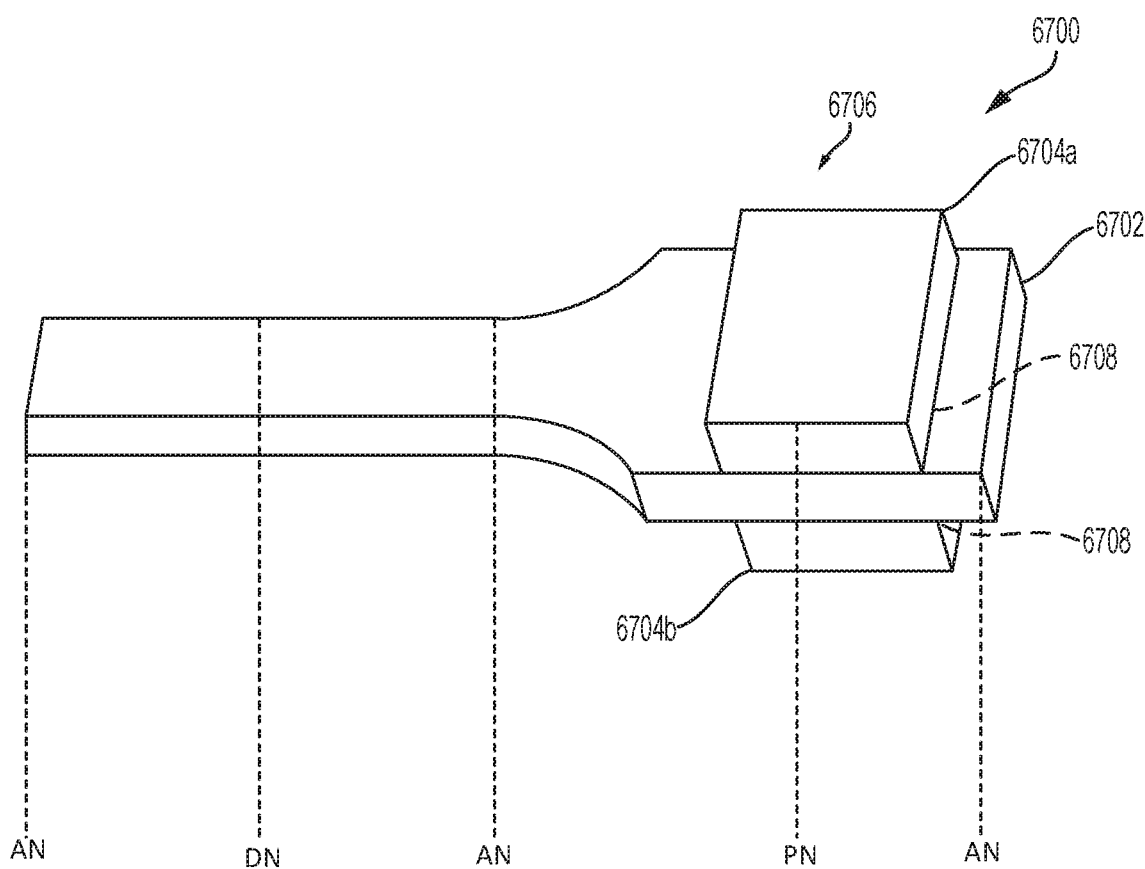
FIG. 92 is a perspective view of an ultrasonic surgical instrument, which is configured to operate in a D31 mode of operation, according to one aspect of this disclosure.

FIG. 92 is a perspective view of an ultrasonic surgical instrument 6700, which is configured to operate in a D31 mode of operation, according to one aspect of this disclosure. The ultrasonic surgical instrument 6700 comprises an ultrasonic waveguide 6702, and piezoelectric elements 6704a, 6704b. The ultrasonic surgical instrument 6700 includes an ultrasonic transducer 6706 that includes the piezoelectric elements 6704a, 6704b. As shown in FIG. 77, the piezoelectric elements 6704a, 6704b are attached to the ultrasonic waveguide 6702 using a bonding material such as a conductive epoxy adhesive 6708 to bond the piezoelectric elements 6704a, 6704b to the ultrasonic waveguide 6702. Specifically, epoxy adhesive 6708 is applied to the area between the bottom surface of the first piezoelectric element 6704a and the top surface of the ultrasonic waveguide 6702. Similarly, epoxy adhesive 6708 is applied to the area between the bottom surface of the ultrasonic waveguide 6702 and the top surface of the second piezoelectric element 6704b. In one aspect, the use of the epoxy adhesive 6708 creates a secure electrical connection between the piezoelectric elements 6704a, 6704b and the ultrasonic waveguide 6702. As described above, the electrical ground connection can be made to the ultrasonic waveguide 6702, which is electrically conductive.

As shown in FIG. 92, the locations of a plurality of nodes and antinodes are depicted. Arrow "PN" and "DN" indicate a proximal and a distal node respectively. Each of the arrows "AN" indicates an anti-node. As described above, a minimum or zero crossing in the vibratory motion standing wave is generally referred to as a node and an absolute value maximum or peak in the standing wave is generally referred to as an anti-node. Conventionally, the electrical ground connection is made at a proximal node, which is denoted by the arrow "PN" in FIG. 92. The location of the proximal node may be represented by a longitudinal line extending through a center portion of the piezoelectric elements 6704a, 6704b and ultrasonic waveguide 6702. Furthermore, the proximal node represents a location of high voltage potential, which enables an electrical ground connection to be made to the ultrasonic waveguide 6702 based on the electrical contact between the piezoelectric elements 6704a, 6704b and the ultrasonic waveguide 6702. In another aspect, the use of the epoxy adhesive 6708 may enable the ultrasonic waveguide 6702 electrical ground connection to be made at an alternate node, such as the distal node, instead of the proximal node. An alternate node may be used because the use of the epoxy adhesive 6708 creates a secure electrical contact between the piezoelectric elements 6704a, 6704b and the ultrasonic waveguide 6702.

Figure 93:
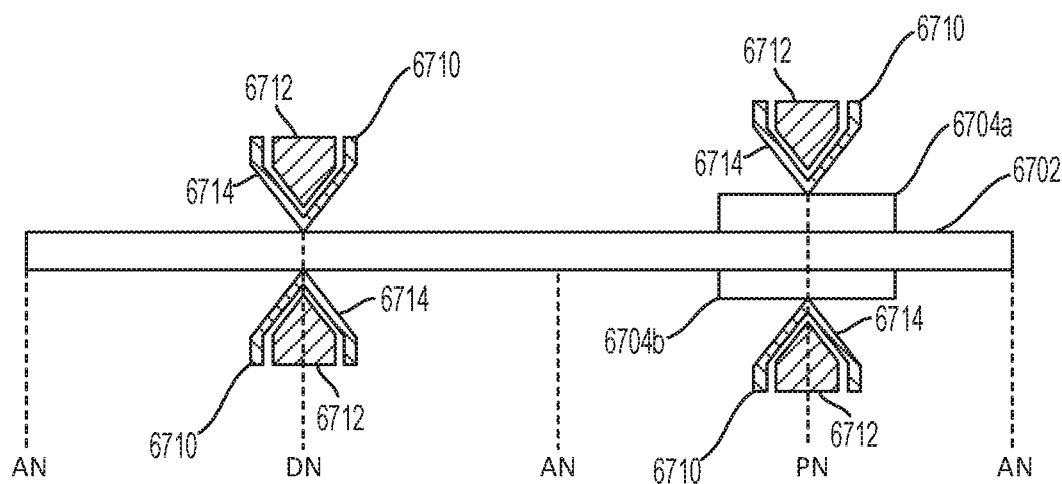
FIG. 93 is a sectional view of the ultrasonic surgical instrument shown in FIG. 92 with electrically conductive electrodes configured to compress the piezoelectric elements and the ultrasonic waveguide, according to one aspect of this disclosure.

FIG. 93 is a sectional view of the ultrasonic surgical instrument 6700 with electrically conductive electrodes 6710 configured to compress the piezoelectric elements 6704a, 6704b and the ultrasonic waveguide 6702, respectively. The electrically conductive electrodes 6710 each comprise a compliant member portion 6712 and a thin metal portion 6714. In one aspect, two conductive electrodes 6710 are positioned on each side of the ultrasonic waveguide 6702. At the proximal node, the thin metal portion 6714 of a first upper conductive electrode 6710 comprises a narrow tip to compress the piezoelectric element 6704a. Similarly, at the proximal node, the thin metal portion 6714 of a first lower conductive electrode 6710 comprises a narrow tip to compress the piezoelectric element 6704a. At the distal node, the thin metal portion 6714 of a second upper conductive electrode 6710 comprises a narrow tip to compress the ultrasonic waveguide 6702. Similarly, at the distal node, the thin metal portion 6714 of a second lower conductive electrode 6710 comprises a narrow tip to compress the ultrasonic waveguide 6702. In another aspect, based on the second upper conductive electrode 6710 and the second lower conductive electrode 6710, an electrical ground connection may be applied to the ultrasonic waveguide at the distal node. Advantages of this configuration may include reduced manufacturing complexity of the ultrasonic surgical instrument 6700.

Figure 94A:
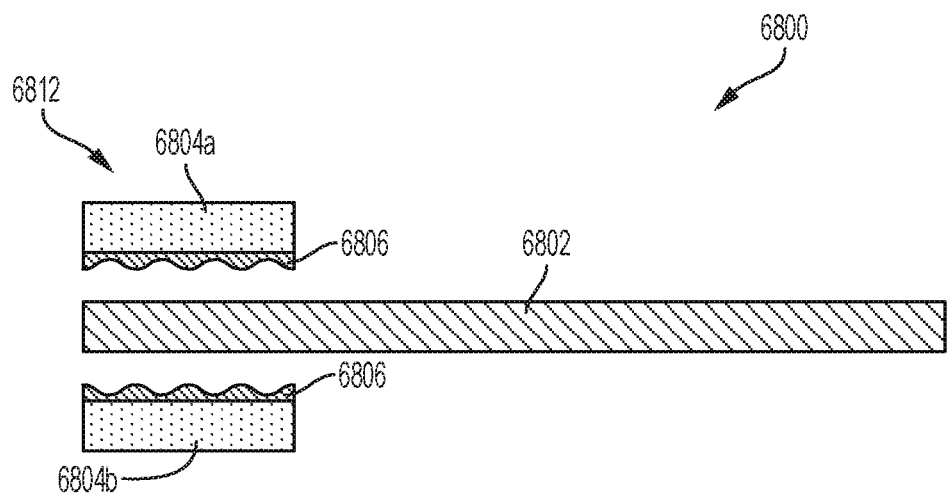
FIG. 94A illustrates an ultrasonic surgical instrument prior to assembly and poling, according to one aspect of this disclosure.
Figure 94B:
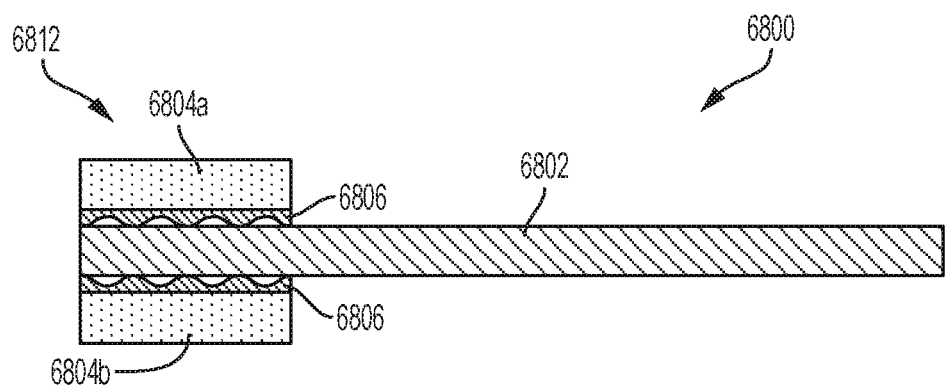
FIG. 94B illustrates the ultrasonic surgical instrument of FIG. 94A prior to poling and the first and second unpoled piezoelectric elements secured to the ultrasonic waveguide in a D31 configuration, according to one aspect of this disclosure.
Figure 94C:
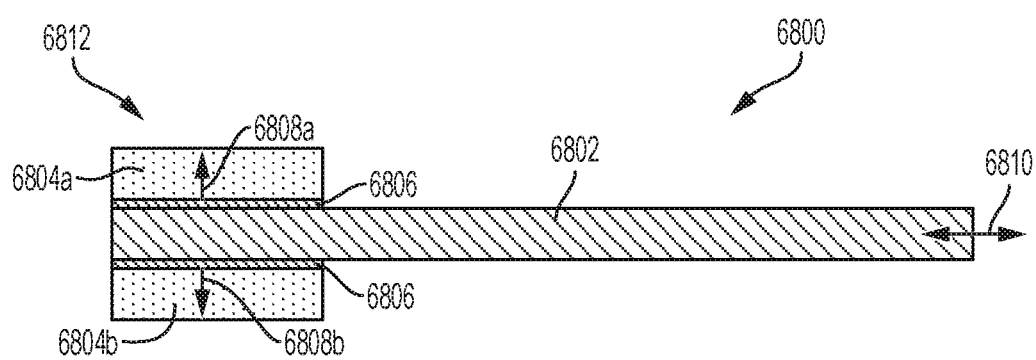
FIG. 94C illustrates the ultrasonic instrument of FIG. 94B prior to poling and the first and second unpoled piezoelectric elements secured to the ultrasonic waveguide in a D31 configuration, according to one aspect of this disclosure.

FIGS. 94A-94C illustrate an ultrasonic surgical instrument 6800 that includes an ultrasonic waveguide 6802 attached to an ultrasonic transducer 6812 by a bonding material, where the ultrasonic surgical instrument 6800 is configured to operate in a D31 mode. The ultrasonic transducer 6812 includes first and second unpoled piezoelectric elements 6804a, 6804b attached to opposite sides of the ultrasonic waveguide 6802 by a bonding material. FIG. 94A illustrates an ultrasonic surgical instrument 6800 prior to assembly and poling, according to one aspect of this disclosure. The ultrasonic surgical instrument 6800 includes a metal ultrasonic waveguide 6802 (e.g., titanium/titanium alloy). A bonding material such as solder paste 6806 is applied to one surface of a first unpoled piezoelectric element 6804a and a second unpoled piezoelectric element 6804b. The solder paste 6806 is a sticky mixture of flux and tiny solder particles, and may be applied to piezoelectric elements 6804a, 6804b with a stainless steel or nickel stencil using a screen printing process. The solder paste 6806 also can be applied to the piezoelectric elements 6804a, 6804b by a jet-printing mechanism, similar to an inkjet printer. After pasting, the piezoelectric elements 6804a, 6804b proceed to a pick-and-place machine or a manual placing process for securing the piezoelectric elements 6804a, 6804b to the ultrasonic waveguide 6802.

FIG. 94B illustrates the ultrasonic surgical instrument 6800 of FIG. 94A prior to poling with the first and second unpoled piezoelectric elements 6804a, 6804b secured to the ultrasonic waveguide 6802 in a D31 configuration, according to one aspect of this disclosure. After pasting, the piezoelectric elements 6804a, 6804b are secured to the ultrasonic waveguide 6802 using an automated or manual process. An insulating clamp may be employed to secure the first and second unpoled piezoelectric elements 6804a, 6804b prior to conveying the secured piezoelectric elements 6804a, 6804b and ultrasonic waveguide 6802 assembly to a reflow soldering oven. Once in the oven, the solder paste 6806 is reflowed to bond the first and second unpoled piezoelectric elements 6804a, 6804b to the ultrasonic waveguide 6802.

FIG. 94C illustrates the ultrasonic instrument 6800 of FIG. 94B after reflow soldering and prior to poling the first and second unpoled piezoelectric elements 6804a, 6804b attached to the ultrasonic waveguide 6802 in a D31 configuration, according to one aspect of this disclosure. Once the secured piezoelectric elements 6804a, 6804b and ultrasonic waveguide 6802 assembly is conveyed to a reflow soldering oven, the solder paste 6806 is reflowed to establish a bond between the first and second unpoled piezoelectric elements 6804a, 6804b and the ultrasonic waveguide 6802. The solder paste 6806 may be reflowed using standard surface mount technology. There are a number of techniques for reflowing the solder 6806. One technique employs infrared lamps and is called infrared reflow. Another technique employs hot gas convection using either standard air or nitrogen gas. Another surface mount technology employs special fluorocarbon liquids with high boiling points which use a method called vapor phase reflow. Each method has its advantages and disadvantages.

After the first and second unpoled piezoelectric elements 6804a, 6804b are attached to the ultrasonic waveguide 6802 using a reflow solder technique, the entire ultrasonic instrument 6800 assembly is poled. A poling process may be carried out in an oil bath with special fixturing. The nature of the piezoelectric effect is closely related to the occurrence of electric dipole moments in solids. The latter may be induced for ions on crystal lattice sites with asymmetric charge surroundings as in piezoelectric elements. The dipole density or polarization (dimensionality (C·m/m$^3$)) may be calculated for crystals by summing up the dipole moments per volume of the crystallographic unit cell. As every dipole is a vector, the dipole density P is a vector field. Dipoles near each other tend to be aligned in regions called Weiss domains. The domains are usually randomly oriented, but can be aligned using the process of poling (not the same as magnetic poling), a process by which a strong electric field is applied across the material, usually at elevated temperatures. Not all piezoelectric materials can be poled. The poling axis (P) of the piezoelectric elements 6804a, 6804b is indicated by the direction arrows 6808a, 6808b, respectively. The motion axis of the ultrasonic waveguide 6802 in response to excitation of the piezoelectric elements 6804a, 6804b is shown by the motion arrow 6810 at the distal end of the ultrasonic waveguide 6802 generally referred to as the ultrasonic blade portion of the ultrasonic waveguide 6802. The motion axis 6810 is orthogonal to the poling axis (P) 6808a, 6808b.

The piezoelectric effect is the change of polarization P under the application of a mechanical stress. This might either be caused by a reconfiguration of the dipole-inducing surrounding or by re-orientation of molecular dipole moments under the influence of the external mechanical stress. Piezoelectricity may manifest in a variety of ways, including the variation of the polarization strength, its direction or both, with the details depending on: the orientation of P within the crystal; crystal symmetry; and the applied mechanical stress. The change in P appears as a variation of surface charge density upon the crystal faces, i.e., as a variation of the electric field extending between the faces caused by a change in dipole density in the bulk. For example, a 1 cm$^3$ cube of quartz with 2 kN (500 lbf) of correctly applied force can produce a voltage of 12500 V.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

An ultrasonic surgical instrument comprising: a transducer base plate comprising a first and second face; a first piezoelectric element positioned on the first face; a second piezoelectric element positioned on the second face, wherein the first and second piezoelectric element are each configured to operate in a D31 mode with respect to a longitudinal axis of a waveguide coupled to the transducer base plate, wherein the waveguide is electrically coupled to the first piezoelectric element and to the second piezoelectric element by a conductive adhesive; an electrode configured to electrically couple the first and second piezoelectric elements to an ultrasonic signal generator; and a thermal conductor configured to conduct thermal energy away from the first and second piezoelectric elements.

Example 2

The ultrasonic surgical instrument of Example 1, wherein the first piezoelectric element has a poling axis in a direction from a first side to a second side of the first piezoelectric element and the second piezoelectric element has a poling axis in a direction from a first side to a second side of the second piezoelectric element to operate in the D31 mode.

Example 3

The ultrasonic surgical instrument of Example 1 or Example 2, wherein a motion axis of the ultrasonic waveguide is orthogonal to the poling axes of the first and second piezoelectric elements.

Example 4

The ultrasonic surgical instrument of one or more of Example 1 through 3, wherein the conductive adhesive is a solder bonding material.

Example 5

The ultrasonic surgical instrument of one or more of Example 1 through Example 4, further comprising an electrical connector positioned at one of a plurality of nodes of the ultrasonic surgical instrument, wherein the waveguide is coupled to the electrical connector to provide an electrical ground.

Example 6

The ultrasonic surgical instrument of one or more of Example 1 through Example 5, further comprising: a first electrically conductive plate attached to a second face of the first piezoelectric element by a second bonding material; and a second electrically conductive plate attached to a second face of the second piezoelectric element by the second bonding material.

Example 7

The ultrasonic surgical instrument of one or more of Example 1 through Example 6, wherein: the thermal conductor is a heat sink that comprises a metal housing including at least one fin, the metal housing comprises two portions interconnected through the waveguide, and the at least one fin is configured to conduct thermal energy away from the first and second piezoelectric elements through a rib of the heat sink.

Example 8

The ultrasonic surgical instrument of Example 7, wherein an electrical connector connected to the ultrasonic signal generator is wedged between the two portions.

Example 9

A method of fabricating an ultrasonic surgical instrument comprising: machining a transducer base plate from a portion of a flat metal stock, wherein the transducer base plate comprises a first and second face; positioning a first piezoelectric element on the first face; positioning a second piezoelectric element on the second face, wherein the first and second piezoelectric element are each configured to operate in a D31 mode with respect to a longitudinal axis of a waveguide coupled to the transducer base plate; coupling, by a first electrically conductive adhesive, the waveguide to the first piezoelectric element and the second piezoelectric element; compressing, by an electrode, against the first and second piezoelectric elements to electrically couple the first and second piezoelectric elements to an ultrasonic signal generator; and conducting, by a thermal conductor, heat away from the first and second piezoelectric elements.

Example 10

The method of Example 9, further comprising: forming a plurality of fins and a rib of the thermal conductor, wherein the conducted heat is conducted through the rib.

Example 11

The method of Example 10, further comprising: forming an interconnection between a first portion of the thermal conductor, the waveguide, and a second portion of the thermal conductor.

Example 12

The method of Example 11, wherein a first fin of the plurality of fins is positioned on the first portion, and a second fin of the plurality of fins is positioned on the second portion.

Example 13

The method of one or more Example 9 through Example 12, further comprising: applying a second electrically conductive adhesive between the electrode and the first and second piezoelectric elements.

Example 14

A transducer base plate comprising: a first and second face, wherein a first piezoelectric element is positioned on the first face and a second piezoelectric element is positioned on the second face, and wherein the first and second piezoelectric element are each configured to operate in a D31 mode with respect to a longitudinal axis of a waveguide coupled to the transducer base plate; a conductive adhesive to electrically couple the first and second piezoelectric elements to the waveguide; an electrode configured to electrically couple the first and second piezoelectric elements to an ultrasonic signal generator; and a thermal conductor configured to conduct heat away from the first and second piezoelectric elements.

Example 15

The transducer base plate of Example 14, further comprising: a third piezoelectric element positioned in a recess of the waveguide; an insulator positioned on a first portion of the electrode, wherein a second portion of the electrode is configured to electrically couple the first, second, and third piezoelectric elements to the ultrasonic signal generator.

Example 16

The transducer base plate of Example 15, wherein the electrode comprises the first portion, the second portion, and a third portion.

Example 17

The transducer base plate of one or more of Example 14 through Example 16, wherein the conductive adhesive comprises a first portion positioned at a proximal end of the first and second piezoelectric elements and a second portion positioned at a distal end of the first and second piezoelectric elements.

Example 18

The transducer base plate of one or more Example 14 through Example 17, further comprising a first recess for receiving the first piezoelectric element and a second recess for receiving the second piezoelectric element, wherein a length of the first recess is greater than a length of the first piezoelectric element such that a gap of the first recess is provided and a length of the second recess is greater than a length of the second piezoelectric element such that a gap of the second recess is provided.

Example 19

An ultrasonic transducer assembly comprising: a stack of a plurality of piezoelectric elements, wherein the stack is configured to operate in a D33 mode with respect to a longitudinal axis of a waveguide coupled to the transducer base plate; a compression plate to compress the stack of the plurality of piezoelectric elements to couple the stack of piezoelectric elements to a waveguide; and a compressive element for applying a compressive force against the compression plate.

Example 20

The ultrasonic transducer assembly of Example 19, wherein the compressive element is a screw fastened to the compression plate.

Example 21

The ultrasonic transducer assembly of Example 19, wherein the compressive element is a wedge element.

Ultrasonic Transducer to Waveguide Acoustic Coupling, Connections, and Configurations FIGS. 95A-95C illustrate a compressed ultrasonic transducer assembly 7000 in a D33 configuration with tuned compression, according to one aspect of this disclosure. In one aspect, the ultrasonic transducer assembly 7000 includes one or more piezoelectric elements 7002a, 7002b, 7002c, 7002d (e.g., PZT) compressed in an opening 7014 defined by a housing 7004 or shell. Once the ultrasonic transducer assembly 7000 is fully compressed, it is provided to a further assembly process, where, for example, a surface of one of the piezoelectric elements 7002a-d in the assembly 7000 is attached to a metal ultrasonic waveguide or waveguide. Applying compression on the piezoelectric elements 7002a-d (especially in the direction of coupled strain) provides higher efficiency and increased ability to drive larger loads. Because the compressed ultrasonic transducer assembly 7000 does not include an axially compressed element, the piezoelectric elements 7002a-d are compressed along the axis of vibration LA and then anchored in place. The shell 7004 or a band disposed about the piezoelectric elements 7002a-d is compressed and the assembly is anchored in place as described below.

FIG. 95A illustrates an installation phase of the ultrasonic transducer assembly 7000 in a pre-compression state. One or more piezoelectric elements 7002a-d are stacked inside the housing 7004. A plug 7006 is aligned with the piezoelectric elements 7002a-d stack. The housing 7004 and plug 7006 elements are made of a metal material. The plug 7006 and the stack of piezoelectric elements 7002a-d are aligned with the axis of vibration LA. The length of the stack of piezoelectric elements 7002a-d prior to compression is labeled as $d_0$.

FIG. 95B illustrates an initial compression state of the compressed ultrasonic transducer assembly 7000. A targeted initial force $F_i$ is applied to the plug 7006 to compress the plug 7006 onto the stack of piezoelectric elements 7002a-d.

FIG. 95C illustrates a final compression state of the compressed ultrasonic transducer assembly 7000. As shown in FIG. 95C, after a final compression force $F_f$ is applied to the stack of piezoelectric elements 7002a-d, the housing 7004 and the plug are anchored together with anchors 7008a, 7008b while the stack of piezoelectric elements 7002a-d is in the compressed state. The compressed length of the stack of piezoelectric elements 7002a-d is labeled as $d_1$, where $d_1 < d_0$. The anchors 7008a, 7008b may be any suitable element that serves to join the plug 7006 to the housing 7004 firmly in place against the piezoelectric elements 7002a-d to maintain the stack of piezoelectric elements 7002a-d under compression. Accordingly, the anchor 7008a, 7008b may be attached or secured by a joint that is formed by welding, soldering, brazing, epoxy, swaging, or any combination thereof.

In another aspect, the anchor 7008a, 7008b may be attached to the metal housing 7004 by threaded connection. In a threaded connection configuration, the metal housing 7004 and the metal plug 7006 each include a threaded end and the components are threadingly coupled. In one aspect, the metal plug 7006 includes external male threads and the housing 7004 includes internal female threads to threadingly engage the male threads of the plug 7006 and the plug 7006 is screwed into the internal portion of the housing 7004. In another aspect, the plug 7006 includes internal female threads and the housing 7004 includes external male threads to threadingly engage the female threads of the plug 7006 and the plug 7006 is screwed onto the external portion of the housing 7004. In the latter configuration, the inside of the plug 7006 includes a boss or other protruding feature inside the plug 7006 to contact and compress the stack of piezoelectric elements 7002a-c. In the threaded anchor configuration, a rotational force is applied to the plug 7006, which applies a compressed force to the stack of piezoelectric elements 7002a-d as the plug 7006 is threadingly engaged with the housing 7004.

Once the transducer assembly 7000 is fully compressed and the anchors 7008a, 7008b are applied, the transducer assembly 7000 is ready to be assembled. In one aspect, an ultrasonic waveguide is acoustically coupled to a first surface 7010 of the transducer assembly 7000 and in another aspect, the ultrasonic waveguide is acoustically couple to a first surface 7010 of the transducer assembly 7000. In other aspects, the plug 7006 may be a component of an ultrasonic waveguide.

The description now turns to techniques for acoustic coupling ceramic piezoelectric elements to ultrasonic waveguides made of titanium or titanium alloys (i.e., Ti6Al4V) in D31 configurations. Advantages of D31 acoustic coupling techniques described herein include low cost, low profile, ease of manufacture and assembly. Additional advantages include the ability to compress the piezoelectric elements (especially in direction of coupled strain) to provide higher efficiency and drive large loads. In a D31 acoustic train configuration, electrical contacts for electrical connection are provided on both sides of the ceramic piezoelectric elements. An electrical ground connection can applied to the ultrasonic waveguide if there is electrical contact from the ceramic piezoelectric elements to the ultrasonic waveguide. In one aspect, low temperature acoustic coupling techniques are employed to minimize or prevent no damage to the ceramic piezoelectric elements (<150° C.). Electrical connections also may be used as a heat sink. Several techniques for acoustic coupling ceramic piezoelectric elements in D31 configurations to titanium/titanium alloy ultrasonic waveguides are described hereinbelow in connection with FIGS. 96-102.

FIG. 96 is a perspective view of an ultrasonic surgical instrument 7100, according to one aspect of this disclosure. The ultrasonic surgical instrument 7100 includes an ultrasonic transducer 7118 attached to an ultrasonic waveguide 7102 by a bonding material, where the ultrasonic surgical instrument 7100 is configured to operate in a D31 mode. FIG. 97 is perspective view of a piezoelectric element 7104 for use with the ultrasonic surgical instrument 7100 shown in FIG. 96, according to one aspect of this disclosure. The ultrasonic transducer 7118 includes first and second piezoelectric elements 7104a, 7104b attached to opposite sides of the ultrasonic waveguide 7102 by a bonding material. The piezoelectric elements 7104a-b may be PZT ceramic elements attached to a metal ultrasonic waveguide 7102 using a ceramic to metal bonding technique described hereinbelow.

FIG. 98 is section view of the ultrasonic surgical instrument 7100 shown in FIG. 96, according to one aspect of this disclosure. The ultrasonic surgical instrument 7100 includes an ultrasonic transducer attached to an ultrasonic waveguide 7102 by a bonding material, where the ultrasonic surgical instrument 7100 is configured to operate in a D31 mode. The ultrasonic transducer includes a first ceramic piezoelectric element 7104a and a second ceramic piezoelectric element 7104b attached to opposite sides of the ultrasonic waveguide 7102 by a bonding material. The bonding material is used to attach the ceramic to metal connections to bond the ceramic piezoelectric elements 7104a, 7104b to the metal ultrasonic waveguide 7102. In the example illustrated in FIG. 98, a bottom surface of the top piezoelectric element 7104a is attached to one side of the ultrasonic waveguide 7102 by a metal bonding material such as a metal alloy solder 7106a. Similarly, a bottom surface of the bottom piezoelectric element 7104b is attached to the opposite side of the ultrasonic waveguide 7102 by a metal bonding material such as a metal alloy solder 7106b. The metal alloy solder 7106a, 7106b may be utilized to bond the ceramic piezoelectric elements 7104a, 7104b, which are made of a PZT material (i.e., $Pb[Zr_xTi_{1-x}]O_3$), to the metal ultrasonic waveguide 7102, which is made of titanium or titanium alloys (i.e., Ti6Al4V), without using flux or pre-coating the piezoelectric elements 7104a, 7104b. The metal alloy solder may be applied at temperatures below the Curie temperature of the ceramic. The metal alloy solder 7106a, 7106b joint is thermally and electrically conductive, provides a hermetic seal, and has high shear strength. Depending on the joining process, the metal alloy solder 7106a, 7106b, may develop a chemical bond between the surfaces of the piezoelectric elements 7104a, 7104b and the ultrasonic waveguide 7102.

In addition, a metal bonding material such as a metal alloy solder 7108a also may be utilized to bond a thin conductive metal element 7110a to a top surface of the top piezoelectric element 7104a. Similarly, a metal bonding material such as a metal alloy solder 7108b can be utilized to bond a thin conductive metal element 7110b to a top surface of the bottom piezoelectric element 7104b. The conductive metal elements 7110a, 7110b are suitable for making positive electrical connections via soldered wire, crimp connection, or spade connection to the piezoelectric elements 7104a, 7104b. At temperatures below the Curie temperature of the piezoelectric elements 7104a, 7104b, bonding may be performed after poling the piezoelectric elements 7104a, 7104b. At temperatures at or above the Curie temperature of the piezoelectric elements 7104a, 7104b, the piezoelectric elements 7104a, 7104b may be poled after bonding the components of the ultrasonic surgical instrument 7100 as an assembly.

In one aspect, a metal bonding material such as a metal alloy solder 7106a, 7106b, 7108a, 7108b suitable for ceramic to metal bonding may be obtained from S-Bond Technologies, for example. Active metal alloy solders are useful for ceramic to metal bonding. Such solder alloys include active elements such as titanium and cerium added to SnAg, SnInAg, and SnBi alloys to create a solder alloy that can be reacted directly with the ceramic surfaces prior to bonding. Solder alloys produce reliable, hermetic joints with all metals, including steel, stainless steels, titanium, nickel alloys, copper and aluminum alloys, for example. Ceramics are generally not compatible with direct wetting processes (molten metal layers adhering) and ceramics and metals have largely different coefficients of thermal expansion (CTE). Solder alloys, by definition melt and thus join at temperatures below 840° F. and normally closer to 480° F. (250° C.). As such, soldered joints are much better at joining ceramics to metals because the joining stresses are much lower due to solidifying from much lower temperatures than brazed joints. The caveat with conventional solders remains that an adherent metal layer must first be placed on the ceramic surface then followed by a solder flux process to disrupt the oxides that form on the metal and metal coating on the ceramic as they are heated on the solder joining process. The metal alloy solder known under the trade name S-BOND is an active solder suitable for joining metal alloys to ceramics by directly bonding ceramic to metal, forming joints without the use flux and without precoating ceramic steps. This process eliminates multiple step coating processes and can be applied at temperatures below 400° F., preventing distortion and softening of metals and preventing ceramic fracture. The joints produced are hermetic, passing $<10^{-9}$ atm-cc/sec, strong (>5,000 psi shear), ductile, based on SnAg or SnIn alloys and thermally conductive.

The poling axis (P) of the piezoelectric elements 7104a, 7104b is indicated by the direction arrows 7114a, 7114b, respectively. The motion axis of the ultrasonic waveguide 7102 in response to excitation of the piezoelectric elements 7104a, 7104b is shown by the motion arrow 7116 at the distal end of the ultrasonic waveguide 7102 generally referred to as the ultrasonic blade portion of the ultrasonic waveguide 7102. The motion axis 7116 is orthogonal to the poling axis (P) 7114a, 7114b.

FIGS. 99-102 illustrate section views of example metal alloy solder joints 7106a, 7106b, 7108a, 7108b suitable for ceramic to metal bonding as shown in FIG. 98, according to one aspect of this disclosure. Two different processes can be used in ceramic to metal bonding. A "mechanically activated" joining process shown in FIGS. 99 and 100 can be carried out at or near the metal alloy solder melting temperature, (e.g., 250° C. for S-Bond 220).

FIG. 99 illustrates an example of an adhesive bond 7120 formed between a metal alloy solder 7122 and a metal 7124, according to one aspect of this disclosure. The bond 7120 can be made by spreading, rubbing, or brushing the molten alloys onto heated surfaces and assembling "hot" in a manner such that the metal alloy solder 7122 surfaces are agitated sufficiently to break the thin oxide skins that form while molten. As shown in FIG. 99, Al, Cr, or Ti atoms 7128 in the metal 7124 and Ti or Ce atoms 7130 in the metal alloy solder 7122 form an adhesive bond at the interface 7126.

FIG. 100 illustrates an example of adhesive bond 7140 between a ceramic 7142 (e.g., PZT) and a metal 7144 (e.g., titanium alloy steel) formed by a metal alloy solder 7146. Metal alloy solder 7146 alloys do bond, but the joint strengths are nominally below 3,000 psi in shear. Such joints on ceramics 7142 and many metals 7144 are adhesive, but have no chemical bond.

FIG. 101 illustrates an example of a metallurgical/chemical bond 7150, according to one aspect of this disclosure. Another metal alloy solder 7154 joining process employs a thermally activated process, which prepares the ceramic 7152 surfaces and develops a chemical bond to the surface through reactions of the active elements in the metal alloy solder 7154. These joints start with an elevated temperature treatment in a protective atmosphere furnace with the metal alloy solder 7154 placed on the surfaces of the ceramic 7152 to be joined. At the elevated temperatures, the active elements in the metal alloy solder 7154 react with the ceramic 7152 to develop a chemical bond (e.g., Al(Ti)—Ag phases or Cu—Sn phases) at the interface 7156 between the ceramic 7152 and the metal alloy solder 7154. A chemical bond and a metal alloy solder 7154 layer in a subsequent joining step provides a much higher level of joint strength and creates high performance ceramic metal joints that are better than most brazed sapphire and ceramic to metal joints made by the multistep MoMn and plating processes.

FIG. 102 is a microstructure illustration of a ceramic 7164 (e.g., PZT) and metal alloy solder 7162 chemical bond 7160, according to one aspect of this disclosure. A reaction zone 7166 is formed at the ceramic 7164 to metal alloy solder 7162 interface 7168. The S-Bond metal alloy solder provides high joint shear strengths. For example, using elevated temperature S-Bond metal alloy solder metallization procedures, the shear strengths of the chemical bond 7160 at the interface 7168 can exceed 7,000 psi and are resistant to thermal cycling from 50-150° C. The S-Bond metal alloy solder is suitable for joining ceramic and metal surfaces without flux or plating and the process is much more tolerant of joint variations due to the high surface tension of the S-Bond metal alloy solder. The S-Bond metal alloy solder joining process does not use chemical fluxes that must be cleaned up or could etch metallic components, leaving cosmetic defects.

In one aspect, the present disclosure provides a process of acoustic coupling of ceramic piezoelectric elements (e.g., PZT) to a metal (e.g., titanium/titanium alloy) ultrasonic waveguide for use in a D31 configuration. The process further includes making electrical connections to both sides of both piezoelectric elements in the D31 acoustic train configuration. Generally, the process includes soldering ceramic piezoelectric elements to a metal ultrasonic waveguide prior to poling the piezoelectric elements and then poling the assembly. Techniques for bonding ceramic to metal are described above in connection with FIGS. 99-102. In one aspect, the process includes securing ceramic piezoelectric elements (e.g., PZT) to a metal (e.g., titanium/titanium alloy) ultrasonic waveguide via solder paste, reflowing the solder paste to bond the piezoelectric elements to the ultrasonic waveguide, and poling the piezoelectric elements as part of the ultrasonic waveguide/piezoelectric elements assembly. One aspect of this process is described hereinbelow in connection with FIGS. 103A-103C.

Figure 103A:
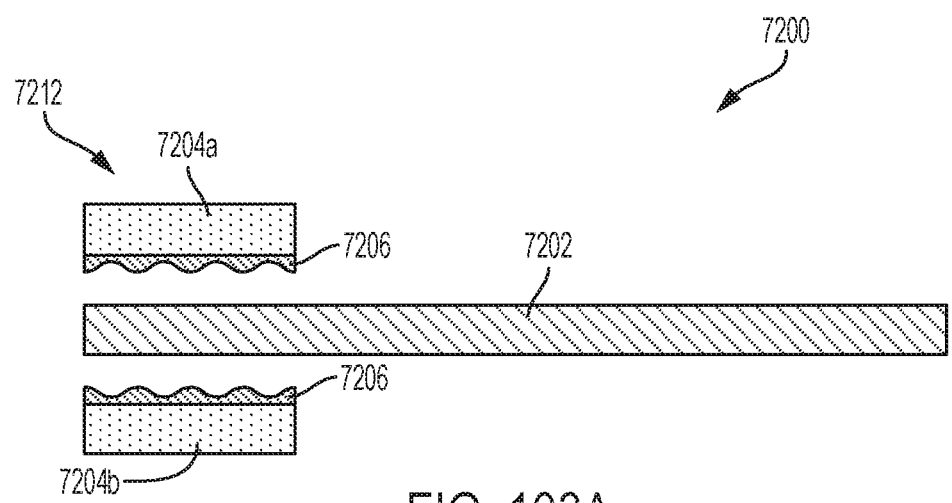
FIG. 103A illustrates an ultrasonic surgical instrument prior to assembly and poling, according to one aspect of this disclosure.
Figure 103B:
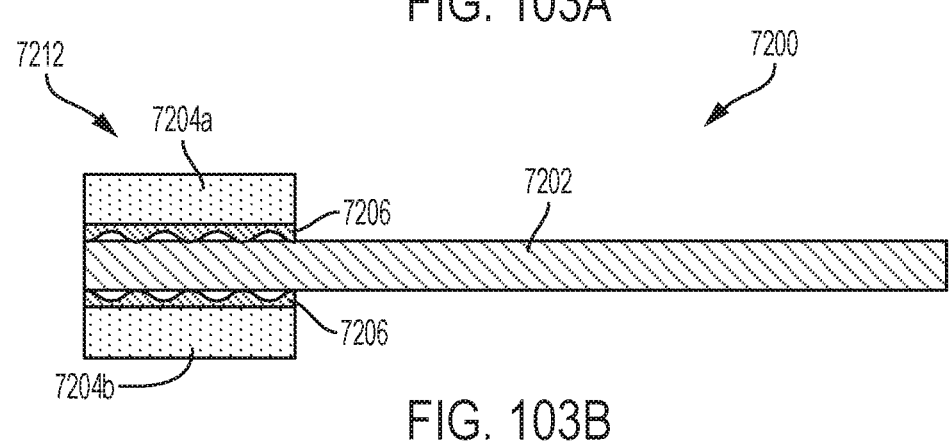
FIG. 103B illustrates the ultrasonic surgical instrument of FIG. 103A prior to poling and the first and second unpoled piezoelectric elements secured to the ultrasonic waveguide in a D31 configuration, according to one aspect of this disclosure.
Figure 103C:
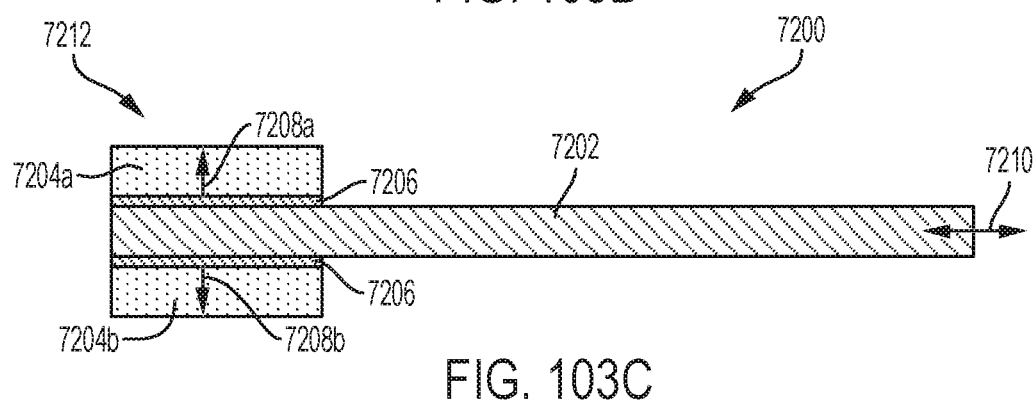
FIG. 103C illustrates the ultrasonic instrument of FIG. 103B prior to poling and the first and second unpoled piezoelectric elements secured to the ultrasonic waveguide in a D31 configuration, according to one aspect of this disclosure.

FIGS. 103A-103C illustrate an ultrasonic surgical instrument 7200 that includes an ultrasonic waveguide 7202 attached to an ultrasonic transducer 7212 by a bonding material, where the ultrasonic surgical instrument 7100 is configured to operate in a D31 mode. The ultrasonic transducer 7212 includes first and second unpoled piezoelectric elements 7204a, 7204b attached to opposite sides of the ultrasonic waveguide 7202 by a bonding material. FIG. 103A illustrates an ultrasonic surgical instrument 7200 prior to assembly and poling, according to one aspect of this disclosure. The ultrasonic surgical instrument 7200 includes a metal ultrasonic waveguide 7202 (e.g., titanium/titanium alloy). A bonding material such as solder paste 7206 is applied to one surface of a first unpoled piezoelectric element 7204a and a second unpoled piezoelectric element 7204b. The solder paste 7206 is a sticky mixture of flux and tiny solder particles, and may be applied to piezoelectric elements 7204a, 7204b with a stainless steel or nickel stencil using a screen printing process. The solder paste 7206 also can be applied to the piezoelectric elements 7204a, 7204b by a jet-printing mechanism, similar to an inkjet printer. After pasting, the piezoelectric elements 7204a, 7204b proceed to a pick-and-place machine or a manual placing process for securing the piezoelectric elements 7204a, 7204b to the ultrasonic waveguide 7202.

FIG. 103B illustrates the ultrasonic surgical instrument 7200 of FIG. 103A prior to poling with the first and second unpoled piezoelectric elements 7204a, 7204b secured to the ultrasonic waveguide 7202 in a D31 configuration, according to one aspect of this disclosure. After pasting, the piezoelectric elements 7204a, 7204b are secured to the ultrasonic waveguide 7202 using an automated or manual process. An insulating clamp may be employed to secure the first and second unpoled piezoelectric elements 7204a, 7204b prior to conveying the secured piezoelectric elements 7204a, 7204b and ultrasonic waveguide 7202 assembly to a reflow soldering oven. Once in the oven, the solder paste 7206 is reflowed to bond the first and second unpoled piezoelectric elements 7204a, 7204b to the ultrasonic waveguide 7202.

FIG. 103C illustrates the ultrasonic instrument 7200 of FIG. 103B after reflow soldering and prior to poling the first and second unpoled piezoelectric elements 7204a, 7204b attached to the ultrasonic waveguide 7202 in a D31 configuration, according to one aspect of this disclosure. Once the secured piezoelectric elements 7204a, 7204b and ultrasonic waveguide 7202 assembly is conveyed to a reflow soldering oven, the solder paste 7206 is reflowed to establish a bond between the first and second unpoled piezoelectric elements 7204a, 7204b and the ultrasonic waveguide 7202. The solder paste 7206 may be reflowed using standard surface mount technology. There are a number of techniques for reflowing the solder 7206. One technique employs infrared lamps and is called infrared reflow. Another technique employs hot gas convection using either standard air or nitrogen gas. Another surface mount technology employs special fluorocarbon liquids with high boiling points which use a method called vapor phase reflow. Each method has its advantages and disadvantages.

After the first and second unpoled piezoelectric elements 7204a, 7204b are attached to the ultrasonic waveguide 7202 using a reflow solder technique, the entire ultrasonic instrument 7200 assembly is poled. A poling process may be carried out in an oil bath with special fixturing. The nature of the piezoelectric effect is closely related to the occurrence of electric dipole moments in solids. The latter may be induced for ions on crystal lattice sites with asymmetric charge surroundings as in piezoelectric elements. The dipole density or polarization (dimensionality $C \cdot m/m^3$) may be calculated for crystals by summing up the dipole moments per volume of the crystallographic unit cell. As every dipole is a vector, the dipole density P is a vector field. Dipoles near each other tend to be aligned in regions called Weiss domains. The domains are usually randomly oriented, but can be aligned using the process of poling (not the same as magnetic poling), a process by which a strong electric field is applied across the material, usually at elevated temperatures. Not all piezoelectric materials can be poled. The poling axis (P) of the piezoelectric elements 7204a, 7204b is indicated by the direction arrows 7208a, 7208b, respectively. The motion axis of the ultrasonic waveguide 7202 in response to excitation of the piezoelectric elements 7204a, 7204b is shown by the motion arrow 7210 at the distal end of the ultrasonic waveguide 7202 generally referred to as the ultrasonic blade portion of the ultrasonic waveguide 7202. The motion axis 7210 is orthogonal to the poling axis (P) 7208a, 7208b.

The piezoelectric effect is the change of polarization P under the application of a mechanical stress. This might either be caused by a reconfiguration of the dipole-inducing surrounding or by re-orientation of molecular dipole moments under the influence of the external stress. Piezoelectricity may manifest in a variation of the polarization strength, its direction or both, with the details depending on: the orientation of P within the crystal; crystal symmetry; and the applied mechanical stress. The change in P appears as a variation of surface charge density upon the crystal faces, i.e., as a variation of the electric field extending between the faces caused by a change in dipole density in the bulk. For example, a 1 $cm^3$ cube of quartz with 2 kN (500 lbf) of correctly applied force can produce a voltage of 12500 V.

Figure 104A:
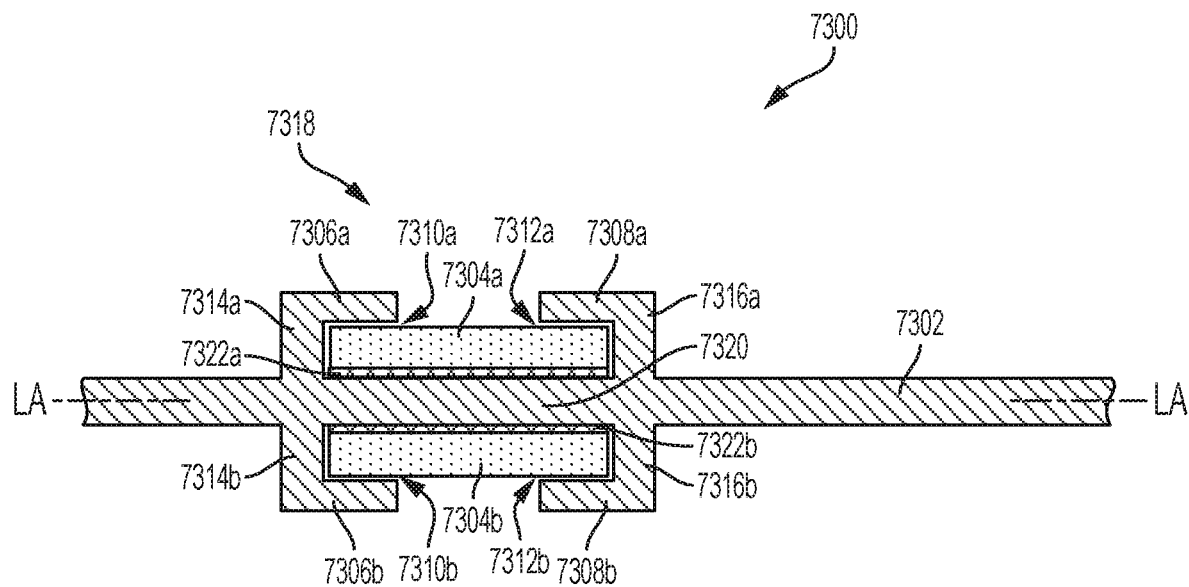
FIG. 104A illustrates an ultrasonic surgical instrument that includes an ultrasonic waveguide configured to hold piezoelectric elements using a bonding material, according to one aspect of this disclosure.

Another technique for acoustic coupling ceramic piezoelectric elements (e.g., PZT) to a metal ultrasonic waveguide (e.g., titanium/titanium alloy) for use in a D31 configuration is described hereinbelow in connection with FIGS. 104A-104O. FIG. 104A illustrates an ultrasonic surgical instrument 7300 that includes an ultrasonic transducer 7318 attached to an ultrasonic waveguide 7302 by a bonding material, where the ultrasonic surgical instrument 7300 is configured to operate in a D31 mode. As shown in FIG. 104A, the ultrasonic surgical instrument 7300 includes an ultrasonic waveguide 7302 configured to hold piezoelectric elements 7304a, 7304b, according to one aspect of this disclosure. The ultrasonic waveguide 7302 includes geometric features to hold the piezoelectric elements 7304a, 7304b. The ultrasonic waveguide 7302 includes a base portion 7320 and a first set of walls 7314a, 7316a extending from one side of the base portion 7320 substantially perpendicular to the longitudinal axis LA. A second set of walls 7314b, 7316b extend from an opposite side of the base portion 7320 substantially perpendicular to the longitudinal axis LA. Ledges 7306a, 7308a project from corresponding walls 7314a, 7316a along the longitudinal axis LA. Ledges 7306b, 7308b project from corresponding walls 7314b, 7316b along the longitudinal axis LA. The ledges 7306a, 7306b, 7308a, 7308b extend over a base portion 7320 of the ultrasonic waveguide 7302 and are substantially parallel to the base portion 7320. In one aspect, the first set of ledges 7306a, 7306b and one side of the base portion 7320 define spaces 7310a, 7310b to receive one end of the piezoelectric elements 7304a, 7304b. The second set of ledges 7308a, 7308b and an opposite side of the base portion 7320 define spaces 7312a, 7312b to receive the other end of the piezoelectric elements 7304a, 7304b.

The ultrasonic transducer 7318 includes first and second piezoelectric elements 7304a, 7304b attached to opposite sides of the base portion 7320 of the ultrasonic waveguide 7302 by a bonding material 7322a, 7322b such as a conductive epoxy, solder, or metal solder alloy. The first piezoelectric element 7304a is slidably received in the first set of spaces 7310a, 7312a. The second piezoelectric element 7304b is slidably received in the second set of spaces 7310b, 7312b.

Once the piezoelectric elements 7304a, 7304b are slidably received in the spaces 7310a, 7310b, 7312a, 7312b, the piezoelectric elements 7304a, 7304b may be attached to the base portion 7320 of the ultrasonic waveguide 7302 using a variety of bonding techniques and bonding materials described above in connection with FIGS. 99-102 or FIGS. 103A-103C.

Figure 104B:
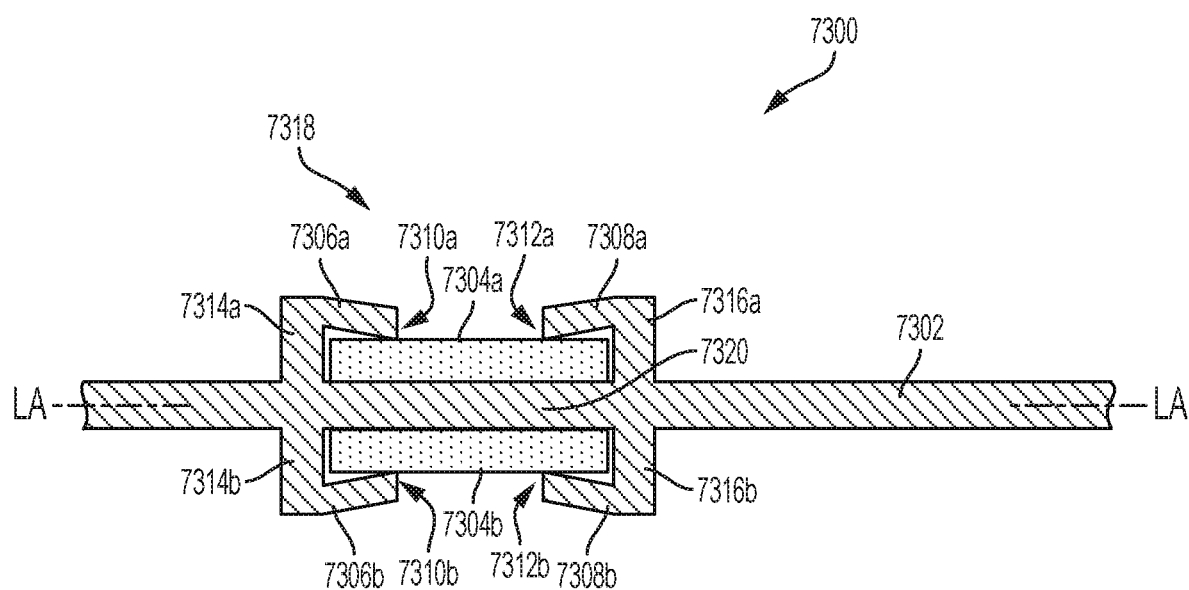
FIG. 104B illustrates an ultrasonic surgical instrument that includes an ultrasonic waveguide configured to hold piezoelectric elements using a biasing force, according to one aspect of this disclosure.

FIG. 104B illustrates an ultrasonic surgical instrument 7330 similar to the ultrasonic surgical instrument 7300 shown in FIG. 104A where the ledges 7306a, 7306b, 7308a, 7308b of the ultrasonic waveguide 7302 are biased, or bent slightly, towards the base portion 7320 of the ultrasonic waveguide 7302 to apply a holding force the piezoelectric elements 7304a, 7304b against the base portion 7320 of the ultrasonic waveguide 7302. The ledges 7306a, 7306b, 7308a, 7308b may be bent before or after the piezoelectric elements 7304a, 7304b are slidably inserted in the spaces 7310a, 7310b, 7312a, 7312b.

Figure 104C:
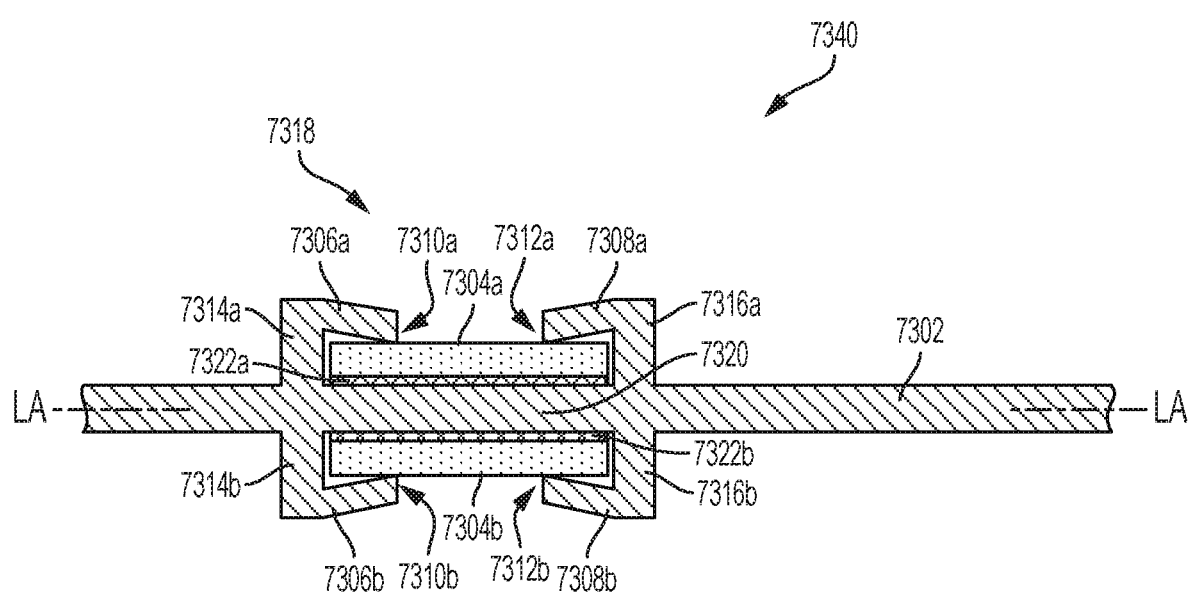
FIG. 104C illustrates an ultrasonic surgical instrument that includes an ultrasonic waveguide configured to hold piezoelectric elements using a combination of a bonding material and a biasing force, according to one aspect of this disclosure.

FIG. 104C illustrates an ultrasonic surgical instrument 7340 similar to the ultrasonic surgical instruments 7300, 7330 shown in FIGS. 104A and 104B, according to one aspect of this disclosure. As shown in FIG. 104C, the piezoelectric elements 7304a, 7304b can be attached to the ultrasonic waveguide 7302 by a combination of applying a bonding material described in connection with FIG. 104 and biasing the ledges 7306a, 7306b, 7308a, 7308b toward the base portion 7320 of the ultrasonic waveguide 7302 to apply a biasing force to the piezoelectric elements 7304a, 7304b as described in connection with FIG. 104B.

Figure 105:
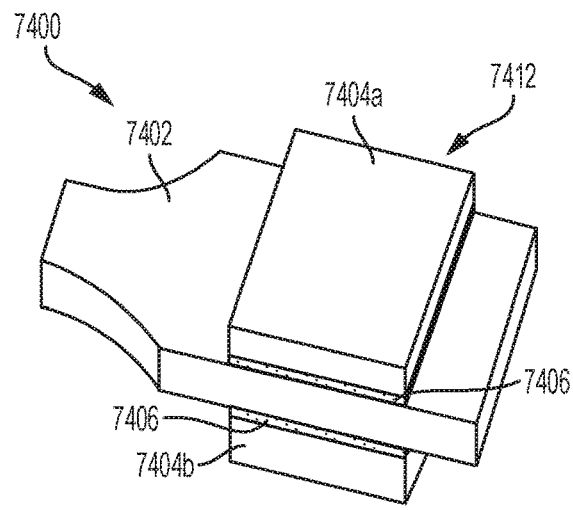
FIG. 105 illustrates an ultrasonic surgical instrument comprising an ultrasonic waveguide fixed to piezoelectric elements arranged in a D31, according to one aspect of this disclosure.
Figure 106:
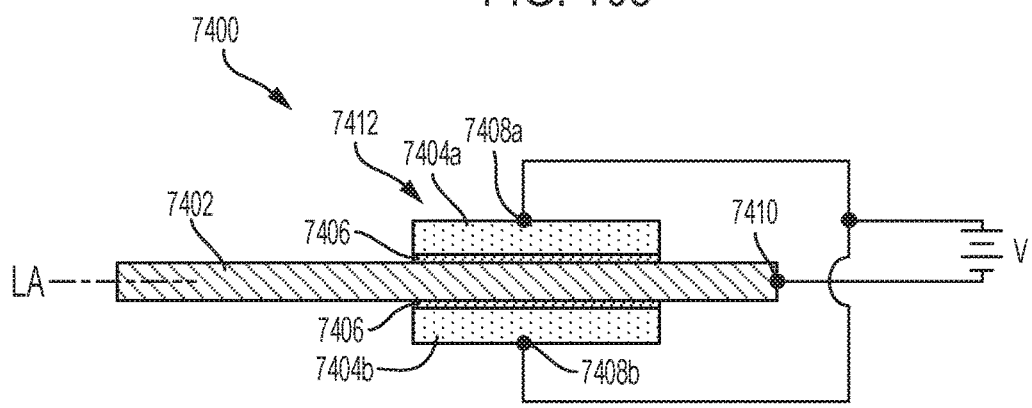
FIG. 106 illustrates the ultrasonic surgical instrument shown in FIG. 105 with a voltage V applied to the piezoelectric elements during a bonding phase, according to one aspect of this disclosure.

In a conventional D33 ultrasonic transducer architecture, the piezoelectric elements (e.g., PZT plates) of an ultrasonic transducer are assembled in a pre-compressed state to ensure that the piezoelectric elements do not operate in tension mode. In a D31 architecture configuration, however, it may be desired to have some pre-compression between each piezoelectric element and the ultrasonic waveguide. FIGS. 105 and 106 illustrate a technique for pre-compressing the piezoelectric elements during a bonding phase of the piezoelectric elements to the ultrasonic waveguide as discussed hereinbelow.

FIG. 105 illustrates an ultrasonic surgical instrument 7400 including an ultrasonic transducer 7412 attached to an ultrasonic waveguide 7402 by a bonding material, where the ultrasonic instrument is configure to operate in a D31 mode, according to one aspect of this disclosure. The ultrasonic transducer 7412 includes first and second piezoelectric elements 7404a, 7404b. FIG. 106 illustrates the ultrasonic surgical instrument 7400 shown in FIG. 105 with a voltage V applied to the piezoelectric elements 7404a, 7404b during a bonding phase, according to one aspect of this disclosure. As shown in FIG. 105, the piezoelectric elements 7404a, 7404b are attached to the ultrasonic waveguide 7402 using a bonding material such as an epoxy adhesive 7406 to bond the piezoelectric elements 7404a, 7404b to the ultrasonic waveguide 7402. In one aspect, pre-compression of the piezoelectric elements 7404a, 7404b may be achieved by applying a voltage to the piezoelectric elements 7404a, 7404b while the epoxy 7406 is curing.

With reference now to FIGS. 105 and 106, accordingly, in a D31 architecture configuration, pre-compression can be obtained between each piezoelectric element 7404a, 7404b and the ultrasonic waveguide 7402 by applying a voltage V to each piezoelectric element 7404a, 7404b during the epoxy 7406 curing process. A positive potential may be applied to electrical connections 7408a, 7408b formed on the free end of each piezoelectric element 7404a, 7404b and a ground potential may be applied to an electrical connection 7410 to the ultrasonic waveguide 7402, for example. As shown in FIG. 106, the voltage V is applied to contract the piezoelectric elements 7404a, 7404b in the direction of the longitudinal axis LA of vibration as described in connection with FIG. 2B, for example. The electrical connections between the ultrasonic waveguide 7402 and the fixed end of the piezoelectric elements 7404a, 7404b may be provided by a conductive epoxy 7406. The piezoelectric elements 7404a, 7404b may be attached to the ultrasonic waveguide 7402 using a variety of bonding materials such as the bonding materials described in connection with FIGS. 99-102 or FIGS. 103A-103O.

In other aspects, in a D31 ultrasonic transducer architecture configuration, the present disclosure provides a method for electrically connecting an energy source to the D31 electrical contacts on both sides of each piezoelectric elements (e.g., PZT plates). The ground connection can be to the ultrasonic waveguide if there is an electrical contact from the piezoelectric elements to the ultrasonic waveguide. In one aspect, the methods are carried out at low temperature to prevent or minimize damage occurs to the piezoelectric elements (<150° C.). The electrical connection may be employed as heat sink. These techniques are described below in connection with FIG. 107.

Figure 107:
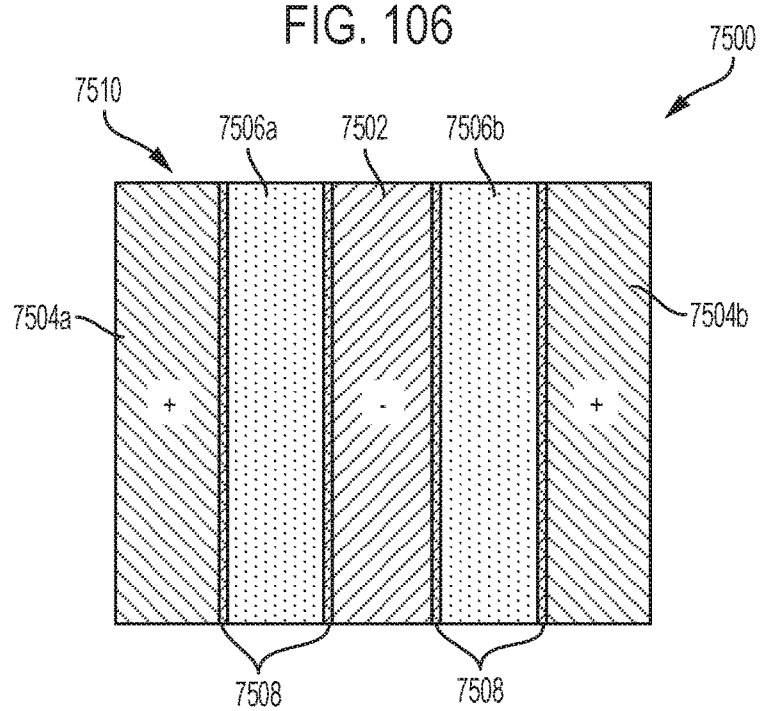
FIG. 107 illustrates a D31 ultrasonic surgical instrument that includes piezoelectric elements attached on one side to an ultrasonic waveguide by a conductive adhesive and attached on another side to electrically conductive plates by a conductive adhesive, according to one aspect of this disclosure.

FIG. 107 illustrates an ultrasonic surgical instrument 7500 including an ultrasonic transducer 7510 attached to an ultrasonic waveguide 7502, by a bonding material, where the ultrasonic surgical instrument 7500 is configured to operate in a D31 mode, according to one aspect of this disclosure. The ultrasonic transducer 7510 includes piezoelectric elements 7506a, 7506b attached on opposite sides of the ultrasonic waveguide 7502 by a bonding material. In one aspect, the bonding material is a conductive adhesive 7508. Conductive plates 7504a, 7504b are attached to the piezoelectric elements 7506a, 7506b, respectively, by a bonding material such as a conductive adhesive 7508, according to one aspect of this disclosure. An electrical connection method includes soldering the piezoelectric elements 7506a, 7506b on side directly to the inside surfaces of the electrically conductive plates 7504a, 7504b (e.g., copper plates or sheets) and on the other side to the ultrasonic waveguide 7502. A conductive epoxy 7508 is applied between the electrically conductive plates 7504a, 7504b and the free ends of the piezoelectric elements 7506a, 7506b. A conductive epoxy 7508 also is applied between the fixed ends of the piezoelectric elements 7506a, 7506b and the ultrasonic waveguide 7502. Electrically conductive elements such as wires may be connected to the electrically conductive plates 7504a, 7504b and to the ultrasonic waveguide 7502. In one aspect, the ultrasonic waveguide 7502 may be formed by stamping and electrical connection features may be added to the ultrasonic waveguide 7502. The electrically conductive plates 7504a, 7504b may be formed of copper sheets and assembled to female electrical connectors on a cable. Crimp connections may be stamped or formed on the ultrasonic waveguide 7502 and the electrically conductive plates 7504a, 7504b (e.g., copper sheets). The connections to wires may be crimped during assembly. In various aspects, the electrical connection process may include any combination of the above.

Figure 108:
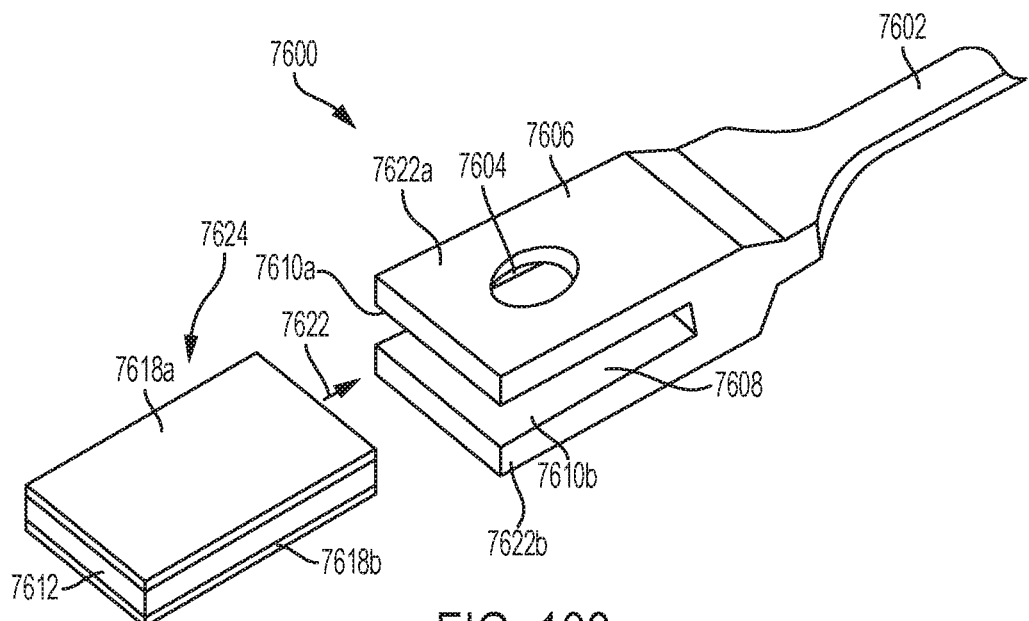
FIG. 108 illustrates an ultrasonic surgical instrument includes a single mid-plane ultrasonic transducer and an ultrasonic waveguide with a tuning-fork-like frame according to one aspect of the present disclosure.
Figure 109:
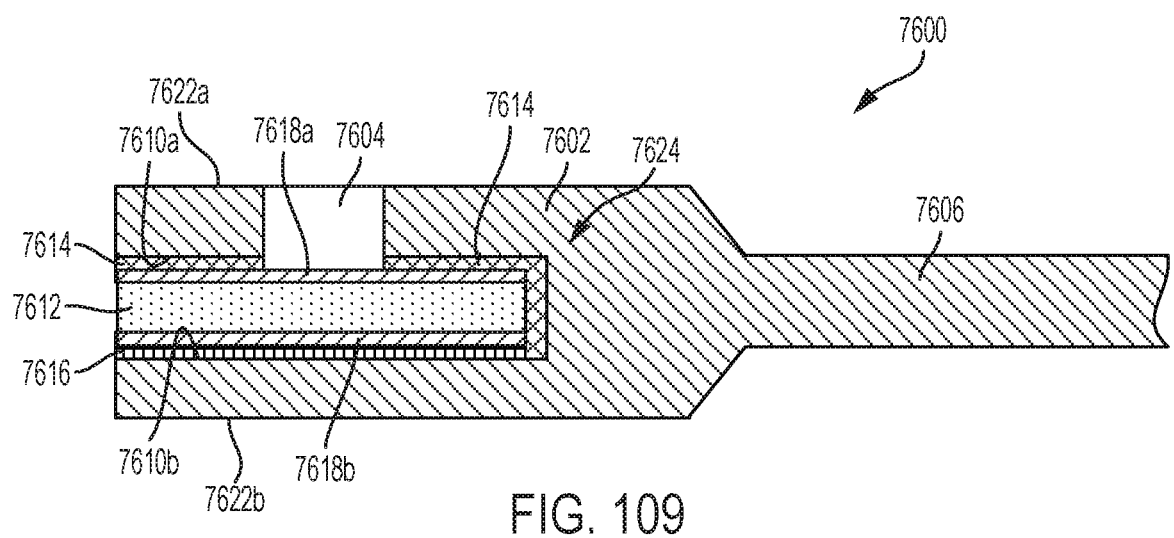
FIG. 109 is a sectional view of the ultrasonic surgical instrument shown in FIG. 108 with the ultrasonic transducer inserted in to the tuning-fork-like frame of the ultrasonic waveguide, according to one aspect of this disclosure.

FIGS. 108 and 109 illustrate an ultrasonic surgical instrument 7600 including an ultrasonic transducer 7624 attached to an ultrasonic waveguide 7602 by a bonding material, where the ultrasonic surgical instrument 7600 is configured to operate in a D31 mode. As shown in FIGS. 108 and 109 the ultrasonic surgical instrument 7600 includes a single mid-plane ultrasonic transducer 7624 acoustically coupled to an ultrasonic waveguide 7602 includes a tuning-fork-like frame 7606, according to one aspect of the present disclosure. The ultrasonic waveguide 7602 and the tuning-fork-like frame 7606 are made of metal such as titanium or titanium alloys as described throughout this disclosure. The tuning-fork-like frame 7606 includes an upper prong 7622a and a lower prong 7622b defining a U-shaped aperture 7608 therebetween to receive the ultrasonic transducer 7624 therein. In one aspect, the tuning-fork-like frame 7606 configuration constrains top and bottom sides of the ultrasonic transducer 7624 to couple more vibratory energy into the ultrasonic waveguide 7602. The single mid-plane ultrasonic transducer 7624 includes a single piezoelectric element 7612 (e.g., PZT) and electrically conductive plates 7618a, 7618b attached to top and bottom sides of the piezoelectric element 7612 by an electrically conductive bonding material such as a conductive epoxy, solder, or metal solder alloy, for example. The upper prong 7622a of the tuning-fork-like frame 7606 defines an aperture 7604 to provide access for an electrical connection to the top electrically conductive plate 7618a. The ultrasonic transducer 7624 is slidably inserted into the U-shaped aperture 7608 in the direction of arrow 7622 and then fixed therein as shown in FIG. 109.

FIG. 109 is a sectional view of the ultrasonic surgical instrument 7600 shown in FIG. 108 with the ultrasonic transducer 7624 inserted in to the U-shaped aperture 7608 defined by the tuning-fork-like frame 7606 of the ultrasonic waveguide 7602, according to one aspect of this disclosure. Prior to inserting the ultrasonic transducer 7624 into the U-shaped aperture 7608, a first bonding material such as an electrically insulative adhesive 7614 (e.g., electrically insulative conductive epoxy) is applied either to an internal surface 7610a of the upper prong 7622a of the tuning-fork-like frame 7606 or the upper electrically conductive plate 7618a, or both. The electrically insulative adhesive 7614 electrically isolates the tuning-fork-like frame 7606 and the ultrasonic waveguide 7602 from the upper electrically conductive element 7618a. Also, prior to inserting the ultrasonic transducer 7624 into the U-shaped aperture 7608, a second bonding material such as an electrically conductive adhesive 7616 (e.g., electrically conductive epoxy) is applied either to an internal surface 7610b of a lower prong 7622b the tuning-fork-like frame 7606 or the lower electrically conductive plate 7618b, or both. The electrically conductive adhesive 7616 electrically couples the lower electrically conductive plate 7618b to the tuning-fork-like frame 7606 and the ultrasonic waveguide 7602.

Once the ultrasonic transducer 7624 is inserted into the U-shaped aperture 7608, the electrically insulative adhesive 7614 and the electrically conductive adhesive 7616 are cured to bond the ultrasonic transducer 7624 to the tuning-fork-like frame 7606 of the ultrasonic waveguide 7602. One pole of an energy source (e.g., positive) is electrically connected to the upper electrically conductive plate 7618a through the aperture 7604. Another pole of the energy source (e.g., negative or ground) is electrically connected to the ultrasonic waveguide 7602 and the tuning-fork-like frame 7606 and to the lower electrically conductive plate 7618b through the electrically conductive adhesive 7616. In general, the positive pole of the energy source is connected to the upper electrically conductive plate 7618a and the negative pole of the energy source or ground is connected to the ultrasonic waveguide 7602 or tuning-fork-like frame 7606. Nevertheless, configurations where the negative or ground pole of the energy source is connected to the upper electrically conductive plate 7618a and the positive pole of the energy source is connected to the ultrasonic waveguide 7602 or tuning-fork-like frame 7606 are contemplated by this disclosure.

In one aspect, the present disclosure provides a D33 ultrasonic transducer configuration where the metal components are joined by a swaging process. D33 piezoelectric elements are located in a tuning-fork-like metal frame and compressed by a metal plug inserted in the proximal end of the frame. The metal plug is joined to the metal frame by a swaging process. Swaging is a forging process in which the dimensions of an item are altered using dies into which the item is forced. Swaging is usually a cold working process, but also may be hot worked. An assembly fixture applies a compressive force during the swaging process to leave a compressed stress in the stack. The compressive force can be measured by measuring the piezoelectric stack voltage. Another configuration includes a U-frame with an opening provided on a distal end of the U-frame. The piezoelectric stack compression is achieved by inserting the ultrasonic horn/waveguide (e.g., titanium or titanium alloy) into the opening and either swaging or threading the components while the piezoelectric stack is under compression. The frame can be made of a different material than the ultrasonic horn/waveguide, e.g., aluminum. These aspects are described hereinbelow in connection with FIGS. 110-112.

Figure 110A:
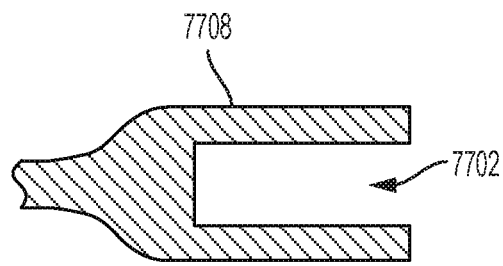
FIGS. 110A and 110B illustrate a D33 ultrasonic transducer configuration, according to one aspect of this disclosure.
Figure 110B:
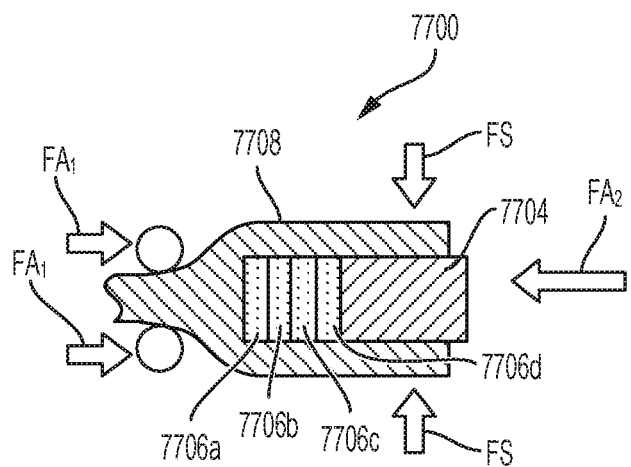

FIGS. 110A and 110B illustrate a D33 ultrasonic transducer 7700 configuration, according to one aspect of this disclosure. In FIG. 110A, a tuning fork-like metal frame 7708 defining a U-shaped aperture 7702 in a proximal end of the metal frame 7708 is provided. The tuning fork-like metal frame 7708 is made of a metal such as titanium or titanium alloy as described herein. As shown in FIG. 110B, a plurality of piezoelectric elements 7706a, 7706b, 7706c, 7706d are inserted into the U-shaped aperture 7702 to form a piezoelectric Langevin stack. A metal plug 7704 is inserted in the proximal end of the tuning fork-like metal frame 7708 until the plug 7704 contacts the piezoelectric stack. An assembly fixture applies compressive forces $FA_1$ from a distal end and a compressive force $FA_2$ from a proximal end to compress the stack of piezoelectric elements 7706a-7706d in the housing 7708. A swaging force FS is applied to the metal plug 7704 to join the metal plug 7704 with the tuning fork-like metal frame 7708 to maintain the piezoelectric elements 7706a-7706d stack under compression.

Figure 111:
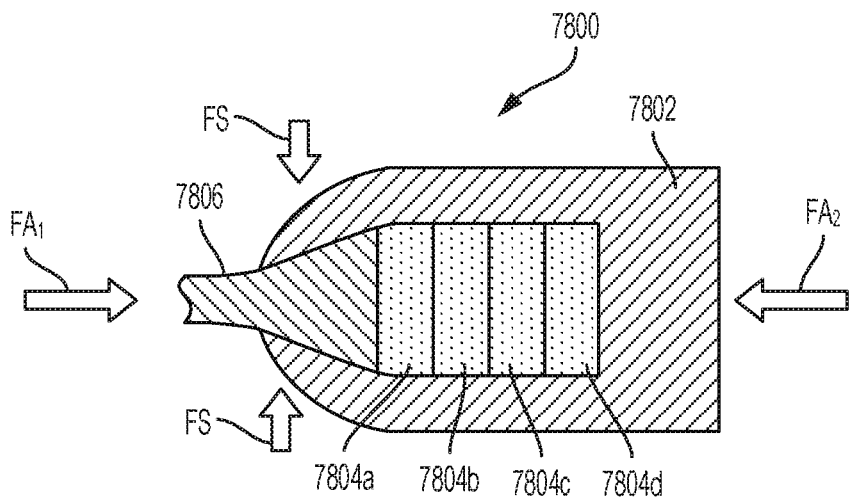
FIG. 111 illustrates a D33 ultrasonic transducer configuration, according to one aspect of this disclosure.

FIG. 111 illustrates a D33 ultrasonic transducer 7800 configuration, according to one aspect of this disclosure. The ultrasonic transducer 7800 includes a U-shaped metal housing 7802 defining an U-shaped aperture where a plurality of piezoelectric elements 7804a, 7804b, 7804c, 7804d are positioned to form a Langevin stack. An ultrasonic horn/waveguide 7806 is inserted in a distal end of the U-shaped metal housing 7802 until the plug 7806 contacts the piezoelectric elements 7804a-7804d stack. An assembly fixture applies compressive forces $FA_1$ from a distal end and a compressive force $FA_2$ from a proximal end to compress the piezoelectric elements 7804a-7804d in the metal housing 7802 (e.g., aluminum). A swaging force FS is applied to the ultrasonic horn/waveguide 7806 to join the ultrasonic horn/waveguide 7806 to the metal housing 7802 to maintain the piezoelectric elements 7804a-7804d stack under compression.

Figure 112:
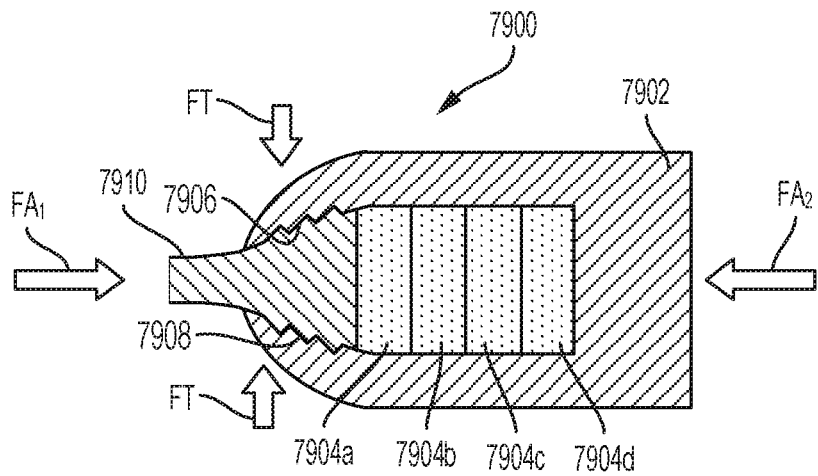
FIG. 112 illustrates a D33 ultrasonic transducer configuration, according to one aspect of this disclosure.

FIG. 112 illustrates a D33 ultrasonic transducer 7900 configuration, according to one aspect of this disclosure. The ultrasonic transducer 7900 includes a U-shaped metal housing 7902 defining a U-shaped aperture to receive a plurality of piezoelectric elements 7904a, 7904b, 7904c, 7904d in the form of a Langevin stack. The distal end of the U-shaped metal housing 7902 includes female threads 7906 and an ultrasonic horn/waveguide 7910 includes male threads 7908. The ultrasonic horn/waveguide 7910 is threadingly engaged to the U-shaped metal housing 7902. An assembly fixture applies compressive forces $FA_1$ from a distal end a compressive force $FA_2$ from a proximal end to compress the piezoelectric elements 7904a-7904d stack in the housing 7902. A threading FT is applied to the ultrasonic horn/waveguide 7910 to threadingly join the ultrasonic horn/waveguide 7910 to the housing 7902 while the piezoelectric elements 7904a-7904d stack is under compression.

Figure 113A:
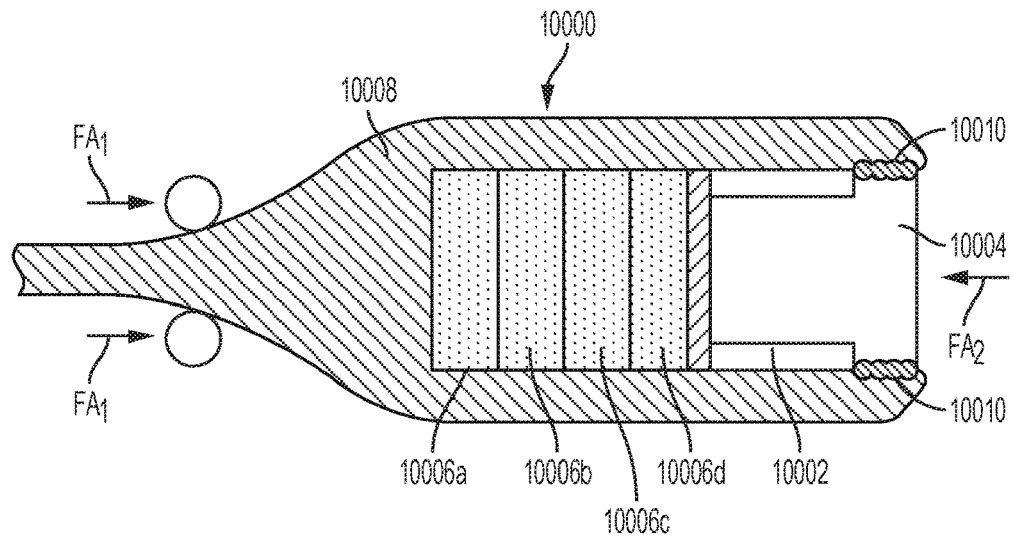
Figure 113B:
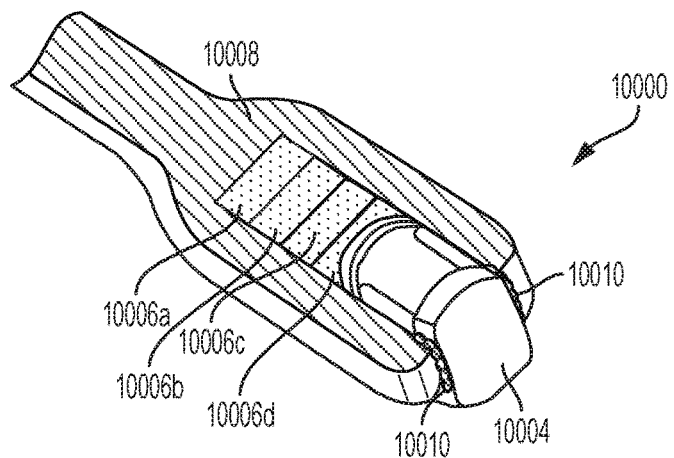
Figure 113C:
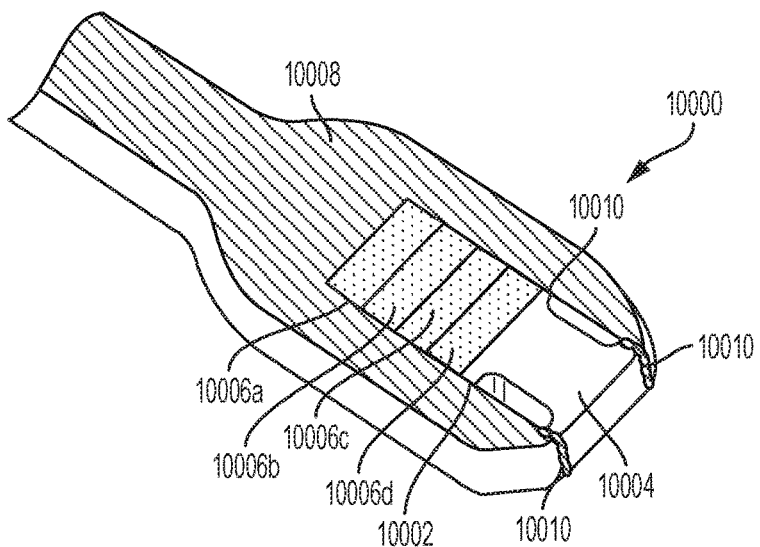
Figure 113D:
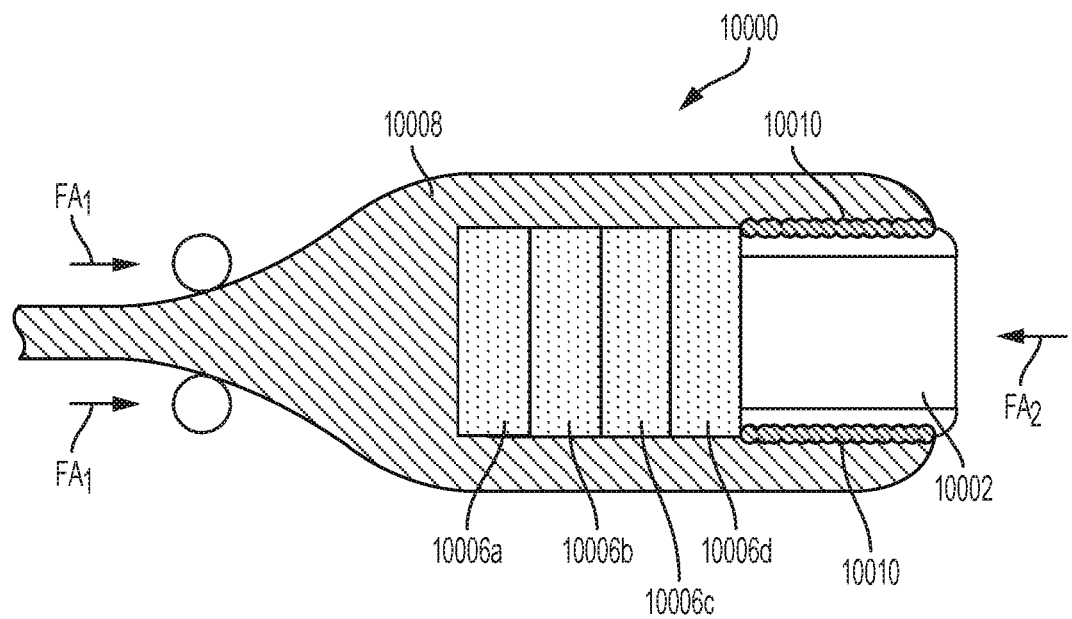

FIGS. 113A-D illustrates a D33 ultrasonic transducer 10000 configuration, according to one aspect of this disclosure. The ultrasonic transducer 10000 includes a U-shaped metal housing 10008 defining an aperture 10002 at the proximal end thereof that is configured to receive a plurality of piezoelectric elements 10006a-d in the form of a Langevin stack. A plug 10004 is inserted in the proximal end of the U-shaped metal housing 10008 until it contacts the stack of piezoelectric elements 10006a-d. The plug 10004 can have a T-shaped configuration as depicted in FIG. 113A, rounded edges as depicted in FIG. 113B, an I-shaped configuration as depicted in FIGS. 113B-C, a rectangular configuration as depicted in FIG. 113D, or any other such suitable configuration. An assembly fixture applies compressive forces $FA_1$ from a distal end and $FA_2$ from a proximal end to compress the piezoelectric elements 10006a-d stack in the housing 10008. Once a desired compressive force is achieved (measured by, e.g., the voltage of the stack of piezoelectric elements 10006a-d), a bond 10010 is applied at the interaction points between the plug 10004 and the housing 10008 while the piezoelectric elements 10006a-d stack is under compression. The assembly fixture can maintain the compressive forces $FA_1$, $FA_2$ until the bond 10010 is sufficiently strong to independently maintain the desired compressive force on the piezoelectric elements 10006a-d stack. The bond 10010 can include, e.g., an adhesive resin or complementary threading, such as is described above with respect to FIG. 112. The bond 10010 can also be achieved through fabrication processes, including, e.g., welding or brazing. If the process for establishing or fabricating the bond 10010 requires a temperature high enough to produce depoling in the piezoelectric elements 10006a-d, then the ultrasonic transducer 10000 can be poled or re-poled after assembly.

FIG. 114 illustrates a D33 ultrasonic transducer 10100 configuration, according to one aspect of this disclosure. The ultrasonic transducer 10100 includes a U-shaped metal housing 10108 defining an aperture at the distal end thereof that is configured to receive a plurality of piezoelectric elements 10106a-d in the form of a Langevin stack. The proximal end 10103 of the ultrasonic waveguide 10102, which defines a plug, is inserted in the distal end of the U-shaped metal housing 10108 until it contacts the stack of piezoelectric elements 10106a-d. An assembly fixture applies compressive forces $FA_1$ from a distal end and $FA_2$ from a proximal end to compress the piezoelectric elements 10106a-d stack in the housing 10108. Once a desired compressive force is achieved (measured by, e.g., the voltage of the stack of piezoelectric elements 10106a-d), a bond 10104 is applied at the interaction points between the ultrasonic waveguide 10102 and the housing 10108 while the piezoelectric elements 10006a-d stack is under compression. The assembly fixture can maintain the compressive forces $FA_1$, $FA_2$ until the bond 10104 is sufficiently strong to independently maintain the desired compressive force on the piezoelectric elements 10106a-d stack. The bond 10104 can include, e.g., an adhesive resin or complementary threading, such as is described above with respect to FIG. 112. The bond 10104 can also be achieved through fabrication processes, including, e.g., welding or brazing. If the process for establishing or fabricating the bond 10104 requires a temperature high enough to produce depoling in the piezoelectric elements 10106a-d, then the ultrasonic transducer 10100 can be poled or re-poled after assembly. The ultrasonic waveguide 10102 can be constructed from the same metal material as the housing 10108 or a different metal material, e.g., aluminum.

FIGS. 115A-C illustrate a D31 ultrasonic transducer 10200 configuration, according to one aspect of this disclosure. The ultrasonic transducer 10200 includes a housing 10202 constructed from a shape-memory alloy, a transducer base plate 10208 (e.g., transducer mounting portion) disposed within the interior of the housing 10202, and an ultrasonic waveguide 10206 extending through a proximal aperture 10210 of the housing 10202. The transducer base plate 10208 comprises flat faces on opposite sides to receive piezoelectric elements. The shape-memory alloy from which the housing 10202 is constructed can include, e.g., CuAlTi and NiTi alloys. In various aspects, the shape-memory alloy of the housing 10202 has a default shape 10212 (i.e., a shape to which the housing 10202 returns when heated) that is smaller than the working shape of the housing 10202 (i.e., the shape at which the housing 10202 is utilized to begin assembly of the ultrasonic transducer 10200), as depicted in FIG. 115C. In one aspect, the default shape 10212 of the housing 10202 is smaller both axially and radially from the working shape of the housing 10202. In alternative aspects, the default shape 10212 can be smaller in any number of dimensions as compared to the working shape of the housing 10202. The dimensions of the default shape 10212 are calculated to correspond to the final desired dimensions of the ultrasonic transducer 10200 wherein all of the components of the ultrasonic transducer 10200 are operably coupled. The housing 10202 can have a variety of shapes such as, e.g., a cylindrical shape.

The housing 10202 includes a plurality of slots 10204a, 10204b that are configured to receive piezoelectric elements therethrough. In the depicted aspect, the slots 10204a, 10204b are arranged longitudinally on the housing 10202 and each slot 10204a, 10204b extends along one side of the transducer base plate 10208 within the housing 10202. A piezoelectric element can be inserted through each of the slots 10204a, 10204b such that each piezoelectric element is positioned on an opposing side of the transducer base plate in a D31 configuration. In alternative aspects, the slots can vary in number and orientation so that the piezoelectric elements can be placed in alternative configurations within the housing 10202, such as a D33 configuration. Once the piezoelectric elements are situated within the slots 10204a, 10204b, the ultrasonic transducer 10200 is heated to a temperature that causes the shape-memory alloy of the housing 10202 to return to the default shape 10212, as depicted in FIG. 115C. As the housing 10202 returns to its default shape 10212, it exerts an axial compression force $F_A$ and a radial compression force $F_R$ on the components therein. One effect of the compressive forces $F_A$, $F_R$ is that the piezoelectric elements are brought securely into contact with the transducer base plate 10208 and held in place in a D31 configuration. The piezoelectric elements can thereafter be electrically excited to induce ultrasonic vibrations, as described above. A second effect is that the compressive forces $F_A$, $F_R$ join the ultrasonic waveguide 10206 to the transducer base plate 10208 and securely hold these components in place such that ultrasonic vibrations can be transmitted through the transducer base plate 10208 to the ultrasonic waveguide 10206. Once assembled, this aspect of the D31 ultrasonic transducer 10200 can be utilized in association with, e.g., a surgical instrument. If the process for heating the shape-memory alloy of the housing 10202 requires a temperature high enough to produce depoling in the piezoelectric elements, then the ultrasonic transducer 10200 can be poled or re-poled after assembly.

FIGS. 116A-C illustrate a D33 ultrasonic transducer 10300 configuration, according to one aspect of this disclosure. The ultrasonic transducer 10300 includes a U-shaped metal housing 10308 defining an aperture 10302 at the proximal end thereof that is configured to receive a plurality of piezoelectric elements 10306a-d in the form of a Langevin stack. A plug 10304a is inserted in the proximal end of the U-shaped metal housing 10308 until it contacts the stack of piezoelectric elements 10306a-d. As the plug 10304a is inserted into the housing 10308, threading 10312 disposed on the plug 10304a engages complementary threading 10310 disposed on the interior surface of the housing 10308, allowing the plug 10304a to be securely tightened against the stack of piezoelectric elements 10306a-d to exert a compressive force thereagainst. Once a desired compressive force is achieved (measured by, e.g., the voltage of the stack of piezoelectric elements 10306a-d), tightening of the plug 10304a can be ceased. Once tightened, the engaged threading 10310, 10312 will maintain the plug 10304a in position. The piezoelectric elements 10306a-d can either be poled prior to assembly of the ultrasonic transducer 10300, or the ultrasonic transducer 10300 can be poled or re-poled after assembly.

FIG. 116D illustrates a D33 ultrasonic transducer 10300 configuration, according to one aspect of this disclosure. In this aspect, the plug 10304b includes threading 10316 that engages with complementary threading 10318 of a nut 10314. When the nut 10314 is threadably engaged with the plug 10304b, tightening the nut 10304b causes the plug 10304b to be driven into the interior of the housing 10308 and contact the stack of piezoelectric elements 10306a-d, exerting a compressive force thereagainst, as described above. In the depicted aspect, the plug 10304b lacks threading that engages with internal threading of the housing 10308. In an alternative aspect, the ultrasonic transducer 10300 can include a combination of the nut 10314 that threadably engages the plug 10304b and the plug threading 10312 that engages with internal threading 13310 of the housing 10308, as described above with respect to FIGS. 116A-C.

FIG. 116E illustrates a D33 ultrasonic transducer configuration, according to one aspect of this disclosure. In this aspect, the ultrasonic transducer 10300 includes one or more fasteners 10322a, 10322b that are configured to extend through the housing 10308 and engage the plug 10304c in order to maintain the plug 10304c in position. The fasteners 10322a, 10322b can include, e.g., screws that are configured to threadably engage the plug 10304c. The fasteners 10322a, 10322b can be configured to, e.g., extend longitudinally through from the distal end of the housing 10308 to the proximal end to engage the plug 10304c. When the fasteners 10322a, 10322b are engaged with the plug 10304c, tightening the fasteners 10322a, 10322b causes the plug 10304c to contact the stack of piezoelectric elements 10306a-d and exert a compressive force thereagainst, as described above. In the depicted aspect, the plug 10304c lacks threading that engages with internal threading of the housing 10308. In an alternative aspect, the ultrasonic transducer 10300 can include a combination of the fasteners 10322a, 10322b engaging the plug 10304c and the plug threading 10312 that engages with internal threading 13310 of the housing 10308, as described above with respect to FIGS. 116A-C.

FIGS. 117A-D illustrate a D33 ultrasonic transducer configuration and an assembly process thereof, according to one aspect of this disclosure. The ultrasonic transducer 10400 includes a U-shaped metal housing 10408 defining an aperture 10402 at the proximal end thereof that is configured to receive a plurality of piezoelectric elements 10406a-d in the form of a Langevin stack. The housing 10408 further includes a channel 10410 extending longitudinally along each of the opposing surfaces defining the aperture 10402. A plug 10404 includes a pair of tabs 10412a, 10412b that are configured to slidably engage the channels 10410 extending along the opposing interior sides of the housing 10408. As depicted in FIG. 117A, the plug 10404 is inserted in the proximal end of the U-shaped metal housing 10408, along the channels 10410, until it contacts the stack of piezoelectric elements 10406a-d. As depicted in FIG. 117C, an assembly fixture then applies a compressive force $F_1$ to the plug 10404 to compress the piezoelectric elements 10406a-d stack in the housing 10008. Once a desired compressive force is achieved (measured by, e.g., the voltage of the stack of piezoelectric elements 10406a-d), a second compressive force $F_2$ is applied to the housing 10408 while the piezoelectric elements 10406a-d stack is under compression, as depicted in FIG. 117D. The compressive force $F_2$ deforms the channels 10410 (and the tabs 10412a, 10412b situated therein), locking the plug 10404 in place. The compressive force $F_2$ can be applied by, e.g., a punch press. The piezoelectric elements 10406a-d can either be poled prior to assembly of the ultrasonic transducer 10400, or the ultrasonic transducer 10400 can be poled or re-poled after assembly.

FIG. 118 illustrates a D31 ultrasonic transducer 10500 configuration, according to one aspect of this disclosure. The ultrasonic transducer 10500 includes a U-shaped metal housing 10508 defining an aperture 10502 at the proximal end thereof that is configured to receive a transducer base plate 10504 (e.g., a transducer mounting portion) that comprises flat faces on opposite sides to receive the piezoelectric elements 10506a-b. The piezoelectric elements 10506a-b can be affixed on the transducer base plate 10504 via, e.g., epoxy layer 10518a-b. The transducer base plate 10504 has a generally T-shaped configuration, including a longitudinal or axial portion 10512 that terminates at a distal end 10514 and a transverse portion 10510 attached to a proximal end of the axial portion 10512. In one aspect, the piezoelectric elements 10506a-b and the axial portion 10512 are dimensioned such that they form a press or interference fit with the interior surface(s) 10524 defining the aperture 10502 when the transducer base plate 10504 is inserted into the aperture 10502. The interference fit compresses the piezoelectric elements 10506a-b in an axial and/or radial direction. This pre-compression of the piezoelectric elements 10506a-b improves the performance of the ultrasonic transducer 10500. The housing 10508 further includes a slot 10516 that is configured to receive the distal end 10514 of the transducer base plate 10504. In one aspect, the distal end 10514 and the slot 10516 are configured to engage in a press or interference fit. In another aspect, the distal end 10514 is bonded to the slot 10516 via an adhesive resin, fasteners, welding, brazing, a physical deformation joint, or another such securement method. When the transducer base plate 10504 is secured to the housing 10508 in the described manner, ultrasonic vibrations generated by the piezoelectric elements 10506a-b are transmitted through the transducer base plate 10504 to the ultrasonic waveguide. The transverse portion 10510 of the transducer base plate 10504 is configured to seal or plug the aperture 10502. In one aspect, one or more surfaces 10520a-b of the transverse portion 10510 are fixed to the opposing surfaces 10522a-b of the housing 10508 via an adhesive resin, fasteners, welding, brazing, a physical deformation joint, or another such securement method. The piezoelectric elements 10506a-b can either be poled prior to assembly of the ultrasonic transducer 10500, or the ultrasonic transducer 10500 can be poled or re-poled after assembly.

FIG. 119 illustrates a D31 ultrasonic transducer 10600 configuration, according to one aspect of this disclosure. The ultrasonic transducer 10600 includes a metal housing 10608 defining one or more recesses 10602 that are each configured to receive a piezoelectric element 10606a-b therein. The dimensions of the recesses 10602 are equal to a close tolerance to the dimensions of the piezoelectric elements 10606a-b, such that the recesses 10602 hold the piezoelectric elements 10606a-b fixed in place when the piezoelectric elements 10606a-b are inserted therein. In the depicted aspect, the metal housing 10608 includes a first recess 10602 and a second recess (not shown) disposed on an opposing side from the first recess 10602. Each recess 10602 includes a plurality of 10610 cavities disposed along the sides thereof. Each cavity 10610 is sized and shaped to securely receive a corresponding tab 10604 disposed along the edges of the piezoelectric elements 10606a-b. The housing 10608 with the recesses 10602 can be fabricated via, e.g., metal injection molding.

As the dimensions of the recesses 10602 are substantially equal to the dimensions of the piezoelectric elements 10606a-b and the tabs 10604 extend beyond the perimeter of the piezoelectric elements 10606a-b, the piezoelectric elements 10606a-b cannot be inserted into the recesses 10602 under standard conditions. In one aspect of assembling the ultrasonic transducer 10600, the housing 10608 is heated to a temperature that causes the material from which the housing 10608 is constructed to expand and/or be rendered malleable. After the housing 10608 is heated to the appropriate temperature, the piezoelectric elements 10606a-b are then inserted into the recesses 10602 so that the tabs 10604 each engage a corresponding cavity 10610. The assembled ultrasonic transducer 10600 is then cooled. In some aspects, the ultrasonic transducer 10600 is additionally compressed as it cools. As the ultrasonic transducer 10600 cools (and optionally undergoes external compression), the recesses 10602 compress around the piezoelectric elements 10606*a-b* therein, causing the tabs 10604 to become secured within the cavities 10610 and thereby fixing the piezoelectric elements 10606*a-b* in place. In aspects wherein the housing 10608 is fabricated utilizing metal injection molding, the piezoelectric elements 10606*a-b* can be inserted into the recesses 10602 prior to the housing 10608 being sintered because the housing 10608 shrinks during the sintering process.

Alternatively, the piezoelectric elements 10606*a-b* can be inserted into the recesses 10602 after the housing 10608 has been sintered, but prior to the hot isostatic press step in the metal injection molding process as the housing 10608 shrinks during the hot isostatic press step as well. In an alternative aspect, the piezoelectric elements 10606*a-b*, rather than the housing 10608, is heated to a temperature that renders the piezoelectric elements 10606*a-b* able to be inserted into the recesses 10602. Once the heated piezoelectric elements 10606*a-b* are placed within the recesses 10602, the ultrasonic transducer 10600 is then cooled as described above, with or without external compression. If the process for heating the ultrasonic transducer 10600 requires a temperature high enough to produce depoling in the piezoelectric elements 10606*a-b*, then the ultrasonic transducer 10600 can be poled or re-poled after assembly.

FIGS. 120A-B illustrate a D31 ultrasonic transducer 10700 configuration, according to one aspect of this disclosure. The ultrasonic transducer 10700 includes a metal housing 10708 defining one or more apertures 10702 extending therethrough. In one aspect, the aperture 10702 is extruded through-holes extending across the housing 10708. The aperture 10702 is configured to receive a piezoelectric element 10706 therein. In the depicted aspect, the ultrasonic transducer 10700 comprises a single aperture 10702; however, the ultrasonic transducer 10700 can include any number of apertures 10702 and corresponding piezoelectric elements 10706. The dimensions of the aperture 10702 are equal to a close tolerance to the dimensions of the piezoelectric element 10706, such that the aperture 10702 holds the piezoelectric element 10706 fixed in place when the piezoelectric elements 10706 when inserted therein. The housing 10708 with the aperture(s) 10702 can be fabricated via, e.g., metal injection molding.

In one aspect of assembly the ultrasonic transducer 10700, the housing 10708 is heated to a temperature that causes the material from which the housing 10708 is constructed to expand and/or be rendered malleable. After the housing 10708 is heated to the appropriate temperature, the piezoelectric element 10706 is then inserted into the aperture 10702. The assembled ultrasonic transducer 10700 is then cooled. In some aspects, the ultrasonic transducer 10700 is additionally compressed as it cools. As the ultrasonic transducer 10700 cools (and optionally undergoes external compression), the recesses 10702 compress around the piezoelectric element 10706 therein, fixing the piezoelectric element 10706 in place due to frictional engagements between the surface of the piezoelectric element 10706 and the surface of the aperture 1702. In aspects wherein the housing 10708 is fabricated utilizing metal injection molding, the piezoelectric element 10706 can be inserted into the aperture 10702 prior to the housing 10708 being sintered because the housing 10708 shrinks during the sintering process. Alternatively, the piezoelectric element 10706 can be inserted into the aperture 10702 after the housing 10708 has been sintered, but prior to the hot isostatic press step in the metal injection molding process as the housing 10708 shrinks during the hot isostatic press step as well. In an alternative aspect, the piezoelectric element 10706, rather than the housing 10708, is heated to a temperature that renders the piezoelectric element 10706 able to be inserted into the aperture 10702. Once the heated piezoelectric element 10706 is placed within the aperture 10702, the process of assembling the ultrasonic transducer 10700 is the same as with the aforementioned aspect. If the process for heating the ultrasonic transducer 10700 requires a temperature high enough to produce depoling in the piezoelectric elements 10706, then the ultrasonic transducer 10700 can be poled or re-poled after assembly.

FIGS. 121A-D illustrate D31 ultrasonic transducer 10800 configurations, according to one aspect of this disclosure. The ultrasonic transducer 10800 includes a transducer base plate 10802, a plurality of piezoelectric elements 1806*a-b* bonded to opposing surfaces of the transducer base plate 10802 (e.g., a transducer mounting portion) in a D31 configuration, and a compression plate 10808*a-b* bonded to the exterior surface of each of the piezoelectric elements 1806*a-b*. The various components of the ultrasonic transducer 10800 can be bonded to each other by, e.g., an electrically conductive epoxy adhesive. In the aspect depicted in FIGS. 121A-B, the transducer base plate 10802, piezoelectric elements 1806*a-b*, and compression plates 10808*a-b* include a series of apertures that are configured to align with each other such that a fastener 10804 can be received therethrough when the components are secured together. The fastener 10804 includes, e.g., a screw having a complementary nut 10810. In an alternative aspect depicted in FIGS. 121C-D, only the compression plates 10808*a-b* include a series of apertures that are configured to align with each other such that fasteners 10804*a-b* can be received therethrough when the components are secured together. These fasteners 10804*a-b* can likewise include, e.g., screws having complementary nuts 10810*a-b*. Tightening the fastener(s) 10804 applies additional compressive force to the ultrasonic transducer 10800, which can improve the performance of the ultrasonic transducer 10800. In some aspects, the compression plates 10808*a-b* are constructed from a metal material, which can aid in heat dissipation of the ultrasonic transducer 10800.

FIG. 122 illustrates a D33 ultrasonic transducer 10900 configuration, according to one aspect of this disclosure. The ultrasonic transducer 10900 includes a metal housing 10908 defining an open interior 10902 that is configured to receive a plurality of piezoelectric elements 10906*a-d* in the form of a Langevin stack. The ultrasonic transducer 10900 further includes a threaded plug or threaded rod 10904 extending through a threaded aperture 10912 disposed at the proximal end of the housing 10908 into the housing interior 10902. As the threaded rod 10904 is tightened, the distal end 10910 thereof contacts the stack of the piezoelectric elements 10906*a-d* and applies a compressive force to compress the piezoelectric elements 10906*a-d* stack in the housing 10908. Once a desired compressive force is achieved, the threaded rod 10904 will be maintained in the particular tightened position due to its engagement with the threaded aperture 10912. The degree of compressive force applied by the threaded rod 10904 can be adjusted by loosening or tightening the threaded rod 10904 in order to tune the frequency of the stack of piezoelectric elements 10906*a-d*, without the need to disassemble the ultrasonic transducer 10900. In some aspects, the ultrasonic transducer 10900 can switch between operating frequencies according to the degree of applied compressive force on the stack of piezoelectric elements 10906a-d. When the ultrasonic transducer 10900 is utilized in conjunction with a surgical instrument, being able to switch between operating frequencies in the field can allow for the ultrasonic transducer 10900 to adjust to tissue effects encountered by the surgical instrument or to different end effector types.

FIGS. 123A-B illustrate D31 ultrasonic transducer 11000 configurations having multiple pairs of piezoelectric elements, according to one aspect of this disclosure. The ultrasonic transducer 11000 includes a first transducer array 11002a disposed on a first face of the transducer base plate 11008 (e.g., a transducer mounting portion) and a second transducer array 11002b disposed on a second face, which opposes the first face, of the transducer base plate 11008. In the aspect depicted in FIG. 123A, the transducer arrays 11002a-b are arranged in a D31 configuration. Each of the transducer arrays 11002a-b includes a first piezoelectric element 11006a and a second piezoelectric element 11006b arranged adjacently to each other. In the depicted aspect, the piezoelectric elements 11006a-b are arranged longitudinally with respect to the longitudinal axis of the transducer base plate 11008. In other aspects, the piezoelectric elements 11006a-b are arranged in other orientations, such as orthogonally, relative to the transducer base plate 10008. In some aspects, the piezoelectric elements 11006a-b of the opposing transducer arrays 11002a-b are arranged in matching pairs. In other words, each of the piezoelectric elements 11006a-b of the first transducer array 10002a is aligned with a corresponding piezoelectric element of the second transducer array 11002b. In the depicted aspect, the piezoelectric elements 11006a-b are rectangular in shape and the transducer array 11002a is square in shape.

In the aspect depicted in FIG. 123B, the transducer array 11002c includes a first piezoelectric element 11006c, a second piezoelectric element 11006d, a third piezoelectric element 11006e, and a fourth piezoelectric element 11006f arranged adjacently to each other. In one aspect, the piezoelectric elements 11006c-f are arranged symmetrically along both the x and y axes of the planar transducer array 11002c. In the depicted aspect, the piezoelectric elements 11006c-f are square in shape and the transducer array 11002c is likewise square in shape.

In various aspects, the transducer arrays 11002a-c depicted in FIGS. 123A-B can be utilized in combination with or in lieu of each other, or other arrays of piezoelectric elements. The piezoelectric elements 11006a-f in the segmented transducer arrays 11002a-c can each be driven individually, thereby allowing the transducer arrays 11002a-c to produce unbalanced vibrations. In previously discussed aspects where the piezoelectric elements on the opposing faces of the transducer base plate 11008 are balanced with respect to each other, non-longitudinal motion of the waveguide and/or end effector is undesired. However, segmented transducer arrays 11002a-c that can be selectively activated in an asymmetric or non-balanced manner can produce two desirable effects. First, if there is unwanted vibration or flexure in the surgical system, then the segmented transducer arrays 11002a-c can be selectively activated in order to counterbalance undesired lateral vibrations and return the system to producing stable, longitudinal motion. Second, in some cases lateral or torsional movement of the end effector is desired. Therefore in these cases, the segmented transducer arrays 11002a-c can be selectively activated in an asymmetric manner in order to induce the desired non-longitudinal movement at the end effector. The activation of the piezoelectric elements 11006a-f in the transducer arrays 11002a-c can be controlled, e.g., by controlling the amount of electrical current applied to the individual piezoelectric elements 11006a-f.

FIGS. 124A-C illustrate D31 ultrasonic transducer 11100, 11200, 11300 configurations having asymmetrically excitable piezoelectric transducer assemblies 11102, 11202, 11302, according to one aspect of this disclosure. As discussed above with respect to FIGS. 124A-B, it can be advantageous for ultrasonic transducers to be able to produce unbalanced or asymmetric vibrations in certain cases, such as for counteracting undesired non-longitudinal vibrations within the surgical system or to intentionally induce non-longitudinal movement at the end effector. In some aspects, asymmetry can be achieved by having the piezoelectric elements arranged asymmetrically relative to the longitudinal axis of the ultrasonic waveguide. In other aspects, asymmetry can be achieved by having the piezoelectric elements arranged symmetrically relative to the longitudinal axis of the ultrasonic waveguide, but selectively activatable in an asymmetric manner. In aspects where the ultrasonic transducers are capable of generating both symmetrical or asymmetrical vibrations depending upon the selective activation of the piezoelectric elements consisting the transducer array, the surgical systems incorporating the ultrasonic transducers can be configured to interchangeably switch between the symmetric and asymmetric activation modes by reversibly activating (i.e., electrically exciting) or deactivating the individual piezoelectric elements.

FIG. 124A illustrates a D31 ultrasonic transducer 11100 configuration including a transducer base plate 11108 (e.g., a transducer mounting portion) comprising flat faces on opposite sides to receive piezoelectric elements 11106a-c thereon. The piezoelectric elements 11106a-c are sized, shaped, and arranged asymmetrically about the longitudinal axis of the waveguide 11104. The first piezoelectric element 11106a and the third piezoelectric element 11106c are roughly triangular in shape and the second piezoelectric element 11106b is irregular in shape. In this aspect, the first piezoelectric element 11106a and the second piezoelectric element 11106b are configured to generate a symmetrical vibration about the longitudinal axis of the waveguide 11104. Likewise, the first piezoelectric element 11106a and the third piezoelectric element 11106c are configured to generate a symmetrical vibration about the longitudinal axis of the waveguide 11104. However, activation of all three piezoelectric elements 11106a-c or activation of the second piezoelectric element 11106b and the third piezoelectric element 11106c is configured to generate an asymmetrical vibration due to the sizes, shapes, and arrangements of the piezoelectric elements 11106a-c.

FIG. 124B illustrates a D31 ultrasonic transducer 11200 configuration including a transducer base plate 11208 (e.g., a transducer mounting portion) comprising flat faces on opposite sides to receive piezoelectric elements 11206a-c thereon. The piezoelectric elements 11206a-c are sized, shaped, and arranged symmetrically about the longitudinal axis of the waveguide 11204, but can be selectively activated to generate asymmetrical vibrations. Specifically, either activation of all three piezoelectric elements 11206a-c or activation of the first piezoelectric element 11206a and the third piezoelectric element 11206c are configured to generate symmetrical vibrations. Conversely, activation of the second piezoelectric element 11206b and one of the first piezoelectric element 11206a or the third piezoelectric element 11206c is configured to generate asymmetrical vibrations.

FIG. 124C illustrates a D31 ultrasonic transducer 11300 configuration including a transducer base plate 11308 (e.g., a transducer mounting portion) comprising flat faces on opposite sides to receive piezoelectric elements 11306a-c thereon. The piezoelectric elements 11306a-c are sized and shaped equivalently to each other, but are arranged asymmetrically about the longitudinal axis of the waveguide 11304. Activation of the first piezoelectric element 11306a and the second piezoelectric element 11306b is configured to generate symmetrical vibrations; however, activation of any other combination of the piezoelectric elements 11306a-c is configured to generate asymmetrical vibrations.

It should be noted that FIGS. 123A-33C are merely exemplary and a variety of other configurations of segmented ultrasonic transducer arrays configured to generate symmetrical vibrations, asymmetrical vibrations, or a combination of symmetrical vibrations or asymmetrical vibrations are contemplated. Furthermore, the descriptions of various aspects of ultrasonic transducer arrays incorporating 2, 3, and 4 piezoelectric elements are merely exemplary. The teachings herein are likewise applicable to ultrasonic transducer arrays incorporating more than 4 piezoelectric elements. Still further, in various aspects the piezoelectric elements of the ultrasonic transducer arrays may be activated synchronously, asynchronously, or with a variety of ultrasound activation signals that may differ in frequency, phase, or amplitude.

FIGS. 125A-B illustrate a D31 ultrasonic transducer 11400 configuration wherein the piezoelectric elements 11406a-b are offset relative to each other, according to one aspect of this disclosure. The ultrasonic transducer 11400 includes a transducer base plate 11408 (e.g., a transducer mounting portion), a first piezoelectric element 11406a disposed on a first face of the transducer base plate 11408, and a second piezoelectric element 11406b disposed on a second face opposing the first face. The first piezoelectric element 11406a and the second piezoelectric element 11406b are longitudinally offset from each. In one aspect, each of the piezoelectric elements 11406a-b are positioned at a node of the acoustic assembly on the transducer base plate 11408. A node is a minimum or zero crossing in the vibratory motion standing wave (i.e., where motion is usually minimal). Therefore, the piezoelectric elements 11406a-b are offset from each other by a distance equal to a one-half wavelength ($\lambda/2$) of the acoustic assembly.

In aspects of ultrasonic transducers incorporating piezoelectric elements that are arranged in an aligned manner (i.e., are not offset from each other) on the transducer base plate 11408, the ultrasonic transducers generate half waves. Conversely, arranging the piezoelectric elements 11406a-b such that they are offset by a one-half wavelength ($\lambda/2$) of the acoustic assembly causes the ultrasonic transducer 11400 to generate a full wave. A full wave vibratory motion can be utilized to introduce non-longitudinal motion to an end effector driven by the acoustic assembly. The ultrasonic transducer 11400 can additionally incorporate one or more balancing features configured to balance or compensate for the bending motion or flexure mode induced by the full wave generated by the offset piezoelectric elements 11406a-b. If additional balancing features are utilized to compensate for the offset piezoelectric elements 11406a-b, the ultrasonic transducer 11400 induces a longitudinal motion at the end effector, as depicted in FIG. 125C. If balancing features are not utilized to compensate for the piezoelectric elements 11406a-b, the ultrasonic transducer 11400 induces a non-longitudinal or bending motion at the end effector, as depicted in FIG. 125D. In some aspects, the balancing features can be selectively activatable, allowing a surgical instrument incorporating the ultrasonic transducer 11400 to switch between longitudinal and non-longitudinal modes for the end effector.

It should be noted that the teachings of any aspect of an ultrasonic transducer assembly depicted as a specific transducer architecture, e.g., a D31 transducer architecture or a D33 transducer architecture, are equally applicable to ultrasonic transducers utilizing other configurations, unless stated otherwise or if such a teaching would be in conflict with the structure of the particular transducer architecture. For example, the teachings of an aspect of an ultrasonic transducer assembly depicted as a D31 transducer architecture, such as in FIGS. 110A-114, 116A-117D, and 122, are likewise applicable to a D33 transducer assembly, such as in FIGS. 115A-C, 118-121D, and 123A-125B, and vice versa (unless they would be in conflict with the structure of the particular transducer architecture).

Figure 126B:
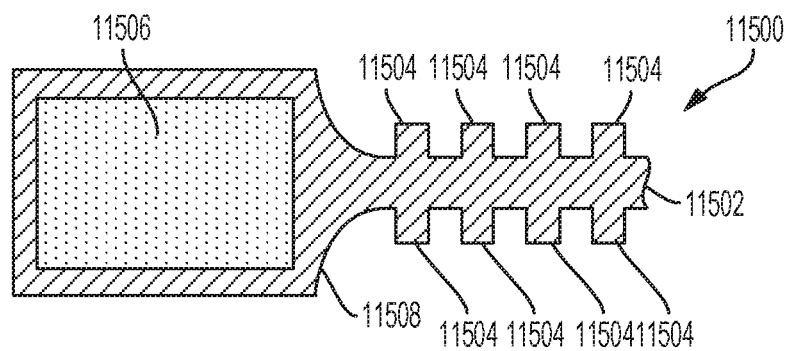
Figure 126C:
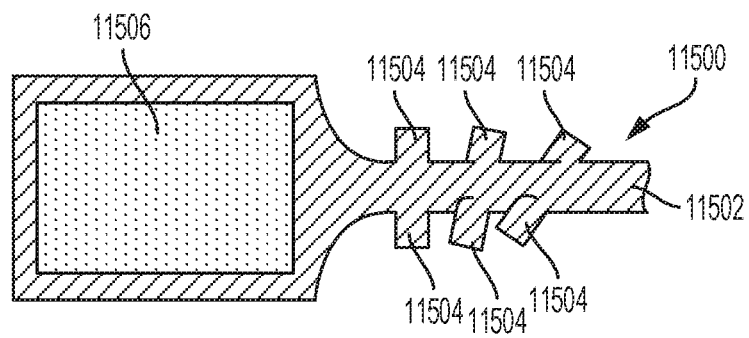
Figure 126D:
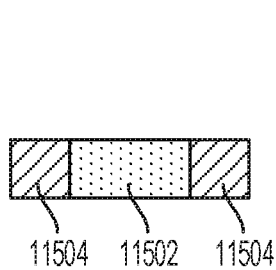
Figure 126E:
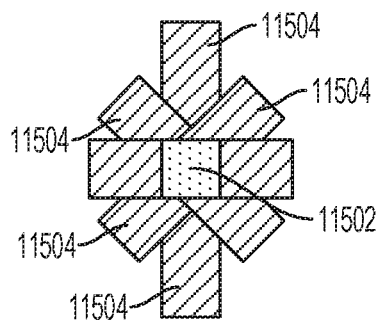

FIGS. 126A-E illustrate various views of a surgical tool 11500 including of a waveguide 11508 of a surgical instrument having complex features and a fabrication process thereof, according to one aspect of this disclosure. The surgical tool 11500 comprises a proximal transducer base plate 11506 (e.g., a transducer mounting portion), a distal end effector 11502, and a longitudinal portion or waveguide 11508 extending therebetween. In various aspects, the waveguide 11508 further comprises a plurality of teeth 11504 disposed along its length. Furthermore, in various aspects the waveguide 11508 is twisted such that the teeth 11504 extend from the longitudinal axis of the waveguide 11508 at a variety of different angles, as depicted in FIG. 126E.

In order to fabricate the surgical instrument 11500, the first step is to fabricate a flat plate surgical tool 11500 comprising a plurality of teeth 11504, as depicted in FIGS. 126B and 35D. The surgical tool 11500 can be fabricated via a variety of manufacturing processes including, e.g., metal injection molding. The teeth 11504 can be formed on the surgical instrument 11500 via the metal injection molding process or via, e.g., forming, machining, cutting, forging, grinding, polishing, de-burring, tumbling, or any other such manufacturing process. Next, the waveguide 11508 is gradually twisted, as depicted in FIG. 126C. The waveguide 11508 can be twisted via a variety of manufacturing processes including, e.g., passing the waveguide 11508 through a series of progressive dies. The twisting may also be used to adjust various features of the waveguide 11508, such as curvature, offset, flex section, and thin or tapered tissue clamping sections. The waveguide 11508 can be twisted at any point along its length. In one aspect, the waveguide is twisted such that the teeth 11504 are symmetrically offset from each other (i.e., adjacent teeth 11504 are angularly separated by a fixed amount). In this aspect, the angularly symmetric teeth 11504 generate both a longitudinal motion and a torsional (i.e., non-longitudinal) motion at the end effector 11502.

FIGS. 127A-D illustrate various views of a D31 ultrasonic transducer 11600 configuration configured to generate non-longitudinal motion and components thereof, according to one aspect of this disclosure. The ultrasonic transducer 11600 includes a metal housing 11608 including a recess 11602 configured to receive a cylindrical piezoelectric element 11604 therein. The ultrasonic transducer 11600 further comprises a cylindrical transducer support 11610 configured to support the cylindrical element 11604 thereon and a plurality of electrodes 11612a-c arranged about the piezoelectric element 11604. In one aspect, the electrodes 11612a-c are angularly offset from each other by a fixed amount (i.e., the electrodes 11612a-c angularly symmetric).

The piezoelectric element 11604 can be affixed to the transducer support 11610 by, e.g., a conductive epoxy. The transducer support 11610 can be affixed to the interior sidewalls of the recess 11602, thereby supporting the piezoelectric element 11604 and electrodes 11612*a-c* within the recess. In various aspects, each of the electrodes 11612*a-c* is asymmetric or unbalanced about at least on axis (i.e., x, y, or z), thereby causing each of the electrodes 11612*a-c* to have a net mass offset. When the ultrasonic transducer 11600 in use, the angularly offset electrodes 11612*a-c* that are asymmetrically weighted cause the ultrasonic transducer 11600 to induce both a longitudinal motion and a torsional (i.e., non-longitudinal) motion at the end effector of the surgical instrument.

FIG. 128 illustrates a perspective view of an electrical connector 11700 to an ultrasonic signal generator for a surgical instrument, according to one aspect of this disclosure. Various surgical instruments, such as ones disclosed in U.S. Pat. No. 10,952,759 entitled "TISSUE LOADING OF A SURGICAL INSTRUMENT," which is herein incorporated by reference in its entirety, include an electrical connector 11700 that is connectable to an ultrasonic signal generator for driving the piezoelectric elements. The electrical connector 11700 includes a first wire 11706*a* and a second wire 11706*b* disposed on an interior side 11704, which is configured to be enclosed within the housing of the surgical instrument, and a first pin 11708*a* and a second pin 11708*b* disposed on the exterior side 11704 that are configured to be connected to an ultrasonic signal generator. The first wire 11706*a* and the second wire 11706*b* are electrically connected to the piezoelectric elements of the ultrasonic transducer and transmit the signal generated by the ultrasonic signal generator thereto.

The interior side 11704 of the electrical connector 11700 is intended to be sealed from the surrounding environment to avoid the ingress of moisture, microbes, and other contaminants that can damage the function of the surgical instrument or otherwise be safety risks for operators and/or patients. If contaminants enter the housing of the surgical instrument, it can be desirable to have the surgical instrument generate an alarm or alert, cease functioning, or perform some other action to notify operators of the instrument that an error has occurred. In this aspect, the electrical connector 11700 comprises a first conductive pathway 11712*a* and a second conductive pathway 11712*b* extending along the interior side 11704 of the electrical connector 11700 from the first wire 11706*a* and the second wire 11706*b*, respectively. The conductive pathways 11712*a-b* can include, e.g., soldered channels. The conductive pathways 11712*a-b* extend towards each other, but terminate such that they are separated by a gap that is sufficiently large to prevent arcing therebetween, but small enough such that a relatively small amount of water can bridge the gap. In one aspect, the gap between the conductive pathways 11712*a-b* is filled with a hydrophilic coating 11714, as depicted in FIG. 128. In another aspect, the geometry of the electrical connector 11700 is configured to channel fluid to the gap between the conductive pathways 11712*a-b* (e.g., the interior side 11704 is constructed as a curved surface with a local or global minimum situated at the gap). In either aspect, if fluid enters the housing of the surgical instrument, it is funneled or attracted to the gap between the conductive pathways 11712*a-b*. When fluid reaches the gap, it causes a short in the electrical system. In one aspect, the short causes the surgical instrument to cease functioning. Therefore, the surgical instrument is prevented from being used if its internal housing is contaminated with moisture. In another aspect, the short causes the circuit of the surgical instrument to generate an error signal, which can in turn be detected and cause an alert or alarm to be generated.

FIGS. 129-132 illustrate various views of a D33 ultrasonic transducer 11800 configuration, according to one aspect of this disclosure. The ultrasonic transducer 11800 includes a metal housing 11808 defining an open interior 11802 that is configured to receive a plurality of piezoelectric elements 11806*a-f* in the form of a Langevin stack. The housing 11816 includes a connector 11816 that is configured to receive an ultrasonic waveguide. The ultrasonic transducer 11800 further includes a threaded plug or threaded rod 11804 extending through a threaded aperture 11814 disposed at the proximal end of the housing 11808 into the housing interior 11802. The ultrasonic transducer 11800 still further includes a plate 11812 situated between the stack of piezoelectric elements 11806*a-f* and the distal end 11810 of the threaded rod 11804. As the threaded rod 11804 is tightened, the distal end 11810 thereof contacts the plate 11812 and applies a compressive force to compress the piezoelectric elements 11806*a-f* stack in the housing 11808. In various aspects, the plate 11812 is constructed from an electrically conductive material.

Once a desired compressive force is achieved, the threaded rod 11804 will be maintained in the particular tightened position due to its engagement with the threaded aperture 11814. The degree of compressive force applied by the threaded rod 11804 can be adjusted by loosening or tightening the threaded rod 11804 in order to tune the frequency of the stack of piezoelectric elements 11806*a-f*, without the need to disassemble the ultrasonic transducer 11800. In some aspects, the ultrasonic transducer 11800 can switch between operating frequencies according to the degree of applied compressive force on the stack of piezoelectric elements 11806*a-d*. When the ultrasonic transducer 11800 is utilized in conjunction with a surgical instrument, being able to switch between operating frequencies in the field can allow for the ultrasonic transducer 11800 to adjust to tissue effects encountered by the surgical instrument or to different end effector types.

The ultrasonic transducer 11800 further includes a first wire 11818 and a second wire 11820 that are electrically coupled to the stack of piezoelectric elements 11806*a-f*. The first wire 11818 can be utilized to deliver a first electrical potential and the second wire 11820 can be utilized to deliver a second electrical potential. In one aspect, the first electrical potential is positive and the second electrical potential is ground or negative. In one aspect, the connection points 11822*a-c* of the first wire 11818 and the connection points 11824*a-d* of the second wire 11820 are attached at the junctions between the plate 11812 and each of the piezoelectric elements 11806*a-f*, which may be connected by, e.g., a conductive adhesive. The connection points 11822*a-c* of the first wire 11818 and the connection points 11824*a-d* of the second wire 11820 can be arranged such that they alternate with each other. In one aspect, the connection points 11824*a-d* of the second wire 11820, representing the negative or ground connection, can be situated at the external connection points 11824*a*, 11824*d* of the stack of piezoelectric elements 11806*a-f*.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

A compressed ultrasonic transducer assembly, comprising: a metal housing defining an opening; at least two piezoelectric elements disposed within the opening and compressed by a compressive force, wherein the at least two piezoelectric elements are configured to work in a D33 mode; and a metal plug joined to the metal housing to close the opening and to maintain the at least two piezoelectric elements in a compressed state within the metal housing.

Example 2

The compressed ultrasonic transducer assembly of Example 1, further comprising a welded joint to join the metal plug to the metal housing.

Example 3

The compressed ultrasonic transducer assembly of Example 1 or Example 2, further comprising an epoxy joint to join the metal plug to the metal housing.

Example 4

The compressed ultrasonic transducer assembly of one or more of Example 1 through Example 3, wherein the metal housing and the metal plug each comprise a threaded end and the metal housing and the metal plug are threadingly coupled.

Example 5

The compressed ultrasonic transducer assembly of one or more of Example 1 through Example 4, further comprising a swaged joint to join the metal plug to the metal housing.

Example 6

The compressed ultrasonic transducer assembly of one or more of Example 1 through Example 5, wherein the metal housing has a fork-like metal frame.

Example 7

An ultrasonic surgical instrument, comprising: an ultrasonic waveguide; an ultrasonic transducer mounted to the ultrasonic waveguide and configured to operated in a D31 mode, ultrasonic transducer comprising: a first ceramic piezoelectric element having a first side attached to a first side of the ultrasonic waveguide by a first bonding material; and a second ceramic piezoelectric element having a first side attached to a second side of the ultrasonic waveguide by the first bonding material, wherein the first side of the ultrasonic waveguide is opposite the second side of the ultrasonic waveguide.

Example 8

The ultrasonic surgical instrument of Example 7, further comprising: a first electrically conductive plate attached to a second side of the first ceramic piezoelectric element by a second bonding material; and a second electrically conductive plate attached to a second side of the second ceramic piezoelectric element by the second bonding material.

Example 9

The ultrasonic surgical instrument of Example 7 or Example 8, wherein the first bonding material is the same as the second bonding material.

Example 10

The ultrasonic surgical instrument of one or more of Example 8 through Example 9, wherein the first bonding material is a solder bonding material and the second bonding material is a conductive epoxy bonding material.

Example 11

The ultrasonic surgical instrument of one or more of Example 8 through Example 10, wherein the solder is a metal solder alloy bonding material.

Example 12

The ultrasonic surgical instrument of one or more of Example 7 through Example 11, wherein the first bonding material is a solder bonding material.

Example 13

The ultrasonic surgical instrument of Example 12, wherein the solder material is a metal solder alloy bonding material.

Example 14

The ultrasonic surgical instrument of one or more of Example 7 through Example 13, wherein the first ceramic piezoelectric element has a poling axis in a direction from the first side to the second side of the first ceramic piezoelectric element and the second ceramic piezoelectric element has a poling axis in a direction from the first side to the second side of the second ceramic piezoelectric element to operate in a D31 mode.

Example 15

The ultrasonic surgical instrument of Example 14, wherein a motion axis of the ultrasonic waveguide is orthogonal to the poling axes of the first and second ceramic piezoelectric elements.

Example 16

The ultrasonic surgical instrument of one or more of Example 14 through Example 15, wherein the first and second piezoelectric elements are unpoled prior to bonding to the respective first and second sides of the ultrasonic waveguide and are poled after the first and second piezoelectric elements are bonded to the respective first and second sides of the ultrasonic waveguide.

Example 17

An ultrasonic surgical instrument, comprising: an ultrasonic waveguide comprising: a base portion; first and second walls extending from one side of the base portion; and first and second ledges projecting from the corresponding first and second walls, wherein a first space is defined between the first ledge and the base portion and wherein a second space is defined between the second ledge and the base portion; and an ultrasonic transducer attached to the ultrasonic waveguide, wherein the ultrasonic transducer comprises at least one piezoelectric element slidably disposed between the first and second spaces and fixed therein.

Example 18

The ultrasonic surgical instrument of Example 17, wherein the at least one piezoelectric element is attached to the base portion of the ultrasonic waveguide by a bonding material.

Example 19

The ultrasonic surgical instrument of Example 17 or Example 18, wherein the first and second ledges are biased toward the base portion of the ultrasonic waveguide to attach the at least one piezoelectric element to the base portion of the ultrasonic waveguide.

Example 20

The ultrasonic surgical instrument of one or more of Example 17 through Example 19, wherein the at least one piezoelectric element is attached to the base portion of the ultrasonic waveguide by a bonding material, and wherein the first and second ledges are biased toward the base portion of the ultrasonic waveguide to attach the at least one piezoelectric element to the base portion of the ultrasonic waveguide in combination with the bonding material.

Example 21

The ultrasonic surgical instrument of one or more of Example 17 through Example 20, wherein the ultrasonic waveguide further comprises third and fourth walls extending from an opposite side of the base portion; third and fourth ledges projecting from the corresponding third and fourth walls, wherein a third space is defined between the third ledge and the base portion and wherein a fourth space is defined between the fourth ledge and the base portion.

Example 22

The ultrasonic surgical instrument of Example 21, wherein the ultrasonic transducer further comprises a second piezoelectric element slidably disposed between the third and fourth spaces and fixed therein.

Example 23

The ultrasonic surgical instrument of Example 22, wherein the second piezoelectric element is attached to the base portion of the ultrasonic waveguide by a bonding material.

Example 24

The ultrasonic surgical instrument of one or more of Example 22 through Example 23, wherein the third and fourth ledges are biased toward the base portion of the ultrasonic waveguide to attach the second piezoelectric element to the base portion of the ultrasonic waveguide.

Example 25

The ultrasonic surgical instrument of one or more of Example 22 through Example 24, wherein the second piezoelectric element is attached to the base portion of the ultrasonic waveguide by a bonding material, and wherein the third and fourth ledges are biased toward the base portion of the ultrasonic waveguide to attach the second piezoelectric element to the base portion of the ultrasonic waveguide in combination with the bonding material.

Example 26

An ultrasonic surgical instrument, comprising: an ultrasonic waveguide; and an ultrasonic transducer attached to the ultrasonic waveguide; wherein the ultrasonic waveguide comprises a tuning-fork-like frame comprising: an upper prong; and a lower prong defining a U-shaped aperture therebetween configured to receive the ultrasonic transducer therein.

Example 27

The ultrasonic instrument of Example 26, wherein the upper prong of the tuning-fork-like frame defines an aperture to provide access for an electrical connection to the ultrasonic transducer.

Example 28

The ultrasonic instrument of Example 26 or Example 27, wherein the ultrasonic transducer comprises: a piezoelectric element; a first electrically conductive plate attached to a top side of the piezoelectric element by an electrically conductive bonding material; and a second electrically conductive plate attached to a bottom top side of the piezoelectric element by an electrically conductive bonding material.

Example 29

The ultrasonic instrument of Example 28, further comprising: an electrically insulative bonding material disposed between the first electrically conductive plate and an internal surface of the upper prong; and an electrically conductive bonding material disposed between the second electrically conductive plate and an internal surface of the lower prong.

Ultrasonic Transducer to Waveguide Joining

FIG. 133 is a side view of an ultrasonic surgical instrument 8000 configured in a D31 ultrasonic transducer architecture comprising separate ultrasonic waveguide 8002 and ultrasonic transducer base plate 8004 (e.g., a transducer mounting portion) components shown in a coupled configuration, according to one aspect of this disclosure. The ultrasonic surgical instrument 8000 may comprise multiple pieces to reduce material waste and provide the ability to use alternate materials and/or manufacturing methods for the waveguide 8002 and the transducer base plate 8004. In one aspect, the waveguide 8002 and the transducer base plate 8004 are made separately from flat metal stock suitable for transmitting ultrasonic vibrations such as titanium, titanium alloy, aluminum, or aluminum alloy, for example, as described herein. For example, the waveguide 8002 and the transducer base plate 8004 are two separate pieces and can be made of the same material or different materials suitable for transmitting ultrasonic energy along the longitudinal axis LA.

The ultrasonic waveguide 8002 and ultrasonic transducer base plate 8004 each define mutually complementary mating geometries and are connected by a jigsaw puzzle joint 8006. A proximal end of the waveguide 8002 includes a connection portion to attach to the transducer base plate 8004. An example of a connection portion is shown in FIGS. 134 and 134B. A distal end of the waveguide 8002 includes an ultrasonic blade 8012. The blade 8012 is used to treat tissue. The transducer base plate 8004 defines flat faces 8005 on opposite sides of the transducer base plate 8004 suitable to attach and support a PZT piezoelectric element on each flat face 8005 similar to the D31 configuration shown by way of example in FIG. 3. The distal end of the transducer base plate 8004 includes a connection portion that is complementary to the connection portion located on the proximal end of the waveguide 8002. The connection portion of the waveguide 8002 may be male, female, or flat and the connection portion of the transducer base plate 8004 may be female, male, or flat, respectively. When fully assembled, the ultrasonic instrument 8000 is configured to transmit ultrasonic energy to the distal end of the waveguide 8002 along the longitudinal axis LA.

In one aspect, the separate waveguide 8002 and transducer base plate 8004 components are coupled at the jigsaw puzzle joint 8006 by plastic deformation of one or both components to enable acoustic transmission along an ultrasonic train. In one aspect, the waveguide 8002 and transducer base plate 8004 components of the ultrasonic instrument 8000 may be coupled to form the jigsaw puzzle joint 8006. Plastic deformation of one or both of the waveguide 8002 and transducer base plate 8004 components can be used to fasten the waveguide 8002 and transducer base plate 8004 components to enable transmission of ultrasonic energy along a longitudinal axis LA of the ultrasonic instrument 8000.

The waveguide 8002 component of the ultrasonic instrument 8000 is acoustically coupled between the transducer base plate 8004 and an ultrasonic blade 8012, or end effector, at the distal end of the waveguide 8002. The transducer base plate 8004 is located at a proximal end of the ultrasonic instrument 8000 and is sized and configured to mount ultrasonic transducer elements, such as, for example, PZT piezoelectric elements, on opposite faces 8005 of the transducer base plate 8004. The ultrasonic blade 8012 is located at a distal end of the ultrasonic instrument 8000. In the surgical instrument 8000 illustrated in FIG. 133, the nodes (N), i.e., where motion is usually minimal, and antinodes (AN), where motion is usually maximal, are indicated along the longitudinal length of the ultrasonic instrument 8000. The distance between an anti-node (AN) and its nearest node (N) is one-quarter wavelength ($\lambda/4$). An AN is located at a distal end of the blade 8012.

FIG. 134A is a section view of a jigsaw puzzle joint 8006A of the waveguide 8002 and transducer base plate 8004 components of the ultrasonic surgical instrument 8000, according to one aspect of this disclosure. A proximal end of the waveguide 8002 component defines a male jigsaw puzzle piece 8008 sized and configured to be received within a complementary mating female jigsaw puzzle piece 8010 defined by a distal end of the transducer base plate 8004 component. To make the jigsaw puzzle joint 8006A, first the male jigsaw puzzle piece 8008 is fitted into the female jigsaw puzzle piece 8010 to achieve a clearance fit. A permanent joint 8012 is created by applying opposing forces F to the distal end of the second component 8004 to plastically deform the second component 8004 by an amount indicated as "d." In other aspects, the proximal end of the waveguide 8002 defines a female connection portion and the distal end of the transducer base plate 8004 defines a male connection portion.

FIG. 134B is a section view of a jigsaw puzzle joint 8006B of the waveguide 8002 and transducer base plate 8004 components of the ultrasonic surgical instrument 8000, according to one aspect of this disclosure. The male jigsaw puzzle piece 8008 of the waveguide 8002 is sized and configured to be received within the female jigsaw puzzle piece 8010 defined at a distal portion of the transducer base plate 8004 to form an interference fit at the joint 8014. The interference fit, also known as a press fit or friction fit, is fastening between two components in which the inner waveguide 8002 component is larger than the outer transducer base plate 8004 component. To achieve the interference fit, a force F is applied during assembly. After the waveguide 8002 component is larger than the outer transducer base plate 8004 component are joined, the mating surfaces will feel pressure due to friction, and deformation of the completed assembly will be observed. In other aspects, the proximal end of the waveguide 8002 defines a female connection portion and the distal end of the transducer base plate 8004 defines a male connection portion.

FIG. 135 is a side view of an ultrasonic surgical instrument 8020 configured in a D31 transducer architecture comprising separate ultrasonic waveguide 8022 and ultrasonic transducer base plate 8024 (e.g., a transducer mounting portion) components shown in a decoupled configuration, according to one aspect of this disclosure. FIG. 136 is an end view of the waveguide 8022 shown in FIG. 135 according to one aspect of this disclosure. FIG. 137 is an end view of the transducer base plate 8024 shown in FIG. 135, according to one aspect of this disclosure. The ultrasonic surgical instrument 8020 may comprise multiple pieces to reduce material waste and provide the ability to use alternate materials and/or manufacturing methods for the waveguide 8022 and the transducer base plate 8024. In one aspect, the waveguide 8022 and the transducer base plate 8024 are made separately from flat metal stock suitable for transmitting ultrasonic vibrations such as titanium, titanium alloy, aluminum, or aluminum alloy, for example, as described herein. For example, the waveguide 8022 and the transducer base plate 8024 are two separate pieces and can be made of the same material or different materials suitable for transmitting ultrasonic energy along the longitudinal axis LA. The transducer base plate 8024 defines flat faces 8023 on opposite sides of the transducer base plate 8024 suitable to attach and support a PZT piezoelectric element on each flat face 8023 similar to the D31 configuration shown by way of example in FIG. 3. When the waveguide 8022 and transducer base plate 8024 are coupled in a D31 configuration, ultrasonic vibrations generated by the PZT piezoelectric elements are transmitted along the waveguide 8022 to an ultrasonic blade at a distal end of the waveguide 8022. When fully assembled, the ultrasonic instrument 8020 is configured to transmit ultrasonic energy to the distal end of the waveguide 8022 along the longitudinal axis LA.

With reference to FIGS. 135-137, the waveguide 8022 and the transducer base plate 8024 are made separately from flat metal stock suitable for transmitting ultrasonic vibrations such as titanium, titanium alloy, aluminum, or aluminum alloy, for example. The waveguide 8022 and the transducer base plate 8024 define a taper through a thickness dimension and are connected by a tapered joint 8039. A proximal end of the waveguide 8022 defines a male connection portion 8028 sized and configured to be received within a complementary mating female connection portion 8032. The male connection portion 8028 defines a tapered neck 8026 and a tapered end 8038, both tapered through the thickness of the male connection portion 8028. The female connection portion 8032 defines a first aperture 8030 to receive the neck portion 8026 of the waveguide 8022 and defines a second aperture 8034 to receive the tapered end 8038 of the waveguide 8022. The complementary mating female connection portion 8032 defines a tapered inner wall 8036 that acts as a lead-in when pressing the waveguide 8022 and the transducer base plate 8024 components together. The waveguide 8022 is coupled to the transducer base plate 8024 to enable transmission of ultrasonic energy along a longitudinal axis LA of the ultrasonic instrument 8020. The width $W_1$ of the bottom portion 8029 of the male connection portion 8028 is wider than the width $W_2$ of the bottom opening 8037 defined by the tapered wall 8036 of defined by the second aperture 8034 to form an interference fit when the waveguide 8022 is press fit into the transducer base plate 8024. The tapered wall 8036 through the thickness of the transducer base plate 8024 may be formed by waterjet or angled laser beam.

FIG. 138 is a side view of the ultrasonic instrument 8020 shown in FIG. 135 in a coupled configuration connected at the tapered joint 8039, according to one aspect of this disclosure. The waveguide 8024 and the transducer base plate 8024 are made separately from flat metal stock suitable for transmitting ultrasonic vibrations such as titanium, titanium alloy, aluminum, or aluminum alloy, for example, as described herein. As shown in FIG. 9, the waveguide 8022 is coupled to the transducer base plate 8024 through a taper through a thickness dimension such that the tapered joint 8039 forms an interference fit. FIGS. 139A and 10B are section views taken along section line 139-139 shown in FIG. 138. FIG. 139A is a section view taken prior to joining the waveguide 8022 to the transducer base plate 8024 and FIG. 139B is a section view taken after partially joining the waveguide 8022 to the transducer base plate 8024.

With reference now to FIGS. 139A and 139B, the neck portion 8026 of the waveguide 8022 is sized and configured to fit in a complementary mating female connection portion 8030. The male connection portion 8028 is sized and configured to form an interference fit when press fit into the complementary mating female connection portion 8032. For example, the top 8025 of the of the neck portion 8026 has a width $W_3$ and the bottom 8027 has a width $W_4$, where $W_4$ is less than $W_3$ to define a taper. The top opening 8031 of the female connection portion 8030 has a width $W_5$ and the bottom opening 8033 has width $W_6$, where $W_6$ is less than $W_5$ to define a complementary taper to receive the neck portion 8026. The taper acts as a lead-in when the waveguide 8022 is press fit with the transducer base plate 8024. The taper results in a more predictable or controlled material flow when press fitting the waveguide 8022 into the transducer base plate 8024. In one aspect, the bottom of the neck portion $W_4$ is wider than the width $W_6$ of the bottom opening 8033 of the complementary mating female connection portion 8030 to form an interference fit as shown in FIG. 139B. The widths $W_3$ and $W_5$ may be the same or, in one aspect, the width $W_3$ may be greater than the width $W_5$. Although not shown, the tapered end 8038 to achieve an interference fit with the complementary second aperture 8034 that defines a tapered inner wall 8036.

FIG. 140 is a side view of an ultrasonic surgical instrument 8040 configured in a D31 transducer architecture comprising separate ultrasonic waveguide 8042 and ultrasonic transducer base plate 8044 (e.g., a transducer mounting portion) components shown in a coupled configuration, according to one aspect of this disclosure. The ultrasonic surgical instrument 8040 may comprise multiple pieces to reduce material waste and provide the ability to use alternate materials and/or manufacturing methods for the waveguide 8042 and the transducer base plate 8044. In one aspect, the waveguide 8042 and the transducer base plate 8044 are made separately from flat metal stock suitable for transmitting ultrasonic vibrations such as titanium, titanium alloy, aluminum, or aluminum alloy, for example, as described herein. For example, the waveguide 8042 and the transducer base plate 8044 are two separate pieces. The waveguide 8042 is configured to transmit ultrasonic energy along a longitudinal axis. The transducer base plate 8044 component is sized and configured to support PZT piezoelectric elements on opposite sides of the transducer base plate 8044. The waveguide 8042 is made of a metal suitable for transmitting ultrasonic vibrations. Generally, the waveguide 8042 may be made of a first metal material such as titanium, titanium alloy, aluminum, or aluminum alloy as described herein. In other aspects, the waveguide 8042 and the transducer base plate 8144 maybe made of the same material. In either case, the material should be suitable for transmitting ultrasonic energy along the longitudinal axis LA.

A proximal end of the waveguide 8042 includes a connection portion to attach to the transducer base plate 8044. A distal end of the waveguide 8042 includes an ultrasonic blade to treat tissue. The transducer base plate 8044 defines flat faces 8045 on opposite sides of the transducer base plate 8044 suitable to attach and support a PZT piezoelectric element on each flat face 8045 similar to the D31 configuration shown by way of example in FIG. 3. The distal end of the transducer base plate 8044 includes a connection portion that is complementary to the connection portion located on the proximal end of the waveguide 8002. The connection portion of the waveguide 8042 may be male, female, or flat and the connection portion of the transducer base plate 8044 may be female, male, or flat, respectively.

The transducer base plate 8044 is made of a second metal material such as aluminum that is different from the first metal material that the waveguide 8042 is made from. When fully assembled, the ultrasonic instrument 8040 is configured to transmit ultrasonic energy to the distal end of the waveguide 8042 along the longitudinal axis LA.

When the waveguide 8042 and transducer base plate 8044 components are coupled in a D31 configuration, ultrasonic vibrations generated by the PZT piezoelectric elements are transmitted along the waveguide 8042 to an ultrasonic blade located at a distal end of the waveguide 8042. Accordingly, ultrasonic energy is transmitted along the longitudinal axis of the waveguide 8042. As shown in FIG. 140, the waveguide 8042 has a width $W_1$ and the transducer base plate 8044 has width $W_2$, where $W_2$ is greater than $W_1$. The waveguide 8042 may be coupled to the transducer base plate 8044 using any of the techniques described herein. The waveguide 8042 and transducer base plate 8044 may be coupled using any of the techniques described herein, including, without limitation, a jigsaw puzzle joint, a C-shaped pin joint, a pin joint, a press fit joint, an interference joint, parallel tang joint, a screw joint, an interference flange joint, an interference pin joint, a wedge joint, a luer lock joint, a swaged joint, among other joints described herein.

FIG. 141 is a section view of the ultrasonic surgical instrument 8040 shown in FIG. 140 taken along section line 141-141 shown in FIG. 140, according to one aspect of this disclosure. In one aspect, the thickness of the transducer base plate 8044 component is greater than the thickness of the waveguide 8042 component. As shown in FIG. 141, the waveguide 8042 component defines a thickness $T_1$ and the transducer base plate 8044 component defines a thickness $T_2$, where $T_2$ is greater than $T_1$. Thus, the flat blade configuration that utilizes two components can generate more gain through the flat/sheet construction than would be created through a single thickness blade part.

FIG. 142 is a section view of an ultrasonic surgical instrument 8050 configured in a D31 transducer architecture comprising multiple plates coupled by a thermal expansion joint, according to one aspect of this disclosure. The ultrasonic surgical instrument 8050 may comprise multiple pieces to reduce material waste and provide the ability to use alternate materials and/or manufacturing methods for the waveguide 8052 and the transducer base plate 8054a, 8054b (e.g., a transducer mounting portion). In one aspect, the waveguide 8052 and the transducer base plate 8054a, 8054b are made separately from flat metal stock suitable for transmitting ultrasonic vibrations such as titanium, titanium alloy, aluminum, or aluminum alloy, for example, as described herein. For example, the waveguide 8052 and the transducer base plate 8054a, 8054b are two separate pieces. The ultrasonic surgical instrument 8050 includes an ultrasonic waveguide 8052 and a two flange plates 8054a, 8054b attached to the waveguide 8052. The waveguide 8052 is made from small rectangular stock of metal such as titanium, titanium alloy, aluminum, or aluminum alloy suitable for transmitting ultrasonic energy. The two flange plates 8054a, 8054b are made from similar stock material or different stock materials. In either case, the material should be suitable for transmitting ultrasonic energy along the longitudinal axis LA The first flange plate 8054a includes one or more male jigsaw puzzle pieces 8056a, 8060a stamped in the body portion of the first flange plate 8054a. The second flange plate 8054b includes one or more male jigsaw puzzle pieces 8058a, 8062a stamped in the body portion of the second flange plate 8054b. One side of the waveguide 8052 includes one or more female jigsaw puzzle pieces 8056b, 8060b stamped in a body portion of the waveguide 8052 sized and configured to mate with the corresponding male jigsaw puzzle pieces 8056a, 8060a. An opposite side of the waveguide 8052 includes one or more female jigsaw puzzle pieces 8058b, 8062b stamped in a body portion of the waveguide 8052 sized and configured to mate with the corresponding male jigsaw puzzle pieces 8058a, 8062a. As shown in FIG. 142, the male and female jigsaw puzzle pieces 8056a-b, 8058a-b, 8060a-b, 8062a-b are disposed on an AN section of the ultrasonic transmission waveguide 8052. When fully assembled, the ultrasonic instrument 8050 is configured to transmit ultrasonic energy to the distal end of the waveguide 8052 along the longitudinal axis LA.

The waveguide 8052 female jigsaw puzzle pieces 8056b, 8058b, 8060b, 8062b are dimensioned smaller than the corresponding dimensions of the male flange jigsaw puzzle pieces 8056a, 8058a, 8060a, 8062a. Thus, the flange plates 8054a, 8054b are nominally larger than the waveguide 8052. The size mismatch prevents assembly of the waveguide 8052 to the flange plates 8054a, 8054b at room temperature. However, by heating the waveguide 8052 to a high temperature, the female jigsaw puzzle pieces 8056b, 8058b, 8060b, 8062b dimensions increase, as shown in FIG. 142 in the expanded configuration, making it possible to mate the waveguide plate 805 and the flange plates 8054a, 8054b. As the waveguide 8052 cools, the jigsaw puzzle type male and female joints contract and achieves an interference fit between the waveguide 8052 and the flange plates 8054a, 8054b. In other aspects, the waveguide 8052 may include male jigsaw puzzle pieces configured to mate with female jigsaw puzzle pieces formed on the flange plates 8054a, 8054b. In another aspect, rather than heating the waveguide 8052, the flange plates 8054a, 8054b may be cooled or frozen to shrink the dimensions prior to mating with the waveguide 8052.

FIG. 143 is side view of an ultrasonic surgical instrument 8070 configured in a D31 transducer architecture comprising separate ultrasonic waveguide 8072 and ultrasonic transducer base plate 8074 (e.g., a transducer mounting portion) shown in a coupled configuration, according to one aspect of this disclosure. The waveguide 8072 is coupled to the transducer base plate 8074 by a C-shaped pin joint 8071 comprising a C-shaped pin 8078 press fit between the waveguide 8072 and the transducer base plate 8074. The ultrasonic surgical instrument 8070 may comprise multiple pieces to reduce material waste and provide the ability to use alternate materials and/or manufacturing methods for the waveguide 8072 and the transducer base plate 8074. In one aspect, the waveguide 8072 and the transducer base plate 8074 are made separately from flat metal stock suitable for transmitting ultrasonic vibrations such as titanium, titanium alloy, aluminum, or aluminum alloy, for example, as described herein. For example, the waveguide 8072 and the transducer base plate 8074 are two separate pieces and can be made of the same material or different materials suitable for transmitting ultrasonic energy along the longitudinal axis LA. The C-shaped pin 8078 may be made of materials that are similar to or different from the materials that the waveguide 8072 or transducer base plate 8074 are made from.

A distal end of the waveguide 8072 defines an ultrasonic blade 8080 and a proximal end of the waveguide 802 defines a male jigsaw puzzle piece 8076 sized and configured to clearance fit within a complementary mating female jigsaw puzzle piece 8079 defined by a distal end of the transducer base plate 8074. The transducer base plate 8074 defines flat faces 8075 on opposite sides of the transducer base plate 8074 suitable to attach and support a PZT piezoelectric element on each flat face 8005 similar to the D31 configuration shown by way of example in FIG. 3. Extending distally from the flat faces 8075 is a neck 8077 that concludes in a female jigsaw puzzle piece 8079. The female jigsaw puzzle piece 8079 also defines a C shape to receive a C-shaped pin 8078. When fully assembled, the ultrasonic instrument 8070 is configured to transmit ultrasonic energy to the distal end of the waveguide 8072 along the longitudinal axis LA.

FIG. 144 is an exploded view and FIG. 145 is a plan view of the C-shaped pin joint 8071 shown in FIG. 143, according to one aspect of this disclosure. FIG. 144 shows the C-shaped pin 8078 in the process of being assembled into an aperture 8073 or gap defined between the male and female jigsaw puzzle pieces 8076, 8079. FIG. 145 shows the C-shaped pin 8078 fully pressed into the aperture 8073 to achieve the C-shaped pin joint 8071. The C-shaped pin 8078 has an outside diameter (OD) that is slightly lager than the diameter of the female jigsaw puzzle piece 8079 and an inside diameter (ID) that is slightly smaller than the diameter of the male jigsaw puzzle piece 8076. The C-shaped clip 8078 is be pressed into the aperture 8073 defined between the female and male jigsaw puzzle pieces 8076, 8079 to lock them in place.

In one aspect, the thermal expansion and contraction properties of the waveguide 8072, transducer base plate 8074, or C-shaped pin 8078 materials may be exploited to achieve a tight joint 8078 at room temperature conditions under which the ultrasonic surgical instrument 8070 will be used. For example, one or ore of the components may be heated to achieve an easier fit to expand the size of the male and female jigsaw puzzle pieces 8076, 8079. In one aspect, the C-shaped pin 8078 may be heated before the C-shaped pin 8078 is press fit into the aperture 8073. In another aspect, the mated male and female jigsaw puzzle pieces 8076, 8079 may be heated before the C-shaped pin 8078. In other aspects, the C-shaped pin 8078 may be sized slightly larger than the aperture 8073 such that the C-shaped pin 8078 is chilled to contract its size prior to press fitting the C-shaped pin 8078 into the aperture 8073. Once the temperature of C-shaped pin 8078 is warmed up to room temperature, the C-shaped pin 8078 expands and achieves a tight fit. In one aspect, the C-shaped pin 8078 may be made of similar or different material to the waveguide 8072 or transducer base plate 8074. In an alternate form, the C-shaped pin 8078 may be replaced by a heated liquid metal that fills the aperture 8073 to achieve the C-shaped pin joint 8071.

FIG. 146 is a side view of an ultrasonic surgical instrument 8100 configured in a D31 transducer architecture comprising separate ultrasonic waveguide 8102 and ultrasonic transducer base plate 8104 (e.g., a transducer mounting portion) components shown in a coupled configuration, according to one aspect of this disclosure. The ultrasonic surgical instrument 8100 may comprise multiple pieces to reduce material waste and provide the ability to use alternate materials and/or manufacturing methods for the waveguide 8102 and the transducer base plate 8104. In one aspect, the waveguide 8102 and the transducer base plate 8104 are made separately from flat metal stock suitable for transmitting ultrasonic vibrations such as titanium, titanium alloy, aluminum, or aluminum alloy, for example, as described herein. For example, the waveguide 8102 and the transducer base plate 8104 are two separate pieces. The transducer base plate 8104 defines flat faces 8103 on opposite sides of the transducer base plate 8104 suitable to attach and support a PZT piezoelectric element on each flat face 8103 similar to the D31 configuration shown by way of example in FIG. 3. The waveguide 8102 and the transducer base plate 8104 are made separately from flat metal stock suitable for transmitting ultrasonic vibrations such as titanium, titanium alloy, aluminum, or aluminum alloy, for example, as described herein. The waveguide 8102 and the transducer base plate 8104 may be made of the same material or different materials suitable for transmitting ultrasonic energy along the longitudinal axis. When fully assembled, the ultrasonic instrument 8100 is configured to transmit ultrasonic energy to the distal end of the waveguide 8102 along the longitudinal axis LA.

FIG. 147 is a section view of the ultrasonic surgical instrument 8100 along section line 147-147 shown in FIG. 146, according to one aspect of this disclosure. With reference to FIGS. 146 and 147, the waveguide 8102 is coupled to an ultrasonic transducer base plate 8104 by slidably receiving the proximal end of the waveguide 8102 into a notch 8105 defined at a distal end of the transducer base plate 8104. A pin 8108 is then press fit through a transverse pin opening 8106 defined by the distal end of the transducer base plate 8104 and a transverse pin opening 8109 defined by the proximal end of the waveguide 8102. The transverse pin openings 8106, 8109 line up when the waveguide 8102 is inserted into the notch 8105 and is seated against a back wall 8101 of the notch 8105. The diameter of the pin 8108 is slightly larger than the diameter of the pin openings 8106, 8109 such that force is required to press fit the pin 8108 into the pin openings 8106, 8109 to achieve an interference pin joint 8107. The waveguide 8102 and the transducer base plate 8104 may be of similar or different materials. The pin 8108, waveguide 8102, and transducer base plate 8104 may be made of similar or different materials. In one aspect, the thermal expansion and thermal contraction properties of the pin 8108, waveguide 8102, and transducer base plate 8104 may be exploited to provide a tight fitting pin joint 8107. For example, in one aspect, the waveguide 8102 and transducer base plate 8104 may be heated to expand the openings 8106, 8109 prior to inserting the pin 8108 into the openings 8106, 8109. Alternatively, the pin 8108 may be chilled prior to inserting the pin 8108 into the openings 8106, 8109.

FIG. 148 is a perspective view an ultrasonic surgical instrument 8110 configured in a D31 transducer architecture comprising separate ultrasonic waveguide 8112 and ultrasonic transducer base plate 8114 (e.g., a transducer mounting portion) components shown in a coupled configuration, according to one aspect of this disclosure. The ultrasonic surgical instrument 8110 may comprise multiple pieces to reduce material waste and provide the ability to use alternate materials and/or manufacturing methods for the waveguide 8112 and the transducer base plate 8114. In one aspect, the waveguide 8112 and the transducer base plate 8114 are made separately from flat metal stock suitable for transmitting ultrasonic vibrations such as titanium, titanium alloy, aluminum, or aluminum alloy, for example, as described herein. In the illustrated aspect, the ultrasonic surgical instrument 8110 is divided into a separate one-piece waveguide 8112 and a one-piece transducer base plate 8114. For example, the waveguide 8112 and the transducer base plate 8114 are two separate pieces and can be made of the same material or different materials suitable for transmitting ultrasonic energy along the longitudinal axis LA.

A proximal end of the waveguide 8112 is coupled to the transducer base plate 8114 within a cutout 8115 defined by the transducer base plate 8114 (see also FIG. 149) to form a press fit joint. The transducer base plate 8114 defines flat faces 8113 on opposite sides of the transducer base plate 8114 suitable to attach and support a PZT piezoelectric element 8116a, 8116b on each flat face 8113 similar to the D31 configuration shown by way of example in FIG. 3. A portion of the waveguide 8119 located beneath and is sandwiched between the piezoelectric elements 8116a, 8116b to form a two-piece divided of the waveguide 8112 and transducer base plate 8114. The waveguide 8112 and the transducer base plate 8114 are made separately from flat metal stock suitable for transmitting ultrasonic vibrations such as titanium, titanium alloy, aluminum, or aluminum alloy, for example, as described herein. When fully assembled, the ultrasonic instrument 8110 is configured to transmit ultrasonic energy to the distal end of the waveguide 8112 along the longitudinal axis LA.

FIG. 149 is a perspective view the ultrasonic surgical instrument 8110 shown in FIG. 148 with the waveguide 8112 and the piezoelectric elements 8116a, 8116b removed to show the cutout 8115 configured to receive a proximal portion of the waveguide 8112, according to one aspect of this disclosure. With reference to FIGS. 148 and 149, in one aspect, the cutout 8115 defined by the transducer base plate 8114 is configured to receive a proximal portion 8118 of the waveguide 8112. The proximal portion waveguide 8119 is inserted in the cutout 8115 defined by the transducer base plate 8114 and is rejoined to the transducer base plate 8114 through the addition of the piezoelectric elements 8116a, 8116b. The transducer base plate 8114 cutout 8115 can have varying shapes to increase retention or minimize material waste. The transducer base plate 8114 can be configured in two or more pieces to increase retention or minimize material waste. Varying materials can be used to join the piezoelectric elements 8116a, 8116b material to the combination of the waveguide portion 8119 and transducer base plate 8114 such as adhesives, welding, soldering, or combinations thereof.

FIG. 150 is a perspective view of an ultrasonic surgical instrument 8120 configured in a D31 transducer architecture comprising ultrasonic waveguide 8122 and ultrasonic transducer base plate 8124a, 8124b (e.g., a transducer mounting portion) components shown in a coupled configuration, according to one aspect of this disclosure. The ultrasonic surgical instrument 8120 may comprise multiple pieces to reduce material waste and provide the ability to use alternate materials and/or manufacturing methods for the waveguide 8122 and the transducer base plate 8124a, 8124b. In one aspect, the waveguide 8122 and the transducer base plate 8124a, 8124b are made separately from flat metal stock suitable for transmitting ultrasonic vibrations such as titanium, titanium alloy, aluminum, or aluminum alloy, for example, as described herein. In the illustrated aspect, the ultrasonic surgical instrument 8120 is divided into separate one-piece waveguide 8122 and two-piece transducer base plate 8124a, 8124b. For example, the waveguide 8122 and the transducer base plate 8124a, 8124b are three separate pieces and can be made of the same material or different materials suitable for transmitting ultrasonic energy along the longitudinal axis LA.

A proximal end of the waveguide 8122 is coupled to the transducer base plate 8124a, 8124b within a cutout 8125 defined by the transducer base plate 8124a, 8124b (see also FIG. 151) to form a press fit joint. The transducer base plate 8124a, 8124b defines flat faces 8123a, 8123b on opposite sides of the transducer base plate 8124a, 8124b suitable to attach and support a PZT piezoelectric element 8126a, 8126b on each flat face 8123a, 8123b similar to the D31 configuration shown by way of example in FIG. 3. A proximal portion of the waveguide 8128 is located beneath and is sandwiched between the piezoelectric elements 8126a, 8126b to form a three-piece divided of the waveguide 8122 and transducer base plate 8124a, 8124b. Another proximal portion of the waveguide 8129 extends through the proximal end of the transducer base plate 8124a, 8124b to divided the transducer base plate 8124a, 8124b into two pieces. The waveguide 8122 and the transducer base plate 8124a, 8124b are made separately from flat metal stock suitable for transmitting ultrasonic vibrations such as titanium, titanium alloy, aluminum, or aluminum alloy, for example, as described herein. When fully assembled, the ultrasonic instrument 8120 is configured to transmit ultrasonic energy to the distal end of the waveguide 8122 along the longitudinal axis LA.

FIG. 151 is a perspective view of the ultrasonic surgical instrument 8120 shown in FIG. 150 with the waveguide 8122 and the piezoelectric elements 8126a, 8126b removed to show the cutout 8125 configured to receive a proximal portion of the waveguide 8122, according to one aspect of this disclosure. With reference to FIGS. 150 and 151, in one aspect, the cutout 8125 is defined by the transducer base plate 8124a, 8124b is configured to receive the proximal portion 8128, 8129 of the waveguide 8122. The proximal portion of the waveguide 8128, 8129 is inserted in the cutout 8125 defined by the transducer base plate 8124a, 8124b and is rejoined to the transducer base plate 8124a, 8124b through the addition of the piezoelectric elements 8126a, 8126b. The transducer base plate 8124a, 8124b cutout 8125 can have varying shapes to increase retention or minimize material waste. The transducer base plate 8124a, 8124b can be configured in three or more pieces to increase retention or minimize material waste. Varying materials can be used to join the piezoelectric elements 8126a, 8126b material to the combination of the proximal portion of the waveguide 8128 and the transducer base plate 8124a, 8124b such as adhesives, welding, soldering, or combinations thereof.

FIG. 152 is a side view of an ultrasonic surgical instrument 8130 configured in a D31 transducer architecture comprising separate ultrasonic waveguide 8132 and ultrasonic transducer base plate 8134 (e.g., a transducer mounting portion) components shown in a decoupled configuration, according to one aspect of this disclosure. FIG. 153 is a section view of the ultrasonic surgical instrument 8130 shown in FIG. 152 with the ultrasonic waveguide 8132 rotated 90° in a decoupled configuration, according to one aspect of this disclosure. The ultrasonic surgical instrument 8130 may comprise multiple pieces to reduce material waste and provide the ability to use alternate materials and/or manufacturing methods for the waveguide 8132 and the transducer base plate 8134. In one aspect, the waveguide 8132 and the transducer base plate 8134 are made separately from flat metal stock suitable for transmitting ultrasonic vibrations such as titanium, titanium alloy, aluminum, or aluminum alloy, for example, as described herein. When fully assembled, the ultrasonic instrument 8130 is configured to transmit ultrasonic energy to the distal end of the waveguide 8152 along the longitudinal axis LA. The waveguide 8132 and transducer base plate 8134 can be made of the same material or different materials suitable for transmitting ultrasonic energy along the longitudinal axis LA.

With reference to FIGS. 152 and 153, a proximal end of the waveguide 8132 includes bump features 8140a, 8140b and the transducer base plate 8134 includes bump features 8138a, 8138b to provide a torqued press fit to join the waveguide 8132 and the transducer base plate 8134. The proximal end of the waveguide 8132 is inserted into an aperture 8136 defined by the transducer base plate 8134. Prior to coupling, the waveguide 8132 is oriented as shown in FIG. 152 where the bump features 8140a, 8140b are not aligned with the bump features 8138a, 8138b such that the waveguide 8132 is slidably received in the aperture 8136 without interference. Once the proximal end of the waveguide 8132 is inserted into the aperture 8136, the waveguide 8132 is rotated as shown in FIG. 153 to provide a torqued press fit joint. The transducer base plate 8134 defines flat faces 8135a, 8135b on opposite sides of the transducer base plate 8134 suitable to attach and support a PZT piezoelectric element on each flat face 8135a, 8135b similar to the D31 configuration shown by way of example in FIG. 3.

FIG. 154 is a section view of the ultrasonic surgical instrument 8130 shown in FIG. 152 with the ultrasonic waveguide 8132 rotated 90° in a coupled configuration, according to one aspect of this disclosure. FIG. 155 is detail view of the joint between the waveguide 8132 and the transducer base plate 8134, according to one aspect of this disclosure. With reference to FIGS. 152-155, once the waveguide 8132 is inserted into the aperture 8136, the waveguide may be rotated as indicated by arrow 8142 such that the bump features 8138a, 8138b on the transducer base plate 8134 and the bump features 8132 on the waveguide 8132 create a torqued press fit connection. As shown in FIG. 155, a lip 8141 defined by a distal end of the transducer base plate 8134 engages with a projection 8143 of the waveguide 8132 to prevent the proximal end of the waveguide 8132 from sliding out of the aperture 8136 after it has been torqued press fit. When fully assembled, the ultrasonic instrument 8130 is configured to transmit ultrasonic energy to the distal end of the waveguide 8152 along the longitudinal axis LA.

FIG. 156 is a perspective view of an ultrasonic surgical instrument 8150 configured in a D31 transducer architecture comprising separate ultrasonic waveguide 8152 and ultrasonic transducer base plate 8154 (e.g., a transducer mounting portion) components shown in a decoupled configuration, according to one aspect of this disclosure. The waveguide 8152 and the transducer base plate 8154 are coupled in a parallel tang joint attachment mechanism. FIG. 157 is a perspective view of the ultrasonic surgical instrument 8150 shown in FIG. 156 in a coupled configuration, according to one aspect of this disclosure. With reference to FIGS. 156 and 157, the ultrasonic surgical instrument 8150 may comprise multiple pieces to reduce material waste and provide the ability to use alternate materials and/or manufacturing methods for the waveguide 8152 and the transducer base plate 8154. In one aspect, the waveguide 8152 and the transducer base plate 8154 are made separately from flat metal stock suitable for transmitting ultrasonic vibrations such as titanium, titanium alloy, aluminum, or aluminum alloy, for example, as described herein. For example, the waveguide 8152 and the transducer base plate 8154 are two separate pieces. The transducer base plate 8154 defines flat faces 8153 on opposite sides of the transducer base plate 8154 suitable to attach and support a PZT piezoelectric element 8156 (not shown) on each flat face 8153 similar to the D31 configuration shown by way of example in FIG. 3.

Still with reference to FIGS. 156 and 157 a parallel tang joint attachment mechanism is disclosed to join the waveguide 8152 and the transducer base plate 8154. A proximal end of the waveguide 8152 is coupled to a distal end of the transducer base plate 8154. A recessed receptacle 8164 in the distal end of the transducer base plate 8154 is configured to accept the profile of a proximal end of the waveguide 8152. Fasteners 8158a, 8158b such as pins, screws, rivets, or other such mechanisms, are disposed through apertures 8160a, 8160b defined at the proximal end of the waveguide 8152 are received in corresponding apertures 8162a, 8162b defined by the recessed receptacle 8164 can be used to lock the waveguide 8152 and the transducer base plate 8154 in place. Alternatively, the waveguide 8152 and the transducer base plate 8154 can be spot welded in the recessed receptacle 8164. When fully assembled, the ultrasonic instrument 8150 is configured to transmit ultrasonic energy to the distal end of the waveguide 8152 along the longitudinal axis LA. The waveguide 8152 and the transducer base plate 8154 can be made of the same material or different materials suitable for transmitting ultrasonic energy along the longitudinal axis LA.

Still with reference to FIGS. 156 and 157, the ultrasonic surgical instrument 8150 may comprise multiple pieces to reduce material waste and provide the ability to use alternate materials and/or manufacturing methods for the waveguide 8152 and the transducer base plate 8154. In one aspect, the waveguide 8152 and the transducer base plate 8154 are made separately from flat metal stock suitable for transmitting ultrasonic vibrations such as titanium, titanium alloy, aluminum, or aluminum alloy, for example, as described herein. For example, the waveguide 8152 and the transducer base plate 8154 are two separate pieces. The transducer base plate 8154 defines flat faces 8153 on opposite sides of the transducer base plate 8154 suitable to attach and support a PZT piezoelectric element 8156 (not shown) on each flat face 8153 similar to the D31 configuration shown by way of example in FIG. 3.

FIG. 158 is a perspective view of an ultrasonic surgical instrument 8160 configured in a D31 transducer architecture comprising separate ultrasonic waveguide 8162 and ultrasonic transducer base plate 8164 (e.g., a transducer mounting portion) components shown in a decoupled configuration, according to one aspect of this disclosure. The waveguide 8162 includes a male threaded section 8166 and the transducer base plate 8164 includes a female threaded section 8172 in a U-shaped slot 8168 of the distal end 8170 of the transducer base plate 8164 to achieve a threaded joint 8171. The ultrasonic surgical instrument 8160 may comprise multiple pieces to reduce material waste and provide the ability to use alternate materials and/or manufacturing methods for the waveguide 8162 and the transducer base plate 8164. In one aspect, the waveguide 8162 and the transducer base plate 8164 are made separately from flat metal stock and can be made of the same material or different materials suitable for transmitting ultrasonic energy along the longitudinal axis LA such as titanium, titanium alloy, aluminum, or aluminum alloy, for example, as described herein. For example, the waveguide 8162 and the transducer base plate 8164 are two separate pieces joined by a threaded connection. The transducer base plate 8164 defines flat faces 8163a, 8163b on opposite sides of the transducer base plate 8164 suitable to attach and support a PZT piezoelectric element 8172a, 8172b on each flat face 8163a, 8163b similar to the D31 configuration shown by way of example in FIG. 3. The waveguide 8162 includes a male threaded section 8166 and the transducer base plate 8164 includes a female threaded section 8172 in a U-shaped slot 8168 of the distal end 8170 of the transducer base plate 8164.

FIG. 159 is a side view of the threaded joint 8171 showing the threaded section 8166 of the waveguide 8162 threaded into the threaded section 8172 of the transducer base plate 8164, according to one aspect of this disclosure. Once the waveguide 8162 is in threaded engagement with the transducer base plate 8164, a forming force F is applied by a forming press 8176 to the external walls of the U-shaped slot 8168 defining the threaded section 8172 to more securely attach the two components in place. The threaded section 8166 of the waveguide 8162 may be made as a separate component using Swiss screw machining, conventional lathe, thread forming on rod stock material, or similar techniques. The threaded section 8166 is joined to the flat waveguide 8162 section by way of lateral forming, forging, or similar process. Accordingly, the threads in the threaded section 8166 are not cut or formed on the flat waveguide 8162 section prior to the joining operation (by forming, forging, or similar process) and thus lowering the cost of the flat section of the waveguide 8162. In one aspect, the threads of the threaded section 8166 of the waveguide 8162 can be made during the forming, forging or similar process. In one aspect, the flat waveguide 8162 section is made from a formable grade of aluminum. The threaded section 8166, however, is made from a material that is harder than the waveguide 8162 material such as titanium.

FIG. 160 is a side view of an alternate threaded joint 7183 where the threaded section 8166 includes a rotational orientation section to provide rotary alignment about the longitudinal axis LA of the threaded section 8166 of the waveguide 8162, according to one aspect of this disclosure. The two joined sections of the waveguide 8162 and the transducer base plate 8164 are maintained by a flat cut 8174 formed on or near the proximal end of the threaded section 8166 of the threaded waveguide 8162, for example, at the very proximal end of the threaded section 8166. The flat cut 8174 is substantially parallel to the sides of the slot 8168 that receives the threaded section 8166 such that when the threaded section 8166 is formed, the flat 8174 portion of the threaded section 1866 section is threadingly engaged with the threaded section 8172 of the slot 8168. In one aspect, a laser may be used to fuse the waveguide 8162 and the transducer base plate 8164 at select points or interfaces of the waveguide 8162 and transducer base plate 8164. In another aspect, adhesive may be used to fuse the waveguide 8162 and the transducer base plate 8164 at select points or interfaces of the waveguide 8162 and transducer base plate 8164.

FIG. 161 is a perspective view of an ultrasonic surgical instrument 8180 configured in a D31 transducer architecture comprising separate ultrasonic waveguide 8182 and ultrasonic transducer base plate 8184 (e.g., a transducer mounting portion) components shown in a coupled configuration, according to one aspect of this disclosure. FIG. 162 is an exploded view of the ultrasonic surgical instrument 8180 shown in FIG. 161, according to one aspect of this disclosure. FIG. 163 is a section view of the ultrasonic surgical instrument 8180 shown in FIG. 161, according to one aspect of this disclosure.

With reference to FIGS. 161-163, the waveguide 8182 is attached to the transducer base plate 8184 by a threaded joint 8188. The ultrasonic surgical instrument 8180 may comprise multiple pieces to reduce material waste and provide the ability to use alternate materials and/or manufacturing methods for the waveguide 8182 and the transducer base plate 8184. In one aspect, the waveguide 8182 is made from round metal stock and the transducer base plate 8184 is made separately from flat metal stock. The metal for both components is suitable for transmitting ultrasonic vibrations and may be titanium, titanium alloy, aluminum, or aluminum alloy, for example, as described herein. For example, the waveguide 8182 and the transducer base plate 8184 are two separate pieces joined by a threaded joint 8188 and can be made of the same material or different materials suitable for transmitting ultrasonic energy along the longitudinal axis LA. This configuration enables the waveguide 8182 or transducer base plate 8184 to be replaced in the field. The transducer base plate 8184 defines flat faces 8183*a*, 8183*b* on opposite sides of the transducer base plate 8184 suitable to attach and support a PZT piezoelectric element 8186*a*, 8186*b* on each flat face 8183*a*, 8183*b* similar to the D31 configuration shown by way of example in FIG. 3.

As shown in FIGS. 161 and 162, the distal end of the waveguide 8182 defines a blade 8198 for treating tissue and a proximal end of the waveguide 8182 defines a conical feature 8190 that matches a complementary conical channel 8194 formed at a distal end of the transducer base plate 8184. The conical channel 8194 meets a cylindrical channel 8195 that is defined through the proximal end of the transducer base plate 8184. The conical feature 8190 of the waveguide 8182 includes female threads 8198 and is bolted to the transducer base plate 8184 by a screw 8192 that is inserted from the proximal end of the transducer base plate 8184 defining a countersunk aperture 8196, for example, through the cylindrical aperture 8195, and screws into the female threads 8198 defined by the conical feature 8190 of the waveguide 8182. In use, the ultrasonic vibrational movement is transmitted from the transducer base plate 8184 to the waveguide 8182 along the longitudinal axis LA through the respective conical surfaces 8190, 8194 in contact. The angle of the conical features is selected such that the compression on their surfaces in contact is high, while the screw is exposed to a low stress, so it can be small. The transducer base plate 8184 can be made of aluminum or other suitable metal material. This is advantageous in terms of low cost, availability, ease of machining, and thermal conductivity for the heat management of the piezoelectric elements 8186*a*, 8186*b*.

FIG. 164 is a perspective view of an ultrasonic surgical instrument 8200 configured in a D31 transducer architecture comprising separate ultrasonic waveguide 8202 and ultrasonic transducer base plate 8204 (e.g., a transducer mounting portion) components shown in a coupled configuration, according to one aspect of this disclosure. FIG. 165 is an exploded view of the ultrasonic surgical instrument 8200 shown in FIG. 164, according to one aspect of this disclosure. With reference to FIGS. 164 and 165, the waveguide 8202 is attached to the transducer base plate 8204 by an interference flange joint 8208. The transducer base plate 8204 defines flat faces 8203*a*, 8203*b* on opposite sides of the transducer base plate 8204 suitable to attach and support a PZT piezoelectric element on each flat face 8203*a*, 8203*b* similar to the D31 configuration shown by way of example in FIG. 3.

The ultrasonic surgical instrument 8200 may comprise multiple pieces to reduce material waste and provide the ability to use alternate materials and/or manufacturing methods for the waveguide 8202 and the transducer base plate 8204. In one aspect, the waveguide 8202 and the transducer base plate 8204 are made separately from flat metal stock. The metal for both components is suitable for transmitting ultrasonic vibrations and may be titanium, titanium alloy, aluminum, or aluminum alloy, for example, as described herein. For example, the waveguide 8202 may be made of titanium or titanium alloy and the transducer base plate 8204 may be made of aluminum or aluminum alloy and joined by the interference flange joint 8208. This configuration enables the waveguide 8202 or transducer base plate 8204 to be replaced in the field. The transducer base plate 8204 can be made of aluminum or other suitable metal material. This is advantageous in terms of low cost, availability, ease of machining, and thermal conductivity for the heat management of the piezoelectric elements. The waveguide 8292 and the transducer base plate 8204 can be made of the same material or different materials suitable for transmitting ultrasonic energy along the longitudinal axis LA.

As shown in FIGS. 164 and 165, the distal end of the waveguide 8202 defines a blade 8216 for treating tissue and a proximal end of the waveguide 8202 defines a flange 8212 that is complementary and mates with a flange 8214 defined at the distal end of the transducer base plate 8204. The waveguide flange 8212 defines an aperture 8210 sized and configured to receive a pin 8206 defined by the transducer base plate flange 8214 sized and configured to achieve an interference flange joint 8208 between the waveguide 8202 and the transducer base plate 8204. In the illustrated example, the transducer base plate 8204 includes an integral machined pin 8206. The waveguide flange 8212 defines a recessed area 8213 that mates with a recessed area 8215 defined by the transducer base plate flange 8214.

FIG. 166 illustrates the waveguide flange 8212, shown in dashed line form, and the transducer base plate flange 8214, shown in solid line form, superimposed in a decoupled configuration, according to one aspect of this disclosure. At room temperature prior to assembly, the length of the waveguide flange 8212 and the transducer base plate flange 8214 is $L_1$. In this arrangement, at room temperature, the length $L_1$ of the flanges 8212, 8214 is slightly longer than the recessed area 8213, 8215 in the mating component, depicted by δ in FIG. 166. Additionally, the aperture 8210 defined by the waveguide flange 8212 is slightly offset on the waveguide flange 8212 such that at room temperature the waveguide 8202 and the transducer base plate 8204 cannot be seated together due to inadequate axial clearance between the pin 8206 and the recess area 8215 in the transducer base plate flange 8214.

FIG. 167 illustrates the waveguide 8202 and the transducer base plate 8204 in a coupled configuration, according to one aspect of this disclosure. To assemble the waveguide 8202 and the transducer base plate 8204, extreme cold is applied to both waveguide 8202 and transducer base plate 8204 components, thereby shrinking the axial extent of the corresponding flanges 8212, 8214. The waveguide 8202 and transducer base plate 8204 components are assembled under the cold condition, and when they return to room temperature or above, the flanges 82122, 8214, pin 8206, and aperture 8210 bind with each other. In the assembled state the length of the waveguide flange 8212 and the transducer base plate flange 8214 is $L_2$, where $L_2 < L_1$. A nominal compressive load therefore exists in the parts at all times and a corresponding shear load, v, at the pin 8206, to achieve an interference flange joint 8208. The pin 8206 configuration accommodates this nominal shear load and for strength of the pin 8206, the transducer base plate 8204 component may be made of a metal that has higher strength than aluminum, such as titanium, for example. Nevertheless, an aluminum alloy may be employed to accommodate the shear force requirements of the pin 8206.

FIG. 168 is a perspective view of an ultrasonic surgical instrument 8220 configured in a D31 transducer architecture comprising separate ultrasonic waveguide 8222 and ultrasonic transducer base plate 8224 (e.g., a transducer mounting portion) components shown in a coupled configuration, according to one aspect of this disclosure. FIG. 169 is an exploded view of the ultrasonic surgical instrument 8220 shown in FIG. 168, according to one aspect of this disclosure. With reference to FIGS. 168 and 169, the waveguide 8222 is attached to the transducer base plate 8224 by an interference pin joint 8228. The transducer base plate 8224 defines flat faces 8223a, 8223b on opposite sides of the transducer base plate 8224 suitable to attach and support a PZT piezoelectric element on each flat face 8223a, 8223b similar to the D31 configuration shown by way of example in FIG. 3.

The ultrasonic surgical instrument 8220 may comprise multiple pieces to reduce material waste and provide the ability to use alternate materials and/or manufacturing methods for the waveguide 8222 and the transducer base plate 8224. In one aspect, the waveguide 8222 and the transducer base plate 8224 are made separately from flat metal stock. The metal for both components is suitable for transmitting ultrasonic vibrations and may be titanium, titanium alloy, aluminum, or aluminum alloy, for example, as described herein. For example, the waveguide 8222 may be made of titanium or titanium alloy and the transducer base plate 8224 may be made of aluminum or aluminum alloy and joined by the interference pin joint 8228. This configuration enables the waveguide 8222 or transducer base plate 8224 to be replaced in the field. The transducer base plate 8224 can be made of aluminum or other suitable metal material. This is advantageous in terms of low cost, availability, ease of machining, and thermal conductivity for the heat management of the piezoelectric elements. The waveguide 8222 and the transducer base plate 8224 can be made of the same material or different materials suitable for transmitting ultrasonic energy along the longitudinal axis LA.

As shown in FIGS. 168 and 169, the distal end of the waveguide 8222 defines a blade 8238 for treating tissue and a proximal end of the waveguide 8222 defines a flange 8234 that matches a flange 8236 defined at the distal end of the transducer base plate 8224. The waveguide flange 8234 defines an aperture 8230 sized and configured to receive a shaft 8228 of a pin 8225, shown in section view in FIG. 170, sized and configured to achieve an interference pin joint 8228 between the waveguide 8222 and the transducer base plate 8224. The aperture 8230 includes a counter bore to accommodate the head 8226 of the pin 8225. In the illustrated example, the transducer base plate 8224 also includes an aperture 8232 sized and configured to receive the shaft 8228 of the pin 8225. The waveguide flange 8212 defines a recessed area 8213 that mates with a recessed area 8215 defined by the transducer base plate flange 8214. The pin 8225 may be made of steel or other metal having high shear strength.

With reference to FIGS. 168-170, joining the dissimilar materials and components of the waveguide 8222 and the transducer base plate 8224 in a D31 configuration is achieved using an interference fit pin joint 8228. The diameter $\Phi_1$ of the shaft 8228 of the joint pin 8225 at very low temperature equals the diameter $\Phi_2$ of both apertures 8230, 8232 in the waveguide 8222 and the transducer base plate 8224 when these components are at high temperature. Assembly of the waveguide 8222 and the transducer base plate 8224 is performed under this thermal mismatch condition and when the waveguide 8222 and transducer base plate 8224 components cool/warm to a uniform temperature, the pin 8225 achieves an interference fit joint 8228 and joins both the waveguide 8222 and the transducer base plate 8224. The interference fit joint 8228 at the pin 8225 creates the continuity of material required to transfer the ultrasonic vibrations along the longitudinal axis LA from the transducer base plate 8224 through the waveguide 8222 to the blade 8238.

FIG. 171 is a perspective view of an ultrasonic surgical instrument 8240 configured in a D31 transducer architecture comprising separate ultrasonic waveguide 8242 and ultrasonic transducer base plate 8244 (e.g., a transducer mounting portion) components shown in a coupled configuration, according to one aspect of this disclosure. FIG. 172 is an exploded view of the ultrasonic surgical instrument 8240 shown in FIG. 171, according to one aspect of this disclosure. With reference to FIGS. 171 and 172, the waveguide 8242 is attached to the transducer base plate 8244 by a wedge joint 8249. The ultrasonic surgical instrument 8240 may comprise multiple pieces to reduce material waste and provide the ability to use alternate materials and/or manufacturing methods for the waveguide 8242 and the transducer base plate 8244. In one aspect, the waveguide 8242 and the transducer base plate 8244 are made separately from flat metal stock. The metal for both components is suitable for transmitting ultrasonic vibrations and may be titanium, titanium alloy, aluminum, or aluminum alloy, for example, as described herein. For example, the waveguide 8242 and the transducer base plate 8244 are two separate pieces joined by a wedge joint 8249. This configuration enables the waveguide 8242 or transducer base plate 8244 to be replaced in the field. The transducer base plate 8244 defines flat faces 8243a, 8243b on opposite sides of the transducer base plate 8244 suitable to attach and support a PZT piezoelectric element 8246a, 8246b on each flat face 8243a, 8243b similar to the D31 configuration shown by way of example in FIG. 3. The transducer base plate 8244 can be made of aluminum. This is advantageous in terms of low cost, availability, ease of machining, and thermal conductivity for the heat management of the piezoelectric elements 8246a, 8246b. The waveguide 8242 and the transducer base plate 8244 can be made of the same material or different materials suitable for transmitting ultrasonic energy along the longitudinal axis LA.

As shown in FIGS. 171 and 172, the distal end of the waveguide 8242 defines a blade 8253 for treating tissue and a proximal end of the waveguide 8242 defines a wedge 8247 feature that matches a notch 8260 in the distal end of the transducer base plate 8244. The wedge 8247 defines two tapered sidewalls 8248a, 8248b that match tapered sidewalls 8258a, 8258b that define the notch 8260. The waveguide 8242 is bolted to the transducer base plate 8244 by two screws 8250a, 8250b that are received through countersunk apertures 8254a, 8254b defined by flanges laterally disposed from the wedge 8247 feature defined by the proximal end of the waveguide 8244. The screws 8250a, 8250b are threadably fastened to the transducer base plate 8244 via threaded apertures 8256a, 8256b. In use, the ultrasonic vibrational movement is transmitted along the longitudinal axis LA from the transducer base late 8244 through the waveguide 8242 to the blade 8253 through the surfaces 8248a, 8248b, 8258a, 8258b of the wedge 8247 and notch 8260. The angle of the wedge 8247 and notch 8260 may be selected such that the compression on their surfaces 8248a, 8248b, 8258a, 8258b in contact is high, while the screws 8250a, 8250b are exposed to a low stress, so they can be small.

FIG. 173 is a perspective view of a luer lock joint 8282 suitable for coupling ultrasonic waveguide 8272 and ultrasonic transducer base plate 8274 (e.g., a transducer mounting portion) components of a two-piece ultrasonic surgical instrument 8270, according to one aspect of this disclosure. FIG. 174 is a section view of the luer lock joint 8282 in a coupled configuration, according to one aspect of this disclosure. FIG. 175 is a luer nut 8276 component of the luer lock joint shown in FIG. 173 and FIG. 176 is perspective view of the luer lock joint 8282 shown in FIG. 173 in a coupled configuration, according to one aspect of this disclosure.

With reference to FIGS. 173-176, the waveguide 8272 is attached to the transducer base plate 8274 by luer lock joint 8282. The ultrasonic surgical instrument 8270 may comprise multiple pieces to reduce material waste and provide the ability to use alternate materials and/or manufacturing methods for the waveguide 8272 and the transducer base plate 8274. In one aspect, the waveguide 8272 and the transducer base plate 8274 are made separately from flat metal stock. The metal for both components is suitable for transmitting ultrasonic vibrations and may be titanium, titanium alloy, aluminum, or aluminum alloy, for example, as described herein. For example, the waveguide 8272 and the transducer base plate 8274 are two separate pieces joined by a luer lock joint 8282. This configuration enables the waveguide 8272 or transducer base plate 8274 to be replaced in the field. Although not shown, the transducer base plate 8274 defines flat faces on opposite sides of the transducer base plate suitable to attach and support a PZT piezoelectric element on each flat face similar to the D31 configuration shown by way of example in FIG. 3. The transducer base plate 8274 can be made of aluminum. This is advantageous in terms of low cost, availability, ease of machining, and thermal conductivity for the heat management of the piezoelectric elements. The waveguide 8272 and the transducer base plate 8274 can be made of the same material or different materials suitable for transmitting ultrasonic energy along the longitudinal axis LA.

With reference now particularly to FIGS. 173 and 174, the luer nut 8276 defines an interior region 8280 to slidably engage the waveguide 8272. As the luer nut 8276 is retracted 8275 proximally the luer nut 8276 (shown in dashed line form) engages male luer lock threads 8278 defined at a distal end of the transducer base plate 8274. Applying a clockwise rotation 8279 causes the threads 8284 defined by a cylindrical sidewall 8286 of the luer nut 8276. Base wall portions 8277a, 8277b act as a stop for the luer nut 8276. Either the transducer base plate 8274 or the waveguide 8272 may have a luer like male thread 8278 made into its shape. In the illustrated example, a half turn luer nut 8276 fits over the waveguide 8272 and screws into the transducer base plate 8274 to lock the two components together. The luer lock thread 8278 is two-dimensional on the screw side at the distal end of the transducer base plate 8274 and is compatible for use with simple shapes like a flat waveguide 8272, for example.

The following description is directed to techniques for manufacturing three-piece ultrasonic surgical instruments. In one aspect, the ultrasonic surgical instrument comprises an ultrasonic transducer base plate, an ultrasonic waveguide shaft, and an ultrasonic transducer. The transducer base plate may be coupled the waveguide shaft by the techniques described herein in connection with FIGS. 133-176, for example. The waveguide shaft may be coupled to the ultrasonic blade by swaging the two components. It will be appreciated that swaging is a forging process in which the dimensions of an item are altered using dies into which the item is forced. Although swaging is usually a cold working process, it also may be hot worked. The term swage may apply to the process or a die or tool used in the process. In one aspect, the swaging process may be employed to join the transducer base plate and the waveguide shaft. Generally, the transducer base plate, waveguide shaft, and ultrasonic blade may be made from dissimilar metals that are suitable for transmitting ultrasonic vibrations along a longitudinal axis. For example, the swaging process may be employed to join aluminum (or alloys thereof) ultrasonic transducer base plates to titanium (or alloys thereof) ultrasonic waveguides. Additionally, the swaging process may be employed to join aluminum waveguides to titanium (or alloys thereof) ultrasonic blades. The following description provides configurations, tooling, and processes suitable for swaging certain aluminum ultrasonic waveguide shafts to certain titanium ultrasonic blades.

Biomedical titanium alloys such as wrought Ti-6Al-4V alloy of extra low interstitial (ELI) grade has been used in the biomedical applications because of its high strength-to-weight ratio and excellent biocompatibility. ELI is the only readily available practical material known to date that has both enough hardness and high enough Q (Resonance Loss Factor Value) to be functionally suitable for use in the ultrasonic medical devices as both an ultrasonic blade and an ultrasonic acoustical waveguide system, i.e., transmitting ultrasonic energy as a transducer core. Wrought Ti-6Al-4V alloy, however, is a relatively expensive material to produce; both in the raw foundry wrought material and followed by machining into a functional part, versus machined wrought Al 6061-T6 or Al7075-T6 alloys, which because they are less hard are less suitable for maintaining the robust surgical ultrasonic blade edge of the medical device. Wrought Al 6061-T6 or Al7075-T6 alloys, however, do have suitable ultrasonic energy transmission properties nearly identical to Ti-6Al-4V ELI alloy at less than half the material and production costs of the one-piece wrought Ti-6Al-4V ELI alloy based ultrasonic medical device.

FIG. 177 is a perspective view of an ultrasonic waveguide 8300 for an ultrasonic surgical instrument comprising an ultrasonic waveguide shaft 8302 made of one metal and coupled to an ultrasonic blade 8306 made of a dissimilar metal, according to aspect of this disclosure. The waveguide shaft 8302 includes a coupler 8304 at a proximal end to increase retention and reduce rotation between the distal tip of the ultrasonic waveguide 8300 and the waveguide shaft 8302. An ultrasonic blade 8306 is coupled to a distal end of the waveguide shaft 8302 at a swaged joint 8309. The proximal end of the ultrasonic blade 8306 includes a cylindrical wall 8309 sized and configured to receive a distal end of the waveguide shaft 8302 for the swaging process. In one aspect the waveguide shaft 8302 may be made of wrought Al 6061-T6 or Al7075-T6 aluminum alloys and the ultrasonic blade 8306 may be made of wrought Ti-6Al-4V ELI titanium alloy.

FIG. 178 is a magnified view of the coupler 8304, according to one aspect of this disclosure. The coupler 8304 comprises a retention feature 8318 in the form of a longitudinal groove to increase retention and reduce rotation between the blade 8306 and the waveguide shaft 8302. The coupler 8304 further comprises cylindrical walls 8312, 8316 and annular grooves 8313, 8314 to couple the waveguide shaft 8302 to an ultrasonic base plate as described herein in connection with FIGS. 133-176, for example. The coupler 8304 may be formed integrally with or coupled to the waveguide shaft 8302. A cylindrical wall 8310 is sized and configured to receive the distal end of the coupler 8304.

Presented here is a unique permanent mechanical swaged joint 8309 design and warm draw die swaging process to achieve a reliable robust mechanical swaged joint 8309 between the ultrasonic waveguide shaft 8302 and the ultrasonic blade 8306 that maintains a desirable elastic acoustic wrought microcrystalline grain structure of both the titanium and aluminum alloy materials that are efficient in transmitting ultrasonic energy with minimal to no loss due to the swaged joint 8309 formed between the two materials, and is as acceptably functional as an titanium alloy (e.g., Ti-6Al-4V ELI titanium alloy) ultrasonic medical device.

This configuration provides an ultrasonic waveguide 8300 at about half the cost to manufacture relative to an all titanium alloy (e.g., Ti-6Al-4V ELI titanium alloy) ultrasonic medical device. Other welding joining processes such as solid state, friction, inertia, ultrasonic, electron beam and laser welding between the aluminum waveguide shaft 8302 and the titanium blade 8306 where tried but did not produce acceptable joints of sufficient functional strength to transmit the required ultrasonic energy without joint failure. Also within the weld zone the material microstructure is changed from wrought (acceptable high Q) to annealed (less than desirable low Q) resulting in local damping of the ultrasonic wave within the waveguide 8300.

FIG. 179 is a section view of a swaged joint 8320 between a two-piece ultrasonic tool comprising an ultrasonic waveguide shaft 8324 made of one metal and an ultrasonic blade 8322 made of a different metal, according to one aspect of his disclosure. Prior to applying the swaging process, the waveguide shaft 8324 defines a cylindrical aperture with a flat perpendicular bottom 8328. The ultrasonic blade 8322 includes a conical male end 8326 defining a conic taper 8323 that is received into the cylindrical aperture defined by the waveguide shaft 8324. The proximal end of the conical male end 8326 defines a flat perpendicular bottom 8325 that should abut the flat perpendicular bottom 8328 defined by the waveguide shaft 8324. After the conical male end 8326 is inserted into the cylindrical aperture defined by the waveguide shaft 8324 the swaging process is applied to produce the swaged joint 8320 shown in FIG. 179.

The swaged joint 8320 is achieved by joining the proximal end of the ultrasonic blade 8322 having a male end 8326 defining a conical shape into the cylindrical aperture defined by the distal end of the waveguide shaft 8324. The length L of conical male end 8326 of the blade 8322 is approximately twice the length of the major diameter $\Phi_1$ of the male end 8326 of the ultrasonic blade 8322 and has a conic taper 8323 of 2°-6° to the minor diameter $\Phi_2$. The conical shape male end 8326 defines a flat perpendicular proximal bottom 8325. In one aspect, the ultrasonic blade 8322 is made of a Ti-6Al-4V ELI titanium alloy and the waveguide shaft 8324 is made of Al 6061-T6 or Al7075-T6 aluminum alloys. The conical shape male end 8326 is located on the proximal end of the Ti-6Al-4V ELI titanium alloy blade 8322 component and fits into the blind cylindrical aperture defined by the Al 6061-T6 or Al7075-T6 aluminum alloy waveguide shaft 8324 component. The blind cylindrical aperture in the waveguide shaft 8324 defines a flat, perpendicular bottom 8328 and is the same diameter $\Phi_1$ as the conical male end 8326 of the blade 8322. A collar 8329 (also see collar 8308 in FIG. 178) of additional material is provided around the outside diameter of the blind cylindrical aperture such that there is additional material (2°-6°) to flow plastically around the shape of the conical male end 8326 during the swaging process, filling the void and resulting in a retained linear compression between the flat bottom 8325 of the conical male end 8326 and the flat bottom 8328 of the blind cylindrical aperture of the waveguide shaft 8324, as well as around the conical male end 8326. The swaged joint 8320 shown in FIG. 50, however, defines gaps $g_1$ and $g_2$, which leads to lower performance. The aspect illustrated in FIG. 180 removes the gaps $g_1$ and $g_2$ during the swaging process.

FIG. 180 is a section view of a swaged joint 8330 achieved between a two-piece ultrasonic waveguide 8300 (FIGS. 177, 178, 184) comprising an ultrasonic waveguide shaft 8334 made of one metal and an ultrasonic blade 8332 made of a different metal, according to one aspect of his disclosure. FIGS. 181-184 show the steps for producing the swaged joint 8330 shown in FIG. 180, according to one aspect of this disclosure, where FIG. 181 is a section view of the waveguide shaft 8334 and the ultrasonic blade 8334 in a decoupled configuration, FIG. 182 is a section view of a pre-assembly 8331 of the waveguide shaft 8334 and the ultrasonic blade 8334 in a coupled configuration prior to applying the swaging process, FIG. 183 is a section view of the waveguide shaft 8334 and the ultrasonic blade 8334 in a coupled after the application of the swaging process, and FIG. 184 is a section view of joined ultrasonic waveguide 8300 showing the waveguide shaft 8334 coupled to the ultrasonic blade 8332, according to one aspect of this disclosure. The ultrasonic blade 8332 comprises a tissue treatment portion 8344 located at a distal end of the ultrasonic blade 8332, which is used to effect tissue in contact therewith.

With reference now to FIGS. 180-184, prior to applying the swaging process, the waveguide shaft 8334 defines a cylindrical aperture 8348 with a flat perpendicular bottom 8338. The ultrasonic blade 8332 includes a male end 8336 defining a conical shape defining a conic taper 8333 that is received into the cylindrical aperture 8348 defined by the waveguide shaft 8334. The proximal end of the conical male end 8336 defines a flat perpendicular bottom 8335 that should abut the flat perpendicular bottom 8338 defined by the waveguide shaft 8334. After the conical male end 8336 is inserted into the cylindrical aperture 8348 defined by the waveguide shaft 8334 the swaging process is applied to produce the swaged joint 8330 shown in FIG. 180. Two circumferential grooves 8340, 8342 are defined about the conical male end 8336 of the blade 8332, one groove 8340 located near or at the smallest diameter $\Phi_2$ and one groove 8342 located between the smallest $\Phi_2$ and largest $\Phi_1$ diameters of the conical male end 8336 of the ultrasonic blade 8332. In one aspect, the one groove 8342 is located mid-way between the smallest $\Phi_2$ and largest $\Phi_1$ diameters of the conical male end 8336. In one aspect, the ultrasonic blade 8322 is made of a Ti-6Al-4V ELI titanium alloy and the waveguide shaft 8324 is made of Al 6061-T6 or Al7075-T6 aluminum alloys. The circumferential grooves 8340, 8342 define a space for the waveguide shaft 8334 material to flow during the swaging process to eliminate the gaps $g_1$, $g_2$ as shown in FIG. 179, thus improving performance loss and providing additional features to improve retention of the ultrasonic blade 8322 component in the waveguide shaft 8334 component.

Other features of the conical male end 836 of the ultrasonic blade 8332 are similar to the features described in connection with FIG. 179. For example, the swaged joint 8330 is achieved by joining the conical male end 8336 of the ultrasonic blade 8332 into the cylindrical aperture 8348 8 defined by the distal end of the waveguide shaft 8334. The length L of conical male end 8336 of the ultrasonic blade 8332 is approximately twice the length of the major diameter $\Phi_1$ of the conical male end 8336 of the ultrasonic blade 8332 and has a conic taper 8333 of 2°-6° to the minor diameter $\Phi_2$. The conical male end 8336 defines a flat perpendicular proximal bottom 8335. In one aspect, the conical male end 8336 is located on the proximal end of a Ti-6Al-4V ELI titanium alloy blade 8322 component and fits into the blind cylindrical aperture 8348 defined by an Al 6061-T6 or Al7075-T6 aluminum alloy waveguide shaft 8334 component. The blind cylindrical aperture 8348 in the waveguide shaft 8334 defines a flat, perpendicular bottom 8338 and is the same diameter $\Phi_1$ as the conical male end 8336 of the ultrasonic blade 8332. A collar 8339 (see also collar 8308 in FIG. 178) of additional material is provided about the outside diameter of the blind cylindrical aperture 8348 such that there is additional material (2°-6°) to flow plastically around the shape of the conical male end 8336 during the swaging process, and filling the void defined by the circumferential grooves 8340, 8342 resulting in a retained linear compression between the flat bottom 8335 of the conical male end 8336 and the flat bottom 8338 of the blind cylindrical aperture 8348 of the waveguide shaft 8334, as well as around the conical male end 8336.

The description now turns to a method of producing the ultrasonic waveguide 8300 by creating the swaged joint 8330 as discussed in connection with FIGS. 180-184 using a warm die swaging process, according to one aspect of this disclosure. FIG. 185 is a section view of a heated draw die tool 8400 and FIG. 186 is a detail section view of the draw die tool 8400 shown in FIG. 185, according to one aspect of this disclosure. With reference now to FIGS. 185 and 186, The heated draw die tool 8400 includes a base clamp 8402 to hold the pre-assembly 8331 (FIG. 182). A draw die 8404 is located above the base clamp 8402. The draw die 8404 defines an aperture 8406 to receive the pre-assembly 8331 (FIG. 182). A cylinder 8408 thermally coupled to a heating element 8410 surrounds the draw die 8404 to heat the draw die 8404. A circular die tool cylinder 8412 defines a sample chamber 8414. The distal end of the pre-assembly 8331 is located in the sample chamber 8414. A load F is applied to the circular die tool cylinder 8412 to press the pre-assembly 8331 through the draw die 8404.

With reference to FIGS. 181-186, the heated draw die process starts by inserting the pre-assembly 8331 through the heated draw die tool 8400, which incorporates mechanical position stops to accurately locate the pre-assembly 8331 with linear straightness respect to each other and in alignment with the location of the draw die 8404. The circular die tool cylinder 8412 presses the pre-assembly 8331 through the draw die 8404, which by generating pressure equally compresses (upsets) the Al 6061-T6 or Al7075-T6 aluminum alloy material of the waveguide shaft 8334 about the external circumference of the pre-assembly 8331 in the exact location of the blind cylindrical hole 8348 and Ti-6Al-4V ELI titanium alloy conical male end 8336 of the ultrasonic blade 8332, causing the Al 6061-T6 or Al7075-T6 aluminum alloy material to become plastic and uniformly reduce the hoop area, accounting for the spring back of the metal, to be permanently formed about the length and circumference of the Ti-6Al-4V ELI titanium alloy conical male end 8336, and retaining the waveguide shaft 8334 and ultrasonic blade 8332 components securely and permanently. Additionally, the Al 6061-T6 or Al7075-T6 aluminum alloy material of the waveguide shaft 8334 is heated by the heating element 8410 and cylinder 8408 to not more than 400° F. to facilitate additional plastic flow without loss of the wrought material properties or cracking/rupturing of the material.

The ultrasonic waveguide 8300 manufactured by this swaging process produces a two-piece assembly comprising the waveguide shaft 8302 and the ultrasonic blade 8306, that function similar to an ultrasonic surgical instrument component produced of a single homogeneous component material. In one aspect, the two-piece swaged ultrasonic waveguide 8300 functions well within the power requirement without significant thermal self-heating, achieves acceptable frequency lock, and achieves functional transverse and longitudinal displacement without breaking. The Al 7075-T6/

Ti-6Al-4V ELI aluminum alloy/titanium alloy two-piece swaged waveguide 8300 functions substantially similar to a one-piece wrought Ti-6Al-4V ELI titanium alloy waveguide.

FIG. 187 is a side view of a two-piece ultrasonic waveguide 8350 comprising a waveguide shaft 8354 coupled to an ultrasonic blade 8352 by a swaged joint 8370 using the swaging process described in connection with FIGS. 177-186, according to one aspect of this disclosure. FIG. 188 is a section view of the swaged joint 8370 formed between the waveguide shaft 8354 and the ultrasonic blade 8352, according to one aspect of this disclosure. A side view of the waveguide shaft 8354 is shown in FIG. 189. A side view of the ultrasonic blade 8352 is shown in FIG. 190 and a plan view of the ultrasonic blade 8352 is shown in FIG. 191. The distal end of the ultrasonic blade 8352 defines a treatment portion 8360 for treating tissue is contact therewith. The proximal end of the ultrasonic blade 8352 is joined to the waveguide shaft 8354 at a collar 8358 portion about the cylindrical aperture located at the distal end of the waveguide shaft 8354. The distal end of the ultrasonic blade defines a male conical end 8356, which is received inside a cylindrical aperture 8362 defined by the collar portion 8359 of the shaft 8354. The male conical end 8356 defines two circumferential grooves 8364, 8366 to improve performance loss and retention of the ultrasonic blade 8352 component in the waveguide shaft 8354 component.

FIG. 192 illustrates an ultrasonic surgical instrument 8500 comprising an ultrasonic waveguide 8502 coupled to an offset ultrasonic transducer baseplate 8504, according to one aspect of this disclosure. The transducer baseplate 8504 defines a flat face 8503a on each side to receive a PZT piezoelectric element 8506a on each side. The transducer baseplate 8504 defines a first longitudinal axis LA1 and the waveguide 8502 defines a second longitudinal axis LA, where the longitudinal axes are offset relative to each other.

FIG. 193 illustrates two metal substrates 8510 components of the ultrasonic surgical instrument 8500 shown in FIG. 192 arranged in a complementary orientation for stamping or punching, according to one aspect of this disclosure. Offsetting the proximal transducer baseplate 8504 end of the ultrasonic surgical instrument allows the substrates 8510 to be oriented in the complementary orientation to minimize material waste and maximize efficiency in material when the substrates are punched or stamped out of sheet metal. In various aspects, the sheet metal is titanium, titanium alloy, aluminum, aluminum alloy, among others.

FIG. 194 is an ultrasonic surgical instrument 8600 configured in a D31 transducer architecture comprising separate ultrasonic waveguide 8602 and ultrasonic transducer base plate 8604 (e.g., a transducer mounting portion) components shown in a coupled configuration, according to one aspect of this disclosure. FIG. 195 is a side view of the ultrasonic blade 8602, according to one aspect of this disclosure. With reference now to FIGS. 194 and 195, the ultrasonic blade 8602 pivots about pivot point 8616 into a groove 8608 formed in the transducer baseplate 8604 with increasing interference as it rotates 8610. The ultrasonic blade 8602 includes a window 8612 defining a slot 8614 to engage a pin 8606 in the groove 8608. The ultrasonic blade 8602 assembles to the transducer base plate 8604 at an angle θ and is then rotated 8610 while the blade 8602 rotating interface increases at the proximal end of the blade 8602 with the groove 8608 in the transducer baseplate 8604.

FIG. 196 is an exploded view of an ultrasonic surgical instrument 8700 configured in a D31 transducer architecture comprising separate ultrasonic waveguide 8702 and symmetric two-piece clamshell housing components 8704a, 8704b to support ultrasonic transducer PZT piezoelectric elements 8706a, 8706b, according to one aspect of this disclosure. FIG. 197 is an assembled view of the ultrasonic surgical instrument 8700 shown in FIG. 196, according to one aspect of this disclosure. With reference now to FIGS. 196 and 197, a proximal end of the ultrasonic blade 6702 defines a T-shaped male connector 8712 that is received in corresponding T-shaped pockets 8714a, 8714b defined in respective top and bottom clamshell housing components 8704a, 8704b. The symmetric two-piece clamshell housing components 8704a, 8704b defines recessed pockets 8716a, 8716b to retain PZT piezoelectric elements 8706a, 8706b. The T-shaped pockets 8714a, 8714b are press fit to the T-shaped male connector 8712 of the ultrasonic blade 8702 when the two-piece clamshell housing components 8704a, 8704b are pressed together. An electrode 8708 is disposed between the PZT piezoelectric elements 8706a, 8706b and an electrically conductive element (e.g., wire tail) is disposed through an aperture 8718 defined in the top clamshell housing component 8704a. Each of the two-piece clamshell housing components 8704a, 8704b is made of an electrically conductive material and act as the other electrode. The clamshell housing components 8704a, 8704b are also thermally conductive and act as a heat sink. The clamshell housing components 8704a, 8704b are either pressed, bolted, banded, or welded together.

FIG. 198 is a perspective view of an ultrasonic surgical instrument 8800 configured in a D31 transducer architecture comprising separate ultrasonic waveguide 8802 and a two-piece ultrasonic transducer base plate 8804a, 8804b (e.g., a transducer mounting portion) to support PZT piezoelectric elements 8808a, 8808b, according to one aspect of this disclosure. FIG. 199 is an exploded view of the ultrasonic surgical instrument 8800 shown in FIG. 198, according to one aspect of this disclosure. With reference now to FIGS. 198 and 199, a distal end of the ultrasonic waveguide 8802 defines a blade 8806 for treating tissue in contact therewith. The ultrasonic surgical instrument 8800 comprises three sections joined together by bonding, resin, or brazing. A central section is the waveguide 8802 and lateral sections 8804a, 8804b are added to increase the width as needed to support the PZT piezoelectric elements 8808a, 8808b. This technique saves material and saves valuable titanium or titanium alloy compared with the method of machining the waveguide and transducer base plate out of a single material blank.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

An ultrasonic surgical instrument, comprising: a waveguide comprising a distal end configured as a blade and a proximal end configured to couple to a transducer base plate; and the transducer base plate comprising a distal end coupled to the proximal end of the waveguide to define a joint at an interface between the waveguide and the transducer base plate, the transducer base plate comprising a first and second sides defining corresponding first and second flat faces, wherein the first flat face is configured to receive a first piezoelectric element and the second flat face is configured to receive a second piezoelectric element, wherein the first and second piezoelectric elements are configured to operate in a D31 mode.

Example 2

The ultrasonic surgical instrument of Example 1, wherein the waveguide is made of a first material and the transducer base plate is made of a second material that is different from the first material.

Example 3

The ultrasonic surgical instrument of Example 1 or Example 2, wherein the first material comprises titanium or a titanium alloy and the second material comprises aluminum or an aluminum alloy.

Example 4

The ultrasonic surgical instrument of one or more of Example 1 through Example 3, wherein the proximal end of the waveguide defines a jigsaw puzzle piece and the distal end of the transducer base plate defines a complementary mating jigsaw puzzle piece configured to receive the jigsaw puzzle piece defined by the proximal end of the waveguide.

Example 5

The ultrasonic surgical instrument of Example 4, wherein the proximal end of the waveguide defines a tapered end and the distal end of the transducer base plate defines an aperture defining a tapered wall, wherein the aperture is configured to receive the tapered end to form an interference joint.

Example 6

The ultrasonic surgical instrument of one or more of Example 4 through Example 5, wherein the waveguide defines at least one female jigsaw puzzle piece on a first side and the transducer base plate defines at least one male jigsaw puzzle piece configured to receive the at least one female jigsaw puzzle piece to form a thermal expansion joint.

Example 7

The ultrasonic surgical instrument of one or more of Example 4 through Example 6, further comprising a C-shaped pin press fit between the proximal end of the waveguide and the distal end of the transducer base plate.

Example 8

The ultrasonic surgical instrument of one or more of Example 1 through Example 7, wherein the proximal end of the waveguide defines at least two bumps and the distal end of the transducer base plate defines an aperture that defines at least two apertures, wherein the aperture is configured to receive the proximal end of the waveguide and the at least two bumps defined on the proximal end of the waveguide form an interference fit with the at least two bumps defined by the aperture.

Example 9

The ultrasonic surgical instrument of one or more of Example 1 through Example 8, wherein the proximal end of the waveguide defines a male threaded end and the distal end of the transducer base plate defines a complementary female threaded end configured to receive the male threaded end defined by the proximal end of the waveguide.

Example 10

The ultrasonic surgical instrument of one or more of Example 1 through Example 9, wherein the proximal end of the waveguide defines a female threaded end and the transducer base plate defines an aperture to receive a screw therethrough and the threadingly engage the female threaded end of the waveguide.

Example 11

The ultrasonic surgical instrument of Example 10, wherein the proximal end of the waveguide defines a conical feature that matches a complementary conical channel defined by the distal end of the transducer base plate.

Example 12

The ultrasonic instrument of one or more of Example 1 through Example 11, wherein the proximal end of the waveguide defines a wedge and the distal end of the transducer baseplate defines a complementary mating notch to receive the wedge, wherein the distal end of the transducer base plate defines female threaded apertures laterally disposed from the notch and the proximal end of the waveguide comprises flanges laterally disposed from the wedge, wherein the flanges defines apertures, and wherein in a coupled configuration the apertures align with the female threaded apertures defined by the distal end of the transducer base plate.

Example 13

The ultrasonic surgical instrument of one or more of Example 1 through Example 12, wherein the distal end of the transducer base plate defines a luer male thread and the waveguide comprises a slidable luer nut configured to engage the luer male thread to define a luer lock joint between the waveguide and the transducer base plate.

Example 14

The ultrasonic surgical instrument of one or more of Example 1 through Example 13, wherein the proximal end of the waveguide defines a first flange that is complementary and mates with a second flange defined at the distal end of the transducer base plate, wherein the first flange defines an aperture sized and configured to receive a pin defined by second flange sized and configured to achieve an interference flange joint between the waveguide and the transducer base plate.

Example 15

The ultrasonic surgical instrument of one or more of Example 1 through Example 14, wherein the proximal end of the waveguide defines a first flange that is complementary and mates with a second flange defined at the distal end of the transducer base plate, wherein the first and second flanges define first and second apertures sized and configured to receive a pin therethrough, wherein the pin and the first and second apertures are sized and configured to achieve an interference joint between the waveguide and the transducer base plate.

Example 16

The ultrasonic surgical instrument of one or more of Example 1 through Example 15, wherein the proximal end of the waveguide defines at least two apertures and a distal end of the transducer base plate defines a recessed receptacle configured to accept a profile of the proximal end of the waveguide, wherein the recessed receptacle defines at least two apertures, wherein the ultrasonic surgical instrument further comprises at least two fasteners disposed through the at least two apertures defined by the waveguide and the at least two apertures defined by the recessed receptacle of the transducer base plate to lock the waveguide and the transducer base plate in place by a parallel tang attachment joint.

Example 17

The ultrasonic surgical instrument of claim one or more of Example 1 through Example 16, wherein the distal end of the transducer base plate defines a notch to receive the proximal end of the waveguide, wherein the distal end of the transducer base plate defines a transverse pin opening and the proximal end of the waveguide defines a transverse pin opening and a pin press fit through the transverse pin openings defined by the distal end of the transducer base plate and the proximal end of the waveguide to achieve an interference pin joint.

Example 18

The ultrasonic surgical instrument one or more of Example 1 through Example 17, wherein the waveguide defines a first longitudinal axis and the transducer base plate defines a second longitudinal axis, wherein the first longitudinal axis is offset from the second longitudinal axis.

Example 19

An ultrasonic waveguide, comprising: a shaft comprising a proximal end and a distal end, wherein the proximal end is configured to couple to an ultrasonic transducer and the distal end defines cylindrical aperture with a flat perpendicular bottom configured to receive a proximal end of a blade; and a blade attached to the shaft, the blade comprising a distal end for treating tissue and a proximal end defining a conical male end defining a flat perpendicular bottom, wherein the conical male end defines a proximal diameter and a distal diameter, wherein the proximal diameter is larger than the distal diameter, and wherein the conical male end is received into the cylindrical aperture defined by the distal end of the shaft.

Example 20

The ultrasonic waveguide of Example 19, wherein the blade is joined to the shaft by a swaged joint.

Example 21

The ultrasonic waveguide of Example 20, wherein the swaged joint is formed by a warm die swaging process.

Example 22

The ultrasonic waveguide of one or more of Example 19 through Example 21, wherein the conical male end defines a first circumferential groove at or near the distal diameter and defines a second circumferential groove between the proximal and distal diameters.

Example 23

The ultrasonic waveguide of one or more of Example 19 through Example 22, wherein the distal end of the shaft defines at a collar about the cylindrical aperture.

Example 24

The ultrasonic waveguide of one or more of Example 19 through Example 23, wherein the shaft is made of a first material and the blade is made of a second material.

Example 25

An ultrasonic surgical instrument, comprising: an ultrasonic waveguide defining a T-shaped male connector at a proximal end; and a symmetric two-piece clamshell housing comprising: first and second T-shaped pockets configured to receive the T-shaped male connector, wherein the T-shaped pockets are press fit to the T-shaped male connector; and first and second recessed pockets configured to support first and a second piezoelectric elements, wherein the first and second piezoelectric elements are configured to operate in a D31 mode.

Example 26

The ultrasonic surgical instrument of Example 25, further comprising a first electrode disposed between the first and second piezoelectric elements and an electrically conductive element disposed through an aperture defined in one of the two-piece clamshell housing.

Example 27

The ultrasonic surgical instrument of Example 25 or Example 26, wherein each of the two-piece clamshell housing components is made of an electrically conductive material to act as a second electrode.

Example 28

The ultrasonic surgical instrument of Example 25 or Example 26, wherein each of the two-piece clamshell housing components is made of a thermally conductive material to act as a heat sink.

Tissue Loading of a Surgical Instrument

FIGS. 200-208 illustrate various views of an ultrasonic surgical instrument 9000. In various aspects, the surgical instrument 9000 can be embodied generally as a pair of ultrasonic shears. More specifically, the surgical instrument 9000 can include a first arm 9002 pivotably connected to a second arm 9004 at a pivot area 9016 by, e.g., a fastener 9006. The surgical instrument 9000 further includes a pair of handles or eye rings 9010, 9012 disposed at the proximal ends of the first arm 9002 and the second arm 9004, respectively. The first arm 9002 includes a jaw 9008 or clamp positioned at its distal end that includes a cooperating surface 9026, which is configured to cooperate with an end effector 9054 extending distally from the second arm 9004. Actuating the first arm 9002 in a first direction causes the jaw 9008 to pivot towards the end effector 9054 and actuating the first arm 9002 in a second direction causes the jaw 9008 to pivot away from the end effector 9054. In some aspects, the cooperating surface 9026 further includes a pad constructed from a polymeric or other compliant material and engages the end effector 9054. The surgical instrument 9000 further includes a transducer assembly, such as is described above with respect to FIGS. 1-3. The transducer assembly can be arranged in, e.g., a D31 or D33 architecture. The surgical instrument 9000 further comprises a housing 9052 enclosing various components of an ultrasonic system 10 (FIG. 1), including first and second piezoelectric elements 9064a, 9064b of an ultrasonic transducer 9062 arranged in a D31 architecture, a transducer base plate 9050 (e.g., a transducer mounting portion) comprising flat faces on opposite sides to receive the piezoelectric elements 9064a, 9064b, and a waveguide 9058 that longitudinally translates vibrations from the ultrasonic transducer 9062 to the end effector 9054. The surgical instrument 9000 further comprises an electrical connector 9056 that is connectable to an ultrasonic signal generator for driving the ultrasonic transducer 9062, as described above. The waveguide 9058 can comprise a plurality of stabilizing silicone rings or compliant supports 9060 positioned at, or at least near, a plurality of nodes (i.e., points located at a minimum or zero crossing in the vibratory motion standing wave). The compliant supports 9060 are configured to dampen undesirable lateral vibration in order to ensure that ultrasonic energy is transmitted longitudinally to the end effector 9054. The waveguide 9058 extends through the housing 9052 and the second arm 9004 and terminates at the end effector 9054, externally to the housing 9052. The end effector 9054 and the jaw 9008 are cooperating elements that are configured to grasp tissue, generally functioning collectively as a clamp 9030. Moving the jaw 9008 towards the end effector 9054 causes tissue situated therebetween to contact the end effector 9054, allowing the end effector 9054 to operate against the grasped tissue. As the end effector 9054 ultrasonically vibrates against the gasped tissue, the end effector 9054 generates frictional forces that cause the tissue to coagulate and eventually sever along the cutting length of the end effector 9054.

In some aspects, the transducer base plate 9050, waveguide 9058, and end effector 9054 assembly is manufactured as a planar member. However, in various aspects, the interior channel of the housing 9052 through which the waveguide 9058 extends is non-linear, as depicted in FIG. 204, because the assembly of the pivot area 9016 at which the first arm 9002 is joined to the second arm 9004 extends into the interior of the housing 9052. When the waveguide 9058 is situated within the housing 9052 during the assembly or manufacture of the surgical instrument 900, the waveguide 9058 is bent or elastically deformed around the interiorly-projecting portion of the pivot area 9016. The interior portion of the housing 9052 is arranged such that the terminal end of the waveguide 9058, i.e., the end effector 9054, extending beyond the housing 9052 is coplanar or aligned with the jaw 9008 and/or the first arm 9002. Conversely, the proximal portion of the waveguide 9058 is not coplanar with the end effector 9054. This curved arrangement allows the waveguide 9058 to avoid the interiorly-projecting portion of the pivot area 9016, e.g., fastener 9006, while still maintaining a slim profile for the housing 9052.

The cutting length of the surgical instrument 9000 corresponds to the lengths of the end effector 9054 and the cooperating surface 9026 of the jaw 9008. Tissue that is held between the end effector 9054 and the cooperating surface 9026 of the jaw 9008 for a sufficient period of time is cut by the end effector 9054, as described above. The end effector 9054 and the corresponding portion of the jaw 9008 can have a variety of shapes. In some aspects, the end effector 9054 is substantially linear in shape, as is depicted in FIGS. 200-204. In other aspects, the end effector 9054 is curved, as is depicted in FIGS. 206-207. In any case, the portion of the jaw 9008 configured to bring tissue into contact with the end effector 9054 corresponds to the shape of the end effector 9054 so that the jaw 9008 is aligned therewith.

In some aspects of the present surgical instrument 9000, there exists a gap 9028 situated proximally to the cooperating surface 9026 of the jaw 9008. If tissue extends into the gap 9028 during the use of the surgical instrument 9000, beyond the cooperating surface 9026 of the jaw 9008, then the coagulation and cutting of this overloaded tissue will be negatively impacted because the cooperating surface 9026 of the jaw 9008 will not be forcing the overloaded tissue to remain in contact with the end effector 9054. Therefore, various aspects of the surgical instrument 9000 include features to mitigate these effects.

In one such aspect wherein the cooperating surface 9026 is shorter in length than the end effector 9054, the region of the jaw 9008 corresponding to the cooperating surface 9026 includes an indicium 9014 or indicia thereon. The indicium 9014 extends across the exterior surface of the jaw 9008 from the distal end of the cooperating surface 9026 to the proximal end thereof. Stated differently, the indicium 9014 is coextensive with the cooperating surface 9026 of the jaw 9008. As the cutting length of the surgical instrument 9000 is equivalent to the length that the end effector 9054 and the cooperating surface 9026 of the jaw 9008 overlap, the indicium 9014 thus visually indicates the cutting length of the end effector 9054 to the operator of the surgical instrument 9000. Indicating the cutting length of the surgical instrument 9000 on the side opposing the end effector 9054, i.e., on the jaw 9008 and/or first arm 9002, can be useful in situations where the operator cannot see the end effector 9054 itself, such as when the surgical instrument 9000 is being utilized to cut tissue that obscures the end effector 9054. In various aspects, the indicium 9014 includes colors, markings (e.g., geometric patterns), protrusions, surface texture, a change in geometry of the end effector 9054 and/or the jaw 9008 (e.g., a curvature), or anything that otherwise visually distinguishes the particular region of the jaw 9008 from the adjacent structure of the surgical instrument 9000. In one particular aspect, the indicium 9014 is a color. In alternative aspects wherein the end effector 9054 is shorter in length than the cooperating surface 9026 of the jaw 9008, the indicium 9014 disposed on the jaw 9008 instead corresponds in length to (i.e., is coextensive with) the end effector 9054. In still other aspects, the indicium 9014 is disposed on the end effector 9054, rather than the jaw 9008.

The housing 9052 and associated structure of the ultrasonic system can be attached to at least one of the first arm 9002 or the second arm 9004 utilizing a variety of different means known in the field. In one aspect depicted in FIG. 200, the housing 9052 is fixedly attached to the second arm 9004 of the surgical instrument 9000 via a collet 9022. In other aspects, the housing 9052 can be attached via adhesives, fasteners, or mechanical connectors, such as clips. In still other aspects, the housing 9052 can be fashioned as a single structural component with at least one of the first arm 9002 or the second arm 9004 via, e.g., injection molding. In yet still other aspects, the housing 9052 can alternatively be fixedly attached to the first arm 9002 of the surgical instrument 9000.

In various aspects, the arm opposing the arm to which the housing 9052 is affixed can be removably connectable to the housing 9052. For example, in one aspect of the surgical instrument 9000 depicted in FIG. 208, the first arm 9002 is removably connectable to the housing 9052 via a first clip 9021 disposed on the first arm 9002 that engages a corresponding second clip 9020 disposed on the housing 9052. In another aspect depicted in FIGS. 200-203, the first arm 9002 is removably connectable to the housing 9052 via a slot 9025 that is configured to frictionally engage a corresponding projection or tab 9024 disposed on the housing 9052. Securing the first arm 9002 to the housing 9052 reduces the profile of the surgical instrument 9000 when it is not in use. In alternative aspects wherein the housing 9052 is fixedly connected to the first arm 9002, the housing 9052 can be removably connected to the second arm 9004 in a variety of manners, as described above.

FIGS. 209-210 illustrate side views of a surgical instrument 9000 clamping a tissue 9900, according to one aspect of this disclosure. In the depicted aspect, the surgical instrument 9000 is configured to detect when the tissue 9900 clamped by the surgical instrument 9000 is overloaded or, stated differently, when the grasped tissue 9900 extends proximally beyond the cooperating surface 9026 of the jaw 9008 and/or end effector 9054. It is desirable to detect such an occurrence for a number of different reasons. For example, when tissue 9900 is positioned in the gap 9028, rather than securely between the cooperating surface 9026 and the end effector 9054, it may not be making consistent contact with end effector 9054, which can negatively impact the performance of the surgical instrument 9000. As another example, if the tissue 9900 that the operator intends to grasp with the clamp 9030 instead enters the proximal gap 9028, the operator of the surgical instrument 9000 may be coagulating and/or cutting an unintended portion of the tissue 9900. As yet another example, if tissue 9900 moves too far proximally, it can become pinched between the first arm 9002 and the second arm 9004, causing damage to the tissue 9900 or otherwise interfering with cutting action of the surgical instrument 9000.

In this aspect, the jaw 9008 comprises a first electrode 9100 having a first electrical potential and a second electrode 9102 having a second electrical potential. The first electrode 9100 corresponds to the position of the cooperating surface 9026 of the jaw 9008. In one aspect, the first electrode 9100 is coextensive with the cooperating surface 9026. The second electrode 9102 corresponds to the position of the gap 9028. In one aspect, the second electrode 9102 is coextensive with the surface of the jaw 9008 corresponding to the gap 9028. When tissue 9900 contacts both the first electrode 9100 and the second electrode 9102, the circuit is completed and a signal is generated indicating that tissue 9900 has been detected in the proximal gap 9028 (i.e., is overloaded). The signal can include an electrical signal transmitted via a wired connection to, e.g., a controller of the surgical instrument 9000. The signal can also include a wireless signal that is received by a corresponding electronic device that is in wireless communication with the surgical instrument 9000. The signal can be utilized to provide an alert to the operator of the surgical instrument 9000, initiate an alarm, deactivate the end effector 9054, or take other corrective action.

In addition to, or in lieu of, components configured to visually indicate the cutting length of the surgical instrument, as described in relation to FIGS. 200-208, or components to detect when tissue is overloaded, as described in relation to FIGS. 209-210, various aspects of the surgical instrument 9000 can be configured to physically prevent grasped from being overloaded. Referring generally now to FIGS. 211-239, there are shown various aspects of ultrasonic surgical instruments 9000 incorporating structural features configured to serve as stops or impediments that physically prevent tissue from loading beyond, i.e., from extending proximally past, the cooperating surface 9026 and/or end effector 9054 when grasped thereby. Such components are referred to collectively as "tissue stops." Each of the tissue stops described herein can be configured to physically obstruct or block tissue from extending proximally beyond the cooperating surface 9026 throughout the range of movement of the jaw 9008 relative to the end effect 9504.

FIGS. 211-212 illustrate various views of an ultrasonic surgical instrument 9000 incorporating a pivotable member 9150 tissue stop, according to one aspect of this disclosure. In one aspect, the pivotable member 9150 comprises a pair of opposing sides 9158a, 9158b and an open interior 9154. The opposing sides 9158a, 9158b are connected to the jaw 9008 and/or the first arm 9002 at a pivot point 9156. The open interior 9154 framed by the opposing sides 9158a, 9158b is greater than or equal in length to the distance from the pivot point 9156 to the distal ends of the end effector 9054 and the jaw 9008, which allows the pivotable member 9150 to pivot from a position stowed against the first arm 9002, around the distal end of the surgical instrument 9000 to a deployed position where the opposing sides 9158a, 9158b extend across the lateral sides of the jaw 9008 and the end effector 9054. In one aspect, when the pivotable member

9150 is in the deployed position, it is oriented generally orthogonally with respect to the end effector 9054. The pivot point 9156 can be positioned on the first arm 9002 and/or the jaw 9008 such that it is aligned with the proximal end of the cooperating surface 9026. Therefore, when the pivotable member 9150 is deployed, the opposing sides 9158*a*, 9158*b* extend downwardly from the pivot point 9156 along the lateral sides of the jaw 9008 and the end effector 9054 at the proximal end of the cooperating surface 9026, physically preventing tissue from extending therebeyond. The pivot point 9156 can additionally include a stop configured to prevent the pivotable member 9150 from rotating beyond a position in which it is oriented generally orthogonally when deployed.

In one aspect, the jaw 9008 and/or first arm 9002 further comprises a channel 9152 or slot that is configured to receive at least a portion of the pivotable member 9150. The depth of the channel 9152 can be, in one aspect, greater than or equal to the height of the pivotable member 9150. In such aspects, the pivotable member 9150 is flush with or recessed from the surface of the surgical instrument 9000 when in the stowed position.

FIGS. 213-215 illustrate various views of an ultrasonic surgical instrument 9000 incorporating a mechanical linkage 9170 tissue stop, according to one aspect of this disclosure. The mechanical linkage 9170 is a rigid member comprising a first end 9172 and a second end 9174. The first end 9172 is pivotably connected to an intermediate linkage 9176, which in turn is pivotably connected to the first arm 9002 adjacent to the jaw 9008. The second end 9174 is pivotably connected to the second arm 9004 adjacent to the end effector 9054. When the jaw 9008 rotates from the open position, depicted in FIG. 214, to the closed position, depicted in FIG. 215, a shelf 9178 positioned adjacently to the proximal end of the jaw 9008 contacts the first end 9172 of the linkage 9170, causing the linkage 9170 to rotate to a position wherein the linkage 9170 rests substantially flush to the proximal end of the jaw 9008. The linkage 9170 thus occupies the space between the proximal end of the jaw 9008 and the first and second arms 9002, 9004, physically preventing tissue gasped between the jaw 9008 and the end effector 9054 from extending proximally beyond the cooperating surface 9026.

FIGS. 216-218 illustrate various side views of an ultrasonic surgical instrument 9000 incorporating a deformable member 9190 tissue stop, according to one aspect of this disclosure. The deformable member 9190 is configured to elastically deform throughout the range of motion of the clamp 9030 between its open position and its closed position in order to block tissue 9900 from extending into the gap 9028. In one aspect, the deformable member 9190 comprises a tubular member constructed from an elastomeric material. The length of the tubular member can be equal to the width of the clamp 9030. The deformable member 9190 can comprise a first end 9192 that is affixed to the second arm 9004 and/or the end effector 9054 and a second end 9194 that is affixed to the first arm 9002 and/or the jaw 9008. In one aspect, the second end 9194 is attached to the first arm 9002 at a position adjacent to the proximal end of the cooperating surface 9026. When the clamp 9030 transitions to an open position, the second arm 9004 exerts a force at the first end 9192 and the first arm 9002 exerts a force at the second end 9194, which in combination causes the deformable member 9190 to expand in as the end effector 9054 and the jaw 9008 pivot away from each other. Likewise, when the clamp 9030 transitions to a closed position, the deformable member 9190 is compressed as the end effector 9054 and the jaw 9008 pivot towards each other. The deformable member 9190 thus occupies the space between the end effector 9054 and the jaw 9008 regardless of their relative positions. The ends 9192, 9194 of the deformable member 9190 can be affixed to their respective portions of the surgical instrument 9000 via, e.g., adhesives, fasteners, mechanical connectors.

FIGS. 219-222 illustrate various views of an ultrasonic surgical instrument 9000 incorporating a curved bar 9200 tissue stop, according to one aspect of this disclosure. In one aspect, the surgical instrument 9000 comprises a curved bar 9200 extending from the distal end of the second arm 9004, adjacent to the end effector 9054. The curved bar 9200 extends from the surface of the second arm 9004 oriented towards the first arm 9002, through a channel 9204 extending through the first arm 9002. The curvature of the curved bar 9200 corresponds to the rotational arc 9201 of the first arm 9002 or jaw 9008 (i.e., the arc along which a fixed point on the first arm 9002 or jaw 9008 travels as the jaw 9008 pivots between the open and closed positions), such that the first arm 9002 can pivot without obstruction from the curved bar 9200. In various aspects, the curved bar 9200 further comprises a head 9202 disposed at its distal end that has a larger width or diameter than at least a portion of the channel 9204 in which the curved bar 9200 is positioned. The head 9202 serves to limit the rotational arc 9201 of the first arm 9002 relative to the second arm 9004, preventing the curved bar 9200 from being withdrawn from the channel 9204 due to over rotation of the first arm 9002.

In various aspects, the curved bar 9200 has a width equal to at least a portion of the width of the cooperating surface 9026 or end effector 9054. As the curved bar 9200 is positioned adjacently to the proximal end of the cooperating surface 9026 and the first arm 9002 slides over the curved bar 9200 throughout the rotational arc 9201 of the first arm 9002, the curved bar 9200 thus serves as a physical obstruction between the open and closed positions of the clamp 9030 preventing grasped tissue from migrating therebeyond.

FIGS. 223-226 illustrates a perspective view of an ultrasonic surgical instrument 9000 incorporating an end effector ring 9250 tissue stop, according to one aspect of this disclosure. The ring 9250 comprises a torus or ring-shaped member including an aperture 9252 extending through the ring 9250 that is configured to receive the end effector 9054 therethrough. In one aspect, the aperture 9252 of the ring 9250 is configured to match the size and shape of the dimensions of the end effector 9054. The aperture 9252 is sized to a close tolerance of the end effector 9054 so that the ring 9250 can be slid along the length of the end effector 9054, but remains securely in place when undisturbed. When placed on the end effector 9054, the ring 9250 is configured to extend to the surface of the jaw 9008 defining the upper bound of the gap 9028 between the jaw 9008 and the end effector 9054. Therefore, when the ring 9250 is placed along the end effector 9054 proximal to the cooperating surface 9026, the ring 9250 serves as a physical barrier preventing tissue from entering the gap 9028. The ring 9250 can be constructed from, e.g., an elastomeric material.

In various aspects, the ring 9250 further comprises a clip 9256 affixed thereto that is configured to assist in securing the ring 9250 in place on the end effector 9054. In one aspect depicted in FIGS. 224-225, the clip 9256 comprises an aperture 9258, which is aligned with the aperture 9252 of the ring 9250, and a plurality of arms 9254. The arms 9254 extend orthogonally from the clip 9256 relative to the end effector 9054. The aperture 9258 of the ring 9250 is likewise configured to receive the end effector 9054 therethrough.

The arms 9254 are elastically biased members defining a slot 9262 that is configured to receive a portion of the jaw 9008. When a portion of the jaw 9008 is inserted into the slot 9262, the arms 9254 frictionally engage the portion of the jaw 9008, which holds the ring 9250 in place. In another aspect depicted in FIG. 226, the clip 9256 comprises an aperture 9258, which is aligned with the aperture 9252 of the ring 9250, and a plurality of arms 9260. The arms 9260 extend longitudinally from the clip 9256 relative to the end effector 9054. The arms 9260 are elastically biased members defining a slot 9264 that is configured to receive a projection (not shown) extending from the interior surface of the jaw 9008. When the arms 9260 are clipped to the projection from the jaw 9008, the arms 9260 frictionally engage the projection, which holds the ring 9250 in place.

FIGS. 227-229 illustrate views of an ultrasonic surgical instrument 9000 incorporating a longitudinally slidable member 9270 tissue stop, according to one aspect of this disclosure. In this aspect, the surgical instrument 9000 comprises a longitudinally slidable member 9270 disposed on the end effector 9054 that is configured to transition between a first or retracted position when the clamp 9030 is opened and a second or extended position when the clamp 9030 is closed. The slidable member 9270 comprises a channel 9280 configured to receive the end effector 9054, a distal surface 9276, and an arm 9278 extending from the proximal end. The channel 9280 further comprises a spring assembly 9272 that biases the slidable member 9270 towards the retracted position. In other words, the spring assembly 9272 is configured to return the slidable member 9270 to the retracted position from the extended position. The surgical instrument 9000 further comprises a projection 9274 extending from the first arm 9002 contacts the arm 9278 of the slidable member 9270 when the jaw 9008 pivots to the closed or clamped position. The contact between the projection 9274 and the arm 9278 drives the slidable member 9270 distally along the end effector 9054, placing the slidable member 9270 in an extended position. When the longitudinally slidable member 9270 is in the extended position, the distal surface 9276 makes contact with the proximal end of the cooperating surface 9026. The surface area of the distal surface 9276 is sufficient to extend from the end effector 9054 to the lower bound of the gap 9028, thereby allowing the slidable member 9270 to serve as a physical barrier preventing tissue from extending beyond the cooperating surface 9026 when the slidable member 9270 is in the extended position. When the jaw 9008 is pivoted away from the end effector 9054 to the open position of the clamp 9030, the projection 9274 disengages from the arm 9278 and the spring assembly 9272 returns the slidable member 9270 to its retracted position.

FIGS. 230-231 illustrate side views of an ultrasonic surgical instrument 9000 incorporating a cam 9290 tissue stop in an open position, according to one aspect of this disclosure. In one aspect, the surgical instrument 9000 comprises a first arm 9002 that is pivotably connected to a second arm 9004 by a pivot pin 9296. The surgical instrument 9000 further includes a cam 9290 that is configured to translate longitudinally between a distal or extended position and a proximal or retracted position. In one aspect, the cam 9290 includes a cam pin 9298 or camming surface that is engaged with a cam slot 9294 disposed on the first arm 9002. In various aspects, the shape of the cam slot 9294 is configured to cause the cam 9290 to be translated distally (i.e., extended) when the jaw 9008 is pivoted away from the end effector 9054 and translated proximally (i.e., retracted) when the jaw 9008 is pivoted towards the end effector 9054.

In one aspect, the cam slot 9294 has a curved or serpentine shape including a first ramp 9302 configured to contact the cam pin 9298 when the jaw 9008 is opened (as depicted in FIG. 231), exerting a first horizontal force on the cam pin 9298. As the cam pin 9298 is fixedly attached to the cam 9290, the first horizontal force causes the cam 9290 to translate distally. The cam slot 9294 further includes a second ramp 9304, opposing the first ramp 9302, configured to contact the cam pin 9298 when the jaw 9008 is closed (as depicted in FIG. 230), exerting a second horizontal force on the cam pin 9298. The second horizontal force exerted by the second ramp 9304 on the cam pin 9298 is oriented oppositely to the first horizontal force, which causes the cam 9290 to translate proximally.

The cam 9290 includes a leading or distal surface 9300 that is configured to serve as a physical impediment or barrier preventing tissue from extending past the cooperating surface 9026 of the jaw 9008 when the surgical instrument 9000 is being utilized to grasp tissue. When the cam 9290 is in the extended position (as depicted in FIG. 231), the distal surface 9300 of the cam 9290 is positioned adjacently to the proximal end of the cooperating surface 9026. When an operator opens the jaw 9008 to grasp tissue, the distal surface 9300 thus blocks tissue from being overloaded. Once tissue is properly loaded and the jaw 9008 is then closed, the cam 9290 retracts.

The cam 9290 further comprises a slot 9292 disposed along its length that receives the pivot pin 9296 connecting the first arm 9002 and the second arm 9004 therethrough. The slot 9292 serves three purposes. First, the slot 9292 prevents the cam 9290 from interfering with the pivotable linkage (i.e., the pivot pin 9296) between the first arm 9002 and the second arm 9004. Second, in some aspects the width of the slot 9292 is equal to a close tolerance of the diameter or width of the pivot pin 9296. The close tolerance between the width of the slot 9292 and the pivot pin 9296 limits the non-longitudinal movement of the cam 9290. Stated differently, the slot 9292 ensures that the cam 9290 translates in a linear or longitudinal manner. Third, the length of the slot 9292 can be configured to serve as an absolute limit on the degree to which the jaw 9008 can be pivoted relative to the end effector 9054. When the proximal end of the slot 9292 contacts the pivot pin 9296 as the cam 9290 moves across the pivot pin 9296, the cam 9290 is prevented from being translated further distally. When the cam 9290 is locked from translating distally, the engagement between the cam pin 9298 and the cam slot 9294 then prevents the first arm 9002 and the jaw 9008 from pivoting further.

FIGS. 232-233 illustrate perspective views of an ultrasonic surgical instrument 9000 incorporating a flexible strip 9350 tissue stop, according to one aspect of this disclosure. In one aspect, the surgical instrument 9000 comprises a flexible strip 9350 including a first end 9352 attached to the second arm 9004 adjacent to the proximal end of the end effector 9054 and a second end 9354 slidably disposed within a channel 9356 positioned on the jaw 9008. The flexible strip 9350 can be constructed from, e.g., an elastomeric material, a series of rigid members flexibly connected together, or another such material or structure that allows the flexible strip 9350 to flex or deform as the jaw 9008 moves relative to the end effector 9054. In the depicted aspect, the flexible strip 9350 is arranged such that when the jaw 9008 pivots towards the end effector 9054, the flexible strip 9350 is retracted into the channel 9356, and when the jaw 9008 pivots away from the end effector 9054, the flexible strip 9350 extends from the channel 9356. However, the second end 9354 of the flexible strip 9350 is maintained within the channel 9356 throughout the range of movement of the jaw 9008. As the flexible strip 9350 slides in and out of the channel 9356 throughout the range of movement between the open and closed positions, the flexible strip 9350 bends or flexes so that a leading portion of the flexible strip 9350 is maintained adjacently to the proximal end of the cooperating surface 9026. The flexible strip 9350 thus serves as a physical barrier preventing tissue from extending beyond the cooperating surface 9026 when the surgical instrument 9000 is in use.

FIGS. 234-236 illustrate perspective views of an ultrasonic surgical instrument 9000 incorporating a flexible strip 9350 tissue stop, according to one aspect of this disclosure. In one aspect, the surgical instrument 9000 comprises a flexible strip 9350 including a first end 9352 slidably attached to the second arm 9004 adjacent to the proximal end of the end effector 9054 and a second end 9354. In one aspect, the first end 9352 is slidably attached to the second arm 9004 by one or more rollers 9358 positioned at the first end 9352 that are slidably disposed along an interior surface of a channel 9360 extending longitudinally along the second arm 9004. In one aspect, the second end 9354 is affixed to the cooperating surface 9026 via, e.g., a living hinge. In some aspects, the flexible strip 9350 and the cooperating surface 9026 are constructed as a continuous strip of material. The flexible strip 9350 can be constructed from, e.g., an elastomeric material, a series of rigid members flexibly connected together, or another such material or structure that allows the flexible strip 9350 to flex or deform as the jaw 9008 moves relative to the end effector 9054. In the depicted aspect, the flexible strip 9350 is arranged such that when the jaw 9008 pivots towards the end effector 9054, the flexible strip 9350 is retracted into the channel 9360, and when the jaw 9008 pivots away from the end effector 9054, the flexible strip 9350 extends from the channel 9360. However, the first end 9352 of the flexible strip 9350 is maintained within the channel 9356 throughout the range of movement of the jaw 9008. As the flexible strip 9350 slides in and out of the channel 9356 throughout the range of movement between the open and closed positions, the flexible strip 9350 bends or flexes so that a leading portion of the flexible strip 9350 is maintained adjacently to the proximal end of the cooperating surface 9026. The flexible strip 9350 thus serves as a physical barrier preventing tissue from extending beyond the cooperating surface 9026 when the surgical instrument 9000 is in use.

FIGS. 237-239 illustrate perspective views of an ultrasonic surgical instrument 9000 incorporating a flexible strip 9350 tissue stop, according to one aspect of this disclosure. In one aspect, the surgical instrument 9000 comprises a flexible strip 9350 including a first end 9352 slidably attached to the second arm 9004 adjacent to the proximal end of the end effector 9054 and a second end 9354. In one aspect, the first end 9352 is slidably attached to the second arm 9004 by one or more rollers 9358 positioned at the first end 9352 that are slidably disposed along an interior surface of a channel 9360 extending longitudinally along the second arm 9004. In one aspect, the second end 9354 is affixed to the jaw 9008 via an adhesive, mechanical fastener, or other such attachment method known in the art. The flexible strip 9350 can be constructed from, e.g., an elastomeric material, a series of rigid members flexibly connected together, or another such material or structure that allows the flexible strip 9350 to flex or deform as the jaw 9008 moves relative to the end effector 9054. In the depicted aspect, the flexible strip 9350 is arranged such that when the jaw 9008 pivots towards the end effector 9054, the flexible strip 9350 is retracted into the channel 9360, and when the jaw 9008 pivots away from the end effector 9054, the flexible strip 9350 extends from the channel 9360. However, the first end 9352 of the flexible strip 9350 is maintained within the channel 9356 throughout the range of movement of the jaw 9008. As the flexible strip 9350 slides in and out of the channel 9356 throughout the range of movement between the open and closed positions, the flexible strip 9350 bends or flexes so that a leading portion of the flexible strip 9350 is maintained adjacently to the proximal end of the cooperating surface 9026. The flexible strip 9350 thus serves as a physical barrier preventing tissue from extending beyond the cooperating surface 9026 when the surgical instrument 9000 is in use.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, in various aspects, such as those depicted in FIGS. 200-212, the end effector is depicted as positioned below the jaw on the surgical instrument; whereas in other aspects, such as those depicted in FIGS. 213-239, the end effector is depicted as positioned above the jaw on the surgical instrument. Notably, these aspects are merely illustrative and the teachings of one type are equally applicable to another type and the various structural characteristics can be utilized interchangeably in alternative aspects. As another example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

An ultrasonic surgical instrument comprising: an end effector; a jaw movable relative to the end effector; a transducer assembly comprising at least two piezoelectric elements configured to ultrasonically oscillate the end effector; and an indicium coextensive with a portion of the jaw overlying the end effector.

Example 2

The ultrasonic surgical instrument of Example 1, wherein the indicia comprises a color.

Example 3

The ultrasonic surgical instrument of Example 1 or Example 2, further comprising: a first electrode; and a second electrode; wherein a tissue contacting both the first electrode and the second electrode generates a signal.

Example 4

The ultrasonic surgical instrument of Example 3, further comprising a cooperating surface disposed on the jaw, the cooperating surface aligned with the end effector, wherein the first electrode is coextensive with the cooperating surface and the second electrode positioned proximally to the cooperating surface.

Example 5

The ultrasonic surgical instrument of one or more Example 1 through Example 4, further comprising: a linkage comprising a first end fixedly attached adjacent to the end effector and a second end pivotably attached adjacent to the jaw; wherein in the jaw closed position, the linkage is configured to pivot and contact a proximal end of the jaw; and wherein in the jaw open position, the linkage is configured to pivot away from the proximal end of the jaw.

Example 6

The ultrasonic surgical instrument of one or more of Example 1 through Example 5, further comprising: a cam movably connected to the jaw via a linkage; wherein in the jaw closed position, the cam is configured to extend and contact a proximal end of the jaw; and wherein in the jaw open position, the cam configured to retract.

Example 7

The ultrasonic surgical instrument of one or more of Example 1 through Example 6, further comprising: a slidable member movable between a retracted position and an extended position, wherein in the slidable member extended position the slidable member is configured to contact a proximal end of the jaw; wherein the member is biased to the retracted position; and a projection, wherein in the jaw closed position the projection is configured to contact the spring-biased member, and wherein in the jaw closed position the projection is configured to move the slidable member to the extended position.

Example 8

The ultrasonic surgical instrument of one or more of Example 1 through Example 7, further comprising a pivotable member configured to pivot from a first position to a second position wherein the pivotable member extends across the lateral sides of the jaw and the end effector.

Example 9

The ultrasonic surgical instrument of one or more of Example 1 through Example 8, further comprising a ring configured to be fitted over the end effector.

Example 10

The ultrasonic surgical instrument of one or more of Example 1 through Example 9, further comprising an elastomeric member disposed between the end effector and the jaw, wherein in the jaw open position the elastomeric member is stretched between the end effector and the jaw, and wherein in the jaw closed position the elastomeric member is compressed between the end effector and the jaw.

Example 11

The ultrasonic surgical instrument of one or more of Example 1 through Example 10, further comprising: a first arm; wherein the jaw disposed at a distal end of the first arm; a second arm pivotably connected to the first arm; wherein the end effector disposed at a distal end of the second arm; and a bar member extending from the second arm through the first arm at a position proximal to the jaw, the bar member comprising a curvature corresponding to a rotational arc of the first arm.

Example 12

The ultrasonic surgical instrument of one or more of Example 1 through Example 11, further comprising: a flexible strip comprising: a first end fixedly attached to the jaw; and a second end; a channel configured to slidably receive the second end; wherein in the jaw closed position the second end retracts into the channel, and wherein in the jaw open position the second end extends from the channel.

Example 13

The ultrasonic surgical instrument of one or more of Example 1 through Example 12, further comprising: a housing enclosing the ultrasonic transducer assembly; and an electrical connector disposed on the housing, the electrical connector electrically coupled to the ultrasonic transducer assembly and couplable to an ultrasonic signal generator; wherein the electrical connector is configured to short when contacted by fluid within the housing.

Example 14

An ultrasonic surgical instrument comprising: an end effector; a jaw movable relative to the end effector between an open position and a closed position; a transducer assembly comprising at least two piezoelectric elements configured to ultrasonically oscillate the end effector; and a cam movably connected to the jaw via a linkage; wherein in the jaw closed position, the cam is configured to extend towards a proximal end of the jaw; and wherein in the jaw open position, the cam is configured to retract.

Example 15

The ultrasonic surgical instrument of Example 14, further comprising: a housing enclosing the transducer assembly; a first arm; a second arm pivotably connected to the first arm; wherein the housing is fixedly connected to the first arm and removably connectable to the second arm.

Example 16

The ultrasonic surgical instrument of Example 14 or Example 15, further comprising: a first electrode; and a second electrode; wherein a tissue contacting both the first electrode and the second electrode generates a signal.

Example 17

The ultrasonic surgical instrument of one or more of Example 14 through Example 16, further comprising: a housing enclosing the ultrasonic transducer assembly; and an electrical connector disposed on the housing, the electrical connector electrically coupled to the ultrasonic transducer assembly and couplable to an ultrasonic signal generator; wherein the electrical connector is configured to short when contacted by fluid within the housing.

Example 18

An ultrasonic surgical instrument comprising: an end effector; a jaw movable relative to the end effector between an open position and a closed position; a transducer assembly comprising at least two piezoelectric elements configured to ultrasonically oscillate the end effector; a slidable member movable between a retracted position and an extended position, wherein in the slidable member extended position the slidable member is configured to contact a proximal end of the jaw; wherein the member is biased to the retracted position; and a projection, wherein in the jaw closed position the projection is configured to contact the spring-biased member, and wherein in the jaw closed position the projection is configured to move the slidable member to the extended position.

Example 19

The ultrasonic surgical instrument of Example 18, wherein the transducer assembly is enclosed within a housing and the housing is removably connectable to at least one of the first arm or the second arm.

Example 20

The ultrasonic surgical instrument of Example 18 or Example 19, further comprising: a first electrode; and a second electrode; wherein a tissue contacting both the first electrode and the second electrode generates a signal.

Example 21

The ultrasonic surgical instrument of example one or more of Example 18 through Example 20, further comprising: a housing enclosing the ultrasonic transducer assembly; and an electrical connector disposed on the housing, the electrical connector electrically coupled to the ultrasonic transducer assembly and couplable to an ultrasonic signal generator; wherein the electrical connector is configured to short when contacted by fluid within the housing.

Example 22

An ultrasonic surgical instrument comprising: a first arm; a second arm pivotably connected to the first arm; a jaw disposed at a distal end of the first arm; an end effector disposed at a distal end of the second arm; wherein the jaw is movable relative to the end effector between an open position and a closed position; a transducer assembly comprising at least two piezoelectric elements configured to ultrasonically oscillate the end effector; and a bar member extending from the second arm through the first arm at a position proximal to the jaw, the bar member comprising a curvature corresponding to a rotational arc of the first arm.

Example 23

The ultrasonic surgical instrument of Example 22, wherein the transducer assembly is enclosed within a housing, which is removably connectable to at least one of the first arm or the second arm.

Example 24

The ultrasonic surgical instrument of Example 22 or Example 23, further comprising: a first electrode; and a second electrode; wherein a tissue contacting both the first electrode and the second electrode generates a signal.

Example 25

The ultrasonic surgical instrument of one or more of Example 22 through Example 24, further comprising: a housing enclosing the ultrasonic transducer assembly; and an electrical connector disposed on the housing, the electrical connector electrically coupled to the ultrasonic transducer assembly and couplable to an ultrasonic signal generator; wherein the electrical connector is configured to short when contacted by fluid within the housing.

Various additional aspects of the subject matter described herein are set out in the following numbered examples:

Example 1

A method of fabricating an ultrasonic medical device comprising: machining a surgical tool from a portion of a flat metal stock, wherein the surgical tool comprises a proximal end, an end effector, and a longitudinal portion therebetween; contacting a face of a first transducer with a first face of the surgical tool, wherein the first transducer is configured to operate in a D31 mode with respect to the longitudinal portion of the surgical tool; and contacting a face of a second transducer with an opposing face of the surgical tool and opposite the first transducer, wherein the second transducer is configured to operate in a D31 mode with respect to the longitudinal portion of the surgical tool; wherein, upon activation, the first transducer and the second transducer are configured to induce a standing wave in the surgical tool; and wherein the induced standing wave comprises a node at a node location in the surgical tool and an antinode at an antinode location in the surgical tool.

Example 2

The method of Example 1, wherein machining a surgical tool from a portion of a flat metal stock comprises machining a surgical tool having a longitudinal axis oriented at an angle with respect to a grain direction of the flat metal stock thereby optimizing an operational characteristic of the surgical tool.

Example 3

The method of Example 1 or Example 2, wherein machining a surgical tool having a longitudinal axis oriented at an angle with respect to a grain direction of the flat metal stock comprises machining a surgical tool having a longitudinal axis oriented parallel to the grain direction of the flat metal stock.

Example 4

The method of one or more of Examples 2 through Example 3, wherein machining a surgical tool having a longitudinal axis oriented at an angle with respect to a grain direction of the flat metal stock comprises machining a surgical tool having a longitudinal axis oriented orthogonal to the grain direction of the flat metal stock.

Example 5

The method of one or more of Examples 2 through Example 4, wherein optimizing an operational characteristic of the surgical tool comprises: maximizing a length of the end effector; minimizing the length of the end effector; or reducing a stress in at least a portion of the surgical tool.

Example 6

A method of fabricating an ultrasonic medical device comprising: machining a surgical tool from a portion of a flat metal stock, wherein the surgical tool comprises a proximal end, an end effector, and a longitudinal portion therebetween; contacting a face of a first transducer with a first face of the surgical tool, wherein the first transducer is configured to operate in a D31 mode with respect to the longitudinal portion of the surgical tool; contacting a face of a second transducer with an opposing face of the surgical tool and opposite the first transducer, wherein the second transducer is configured to operate in a D31 mode with respect to the longitudinal portion of the surgical tool; and subjecting the surgical tool to one or more metalworking processes; wherein, upon activation, the first transducer and the second transducer are configured to induce a standing wave in the surgical tool; and wherein the induced standing wave comprises a node at a node location in the surgical tool and an antinode at an antinode location in the surgical tool.

Example 7

The method of Example 6, wherein subjecting the surgical tool to one or more metalworking processes comprises applying a metalworking process to a portion of the surgical tool proximal to the anti-node location in the surgical tool.

Example 8

The method of Example 6 or Example 7, wherein subjecting the surgical tool to one or more metalworking processes comprises removing a portion of mass of the surgical tool in a region bounded by the anti-node location in the surgical tool and a second anti-node location in the surgical tool.

Example 9

The method of one or more of Example 6 through Example 8, wherein subjecting the surgical tool to one or more metalworking processes comprises subjecting the surgical tool to machining, skiving, coining, forming, forging, milling, end milling, chamfering, tumbling, sand blasting, bead blasting, or electropolishing, or any combination or combinations thereof.

Example 10

The method of one or more of Example 6 through Example 9, wherein subjecting the surgical tool to one or more metalworking processes comprises removing a portion of mass of the surgical tool in a section of the longitudinal portion and bending the surgical tool in the section of the longitudinal portion.

Example 11

The method of one or more of Example 6 through Example 10, wherein subjecting the surgical tool to one or more metalworking processes comprises machining a plurality of female screw threads into the proximal end of the surgical tool, wherein the female screw threads are oriented along a longitudinal axis thereof.

Example 12

The method of Example 11, wherein machining a plurality of female screw threads into the proximal end of the surgical tool comprises machining a plurality of female screw threads configured to receive a component having mating male threads that have a major dimension less than or equal to a thickness of the surgical tool, wherein the thickness comprises a distance between the first face of the surgical tool and the second face of the surgical tool.

Example 13

The method of Example 11 or Example 12, wherein machining a plurality of female screw threads into the proximal end of the surgical tool comprises machining a plurality of female screw threads configured to receive a component having mating male threads that have a major dimension greater than a thickness of the surgical tool, wherein the thickness comprises a distance between the first face of the surgical tool and the second face of the surgical tool.

Example 14

A method of fabricating an ultrasonic medical device comprising: machining a surgical tool from a portion of a flat metal stock, wherein the surgical tool comprises a proximal end, an end effector, and a longitudinal portion therebetween; contacting a face of a first transducer with a first face of the surgical tool, wherein the first transducer is configured to operate in a D31 mode with respect to the longitudinal portion of the surgical tool; and contacting a face of a second transducer with an opposing face of the surgical tool and opposite the first transducer, wherein the second transducer is configured to operate in a D31 mode with respect to the longitudinal portion of the surgical tool; wherein, upon activation, the first transducer and the second transducer are configured to induce a standing wave in the surgical tool; wherein the induced standing wave comprises a node at a node location in the surgical tool and an antinode at an antinode location in the surgical tool; and wherein machining a surgical tool from a portion of a flat metal stock comprises laser machining, laser machining with a tilt degree of freedom, electrical discharge machining, milling, stamping, or fine blanking.

Example 15

The method of Example 14, wherein machining a surgical tool from a portion of a flat metal stock comprises machining a surgical tool further comprising a first flange and a second flange, wherein the first flange extends from a first side of the surgical tool and the second flange extends from an opposing side of the surgical tool.

Example 16

The method of Example 14 or Example 15, wherein machining a surgical tool from a portion of a flat metal stock comprises machining a surgical tool further comprising a first flange and a second flange wherein each of the first flange and the second flange is symmetrically disposed about the node location in the surgical device.

Example 17

The method of one or more of Example 14 through Example 16, wherein machining a surgical tool from a portion of a flat metal stock comprises machining a surgical tool from a flat metal stock comprising aluminum or titanium.

Example 18

The method of one or more of Example 14 through Example 17, wherein contacting a face of a first transducer with a first face of the surgical tool comprises fixing a face of a first transducer to a first face of the surgical tool with a conductive adhesive at the node location in the surgical tool and with a high strength adhesive at a location away from the node location in the surgical tool.

Example 19

The method of Example 18, wherein contacting a face of a second transducer with an opposing face of the surgical tool and opposite the first transducer comprises fixing a face of a second transducer to an opposing face of the surgical tool and opposite the first transducer with a conductive adhesive at the node location in the surgical tool and with a high strength adhesive at a location away from the node location in the surgical tool.

Example 20

A method of fabricating an ultrasonic waveguide, comprising swaging an ultrasonic waveguide shaft made of a first metal to an ultrasonic blade made of a second metal.

The invention claimed is:

1. A method of fabricating an ultrasonic medical device comprising:
   machining a surgical tool from a portion of a flat metal stock, wherein the surgical tool comprises a proximal end having a first flat face and a second flat face outwardly facing 180 degrees opposite the first flat face, an end effector, and a longitudinal portion in between the proximal end and the end effector;
   contacting a face of a first transducer with the first flat face of the surgical tool, wherein the first transducer is configured to operate in a D31 mode with respect to the longitudinal portion of the surgical tool, and wherein the first transducer is mounted to the surgical tool with a first transducer mounting portion fabricated in the form of a triangular prism; and
   contacting a face of a second transducer with the second flat face of the surgical tool and opposite the first transducer, such that the first transducer outwardly faces a first direction and the second transducer outwardly faces a second direction 180 degrees opposite the first direction, wherein the second transducer is configured to operate in a D31 mode with respect to the longitudinal portion of the surgical tool, and wherein the second transducer is mounted to the surgical tool with a second transducer mounting portion fabricated in the form of a triangular prism;
   wherein, upon activation, the first transducer and the second transducer are configured to induce a standing wave in the surgical tool,
   wherein the induced standing wave comprises a node at a node location in the surgical tool and an antinode at an antinode location in the surgical tool,
   wherein the longitudinal portion defines a third direction that extends from the proximal end to the end effector, and
   wherein the third direction is orthogonal to the first direction and the second direction.

2. The method of claim 1, wherein machining the surgical tool from the portion of the flat metal stock comprises machining the surgical tool having a longitudinal axis oriented at an angle with respect to a grain direction of the flat metal stock thereby optimizing an operational characteristic of the surgical tool.

3. The method of claim 2, wherein machining the surgical tool having the longitudinal axis oriented at the angle with respect to the grain direction of the flat metal stock comprises machining the surgical tool having the longitudinal axis oriented parallel to the grain direction of the flat metal stock.

4. The method of claim 2, wherein machining the surgical tool having the longitudinal axis oriented at the angle with respect to the grain direction of the flat metal stock comprises machining the surgical tool having the longitudinal axis oriented orthogonal to the grain direction of the flat metal stock.

5. The method of claim 2, wherein optimizing the operational characteristic of the surgical tool comprises:
   maximizing a length of the end effector;
   minimizing the length of the end effector; or
   reducing a stress in at least a portion of the surgical tool.

6. The method of claim 1, wherein contacting the face of the first transducer with the first flat face of the surgical tool comprises:
   identifying the node location based on a wavelength of the standing wave induced in the surgical tool;
   applying an electrically conductive adhesive to the face of the first transducer;
   applying a high strength adhesive to the first flat face of the surgical tool away from the node location; and
   applying the electrically conductive adhesive on the face of the first transducer to the first flat face of the surgical tool, centered around the node location, such that the high strength adhesive also contacts the face of the first transducer.

7. A method of fabricating an ultrasonic medical device comprising:

machining a surgical tool from a portion of a flat metal stock, wherein the surgical tool comprises a proximal end having a first flat face and a second flat face outwardly facing 180 degrees opposite the first flat face, an end effector, and a longitudinal portion in between the proximal end and the end effector;

contacting a face of a first transducer with the first flat face of the surgical tool, wherein the first transducer is configured to operate in a D31 mode with respect to the longitudinal portion of the surgical tool, and wherein the first transducer is mounted to the surgical tool with a first transducer mounting portion fabricated in the form of a triangular prism; and contacting a face of a second transducer with the second flat face of the surgical tool and opposite the first transducer, such that the first transducer outwardly faces a first direction and the second transducer outwardly faces a second direction 180 degrees opposite the first direction, wherein the second transducer is configured to operate in a D31 mode with respect to the longitudinal portion of the surgical tool, and wherein the second transducer is mounted to the surgical tool with a second transducer mounting portion fabricated in the form of a triangular prism;

wherein, upon activation, the first transducer and the second transducer are configured to induce a standing wave in the surgical tool;

wherein the induced standing wave comprises a node at a node location in the surgical tool and an antinode at an antinode location in the surgical tool, wherein machining the surgical tool from the portion of the flat metal stock comprises laser machining, laser machining with a tilt degree of freedom, electrical discharge machining, milling, stamping, or fine blanking, wherein the longitudinal portion defines a third direction that extends from the proximal end to the end effector, and wherein the third direction is orthogonal to the first direction and the second direction.

8. The method of claim 7, wherein the surgical tool further comprises a first flange and a second flange, wherein the first flange extends from a first side of the surgical tool and the second flange extends from an opposing side of the surgical tool.

9. The method of claim 8, wherein each of the first flange and the second flange is symmetrically disposed about the node location in the surgical tool.

10. The method of claim 7, wherein the flat metal stock comprises aluminum or titanium.

11. The method of claim 7, wherein contacting the face of the first transducer with the first flat face of the surgical tool comprises fixing the face of the first transducer to the first flat face of the surgical tool with a conductive adhesive at the node location in the surgical tool and with a high strength adhesive at a location away from the node location in the surgical tool.

12. The method of claim 11, wherein contacting the face of the second transducer with the second flat face of the surgical tool and opposite the first transducer comprises fixing the face of the second transducer to the second flat face of the surgical tool and opposite the first transducer with a conductive adhesive at the node location in the surgical tool and with a high strength adhesive at a location away from the node location in the surgical tool.

13. The method of claim 7, wherein contacting the face of the first transducer with the first flat face of the surgical tool comprises:
  identifying the node location based on a wavelength of the standing wave induced in the surgical tool;
  applying an electrically conductive adhesive to the face of the first transducer;
  applying a high strength adhesive to the first flat face of the surgical tool away from the node location; and
  applying the electrically conductive adhesive on the face of the first transducer to the first flat face of the surgical tool, centered around the node location, such that the high strength adhesive also contacts the face of the first transducer.

* * * * *